US009758485B2

(12) United States Patent
Hallenbach et al.

(10) Patent No.: US 9,758,485 B2
(45) Date of Patent: *Sep. 12, 2017

(54) COMPOUNDS FOR CONTROLLING ARTHROPODS

(71) Applicant: BAYER CROPSCIENCE AKTIENGESELLSCHAFT, Monheim am Rhein (DE)

(72) Inventors: Werner Hallenbach, Monheim (DE); Hans-Georg Schwarz, Dorsten (DE); Kerstin Ilg, Cologne (DE); Ulrich Goergens, Ratingen (DE); Johannes Koebberling, Neuss (DE); Andreas Turgerg, Haan (DE); Niels Boehnke, Berlin (DE); Michael Maue, Langenfeld (DE); Robert Velten, Langenfeld (DE); Tobias Harschneck, Duesseldorf (DE); Julia Johanna Hahn, Duesseldorf (DE); Sebastian Horstmann, Leverkusen (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/033,415

(22) PCT Filed: Nov. 5, 2014

(86) PCT No.: PCT/EP2014/073795
§ 371 (c)(1),
(2) Date: Apr. 29, 2016

(87) PCT Pub. No.: WO2015/067647
PCT Pub. Date: May 14, 2015

(65) Prior Publication Data
US 2016/0278379 A1    Sep. 29, 2016

(30) Foreign Application Priority Data

Nov. 5, 2013  (EP) ................................. 13191610
Aug. 15, 2014 (EP) ................................. 14181149

(51) Int. Cl.
| | | |
|---|---|---|
| A01N 43/56 | (2006.01) |
| A01N 43/54 | (2006.01) |
| A01N 43/36 | (2006.01) |
| A01N 43/80 | (2006.01) |
| C07D 231/12 | (2006.01) |
| C07D 261/08 | (2006.01) |
| C07D 401/04 | (2006.01) |
| C07D 413/04 | (2006.01) |
| C07D 403/04 | (2006.01) |
| C07D 207/337 | (2006.01) |
| A01N 43/40 | (2006.01) |

(Continued)

(52) U.S. Cl.
CPC ........... *C07D 231/12* (2013.01); *A01N 43/36* (2013.01); *A01N 43/40* (2013.01); *A01N 43/54* (2013.01); *A01N 43/56* (2013.01); *A01N 43/80* (2013.01); *C07D 207/337* (2013.01); *C07D 231/00* (2013.01); *C07D 261/00* (2013.01); *C07D 261/08* (2013.01); *C07D 401/04* (2013.01); *C07D 403/04* (2013.01); *C07D 413/04* (2013.01)

(58) Field of Classification Search
CPC ........ A01N 43/56; A01N 43/54; A01N 43/36; A01N 43/80; C07D 231/12; C07D 261/08; C07D 401/04; C07D 413/04
See application file for complete search history.

(56) References Cited

U.S. PATENT DOCUMENTS

| | | | |
|---|---|---|---|
| 6,869,969 B2 * | 3/2005 | Huebner | ............ C07D 261/08 514/378 |
| 8,946,234 B2 | 2/2015 | Maue et al. | |

(Continued)

FOREIGN PATENT DOCUMENTS

| | | | |
|---|---|---|---|
| CH | WO 2011009484 A1 * | 1/2011 | ........... C07D 231/12 |
| EP | 1 911 751 A1 | 4/2008 | |

(Continued)

*Primary Examiner* — Samira Jean-Louis
(74) *Attorney, Agent, or Firm* — McBee Moore Woodward Vanik IP LLC

(57) ABSTRACT

The invention relates inter alia to compounds of the general formula (I)

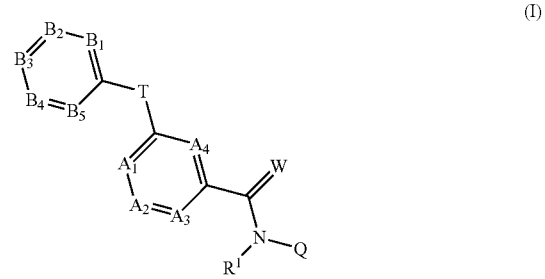

in which the $A_1$-$A_4$, T, n, W, Q, $R^1$ and $B_1$-$B_4$ radicals are each as defined in the description. Also described are processes for preparing the compounds of the formula (I). The inventive compounds are especially suitable for controlling insects, arachnids and nematodes in agriculture, and ectoparasites in veterinary medicine.

17 Claims, No Drawings

(51) Int. Cl.
*C07D 231/00* (2006.01)
*C07D 261/00* (2006.01)

(56) References Cited

U.S. PATENT DOCUMENTS

| | | | | |
|---|---|---|---|---|
| 2010/0144672 A1* | 6/2010 | Frackenpohl | ........ | C07D 401/14 514/63 |
| 2010/0179141 A1* | 7/2010 | Belanger | .............. | C07D 213/81 514/233.8 |
| 2010/0286135 A1* | 11/2010 | Reddy | .................. | C07D 401/14 514/230.5 |

FOREIGN PATENT DOCUMENTS

| | | |
|---|---|---|
| WO | 2010/051926 A2 | 5/2010 |
| WO | 2011/113756 A1 | 9/2011 |
| WO | 2012/069366 A1 | 5/2012 |
| WO | 2012080376 A1 | 6/2012 |
| WO | 2012/107434 A1 | 8/2012 |
| WO | 2012/175474 A1 | 12/2012 |

* cited by examiner

COMPOUNDS FOR CONTROLLING ARTHROPODS

CROSS REFERENCE TO RELATED APPLICATIONS

This application is a §371 National State Application of PCT/EP2014/073795, filed Nov. 5, 2014, which claims priority to European Application Nos. 13191610.8 filed Nov. 5, 2013 and European Application No. 14181149.7 filed Aug. 15, 2014.

BACKGROUND OF THE INVENTION

Field of the Invention

INTRODUCTION

The present application relates to trifluoro novel compounds, to processes for preparation thereof and to use thereof for controlling animal pests, in particular arthropods and especially insects, arachnids and nematodes.

Description of Related Art

It is known that particular halogen-substituted compounds have insecticidal activity (EP 1 911 751, WO2012/069366, WO2012/080376, WO2012/107434 and WO2012/175474).

WO 2011/113756 discloses triazole derivatives having insecticidal activity.

It is also known that particular halogen-substituted compounds have cytokine-inhibiting activities (WO 2000/07980).

Modern crop protection compositions have to meet many demands, for example in relation to efficacy, persistence and spectrum of action, and possible use. Questions of toxicity and of combinability with other active ingredients or formulation auxiliaries play a role, as does the question of the expense that the synthesis of an active ingredient requires. In addition, resistances can occur. For all these reasons, the search for novel crop protection agents can never be considered to be complete, and there is a constant need for novel compounds having properties improved over the known compounds at least in relation to individual aspects.

SUMMARY

It was an object of the present invention to provide compounds which widen the spectrum of the pesticides in various aspects and/or improve their activity.

It has now been found that, surprisingly, particular halogen-substituted compounds and salts thereof have biological properties and are especially suitable for controlling animal pests, and therefore have particularly good usability in the agrochemical sector and in the animal health sector.

Similar compounds are already known from WO 2010/051926.

Novel halogen-substituted compounds which have insecticidal, acaricidal and/or parasiticidal activity and are of the general formula (I) have been found:

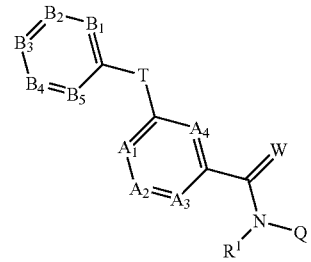

in which
R$^1$ is H, in each case optionally substituted C$_2$-C$_6$-alkenyl, C$_2$-C$_6$-alkynyl, C$_3$-C$_7$-cycloalkyl, C$_1$-C$_6$-alkylcarbonyl, C$_1$-C$_6$-alkoxycarbonyl, aryl(C$_1$-C$_3$)-alkyl, heteroaryl(C$_1$-C$_3$)-alkyl, or is optionally substituted C$_1$-C$_6$-alkyl, preferably H or preferably C$_1$-C$_2$-alkyl, most preferably H or methyl, especially H, the following moieties are as follows:
A$_1$ is CR$^2$ or N,
A$_2$ is CR$^3$ or N,
A$_3$ is CR$^4$ or N,
A$_4$ is CR$^5$ or N,
B$_1$ is CR$^6$ or N,
B$_2$ is CR$^7$ or N,
B$_3$ is CR$^8$ or N,
B$_4$ is CR$^9$ or N, and
B$_5$ is CR$^{10}$ or N,
but not more than three of the A$_1$ to A$_4$ moieties are N and not more than three of the B$_1$ to B$_5$ moieties are N;
R$^2$, R$^3$, R$^4$, R$^5$, R$^6$, R$^7$, R$^9$ and R$^{10}$ are each independently H, halogen, cyano, nitro, in each case optionally substituted C$_1$-C$_6$-alkyl, C$_3$-C$_6$-cycloalkyl, C$_1$-C$_6$-alkoxy, N—C$_1$-C$_6$-alkoxyimino-C$_1$-C$_3$-alkyl, C$_1$-C$_6$-alkylsulphanyl, C$_1$-C$_6$-alkylsulphinyl, C$_1$-C$_6$-alkylsulphonyl, N—C$_1$-C$_6$-alkylamino, N,N-di-C$_1$-C$_6$-alkylamino or N—C$_1$-C$_3$-alkoxy-C$_1$-C$_4$-alkylamino or 1-pyrrolidinyl;
if neither of the A$_2$ and A$_3$ moieties is N, R$^3$ and R$^4$ together with the carbon atom to which they are bonded may form a 5- or 6-membered ring containing 0, 1 or 2 nitrogen atoms and/or 0 or 1 oxygen atom and/or 0 or 1 sulphur atom; or
if neither of the A$_1$ and A$_2$ moieties is N, R$^2$ and R$^3$ together with the carbon atom to which they are bonded may form a 6-membered ring containing 0, 1 or 2 nitrogen atoms;
R$^8$ is halogen, cyano, nitro, in each case optionally substituted C$_1$-C$_6$-alkyl, C$_3$-C$_6$-cycloalkyl, C$_1$-C$_6$-alkoxy, N—C$_1$-C$_6$-alkoxyimino-C$_1$-C$_3$-alkyl, C$_1$-C$_6$-alkylsulphanyl, C$_1$-C$_6$-alkylsulphinyl, C$_1$-C$_6$-alkylsulphonyl, N—C$_1$-C$_6$-alkylamino or N,N-di-C$_1$-C$_6$-alkylamino;
W is O or S;
Q is H, formyl, hydroxyl, amino or in each case optionally substituted C$_1$-C$_6$-alkyl, C$_2$-C$_6$-alkenyl, C$_2$-C$_6$-alkynyl, C$_3$-C$_6$-cycloalkyl, C$_1$-C$_5$-heterocycloalkyl, C$_1$-C$_4$-alkoxy, C$_1$-C$_6$-alkyl-C$_3$-C$_6$-cycloalkyl, C$_3$-C$_6$-cycloalkyl-C$_1$-C$_6$-alkyl, C$_6$-,C$_{10}$-C$_{14}$-aryl, C$_1$-C$_5$-heteroaryl, C$_6$-,C$_{10}$-,C$_{14}$-aryl-(C$_1$-C$_3$)-alkyl, C$_1$-C$_5$-heteroaryl-(C$_1$-C$_3$)-alkyl, N—C$_1$-C$_4$-alkylamino, N—C$_1$-C$_4$-alkylcarbonylamino, or N,N-di-C$_1$-C$_4$-alkylamino; or
is an optionally poly-V-substituted unsaturated 6-membered carbocycle; or
is an optionally poly-V-substituted unsaturated 4-, 5- or 6-membered heterocyclic ring, where V is independently halogen, cyano, nitro, in each case optionally substituted $C_1$-$C_6$-alkyl, $C_1$-$C_4$-alkenyl, $C_1$-$C_4$-alkynyl, $C_3$-$C_6$-cycloalkyl, $C_1$-$C_6$-alkoxy, N—$C_1$-$C_6$-alkoxyimino-$C_1$-$C_3$-alkyl, $C_1$-$C_6$-alkylsulphanyl, $C_1$-$C_6$-alkylsulphinyl, $C_1$-$C_6$-alkylsulphonyl, or N,N-di-($C_1$-$C_6$-alkyl)amino;

T is an optionally substituted 5-membered heteroaromatic system containing not more than 2 heteroatoms (1 or 2 heteroatoms), such as four carbon atoms and one (1) heteroatom, preferably one (1) nitrogen, one (1) oxygen or one (1) sulphur atom or three carbon atoms and two heteroatoms, preferably two nitrogen atoms, one (1) nitrogen and one (1) oxygen atom, or one (1) nitrogen and one (1) sulphur atom, and salts, N-oxides and tautomeric forms of the compound of the formula (I).

One aspect of the present invention relates to compounds of the formula (Ia)

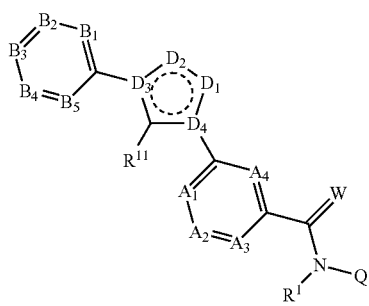

(Ia)

in which the $D_1$, $D_2$ moieties are each independently C—$R^{11}$ or a heteroatom selected from N and O;

the $D_3$ and $D_4$ moieties are each independently C or a heteroatom selected from N (i.e. the $D_3$ and $D_4$ moieties are each independently C or N);

where not more than one (1) or two moieties selected from $D_1$, $D_2$, $D_3$ and $D_4$ is/are a heteroatom, where one (1) or two moiety selected from $D_1$, $D_2$, $D_3$ and $D_4$ is a heteroatom selected from N and O in the case of D, and $D_2$, or N in the case of $D_3$ and $D_4$;

is an aromatic system; and $R^1$, $A_1$, $A_2$, $A_3$, $A_4$, $B_1$, $B_2$, $B_3$, $B_4$, $B_5$, $R^2$, $R^3$, $R^4$, $R^5$, $R^6$, $R^7$, $R^8$, $R^9$, $R^{10}$, $R^{11}$, W, Q, V, and T are each defined as described herein, where not more than one moiety selected from $A_1$, $A_2$, $A_3$, $A_4$ is N and not more than one moiety selected from $B_1$, $B_2$, $B_3$, $B_4$ and $B_5$ is N; or where one or two moieties selected from $A_1$, $A_2$, $A_3$, $A_4$ may be N and not more than one moiety selected from $B_1$, $B_2$, $B_3$, $B_4$ and $B_5$ is N, and salts, N-oxides and tautomeric forms of the compounds of the formula (I).

DETAILED DESCRIPTION OF A PREFERRED EMBODIMENT

One embodiment of the present invention relates to compounds of the formula (Ia')

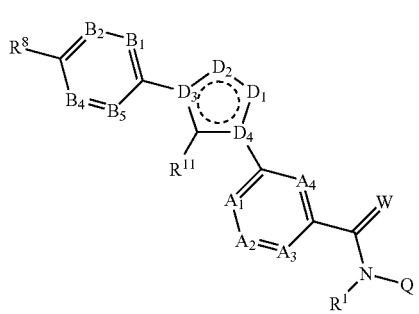

(Ia')

in which $R^1$, $R^{11}$, Q, W, $A_1$, $A_2$, $A_3$, $A_4$, $B_1$, $B_2$, $B_4$ and $B_5$ are each defined as described herein, where not more than one moiety selected from $A_1$, $A_2$, $A_3$, $A_4$ is N and not more than one moiety selected from $B_1$, $B_2$, $B_3$, $B_4$ and $B_5$ is N; or where one or two moieties selected from $A_1$, $A_2$, $A_3$, $A_4$ may be N and not more than one moiety selected from $B_1$, $B_2$, $B_3$, $B_4$ and $B_5$ is N;

$D_1$ and $D_2$ are each independently C—$R^{11}$ or a heteroatom, preferably C—$R^{11}$ or a heteroatom selected from N, O and S, more preferably C—$R^{11}$ or a heteroatom selected from N and O;

the $D_3$ and $D_4$ moieties are each independently C or a heteroatom selected from N;

where not more than one (1) or two moieties selected from $D_1$, $D_2$, $D_3$ and $D_4$ is/are a heteroatom, where one (1) or two moieties selected from $D_1$, $D_2$, $D_3$ and $D_4$ is a heteroatom selected from N and O in the case of $D_1$ and $D_2$, or N in the case of $D_3$ and $D_4$;

is an aromatic system
and $R^8$ is as defined herein, preferably perfluorinated $C_1$-$C_4$-alkyl.

A further embodiment of the present invention relates to compounds of the formula (Ia")

(Ia")

where
$D_1$ is C—$R^{11}$ or a heteroatom selected from N and O;
$D_2$ is C—$R^{11}$ or a heteroatom selected from N and O;
$D_3$ is C or N;
$D_4$ is C or N;
$D_5$ is C—$R^{11}$ or N;

where not more than one (1) or two moieties selected from D$_1$, D$_2$, D$_3$, D$_4$ and D$_5$ are a heteroatom;

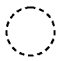

is an aromatic system; and

R$^1$ is H, in each case optionally substituted C$_2$-C$_6$-alkenyl, C$_2$-C$_6$-alkynyl, C$_3$-C$_7$-cycloalkyl, C$_1$-C$_6$-alkylcarbonyl, C$_1$-C$_6$-alkoxycarbonyl, aryl(C$_1$-C$_3$)-alkyl, or heteroaryl(C$_1$-C$_3$)-alkyl, or optionally substituted C$_1$-C$_6$-alkyl, more preferably H;

the following moieties are as follows:
A$_1$ is CR$^2$ or N,
A$_2$ is CR$^3$ or N,
A$_3$ is CR$^4$ or N,
A$_4$ is CR$^5$ or N,
B$_1$ is CR$^6$ or N,
B$_2$ is CR$^7$ or N,
B$_3$ is CR$^8$ or N,
B$_4$ is CR$^9$ or N, and
B$_5$ is CR$^{10}$ or N,
but not more than three of the A$_1$ to A$_4$ moieties are N and not more than three of the B$_1$ to B$_5$ moieties are simultaneously N;

R$^2$, R$^3$, R$^4$, R$^5$, R$^6$, R$^7$, R$^9$ and R$^{10}$ are each independently H, halogen, cyano, nitro, in each case optionally substituted C$_1$-C$_6$-alkyl, C$_3$-C$_6$-cycloalkyl, C$_1$-C$_6$-alkoxy, N—C$_1$-C$_6$-alkoxyimino-C$_1$-C$_3$-alkyl, C$_1$-C$_6$-alkylsulphanyl, C$_1$-C$_6$-alkylsulphinyl, C$_1$-C$_6$-alkylsulphonyl, N—C$_1$-C$_6$-alkylamino or N,N-di-C$_1$-C$_6$-alkylamino;
  if neither of the A$_2$ and A$_3$ moieties is N, R$^3$ and R$^4$ together with the carbon atom to which they are bonded may form a 5- or 6-membered ring containing 0, 1 or 2 nitrogen atoms and/or 0 or 1 oxygen atom and/or 0 or 1 sulphur atom, or
  if neither of the A$_1$ and A$_2$ moieties is N, R$^2$ and R$^3$ together with the carbon atom to which they are bonded may form a 6-membered ring containing 0, 1 or 2 nitrogen atoms;

R$^8$ is halogen, cyano, nitro, in each case optionally substituted C$_1$-C$_6$-alkyl, C$_3$-C$_6$-cycloalkyl, C$_1$-C$_6$-alkoxy, N—C$_1$-C$_6$-alkoxyimino-C$_1$-C$_3$-alkyl, C$_1$-C$_6$-alkylsulphanyl, C$_1$-C$_6$-alkylsulphinyl, C$_1$-C$_6$-alkylsulphonyl, N—C$_1$-C$_6$-alkylamino or N,N-di-C$_1$-C$_6$-alkylamino;

R$^{11}$ is independently H, halogen, cyano, nitro, amino or an optionally substituted C$_1$-C$_6$-alkyl, C$_1$-C$_6$-alkyloxy, C$_1$-C$_6$-alkylcarbonyl, C$_1$-C$_6$-alkylsulphanyl, C$_1$-C$_6$-alkylsulphinyl, C$_1$-C$_6$-alkylsulphonyl, preferably H;

W is O or S;

Q is H, formyl, hydroxyl, amino or in each case optionally substituted C$_1$-C$_6$-alkyl, C$_2$-C$_6$-alkenyl, C$_2$-C$_6$-alkynyl, C$_3$-C$_6$-cycloalkyl, C$_1$-C$_5$-heterocycloalkyl, C$_1$-C$_4$-alkoxy, C$_1$-C$_6$-alkyl-C$_3$-C$_6$-cycloalkyl, C$_3$-C$_6$-cycloalkyl-C$_1$-C$_6$-alkyl, C$_6$-,C$_{10}$-C$_{14}$-aryl, C$_1$-C$_5$-heteroaryl, C$_6$-,C$_{10}$-,C$_{14}$-aryl-(C$_1$-C$_3$)-alkyl, C$_1$-C$_5$-heteroaryl-(C$_1$-C$_3$)-alkyl, N—C$_1$-C$_4$-alkylamino, N—C$_1$-C$_4$-alkylcarbonylamino, or N,N-di-C$_1$-C$_4$-alkylamino; or
  is an optionally poly-V-substituted unsaturated 6-membered carbocycle; or
  is an optionally poly-V-substituted unsaturated 4-, 5- or 6-membered heterocyclic ring, where V is independently halogen, cyano, nitro, in each case optionally substituted C$_1$-C$_6$-alkyl, C$_1$-C$_4$-alkenyl, C$_1$-C$_4$-alkynyl, C$_3$-C$_6$-cycloalkyl, C$_1$-C$_6$-alkoxy, N—C$_1$-C$_6$-alkoxyimino-C$_1$-C$_3$-alkyl, C$_1$-C$_6$-alkylsulphanyl, C$_1$-C$_6$-alkylsulphinyl, C$_1$-C$_6$-alkylsulphonyl, or N,N-di-(C$_1$-C$_6$-alkyl)amino;

and salts, N-oxides and tautomeric forms of the compounds of the formula (Ia").

A further embodiment of the present invention relates to compounds of the formula (Ia"), where the compounds of the formula (Ia") are compounds of the formula (I-T3)

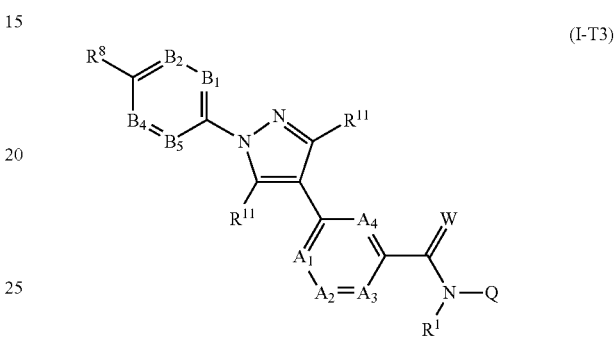

(I-T3)

in which R$^1$, A$_1$, A$_2$, A$_3$, A$_4$, R$^{11}$, B$_1$, B$_2$, B$_4$, B$_5$, R$^8$, Q and W are each defined as described herein, where not more than one moiety selected from A$_1$, A$_2$, A$_3$, A$_4$ is N and not more than one moiety selected from B$_1$, B$_2$, B$_3$, B$_4$ and B$_5$ is N; or where one or two moieties selected from A$_1$, A$_2$, A$_3$, A$_4$ may be N and not more than one moiety selected from B$_1$, B$_2$, B$_3$, B$_4$ and B$_5$ is N.

A further embodiment of the present invention relates to compounds of the formula (Ia"), where the compounds of the formula (Ia") are compounds of the formula (I-T2)

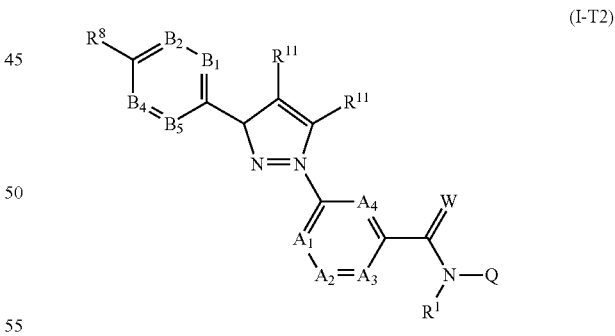

(I-T2)

in which R$^1$, A$_1$, A$_2$, A$_3$, A$_4$, R$^{11}$, B$_1$, B$_2$, B$_4$, B$_5$, R$^8$, Q and W are each defined as described herein, where not more than one moiety selected from A$_1$, A$_2$, A$_3$, A$_4$ is N and not more than one moiety selected from B$_1$, B$_2$, B$_3$, B$_4$ and B$_5$ is N; or where one or two moieties selected from A$_1$, A$_2$, A$_3$, A$_4$ may be N and not more than one moiety selected from B$_1$, B$_2$, B$_3$, B$_4$ and B$_5$ is N.

A further embodiment of the present invention relates to compounds of the formula (Ia"), where the compounds of the formula (Ia") are compounds of the formula (I-T4)

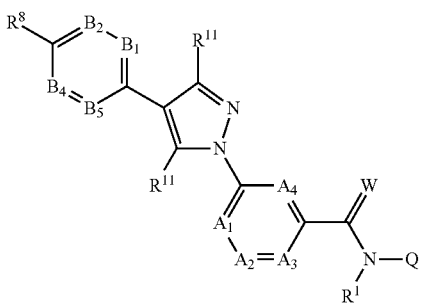

(I-T4)

in which $R^1$, $A_1$, $A_2$, $A_3$, $A_4$, $R^{11}$, $B_1$, $B_2$, $B_4$, $B_5$, $R^8$, Q and W are each defined as described herein, where not more than one moiety selected from $A_1$, $A_2$, $A_3$, $A_4$ is N and not more than one moiety selected from $B_1$, $B_2$, $B_3$, $B_4$ and $B_5$ is N; or where one or two moieties selected from $A_1$, $A_2$, $A_3$, $A_4$ may be N and not more than one moiety selected from $B_1$, $B_2$, $B_3$, $B_4$ and $B_5$ is N.

A further embodiment of the present invention relates to compounds of the formula (Ia"), where the compounds of the formula (Ia") are compounds of the formula (I-T22)

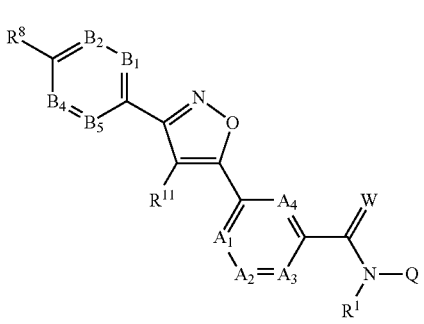

(I-T-22)

in which $R^1$, $A_1$, $A_2$, $A_3$, $A_4$, $R^{11}$, $B_1$, $B_2$, $B_4$, $B_5$, $R^8$, Q and W are each defined as described herein, where not more than one moiety selected from $A_1$, $A_2$, $A_3$, $A_4$ is N and not more than one moiety selected from $B_1$, $B_2$, $B_3$, $B_4$ and $B_5$ is N; or where one or two moieties selected from $A_1$, $A_2$, $A_3$, $A_4$ may be N and not more than one moiety selected from $B_1$, $B_2$, $B_3$, $B_4$ and $B_5$ is N.

A further embodiment of the present invention relates to compounds of the formula (Ia"), where the compounds of the formula (Ia") are compounds of the formula (I-T23)

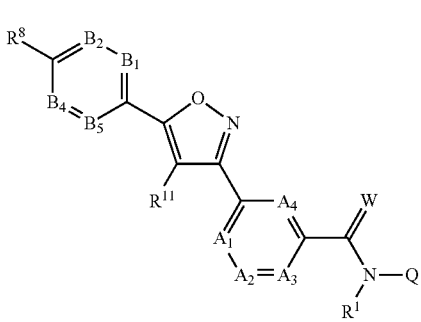

(I-T23)

in which $R^1$, $A_1$, $A_2$, $A_3$, $A_4$, $R^{11}$, $B_1$, $B_2$, $B_4$, $B_5$, $R^8$, Q and W are each defined as described herein, where not more than one moiety selected from $A_1$, $A_2$, $A_3$, $A_4$ is N and not more than one moiety selected from $B_1$, $B_2$, $B_3$, $B_4$ and $B_5$ is N; or where one or two moieties selected from $A_1$, $A_2$, $A_3$, $A_4$ may be N and not more than one moiety selected from $B_1$, $B_2$, $B_3$, $B_4$ and $B_5$ is N.

A further embodiment of the present invention relates to compounds of the formulae and embodiments described herein, where $R^{11}$ is independently H and W is O.

A further embodiment of the present invention relates to compounds of the formulae and embodiments described herein, where $R^{11}$ is independently H and W is O and $B_3$ is C—$R^8$, $R^8$ is halogen-substituted $C_1$-$C_3$-alkyl (preferably perhalogenated $C_1$-$C_3$-alkyl, more preferably perfluorinated $C_1$-$C_3$-alkyl) or halogen-substituted $C_1$-$C_3$-alkoxy (preferably perhalogenated $C_1$-$C_3$-alkoxy, more preferably perfluorinated $C_1$-$C_3$-alkoxy).

A further embodiment of the present invention relates to compounds of the formulae and embodiments described herein, where the $A_1$ to $A_4$ and $B_1$ to $B_5$ moieties are as follows:

$A_1$ is C—H,
$A_2$ is $CR^3$ or N,
$A_3$ is $CR^4$,
$A_4$ is C—H,
$B_1$ is $CR^6$ or N,
$B_2$ is C—H,
$B_3$ is $CR^8$,
$B_4$ is C—H and
$B_5$ is $CR^{10}$ or N.

A further embodiment of the present invention relates to compounds of the formulae and embodiments described herein, where $R^1$ is H.

A further embodiment of the present invention relates to compounds of the formulae and embodiments described herein, where Q is fluorine-substituted $C_1$-$C_4$-alkyl, $C_3$-$C_4$-cycloalkyl, optionally cyano- or fluorine-substituted $C_3$-$C_4$-cycloalkyl, $C_4$-$C_6$-heterocycloalkyl, 1-oxidothietan-3-yl, 1,1-dioxidothietan-3-yl, benzyl, pyridin-2-ylmethyl, methylsulphonyl or 2-oxo-2-(2,2,2-trifluoroethylamino)ethyl.

A further embodiment of the present invention relates to compounds of the formulae and embodiments described herein, where $R^8$ is halogen or halogen-substituted $C_1$-$C_4$-alkyl.

Yet a further embodiment of the present invention relates to compounds of the formulae described herein, where $R^{11}$ is independently H.

Yet a further embodiment of the present invention relates to compounds of the formulae described herein, where $R^6$, $R^7$, $R^9$ and $R^{10}$ are each independently H, halogen, cyano, nitro, in each case optionally substituted $C_1$-$C_4$-alkyl, $C_3$-$C_4$-cycloalkyl, $C_1$-$C_4$-alkoxy, N-alkoxyiminoalkyl, $C_1$-$C_4$-alkylsulphanyl, $C_1$-$C_4$-alkylsulphinyl, $C_1$-$C_4$-alkylsulphonyl, N—$C_1$-$C_4$-alkylamino, N,N-di-$C_1$-$C_4$-alkylamino.

Yet a further embodiment of the present invention relates to compounds of the formulae described herein, where $R^2$, $R^3$, $R^4$ and $R^5$ are each independently H, halogen, cyano, nitro, in each case optionally substituted $C_1$-$C_4$-alkyl, $C_3$-$C_4$-cycloalkyl, $C_1$-$C_4$-alkoxy, N—$C_1$-$C_4$-alkoxyimino-$C_1$-$C_4$-alkyl, $C_1$-$C_4$-alkylsulphanyl, $C_1$-$C_4$-alkylsulphinyl, $C_1$-$C_4$-alkylsulphonyl, N—$C_1$-$C_4$-alkylamino or N,N-di-$C_1$-$C_4$-alkylamino.

Yet a further embodiment of the present invention relates to compounds of the formulae described herein, where the $A_1$ to $A_4$ and $B_1$ to $B_5$ moieties are as follows:

$A_1$ is C—H,
$A_2$ is $CR^3$ or N,
$A_3$ is $CR^4$,
$A_4$ is C—H,
$B_1$ is $CR^6$ or N,
$B_2$ is C—H,
$B_3$ is $CR^8$,
$B_4$ is C—H and
$B_5$ is $CR^{10}$ or N.

Yet a further embodiment of the present invention relates to compounds of the formulae described herein, where $R^1$ is H.

Yet a further embodiment of the present invention relates to compounds of the formulae described herein, where Q is $C_1$-$C_4$-alkyl substituted by fluorine or by carbonamide (—C(=O)N(R)$_2$ where R is independently H, $C_1$-$C_3$-alkyl or halogen-substituted $C_1$-$C_3$-alkyl), optionally cyano- or fluorine-substituted $C_3$-$C_4$-cycloalkyl, $C_4$-$C_6$-heterocycloalkyl, 1-oxidothietan-3-yl, 1,1-dioxidothietan-3-yl, benzyl, pyridin-2-ylmethyl, methylsulphonyl or 2-oxo-2-(2,2,2-trifluoroethylamino)ethyl.

Yet a further embodiment of the present invention relates to compounds of the formulae described herein, where Q is 2,2,2-trifluoroethyl, 2,2-difluoroethyl, 3,3,3-trifluoropropyl, cyclopropyl, cyclobutyl, cyclopropyl, cyclobutyl, 1-cyanocyclopropyl, trans-2-fluorocyclopropyl, or cis-2-fluorocyclopropyl, oxetan-3-yl, thietan-3-yl, 1-oxidothietan-3-yl, 1,1-dioxidothietan-3-yl, benzyl, pyridin-2-ylmethyl, methylsulphonyl or 2-oxo-2-(2,2,2-trifluoroethylamino)ethyl.

Yet a further embodiment of the present invention relates to compounds of the formulae described herein, where $R^8$ is halogen or halogen-substituted $C_1$-$C_4$-alkyl.

A further aspect relates to insecticidal compositions, characterized by a content of at least one compound of the formula (I) as described herein and an extender and/or a surface-active substance.

A further aspect relates to a method for protecting transgenic or conventional seed and the plant that arises therefrom from infestation by pests, characterized in that the seed is treated with at least one compound of the formula (I) as described herein.

Yet a further aspect relates to the use of compounds of the formula (I) as described herein or of an insecticidal composition as described herein for controlling pests.

A further aspect relates to the use of compounds of the formula (I) as described herein in vector control.

Yet a further aspect relates to seed in which a compound of the formula (I) as described herein has been applied to the seed as a constituent of a coating or as a further layer or further layers in addition to a coating.

Accordingly, a further aspect relates to a method for applying a coating comprising at least one compound of the formula (I) as described herein or for applying a compound of the formula (I) as described herein, which is applied to seed as a layer or further layers in addition to a coating, comprising the steps of a) mixing seeds with a coating material consisting of or comprising a compound of the formula (I) as described herein, b) enriching the coated seed composition obtained, c) drying the enriched seed composition obtained, d) dis- or deagglomerating the dried seed composition obtained.

Depending on the nature of the substituents, the compounds of the formula (I) described here may optionally be in the form of geometric and/or optically active isomers or corresponding isomer mixtures in different compositions. The invention relates both to the pure isomers and to the isomer mixtures.

The inventive compounds may also be in the form of metal complexes.

Definitions

The person skilled in the art is aware that, if not stated explicitly, the expressions "a" or "an" as used in the present application may, depending on the situation, mean "one (1)", "one (1) or more" or "at least one (1)".

For all the structures described herein, such as ring systems and groups, adjacent atoms must not be —O—O— or —O—S—.

Structures having a variable number of possible carbon atoms (C atoms) may be referred to in the present application as $C_{lower\ limit\ of\ carbon\ atoms}$—$C_{upper\ limit\ of\ carbon\ atoms}$ structures ($C_{LL}$—$C_{UL}$ structures), in order thus to be stipulated more specifically. Example: an alkyl group may consist of 3 to 10 carbon atoms and in that case corresponds to $C_3$-$C_{10}$-alkyl. Ring structures composed of carbon atoms and heteroatoms may be referred to as "LL- to UL-membered" structures. One example of a 6-membered ring structure is toluene (a 6-membered ring structure substituted by a methyl group).

If a collective term for a substituent, for example ($C_{LL}$—$C_{UL}$)-alkyl, is at the end of a composite substituent, for example ($C_{LL}$—$C_{UL}$)-cycloalkyl-($C_{LL}$—$C_{UL}$)-alkyl, the constituent at the start of the composite substituent, for example the ($C_{LL}$—$C_{UL}$)-cycloalkyl, may be mono- or polysubstituted identically or differently and independently by the latter substituent, for example ($C_{LL}$—$C_{UL}$)-alkyl. All the collective terms used in this application for chemical groups, cyclic systems and cyclic groups can be stipulated more specifically through the addition "$C_{LL}$—$C_{UL}$" or "LL- to UL-membered".

Unless defined differently, the definition of collective terms also applies to these collective terms in composite substituents. Example: the definition of $C_{LL}$—$C_{UL}$-alkyl also applies to $C_{LL}$—$C_{UL}$-alkyl as part of a composite substituent, for example $C_{LL}$—$C_{UL}$-cycloalkyl-$C_{LL}$—$C_{LL}$-alkyl.

It will be clear to the person skilled in the art that examples cited in the present application should not be considered in a restrictive manner, but merely describe some embodiments in detail.

In the definitions of the symbols given in the above formulae, collective terms which are generally representative of the following substituents were used:

Halogen relates to elements of the 7th main group, preferably fluorine, chlorine, bromine and iodine, more preferably fluorine, chlorine and bromine, and even more preferably fluorine and chlorine.

Examples of heteroatom are N, O, S, P, B, Si. Preferably, the term "heteroatom" relates to N, S and O.

According to the invention, "alkyl"—on its own or as part of a chemical group—represents straight-chain or branched hydrocarbons preferably having 1 to 6 carbon atoms, for example methyl, ethyl, n-propyl, isopropyl, n-butyl, isobutyl, s-butyl, t-butyl, pentyl, 1-methylbutyl, 2-methylbutyl, 3-methylbutyl, 1,2-dimethylpropyl, 1,1-dimethylpropyl, 2,2-dimethylpropyl, 1-ethylpropyl, hexyl, 1-methylpentyl, 2-methylpentyl, 3-methylpentyl, 4-methylpentyl, 1,2-dimethylbutyl, 1,3-dimethylbutyl, 1,4-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl and 2-ethylbutyl. Preference is also given to alkyls having 1 to 4 carbon atoms such as, inter alia, methyl, ethyl, n-propyl, isopropyl, n-butyl, isobutyl, s-butyl or t-butyl. The inventive alkyls may be substituted by one or more identical or different radicals.

According to the invention, "alkenyl"—on its own or as part of a chemical group—represents straight-chain or branched hydrocarbons preferably having 2 to 6 carbon atoms and at least one double bond, for example vinyl, 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl and 1-ethyl-2-methyl-2-propenyl. Preference is also given to alkenyls having 2 to 4 carbon atoms such as, inter alia, 2-propenyl, 2-butenyl or 1-methyl-2-propenyl. The inventive alkenyls may be substituted by one or more identical or different radicals.

According to the invention, "alkynyl"—on its own or as part of a chemical group—represents straight-chain or branched hydrocarbons preferably having 2 to 6 carbon atoms and at least one triple bond, for example 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-3-butynyl, 1,2-dimethyl-3-butynyl, 2,2-dimethyl-3-butynyl, 1-ethyl-3-butynyl, 2-ethyl-3-butynyl, 1-ethyl-1-methyl-2-propynyl and 2,5-hexadiynyl. Preference is also given to alkynyls having 2 to 4 carbon atoms such as, inter alia, ethynyl, 2-propynyl or 2-butynyl-2-propenyl. The inventive alkynyls may be substituted by one or more identical or different radicals.

According to the invention, "cycloalkyl"—on its own or as part of a chemical group—represents mono-, bi- or tricyclic hydrocarbons preferably having 3 to 10 carbons, for example cyclopropyl, cyclobutyl, cyclopentyl, cyclohexyl, cycloheptyl, cyclooctyl, bicyclo[2.2.1]heptyl, bicyclo[2.2.2]octyl or adamantyl. Preference is also given to cycloalkyls having 3, 4, 5, 6 or 7 carbon atoms such as, inter alia, cyclopropyl or cyclobutyl. The inventive cycloalkyls may be substituted by one or more identical or different radicals.

According to the invention, "alkylcycloalkyl" represents mono-, bi- or tricyclic alkylcycloalkyl preferably having 4 to 10 or 4 to 7 carbon atoms, for example methylcyclopropyl, ethylcyclopropyl, isopropylcyclobutyl, 3-methylcyclopentyl and 4-methylcyclohexyl. Preference is also given to alkylcycloalkyls having 4, 5 or 7 carbon atoms such as, inter alia, ethylcyclopropyl or 4-methylcyclohexyl. The inventive alkylcycloalkyls may be substituted by one or more identical or different radicals.

According to the invention, "cycloalkylalkyl" represents mono-, bi- or tricyclic cycloalkylalkyl preferably having 4 to 10 or 4 to 7 carbon atoms, for example cyclopropylmethyl, cyclobutylmethyl, cyclopentylmethyl, cyclohexylmethyl and cyclopentylethyl. Preference is also given to cycloalkylalkyls having 4, 5 or 7 carbon atoms such as, inter alia, cyclopropylmethyl or cyclobutylmethyl. The inventive cycloalkylalkyls may be substituted by one or more identical or different radicals.

According to the invention, "hydroxyalkyl" represents a straight-chain or branched alcohol preferably having 1 to 6 carbon atoms, for example methanol, ethanol, n-propanol, isopropanol, n-butanol, isobutanol, s-butanol and t-butanol. Preference is also given to hydroxyalkyl groups having 1 to 4 carbon atoms. The inventive hydroxyalkyl groups may be substituted by one or more identical or different radicals.

According to the invention, "alkoxy" represents a straight-chain or branched O-alkyl preferably having 1 to 6 carbon atoms, for example methoxy, ethoxy, n-propoxy, isopropoxy, n-butoxy, isobutoxy, s-butoxy and t-butoxy. Preference is also given to alkoxy groups having 1 to 4 carbon atoms. The inventive alkoxy groups may be substituted by one or more identical or different radicals.

According to the invention, "alkylsulphanyl" represents straight-chain or branched S-alkyl preferably having 1 to 6 carbon atoms, for example methylthio, ethylthio, n-propylthio, isopropylthio, n-butylthio, isobutylthio, s-butylthio and t-butylthio. Preference is also given to alkylsulphanyl groups having 1 to 4 carbon atoms. The inventive alkylsulphanyl groups may be substituted by one or more identical or different radicals.

According to the invention, "alkylsulphinyl" represents straight-chain or branched alkylsulphinyl preferably having 1 to 6 carbon atoms, for example methylsulphinyl, ethylsulphinyl, n-propylsulphinyl, isopropylsulphinyl, n-butylsulphinyl, isobutylsulphinyl, s-butylsulphinyl and t-butylsulphinyl. Preference is also given to alkylsulphinyl groups having 1 to 4 carbon atoms. The inventive alkylsulphinyl groups may be substituted by one or more identical or different radicals.

According to the invention, "alkylsulphonyl" represents straight-chain or branched alkylsulphonyl preferably having 1 to 6 carbon atoms, for example methylsulphonyl, ethylsulphonyl, n-propylsulphonyl, isopropylsulphonyl, n-butylsulphonyl, isobutylsulphonyl, s-butylsulphonyl and t-butylsulphonyl. Preference is also given to alkylsulphonyl groups having 1 to 4 carbon atoms. The inventive alkylsulphonyl groups may be substituted by one or more identical or different radicals.

According to the invention, "alkylcarbonyl" represents straight-chain or branched alkyl-C(=O) preferably having 2 to 7 carbon atoms such as methylcarbonyl, ethylcarbonyl, n-propylcarbonyl, isopropylcarbonyl, s-butylcarbonyl and t-butylcarbonyl. Preference is also given to alkylcarbonyls having 1 to 4 carbon atoms. The inventive alkylcarbonyls may be substituted by one or more identical or different radicals.

According to the invention, "cycloalkylcarbonyl" represents straight-chain or branched cycloalkylcarbonyl preferably having 3 to 10 carbon atoms in the cycloalkyl moiety, for example cyclopropylcarbonyl, cyclobutylcarbonyl, cyclopentylcarbonyl, cyclohexylcarbonyl, cycloheptylcarbonyl, cyclooctylcarbonyl, bicyclo[2.2.1]heptyl, bicyclo[2.2.2]octylcarbonyl and adamantylcarbonyl. Preference is also given to cycloalkylcarbonyl having 3, 5 or 7 carbon atoms in the cycloalkyl moiety. The inventive cycloalkylcarbonyl groups may be substituted by one or more identical or different radicals.

According to the invention, "alkoxycarbonyl"—alone or as a constituent of a chemical group—represents straight-chain or branched alkoxycarbonyl, preferably having 1 to 6 carbon atoms or having 1 to 4 carbon atoms in the alkoxy moiety, for example methoxycarbonyl, ethoxycarbonyl, n-propoxycarbonyl, isopropoxycarbonyl, s-butoxycarbonyl and t-butoxycarbonyl. The inventive alkoxycarbonyl groups may be substituted by one or more identical or different radicals.

According to the invention, "alkylaminocarbonyl" represents straight-chain or branched alkylaminocarbonyl having preferably 1 to 6 carbon atoms or 1 to 4 carbon atoms in the alkyl moiety, for example methylaminocarbonyl, ethylaminocarbonyl, n-propylaminocarbonyl, isopropylaminocarbonyl, s-butylaminocarbonyl and t-butylaminocarbonyl. The inventive alkylaminocarbonyl groups may be substituted by one or more identical or different radicals.

According to the invention, "N,N-dialkylaminocarbonyl" represents straight-chain or branched N,N-dialkylaminocarbonyl having preferably 1 to 6 carbon atoms or 1 to 4 carbon atoms in the alkyl moiety, for example N,N-dimethylaminocarbonyl, N,N-diethylaminocarbonyl, N,N-di(n-propylamino)carbonyl, N,N-di(isopropylamino)carbonyl and N,N-di-(s-butylamino)carbonyl. The inventive N,N-dialkylaminocarbonyl groups may be substituted by one or more identical or different radicals.

According to the invention, "aryl" represents a mono-, bi- or polycyclic aromatic system having preferably 6 to 14, especially 6 to 10, ring carbon atoms, for example phenyl, naphthyl, anthryl, phenanthrenyl, preferably phenyl. In addition, aryl also represents polycyclic systems such as tetrahydronaphthyl, indenyl, indanyl, fluorenyl, biphenyl, where the bonding site is on the aromatic system. The inventive aryl groups may be substituted by one or more identical or different radicals.

Examples of substituted aryls are the arylalkyls, which may likewise be substituted by one or more identical or different radicals in the $C_1$-$C_4$-alkyl and/or $C_6$-$C_{14}$-aryl moiety. Examples of such arylalkyls include benzyl and 1-phenylethyl.

According to the invention, "heterocycle", "heterocyclic ring" or "heterocyclic ring system" represents a carbocyclic ring system having at least one ring in which at least one carbon atom is replaced by a heteroatom, preferably by a heteroatom from the group consisting of N, O, S, P, B, Si, Se, and which is saturated, unsaturated or heteroaromatic and may be unsubstituted or substituted, where the bonding site is on a ring atom. Unless defined differently, the heterocyclic ring contains preferably 3 to 9 ring atoms, especially 3 to 6 ring atoms, and one or more, preferably 1 to 4, especially 1, 2 or 3, heteroatoms in the heterocyclic ring, preferably from the group consisting of N, O, and S, although no two oxygen atoms should be directly adjacent. The heterocyclic rings usually contain not more than 4 nitrogen atoms and/or not more than 2 oxygen atoms and/or not more than 2 sulphur atoms. When the heterocyclyl radical or the heterocyclic ring is optionally substituted, it may be fused to other carbocyclic or heterocyclic rings. In the case of optionally substituted heterocyclyl, the invention also embraces polycyclic systems, for example 8-azabicyclo[3.2.1]octanyl or 1-azabicyclo[2.2.1]heptyl. In the case of optionally substituted heterocyclyl, the invention also embraces spirocyclic systems, for example 1-oxa-5-azaspiro[2.3]hexyl.

Inventive heterocyclyl groups are, for example, piperidinyl, piperazinyl, morpholinyl, thiomorpholinyl, dihydropyranyl, tetrahydropyranyl, dioxanyl, pyrrolinyl, pyrrolidinyl, imidazolinyl, imidazolidinyl, thiazolidinyl, oxazolidinyl, dioxolanyl, dioxolyl, pyrazolidinyl, tetrahydrofuranyl, dihydrofuranyl, oxetanyl, oxiranyl, azetidinyl, aziridinyl, oxazetidinyl, oxaziridinyl, oxazepanyl, oxazinanyl, azepanyl, oxopyrrolidinyl, dioxopyrrolidinyl, oxomorpholinyl, oxopiperazinyl and oxepanyl.

Of particular significance are heteroaryls, i.e. heteroaromatic systems. According to the invention, the term heteroaryl represents heteroaromatic compounds, i.e. completely unsaturated aromatic heterocyclic compounds which fall under the above definition of heterocycles. Preference is given to 5- to 7-membered rings having 1 to 3, preferably 1 or 2, identical or different heteroatoms from the group above. Inventive heteroaryls are, for example, furyl, thienyl, pyrazolyl, imidazolyl, 1,2,3- and 1,2,4-triazolyl, isoxazolyl, thiazolyl, isothiazolyl, 1,2,3-, 1,3,4-, 1,2,4- and 1,2,5-oxadiazolyl, azepinyl, pyrrolyl, pyridyl, pyridazinyl, pyrimidinyl, pyrazinyl, 1,3,5-, 1,2,4- and 1,2,3-triazinyl, 1,2,4-, 1,3,2-, 1,3,6- and 1,2,6-oxazinyl, oxepinyl, thiepinyl, 1,2,4-triazolonyl and 1,2,4-diazepinyl. The inventive heteroaryl groups may also be substituted by one or more identical or different radicals.

The term "(optionally) substituted" groups/substituents, such as a substituted alkyl, alkenyl, alkynyl, alkoxy, alkylsulphanyl, alkylsulphinyl, alkylsulphonyl, cycloalkyl, aryl, phenyl, benzyl, heterocyclyl and heteroaryl radical, means, for example, a substituted radical derived from the unsubstituted base structure, where the substituents, for example, one (1) substituent or a plurality of substituents, preferably 1, 2, 3, 4, 5, 6 or 7, are selected from a group consisting of amino, hydroxyl, halogen, nitro, cyano, isocyano, mercapto, isothiocyanato, $C_1$-$C_4$-carboxyl, carbonamide, $SF_5$, aminosulphonyl, $C_1$-$C_4$-alkyl, $C_3$-$C_4$-cycloalkyl, $C_2$-$C_4$-alkenyl, $C_3$-$C_4$-cycloalkenyl, $C_2$-$C_4$-alkynyl, N-mono-$C_1$-$C_4$-alkylamino, N,N-di-$C_1$-$C_4$-alkylamino, N—$C_1$-$C_4$-alkanoylamino, $C_1$-$C_4$-alkoxy, $C_2$-$C_4$-alkenyloxy, $C_2$-$C_4$-alkynyloxy, $C_3$-$C_4$-cycloalkoxy, $C_3$-$C_4$-cycloalkenyloxy, $C_1$-$C_4$-alkoxycarbonyl, $C_2$-$C_4$-$C_2$-$C_4$-alkenyloxycarbonyl, $C_2$-$C_4$-alkynyloxycarbonyl, $C_6$-,$C_{10}$-,$C_{14}$-aryloxycarbonyl, $C_1$-$C_4$-alkanoyl, $C_2$-$C_4$-alkenylcarbonyl, $C_2$-$C_4$-alkynylcarbonyl, $C_6$-,$C_{10}$-,$C_{14}$-arylcarbonyl, $C_1$-$C_4$-alkylsulphanyl, $C_3$-$C_4$-cycloalkylsulphanyl, $C_1$-$C_4$-alkylthio, $C_2$-$C_4$-alkenylthio, $C_3$-$C_4$-cycloalkenylthio, $C_2$-$C_4$-alkynylthio, $C_1$-$C_4$-alkylsulphenyl and $C_1$-$C_4$-alkylsulphinyl, including both enantiomers of the $C_1$-$C_4$-alkylsulphinyl group, $C_1$-$C_4$-alkylsulphonyl, N-mono-$C_1$-$C_4$-alkylaminosulphonyl, N,N-di-$C_1$-$C_4$-alkylaminosulphonyl, $C_1$-$C_4$-alkylphosphinyl, $C_1$-$C_4$-alkylphosphonyl, including both enantiomers of $C_1$-$C_4$-alkylphosphinyl and $C_1$-$C_4$-alkylphosphonyl, N—$C_1$-$C_4$-alkylaminocarbonyl, N,N-di-$C_1$-$C_4$-alkylaminocarbonyl, N—$C_1$-$C_4$-alkanoylaminocarbonyl, N—$C_1$-$C_4$-alkanoyl-N—$C_1$-$C_4$-alkylaminocarbonyl, $C_6$-,$C_{10}$-,$C_{14}$-aryl, $C_6$-,$C_{10}$-,$C_{14}$-aryloxy, benzyl, benzyloxy, benzylthio, $C_6$-,$C_{10}$-, $C_{14}$-arylthio, $C_6$-,$C_{10}$-,$C_{14}$-arylamino, benzylamino, heterocyclyl and trialkylsilyl, substituents bonded via a double bond, such as $C_1$-$C_4$-alkylidene (e.g. methylidene or ethylidene), an oxo group, a thioxo group, an imino group and a substituted imino group. When two or more radicals form one or more rings, these may be carbocyclic, heterocyclic, saturated, partly saturated, unsaturated, for example including aromatic rings and with further substitution.

The substituents mentioned by way of example ("first substituent level") may, if they contain hydrocarbonaceous components, optionally have further substitution therein ("second substituent level"), for example by one or more of the substituents each independently selected from halogen, hydroxyl, amino, nitro, cyano, isocyano, azido, acylamino, an oxo group and an imino group. The term "(optionally) substituted" group preferably embraces just one or two substituent levels.

The inventive halogen-substituted chemical groups or halogenated groups (for example alkyl or alkoxy) are mono- or polysubstituted by halogen up to the maximum possible number of substituents. Such groups are also referred to as halo groups (for example haloalkyl). In the case of polysubstitution by halogen, the halogen atoms may be the same or different, and may all be bonded to one carbon atom or may be bonded to a plurality of carbon atoms. Halogen is especially fluorine, chlorine, bromine or iodine, preferably fluorine, chlorine or bromine and more preferably fluorine. More particularly, halogen-substituted groups are monohalocycloalkyl such as 1-fluorocyclopropyl, 2-fluorocyclopropyl or 1-fluorocyclobutyl, monohaloalkyl such as 2-chloroethyl, 2-fluoroethyl, 1-chloroethyl, 1-fluoroethyl, chloromethyl, or fluoromethyl; perhaloalkyl such as trichloromethyl or trifluoromethyl or $CF_2CF_3$, polyhaloalkyl such as difluoromethyl, 2-fluoro-2-chloroethyl, dichloromethyl, 1,1,2,2-tetrafluoroethyl or 2,2,2-trifluoroethyl. Further examples of haloalkyls are trichloromethyl, chlorodifluoromethyl, dichlorofluoromethyl, chloromethyl, bromomethyl, 1-fluoroethyl, 2-fluoroethyl, 2,2-difluoroethyl, 2,2,2-trifluoroethyl, 2,2,2-trichloroethyl, 2-chloro-2,2-difluoroethyl, pentafluoroethyl, 3,3,3-trifluoropropyl and pentafluoro-t-butyl. Preference is given to haloalkyls having 1 to 4 carbon atoms and 1 to 9, preferably 1 to 5, identical or different halogen atoms selected from fluorine, chlorine and bromine. Particular preference is given to haloalkyls having 1 or 2 carbon atoms and 1 to 5 identical or different halogen atoms selected from fluorine and chlorine, such as, inter alia, difluoromethyl, trifluoromethyl or 2,2-difluoroethyl. Further examples of halogen-substituted compounds are haloalkoxy such as $OCF_3$, $OCHF_2$, $OCH_2F$, $OCF_2CF_3$, $OCH_2CF_3$, $OCH_2CHF_2$ and $OCH_2CH_2Cl$, haloalkylsulphanyls such as difluoromethylthio, trifluoromethylthio, trichloromethylthio, chlorodifluoromethylthio, 1-fluoroethylthio, 2-fluoroethylthio, 2,2-difluoroethylthio, 1,1,2,2-tetrafluoroethylthio, 2,2,2-trifluoroethylthio or 2-chloro-1,1,2-trifluoroethylthio, haloalkylsulphinyls such as difluoromethylsulphinyl, trifluoromethylsulphinyl, trichloromethylsulphinyl, chlorodifluoromethylsulphinyl, 1-fluoroethylsulphinyl, 2-fluoroethylsulphinyl, 2,2-difluoroethylsulphinyl, 1,1,2,2-tetrafluoroethylsulphinyl, 2,2,2-trifluoroethylsulphinyl and 2-chloro-1,1,2-trifluoroethylsulphinyl, haloalkylsulphinyls such as difluoromethylsulphinyl, trifluoromethylsulphinyl, trichloromethylsulphinyl, chlorodifluoromethylsulphinyl, 1-fluoroethylsulphinyl, 2-fluoroethylsulphinyl, 2,2-difluoroethylsulphinyl, 1,1,2,2-tetrafluoroethylsulphinyl, 2,2,2-trifluoroethylsulphinyl and 2-chloro-1,1,2-trifluoroethylsulphinyl, haloalkylsulphonyl groups such as difluoromethylsulphonyl, trifluoromethylsulphonyl, trichloromethylsulphonyl, chlorodifluoromethylsulphonyl, 1-fluoroethylsulphonyl, 2-fluoroethylsulphonyl, 2,2-difluoroethylsulphonyl, 1,1,2,2-tetrafluoroethylsulphonyl, 2,2,2-trifluoroethylsulphonyl and 2-chloro-1,1,2-trifluoroethylsulphonyl.

In the case of radicals having carbon atoms, preference is given to those having 1 to 4 carbon atoms, especially 1 or 2 carbon atoms. Preference is generally given to substituents from the group of halogen, e.g. fluorine and chlorine, $(C_1-C_4)$-alkyl, preferably methyl or ethyl, $(C_1-C_4)$-haloalkyl, preferably trifluoromethyl, $(C_1-C_4)$-alkoxy, preferably methoxy or ethoxy, $(C_1-C_4)$-haloalkoxy, nitro and cyano. Particular preference is given here to the substituents methyl, methoxy, fluorine and chlorine.

Substituted amino such as mono- or disubstituted amino means a radical from the group of the substituted amino radicals which are N-substituted, for example, by one or two identical or different radicals from the group of alkyl, hydroxy, amino, alkoxy, acyl and aryl; preferably N-mono- and N,N-dialkylamino, (for example methylamino, ethylamino, N,N-dimethylamino, N,N-diethylamino, N,N-di-n-propylamino, N,N-diisopropylamino or N,N-dibutylamino), N-mono- or N,N-dialkoxyalkylamino groups (for example N-methoxymethylamino, N-methoxyethylamino, N,N-di(methoxymethyl)amino or N,N-di(methoxyethyl)amino), N-mono- and N,N-diarylamino, such as optionally substituted anilines, acylamino, N,N-diacylamino, N-alkyl-N-arylamino, N-alkyl-N-acylamino and also saturated N-heterocycles; preference is given here to alkyl radicals having 1 to 4 carbon atoms; here, aryl is preferably phenyl or substituted phenyl; for acyl, the definition given further below applies, preferably $(C_1-C_4)$-alkanoyl. The same applies to substituted hydroxylamino or hydrazino.

According to the invention, the term "cyclic amino groups" embraces heteroaromatic or aliphatic ring systems having one or more nitrogen atoms. The heterocycles are saturated or unsaturated, consist of one or more optionally fused ring systems and optionally contain further heteroatoms, for example one or two nitrogen, oxygen and/or sulphur atoms. In addition, the term also embraces groups having a spiro ring or a bridged ring system. The number of atoms which form the cyclic amino group is not limited and may consist, for example, in the case of a one-ring system of 3 to 8 ring atoms, and in the case of a two-ring system of 7 to 11 atoms.

Examples of cyclic amino groups having saturated and unsaturated monocyclic groups having a nitrogen atom as heteroatom include 1-azetidinyl, pyrrolidino, 2-pyrrolidin-1-yl, 1-pyrrolyl, piperidino, 1,4-dihydropyrazin-1-yl, 1,2,5,6-tetrahydropyrazin-1-yl, 1,4-dihydropyridin-1-yl, 1,2,5,6-tetrahydropyridin-1-yl, homopiperidinyl; examples of cyclic amino groups having saturated and unsaturated monocyclic groups having two or more nitrogen atoms as heteroatoms include 1-imidazolidinyl, 1-imidazolyl, 1-pyrazolyl, 1-triazolyl, 1-tetrazolyl, 1-piperazinyl, 1-homopiperazinyl, 1,2-dihydropiperazin-1-yl, 1,2-dihydropyrimidin-1-yl, perhydropyrimidin-1-yl, 1,4-diazacycloheptan-1-yl; examples of cyclic amino groups having saturated and unsaturated monocyclic groups having one or two oxygen atoms and one to three nitrogen atoms as heteroatoms, for example, oxazolidin-3-yl, 2,3-dihydroisoxazol-2-yl, isoxazol-2-yl, 1,2,3-oxadiazin-2-yl, morpholino, examples of cyclic amino groups having saturated and unsaturated monocyclic groups having one to three nitrogen atoms and one to two sulphur atoms as heteroatoms include thiazolidin-3-yl, isothiazolin-2-yl, thiomorpholino, or dioxothiomorpholino; examples of cyclic amino groups having saturated and unsaturated fused cyclic groups include indol-1-yl, 1,2-dihydrobenzimidazol-1-yl, perhydropyrrolo[1,2-a]pyrazin-2-yl; examples of cyclic amino groups having spirocyclic groups include 2-azaspiro[4,5]decan-2-yl; examples of cyclic amino groups having bridged heterocyclic groups include 2-azabicyclo[2.2.1]heptan-7-yl.

Substituted amino also includes quaternary ammonium compounds (salts) having four organic substituents on the nitrogen atom.

Optionally substituted phenyl is preferably phenyl which is unsubstituted or mono- or polysubstituted, preferably up to trisubstituted, by identical or different radicals from the group of halogen, ($C_1$-$C_4$)-alkyl, ($C_1$-$C_4$)-alkoxy, ($C_1$-$C_4$)-alkoxy-($C_1$-$C_4$)-alkoxy, ($C_1$-$C_4$)-alkoxy-($C_1$-$C_4$)-alkyl, ($C_1$-$C_4$)-haloalkyl, ($C_1$-$C_4$)-haloalkoxy, ($C_1$-$C_4$)-alkylsulphanyl, ($C_1$-$C_4$)-haloalkylsulphanyl, cyano, isocyano and nitro, for example o-, m- and p-tolyl, dimethylphenyls, 2-, 3- and 4-chlorophenyl, 2-, 3- and 4-fluorophenyl, 2-, 3- and 4-trifluoromethyl- and -trichloromethylphenyl, 2,4-, 3,5-, 2,5- and 2,3-dichlorophenyl, o-, m- and p-methoxyphenyl, 4-heptafluorophenyl.

Optionally substituted cycloalkyl is preferably cycloalkyl which is unsubstituted or mono- or polysubstituted, preferably up to trisubstituted, by identical or different radicals from the group of halogen, cyano, ($C_1$-$C_4$)-alkyl, ($C_1$-$C_4$)-alkoxy, ($C_1$-$C_4$)-alkoxy-($C_1$-$C_4$)-alkoxy, ($C_1$-$C_4$)-alkoxy-($C_1$-$C_4$)-alkyl, ($C_1$-$C_4$)-haloalkyl and ($C_1$-$C_4$)-haloalkoxy, especially by one or two ($C_1$-$C_4$)-alkyl radicals.

Optionally substituted heterocyclyl is preferably heterocyclyl which is unsubstituted or mono- or polysubstituted, preferably up to trisubstituted, by identical or different radicals from the group of halogen, cyano, ($C_1$-$C_4$)-alkyl, ($C_1$-$C_4$)-alkoxy, ($C_1$-$C_4$)-alkoxy-($C_1$-$C_4$)-alkoxy, ($C_1$-$C_4$)-alkoxy-($C_1$-$C_4$)-alkyl, ($C_1$-$C_4$)-haloalkyl, ($C_1$-$C_4$)-haloalkoxy, nitro and oxo, especially mono- or polysubstituted by radicals from the group of halogen, ($C_1$-$C_4$)-alkyl, ($C_1$-$C_4$)-alkoxy, ($C_1$-$C_4$)-haloalkyl and oxo, most preferably substituted by one or two ($C_1$-$C_4$)-alkyl radicals.

Examples of alkyl-substituted heteroaryls are furylmethyl, thienylmethyl, pyrazolylmethyl, imidazolylmethyl, 1,2,3- and 1,2,4-triazolylmethyl, isoxazolylmethyl, thiazolylmethyl, isothiazolylmethyl, 1,2,3-, 1,3,4-, 1,2,4- and 1,2,5-oxadiazolylmethyl, azepinylmethyl, pyrrolylmethyl, pyridylmethyl, pyridazinylmethyl, pyrimidinylmethyl, pyrazinylmethyl, 1,3,5-, 1,2,4- and 1,2,3-triazinylmethyl, 1,2,4-, 1,3,2-, 1,3,6- and 1,2,6-oxazinylmethyl, oxepinylmethyl, thiepinylmethyl and 1,2,4-diazepinylmethyl.

Inventive compounds may occur in preferred embodiments. Individual embodiments described herein may be combined with one another. Not included are combinations which contravene the laws of nature and which the person skilled in the art would therefore rule out on the basis of his/her expert knowledge. Ring structures having three or more adjacent oxygen atoms, for example, are excluded.

Embodiments of the Inventive Compounds

It will be obvious to the person skilled in the art that all the embodiments may be present alone or in combination. The compounds of the formula (I), especially compounds of the formulae (Ia), (Ib), (I-T2), (I-T3), (I-T4), (I-T22) and (I-T23), may, where appropriate, depending on the nature of the substituents, be in the form of salts, tautomers, geometric and/or optically active isomers or corresponding isomer mixtures in different compositions.

Where appropriate, the inventive compounds may be in various polymorphic forms or in the form of a mixture of different polymorphic forms. Both the pure polymorphs and the polymorph mixtures form part of the subject-matter of the invention and can be used in accordance with the invention.

Embodiments of the compounds of the formula (I) are described in detail below:

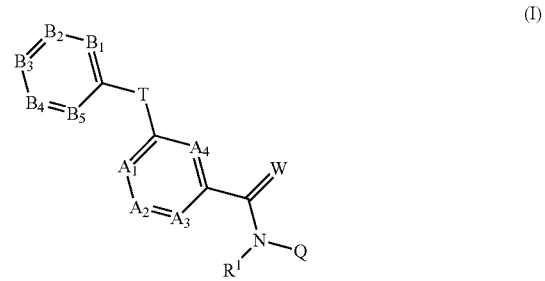

(I)

in which
R$^1$ is H, in each case optionally substituted $C_2$-$C_6$-alkenyl, $C_2$-$C_6$-alkynyl, $C_3$-$C_7$-cycloalkyl, $C_1$-$C_6$-alkylcarbonyl, $C_1$-$C_6$-alkoxycarbonyl, aryl($C_1$-$C_3$)-alkyl, heteroaryl($C_1$-$C_3$)-alkyl, or is optionally substituted $C_1$-$C_6$-alkyl, preferably H or preferably $C_1$-$C_2$-alkyl, most preferably H or methyl, the following moieties are as follows:
A$_1$ is CR$^2$ or N,
A$_2$ is CR$^3$ or N,
A$_3$ is CR$^4$ or N,
A$_4$ is CR$^5$ or N,
B$_1$ is CR$^6$ or N,
B$_2$ is CR$^7$ or N,
B$_3$ is CR$^8$ or N,
B$_4$ is CR$^9$ or N, and
B$_5$ is CR$^{10}$ or N,
but not more than three of the A$_1$ to A$_4$ moieties are N and not more than three of the B$_1$ to B$_5$ moieties are simultaneously N;

R$^2$, R$^3$, R$^4$, R$^5$, R$^6$, R$^7$, R$^9$ and R$^{10}$ are each independently H, halogen, cyano, nitro, in each case optionally substituted $C_1$-$C_6$-alkyl, $C_3$-$C_6$-cycloalkyl, $C_1$-$C_6$-alkoxy, N—$C_1$-$C_6$-alkoxyimino-$C_1$-$C_3$-alkyl, $C_1$-$C_6$-alkylsulphanyl, $C_1$-$C_6$-alkylsulphinyl, $C_1$-$C_6$-alkylsulphonyl, N—$C_1$-$C_6$-alkylamino, N,N-di-$C_1$-$C_6$-alkylamino or N—$C_1$-$C_3$-alkoxy-$C_1$-$C_4$-alkylamino or 1-pyrrolidinyl;

if neither of the A$_2$ and A$_3$ moieties is N, R$^3$ and R$^4$ together with the carbon atom to which they are bonded may form a 5- or 6-membered ring containing 0, 1 or 2 nitrogen atoms and/or 0 or 1 oxygen atom and/or 0 or 1 sulphur atom, or if neither of the A$_1$ and A$_2$ moieties is N, R$^2$ and R$^3$ together with the carbon atom to which they are bonded may form a 6-membered ring containing 0, 1 or 2 nitrogen atoms;

R$^8$ is halogen, cyano, nitro, in each case optionally substituted $C_1$-$C_6$-alkyl, $C_3$-$C_6$-cycloalkyl, $C_1$-$C_6$-alkoxy, N—$C_1$-$C_6$-alkoxyimino-$C_1$-$C_3$-alkyl, $C_1$-$C_6$-alkylsulphanyl, $C_1$-$C_6$-alkylsulphinyl, $C_1$-$C_6$-alkylsulphonyl, N—$C_1$-$C_6$-alkylamino or N,N-di-$C_1$-$C_6$-alkylamino;

W is O or S;

Q is H, formyl, hydroxyl, amino or in each case optionally substituted $C_1$-$C_6$-alkyl, $C_2$-$C_6$-alkenyl, $C_2$-$C_6$-alkynyl, $C_3$-$C_6$-cycloalkyl, $C_1$-$C_5$-heterocycloalkyl, $C_1$-$C_4$-alkoxy, $C_1$-$C_6$-alkyl-$C_3$-$C_6$-cycloalkyl, $C_3$-$C_6$-cycloalkyl-$C_1$-$C_6$-alkyl, $C_6$-$C_{10}$-$C_{14}$-aryl, $C_1$-$C_5$-heteroaryl, $C_6$-$C_{10}$-$C_{14}$-aryl-$C_1$-$C_3$-alkyl, $C_1$-$C_5$-heteroaryl-$C_1$-$C_3$-alkyl, N—$C_1$-$C_4$-alkylamino, N—$C_1$-$C_4$-alkylcarbonylamino, or N,N-di-$C_1$-$C_4$-alkylamino; or is an optionally poly-V-substituted unsaturated 6-membered carbocycle; or is an optionally poly-V-substituted unsaturated 4-, 5- or 6-membered heterocyclic ring, where V is independently halogen, cyano, nitro, in each case optionally substituted $C_1$-$C_6$-alkyl, $C_1$-$C_4$-alkenyl, $C_1$-$C_4$-alkynyl, $C_3$-$C_6$-cycloalkyl, $C_1$-$C_6$-alkoxy, N—$C_1$-$C_6$-alkoxyimino-$C_1$-$C_3$-alkyl, $C_1$-$C_6$-alkylsulphanyl, $C_1$-$C_6$-alkylsulphinyl, $C_1$-$C_6$-alkylsulphonyl, or N,N-di-($C_1$-$C_6$-alkyl)amino;

T is an optionally substituted 5-membered heteroaromatic system containing not more than 2 heteroatoms, such as four carbon atoms and one (1) heteroatom, preferably one (1) nitrogen, one (1) oxygen or one (1) sulphur atom or three carbon atoms and two heteroatoms, preferably two nitrogen atoms, one (1) nitrogen and one (1) oxygen atom, or one (1) nitrogen and one (1) sulphur atom, and salts, N-oxides and tautomeric forms of the compounds of the formula (I).

$R^1$

In a preferred embodiment, $R^1$ in a compound of the formula (I) is H, in each case optionally substituted methyl, ethyl, n-propyl, isopropyl, n-butyl, isobutyl, s-butyl, t-butyl, methoxymethyl, ethoxymethyl, propoxymethyl, methylcarbonyl, ethylcarbonyl, n-propylcarbonyl, isopropylcarbonyl, s-butylcarbonyl, t-butylcarbonyl, methoxycarbonyl, ethoxycarbonyl, n-propoxycarbonyl, isopropoxycarbonyl, s-butoxycarbonyl, t-butoxycarbonyl, cyanomethyl, 2-cyanoethyl, benzyl, 4-methoxybenzyl, pyrid-2-ylmethyl, pyrid-3-ylmethyl, pyrid-4-ylmethyl, 4-chloropyrid-3-ylmethyl.

In an even more preferred embodiment, $R^1$ is H.

W

In a further preferred embodiment, W is O.

Q

In a further preferred embodiment, Q is H, in each case optionally substituted methyl, ethyl, n-propyl, 1-methylethyl, 1,1-dimethylethyl, 1-methylpropyl, n-butyl, 2-methylpropyl, 2-methylbutyl, hydroxymethyl, 2-hydroxypropyl, cyanomethyl, 2-cyanoethyl, 2-fluoroethyl, 2,2-difluoroethyl, 2,2,2-trifluoroethyl, 1-trifluoromethylethyl, 2,2-difluoropropyl, 3,3,3-trifluoropropyl, 2,2-dimethyl-3-fluoropropyl, cyclopropyl, 1-cyanocyclopropyl, 1-methoxycarbonylcyclopropyl, 1-(N-methylcarbamoyl)cyclopropyl, 1-(N-cyclopropylcarbamoyl)cyclopropyl, 1-(thiocarbamoyl)cyclopropyl, cyclopropylmethyl, cyclobutyl, cyclopentyl, cyclohexyl, 1-cyclopropylethyl, bis(cyclopropyl)methyl, 2,2-dimethylcyclopropylmethyl, 2-phenylcyclopropyl, 2,2-dichlorocyclopropyl, trans-2-chlorocyclopropyl, cis-2-chlorocyclopropyl, 2,2-difluorocyclopropyl, trans-2-fluorocyclopropyl, cis-2-fluorocyclopropyl, trans-4-hydroxycyclohexyl, 4-trifluoromethylcyclohexyl, prop-2-enyl, 2-methylprop-2-enyl, prop-2-ynyl, 1,1-dimethylbut-2-ynyl, 3-chloroprop-2-enyl, 3,3-dichloroprop-2-enyl, 3,3-dichloro-1,1-dimethylprop-2-enyl, phenyl, 2-chlorophenyl, 3-chlorophenyl, 4-chlorophenyl, oxetan-3-yl, thietan-3-yl, 1-oxidothietan-3-yl, 1,1-dioxidothietan-3-yl, isoxazol-3-ylmethyl, 2-oxo-2-(2,2,2-trifluoroethylamino)ethyl, 1,2,4-triazol-3-ylmethyl, 3-methyloxetan-3-ylmethyl, benzyl, 2,6-difluorophenylmethyl, 3-fluorophenylmethyl, 2-fluorophenylmethyl, 2,5-difluorophenylmethyl, 1-phenylethyl, 4-chlorophenylethyl, 2-trifluoromethylphenylethyl, 1-pyridin-2-ylethyl, pyridin-2-ylmethyl, 5-fluoropyridin-2-ylmethyl, (6-chloropyridin-3-yl)methyl, pyrimidin-2-ylmethyl, methoxy, 2-ethoxyethyl, 2-(methylsulphanyl)ethyl, 1-methyl-2-(ethylsulphanyl)ethyl, 2-methyl-1-(methylsulphanyl)propan-2-yl, methoxycarbonyl, methoxycarbonylmethyl, $NH_2$, N-ethylamino, N-allylamino, N,N-dimethylamino, N,N-diethylamino; or Q is one of the following, each substituted by 0-4 V substituents: phenyl, naphthyl, pyridazine, pyrazine, pyrimidine, triazine, pyridine, pyrazole, thiazole, isothiazole, oxazole, isoxazole, triazole, imidazole, furan, thiophene, pyrrole, oxadiazole, thiadiazole, where V is independently F, Cl, Br, I, cyano, nitro, methyl, ethyl, difluoromethyl, trichloromethyl, chlorodifluoromethyl, dichlorofluoromethyl, trifluoromethyl, chloromethyl, bromomethyl, 1-fluoroethyl, 2-fluoroethyl, 2,2-difluoroethyl, 2,2,2-trifluoroethyl, 1,2,2,2-tetrafluoroethyl, 1-chloro-1,2,2,2-tetrafluoroethyl, 2,2,2-trichloroethyl, 2-chloro-2,2-difluoroethyl, 1,1-difluoroethyl, pentafluoroethyl, heptafluoro-n-propyl, heptafluoroisopropyl, nonafluoro-n-butyl, cyclopropyl, cyclobutyl, methoxy, ethoxy, n-propoxy, 1-methylethoxy, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, N-methoxyiminomethyl, 1-(N-methoxyimino)ethyl, methylsulphanyl, methylsulphonyl, methylsulphinyl, trifluoromethylsulphonyl, trifluoromethylsulphinyl, trifluoromethylsulphanyl, N,N-dimethylamino.

In a further preferred embodiment, Q is optionally substituted $C_1$-$C_4$-alkyl or optionally substituted $C_3$-$C_6$-cycloalkyl or an unsaturated 4-, 5- or 6-membered heterocyclic ring optionally substituted by one, two or three V substituents, where V is independently halogen, cyano, nitro, oxo (=O), optionally halogen-substituted $C_1$-$C_6$-alkyl, $C_1$-$C_4$-alkenyl, $C_1$-$C_6$-alkoxy, $C_1$-$C_6$-alkylsulphanyl, $C_1$-$C_6$-alkylsulphinyl, $C_1$-$C_6$-alkylsulphonyl. Preferably, Q is halogen-substituted $C_1$-$C_3$-alkyl; with cyano, hydroxyl or carbonamide (—C(=O)N(R)$_2$ where R is independently H or $C_1$-$C_3$-alkyl, substituted $C_1$-$C_3$-alkyl; $C_3$-cycloalkyl; cyano-substituted, halogen-substituted, nitro-substituted or halogenated $C_1$-$C_2$-alkyl-substituted $C_3$-cycloalkyl; an unsaturated 4-, 5- or 6-membered heterocyclic ring optionally substituted by one, two or three V and containing one or two heteroatoms selected from a group consisting of N, O and S, where V is independently halogen, cyano, nitro, oxo (=O), optionally halogen-substituted $C_1$-$C_6$-alkyl. More preferably, Q is fluorinated $C_1$-$C_3$-alkyl such as $CF_3$, $CH_2CF_3$ or $CH_2CH_2CF_3$; $C_1$-$C_3$-alkyl substituted by carbonamide (—C(=O)N(R)$_2$ where R is independently H, $C_1$-$C_3$-alkyl or halogen-substituted $C_1$-$C_3$-alkyl, such as 2-oxo-2-(2,2,2-trifluoroethylamino)ethyl; cyclopropyl; cyano-substituted or fluorinated $C_1$-$C_2$-alkyl-substituted cyclopropyl such as 1-(cyano)cyclopropyl or 1-(trifluoromethyl)cyclopropyl); a 4-membered heterocyclic ring containing one heteroatom selected from a group consisting of N, O and S, such as thietan-3-yl.

In a more preferred embodiment, Q is fluorine-substituted $C_1$-$C_4$-alkyl such as 2,2,2-trifluoroethyl, 2,2-difluoroethyl, 3,3,3-trifluoropropyl; $C_3$-$C_4$-cycloalkyl such as cyclopropyl or cyclobutyl; optionally substituted $C_3$-$C_4$-cycloalkyl such as 1-trifluoromethylcyclopropyl, 1-tert-butylcyclopropyl, 1-thiocarbamoylcyclopropyl, 1-cyanocyclopropyl, trans-2-fluorocyclopropyl, cis-2-fluorocyclopropyl; $C_4$-$C_6$-heterocycloalkyl such as oxetan-3-yl, thietan-3-yl, 1-oxidothietan-3-yl or 1,1-dioxidothietan-3-yl; benzyl; pyridin-2-ylmethyl; methylsulphonyl; or 2-oxo-2-(2,2,2-trifluoroethylamino) ethyl.

In a particularly preferred embodiment, Q is fluorine-substituted $C_1$-$C_3$-alkyl such as 2,2,2-trifluoroethyl or 3,3,3-trifluoropropyl; cyclopropyl; optionally substituted cyclopropyl such as 1-cyanocyclopropyl or 1-trifluoromethylcyclopropyl, thietan-3-yl; or 2-oxo-2-(2,2,2-trifluoroethyl)aminoethyl.

A1 to A4

In a preferred embodiment, not more than one (1) $A_1$ to $A_4$ moiety is N (in other words: one (1) $A_1$ to $A_4$ (preferably $A_2$) is N); or no (0) $A_1$ to $A_4$ is N (in other words: $A_1$ to $A_4$ are each $CR^2$, $CR^3$, $CR^4$, and $CR^5$); or one or two moieties selected from $A_1$, $A_2$, $A_3$, $A_4$ may be N and not more than one moiety selected from $B_1$, $B_2$, $B_3$, $B_4$ and $B_5$ is N.

In a further preferred embodiment, $R^2$, $R^3$, $R^4$ and $R^5$ (if the corresponding A moiety is CR) in a compound of the formula (I) are each independently H, halogen, cyano, nitro, in each case optionally substituted $C_1$-$C_4$-alkyl, $C_3$-$C_4$-cycloalkyl, $C_1$-$C_4$-alkoxy, N—$C_1$-$C_4$-alkoxyimino-$C_1$-$C_4$-alkyl, $C_1$-$C_4$-alkylsulphanyl, $C_1$-$C_4$-alkylsulphinyl, $C_1$-$C_4$-alkylsulphonyl, N—$C_1$-$C_4$-alkylamino, N,N-di-$C_1$-$C_4$-alkylamino or N—$C_1$-$C_3$-alkoxy-$C_1$-$C_4$-alkylamino or 1-pyrrolidinyl.

In a further preferred embodiment, $R^2$ and $R^5$ are each independently H, methyl, F and Cl.

In a further preferred embodiment, $R^3$ and $R^4$ are each independently H, F, Cl, Br, I, cyano, nitro, methyl, ethyl, fluoromethyl, difluoromethyl, chlorodifluoromethyl, trifluoromethyl, 2,2,2-trifluoroethyl, methoxy, ethoxy, n-propoxy, 1-methylethoxy, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, N-methoxyiminomethyl, 1-(N-methoxyimino)ethyl, methylsulphanyl, trifluoromethylsulphanyl, methylsulphonyl, methylsulphinyl, trifluoromethylsulphonyl, trifluoromethylsulphinyl.

B1 to B5

In a preferred embodiment, not more than one (1) $B_1$ to $B_5$ moiety is N (in other words: one (1) $B_1$ to $B_5$ is N); or no (0) $B_1$ to $B_5$ is N ($B_1$ to $B_5$ are each $CR^6$, $CR^7$, $CR^8$, $CR^9$ and $CR^{10}$).

In a further preferred embodiment, $R^6$, $R^7$, $R^9$ and $R^{10}$ (when the corresponding B moiety is CR) are each independently H, halogen, cyano, nitro, in each case optionally substituted $C_1$-$C_4$-alkyl, $C_3$-$C_4$-cycloalkyl, $C_1$-$C_4$-alkoxy, N-alkoxyiminoalkyl, $C_1$-$C_4$-alkylsulphanyl, $C_1$-$C_4$-alkylsulphinyl, $C_1$-$C_4$-alkylsulphonyl, N—$C_1$-$C_4$-alkylamino, N,N-di-$C_1$-$C_4$-alkylamino.

In a further preferred embodiment, $R^6$, $R^7$, $R^9$ and $R^{10}$ are each independently H, halogen, cyano, nitro, methyl, ethyl, fluoromethyl, difluoromethyl, chlorodifluoromethyl, trifluoromethyl, 2,2,2-trifluoroethyl, methoxy, ethoxy, n-propoxy, 1-methylethoxy, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, N-methoxyiminomethyl, 1-(N-methoxyimino)ethyl, methylsulphanyl, trifluoromethylsulphanyl, methylsulphonyl, methylsulphinyl, trifluoromethylsulphonyl, trifluoromethylsulphinyl.

In a further preferred embodiment, $R^6$ and $R^{10}$ are each independently H, halogen (especially chlorine, bromine, fluorine), cyano, nitro, methyl, ethyl, difluoromethyl, chlorodifluoromethyl, trifluoromethyl, methoxy, ethoxy, 1-methylethoxy, difluoromethoxy, chlorodifluoromethoxy, dichlorofluoromethoxy, trifluoromethoxy, 2,2,2-trifluoroethoxy, 2-chloro-2,2-difluoroethoxy, methylsulphanyl, trifluoromethylsulphanyl, methylsulphonyl, methylsulphinyl, trifluoromethylsulphonyl, trifluoromethylsulphinyl.

In a further preferred embodiment, $R^6$ and $R^{10}$ are the substituents described herein, but $R^6$ and $R^{10}$ in one compound are not both H. In other words, when $R^6$ in a compound is H, $R^{10}$ is one of the other substituents described herein, and vice versa.

In a further preferred embodiment, $R^6$ and $R^{10}$ are each a substituent selected from halogen (preferably Cl, Br or F), $C_1$-$C_3$-alkyl, halogen-substituted $C_1$-$C_3$-alkyl, $C_1$-$C_3$-alkoxy and halogen-substituted $C_1$-$C_3$-alkoxy.

In a further preferred embodiment, $R^6$ and $R^{10}$ are each halogen (such as Cl, Br or F), are each $C_1$-$C_3$-alkyl, or are each halogen-substituted $C_1$-$C_3$-alkyl, for example perfluorinated $C_1$-$C_3$-alkyl (perfluoromethyl, perfluoroethyl or perfluoropropyl).

In a further preferred embodiment, $R^6$ is perfluorinated $C_1$-$C_3$-alkyl (e.g. perfluoromethyl) and $R^{10}$ is Cl, Br or F, more preferably Cl or Br.

R8

In a particularly preferred embodiment, $B_3$ is C—$R^8$ in which $R^8$ is halogen, cyano, nitro, halogen-substituted $C_1$-$C_4$-alkyl, $C_3$-$C_4$-cycloalkyl, $C_1$-$C_4$-alkoxy, N—$C_1$-$C_4$-alkoxyimino-$C_1$-$C_4$-alkyl, $C_1$-$C_4$-alkylsulphanyl, $C_1$-$C_4$-alkylsulphinyl, $C_1$-$C_4$-alkylsulphonyl, N—$C_1$-$C_4$-alkylamino or N,N-di-$C_1$-$C_4$-alkylamino.

In a further preferred embodiment, $R^8$ is halogen such as fluorine, chlorine, bromine, iodine, or halogen-substituted $C_1$-$C_4$-alkyl, cyano, nitro, methyl, ethyl, difluoromethyl, trichloromethyl, chlorodifluoromethyl, dichlorofluoromethyl, trifluoromethyl, chloromethyl, bromomethyl, 1-fluoroethyl, 2-fluoroethyl, 2,2-difluoroethyl, 2,2,2-trifluoroethyl, 1,2,2,2-tetrafluoroethyl, 1-chloro-1,2,2,2-tetrafluoroethyl, 2,2,2-trichloroethyl, 2-chloro-2,2-difluoroethyl, 1,1-difluoroethyl, pentafluoroethyl, pentafluoro-tert-butyl, heptafluoro-n-propyl, heptafluoroisopropyl, nonafluoro-n-butyl, nonafluoro-sec-butyl, cyclopropyl, cyclobutyl, methoxy, ethoxy, n-propoxy, 1-methylethoxy, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, N-methoxyiminomethyl, 1-(N-methoxyimino)ethyl, methylsulphanyl, methylsulphonyl, methylsulphinyl, trifluoromethylsulphonyl, trifluoromethylsulphinyl, trifluoromethylsulphanyl, N,N-dimethylamino.

In a more preferred embodiment, $R^8$ is difluoromethyl, trichloromethyl, chlorodifluoromethyl, dichlorofluoromethyl, trifluoromethyl, 1-fluoroethyl, 2-fluoroethyl, 2,2-difluoroethyl, 2,2,2-trifluoroethyl, 1,2,2,2-tetrafluoroethyl, 1-chloro-1,2,2,2-tetrafluoroethyl, 2,2,2-trichloroethyl, 2-chloro-2,2-difluoroethyl, 1,1-difluoroethyl, pentafluoroethyl, pentafluoro-tert-butyl, heptafluoro-n-propyl, heptafluoroisopropyl, nonafluoro-n-butyl, nonafluoro-sec-butyl, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, trifluoromethylsulphonyl, trifluoromethylsulphinyl, trifluoromethylsulphanyl.

In a further more preferred embodiment, $R^8$ is halogen-substituted $C_1$-$C_3$-alkyl (preferably perfluorinated $C_1$-$C_3$-alkyl ($CF_3$, $C_2F_5$ or $C_3F_7$)) or halogen-substituted alkoxy (preferably perfluorinated $C_1$-$C_3$-alkoxy ($OCF_3$, $OC_2F_5$ or $OC_3F_7$)).

In a particularly preferred embodiment, $R^8$ is perfluorinated $C_1$-$C_3$-alkyl such as perfluorinated n- or i-propyl (—$C_3F_7$), perfluorinated ethyl ($C_2F_5$) or perfluorinated methyl ($CF_3$), more preferably perfluorinated n- or i-propyl (—$C_3F_7$) or perfluorinated methyl.

A and B

In a further preferred embodiment, the $A_1$ to $A_4$ and $B_1$ to $B_5$ moieties in compounds of the formula (I) are as follows:

$A_1$ is C—H,
$A_2$ is $CR^3$ or N,
$A_3$ is $CR^4$,
$A_4$ is $CR^5$ or N,
$B_1$ is $CR^6$ or N,
$B_2$ is $CR^7$,
$B_3$ is $CR^8$, $B_4$ is $CR^9$ and
$B_5$ is $CR^{10}$ or N.

In an even more preferred embodiment, the $A_1$ to $A_4$ and $B_1$ to $B_5$ moieties in compounds of the formula (I) are as follows:
$A_1$ is C—H,
$A_2$ is $CR^3$ or N,
$A_3$ is $CR^4$,
$A_4$ is C—H,
$B_1$ is $CR^6$ or N,
$B_2$ is C—H,
$B_3$ is $CR^8$,
$B_4$ is C—H and
$B_5$ is $CR^{10}$ or N.

In an even more preferred embodiment, the $A_1$ to $A_4$ and $B_1$ to $B_5$ moieties in compounds of the formula (I) are as follows:
$A_1$ is C—H,
$A_2$ is $CR^3$ or N,
$A_3$ is $CR^4$,
$A_4$ is C—H oder N,
$B_1$ is $CR^6$,
$B_2$ is C—H,
$B_3$ is $CR^8$,
$B_4$ is C—H and
$B_5$ is $CR^{10}$ or N.

T

In a further preferred embodiment, T is one of the 5-membered heteroaromatic systems shown below, where the bond to the carbon atom of the (C—$B_1$-$B_5$) ring system is identified by a dotted bond marked with an asterisk, and the bond to the carbon atom of the (C-$A_1$-$A_2$-$A_3$-C-$A_4$)-ring system by a dotted bond.

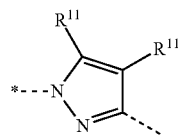

T1

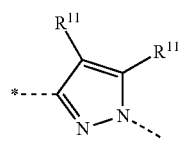

T2

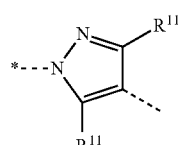

T3

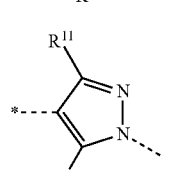

T4

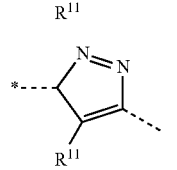

T5

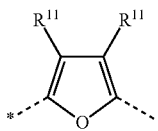

T8

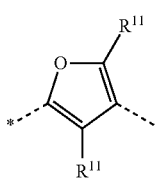

T9

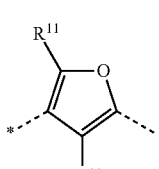

T10

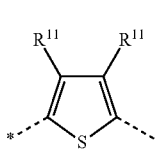

T11

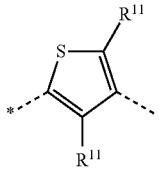

T12

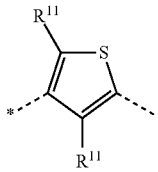

T13

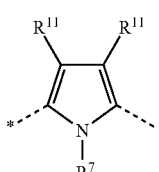

T14

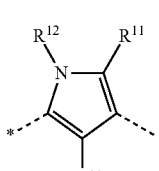

T15

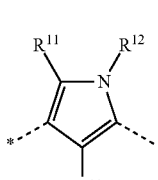

T16

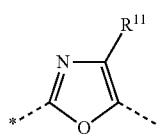 T18
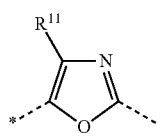 T19
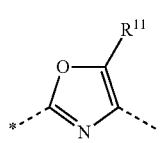 T20
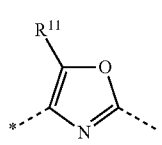 T21
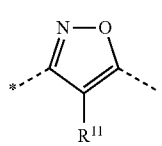 T22
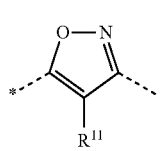 T23
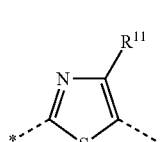 T24
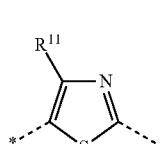 T25
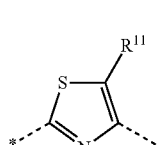 T26
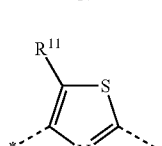 T27
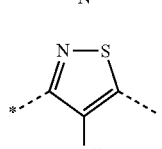 T28
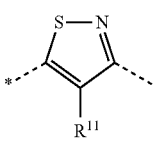 T29
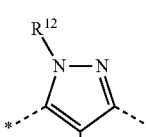 T30
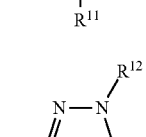 T31
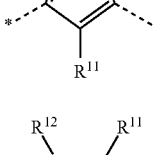 T32
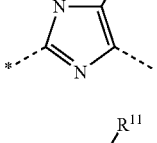 T33
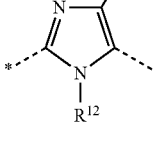 T34
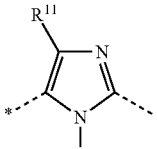 T35
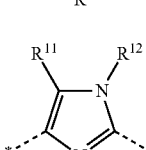 T45
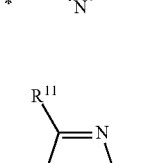 T46

-continued

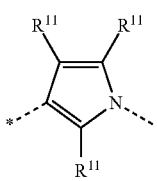
T47 where

R$^{11}$ is independently H, halogen, cyano, nitro, amino or an optionally substituted C$_1$-C$_6$-alkyl, C$_1$-C$_6$-alkyloxy, C$_1$-C$_6$-alkylcarbonyl, C$_1$-C$_6$-alkylsulphanyl, C$_1$-C$_6$-alkylsulphinyl, C$_1$-C$_6$-alkylsulphonyl, preferably H; and R$^{12}$ is H, halogen, cyano, nitro, amino or an optionally substituted C$_1$-C$_6$-alkyl, C$_1$-C$_6$-alkyloxy, C$_1$-C$_6$-alkylcarbonyl, C$_1$-C$_6$-alkylsulphanyl, C$_1$-C$_6$-alkylsulphinyl, C$_1$-C$_6$-alkylsulphonyl, preferably H or methyl.

In a further preferred embodiment, R$^{11}$ is independently halogen, cyano, nitro, amino, methyl, ethyl, 1-methylethyl, tert-butyl, trifluoromethyl, difluoromethyl, methoxy, ethoxy, trifluoromethoxy, 2,2-difluoroethoxy, 2,2,2-trifluoroethoxy, methylcarbonyl, ethylcarbonyl, trifluoromethylcarbonyl, methylsulphanyl, methylsulphinyl, methylsulphonyl, trifluoromethylsulphonyl, trifluoromethylsulphanyl or trifluoromethylsulphinyl.

In a more preferred embodiment, R$^{11}$ is independently H, methyl, ethyl, 2-methylethyl, 2,2-dimethylethyl, fluorine, chlorine, bromine, iodine, nitro, trifluoromethyl or amino.

In a further preferred embodiment, T is one of the 5-membered heteroaromatic systems shown below, where the bond to the carbon atom of the (C—B$_1$-B$_5$) ring system is identified by a dotted bond marked with an asterisk, and the bond to the carbon atom of the (C-A$_1$-A$_2$-A$_3$-C-A$_4$)-ring system by a dotted bond.

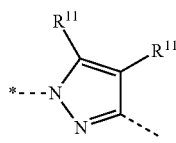
T1

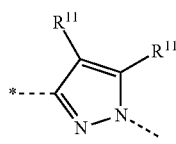
T2

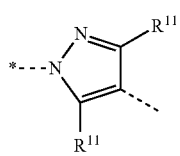
T3

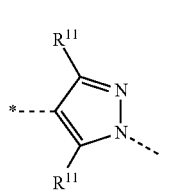
T4

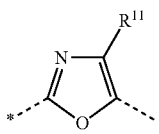
T18

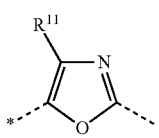
T19

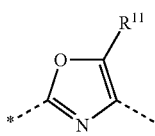
T20

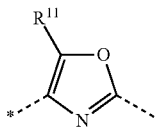
T21

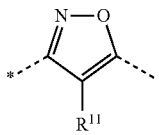
T22

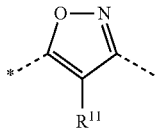
T23

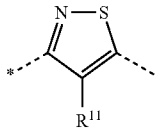
T28

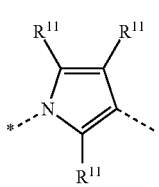
T29

T45

T46

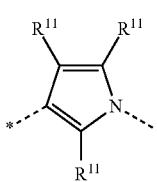
T47 where R¹¹ is independently defined as described herein.

In a more preferred embodiment, T is one of the 5-membered heteroaromatic systems shown below, where the bond to the carbon atom of the (C—B₁-B₅) ring system is identified by a dotted bond marked with an asterisk, and the bond to the carbon atom of the (C-A₁-A₂-A₃-C-A₄)-ring system by a dotted bond.

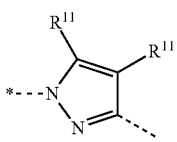
T1

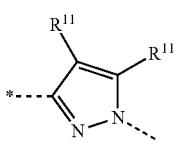
T2

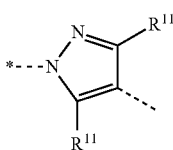
T3

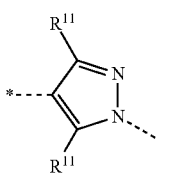
T4

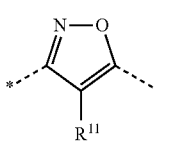
T22

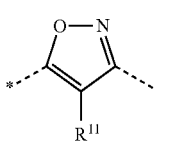
T23

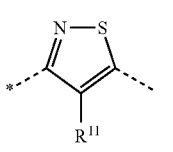
T28

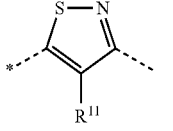
T29

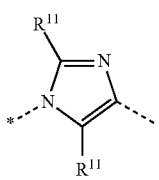
T45

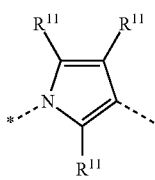
T46

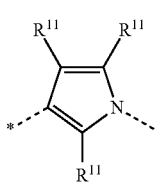
T47 where R¹¹ is defined as described herein and n has the values of 1 or 2.

In a particularly preferred embodiment, T is one of the 5-membered heteroaromatic systems shown below, where the bond to the carbon atom of the (C—B₁-B₅) ring system is identified by a dotted bond marked with an asterisk, and the bond to the carbon atom of the (C-A₁-A₂-A₃-C-A₄)-ring system by a dotted bond.

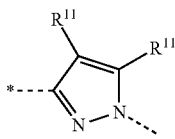
T2

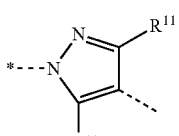
T3

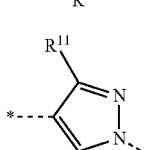
T4

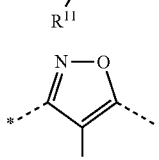
T22

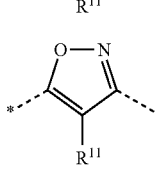
T23

-continued

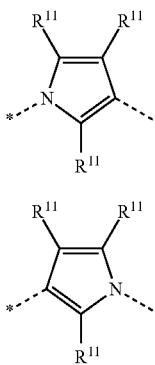

where $R^{11}$ is independently defined as described herein.

In a further particularly preferred embodiment, T is one of the 5-membered heteroaromatic systems shown below, where the bond to the carbon atom of the (C—$B_1$-$B_5$) ring system is identified by a dotted bond marked with an asterisk, and the bond to the carbon atom of the (C-$A_1$-$A_2$-$A_3$-C-$A_4$)-ring system by a dotted bond.

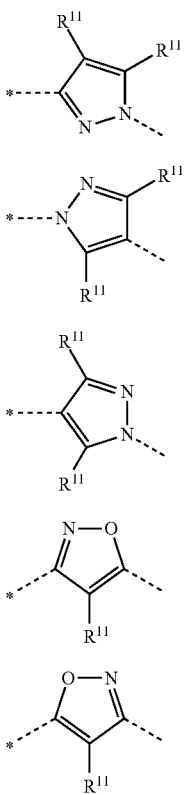

where $R^{11}$ is independently defined as described herein.

In an even more preferred embodiment, in the formula (I) and further general formulae detailed herein,
$A_1$ is C—$R^2$ or N, preferably C—$R^2$,
$A_2$ is $CR^3$ or N,
$A_3$ is $CR^4$,
$A_4$ is C—$R^5$ or N,
$B_1$ is $CR^6$,
$B_2$ is C—H,
$B_3$ is $CR^8$,
$B_4$ is C—H,
$B_5$ is $CR^{10}$ or N,
$R^1$ is hydrogen,
$R^2$ is hydrogen, $C_1$-$C_3$-alkyl, fluorine or chlorine, preferably H,
$R^3$ is hydrogen or halogen-substituted $C_1$-$C_3$-alkyl (preferably perfluorinated $C_1$-$C_3$-alkyl ($CF_3$, $C_2F_5$ or $C_3F_7$)),
$R^4$ is hydrogen, chlorine, fluorine, $C_1$-$C_3$-alkyl (such as —$CH_3$), cyclopropyl, $C_1$-$C_3$-alkoxy (such as —O—$CH_3$), N—$C_1$-$C_4$-alkylamino (—NH—$C_1$-$C_3$-alkyl such as —NH—$CH_3$), $C_3$-cycloalkylamino (such as —NH—$C_3H_5$), N—$C_1$-$C_3$-alkoxy-$C_1$-$C_3$-alkylamino (such as —NH—$C_2H_4$—O—$CH_3$) or 1-pyrrolidinyl, more preferably chlorine,
$R^5$ is hydrogen or fluorine, preferably H,
$R^6$ and $R^{10}$ are each independently hydrogen, $C_1$-$C_3$-alkyl (preferably, $R^6$ and $R^{10}$ are each $C_1$-$C_3$-alkyl), $C_1$-$C_3$-alkoxy, halogen-substituted $C_1$-$C_3$-alkyl (preferably perfluorinated $C_1$-$C_3$-alkyl ($CF_3$, $C_2F_5$ or $C_3F_7$)), halogen-substituted $C_1$-$C_3$-alkoxy (preferably perfluorinated $C_1$-$C_3$-alkoxy ($OCF_3$, $OC_2F_5$ or $OC_3F_7$)), $C_1$-$C_3$-alkylsulphanyl, $C_1$-$C_3$-alkylsulphinyl, $C_1$-$C_3$-alkylsulphonyl, fluorine, bromine or chlorine (preferably, $R^6$ and $R^{10}$ are each chlorine),
$R^8$ is halogen-substituted $C_1$-$C_3$-alkyl (preferably perfluorinated $C_1$-$C_3$-alkyl ($CF_3$, $C_2F_5$ or $C_3F_7$)) or halogen-substituted $C_1$-$C_3$-alkoxy (preferably perfluorinated $C_1$-$C_3$-alkoxy ($OCF_3$, $OC_2F_5$ or $OC_3F_7$)),
$R^{11}$ is hydrogen, cyano (CN) or amino ($NH_2$),
W is oxygen or sulphur, preferably oxygen,
Q is $C_1$-$C_3$-alkyl, cyclopropyl, 1-(cyano)cyclopropyl, 1-(perfluorinated $C_1$-$C_3$-alkyl)cyclopropyl (such as (1-(trifluoromethyl)cyclopropyl), 1-($C_1$-$C_4$-alkyl)cyclopropyl (such as 1-(tert-butyl)cyclopropyl), 1-(thiocarbamoyl)cyclopropyl, halogen-substituted $C_1$-$C_3$-alkyl (e.g. $CH_2CF_3$, $CH_2CH_2CF_3$), thietan-3-yl, N-methylpyrazol-3-yl, 2-oxo-2(2,2,2-trifluoroethylamino)ethyl, and
T is a T selected from the group consisting of T1 to T47, preferably T2, T3, T4, T22 or T23 (more preferably T22 or T23).

In a further even more preferred embodiment, in the formula (I) and further general formulae detailed herein,
$A_1$ is C—$R^2$ or N, preferably C—$R^2$,
$A_2$ is $CR^3$ or N,
$A_3$ is $CR^4$,
$A_4$ is C—$R^5$ or N,
$B_1$ is $CR^6$,
$B_2$ is C—H,
$B_3$ is $CR^8$,
$B_4$ is C—H,
$B_5$ is $CR^{10}$ or N,
$R^1$ is $C_1$-$C_2$-alkyl (methyl or ethyl, more preferably methyl),
$R^2$ is hydrogen, $C_1$-$C_3$-alkyl, fluorine or chlorine, preferably H,
$R^3$ is hydrogen or halogen-substituted $C_1$-$C_3$-alkyl (preferably perfluorinated $C_1$-$C_3$-alkyl ($CF_3$, $C_2F_5$ or $C_3F_7$)),
$R^4$ is hydrogen, chlorine, fluorine, $C_1$-$C_3$-alkyl (such as —$CH_3$), cyclopropyl, $C_1$-$C_3$-alkoxy (such as —O—$CH_3$), N—$C_1$-$C_4$-alkylamino (—NH—$C_1$-$C_3$-alkyl such as —NH—$CH_3$), $C_3$-cycloalkylamino (such as —NH—$C_3H_5$), N—$C_1$-$C_3$-alkoxy-$C_1$-$C_3$-alkylamino (such as —NH—$C_2H_4$—O—$CH_3$) or 1-pyrrolidinyl, more preferably chlorine,
$R^5$ is hydrogen or fluorine, preferably H,
$R^6$ and $R^{10}$ are each independently hydrogen, $C_1$-$C_3$-alkyl (preferably, $R^6$ and $R^{10}$ are each $C_1$-$C_3$-alkyl), $C_1$-$C_3$- alkoxy, halogen-substituted $C_1$-$C_3$-alkyl (preferably perfluorinated $C_1$-$C_3$-alkyl ($CF_3$, $C_2F_5$ or $C_3F_7$)), halogen-substituted $C_1$-$C_3$-alkoxy (preferably perfluorinated $C_1$-$C_3$-alkoxy ($OCF_3$, $OC_2F_5$ or $OC_3F_7$)), $C_1$-$C_3$-alkylsulphanyl, $C_1$-$C_3$-alkylsulphinyl, $C_1$-$C_3$-alkylsulphonyl, fluorine, bromine or chlorine (preferably, $R^6$ and $R^{10}$ are each chlorine), $R^8$ is halogen-substituted $C_1$-$C_3$-alkyl (preferably perfluorinated $C_1$-$C_3$-alkyl ($CF_3$, $C_2F_5$ or $C_3F_7$)) or halogen-substituted $C_1$-$C_3$-alkoxy (preferably perfluorinated $C_1$-$C_3$-alkoxy ($OCF_3$, $OC_2F_5$ or $OC_3F_7$)), $R^{11}$ is hydrogen, cyano (CN) or amino ($NH_2$), W is oxygen or sulphur, preferably oxygen, Q is $C_1$-$C_3$-alkyl, cyclopropyl, 1-(cyano)cyclopropyl, 1-(perfluorinated $C_1$-$C_3$-alkyl)cyclopropyl (such as (1-(trifluoromethyl)cyclopropyl), 1-($C_1$-$C_4$-alkyl)cyclopropyl (such as 1-(tert-butyl)cyclopropyl), 1-(thiocarbamoyl)cyclopropyl, halogen-substituted $C_1$-$C_3$-alkyl (e.g. $CH_2CF_3$, $CH_2CH_2CF_3$), thietan-3-yl, N-methylpyrazol-3-yl, 2-oxo-2(2,2,2-trifluoroethylamino)ethyl, and T is a T selected from the group consisting of T1 to T47, preferably T2, T3, T4, T22 or T23 (more preferably T22 or T23).

A further preferred embodiment additionally relates to compounds of the formula (Ia)

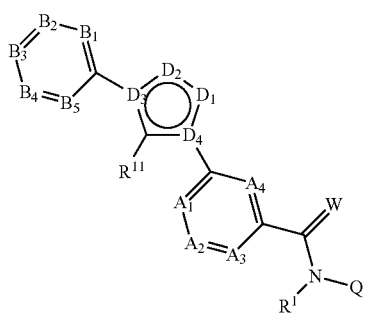

(Ia)

in which
$R^1$, $R^{11}$, Q, W, $A_1$, $A_2$, $A_3$, $A_4$, $B_1$, $B_2$, $B_3$, $B_4$ and $B_5$ are each defined as described herein, where not more than one moiety selected from $A_1$, $A_2$, $A_3$, $A_4$ is N and not more than one moiety selected from $B_1$, $B_2$, $B_3$, $B_4$ and $B_5$ is N; or where one or two moieties selected from $A_1$, $A_2$, $A_3$, $A_4$ may be N and not more than one moiety selected from $B_1$, $B_2$, $B_3$, $B_4$ and $B_5$ is N; and $D_1$ and $D_2$ are each independently C—$R^{11}$ or a heteroatom, preferably C—$R^{11}$ or a heteroatom selected from N, O and S, more preferably C—$R^{11}$ or a heteroatom selected from N and O;

the $D_3$ and $D_4$ moieties are each independently C or a heteroatom selected from N;

where one (1) or two moieties selected from $D_1$, $D_2$, $D_3$ and $D_4$ are a heteroatom;

is an aromatic system.

A further preferred embodiment additionally relates to compounds of the formula (Ia')

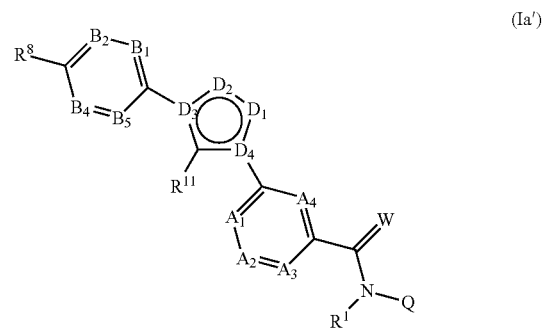

(Ia')

in which
$R^1$, $R^{11}$, Q, W, $A_1$, $A_2$, $A_3$, $A_4$, $B_1$, $B_2$, $B_4$ and $B_5$ are each defined as described herein, where not more than one moiety selected from $A_1$, $A_2$, $A_3$, $A_4$ is N and not more than one moiety selected from $B_1$, $B_2$, $B_3$, $B_4$ and $B_5$ is N; or where one or two moieties selected from $A_1$, $A_2$, $A_3$, $A_4$ may be N and not more than one moiety selected from $B_1$, $B_2$, $B_3$, $B_4$ and $B_5$ is N;

$D_1$ and $D_2$ are each independently C—$R^{11}$ or a heteroatom, preferably C—$R^{11}$ or a heteroatom selected from N, O and S, more preferably C—$R^{11}$ or a heteroatom selected from N and O;

the $D_3$ and $D_4$ moieties are each independently C or a heteroatom selected from N;

where one (1) or two moieties selected from $D_1$, $D_2$, $D_3$ and $D_4$ are a heteroatom; in other words, where not more than one (1) or two moieties selected from $D_1$, $D_2$, $D_3$ and $D_4$ is/are a heteroatom, where one (1) or two moieties selected from $D_1$, $D_2$, $D_3$ and $D_4$ is a heteroatom selected from N and O in the case of $D_1$ and $D_2$, or N in the case of $D_3$ and $D_4$;

is an aromatic system
and $R^8$ is as defined herein, preferably perfluorinated $C_1$-$C_4$-alkyl.

A further preferred embodiment relates to compounds of the formula (Ib)

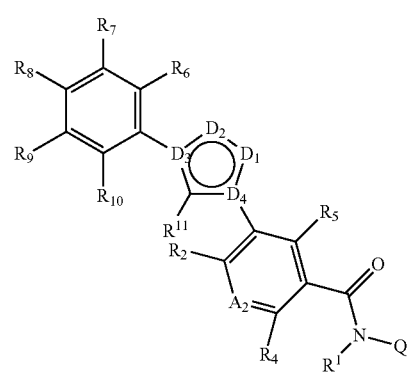

(Ib)

in which $R_1$, $R_2$, $R_4$, $R_5$, $R_6$, $R_7$, $R_8$, $R_9$, $R_{10}$, $R_{11}$, $A_2$, Q, $D_1$, $D_2$, $D_3$ $D_4$ and

are each defined as described herein, and where one (1) or two moieties selected from $D_1$, $D_2$, $D_3$ and $D_4$ are a heteroatom.

Two particularly preferred embodiments relate to compounds of the formula (Ib) and (Id) in which $D_1$ is N, $D_2$ is O and $D_3$ and $D_4$ are C; or $D_1$ is C—$R^{13}$, $D_2$ is N and $D_3$ is N and $D_4$ is C, where $R_{13}$ is H, halogen, cyano, nitro, amino or an optionally substituted $C_1$-$C_6$-alkyl, $C_1$-$C_6$-alkyloxy, $C_1$-$C_6$-alkylcarbonyl, $C_1$-$C_6$-alkylsulphanyl, $C_1$-$C_6$-alkylsulphinyl, $C_1$-$C_6$-alkylsulphonyl, preferably H or halogen such as F, Cl, Br or I, and more preferably H; and $R_1$ is preferably H or $R_1$ is preferably methyl.

A further particularly preferred embodiment relates to compounds of the formula (Ib) and (Id) in which $D_1$ is O, $D_2$ is N and $D_3$ and $D_4$ are C; where $R_{13}$ is H, halogen, cyano, nitro, amino or an optionally substituted $C_1$-$C_6$-alkyl, $C_1$-$C_6$-alkyloxy, $C_1$-$C_6$-alkylcarbonyl, $C_1$-$C_6$-alkylsulphanyl, $C_1$-$C_6$-alkylsulphinyl, $C_1$-$C_6$-alkylsulphonyl, preferably H or halogen such as F, Cl, Br or I, and more preferably H; and $R_1$ is preferably H or $R_1$ is preferably methyl.

A further preferred embodiment relates to compounds of the formula (Ic)

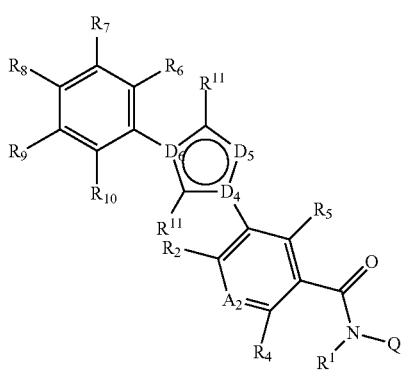

in which $R_1$, $R_2$, $R_4$, $R_5$, $R_6$, $R_7$, $R_8$, $R_9$, $R_{10}$, $R_{11}$, $A_2$ and Q are each defined as described herein and

is an aromatic system; and a moiety selected from $D_4$ and $D_6$ is N, where the respective other moiety selected from $D_4$ and $D_6$ is N or C; and $D_5$ is N or C—$R^{11}$;

under the condition that not more than two moieties selected from $D_4$, $D_5$ and $D_6$ are N.

Preferred embodiments relate to compounds of the formula (Ic) in which $D_4$ is N and $D_5$ and $D_6$ are each C—$R^{11}$; in which $D_6$ is N and $D_5$ and $D_4$ are each C—$R^{11}$; or in which $D_4$ and $D_5$ are each N and $D_6$ is C—$R^{11}$.

A further preferred embodiment relates to compounds of the formula (Id)

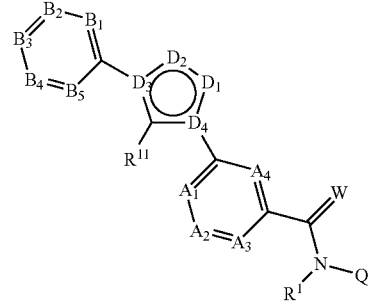

where $R^1$, $R^{11}$, Q, W, $A_1$, $A_2$, $A_3$, $A_4$, $B_1$, $B_2$, $B_3$, $B_4$ and $B_5$, $D_1$, $D_2$, $D_3$ and $D_4$ and are each defined as described herein, where not more than one (1) or two moieties selected from $D_1$, $D_2$, $D_3$ and $D_4$ are a heteroatom and where not more than one moiety selected from $A_1$, $A_2$, $A_3$, $A_4$ is N and not more than one moiety selected from $B_1$, $B_2$, $B_3$, $B_4$ and $B_5$ is N.

A particularly preferred embodiment relates to compounds of the formula (Ia), (Ib), (Ic) or (Id) in which $R^8$ is $C_1$-$C_6$-alkyl, halogen-substituted $C_1$-$C_6$-alkyl, $C_3$-$C_6$-cycloalkyl, halogen-substituted $C_3$-$C_6$-cycloalkyl, $C_1$-$C_6$-alkoxy, halogen-substituted $C_1$-$C_6$-alkoxy, N-alkoxyiminoalkyl, halogen-substituted $C_1$-$C_6$-alkylsulphanyl, halogen-substituted $C_1$-$C_6$-alkylsulphinyl, halogen-substituted $C_1$-$C_6$-alkylsulphonyl, N—$C_1$-$C_6$-alkylamino, N,N-di-$C_1$-$C_4$-alkylamino, and is halogen, cyano or nitro. Examples are fluorine, chlorine, bromine, iodine, cyano, nitro, methyl, ethyl, difluoromethyl, trichloromethyl, chlorodifluoromethyl, dichlorofluoromethyl, trifluoromethyl, chloromethyl, bromomethyl, 1-fluoroethyl, 2-fluoroethyl, 2,2-difluoroethyl, 2,2,2-trifluoroethyl, 1,2,2,2-tetrafluoroethyl, 1-chloro-1,2,2,2-tetrafluoroethyl, 2,2,2-trichloroethyl, 2-chloro-2,2-difluoroethyl, 1,1-difluoroethyl, pentafluoroethyl, pentafluoro-tert-butyl, heptafluoro-n-propyl, heptafluoroisopropyl, nonafluoro-n-butyl, nonafluoro-sec-butyl, cyclopropyl, cyclobutyl, methoxy, ethoxy, n-propoxy, 1-methylethoxy, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, N-methoxyiminomethyl, 1-(N-methoxyimino)ethyl, methylsulphanyl, methylsulphonyl, methylsulphinyl, trifluoromethylsulphonyl, trifluoromethylsulphinyl, trifluoromethylsulphanyl, N,N-dimethylamino. More preferably, $R^8$ is halogen-substituted $C_1$-$C_4$-alkyl such as difluoromethyl, trichloromethyl, chlorodifluoromethyl, dichlorofluoromethyl, trifluoromethyl, 1-fluoroethyl, 2-fluoroethyl, 2,2-difluoroethyl, 2,2,2-trifluoroethyl, 1,2,2,2-tetrafluoroethyl, 1-chloro-1,2,2,2-tetrafluoroethyl, 2,2,2-trichloroethyl, 2-chloro-2,2-difluoroethyl, 1,1-difluoroethyl, pentafluoroethyl, pentafluoro-tert-butyl, heptafluoro-n-propyl, heptafluoroisopropyl, nonafluoro-n-butyl, nonafluoro-sec-butyl; halogen-substituted $C_1$-$C_4$-alkoxy such as fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy; trifluoromethylsulphonyl; trifluoromethylsulphinyl; or trifluoromethylsulphanyl. Even more preferably, $R^8$ is difluoromethyl, trichloromethyl, chlorodifluoromethyl, dichlorofluoromethyl, trifluoromethyl, 1-fluoroethyl, 2-fluoroethyl, 2,2-difluoroethyl, 2,2,2-trifluoroethyl, 1,2,2,2-tetrafluoroethyl, 1-chloro-1,2,2,2-tetrafluoroethyl, 2,2,2-trichloroethyl, 2-chloro-2,2-difluoroethyl, 1,1-difluoroethyl, pentafluoroethyl, pentafluoro-tert-butyl, heptafluoro-n-propyl, heptafluoroisopropyl, nonafluoro-n-butyl, nonafluoro-sec-butyl, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, trifluoromethylsulphonyl, trifluoromethylsulphinyl or trifluoromethylsulphanyl. More preferably, $R^8$ in compounds of the formula (Ib) is perfluorinated $C_1$-$C_3$-alkyl such as perfluorinated propyl (—$C_3F_7$), perfluorinated ethyl ($C_2F_5$) or perfluorinated methyl ($CF_3$), most preferably perfluorinated propyl (—$C_3F_7$) or perfluorinated methyl.

Particularly preferred compounds corresponding to the compounds of the formula (Ia) are compounds of the formula (I-T2), (I-T3), (I-T4), (I-T22) and (I-T23).

One embodiment of the present invention relates to compounds of the formula (I-T2) and (I-T4).

A further embodiment relates to compounds of the formula (I-T3).

A further embodiment relates to compounds of the formulae (I-T22) and (I-T23).

Therefore, a very particularly preferred embodiment relates to compounds of the formula (I-T2). A preferred embodiment relates in turn to compounds of the formula (I-T2) in which $R^1$ is H. A further preferred embodiment relates in turn to compounds of the formula (I-T2) in which $R^1$ is methyl.

A further very particularly preferred embodiment relates to compounds of the formula (I-T3). A preferred embodiment relates in turn to compounds of the formula (I-T3) in which $R^1$ is H. A further preferred embodiment relates in turn to compounds of the formula (I-T3) in which $R^1$ is methyl.

A further very particularly preferred embodiment relates to compounds of the formula (I-T4). A preferred embodiment relates in turn to compounds of the formula (I-T4) in which $R^1$ is H. A further preferred embodiment relates in turn to compounds of the formula (I-T4) in which $R^1$ is methyl.

A further very particularly preferred embodiment relates to compounds of the formula (I-T22). A preferred embodiment relates in turn to compounds of the formula (I-T22) in which $R^1$ is H. A further preferred embodiment relates in turn to compounds of the formula (I-T22) in which $R^1$ is methyl.

A further very particularly preferred embodiment relates to compounds of the formula (I-T23). A preferred embodiment relates in turn to compounds of the formula (I-T23) in which $R^1$ is H. A further preferred embodiment relates in turn to compounds of the formula (I-T23) in which $R^1$ is methyl.

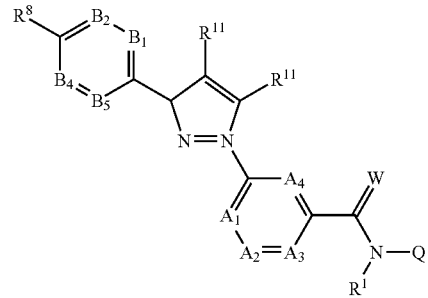

(I-T2)

in which $R^1$, $A_1$, $A_2$, $A_3$, $A_4$, $R^{11}$, $B_1$, $B_2$, $B_4$, $B_5$, $R^8$, $R^{11}$, Q and W are each defined as described herein, where not more than one moiety selected from $A_1$, $A_2$, $A_3$, $A_4$ is N and not more than one moiety selected from $B_1$, $B_2$, $B_3$, $B_4$ and $B_5$ is N; or where one or two moieties selected from $A_1$, $A_2$, $A_3$, $A_4$ may be N and not more than one moiety selected from $B_1$, $B_2$, $B_3$, $B_4$ and $B_5$ is N; or

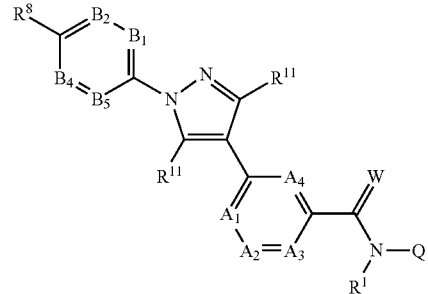

(I-T3)

in which $R^1$, $A_1$, $A_2$, $A_3$, $A_4$, $R^{11}$, $B_1$, $B_2$, $B_4$, $B_5$, $R^8$, $R^{11}$, Q and W are each defined as described herein, where not more than one moiety selected from $A_1$, $A_2$, $A_3$, $A_4$ is N and not more than one moiety selected from $B_1$, $B_2$, $B_3$, $B_4$ and $B_5$ is N; or where one or two moieties selected from $A_1$, $A_2$, $A_3$, $A_4$ may be N and not more than one moiety selected from $B_1$, $B_2$, $B_3$, $B_4$ and $B_5$ is N; or

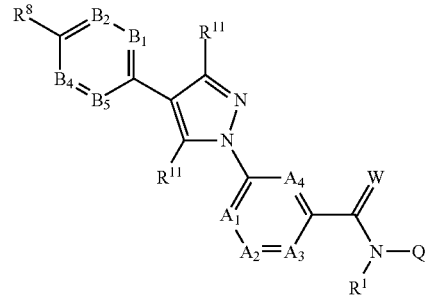

(I-T4)

in which

R¹, A₁, A₂, A₃, A₄, R¹¹, B₁, B₂, B₄, B₅, R⁸, R¹¹, Q and W are each defined as described herein, where not more than one moiety selected from A₁, A₂, A₃, A₄ is N and not more than one moiety selected from B₁, B₂, B₃, B₄ and B₅ is N; or where one or two moieties selected from A₁, A₂, A₃, A₄ may be N and not more than one moiety selected from B₁, B₂, B₃, B₄ and B₅ is N; or

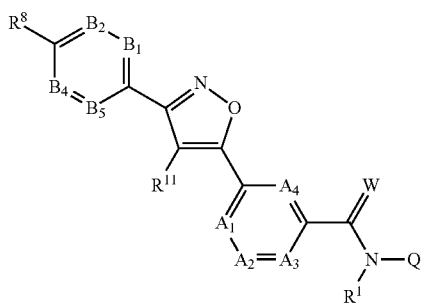

(T-22)

in which

R¹, A₁, A₂, A₃, A₄, R¹¹, B₁, B₂, B₄, B₅, R⁸, R¹¹, Q and W are each defined as described herein, where not more than one moiety selected from A₁, A₂, A₃, A₄ is N and not more than one moiety selected from B₁, B₂, B₃, B₄ and B₅ is N; or where one or two moieties selected from A₁, A₂, A₃, A₄ may be N and not more than one moiety selected from B₁, B₂, B₃, B₄ and B₅ is N; or

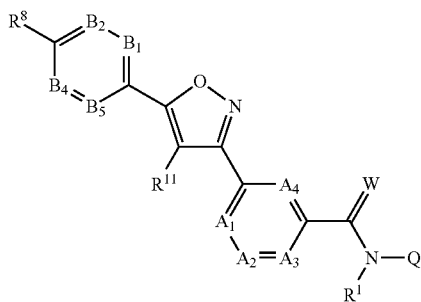

(I-T23)

in which

R¹, A₁, A₂, A₃, A₄, R¹¹, B₁, B₂, B₄, B₅, R⁸, R¹¹, Q and W are each defined as described herein, where not more than one moiety selected from A₁, A₂, A₃, A₄ is N and not more than one moiety selected from B₁, B₂, B₃, B₄ and B₅ is N; or where one or two moieties selected from A₁, A₂, A₃, A₄ may be N and not more than one moiety selected from B₁, B₂, B₃, B₄ and B₅ is N.

A further preferred embodiment relates to compounds of the formula (In) (T=T2)

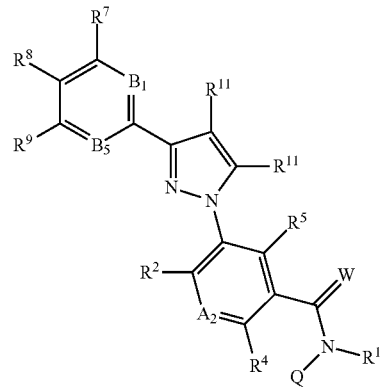

(In)

in which R¹, Q, W, A₂, B₁, B₅, R², R⁴, R⁵, R⁶, R⁷, R⁸, R⁹ and R¹¹ are each defined as described herein, in which R¹ represents H or in which R¹ represents methyl.

A further-preferred embodiment relates to compounds of the formula (In) in which W is O;

Q is optionally substituted $C_1$-$C_4$-alkyl or optionally substituted $C_3$-$C_6$-cycloalkyl or an unsaturated 4-, 5- or 6-membered heterocyclic ring optionally substituted by one, two or three V substituents, where V is independently halogen, cyano, nitro, oxo (=O), optionally halogen-substituted $C_1$-$C_6$-alkyl, $C_1$-$C_4$-alkenyl, $C_1$-$C_6$-alkoxy, $C_1$-$C_6$-alkylsulphanyl, $C_1$-$C_6$-alkylsulphinyl, $C_1$-$C_6$-alkylsulphonyl;
preferably halogen-substituted $C_1$-$C_3$-alkyl; with cyano, hydroxyl or carbonamide (—C(=O)N(R)₂ where R is independently H or $C_1$-$C_3$-alkyl, substituted $C_1$-$C_3$-alkyl; $C_3$-cycloalkyl; cyano-substituted, halogen-substituted, nitro-substituted or halogenated $C_1$-$C_2$-alkyl-substituted $C_3$-cycloalkyl; an unsaturated 4-, 5- or 6-membered heterocyclic ring optionally substituted by one, two or three V and containing one or two heteroatoms selected from a group consisting of N, O and S, where V is independently halogen, cyano, nitro, oxo (=O), optionally halogen-substituted $C_1$-$C_6$-alkyl;
more preferably fluorinated $C_1$-$C_3$-alkyl such as CF₃, CH₂CF₃ or CH₂CH₂CF₃; $C_1$-$C_3$-alkyl substituted by carbonamide (—C(=O)N(R)₂ where R is independently H, $C_1$-$C_3$-alkyl or halogen-substituted $C_1$-$C_3$-alkyl), such as 2-oxo-2-(2,2,2-trifluoroethylamino) ethyl; cyclopropyl; cyano-substituted or fluorinated $C_1$-$C_2$-alkyl-substituted cyclopropyl such as 1-(cyano) cyclopropyl or 1-(trifluoromethyl)cyclopropyl); a 4-membered heterocyclic ring containing one heteroatom selected from a group consisting of N, O and S, such as thietan-3-yl;

R⁷ and R⁹ are each H;
R¹¹ in each case is H;
R¹ is H;
R² is H, halogen or $C_1$-$C_4$-alkyl, preferably H, fluorine, chlorine or methyl;
R⁴ is H or halogen, preferably H, fluoro or chloro;
R⁵ is H or halogen, preferably H, fluoro or chloro;
B₅ is N or C—R¹⁰, preferably C—R¹⁰ in which
R¹⁰ is hydrogen, $C_1$-$C_3$-alkyl, $C_1$-$C_3$-alkoxy, halogen-substituted $C_1$-$C_3$-alkyl (preferably perfluorinated $C_1$-$C_3$-alkyl (CF₃, C₂F₅ or C₃F₇)), halogen-substituted $C_1$-$C_3$-alkoxy (preferably perfluorinated $C_1$-$C_3$-alkoxy (OCF₃, OC₂F₅ or OC₃F₇)), $C_1$-$C_3$-alkylsulphanyl, $C_1$-$C_3$-alkylsulphinyl, $C_1$-$C_3$-alkylsulphonyl, fluorine, bromine or chlorine;

$A_2$ is N or C—$R^3$, preferably C—$R^3$ in which
$R^3$ is H, halogen, or optionally substituted $C_1$-$C_4$-alkyl, preferably H, fluorine, chlorine or optionally halogen-substituted $C_1$-$C_2$-alkyl, more preferably H or fluoro-substituted methyl, for example perfluoromethyl;
$R^6$ is hydrogen, $C_1$-$C_3$-alkyl, $C_1$-$C_3$-alkoxy, halogen-substituted $C_1$-$C_3$-alkyl (preferably perfluorinated $C_1$-$C_3$-alkyl ($CF_3$, $C_2F_5$ or $C_3F_7$)), halogen-substituted $C_1$-$C_3$-alkoxy (preferably perfluorinated $C_1$-$C_3$-alkoxy ($OCF_3$, $OC_2F_5$ or $OC_3F_7$)), $C_1$-$C_3$-alkylsulphanyl, $C_1$-$C_3$-alkylsulphinyl, $C_1$-$C_3$-alkylsulphonyl, fluorine, chlorine or bromine, preferably fluorine, chlorine, bromine, $C_1$-$C_2$-alkyl, halogen-substituted $C_1$-$C_2$-alkyl (e.g. perfluoromethyl) or optionally halogen-substituted $C_1$-$C_2$-alkoxy, more preferably fluorine, bromine, chlorine, methyl, ethyl, fluorinated methyl or fluorinated ethyl (more preferably perfluoromethyl or perfluoroethyl), fluorinated methoxy or fluorinated ethoxy (more preferably perfluoromethoxy);
$R^8$ is halogen or optionally halogen-substituted $C_1$-$C_4$-alkyl or optionally halogen-substituted $C_1$-$C_4$-alkoxy, preferably halogen-substituted $C_1$-$C_3$-alkyl or halogen-substituted $C_1$-$C_3$-alkoxy, more preferably halogen-substituted $C_1$-$C_3$-alkyl such as fluorinated $C_1$-$C_3$-alkyl (e.g. fluorinated $C_3$-alkyl such as perfluoropropyl).

A further-preferred embodiment relates to compounds of the formula (In) in which
W is O;
Q is optionally substituted $C_1$-$C_4$-alkyl or optionally substituted $C_3$-$C_6$-cycloalkyl or an unsaturated 4-, 5- or 6-membered heterocyclic ring optionally substituted by one, two or three V substituents, where V is independently halogen, cyano, nitro, oxo (=O), optionally halogen-substituted $C_1$-$C_6$-alkyl, $C_1$-$C_4$-alkenyl, $C_1$-$C_6$-alkoxy, $C_1$-$C_6$-alkylsulphanyl, $C_1$-$C_6$-alkylsulphinyl, $C_1$-$C_6$-alkylsulphonyl;
preferably halogen-substituted $C_1$-$C_3$-alkyl; with cyano, hydroxyl or carbonamide (—C(=O)N(R)$_2$ where R is independently H or $C_1$-$C_3$-alkyl, substituted $C_1$-$C_3$-alkyl; $C_3$-cycloalkyl; cyano-substituted, halogen-substituted, nitro-substituted or halogenated $C_1$-$C_2$-alkyl-substituted $C_3$-cycloalkyl; an unsaturated 4-, 5- or 6-membered heterocyclic ring optionally substituted by one, two or three V and containing one or two heteroatoms selected from a group consisting of N, O and S, where V is independently halogen, cyano, nitro, oxo (=O), optionally halogen-substituted $C_1$-$C_6$-alkyl;
more preferably fluorinated $C_1$-$C_3$-alkyl such as $CF_3$, $CH_2CF_3$ or $CH_2CH_2CF_3$; $C_1$-$C_3$-alkyl substituted by carbonamide (—C(=O)N(R)$_2$ where R is independently H, $C_1$-$C_3$-alkyl or halogen-substituted $C_1$-$C_3$-alkyl), such as 2-oxo-2-(2,2,2-trifluoroethylamino) ethyl; cyclopropyl; cyano-substituted or fluorinated $C_1$-$C_2$-alkyl-substituted cyclopropyl such as 1-(cyano)cyclopropyl or 1-(trifluoromethyl)cyclopropyl); a 4-membered heterocyclic ring containing one heteroatom selected from a group consisting of N, O and S, such as thietan-3-yl;
$R^7$ and $R^9$ are each H;
$R^{11}$ in each case is H;
$R^1$ is methyl;
$R^2$ is H, halogen or $C_1$-$C_4$-alkyl, preferably H, fluorine, chlorine or methyl;
$R^4$ is H or halogen, preferably H, fluoro or chloro;
$R^5$ is H or halogen, preferably H, fluoro or chloro;
$B_5$ is N or C—$R^{10}$, preferably C—$R^{10}$ in which
$R^{10}$ is hydrogen, $C_1$-$C_3$-alkyl, $C_1$-$C_3$-alkoxy, halogen-substituted $C_1$-$C_3$-alkyl (preferably perfluorinated $C_1$-$C_3$-alkyl ($CF_3$, $C_2F_5$ or $C_3F_7$)), halogen-substituted $C_1$-$C_3$-alkoxy (preferably perfluorinated $C_1$-$C_3$-alkoxy ($OCF_3$, $OC_2F_5$ or $OC_3F_7$)), $C_1$-$C_3$-alkylsulphanyl, $C_1$-$C_3$-alkylsulphinyl, $C_1$-$C_3$-alkylsulphonyl, fluorine, bromine or chlorine;
$A_2$ is N or C—$R^3$, preferably C—$R^3$ in which
$R^3$ is H, halogen, or optionally substituted $C_1$-$C_4$-alkyl, preferably H, fluorine, chlorine or optionally halogen-substituted $C_1$-$C_2$-alkyl, more preferably H or fluoro-substituted methyl, for example perfluoromethyl;
$R^6$ is hydrogen, $C_1$-$C_3$-alkyl, $C_1$-$C_3$-alkoxy, halogen-substituted $C_1$-$C_3$-alkyl (preferably perfluorinated $C_1$-$C_3$-alkyl ($CF_3$, $C_2F_5$ or $C_3F_7$)), halogen-substituted $C_1$-$C_3$-alkoxy (preferably perfluorinated $C_1$-$C_3$-alkoxy ($OCF_3$, $OC_2F_5$ or $OC_3F_7$)), $C_1$-$C_3$-alkylsulphanyl, $C_1$-$C_3$-alkylsulphinyl, $C_1$-$C_3$-alkylsulphonyl, fluorine, chlorine or bromine, preferably fluorine, chlorine, bromine, $C_1$-$C_2$-alkyl, halogen-substituted $C_1$-$C_2$-alkyl (e.g. perfluoromethyl) or optionally halogen-substituted $C_1$-$C_2$-alkoxy, more preferably fluorine, bromine, chlorine, methyl, ethyl, fluorinated methyl or fluorinated ethyl (more preferably perfluoromethyl or perfluoroethyl), fluorinated methoxy or fluorinated ethoxy (more preferably perfluoromethoxy);
$R^8$ is halogen or optionally halogen-substituted $C_1$-$C_4$-alkyl or optionally halogen-substituted $C_1$-$C_4$-alkoxy, preferably halogen-substituted $C_1$-$C_3$-alkyl or halogen-substituted $C_1$-$C_3$-alkoxy, more preferably halogen-substituted $C_1$-$C_3$-alkyl such as fluorinated $C_1$-$C_3$-alkyl (e.g. fluorinated $C_3$-alkyl such as perfluoropropyl).

A further preferred embodiment relates to compounds of the formula (Ie) (T=T3)

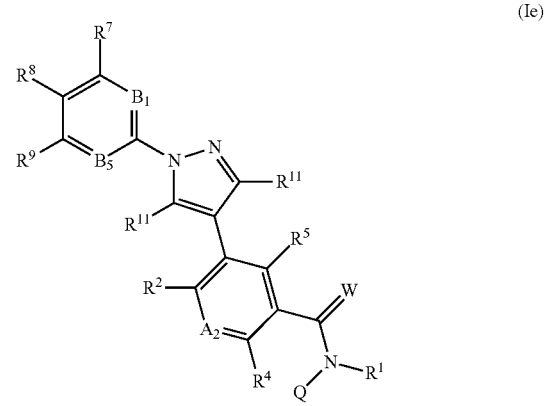

(Ie)

in which $R^1$, Q, W, $A_2$, $B_1$, $B_5$, $R^2$, $R^4$, $R^5$, $R^6$, $R^7$, $R^8$, $R^9$ and $R^{11}$ are each defined as described herein, in which $R^1$ represents H or in which $R^1$ represents methyl.

A further-preferred embodiment relates to compounds of the formula (Ie) in which
W is O;
Q is optionally substituted $C_1$-$C_4$-alkyl or optionally substituted $C_3$-$C_6$-cycloalkyl or an unsaturated 4-, 5- or 6-membered heterocyclic ring optionally substituted by one, two or three V substituents, where V is independently halogen, cyano, nitro, oxo (=O), optionally halogen-substituted $C_1$-$C_6$-alkyl, $C_1$-$C_4$-alkenyl, $C_1$-$C_6$-alkoxy, $C_1$-$C_6$-alkylsulphanyl, $C_1$-$C_6$-alkylsulphinyl, $C_1$-$C_6$-alkylsulphonyl;
preferably halogen-substituted $C_1$-$C_3$-alkyl; with cyano, hydroxyl or carbonamide (—C(=O)N(R)$_2$ where R is independently H or $C_1$-$C_3$-alkyl, substituted $C_1$-$C_3$-alkyl; $C_3$-cycloalkyl; cyano-substituted, halogen-substituted, nitro-substituted or halogenated $C_1$-$C_2$-alkylsubstituted $C_3$-cycloalkyl; an unsaturated 4-, 5- or 6-membered heterocyclic ring optionally substituted by one, two or three V and containing one or two heteroatoms selected from a group consisting of N, O and S, where V is independently halogen, cyano, nitro, oxo (=O), optionally halogen-substituted $C_1$-$C_6$-alkyl;

more preferably fluorinated $C_1$-$C_3$-alkyl such as $CF_3$, $CH_2CF_3$ or $CH_2CH_2CF_3$; $C_1$-$C_3$-alkyl substituted by carbonamide (—C(=O)N(R)$_2$ where R is independently H, $C_1$-$C_3$-alkyl or halogen-substituted $C_1$-$C_3$-alkyl), such as 2-oxo-2-(2,2,2-trifluoroethylamino)ethyl; cyclopropyl; cyano-substituted or fluorinated $C_1$-$C_2$-alkyl-substituted cyclopropyl such as 1-(cyano)cyclopropyl or 1-(trifluoromethyl)cyclopropyl); a 4-membered heterocyclic ring containing one heteroatom selected from a group consisting of N, O and S, such as thietan-3-yl;

$R^7$ and $R^9$ are each H;
$R^{11}$ in each case is H;
$R^1$ is H;
$R^2$ is H, halogen or $C_1$-$C_4$-alkyl, preferably H, fluorine, chlorine or methyl;
$R^4$ is H or halogen, preferably H, fluoro or chloro;
$R^5$ is H or halogen, preferably H, fluoro or chloro;
$B_5$ is N or C—$R^{10}$, preferably C—$R^{10}$ in which
$R^{10}$ is hydrogen, $C_1$-$C_3$-alkyl, $C_1$-$C_3$-alkoxy, halogen-substituted $C_1$-$C_3$-alkyl (preferably perfluorinated $C_1$-$C_3$-alkyl ($CF_3$, $C_2F_5$ or $C_3F_7$)), halogen-substituted $C_1$-$C_3$-alkoxy (preferably perfluorinated $C_1$-$C_3$-alkoxy ($OCF_3$, $OC_2F_5$ or $OC_3F_7$)), $C_1$-$C_3$-alkylsulphanyl, $C_1$-$C_3$-alkylsulphinyl, $C_1$-$C_3$-alkylsulphonyl, fluorine, bromine or chlorine;
$A_2$ is N or C—$R^3$, preferably C—$R^3$ in which
$R^3$ is H, halogen, or optionally substituted $C_1$-$C_4$-alkyl, preferably H, fluorine, chlorine or optionally halogen-substituted $C_1$-$C_2$-alkyl, more preferably H or fluoro-substituted methyl, for example perfluoromethyl;
$R^6$ is hydrogen, $C_1$-$C_3$-alkyl, $C_1$-$C_3$-alkoxy, halogen-substituted $C_1$-$C_3$-alkyl (preferably perfluorinated $C_1$-$C_3$-alkyl ($CF_3$, $C_2F_5$ or $C_3F_7$)), halogen-substituted $C_1$-$C_3$-alkoxy (preferably perfluorinated $C_1$-$C_3$-alkoxy ($OCF_3$, $OC_2F_5$ or $OC_3F_7$)), $C_1$-$C_3$-alkylsulphanyl, $C_1$-$C_3$-alkylsulphinyl, $C_1$-$C_3$-alkylsulphonyl, fluorine, chlorine or bromine, preferably fluorine, chlorine, bromine, $C_1$-$C_2$-alkyl, halogen-substituted $C_1$-$C_2$-alkyl (e.g. perfluoromethyl) or optionally halogen-substituted $C_1$-$C_2$-alkoxy, more preferably fluorine, bromine, chlorine, methyl, ethyl, fluorinated methyl or fluorinated ethyl (more preferably perfluoromethyl or perfluoroethyl), fluorinated methoxy or fluorinated ethoxy (more preferably perfluoromethoxy);
$R^8$ is halogen or optionally halogen-substituted $C_1$-$C_4$-alkyl or optionally halogen-substituted $C_1$-$C_4$-alkoxy, preferably halogen-substituted $C_1$-$C_3$-alkyl or halogen-substituted $C_1$-$C_3$-alkoxy, more preferably halogen-substituted $C_1$-$C_3$-alkyl such as fluorinated $C_1$-$C_3$-alkyl (e.g. fluorinated $C_3$-alkyl such as perfluoropropyl).

A further-preferred embodiment relates to compounds of the formula (Ie) in which
W is O;
Q is optionally substituted $C_1$-$C_4$-alkyl or optionally substituted $C_3$-$C_6$-cycloalkyl or an unsaturated 4-, 5- or 6-membered heterocyclic ring optionally substituted by one, two or three V substituents, where V is independently halogen, cyano, nitro, oxo (=O), optionally halogen-substituted $C_1$-$C_6$-alkyl, $C_1$-$C_4$-alkenyl, $C_1$-$C_6$-alkoxy, $C_1$-$C_6$-alkylsulphanyl, $C_1$-$C_6$-alkylsulphinyl, $C_1$-$C_6$-alkylsulphonyl; preferably halogen-substituted $C_1$-$C_3$-alkyl; with cyano, hydroxyl or carbonamide (—C(=O)N(R)$_2$ where R is independently H or $C_1$-$C_3$-alkyl, substituted $C_1$-$C_3$-alkyl; $C_3$-cycloalkyl; cyano-substituted, halogen-substituted, nitro-substituted or halogenated $C_1$-$C_2$-alkyl-substituted $C_3$-cycloalkyl; an unsaturated 4-, 5- or 6-membered heterocyclic ring optionally substituted by one, two or three V and containing one or two heteroatoms selected from a group consisting of N, O and S, where V is independently halogen, cyano, nitro, oxo (=O), optionally halogen-substituted $C_1$-$C_6$-alkyl;

more preferably fluorinated $C_1$-$C_3$-alkyl such as $CF_3$, $CH_2CF_3$ or $CH_2CH_2CF_3$; $C_1$-$C_3$-alkyl substituted by carbonamide (—C(=O)N(R)$_2$ where R is independently H, $C_1$-$C_3$-alkyl or halogen-substituted $C_1$-$C_3$-alkyl), such as 2-oxo-2-(2,2,2-trifluoroethylamino)ethyl; cyclopropyl; cyano-substituted or fluorinated $C_1$-$C_2$-alkyl-substituted cyclopropyl such as 1-(cyano)cyclopropyl or 1-(trifluoromethyl)cyclopropyl); a 4-membered heterocyclic ring containing one heteroatom selected from a group consisting of N, O and S, such as thietan-3-yl;

$R^7$ and $R^9$ are each H;
$R^{11}$ in each case is H;
$R^1$ is methyl;
$R^2$ is H, halogen or $C_1$-$C_4$-alkyl, preferably H, fluorine, chlorine or methyl;
$R^4$ is H or halogen, preferably H, fluoro or chloro;
$R^5$ is H or halogen, preferably H, fluoro or chloro;
$B_5$ is N or C—$R^{10}$, preferably C—$R^{10}$ in which
$R^{10}$ is hydrogen, $C_1$-$C_3$-alkyl, $C_1$-$C_3$-alkoxy, halogen-substituted $C_1$-$C_3$-alkyl (preferably perfluorinated $C_1$-$C_3$-alkyl ($CF_3$, $C_2F_5$ or $C_3F_7$)), halogen-substituted $C_1$-$C_3$-alkoxy (preferably perfluorinated $C_1$-$C_3$-alkoxy ($OCF_3$, $OC_2F_5$ or $OC_3F_7$)), $C_1$-$C_3$-alkylsulphanyl, $C_1$-$C_3$-alkylsulphinyl, $C_1$-$C_3$-alkylsulphonyl, fluorine, bromine or chlorine;
$A_2$ is N or C—$R^3$, preferably C—$R^3$ in which
$R^3$ is H, halogen, or optionally substituted $C_1$-$C_4$-alkyl, preferably H, fluorine, chlorine or optionally halogen-substituted $C_1$-$C_2$-alkyl, more preferably H or fluoro-substituted methyl, for example perfluoromethyl;
$R^6$ is hydrogen, $C_1$-$C_3$-alkyl, $C_1$-$C_3$-alkoxy, halogen-substituted $C_1$-$C_3$-alkyl (preferably perfluorinated $C_1$-$C_3$-alkyl ($CF_3$, $C_2F_5$ or $C_3F_7$)), halogen-substituted $C_1$-$C_3$-alkoxy (preferably perfluorinated $C_1$-$C_3$-alkoxy ($OCF_3$, $OC_2F_5$ or $OC_3F_7$)), $C_1$-$C_3$-alkylsulphanyl, $C_1$-$C_3$-alkylsulphinyl, $C_1$-$C_3$-alkylsulphonyl, fluorine, chlorine or bromine, preferably fluorine, chlorine, bromine, $C_1$-$C_2$-alkyl, halogen-substituted $C_1$-$C_2$-alkyl (e.g. perfluoromethyl) or optionally halogen-substituted $C_1$-$C_2$-alkoxy, more preferably fluorine, bromine, chlorine, methyl, ethyl, fluorinated methyl or fluorinated ethyl (more preferably perfluoromethyl or perfluoroethyl), fluorinated methoxy or fluorinated ethoxy (more preferably perfluoromethoxy);
$R^8$ is halogen or optionally halogen-substituted $C_1$-$C_4$-alkyl or optionally halogen-substituted $C_1$-$C_4$-alkoxy, preferably halogen-substituted $C_1$-$C_3$-alkyl or halogen-substituted $C_1$-$C_3$-alkoxy, more preferably halogen-substituted $C_1$-$C_3$-alkyl such as fluorinated $C_1$-$C_3$-alkyl (e.g. fluorinated $C_3$-alkyl such as perfluoropropyl).

A further-preferred embodiment relates to compounds of the formula (If) (T=T23)

(If)

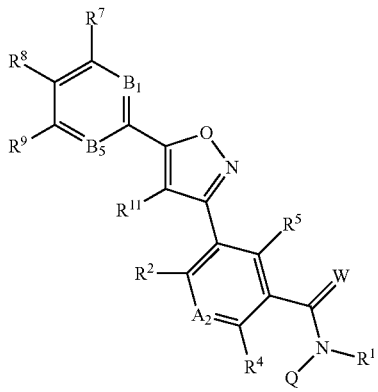

in which $R^1$, Q, W, $A_2$, $B_1$, $B_5$, $R^2$, $R^4$, $R^5$, $R^6$, $R^7$, $R^8$, $R^9$ and $R^{11}$ are each defined as described herein, in which $R^1$ represents H or in which $R^1$ represents methyl.

A preferred embodiment relates to compounds of the formula (If) in which

W is O;

Q is optionally substituted $C_1$-$C_4$-alkyl or optionally substituted $C_3$-$C_6$-cycloalkyl or an unsaturated 4-, 5- or 6-membered heterocyclic ring optionally substituted by one, two or three V substituents, where V is independently halogen, cyano, nitro, oxo (═O), optionally halogen-substituted $C_1$-$C_6$-alkyl, $C_1$-$C_4$-alkenyl, $C_1$-$C_6$-alkoxy, $C_1$-$C_6$-alkylsulphanyl, $C_1$-$C_6$-alkylsulphinyl, $C_1$-$C_6$-alkylsulphonyl;
preferably halogen-substituted $C_1$-$C_3$-alkyl; with cyano, hydroxyl or carbonamide (—C(═O)N(R)$_2$ where R is independently H or $C_1$-$C_3$-alkyl, substituted $C_1$-$C_3$-alkyl; $C_3$-cycloalkyl; cyano-substituted, halogen-substituted, nitro-substituted or halogenated $C_1$-$C_2$-alkyl-substituted $C_3$-cycloalkyl; an unsaturated 4-, 5- or 6-membered heterocyclic ring optionally substituted by one, two or three V and containing one or two heteroatoms selected from a group consisting of N, O and S, where V is independently halogen, cyano, nitro, oxo (═O), optionally halogen-substituted $C_1$-$C_6$-alkyl;
more preferably fluorinated $C_1$-$C_3$-alkyl such as $CF_3$, $CH_2CF_3$ or $CH_2CH_2CF_3$; $C_1$-$C_3$-alkyl substituted by carbonamide (—C(═O)N(R)$_2$ where R is independently H, $C_1$-$C_3$-alkyl or halogen-substituted $C_1$-$C_3$-alkyl), such as 2-oxo-2-(2,2,2-trifluoroethylamino) ethyl; cyclopropyl; cyano-substituted or fluorinated $C_1$-$C_2$-alkyl-substituted cyclopropyl such as 1-(cyano)cyclopropyl or 1-(trifluoromethyl)cyclopropyl); a 4-membered heterocyclic ring containing one heteroatom selected from a group consisting of N, O and S, such as thietan-3-yl;

$R^7$ and $R^9$ are each H;
$R^{11}$ in each case is H;
$R^1$ is H;
$R^2$ is H, halogen or $C_1$-$C_4$-alkyl, preferably H, fluorine, chlorine or methyl;
$R^4$ is H or halogen, preferably H, fluorine or chlorine;
$R^5$ is H or halogen, preferably H, fluorine or chlorine;
$B_5$ is N or C—$R^{10}$, preferably C—$R^{10}$ in which
$R^{10}$ is H, halogen, $C_1$-$C_4$-alkyl or $C_1$-$C_4$-alkoxy, preferably H, fluorine, bromine, chlorine, $C_1$-$C_2$-alkyl or $C_1$-$C_2$-alkoxy, more preferably H, chlorine, bromine, fluorine, methyl or methoxy;
$A_2$ is N or C—$R^3$, preferably C—$R^3$ in which $R^3$ is H, halogen, or optionally substituted $C_1$-$C_4$-alkyl, preferably H, fluorine, chlorine or optionally halogen-substituted $C_1$-$C_2$-alkyl, more preferably H or fluorine-substituted methyl, for example perfluoromethyl;
$R^6$ is H, halogen, optionally substituted $C_1$-$C_4$-alkyl or optionally substituted $C_1$-$C_4$-alkoxy, preferably fluorine, chlorine, $C_1$-$C_2$-alkyl, halogen-substituted $C_1$-$C_2$-alkyl (e.g. perfluoromethyl) or optionally halogen-substituted $C_1$-$C_2$-alkoxy, more preferably fluorine, bromine, chlorine, methyl, ethyl, fluorinated methyl or fluorinated ethyl (more preferably perfluoromethyl or perfluoroethyl), fluorinated methoxy or fluorinated ethoxy (more preferably perfluoromethoxy);
$R^8$ is halogen or optionally halogen-substituted $C_1$-$C_4$-alkyl or optionally halogen-substituted $C_1$-$C_4$-alkoxy, preferably halogen-substituted $C_1$-$C_3$-alkyl or halogen-substituted $C_1$-$C_3$-alkoxy, more preferably halogen-substituted $C_1$-$C_3$-alkyl such as fluorinated $C_1$-$C_3$-alkyl (e.g. fluorinated $C_3$-alkyl such as perfluoropropyl).

A preferred embodiment relates to compounds of the formula (If) in which

W is O;
Q is optionally substituted $C_1$-$C_4$-alkyl or optionally substituted $C_3$-$C_6$-cycloalkyl or an unsaturated 4-, 5- or 6-membered heterocyclic ring optionally substituted by one, two or three V substituents, where V is independently halogen, cyano, nitro, oxo (═O), optionally halogen-substituted $C_1$-$C_6$-alkyl, $C_1$-$C_4$-alkenyl, $C_1$-$C_6$-alkoxy, $C_1$-$C_6$-alkylsulphanyl, $C_1$-$C_6$-alkylsulphinyl, $C_1$-$C_6$-alkylsulphonyl;
preferably halogen-substituted $C_1$-$C_3$-alkyl; with cyano, hydroxyl or carbonamide (—C(═O)N(R)$_2$ where R is independently H or $C_1$-$C_3$-alkyl, substituted $C_1$-$C_3$-alkyl; $C_3$-cycloalkyl; cyano-substituted, halogen-substituted, nitro-substituted or halogenated $C_1$-$C_2$-alkyl-substituted $C_3$-cycloalkyl; an unsaturated 4-, 5- or 6-membered heterocyclic ring optionally substituted by one, two or three V and containing one or two heteroatoms selected from a group consisting of N, O and S, where V is independently halogen, cyano, nitro, oxo (═O), optionally halogen-substituted $C_1$-$C_6$-alkyl;
more preferably fluorinated $C_1$-$C_3$-alkyl such as $CF_3$, $CH_2CF_3$ or $CH_2CH_2CF_3$; $C_1$-$C_3$-alkyl substituted by carbonamide (—C(═O)N(R)$_2$ where R is independently H, $C_1$-$C_3$-alkyl or halogen-substituted $C_1$-$C_3$-alkyl), such as 2-oxo-2-(2,2,2-trifluoroethylamino) ethyl; cyclopropyl; cyano-substituted or fluorinated $C_1$-$C_2$-alkyl-substituted cyclopropyl such as 1-(cyano)cyclopropyl or 1-(trifluoromethyl)cyclopropyl); a 4-membered heterocyclic ring containing one heteroatom selected from a group consisting of N, O and S, such as thietan-3-yl;
$R^7$ and $R^9$ are each H;
$R^{11}$ in each case is H;
$R^1$ is methyl;
$R^2$ is H, halogen or $C_1$-$C_4$-alkyl, preferably H, fluorine, chlorine or methyl;
$R^4$ is H or halogen, preferably H, fluorine or chlorine;
$R^5$ is H or halogen, preferably H, fluorine or chlorine;
$B_5$ is N or C—$R^{10}$, preferably C—$R^{10}$ in which
$R^{10}$ is hydrogen, $C_1$-$C_3$-alkyl, $C_1$-$C_3$-alkoxy, halogen-substituted $C_1$-$C_3$-alkyl (preferably perfluorinated $C_1$-$C_3$-alkyl ($CF_3$, $C_2F_5$ or $C_3F_7$)), halogen-substituted $C_1$-$C_3$-alkoxy (preferably perfluorinated $C_1$-$C_3$-alkoxy ($OCF_3$, $OC_2F_5$ or $OC_3F_7$)), $C_1$-$C_3$-alkylsulphanyl, $C_1$-$C_3$-alkylsulphinyl, $C_1$-$C_3$-alkylsulphonyl, fluorine, bromine or chlorine;
$A_2$ is N or C—$R^3$, preferably C—$R^3$ in which R³ is H, halogen, or optionally substituted $C_1$-$C_4$-alkyl, preferably H, fluorine, chlorine or optionally halogen-substituted $C_1$-$C_2$-alkyl, more preferably H or fluoro-substituted methyl, for example perfluoromethyl;

R⁶ is hydrogen, $C_1$-$C_3$-alkyl, $C_1$-$C_3$-alkoxy, halogen-substituted $C_1$-$C_3$-alkyl (preferably perfluorinated $C_1$-$C_3$-alkyl ($CF_3$, $C_2F_5$ or $C_3F_7$)), halogen-substituted $C_1$-$C_3$-alkoxy (preferably perfluorinated $C_1$-$C_3$-alkoxy ($OCF_3$, $OC_2F_5$ or $OC_3F_7$)), $C_1$-$C_3$-alkylsulphanyl, $C_1$-$C_3$-alkylsulphinyl, $C_1$-$C_3$-alkylsulphonyl, fluorine, chlorine or bromine, preferably fluorine, chlorine, bromine, $C_1$-$C_2$-alkyl, halogen-substituted $C_1$-$C_2$-alkyl (e.g. perfluoromethyl) or optionally halogen-substituted $C_1$-$C_2$-alkoxy, more preferably fluorine, bromine, chlorine, methyl, ethyl, fluorinated methyl or fluorinated ethyl (more preferably perfluoromethyl or perfluoroethyl), fluorinated methoxy or fluorinated ethoxy (more preferably perfluoromethoxy);

R⁸ is halogen or optionally halogen-substituted $C_1$-$C_4$-alkyl or optionally halogen-substituted $C_1$-$C_4$-alkoxy, preferably halogen-substituted $C_1$-$C_3$-alkyl or halogen-substituted $C_1$-$C_3$-alkoxy, more preferably halogen-substituted $C_1$-$C_3$-alkyl such as fluorinated $C_1$-$C_3$-alkyl (e.g. fluorinated $C_3$-alkyl such as perfluoropropyl).

A further-preferred embodiment relates to compounds of the formula (Ig) (T=T4)

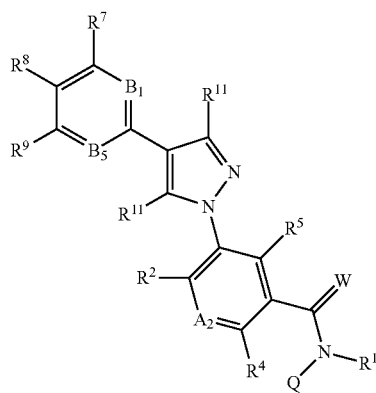

(Ig)

in which R¹, Q, W, A₂, B₁, B₅, R², R⁴, R⁵, R⁶, R⁷, R⁸, R⁹ and R¹¹ are each defined as described herein, in which R¹ represents H or in which R¹ represents methyl.

A preferred embodiment relates to compounds of the formula (Ig) in which

W is O;

Q is optionally substituted $C_1$-$C_4$-alkyl or optionally substituted $C_3$-$C_6$-cycloalkyl or an unsaturated 4-, 5- or 6-membered heterocyclic ring optionally substituted by one, two or three V substituents, where V is independently halogen, cyano, nitro, oxo (=O), optionally halogen-substituted $C_1$-$C_6$-alkyl, $C_1$-$C_4$-alkenyl, $C_1$-$C_6$-alkoxy, $C_1$-$C_6$-alkylsulphanyl, $C_1$-$C_6$-alkylsulphinyl, $C_1$-$C_6$-alkylsulphonyl; preferably halogen-substituted $C_1$-$C_3$-alkyl; with cyano, hydroxyl or carbonamide (—C(=O)N(R)₂ where R is independently H or $C_1$-$C_3$-alkyl, substituted $C_1$-$C_3$-alkyl; $C_3$-cycloalkyl; cyano-substituted, halogen-substituted, nitro-substituted or halogenated $C_1$-$C_2$-alkyl-substituted $C_3$-cycloalkyl; an unsaturated 4-, 5- or 6-membered heterocyclic ring optionally substituted by one, two or three V and containing one or two heteroatoms selected from a group consisting of N, O and S, where V is independently halogen, cyano, nitro, oxo (=O), optionally halogen-substituted $C_1$-$C_6$-alkyl;

more preferably fluorinated $C_1$-$C_3$-alkyl such as $CF_3$, $CH_2CF_3$ or $CH_2CH_2CF_3$; $C_1$-$C_3$-alkyl substituted by carbonamide (—C(=O)N(R)₂ where R is independently H, $C_1$-$C_3$-alkyl or halogen-substituted $C_1$-$C_3$-alkyl), such as 2-oxo-2-(2,2,2-trifluoroethylamino) ethyl; cyclopropyl; cyano-substituted or fluorinated $C_1$-$C_2$-alkyl-substituted cyclopropyl such as 1-(cyano) cyclopropyl or 1-(trifluoromethyl)cyclopropyl); a 4-membered heterocyclic ring containing one heteroatom selected from a group consisting of N, O and S, such as thietan-3-yl;

R⁷ and R⁹ are each H;
R¹¹ in each case is H;
R¹ is H;
R² is H, halogen or $C_1$-$C_4$-alkyl, preferably H, fluorine, chlorine or methyl;
R⁴ is H or halogen, preferably H, fluorine or chlorine;
R⁵ is H or halogen, preferably H, fluorine or chlorine;
B₅ is N or C—R¹⁰, preferably C—R¹⁰ in which
R¹⁰ is hydrogen, $C_1$-$C_3$-alkyl, $C_1$-$C_3$-alkoxy, halogen-substituted $C_1$-$C_3$-alkyl (preferably perfluorinated $C_1$-$C_3$-alkyl ($CF_3$, $C_2F_5$ or $C_3F_7$)), halogen-substituted $C_1$-$C_3$-alkoxy (preferably perfluorinated $C_1$-$C_3$-alkoxy ($OCF_3$, $OC_2F_5$ or $OC_3F_7$)), $C_1$-$C_3$-alkylsulphanyl, $C_1$-$C_3$-alkylsulphinyl, $C_1$-$C_3$-alkylsulphonyl, fluorine, bromine or chlorine;

A₂ is N or C—R³, preferably C—R³ in which
R³ is H, halogen, or optionally substituted $C_1$-$C_4$-alkyl, preferably H, fluorine, chlorine or optionally halogen-substituted $C_1$-$C_2$-alkyl, more preferably H or fluoro-substituted methyl, for example perfluoromethyl;

R⁶ is hydrogen, $C_1$-$C_3$-alkyl, $C_1$-$C_3$-alkoxy, halogen-substituted $C_1$-$C_3$-alkyl (preferably perfluorinated $C_1$-$C_3$-alkyl ($CF_3$, $C_2F_5$ or $C_3F_7$)), halogen-substituted $C_1$-$C_3$-alkoxy (preferably perfluorinated $C_1$-$C_3$-alkoxy ($OCF_3$, $OC_2F_5$ or $OC_3F_7$)), $C_1$-$C_3$-alkylsulphanyl, $C_1$-$C_3$-alkylsulphinyl, $C_1$-$C_3$-alkylsulphonyl, fluorine, chlorine or bromine, preferably fluorine, chlorine, bromine, $C_1$-$C_2$-alkyl, halogen-substituted $C_1$-$C_2$-alkyl (e.g. perfluoromethyl) or optionally halogen-substituted $C_1$-$C_2$-alkoxy, more preferably fluorine, bromine, chlorine, methyl, ethyl, fluorinated methyl or fluorinated ethyl (more preferably perfluoromethyl or perfluoroethyl), fluorinated methoxy or fluorinated ethoxy (more preferably perfluoromethoxy);

R⁸ is halogen or optionally halogen-substituted $C_1$-$C_4$-alkyl or optionally halogen-substituted $C_1$-$C_4$-alkoxy, preferably halogen-substituted $C_1$-$C_3$-alkyl or halogen-substituted $C_1$-$C_3$-alkoxy, more preferably halogen-substituted $C_1$-$C_3$-alkyl such as fluorinated $C_1$-$C_3$-alkyl (e.g. fluorinated $C_3$-alkyl such as perfluoropropyl).

A preferred embodiment relates to compounds of the formula (Ig) in which

W is O;

Q is optionally substituted $C_1$-$C_4$-alkyl or optionally substituted $C_3$-$C_6$-cycloalkyl or an unsaturated 4-, 5- or 6-membered heterocyclic ring optionally substituted by one, two or three V substituents, where V is independently halogen, cyano, nitro, oxo (=O), optionally halogen-substituted $C_1$-$C_6$-alkyl, $C_1$-$C_4$-alkenyl, $C_1$-$C_6$-alkoxy, $C_1$-$C_6$-alkylsulphanyl, $C_1$-$C_6$-alkylsulphinyl, $C_1$-$C_6$-alkylsulphonyl; preferably halogen-substituted $C_1$-$C_3$-alkyl; with cyano, hydroxyl or carbonamide (—C(=O)N(R)₂ where R is independently H or $C_1$-$C_3$-alkyl, substituted $C_1$-$C_3$-alkyl; $C_3$-cycloalkyl; cyano-substituted, halogen-substituted, nitro-substituted or halogenated $C_1$-$C_2$-alkyl-substituted $C_3$-cycloalkyl; an unsaturated 4-, 5- or 6-membered heterocyclic ring optionally substituted by one, two or three V and containing one or two heteroatoms selected from a group consisting of N, O and S, where V is independently halogen, cyano, nitro, oxo (=O), optionally halogen-substituted $C_1$-$C_6$-alkyl;

more preferably fluorinated $C_1$-$C_3$-alkyl such as $CF_3$, $CH_2CF_3$ or $CH_2CH_2CF_3$; $C_1$-$C_3$-alkyl substituted by carbonamide (—C(=O)N(R)$_2$ where R is independently H, $C_1$-$C_3$-alkyl or halogen-substituted $C_1$-$C_3$-alkyl), such as 2-oxo-2-(2,2,2-trifluoroethylamino) ethyl; cyclopropyl; cyano-substituted or fluorinated $C_1$-$C_2$-alkyl-substituted cyclopropyl such as 1-(cyano)cyclopropyl or 1-(trifluoromethyl)cyclopropyl); a 4-membered heterocyclic ring containing one heteroatom selected from a group consisting of N, O and S, such as thietan-3-yl;

$R^7$ and $R^9$ are each H;

$R^{11}$ in each case is H;

$R^1$ is methyl;

$R^2$ is H, halogen or $C_1$-$C_4$-alkyl, preferably H, fluorine, chlorine or methyl;

$R^4$ is H or halogen, preferably H, fluorine or chlorine;

$R^5$ is H or halogen, preferably H, fluorine or chlorine;

$B_5$ is N or C—$R^{10}$, preferably C—$R^{10}$ in which $R^{10}$ is hydrogen, $C_1$-$C_3$-alkyl, $C_1$-$C_3$-alkoxy, halogen-substituted $C_1$-$C_3$-alkyl (preferably perfluorinated $C_1$-$C_3$-alkyl ($CF_3$, $C_2F_5$ or $C_3F_7$)), halogen-substituted $C_1$-$C_3$-alkoxy (preferably perfluorinated $C_1$-$C_3$-alkoxy ($OCF_3$, $OC_2F_5$ or $OC_3F_7$)), $C_1$-$C_3$-alkylsulphanyl, $C_1$-$C_3$-alkylsulphinyl, $C_1$-$C_3$-alkylsulphonyl, fluorine, bromine or chlorine;

$A_2$ is N or C—$R^3$, preferably C—$R^3$ in which $R^3$ is H, halogen, or optionally substituted $C_1$-$C_4$-alkyl, preferably H, fluorine, chlorine or optionally halogen-substituted $C_1$-$C_2$-alkyl, more preferably H or fluoro-substituted methyl, for example perfluoromethyl;

$R^6$ is hydrogen, $C_1$-$C_3$-alkyl, $C_1$-$C_3$-alkoxy, halogen-substituted $C_1$-$C_3$-alkyl (preferably perfluorinated $C_1$-$C_3$-alkyl ($CF_3$, $C_2F_5$ or $C_3F_7$)), halogen-substituted $C_1$-$C_3$-alkoxy (preferably perfluorinated $C_1$-$C_3$-alkoxy ($OCF_3$, $OC_2F_5$ or $OC_3F_7$)), $C_1$-$C_3$-alkylsulphanyl, $C_1$-$C_3$-alkylsulphinyl, $C_1$-$C_3$-alkylsulphonyl, fluorine, chlorine or bromine, preferably fluorine, chlorine, bromine, $C_1$-$C_2$-alkyl, halogen-substituted $C_1$-$C_2$-alkyl (e.g. perfluoromethyl) or optionally halogen-substituted $C_1$-$C_2$-alkoxy, more preferably fluorine, bromine, chlorine, methyl, ethyl, fluorinated methyl or fluorinated ethyl (more preferably perfluoromethyl or perfluoroethyl), fluorinated methoxy or fluorinated ethoxy (more preferably perfluoromethoxy);

$R^8$ is halogen or optionally halogen-substituted $C_1$-$C_4$-alkyl or optionally halogen-substituted $C_1$-$C_4$-alkoxy, preferably halogen-substituted $C_1$-$C_3$-alkyl or halogen-substituted $C_1$-$C_3$-alkoxy, more preferably halogen-substituted $C_1$-$C_3$-alkyl such as fluorinated $C_1$-$C_3$-alkyl (e.g. fluorinated $C_3$-alkyl such as perfluoropropyl).

A further-preferred embodiment relates to compounds of the formula (Io) (T=T22)

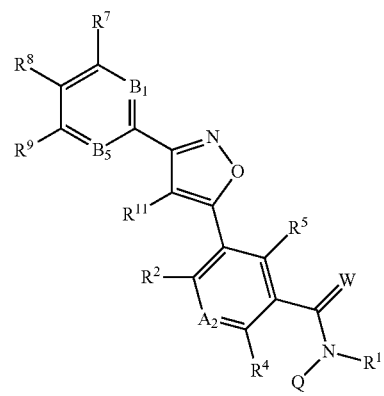

(Io)

in which $R^1$, Q, W, $A_2$, $B_1$, $B_5$, $R^2$, $R^4$, $R^5$, $R^6$, $R^7$, $R^8$, $R^9$ and $R^{11}$ are each defined as described herein, in which $R^1$ represents H or in which $R^1$ represents methyl.

A preferred embodiment relates to compounds of the formula (Io) in which

W is O;

Q is optionally substituted $C_1$-$C_4$-alkyl or optionally substituted $C_3$-$C_6$-cycloalkyl or an unsaturated 4-, 5- or 6-membered heterocyclic ring optionally substituted by one, two or three V substituents, where V is independently halogen, cyano, nitro, oxo (=O), optionally halogen-substituted $C_1$-$C_6$-alkyl, $C_1$-$C_4$-alkenyl, $C_1$-$C_6$-alkoxy, $C_1$-$C_6$-alkylsulphanyl, $C_1$-$C_6$-alkylsulphinyl, $C_1$-$C_6$-alkylsulphonyl;

preferably halogen-substituted $C_1$-$C_3$-alkyl; with cyano, hydroxyl or carbonamide (—C(=O)N(R)$_2$ where R is independently H or $C_1$-$C_3$-alkyl, substituted $C_1$-$C_3$-alkyl; $C_3$-cycloalkyl; cyano-substituted, halogen-substituted, nitro-substituted or halogenated $C_1$-$C_2$-alkyl-substituted $C_3$-cycloalkyl; an unsaturated 4-, 5- or 6-membered heterocyclic ring optionally substituted by one, two or three V and containing one or two heteroatoms selected from a group consisting of N, O and S, where V is independently halogen, cyano, nitro, oxo (=O), optionally halogen-substituted $C_1$-$C_6$-alkyl;

more preferably fluorinated $C_1$-$C_3$-alkyl such as $CF_3$, $CH_2CF_3$ or $CH_2CH_2CF_3$; $C_1$-$C_3$-alkyl substituted by carbonamide (—C(=O)N(R)$_2$ where R is independently H, $C_1$-$C_3$-alkyl or halogen-substituted $C_1$-$C_3$-alkyl), such as 2-oxo-2-(2,2,2-trifluoroethylamino) ethyl; cyclopropyl; cyano-substituted or fluorinated $C_1$-$C_2$-alkyl-substituted cyclopropyl such as 1-(cyano) cyclopropyl or 1-(trifluoromethyl)cyclopropyl); a 4-membered heterocyclic ring containing one heteroatom selected from a group consisting of N, O and S, such as thietan-3-yl;

$R^7$ and $R^9$ are each H;

$R^{11}$ in each case is H;

$R^1$ is H;

$R^2$ is H, halogen or $C_1$-$C_4$-alkyl, preferably H, fluorine, chlorine or methyl;

$R^4$ is H or halogen, preferably H, fluorine or chlorine;

$R^5$ is H or halogen, preferably H, fluorine or chlorine;

$B_5$ is N or C—$R^{10}$, preferably C—$R^{10}$ in which $R^{10}$ is hydrogen, $C_1$-$C_3$-alkyl, $C_1$-$C_3$-alkoxy, halogen-substituted $C_1$-$C_3$-alkyl (preferably perfluorinated $C_1$-$C_3$-alkyl ($CF_3$, $C_2F_5$ or $C_3F_7$)), halogen-substituted $C_1$-$C_3$-alkoxy (preferably perfluorinated $C_1$-$C_3$-alkoxy ($OCF_3$, $OC_2F_5$ or $OC_3F_7$)), $C_1$-$C_3$-alkylsulphanyl, $C_1$-$C_3$-alkylsulphinyl, $C_1$-$C_3$-alkylsulphonyl, fluorine, bromine or chlorine;

$A_2$ is N or C—$R^3$, preferably C—$R^3$ in which $R^3$ is H, halogen, or optionally substituted $C_1$-$C_4$-alkyl, preferably H, fluorine, chlorine or optionally halogen-substituted $C_1$-$C_2$-alkyl, more preferably H or fluoro-substituted methyl, for example perfluoromethyl;

$R^6$ is hydrogen, $C_1$-$C_3$-alkyl, $C_1$-$C_3$-alkoxy, halogen-substituted $C_1$-$C_3$-alkyl (preferably perfluorinated $C_1$-$C_3$-alkyl ($CF_3$, $C_2F_5$ or $C_3F_7$)), halogen-substituted $C_1$-$C_3$-alkoxy (preferably perfluorinated $C_1$-$C_3$-alkoxy ($OCF_3$, $OC_2F_5$ or $OC_3F_7$)), $C_1$-$C_3$-alkylsulphanyl, $C_1$-$C_3$-alkylsulphinyl, $C_1$-$C_3$-alkylsulphonyl, fluorine, chlorine or bromine, preferably fluorine, chlorine, bromine, $C_1$-$C_2$-alkyl, halogen-substituted $C_1$-$C_2$-alkyl (e.g. perfluoromethyl) or optionally halogen-substituted $C_1$-$C_2$-alkoxy, more preferably fluorine, bromine, chlorine, methyl, ethyl, fluorinated methyl or fluorinated ethyl (more preferably perfluoromethyl or perfluoroethyl), fluorinated methoxy or fluorinated ethoxy (more preferably perfluoromethoxy);

$R^8$ is halogen or optionally halogen-substituted $C_1$-$C_4$-alkyl or optionally halogen-substituted $C_1$-$C_4$-alkoxy, preferably halogen-substituted $C_1$-$C_3$-alkyl or halogen-substituted $C_1$-$C_3$-alkoxy, more preferably halogen-substituted $C_1$-$C_3$-alkyl such as fluorinated $C_1$-$C_3$-alkyl (e.g. fluorinated $C_3$-alkyl such as perfluoropropyl).

A preferred embodiment relates to compounds of the formula (Io) in which

W is O;

Q is optionally substituted $C_1$-$C_4$-alkyl or optionally substituted $C_3$-$C_6$-cycloalkyl or an unsaturated 4-, 5- or 6-membered heterocyclic ring optionally substituted by one, two or three V substituents, where V is independently halogen, cyano, nitro, oxo (=O), optionally halogen-substituted $C_1$-$C_6$-alkyl, $C_1$-$C_4$-alkenyl, $C_1$-$C_6$-alkoxy, $C_1$-$C_6$-alkylsulphanyl, $C_1$-$C_6$-alkylsulphinyl, $C_1$-$C_6$-alkylsulphonyl;

preferably halogen-substituted $C_1$-$C_3$-alkyl; with cyano, hydroxyl or carbonamide (—C(=O)N(R)$_2$ where R is independently H or $C_1$-$C_3$-alkyl, substituted $C_1$-$C_3$-alkyl; $C_3$-cycloalkyl; cyano-substituted, halogen-substituted, nitro-substituted or halogenated $C_1$-$C_2$-alkyl-substituted $C_3$-cycloalkyl; an unsaturated 4-, 5- or 6-membered heterocyclic ring optionally substituted by one, two or three V and containing one or two heteroatoms selected from a group consisting of N, O and S, where V is independently halogen, cyano, nitro, oxo (=O), optionally halogen-substituted $C_1$-$C_6$-alkyl;

more preferably fluorinated $C_1$-$C_3$-alkyl such as $CF_3$, $CH_2CF_3$ or $CH_2CH_2CF_3$; $C_1$-$C_3$-alkyl substituted by carbonamide (—C(=O)N(R)$_2$ where R is independently H, $C_1$-$C_3$-alkyl or halogen-substituted $C_1$-$C_3$-alkyl), such as 2-oxo-2-(2,2,2-trifluoroethylamino) ethyl; cyclopropyl; cyano-substituted or fluorinated $C_1$-$C_2$-alkyl-substituted cyclopropyl such as 1-(cyano) cyclopropyl or 1-(trifluoromethyl)cyclopropyl); a 4-membered heterocyclic ring containing one heteroatom selected from a group consisting of N, O and S, such as thietan-3-yl;

$R^7$ and $R^9$ are each H;

$R^{11}$ in each case is H;

$R^1$ is methyl;

$R^2$ is H, halogen or $C_1$-$C_4$-alkyl, preferably H, fluorine, chlorine or methyl;

$R^4$ is H or halogen, preferably H, fluorine or chlorine;

$R^5$ is H or halogen, preferably H, fluorine or chlorine;

$B_5$ is N or C—$R^{10}$, preferably C—$R^{10}$ in which $R^{10}$ is hydrogen, $C_1$-$C_3$-alkyl, $C_1$-$C_3$-alkoxy, halogen-substituted $C_1$-$C_3$-alkyl (preferably perfluorinated $C_1$-$C_3$-alkyl ($CF_3$, $C_2F_5$ or $C_3F_7$)), halogen-substituted $C_1$-$C_3$-alkoxy (preferably perfluorinated $C_1$-$C_3$-alkoxy ($OCF_3$, $OC_2F_5$ or $OC_3F_7$)), $C_1$-$C_3$-alkylsulphanyl, $C_1$-$C_3$-alkylsulphinyl, $C_1$-$C_3$-alkylsulphonyl, fluorine, bromine or chlorine;

$A_2$ is N or C—$R^3$, preferably C—$R^3$ in which $R^3$ is H, halogen, or optionally substituted $C_1$-$C_4$-alkyl, preferably H, fluorine, chlorine or optionally halogen-substituted $C_1$-$C_2$-alkyl, more preferably H or fluoro-substituted methyl, for example perfluoromethyl;

$R^6$ is hydrogen, $C_1$-$C_3$-alkyl, $C_1$-$C_3$-alkoxy, halogen-substituted $C_1$-$C_3$-alkyl (preferably perfluorinated $C_1$-$C_3$-alkyl ($CF_3$, $C_2F_5$ or $C_3F_7$)), halogen-substituted $C_1$-$C_3$-alkoxy (preferably perfluorinated $C_1$-$C_3$-alkoxy ($OCF_3$, $OC_2F_5$ or $OC_3F_7$)), $C_1$-$C_3$-alkylsulphanyl, $C_1$-$C_3$-alkylsulphinyl, $C_1$-$C_3$-alkylsulphonyl, fluorine, chlorine or bromine, preferably fluorine, chlorine, bromine, $C_1$-$C_2$-alkyl, halogen-substituted $C_1$-$C_2$-alkyl (e.g. perfluoromethyl) or optionally halogen-substituted $C_1$-$C_2$-alkoxy, more preferably fluorine, bromine, chlorine, methyl, ethyl, fluorinated methyl or fluorinated ethyl (more preferably perfluoromethyl or perfluoroethyl), fluorinated methoxy or fluorinated ethoxy (more preferably perfluoromethoxy);

$R^8$ is halogen or optionally halogen-substituted $C_1$-$C_4$-alkyl or optionally halogen-substituted $C_1$-$C_4$-alkoxy, preferably halogen-substituted $C_1$-$C_3$-alkyl or halogen-substituted $C_1$-$C_3$-alkoxy, more preferably halogen-substituted $C_1$-$C_3$-alkyl such as fluorinated $C_1$-$C_3$-alkyl (e.g. fluorinated $C_3$-alkyl such as perfluoropropyl).

Examples of compounds of the formula (I) include the following structures:

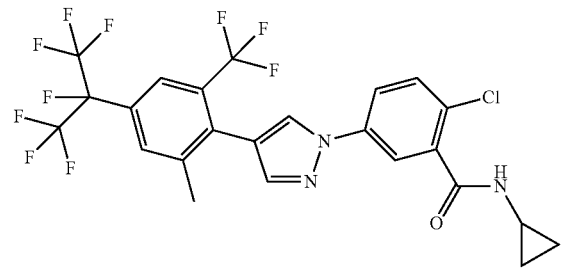 [SMILES: Cc1cc(C(F)(C(F)(F)F)C(F)(F)F)cc(C(F)(F)F)c1-c1cnn(-c2ccc(Cl)c(C(=O)NC3CC3)c2)c1]

2-chloro-N-cyclopropyl-5-[1-[4-(1,1,1,2,3,3,3-heptafluoropropan-2-yl)-2-methyl-6-(trifluoromethyl)phenyl]-1H-pyrazol-4-yl]benzamide,

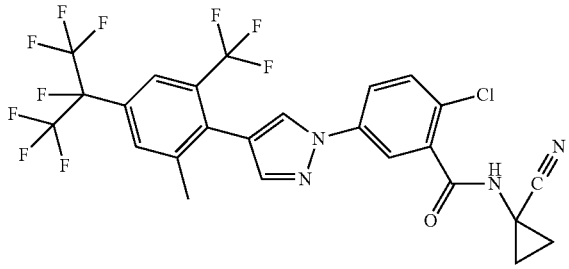 [SMILES: Cc1cc(C(F)(C(F)(F)F)C(F)(F)F)cc(C(F)(F)F)c1-c1cnn(-c2ccc(Cl)c(C(=O)NC3(C#N)CC3)c2)c1]

2-chloro-N-(1-cyanocyclopropyl-5-[1-[4-(1,1,1,2,3,3,3-heptafluoropropan-2-yl)-2-methyl-6-(trifluoromethyl) phenyl]-1H-pyrazol-4-yl]benzamide,

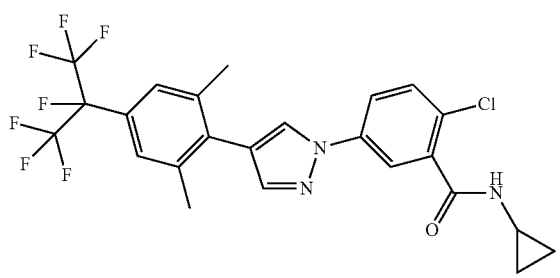 [SMILES: Cc1cc(C(F)(C(F)(F)F)C(F)(F)F)cc(C)c1-c1cnn(-c2ccc(Cl)c(C(=O)NC3CC3)c2)c1]

2-chloro-N-cyclopropyl-5-[4-[2,6-dimethyl-4-[1,2,2,2-tetrafluoro-1-(trifluoromethyl)ethyl]phenyl]pyrazol-1-yl]benzamide,

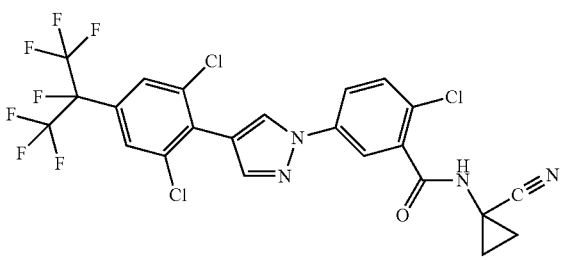 [SMILES: N#CC1(NC(=O)c2cc(-n3cc(-c4c(Cl)cc(C(F)(C(F)(F)F)C(F)(F)F)cc4Cl)cn3)ccc2Cl)CC1]

2-chloro-N-(1-cyanocyclopropyl)-5-[4-[2,6-dichloro-4-[1,2,2,2-tetrafluoro-1-(trifluoromethyl)ethyl]phenyl]pyrazol-1-yl]benzamide,

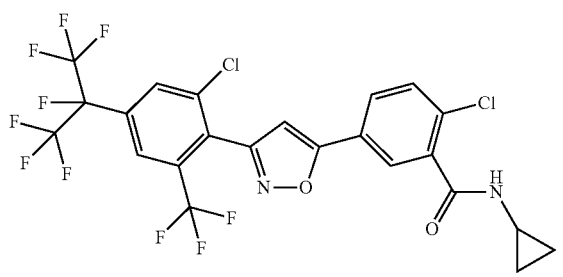 [SMILES: O=C(NC1CC1)c1cc(-c2cc(-c3c(Cl)cc(C(F)(C(F)(F)F)C(F)(F)F)cc3C(F)(F)F)no2)ccc1Cl]

2-chloro-5-[3-[2-chloro-4-[1,2,2,2-tetrafluoro-1-(trifluoromethyl)ethyl]-6-(trifluoromethyl)phenyl]isoxazol-5-yl]-N-cyclopropylbenzamide,

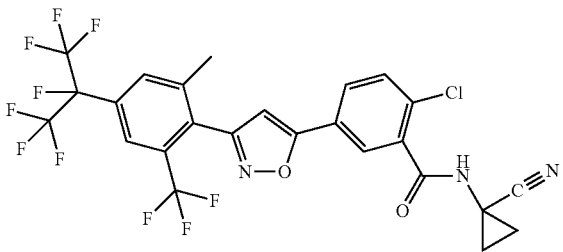 [SMILES: Cc1cc(C(F)(C(F)(F)F)C(F)(F)F)cc(C(F)(F)F)c1-c1cc(-c2ccc(Cl)c(C(=O)NC3(C#N)CC3)c2)on1]

2-chloro-N-(1-cyanocyclopropyl)-5-[3-[2-methyl-4-[1,2,2,2-tetrafluoro-1-(trifluoromethyl)ethyl]-6-(trifluoromethyl)phenyl]isoxazol-5-yl]benzamide, Further inventive compounds are

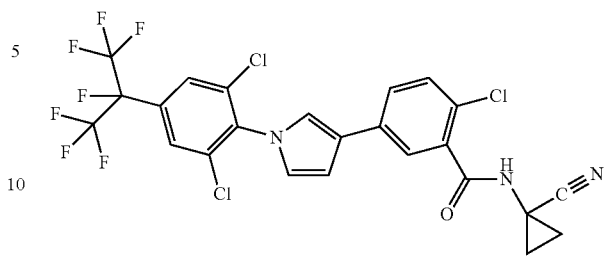

2-chloro-N-(1-cyanocyclopropyl)-5-[1-[2,6-dichloro-4-[1,2,2,2-tetrafluoro-1-(trifluoromethyl)ethyl]phenyl]pyrrol-3-yl]benzamide,

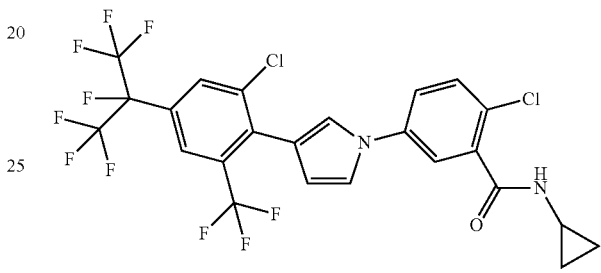

2-chloro-5-[3-[2-chloro-4-[1,2,2,2-tetrafluoro-1-(trifluoromethyl)ethyl]-6-(trifluoromethyl)phenyl]pyrrol-1-yl]-N-cyclopropylbenzamide.

R1 Methyl

A preferred embodiment relates to compounds of the formula (I) in which $R^1$ is methyl and all the other parameters are as defined above.

T3—Methyl

A further preferred embodiment relates to compounds of the formula (I) in which $R^1$ is methyl, T is T3, $R^{11}$ in T3 is H, W is O and all the other parameters are as defined above.

A further preferred embodiment relates to compounds of the formula (I) in which $R^1$ is methyl, T is T3, $R^{11}$ in T3 is H, W is O, $A_1$ is $CR^2$, $A_2$ is $CR^3$ or N, $A_3$ is $CR^4$, $A_4$ is $CR^5$, $B_1$ is $CR^6$, $B_2$ is $CR^7$, $B_3$ is $CR^8$, $B_4$ is $CR^9$, $B_5$ is $CR^{10}$ and all the other parameters are as defined above.

A further preferred embodiment relates to compounds of the formula (I) in which $R^1$ is methyl, T is T3, $R^{11}$ in T3 is H, W is O, $A_1$ is CH, $A_2$ is CH or N, $A_3$ is $CR^4$, $A_4$ is CH, $B_1$ is $CR^6$, $B_2$ is CH, $B_3$ is $CR^8$, $B_4$ is CH, $B_5$ is $CR^{10}$, where $R^6$ and $R^{10}$ are each a substituent selected from halogen (preferably chlorine, bromine or fluorine), $C_1$-$C_3$-alkyl, halogen-substituted $C_1$-$C_3$-alkyl, $C_1$-$C_3$-alkoxy or halogen-substituted $C_1$-$C_3$-alkoxy, and all the other parameters are as defined.

A further preferred embodiment relates to compounds of the formula (I) in which $R^1$ is methyl, T is T3, $R^{11}$ in T3 is H, W is O, $A_1$ is CH, $A_2$ is CH or N, $A_3$ is $CR^4$, $A_4$ is CH, $B_1$ is $CR^6$, $B_2$ is CH, $B_3$ is $CR^8$, $B_4$ is CH, $B_5$ is $CR^{10}$, where $R^6$ and $R^{10}$ are each a substituent selected from halogen (preferably chlorine, bromine or fluorine), $C_1$-$C_3$-alkyl, halogen-substituted $C_1$-$C_3$-alkyl, $C_1$-$C_3$-alkoxy or halogen-substituted $C_1$-$C_3$-alkoxy, and all the other parameters are as defined above.

T2—Methyl

A further preferred embodiment relates to compounds of the formula (I) in which $R^1$ is methyl, T is T2, $R^{11}$ in T2 is H, W is O and all the other parameters are as defined above.

A further preferred embodiment relates to compounds of the formula (I) in which $R^1$ is methyl, T is T2, $R^{11}$ in T2 is H, W is O, $A_1$ is $CR^2$, $A_2$ is $CR^3$ or N, $A_3$ is $CR^4$, $A_4$ is $CR^5$, $B_1$ is $CR^6$, $B_2$ is $CR^7$, $B_3$ is $CR^8$, $B_4$ is $CR^9$, $B_5$ is $CR^{10}$ and all the other parameters are as defined in above.

A further preferred embodiment relates to compounds of the formula (I) in which $R^1$ is methyl, T is T2, $R^{11}$ in T2 is H, W is O, $A_1$ is CH, $A_2$ is CH or N, $A_3$ is $CR^4$, $A_4$ is CH, $B_1$ is $CR^6$, $B_2$ is CH, $B_3$ is $CR^8$, $B_4$ is CH, $B_5$ is $CR^{10}$, where $R^6$ and $R^{10}$ are each a substituent selected from halogen (preferably chlorine, bromine or fluorine), $C_1$-$C_3$-alkyl, halogen-substituted $C_1$-$C_3$-alkyl, $C_1$-$C_3$-alkoxy or halogen-substituted $C_1$-$C_3$-alkoxy, and all the other parameters are as defined in above.

A further preferred embodiment relates to compounds of the formula (I) in which $R^1$ is methyl, T is T2, $R^{11}$ in T2 is H, W is O, $A_1$ is CH, $A_2$ is CH or N, $A_3$ is $CR^4$, $A_4$ is CH, $B_1$ is $CR^6$, $B_2$ is CH, $B_3$ is $CR^8$, $B_4$ is CH, $B_5$ is $CR^{10}$, where $R^6$ and $R^{10}$ are each a substituent selected from halogen (preferably chlorine, bromine or fluorine), $C_1$-$C_3$-alkyl, halogen-substituted $C_1$-$C_3$-alkyl, $C_1$-$C_3$-alkoxy or halogen-substituted $C_1$-$C_3$-alkoxy, and all the other parameters are as defined above.

T4—Methyl

A further preferred embodiment relates to compounds of the formula (I) in which $R^1$ is methyl, T is T4, $R^{11}$ in T4 is H, W is O and all the other parameters are as defined above.

A further preferred embodiment relates to compounds of the formula (I) in which $R^1$ is methyl, T is T4, $R^{11}$ in T4 is H, W is O, $A_1$ is $CR^2$, $A_2$ is $CR^3$ or N, $A_3$ is $CR^4$, $A_4$ is $CR^5$, $B_1$ is $CR^6$, $B_2$ is $CR^7$, $B_3$ is $CR^8$, $B_4$ is $CR^9$, $B_5$ is $CR^{10}$ and all the other parameters are as defined above.

A further preferred embodiment relates to compounds of the formula (I) in which $R^1$ is methyl, T is T4, $R^{11}$ in T4 is H, W is O, $A_1$ is CH, $A_2$ is CH or N, $A_3$ is $CR^4$, $A_4$ is CH, $B_1$ is $CR^6$, $B_2$ is Ch, $B_3$ is $CR^8$, $B_4$ is CH, $B_5$ is $CR^{10}$, where $R^6$ and $R^{10}$ are each a substituent selected from halogen (preferably chlorine, bromine or fluorine), $C_1$-$C_3$-alkyl, halogen-substituted $C_1$-$C_3$-alkyl, $C_1$-$C_3$-alkoxy or halogen-substituted $C_1$-$C_3$-alkoxy, and all the other parameters are as defined above.

A further preferred embodiment relates to compounds of the formula (I) in which $R^1$ is methyl, T is T4, $R^{11}$ in T4 is H, W is O, $A_1$ is CH, $A_2$ is CH or N, $A_3$ is $CR^4$, $A_4$ is CH, $B_1$ is $CR^6$, $B_2$ is CH, $B_3$ is $CR^8$, $B_4$ is CH, $B_5$ is $CR^{10}$, where $R^6$ and $R^{10}$ are each a substituent selected from halogen (preferably chlorine, bromine or fluorine), $C_1$-$C_3$-alkyl, halogen-substituted $C_1$-$C_3$-alkyl, $C_1$-$C_3$-alkoxy or halogen-substituted $C_1$-$C_3$-alkoxy, and all the other parameters are as defined above.

T22—Methyl

A further preferred embodiment relates to compounds of the formula (I) in which $R^1$ is methyl, T is T22, $R^{11}$ in T22 is H, W is O and all the other parameters are as defined above.

A further preferred embodiment relates to compounds of the formula (I) in which $R^1$ is methyl, T is T22, $R^{11}$ in T22 is H, W is O, $A_1$ is $CR^2$, $A_2$ is $CR^3$ or N, $A_3$ is $CR^4$, $A_4$ is $CR^5$, $B_1$ is $CR^6$, $B_2$ is $CR^7$, $B_3$ is $CR^8$, $B_4$ is $CR^9$, $B_5$ is $CR^{10}$ and all the other parameters are as defined above.

A further preferred embodiment relates to compounds of the formula (I) in which $R^1$ is methyl, T is T22, $R^{11}$ in T22 is H, W is O, $A_1$ is CH, $A_2$ is CH or N, $A_3$ is $CR^4$, $A_4$ is CH, $B_1$ is $CR^6$, $B_2$ is CH, $B_3$ is $CR^8$, $B_4$ is CH, $B_5$ is $CR^{10}$, where $R^6$ and $R^{10}$ are each a substituent selected from halogen (preferably chlorine, bromine or fluorine), $C_1$-$C_3$-alkyl, halogen-substituted $C_1$-$C_3$-alkyl, $C_1$-$C_3$-alkoxy or halogen-substituted $C_1$-$C_3$-alkoxy, and all the other parameters are as defined above.

A further preferred embodiment relates to compounds of the formula (I) in which $R^1$ is methyl, T is T22, $R^{11}$ in T22 is H, W is O, $A_1$ is CH, $A_2$ is CH or N, $A_3$ is $CR^4$, $A_4$ is CH, $B_1$ is $CR^6$, $B_2$ is CH, $B_3$ is $CR^8$, $B_4$ is CH, $B_5$ is $CR^{10}$, where $R^6$ and $R^{10}$ are each a substituent selected from halogen (preferably chlorine, bromine or fluorine), $C_1$-$C_3$-alkyl, halogen-substituted $C_1$-$C_3$-alkyl, $C_1$-$C_3$-alkoxy or halogen-substituted $C_1$-$C_3$-alkoxy, and all the other parameters are as defined above.

T23—Methyl

A further preferred embodiment relates to compounds of the formula (I) in which $R^1$ is methyl, T is T23, $R^{11}$ in T23 is H, W is O and all the other parameters are as defined above.

A further preferred embodiment relates to compounds of the formula (I) in which $R^1$ is methyl, T is T23, $R^{11}$ in T23 is H, W is O, $A_1$ is $CR^2$, $A_2$ is $CR^3$ or N, $A_3$ is $CR^4$, $A_4$ is $CR^5$, $B_1$ is $CR^6$, $B_2$ is $CR^7$, $B_3$ is $CR^8$, $B_4$ is $CR^9$, $B_5$ is $CR^{10}$ and all the other parameters are as defined above.

A further preferred embodiment relates to compounds of the formula (I) in which $R^1$ is methyl, T is T23, $R^{11}$ in T23 is H, W is O, $A_1$ is CH, $A_2$ is CH or N, $A_3$ is $CR^4$, $A_4$ is CH, $B_1$ is $CR^6$, $B_2$ is CH, $B_3$ is $CR^8$, $B_4$ is CH, $B_5$ is $CR^{10}$, where $R^6$ and $R^{10}$ are each a substituent selected from halogen (preferably chlorine, bromine or fluorine), $C_1$-$C_3$-alkyl, halogen-substituted $C_1$-$C_3$-alkyl, $C_1$-$C_3$-alkoxy or halogen-substituted $C_1$-$C_3$-alkoxy, and all the other parameters are as defined above.

A further preferred embodiment relates to compounds of the formula (I) in which $R^1$ is methyl, T is T23, $R^{11}$ in T23 is H, W is O, $A_1$ is CH, $A_2$ is CH or N, $A_3$ is $CR^4$, $A_4$ is CH, $B_1$ is $CR^6$, $B_2$ is CH, $B_3$ is $CR^8$, $B_4$ is CH, $B_5$ is $CR^{10}$, where $R^6$ and $R^{10}$ are each a substituent selected from halogen (preferably chlorine, bromine or fluorine), $C_1$-$C_3$-alkyl, halogen-substituted $C_1$-$C_3$-alkyl, $C_1$-$C_3$-alkoxy or halogen-substituted $C_1$-$C_3$-alkoxy, and all the other parameters are as defined above.

T3—H

A preferred embodiment relates to compounds of the formula (I) in which $R^1$ is hydrogen (H) and all the other parameters are as defined above.

A further preferred embodiment relates to compounds of the formula (I) in which $R^1$ is H, T is T3, $R^{11}$ in T3 is H, W is O and all the other parameters are as defined above A further preferred embodiment relates to compounds of the formula (I) in which $R^1$ is H, T is T3, $R^{11}$ in T3 is H, W is O, $A_1$ is $CR^2$, $A_2$ is $CR^3$ or N, $A_3$ is $CR^4$, $A_4$ is $CR^5$, $B_1$ is $CR^6$, $B_2$ is $CR^7$, $B_3$ is $CR^8$, $B_4$ is $CR^9$, $B_5$ is $CR^{10}$ and all the other parameters are as defined above.

A further preferred embodiment relates to compounds of the formula (I) in which $R^1$ is H, T is T3, $R^{11}$ in T3 is H, W is O, $A_1$ is CH, $A_2$ is CH or N, $A_3$ is $CR^4$, $A_4$ is CH, $B_1$ is $CR^6$, $B_2$ is CH, $B_3$ is $CR^8$, $B_4$ is CH, $B_5$ is $CR^{10}$, where $R^6$ and $R^{10}$ are each a substituent selected from halogen (preferably chlorine, bromine or fluorine), $C_1$-$C_3$-alkyl, halogen-substituted $C_1$-$C_3$-alkyl, $C_1$-$C_3$-alkoxy or halogen-substituted $C_1$-$C_3$-alkoxy, and all the other parameters are as defined above.

A further preferred embodiment relates to compounds of the formula (I) in which $R^1$ is H, T is T3, $R^{11}$ in T3 is H, W is O, $A_1$ is CH, $A_2$ is CH or N, $A_3$ is $CR^4$, $A_4$ is CH, $B_1$ is $CR^6$, $B_2$ is CH, $B_3$ is $CR^8$, $B_4$ is CH, $B_5$ is $CR^{10}$, where $R^6$ and $R^{10}$ are each a substituent selected from halogen (preferably chlorine, bromine or fluorine), $C_1$-$C_3$-alkyl, halogen-substituted $C_1$-$C_3$-alkyl, $C_1$-$C_3$-alkoxy or halogen-substituted $C_1$-$C_3$-alkoxy, and all the other parameters are as defined above.

T2-H

A further preferred embodiment relates to compounds of the formula (I) in which $R^1$ is H, T is T2, $R^{11}$ in T2 is H, W is O and all the other parameters are as defined above.

A further preferred embodiment relates to compounds of the formula (I) in which $R^1$ is H, T is T2, $R^{11}$ in T2 is H, W is O, $A_1$ is $CR^2$, $A_2$ is $CR^3$ or N, $A_3$ is $CR^4$, $A_4$ is $CR^5$, $B_1$ is $CR^6$, $B_2$ is $CR^7$, $B_3$ is $CR^8$, $B_4$ is $CR^9$, $B_5$ is $CR^{10}$ and all the other parameters are as defined above.

A further preferred embodiment relates to compounds of the formula (I) in which $R^1$ is H, T is T2, $R^{11}$ in T2 is H, W is O, $A_1$ is CH, $A_2$ is CH or N, $A_3$ is $CR^4$, $A_4$ is CH, $B_1$ is $CR^6$, $B_2$ is CH, $B_3$ is $CR^8$, $B_4$ is CH, $B_5$ is $CR^{10}$, where $R^6$ and $R^{10}$ are each a substituent selected from halogen (preferably chlorine, bromine or fluorine), $C_1$-$C_3$-alkyl, halogen-substituted $C_1$-$C_3$-alkyl, $C_1$-$C_3$-alkoxy or halogen-substituted $C_1$-$C_3$-alkoxy, and all the other parameters are as defined above.

A further preferred embodiment relates to compounds of the formula (I) in which $R^1$ is H, T is T2, $R^{11}$ in T2 is H, W is O, $A_1$ is CH, $A_2$ is CH or N, $A_3$ is $CR^4$, $A_4$ is CH, $B_1$ is $CR^6$, $B_2$ is CH, $B_3$ is $CR^8$, $B_4$ is CH, $B_5$ is $CR^{10}$, where $R^6$ and $R^{10}$ are each a substituent selected from halogen (preferably chlorine, bromine or fluorine), $C_1$-$C_3$-alkyl, halogen-substituted $C_1$-$C_3$-alkyl, $C_1$-$C_3$-alkoxy or halogen-substituted $C_1$-$C_3$-alkoxy, and all the other parameters are as defined above.

T4-H

A further preferred embodiment relates to compounds of the formula (I) in which $R^1$ is H, T is T4, $R^{11}$ in T4 is H, W is O and all the other parameters are as defined above.

A further preferred embodiment relates to compounds of the formula (I) in which $R^1$ is H, T is T4, $R^{11}$ in T4 is H, W is O, $A_1$ is $CR^2$, $A_2$ is $CR^3$ or N, $A_3$ is $CR^4$, $A_4$ is $CR^5$, $B_1$ is $CR^6$, $B_2$ is $CR^7$, $B_3$ is $CR^8$, $B_4$ is $CR^9$, $B_5$ is $CR^{10}$ and all the other parameters are as defined above.

A further preferred embodiment relates to compounds of the formula (I) in which $R^1$ is H, T is T4, $R^{11}$ in T4 is H, W is O, $A_1$ is CH, $A_2$ is CH or N, $A_3$ is $CR^4$, $A_4$ is CH, $B_1$ is $CR^6$, $B_2$ is CH, $B_3$ is $CR^8$, $B_4$ is CH, $B_5$ is $CR^{10}$, where $R^6$ and $R^{10}$ are each a substituent selected from halogen (preferably chlorine, bromine or fluorine), $C_1$-$C_3$-alkyl, halogen-substituted $C_1$-$C_3$-alkyl, $C_1$-$C_3$-alkoxy or halogen-substituted $C_1$-$C_3$-alkoxy, and all the other parameters are as defined above.

A further preferred embodiment relates to compounds of the formula (I) in which $R^1$ is H, T is T4, $R^{11}$ in T4 is H, W is O, $A_1$ is CH, $A_2$ is CH or N, $A_3$ is $CR^4$, $A_4$ is CH, $B_1$ is $CR^6$, $B_2$ is CH, $B_3$ is $CR^8$, $B_4$ is CH, $B_5$ is $CR^{10}$, where $R^6$ and $R^{10}$ are each a substituent selected from halogen (preferably chlorine, bromine or fluorine), $C_1$-$C_3$-alkyl, halogen-substituted $C_1$-$C_3$-alkyl, $C_1$-$C_3$-alkoxy or halogen-substituted $C_1$-$C_3$-alkoxy, and all the other parameters are as defined above.

T22—H

A further preferred embodiment relates to compounds of the formula (I) in which $R^1$ is H, T is T22, $R^{11}$ in T22 is H, W is O and all the other parameters are as defined above.

A further preferred embodiment relates to compounds of the formula (I) in which $R^1$ is H, T is T22, $R^{11}$ in T22 is H, W is O, $A_1$ is $CR^2$, $A_2$ is $CR^3$ or N, $A_3$ is $CR^4$, $A_4$ is $CR^5$, $B_1$ is $CR^6$, $B_2$ is $CR^7$, $B_3$ is $CR^8$, $B_4$ is $CR^9$, $B_5$ is $CR^{10}$ and all the other parameters are as defined above.

A further preferred embodiment relates to compounds of the formula (I) in which $R^1$ is H, T is T22, $R^{11}$ in T22 is H, W is O, $A_1$ is CH, $A_2$ is CH or N, $A_3$ is $CR^4$, $A_4$ is CH, $B_1$ is $CR^6$, $B_2$ is CH, $B_3$ is $CR^8$, $B_4$ is CH, $B_5$ is $CR^{10}$, where $R^6$ and $R^{10}$ are each a substituent selected from halogen (preferably chlorine, bromine or fluorine), $C_1$-$C_3$-alkyl, halogen-substituted $C_1$-$C_3$-alkyl, $C_1$-$C_3$-alkoxy or halogen-substituted $C_1$-$C_3$-alkoxy, and all the other parameters are as defined above.

A further preferred embodiment relates to compounds of the formula (I) in which $R^1$ is H, T is T22, $R^{11}$ in T22 is H, W is O, $A_1$ is CH, $A_2$ is CH or N, $A_3$ is $CR^4$, $A_4$ is CH, $B_1$ is $CR^6$, $B_2$ is CH, $B_3$ is $CR^8$, $B_4$ is CH, $B_5$ is $CR^{10}$, where $R^6$ and $R^{10}$ are each a substituent selected from halogen (preferably chlorine, bromine or fluorine), $C_1$-$C_3$-alkyl, halogen-substituted $C_1$-$C_3$-alkyl, $C_1$-$C_3$-alkoxy or halogen-substituted $C_1$-$C_3$-alkoxy, and all the other parameters are as defined above.

T23—H

A further preferred embodiment relates to compounds of the formula (I) in which $R^1$ is H, T is T23, $R^{11}$ in T23 is H, W is O and all the other parameters are as defined above.

A further preferred embodiment relates to compounds of the formula (I) in which $R^1$ is H, T is T23, $R^{11}$ in T23 is H, W is O, $A_1$ is $CR^2$, $A_2$ is $CR^3$ or N, $A_3$ is $CR^4$, $A_4$ is $CR^5$, $B_1$ is $CR^6$, $B_2$ is $CR^7$, $B_3$ is $CR^8$, $B_4$ is $CR^9$, $B_5$ is $CR^{10}$ and all the other parameters are as defined above.

A further preferred embodiment relates to compounds of the formula (I) in which $R^1$ is H, T is T23, $R^{11}$ in T23 is H, W is O, $A_1$ is CH, $A_2$ is CH or N, $A_3$ is $CR^4$, $A_4$ is CH, $B_1$ is $CR^6$, $B_2$ is CH, $B_3$ is $CR^8$, $B_4$ is CH, $B_5$ is $CR^{10}$, where $R^6$ and $R^{10}$ are each a substituent selected from halogen (preferably chlorine, bromine or fluorine), $C_1$-$C_3$-alkyl, halogen-substituted $C_1$-$C_3$-alkyl, $C_1$-$C_3$-alkoxy or halogen-substituted $C_1$-$C_3$-alkoxy, and all the other parameters are as defined above.

A further preferred embodiment relates to compounds of the formula (I) in which $R^1$ is H, T is T23, $R^{11}$ in T23 is H, W is O, $A_1$ is CH, $A_2$ is CH or N, $A_3$ is $CR^4$, $A_4$ is CH, $B_1$ is $CR^6$, $B_2$ is CH, $B_3$ is $CR^8$, $B_4$ is CH, $B_5$ is $CR^{10}$, where $R^6$ and $R^{10}$ are each a substituent selected from halogen (preferably chlorine, bromine or fluorine), $C_1$-$C_3$-alkyl, halogen-substituted $C_1$-$C_3$-alkyl, $C_1$-$C_3$-alkoxy or halogen-substituted $C_1$-$C_3$-alkoxy, and all the other parameters are as defined above.

A further preferred embodiment relates to compounds of the formula (I) in which $B_1$ is C—$R^6$ and $R^6$ is halogen (preferably chlorine or fluorine), $C_1$-$C_4$-alkyl, $C_1$-$C_4$-alkoxy, $C_1$-$C_4$-haloalkyl (preferably perfluorinated $C_1$-$C_4$-alkyl), $C_1$-$C_4$-haloalkoxy (preferably perfluorinated $C_1$-$C_4$-alkoxy), $C_1$-$C_4$-alkylsulphanyl or $C_1$-$C_4$-alkylsulphonyl.

Salts of the inventive compounds that are suitable in accordance with the invention, for example salts with bases or acid addition salts, are all customary non-toxic salts, preferably agriculturally and/or physiologically acceptable salts. Preference is given to salts with inorganic bases, for example alkali metal salts (e.g. sodium, potassium or caesium salts), alkaline earth metal salts (e.g. calcium or magnesium salts), ammonium salts or salts with organic bases, in particular with organic amines, for example triethylammonium, dicyclohexylammonium, N,N'-dibenzylethylenediammonium, pyridinium, picolinium or ethanolammonium salts, salts with inorganic acids (e.g. hydrochlorides, hydrobromides, dihydrosulphates, trihydrosulphates or phosphates), salts with organic carboxylic acids or organic sulpho acids (e.g. formates, acetates, trifluoroacetates, maleates, tartrates, methanesulphonates, benzenesulphonates or 4-toluenesulphonates). It is well known that t-amines, for example some of the inventive compounds, are capable of forming N-oxides, which are likewise inventive salts.

Depending on the nature of the substituents, the compounds of the formula (I) may be in the form of geometric and/or optically active isomers or corresponding isomer mixtures in different compositions. These stereoisomers are, for example, enantiomers, diastereomers, atropisomers or geometric isomers. Accordingly, the invention encompasses both pure stereoisomers and any mixtures of these isomers.

The invention also relates to methods for controlling animal pests, in which compounds of the formula (I) are allowed to act on animal pests and/or their habitat. The control of the animal pests is preferably conducted in agriculture and forestry, and in material protection. Preferably excluded from this are methods for the surgical or therapeutic treatment of the human or animal body and diagnostic methods carried out on the human or animal body.

The invention further relates to the use of the compounds of the formula (I) as pesticides, especially crop protection agents.

In the context of the present application, the term "pesticide" also always encompasses the term "crop protection agent".

The compounds of the formula (I), given good plant tolerance, favourable homeotherm toxicity and good environmental compatibility, are suitable for protecting plants and plant organs against biotic and abiotic stress factors, for increasing harvest yields, for improving the quality of the harvested material and for controlling animal pests, especially insects, arachnids, helminths, nematodes and molluscs, which are encountered in agriculture, in horticulture, in animal husbandry, in aquatic cultures, in forests, in gardens and leisure facilities, in the protection of stored products and of materials, and in the hygiene sector. They can preferably be used as pesticides. They are effective against normally sensitive and resistant species and against all or some stages of development. The abovementioned pests include:

pests from the phylum of the Arthropoda, especially from the class of the Arachnida, for example *Acarus* spp., for example *Acarus siro, Aceria kuko, Aceria sheldoni, Aculops* spp., *Aculus* spp., *for example Aculus fockeui, Aculus schlechtendali, Amblyomma* spp., *Amphitetranychus viennensis, Argas* spp., *Boophilus* spp., *Brevipalpus* spp., for example *Brevipalpus phoenicis, Bryobia graminum, Bryobia praetiosa, Centruroides* spp., *Chorioptes* spp., *Dermanyssus gallinae, Dermatophagoides pteronyssinus, Dermatophagoides farinae, Dermacentor* spp., *Eotetranychus* spp., *for example Eotetranychus hicoriae, Epitrimerus pyri, Eutetranychus* spp., for example *Eutetranychus banksi, Eriophyes* spp., for example *Eriophyes pyri, Glycyphagus domesticus, Halotydeus destructor, Hemitarsonemus* spp., for example *Hemitarsonemus latus (=Polyphagotarsonemus latus), Hyalomma* spp., *Ixodes* spp., *Latrodectus* spp., *Loxosceles* spp., *Neutrombicula autumnalis, Nuphersa* spp., *Oligonychus* spp., for example *Oligonychus coniferarum, Oligonychus ilicis, Oligonychus indicus, Oligonychus mangiferus, Oligonychus pratensis, Oligonychus punicae, Oligonychus yothersi, Ornithodorus* spp., *Ornithonyssus* spp., *Panonychus* spp., for example *Panonychus citri (=Metatetranychus citri), Panonychus ulmi (=Metatetranychus ulmi), Phyllocoptruta oleivora, Platytetranychus multidigituli, Polyphagotarsonemus latus, Psoroptes* spp., *Rhipicephalus* spp., *Rhizoglyphus* spp., *Sarcoptes* spp., *Scorpio maurus, Steneotarsonemus* spp., *Steneotarsonemus spinki, Tarsonemus* spp., for example *Tarsonemus confusus, Tarsonemus pallidus, Tetranychus* spp., for example *Tetranychus canadensis, Tetranychus cinnabarinus, Tetranychus turkestani, Tetranychus urticae, Trombicula alfreddugesi, Vaejovis* spp., *Vasates lycopersici;* from the class of the Chilopoda, for example *Geophilus* spp., *Scutigera* spp.;

from the order or the class of the Collembola, for example *Onychiurus armatus; Sminthurus viridis;* from the class of the Diplopoda, for example *Blaniulus guttulatus;* from the class of the Insecta, for example from the order of the Blattodea, for example *Blatta orientalis, Blattella asahinai, Blattella germanica, Leucophaea maderae, Panchlora* spp., *Parcoblatta* spp., *Periplaneta* spp., for example *Periplaneta americana, Periplaneta australasiae, Supella longipalpa;* from the order of the Coleoptera, for example *Acalymma vittatum, Acanthoscelides obtectus, Adoretus* spp., *Agelastica alni, Agriotes* spp., for example *Agriotes linneatus, Agriotes mancus, Alphitobius diaperinus, Amphimallon solstitialis, Anobium punctatum, Anoplophora* spp., *Anthonomus* spp., for example *Anthonomus grandis, Anthrenus* spp., *Apion* spp., *Apogonia* spp., *Atomaria* spp., for example *Atomaria linearis, Attagenus* spp., *Baris caerulescens, Bruchidius obtectus, Bruchus* spp., for example *Bruchus pisorum, Bruchus rufimanus, Cassida* spp., *Cerotoma trifurcata, Ceutorrhynchus* spp., for example *Ceutorrhynchus assimilis, Ceutorrhynchus quadridens, Ceutorrhynchus rapae, Chaetocnema* spp., for example *Chaetocnema confinis, Chaetocnema denticulata, Chaetocnema ectypa, Cleonus mendicus, Conoderus* spp., *Cosmopolites* spp., for example *Cosmopolites sordidus, Costelytra zealandica, Ctenicera* spp., *Curculio* spp., for example *Curculio caryae, Curculio caryatrypes, Curculio obtusus, Curculio sayi, Cryptolestes ferrugineus, Cryptolestes pusillus, Cryptorhynchus lapathi, Cryptorhynchus mangiferae, Cylindrocopturus* spp., *Cylindrocopturus adspersus, Cylindrocopturus furnissi, Dermestes* spp., *Diabrotica* spp., for example *Diabrotica balteata, Diabrotica barberi, Diabrotica undecimpunctata howardi, Diabrotica undecimpunctata undecimpunctata, Diabrotica virgifera virgifera, Diabrotica virgifera zeae, Dichocrocis* spp., *Dicladispa armigera, Diloboderus* spp., *Epilachna* spp., for example *Epilachna borealis, Epilachna varivestis, Epitrix* spp., for example *Epitrix cucumeris, Epitrix fuscula, Epitrix hirtipennis, Epitrix subcrinita, Epitrix tuberis, Faustinus* spp., *Gibbium psylloides, Gnathocerus cornutus, Hellula undalis, Heteronychus arator, Heteronyx* spp., *Hylamorpha elegans, Hylotrupes bajulus, Hypera postica, Hypomeces squamosus, Hypothenemus* spp., *for example Hypothenemus hampei, Hypothenemus obscurus, Hypothenemus pubescens, Lachnosterna consanguinea, Lasioderma serricorne, Latheticus oryzae, Lathridius* spp., *Lema* spp., *Leptinotarsa decemlineata, Leucoptera* spp., for example *Leucoptera coffeella, Lissorhoptrus oryzophilus, Lixus* spp., *Luperomorpha xanthodera, Luperodes* spp., *Lyctus* spp., *Megascelis* spp., *Melanotus* spp., *for example Melanotus longulus oregonensis, Meligethes aeneus, Melolontha* spp., for example *Melolontha melolontha, Migdolus* spp., *Monochamus* spp., *Naupactus xanthographus, Necrobia* spp., *Niptus hololeucus, Oryctes rhinoceros, Oryzaephilus surinamensis, Oryzaphagus oryzae, Otiorhynchus* spp., for example *Otiorhynchus cribricollis, Otiorhynchus ligustici, Otiorhynchus ovatus, Otiorhynchus rugosostriarus, Otiorhynchus sulcatus, Oxycetonia jucunda, Phaedon cochleariae, Phyllophaga* spp., *Phyllophaga helleri, Phyllotreta* spp., for example *Phyllotreta armoraciae, Phyllotreta pusilla, Phyllotreta ramosa, Phyllotreta striolata, Popillia japonica, Premnotrypes* spp., *Prostephanus truncatus, Psylliodes* spp., for example *Psylliodes affinis, Psylliodes chrysocephala, Psylliodes punctulata, Ptinus* spp., *Rhizobius ventralis, Rhizopertha dominica, Sitophilus* spp., for example *Sitophilus granarius, Sitophilus linearis, Sitophilus oryzae, Sitophilus zeamais, Sphenophorus* spp., *Stegobium paniceum, Sternechus* spp., for example *Sternechus paludatus, Symphyletes* spp., *Tanymecus* spp., for example *Tanymecus dilaticollis, Tanymecus indicus, Tanymecus palliatus, Tenebrio molitor, Tenebrioides mauretanicus, Tribolium* spp., for example *Tribolium audax, Tribolium castaneum, Tribolium confusum, Trogoderma* spp., *Tychius* spp., *Xylotrechus* spp., *Zabrus* spp., for example *Zabrus tenebrioides*;

from the order of the Diptera, for example *Aedes* spp., for example *Aedes aegypti, Aedes albopictus, Aedes sticticus, Aedes vexans, Agromyza* spp., for example *Agromyza frontella, Agromyza parvicornis, Anastrepha* spp., *Anopheles* spp., for example *Anopheles quadrimaculatus, Anopheles gambiae, Asphondylia* spp., *Bactrocera* spp., for example *Bactrocera cucurbitae, Bactrocera dorsalis, Bactrocera oleae, Bibio hortulanus, Calliphora erythrocephala, Calliphora vicina, Ceratitis capitata, Chironomus* spp., *Chrysomya* spp., *Chrysops* spp., *Chrysozona pluvialis, Cochliomya* spp., *Contarinia* spp., for example *Contarinia johnsoni, Contarinia nasturtii, Contarinia pyrivora, Contarinia schulzi, Contarinia sorghicola, Contarinia tritici, Cordylobia anthropophaga, Cricotopus sylvestris, Culex* spp., *for example Culex pipiens, Culex quinquefasciatus, Culicoides* spp., *Culiseta* spp., *Cuterebra* spp., *Dacus oleae, Dasineura* spp., for example *Dasineura brassicae, Delia* spp., for example *Delia antiqua, Delia coarctata, Delia florilega, Delia platura, Delia radicum, Dermatobia hominis, Drosophila* spp., *for example Drosphila melanogaster, Drosophila suzukii, Echinocnemus* spp., *Fannia* spp., *Gasterophilus* spp., *Glossina* spp., *Haematopota* spp., *Hydrellia* spp., *Hydrellia griseola, Hylemya* spp., *Hippobosca* spp., *Hypoderma* spp., *Liriomyza* spp., for example *Liriomyza brassicae, Liriomyza huidobrensis, Liriomyza sativae, Lucilia* spp., for example *Lucilia cuprina, Lutzomyia* spp., *Mansonia* spp., *Musca* spp., for example *Musca domestica, Musca domestica vicina, Oestrus* spp., *Oscinella frit, Paratanytarsus* spp., *Paralauterborniella subcincta, Pegomya* spp., for example *Pegomya betae, Pegomya hyoscyami, Pegomya rubivora, Phlebotomus* spp., *Phorbia* spp., *Phormia* spp., *Piophila casei, Prodiplosis* spp., *Psila rosae, Rhagoletis* spp., for example *Rhagoletis cingulata, Rhagoletis completa, Rhagoletis fausta, Rhagoletis indifferens, Rhagoletis mendax, Rhagoletis pomonella, Sarcophaga* spp., *Simulium* spp., for example *Simulium meridionale, Stomoxys* spp., *Tabanus* spp., *Tetanops* spp., *Tipula* spp., *for example Tipula paludosa, Tipula simplex*;

from the order of the Heteroptera, for example *Anasa tristis, Antestiopsis* spp., *Boisea* spp., *Blissus* spp., *Calocoris* spp., *Campylomma livida, Cavelerius* spp., *Cimex* spp., for example *Cimex adjunctus, Cimex hemipterus, Cimex lectularius, Cimex pilosellus, Collaria* spp., *Creontiades dilutus, Dasynus piperis, Dichelops furcatus, Diconocoris hewetti, Dysdercus* spp., *Euschistus* spp., for example *Euschistus heros, Euschistus servus, Euschistus tristigmus, Euschistus variolarius, Eurygaster* spp., *Halyomorpha halys, Heliopeltis* spp., *Horcias nobilellus, Leptocorisa* spp., *Leptocorisa varicornis, Leptoglossus occidentalis, Leptoglossus phyllopus, Lygocoris* spp., *for example Lygocoris pabulinus, Lygus* spp., *for example Lygus elisus, Lygus hesperus, Lygus lineolaris, Macropes excavatus, Monalonion atratum, Nezara* spp., *for example Nezara viridula, Oebalus* spp., *Piesma quadrata, Piezodorus* spp., for example *Piezodorus guildinii, Psallus* spp., *Pseudacysta persea, Rhodnius* spp., *Sahlbergella singularis, Scaptocoris castanea, Scotinophora* spp., *Stephanitis nashi, Tibraca* spp., *Triatoma* spp.;

from the order of the Homoptera, for example *Acizzia acaciaebaileyanae, Acizzia dodonaeae, Acizzia uncatoides, Acrida turrita, Acyrthosipon* spp., for example *Acyrthosiphon pisum, Acrogonia* spp., *Aeneolamia* spp., *Agonoscena* spp., *Aleyrodes proletella, Aleurolobus barodensis, Aleurothrixus floccosus, Allocaridara malayensis, Amrasca* spp., for example *Amrasca bigutulla, Amrasca devastans, Anuraphis cardui, Aonidiella* spp., for example *Aonidiella aurantii, Aonidiella citrina, Aonidiella inornata, Aphanostigma piri, Aphis* spp., for example *Aphis craccivora, Aphis fabae, Aphis forbesi, Aphis glycines, Aphis gossypii, Aphis hederae, Aphis illinoisensis, Aphis middletoni, Aphis nasturtii, Aphis nerii, Aphis pomi, Aphis spiraecola, Aphis viburniphila, Arboridia apicalis, Arytainilla* spp., *Aspidiella* spp., *Aspidiotus* spp., for example *Aspidiotus nerii, Atanus* spp., *Aulacorthum solani, Bemisia tabaci, Blastopsylla occidentalis, Boreioglycaspis melaleucae, Brachycaudus helichrysi, Brachycolus* spp., *Brevicoryne brassicae, Cacopsylla* spp., for example *Cacopsylla pyricola, Calligypona marginata, Cameocephala fulgida, Ceratovacuna lanigera, Cercopidae, Ceroplastes* spp., *Chaetosiphon fragaefolii, Chionaspis tegalensis, Chlorita onukii, Chondracris rosea, Chromaphis juglandicola, Chrysomphalus ficus, Cicadulina mbila, Coccomytilus halli, Coccus* spp., for example *Coccus hesperidum, Coccus longulus, Coccus pseudomagnoliarum, Coccus viridis, Cryptomyzus ribis, Cryptoneossa* spp., *Ctenarytaina* spp., *Dalbulus* spp., *Dialeurodes citri, Diaphorina citri, Diaspis* spp., *Drosicha* spp., *Dysaphis* spp., for example *Dysaphis apiifolia, Dysaphis plantaginea, Dysaphis tulipae, Dysmicoccus* spp., *Empoasca* spp., for example *Empoasca abrupta, Empoasca fabae, Empoasca maligna, Empoasca solana, Empoasca stevensi, Eriosoma* spp., for example *Eriosoma americanum, Eriosoma lanigerum, Eriosoma pyricola, Erythroneura* spp., *Eucalyptolyma* spp., *Euphyllura* spp., *Euscelis bilobatus, Ferrisia* spp., *Geococcus coffeae, Glycaspis* spp., *Heteropsylla cubana, Heteropsylla spinulosa, Homalodisca coagulata, Hyalopterus arundinis, Hyalopterus pruni, Icerya* spp., for example *Icerya purchasi, Idiocerus* spp., *Idioscopus* spp., *Laodelphax striatellus, Lecanium* spp., *for example Lecanium comi (=Parthenolecanium comi), Lepidosaphes* spp., for example *Lepidosaphes ulmi, Lipaphis erysimi, Macrosiphum* spp., for example *Macrosiphum euphorbiae, Macrosiphum lilii, Macrosiphum rosae, Macrosteles facifrons, Mahanarva* spp., *Melanaphis sacchari, Metcalfiella* spp., *Metopolophium dirhodum, Monellia costalis, Monelliopsis pecanis, Myzus* spp., for example *Myzus ascalonicus, Myzus cerasi, Myzus ligustri, Myzus ornatus, Myzus persicae, Myzus nicotianae, Nasonovia ribisnigri, Nephotettix* spp., for example *Nephotettix cincticeps, Nephotettix nigropictus, Nilaparvata lugens, Oncometopia* spp., *Orthezia praelonga, Oxya chinensis, Pachypsylla* spp., *Parabemisia myricae, Paratrioza* spp., for example *Paratrioza cockerelli, Parlatoria* spp., *Pemphigus* spp., for example *Pemphigus bursarius, Pemphigus populivenae, Peregrinus maidis, Phenacoccus* spp., for example *Phenacoccus madeirensis, Phloeomyzus passerinii, Phorodon humuli, Phylloxera* spp., for example *Phylloxera devastatrix, Phylloxera notabilis, Pinnaspis aspidistrae, Planococcus* spp., for example *Planococcus citri, Prosopidopsylla flava, Protopulvinaria pyriformis, Pseudaulacaspis pentagona, Pseudococcus* spp., for example *Pseudococcus calceolariae, Pseudococcus com-*

*stocki, Pseudococcus longispinus, Pseudococcus maritimus, Pseudococcus vibumi, Psyllopsis* spp., *Psylla* spp., for example *Psylla buxi, Psylla mali, Psylla pyri, Pteromalus* spp., *Pyrilla* spp., *Quadraspidiotus* spp., for example *Quadraspidiotus juglansregiae, Quadraspidiotus ostreaeformis, Quadraspidiotus pemiciosus, Quesada gigas, Rastrococcus* spp., *Rhopalosiphum* spp., for example *Rhopalosiphum maidis, Rhopalosiphum oxyacanthae, Rhopalosiphum padi, Rhopalosiphum rufiabdominale, Saissetia* spp., for example *Saissetia coffeae, Saissetia miranda, Saissetia neglecta, Saissetia oleae, Scaphoideus titanus, Schizaphis graminum, Selenaspidus articulatus, Sitobion avenae, Sogata* spp., *Sogatella furcifera, Sogatodes* spp., *Stictocephala festina, Siphoninus phillyreae, Tenalaphara malayensis, Tetragonocephela* spp., *Tinocallis caryaefoliae, Tomaspis* spp., *Toxoptera* spp., for example *Toxoptera aurantii, Toxoptera citricidus, Trialeurodes vaporariorum, Trioza* spp., for example *Trioza diospyri, Typhlocyba* spp., *Unaspis* spp., *Viteus vitifolii, Zygina* spp.;

from the order of the Hymenoptera, for example *Acromyrmex* spp., *Athalia* spp., for example *Athalia rosae, Atta* spp., *Diprion* spp., for example *Diprion similis, Hoplocampa* spp., for example *Hoplocampa cookei, Hoplocampa testudinea, Lasius* spp., *Monomorium pharaonis, Sirex* spp., *Solenopsis invicta, Tapinoma* spp., *Urocerus* spp., *Vespa* spp., for example *Vespa crabro, Xeris* spp.;

from the order of the Isopoda, for example *Armadillidium vulgare, Oniscus asellus, Porcellio scaber;* from the order of the Isoptera, for example *Coptotermes* spp., for example *Coptotermes formosanus, Comitermes cumulans, Cryptotermes* spp., *Incisitermes* spp., *Microtermes obesi, Odontotermes* spp., *Reticulitermes* spp., for example *Reticulitermes flavipes, Reticulitermes hesperus;* from the order of the Lepidoptera, for example *Achroia grisella, Acronicta major, Adoxophyes* spp., for example *Adoxophyes orana, Aedia leucomelas, Agrotis* spp., for example *Agrotis segetum, Agrotis ipsilon, Alabama* spp., for example *Alabama argillacea, Amyelois transitella, Anarsia* spp., *Anticarsia* spp., for example *Anticarsia gemmatalis, Argyroploce* spp., *Barathra brassicae, Borbo cinnara, Bucculatrix thurberiella, Bupalus piniarius, Busseola* spp., *Cacoecia* spp., *Caloptilia theivora, Capua reticulana, Carpocapsa pomonella, Carposina niponensis, Cheimatobia brumata, Chilo* spp., for example *Chilo plejadellus, Chilo suppressalis, Choristoneura* spp., *Clysia ambiguella, Cnaphalocerus* spp., *Cnaphalocrocis medinalis, Cnephasia* spp., *Conopomorpha* spp., *Conotrachelus* spp., *Copitarsia* spp., *Cydia* spp., for example *Cydia nigricana, Cydia pomonella, Dalaca noctuides, Diaphania* spp., *Diatraea saccharalis, Earias* spp., *Ecdytolopha aurantium, Elasmopalpus lignosellus, Eldana saccharina, Ephestia* spp., for example *Ephestia elutella, Ephestia kuehniella, Epinotia* spp., *Epiphyas postvittana, Etiella* spp., *Eulia* spp., *Eupoecilia ambiguella, Euproctis* spp., for example *Euproctis chrysorrhoea, Euxoa* spp., *Feltia* spp., *Galleria mellonella, Gracillaria* spp., *Grapholitha* spp., for example *Grapholita molesta, Grapholita prunivora, Hedylepta* spp., *Helicoverpa* spp., for example *Helicoverpa armigera, Helicoverpa zea, Heliothis* spp., for example *Heliothis virescens, Hofmannophila pseudospretella, Homoeosoma* spp., *Homona* spp., *Hyponomeuta padella, Kakivoria flavofasciata, Laphygma* spp., *Leucinodes orbonalis, Leucoptera* spp., for example *Leucoptera coffeella, Lithocolletis* spp., for example *Lithocolletis blancardella, Lithophane antennata, Lobesia* spp., for example *Lobesia botrana, Loxagrotis albicosta, Lymantria* spp., for example *Lymantria dispar, Lyonetia* spp., for example *Lyonetia clerkella, Malacosoma neustria, Maruca testulalis, Mamestra brassicae, Melanitis leda, Mocis* spp., *Monopis obviella, Mythimna separata, Nemapogon cloacellus, Nymphula* spp., *Oiketicus* spp., *Oria* spp., *Orthaga* spp., *Ostrinia* spp., for example *Ostrinia nubilalis, Oulema melanopus, Oulema oryzae, Panolis flammea, Parnara* spp., *Pectinophora* spp., for example *Pectinophora gossypiella, Perileucoptera* spp., *Phthorimaea* spp., for example *Phthorimaea operculella, Phyllocnistis citrella, Phyllonorycter* spp., for example *Phyllonorycter blancardella, Phyllonorycter crataegella, Pieris* spp., for example *Pieris rapae, Platynota stultana, Plodia interpunctella, Plusia* spp., *Plutella xylostella* (=*Plutella maculipennis*), *Prays* spp., *Prodenia* spp., *Protoparce* spp., *Pseudaletia* spp., for example *Pseudaletia unipuncta, Pseudoplusia includens, Pyrausta nubilalis, Rachiplusia nu, Schoenobius* spp., for example *Schoenobius bipunctifer, Scirpophaga* spp., for example *Scirpophaga innotata, Scotia segetum, Sesamia* spp., for example *Sesamia inferens, Sparganothis* spp., *Spodoptera* spp., for example *Spodoptera eradiana, Spodoptera exigua, Spodoptera frugiperda, Spodoptera praefica, Stathmopoda* spp., *Stomopteryx subsecivella, Synanthedon* spp., *Tecia solanivora, Thermesia gemmatalis, Tinea cloacella, Tinea pellionella, Tineola bisselliella, Tortrix* spp., *Trichophaga tapetzella, Trichoplusia* spp., for example *Trichoplusia ni, Tryporyza incertulas, Tuta absoluta, Virachola* spp.;

from the order of the Orthoptera or *Saltatoria*, for example *Acheta domesticus, Dichroplus* spp., *Gryllotalpa* spp., for example *Gryllotalpa gryllotalpa, Hieroglyphus* spp., *Locusta* spp., for example *Locusta migratoria, Melanoplus* spp., for example *Melanoplus devastator, Schistocerca gregaria;* from the order of the Phthiraptera, for example *Damalinia* spp., *Haematopinus* spp., *Linognathus* spp., *Pediculus* spp., *Phylloxera vastatrix, Phthirus pubis, Trichodectes* spp.;

from the order of the Psocoptera, for example *Lepinotus* spp., *Liposcelis* spp.;

from the order of the Siphonaptera, for example, *Ceratophyllus* spp., *Ctenocephalides* spp., for example *Ctenocephalides canis, Ctenocephalides felis, Pulex irritans, Tunga penetrans, Xenopsylla cheopis;* from the order of the Thysanoptera, for example *Anaphothrips obscurus, Baliothrips biformis, Drepanothrips reuteri, Enneothrips flavens, Frankliniella* spp., for example *Frankliniella fusca, Frankliniella occidentalis, Frankliniella schultzei, Frankliniella tritici, Frankliniella vaccinii, Frankliniella williamsi, Heliothrips* spp., *Hercinothrips femoralis, Rhipiphorothrips cruentatus, Scirtothrips* spp., *Taeniothrips cardamomi, Thrips* spp., for example *Thrips palmi, Thrips tabaci;* from the order of the Zygentoma (=*Thysanura*), for example *Ctenolepisma* spp., *Lepisma saccharina, Lepismodes inquilinus, Thermobia domestica;* from the class of the Symphyla, for example *Scutigerella* spp., for example *Scutigerella immaculata;* pests from the phylum of the Mollusca, for example from the class of the Bivalvia, for example *Dreissena* spp., and also from the class of the Gastropoda, for example *Arion* spp., for example *Arion ater rufus, Biomphalaria* spp., *Bulinus* spp., *Deroceras* spp., for example *Deroceras laeve, Galba* spp., *Lymnaea* spp., *Oncomelania* spp., *Pomacea* spp., *Succinea* spp.;

animal parasites from the phyla of the Plathelminthes and Nematoda, for example *Ancylostoma* spp., for example *Ancylostoma duodenale, Ancylostoma ceylanicum, Ancylostoma braziliensis, Ascaris* spp., *Brugia malayi, Brugia timori, Bunostomum* spp., *Chabertia* spp., *Clonorchis* spp., *Cooperia* spp., *Dicrocoelium* spp., *Dictyocaulus filaria,*

*Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercoralis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichiura, Wuchereria bancrofti;* plant pests from the phylum of the Nematoda, i.e. *phytoparasitic nematodes*, especially *Aglenchus* spp., for example *Aglenchus agricola, Anguina* spp., for example *Anguina tritici, Aphelenchoides* spp., for example *Aphelenchoides arachidis, Aphelenchoides fragariae, Belonolaimus* spp., for example *Belonolaimus gracilis, Belonolaimus longicaudatus, Belonolaimus nortoni, Bursaphelenchus* spp., for example *Bursaphelenchus cocophilus, Bursaphelenchus eremus, Bursaphelenchus xylophilus, Cacopaurus* spp., for example *Cacopaurus pestis, Criconemella* spp., for example *Criconemella curvata, Criconemella onoensis, Criconemella ornata, Criconemella rusium, Criconemella xenoplax (=Mesocriconema xenoplax), Criconemoides* spp., for example *Criconemoides ferniae, Criconemoides onoense, Criconemoides ornatum, Ditylenchus* spp., for example *Ditylenchus dipsaci, Dolichodorus* spp., *Globodera* spp., for example *Globodera pallida, Globodera rostochiensis, Helicotylenchus* spp., for example *Helicotylenchus dihystera, Hemicriconemoides* spp., *Hemicycliophora* spp., *Heterodera* spp., for example *Heterodera avenae, Heterodera glycines, Heterodera schachtii, Hoplolaimus* spp., *Longidorus* spp., for example *Longidorus africanus, Meloidogyne* spp., for example *Meloidogyne chitwoodi, Meloidogyne fallax, Meloidogyne hapla, Meloidogyne incognita, Meloinema* spp., *Nacobbus* spp., *Neotylenchus* spp., *Paraphelenchus* spp., *Paratrichodorus* spp., for example *Paratrichodorus minor, Pratylenchus* spp., for example *Pratylenchus penetrans, Pseudohalenchus* spp., *Psilenchus* spp., *Punctodera* spp., *Quinisulcius* spp., *Radopholus* spp., *for example Radopholus citrophilus, Radopholus similis, Rotylenchulus* spp., *Rotylenchus* spp., *Scutellonema* spp., *Subanguina* spp., *Trichodorus* spp., for example *Trichodorus obtusus, Trichodorus primitivus, Tylenchorhynchus* spp., for example *Tylenchorhynchus annulatus, Tylenchulus* spp., for example *Tylenchulus semipenetrans, Xiphinema* spp., for example *Xiphinema index.*

In addition, it is possible to control, from the sub-kingdom of the Protozoa, the order of the Coccidia, for example, *Eimeria* spp.

The compounds of the formula (I) can optionally, at certain concentrations or application rates, also be used as herbicides, safeners, growth regulators or agents to improve plant properties, as microbicides or gametocides, for example as fungicides, antimycotics, bactericides, virucides (including agents against viroids) or as agents against MLO (*mycoplasma*-like organisms) and RLO (*rickettsia*-like organisms). If appropriate, they can also be used as intermediates or precursors for the synthesis of other active ingredients.

The present invention further relates to formulations and use forms prepared therefrom as pesticides, for example drench, drip and spray liquors, comprising at least one compound of the formula (I). In some cases, the use forms comprise further pesticides and/or adjuvants which improve action, such as penetrants, e.g. vegetable oils, for example rapeseed oil, sunflower oil, mineral oils, for example paraffin oils, alkyl esters of vegetable fatty acids, for example rapeseed oil methyl ester or soya oil methyl ester, or alkanol alkoxylates and/or spreaders, for example alkylsiloxanes and/or salts, for example organic or inorganic ammonium or phosphonium salts, for example ammonium sulphate or diammonium hydrogenphosphate and/or retention promoters, for example dioctyl sulphosuccinate or hydroxypropyl guar polymers and/or humectants, for example glycerol and/or fertilizers, for example ammonium-, potassium- or phosphorus-containing fertilizers.

Customary formulations are, for example, water-soluble liquids (SL), emulsion concentrates (EC), emulsions in water (EW), suspension concentrates (SC, SE, FS, OD), water-dispersible granules (WG), granules (GR) and capsule concentrates (CS); these and further possible formulation types are described, for example, by Crop Life International and in Pesticide Specifications, Manual on development and use of FAO and WHO specifications for pesticides, FAO Plant Production and Protection Papers—173, prepared by the FAO/WHO Joint Meeting on Pesticide Specifications, 2004, ISBN: 9251048576. The formulations, in addition to one or more compounds of the formula (I), optionally comprise further agrochemically active ingredients.

These are preferably formulations or use forms which comprise auxiliaries, for example extenders, solvents, spontaneity promoters, carriers, emulsifiers, dispersants, frost protectants, biocides, thickeners and/or further auxiliaries, for example adjuvants. An adjuvant in this context is a component which enhances the biological effect of the formulation, without the component itself having any biological effect. Examples of adjuvants are agents which promote retention, spreading, attachment to the leaf surface or penetration.

These formulations are produced in a known manner, for example by mixing the compounds of the formula (I) with auxiliaries, for example extenders, solvents and/or solid carriers and/or other auxiliaries, for example surfactants. The formulations are produced either in suitable facilities or else before or during application.

Auxiliaries used may be substances suitable for imparting special properties, such as particular physical, technical and/or biological properties, to the formulation of the compounds of the formula (I), or to the use forms prepared from these formulations (for example ready-to-use pesticides such as spray liquors or seed dressing products).

Suitable extenders are, for example, water, polar and nonpolar organic chemical liquids, for example from the classes of the aromatic and nonaromatic hydrocarbons (such as paraffins, alkylbenzenes, alkylnaphthalenes, chlorobenzenes), the alcohols and polyols (which may optionally also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender utilized is water, it is also possible to use, for example, organic solvents as auxiliary solvents. Useful liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, and also water.

In principle, it is possible to use all suitable solvents. Examples of suitable solvents are aromatic hydrocarbons such as xylene, toluene or alkylnaphthalenes, chlorinated aromatic or aliphatic hydrocarbons such as chlorobenzene, chloroethylene or methylene chloride, aliphatic hydrocarbons such as cyclohexane, paraffins, mineral oil fractions, mineral and vegetable oils, alcohols such as methanol, ethanol, isopropanol, butanol or glycol and their ethers and esters, ketones such as acetone, methyl ethyl ketone, methyl isobutyl ketone or cyclohexanone, strongly polar solvents such as dimethyl sulphoxide, and water.

In principle, it is possible to use all suitable carriers. Useful carriers especially include: for example ammonium salts and ground natural minerals such as kaolins, clays, talc, chalk, quartz, attapulgite, montmorillonite or diatomaceous earth, and ground synthetic materials such as finely divided silica, alumina and natural or synthetic silicates, resins, waxes and/or solid fertilizers. Mixtures of such carriers can likewise be used. Useful carriers for granules include: for example crushed and fractionated natural rocks such as calcite, marble, pumice, sepiolite, dolomite, and synthetic granules of inorganic and organic meals, and also granules of organic material such as sawdust, paper, coconut shells, corn cobs and tobacco stalks.

Liquefied gaseous extenders or solvents can also be used. Particularly suitable extenders or carriers are those which are gaseous at ambient temperature and under atmospheric pressure, for example aerosol propellant gases, such as halohydrocarbons, and also butane, propane, nitrogen and carbon dioxide.

Examples of emulsifiers and/or foam generators, dispersants or wetting agents having ionic or nonionic properties, or mixtures of these surfactants, are salts of polyacrylic acid, salts of lignosulphonic acid, salts of phenolsulphonic acid or naphthalenesulphonic acid, polycondensates of ethylene oxide with fatty alcohols or with fatty acids or with fatty amines, with substituted phenols (preferably alkylphenols or arylphenols), salts of sulphosuccinic esters, taurine derivatives (preferably alkyl taurates), phosphoric esters of polyethoxylated alcohols or phenols, fatty acid esters of polyols, and derivatives of the compounds comprising sulphates, sulphonates and phosphates, e.g. alkylaryl polyglycol ethers, alkylsulphonates, alkyl sulphates, arylsulphonates, protein hydrolysates, lignosulphite waste liquors, and methyl cellulose. The presence of a surfactant is advantageous if one of the compounds of the formula (I) and/or one of the inert carriers is insoluble in water and when the application takes place in water.

Further auxiliaries which may be present in the formulations and the use forms derived therefrom include dyes such as inorganic pigments, for example iron oxide, titanium oxide and Prussian Blue, and organic dyes such as alizarin dyes, azo dyes and metal phthalocyanine dyes, and nutrients and trace nutrients such as salts of iron, manganese, boron, copper, cobalt, molybdenum and zinc.

Additional components may be stabilizers, such as cold stabilizers, preservatives, antioxidants, light stabilizers, or other agents which improve chemical and/or physical stability. Foam generators or antifoams may also be present.

In addition, the formulations and the use forms derived therefrom may also comprise, as additional auxiliaries, stickers such as carboxymethyl cellulose and natural and synthetic polymers in the form of powders, granules or latices, such as gum arabic, polyvinyl alcohol and polyvinyl acetate, or else natural phospholipids such as cephalins and lecithins and synthetic phospholipids. Further possible auxiliaries are mineral and vegetable oils.

Optionally, further auxiliaries may be present in the formulations and the use forms derived therefrom. Examples of such additives include fragrances, protective colloids, binders, adhesives, thickeners, thixotropic agents, penetrants, retention promoters, stabilizers, sequestrants, complexing agents, humectants, spreaders. In general, the compounds of the formula (I) can be combined with any solid or liquid additive commonly used for formulation purposes.

Useful retention promoters include all those substances which reduce the dynamic surface tension, for example dioctyl sulphosuccinate, or increase the viscoelasticity, for example hydroxypropylguar polymers.

Useful penetrants in the present context are all those substances which are typically used to improve the penetration of active agrochemical ingredients into plants. Penetrants are defined in this context by their ability to penetrate from the (generally aqueous) application liquor and/or from the spray coating into the cuticle of the plant and thereby increase the mobility of active ingredients in the cuticle. The method described in the literature (Baur et al., 1997, Pesticide Science 51, 131-152) can be used for determining this property. Examples include alcohol alkoxylates such as coconut fatty ethoxylate (10) or isotridecyl ethoxylate (12), fatty acid esters, for example rapeseed oil methyl ester or soya oil methyl ester, fatty amine alkoxylates, for example tallowamine ethoxylate (15), or ammonium and/or phosphonium salts, for example ammonium sulphate or diammonium hydrogenphosphate.

The formulations preferably contain between 0.00000001% and 98% by weight of the compound of the formula (I), more preferably between 0.01% and 95% by weight of the compound of the formula (I), most preferably between 0.5% and 90% by weight of the compound of the formula (I), based on the weight of the formulation.

The content of the compound of the formula (I) in the use forms prepared from the formulations (especially pesticides) may vary within wide ranges. The concentration of the compound of the formula (I) in the use forms may typically be between 0.00000001% and 95% by weight of the compound of the formula (I), preferably between 0.00001% and 1% by weight, based on the weight of the use form. Application is accomplished in a customary manner appropriate for the use forms.

The compounds of the formula (I) can also be used in a mixture with one or more suitable fungicides, bactericides, acaricides, molluscicides, nematicides, insecticides, microbiologicals, beneficial organisms, herbicides, fertilizers, bird repellents, phytotonics, sterilants, safeners, semiochemicals and/or plant growth regulators, in order thus, for example, to broaden the spectrum of action, to prolong the duration of action, to increase the rate of action, to prevent repulsion or prevent evolution of resistance. In addition, active ingredient combinations of this kind can improve plant growth and/or tolerance to abiotic factors, for example high or low temperatures, to drought or to elevated water content or soil salinity. It is also possible to improve flowering and fruiting performance, optimize germination capacity and root development, facilitate harvesting and improve yields, influence maturation, improve the quality and/or the nutritional value of the harvested products, prolong storage life and/or improve the processability of the harvested products.

In addition, the compounds of the formula (I) may be present in a mixture with other active ingredients or semiochemicals such as attractants and/or bird repellents and/or plant activators and/or growth regulators and/or fertilizers.

Likewise, the compounds of the formula (I) can be used in mixtures with agents to improve plant properties, for example growth, yield and quality of the harvested material.

In a particular embodiment of the invention, the compounds of the formula (I) are in the form of formulations or the use forms prepared from these formulations in a mixture with further compounds, preferably those as described below.

If one of the compounds mentioned below can occur in various tautomeric forms, these forms are also included even if not explicitly mentioned in each case.

Insecticides/Acaricides/Nematicides

The active ingredients specified here with their "common names" are known and are described for example in The Pesticide Manual, 16th ed., British Crop Protection Council 2012, or can be searched for on the Internet (e.g. http://www.alanwood.net/pesticides).

(1) Acetylcholinesterase (AChE) inhibitors, for example carbamates, e.g. alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, e.g. acephate, azamethiphos, azinphos-ethyl, azinphos-methyl, cadusafos, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothiophosphoryl)salicylate, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion.

(2) GABA-gated chloride channel antagonists, for example cyclodiene-organochlorines, e.g. chlordane and endosulfan or phenylpyrazoles (fiproles), e.g. ethiprole and fipronil.

(3) Sodium channel modulators/voltage-gated sodium channel blockers, for example pyrethroids, e.g. acrinathrin, allethrin, d-cis-trans allethrin, d-trans allethrin, bifenthrin, bioallethrin, bioallethrin s-cyclopentenyl isomer, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans isomer], deltamethrin, empenthrin [(EZ)-(1R) isomer], esfenvalerate, etofenprox, fenpropathrin, fenvalerate, flucythrinate, flumethrin, tau-fluvalinate, halfenprox, imiprothrin, kadethrin, permethrin, phenothrin [(1R)-trans isomer], prallethrin, pyrethrins (pyrethrum), resmethrin, silafluofen, tefluthrin, tetramethrin, tetramethrin [(1R) isomer)], tralomethrin and transfluthrin or DDT or methoxychlor.

(4) Nicotinergic acetylcholine receptor (nAChR) agonists, for example neonicotinoids, e.g. acetamiprid, clothianidin, dinotefuran, imidacloprid, nitenpyram, thiacloprid and thiamethoxam or nicotine or sulfoxaflor.

(5) Allosteric activators of the nicotinergic acetylcholine receptor (nAChR), for example spinosyns, e.g. spinetoram and spinosad.

(6) Chloride channel activators, for example, avermectins/milbemycins, e.g. abamectin, emamectin benzoate, lepimectin and milbemectin.

(7) Juvenile hormone imitators, for example, juvenile hormone analogues e.g. hydroprene, kinoprene and methoprene or fenoxycarb or pyriproxyfen.

(8) Active ingredients with unknown or nonspecific mechanisms of action, for example alkyl halides, e.g. methyl bromide and other alkyl halides; or chloropicrine or sulphuryl fluoride or borax or tartar emetic.

(9) Selective antifeedants, e.g. pymetrozine or flonicamid.

(10) Mite growth inhibitors, e.g. clofentezine, hexythiazox and diflovidazin or etoxazole.

(11) Microbial disruptors of the insect gut membrane, e.g. *Bacillus thuringiensis* subspecies *israelensis, Bacillus sphaericus, Bacillus thuringiensis* subspecies *aizawai, Bacillus thuringiensis* subspecies *kurstaki, Bacillus thuringiensis* subspecies *tenebrionis*, and BT plant proteins: Cry1Ab, Cry1Ac, Cry1Fa, Cry2Ab, mCry3A, Cry3Ab, Cry3Bb, Cry34/35Ab1.

(12) Oxidative phosphorylation inhibitors, ATP disruptors, for example diafenthiuron or organotin compounds, e.g. azocyclotin, cyhexatin and fenbutatin oxide or propargite or tetradifon.

(13) Oxidative phosphorylation decouplers that interrupt the H proton gradient, for example chlorfenapyr, DNOC and sulfluramid.

(14) Nicotinergic acetylcholine receptor antagonists, for example bensultap, cartap hydrochloride, thiocyclam, and thiosultap-sodium.

(15) Chitin biosynthesis inhibitors, type 0, for example bistrifluron, chlorfluazuron, diflubenzuron, flucycloxuron, flufenoxuron, hexaflumuron, lufenuron, novaluron, noviflumuron, teflubenzuron and triflumuron.

(16) Chitin biosynthesis inhibitors, type 1, for example buprofezin.

(17) Moulting inhibitors (especially for Diptera, i.e. dipterans), for example cyromazine.

(18) Ecdysone receptor agonists, for example chromafenozide, halofenozide, methoxyfenozide and tebufenozide.

(19) Octopaminergic agonists, for example amitraz.

(20) Complex-III electron transport inhibitors, for example hydramethylnon; or acequinocyl; or fluacrypyrim.

(21) Complex-I electron transport inhibitors, for example from the group of the METI acaricides, e.g. fenazaquin, fenpyroximate, pyrimidifen, pyridaben, tebufenpyrad and tolfenpyrad or rotenone (Derris).

(22) Voltage-gated sodium channel blockers, for example indoxacarb or metaflumizone.

(23) Inhibitors of acetyl-CoA carboxylase, for example tetronic and tetramic acid derivatives, e.g. spirodiclofen, spiromesifen and spirotetramat.

(24) Complex-IV electron transport inhibitors, for example phosphines, e.g. aluminium phosphide, calcium phosphide, phosphine and zinc phosphide or cyanide.

(25) Complex-II electron transport inhibitors, for example cyenopyrafen and cyflumetofen.

(28) Ryanodine receptor effectors, for example diamides, e.g. chlorantraniliprole, cyantraniliprole and flubendiamide, further active ingredients, for example afidopyropen, azadirachtin, benclothiaz, benzoximate, bifenazate, bromopropylate, chinomethionat, cryolite, dicofol, diflovidazin, fluensulfone, flometoquin, flufenerim, flufenoxystrobin, flufiprole, fluopyram, flupyradifurone, fufenozide, heptafluthrin, imidaclothiz, iprodione, meperfluthrin, paichongding, pyflubumide, pyrifluquinazon, pyriminostrobin, tetramethylfluthrin and iodomethane; and also preparations based on *Bacillus firmus* (I-1582, BioNeem, Votivo), and also the following compounds: 3-bromo-N-{2-bromo-4-chloro-6-[(1-cyclopropylethyl)carbamoyl]phenyl}-1-(3-chloropyridin-2-yl)-1H-pyrazole-5-carboxamide (known from WO2005/077934) and 1-{2-fluoro-4-methyl-5-[(2,2,2-trifluoroethyl)sulphinyl]phenyl}-3-(trifluoromethyl)-1H-1,2,4-triazole-5-amine (known from WO2006/043635), {1'-[(2E)-3-(4-chlorophenyl)prop-2-en-1-yl]-5-fluorospiro[indole-3,4'-piperidin]-1(2H)-yl}(2-chloropyridin-4-yl)methanone (known from WO2003/106457), 2-chloro-N-[2-{1-[(2E)-3-(4-chlorophenyl)prop-2-en-1-yl]piperidin-4-yl}-4-(trifluoromethyl)phenyl] isonicotinamide (known from WO2006/003494), 3-(2,5-dimethylphenyl)-4-hydroxy-8-methoxy-1,8-diazaspiro[4.5]dec-3-en-2-one (known from WO2009/049851), 3-(2,5-dimethylphenyl)-8-methoxy-2-oxo-1,8-diazaspiro[4.5]dec-3-en-4-yl-ethylcarbonate (known from WO2009/049851), 4-(but-2-yn-1-yloxy)-6-(3,5-dimethylpiperidin-1-yl)-5-fluoropyrimidine (known from WO2004/099160), 4-(but-2-yn-1-yloxy)-6-(3-chlorophenyl)pyrimidine (known from WO2003/076415), PF1364 (CAS Reg. No. 1204776-60-2), 4-[5-(3,5-dichlorophenyl)-5-(trifluoromethyl)-4,5-dihydro-1,2-oxazol-3-yl]-2-methyl-N-{2-oxo-2-[(2,2,2-trifluoroethyl)amino]ethyl}benzamide (known from WO2005/085216), 4-{5-[3-chloro-5-(trifluoromethyl)phenyl]-5-(trifluoromethyl)-4,5-dihydro-1,2-oxazol-3-yl}-N-{2-oxo-2-[(2,2,2-trifluoroethyl)amino]ethyl}-1-naphthamide (known from WO2009/002809), methyl 2-[2-({[3-bromo-1-(3-chloropyridin-2-yl)-1H-pyrazol-5-yl]carbonyl}amino)-5-chloro-3-methylbenzoyl]-2-methylhydrazinecarboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-ethylhydrazinecarboxylate (known from WO2005/085216), methyl 2-[2-({[3-bromo-1-(3-chloropyridin-2-yl)-1H-pyrazol-5-yl]carbony}amino)-5-cyano-3-methylbenzoyl]-2-methylhydrazinecarboxylate (known from WO2005/085216), methyl 2-[3,5-dibromo-2-({[3-bromo-1-(3-chloropyridin-2-yl)-1H-pyrazol-5-yl]carbonyl}amino)benzoyl]-2-ethylhydrazinecarboxylate (known from WO2005/085216), 1-(3-chloropyridin-2-yl)-N-[4-cyano-2-methyl-6-(methylcarbamoyl)phenyl]-3-{[5-(trifluoromethyl)-2H-tetrazol-2-yl]methyl}-1H-pyrazole-5-carboxamide (known from WO2010/069502), N-[2-(5-amino-1,3,4-thiadiazol-2-yl)-4-chloro-6-methylphenyl]-3-bromo-1-(3-chloropyridin-2-yl)-1H-pyrazole-5-carboxamide (known from CN102057925), 3-chloro-N-(2-cyanopropan-2-yl)-N-[4-(1,1,1,2,3,3,3-heptafluoropropan-2-yl)-2-methylphenyl]phthalamide (known from WO2012/034472), 8-chloro-N-[(2-chloro-5-methoxyphenyl) sulphonyl]-6-(trifluoromethyl)imidazo[1,2-a]pyridine-2-carboxamide (known from WO2010/129500), 4-[5-(3,5-dichlorophenyl)-5-(trifluoromethyl)-4,5-dihydro-1,2-oxazol-3-yl]-2-methyl-N-(1-oxidothietan-3-yl)benzamide (known from WO2009/080250), 4-[5-(3,5-dichlorophenyl)-5-(trifluoromethyl)-4,5-dihydro-1,2-oxazol-3-yl]-2-methyl-N-(1-oxidothietan-3-yl)benzamide (known from WO2012/029672), 1-[(2-chloro-1,3-thiazol-5-yl)methyl]-4-oxo-3-phenyl-4H-pyrido[1,2-a]pyrimidin-1-ium-2-olate (known from WO2009/099929), 1-[(6-chloropyridin-3-yl)methyl]-4-oxo-3-phenyl-4H-pyrido[1,2-a]pyrimidin-1-ium-2-olate (known from WO2009/099929), (5S,8R)-1-[(6-chloropyridin-3-yl)methyl]-9-nitro-2,3,5,6,7,8-hexahydro-1H-5,8-epoxyimidazo[1,2-a]azepine (known from WO2010/069266), (2E)-1-[(6-chloropyridin-3-yl)methyl]-N'-nitro-2-pentylidenehydrazinecarboximidamide (known from WO2010/060231), 4-(3-{2,6-dichloro-4-[(3,3-dichloroprop-2-en-1-yl)oxy]phenoxy}propoxy)-2-methoxy-6-(trifluoromethyl) pyrimidine (known from CN101337940), N-[2-(tert-butylcarbamoyl)-4-chloro-6-methylphenyl]-1-(3-chloropyridin-2-yl)-3-(fluoromethoxy)-1H-pyrazole-5-carboxamide (known from WO2008/134969).

Fungicides

The active ingredients specified herein by their common name are known and described, for example, in the "Pesticide Manual" or on the Internet (for example: http://www.alanwood.net/pesticides).

(1) Ergosterol biosynthesis inhibitors, for example (1.1) aldimorph, (1.2) azaconazole, (1.3) bitertanol, (1.4) bromuconazole, (1.5) cyproconazole, (1.6) diclobutrazole, (1.7) difenoconazole, (1.8) diniconazole, (1.9) diniconazole-M, (1.10) dodemorph, (1.11) dodemorph acetate, (1.12) epoxiconazole, (1.13) etaconazole, (1.14) fenarimol, (1.15) fenbuconazole, (1.16) fenhexamid, (1.17) fenpropidin, (1.18) fenpropimorph, (1.19) fluquinconazole, (1.20) flurprimidol, (1.21) flusilazole, (1.22) flutriafole, (1.23) furconazole, (1.24) furconazole-cis, (1.25) hexaconazole, (1.26) imazalil, (1.27) imazalil sulphate, (1.28) imibenconazole, (1.29) ipconazole, (1.30) metconazole, (1.31) myclobutanil, (1.32) naftifin, (1.33) nuarimol, (1.34) oxpoconazole, (1.35) paclobutrazole, (1.36) pefurazoate, (1.37) penconazole, (1.38) piperalin, (1.39) prochloraz, (1.40) propiconazole, (1.41) prothioconazole, (1.42) pyributicarb, (1.43) pyrifenox, (1.44) quinconazole, (1.45) simeconazole, (1.46) spiroxamine, (1.47) tebuconazole, (1.48) terbinafin, (1.49) tetraconazole, (1.50) triadimefon, (1.51) triadimenol, (1.52) tridemorph, (1.53) triflumizole, (1.54) triforine, (1.55) triticonazole, (1.56) uniconazole, (1.57) uniconazole-P, (1.58) viniconazole, (1.59) voriconazole, (1.60) 1-(4-chlorophenyl)-2-(1H-1,2,4-triazol-1-yl)cycloheptanol, (1.61) methyl 1-(2,2-dimethyl-2,3-dihydro-1H-inden-1-yl)-1H-imidazole-5-carboxylate, (1.62) N'-{5-(difluoromethyl)-2-methyl-4-[3-(trimethylsilyl)propoxy]phenyl}-N-ethyl-N-methylimidoformamide, (1.63) N-ethyl-N-methyl-N'-{2-methyl-5-(trifluoromethyl)-4-[3-(trimethylsilyl)propoxy]phenyl}imidoformamide and (1.64) O-[1-(4-methoxyphenoxy)-3,3-dimethylbutan-2-yl]-1H-imidazole-1-carbothioate, (1.65) pyrisoxazole.

(2) Respiration inhibitors (respiratory chain inhibitors), for example (2.1) bixafen, (2.2) boscalid, (2.3) carboxin, (2.4) diflumetorim, (2.5) fenfuram, (2.6) fluopyram, (2.7) flutolanil, (2.8) fluxapyroxad, (2.9) furametpyr, (2.10) furmecyclox, (2.11) isopyrazam mixture of the syn-epimeric racemate 1RS,4SR,9RS and the anti-empimeric racemate 1RS,4SR,9SR, (2.12) isopyrazam (anti-epimeric racemate), (2.13) isopyrazam (anti-epimeric enantiomer 1R,4S,9S), (2.14) isopyrazam (anti-epimeric enantiomer 1S,4R,9R), (2.15) isopyrazam (syn-epimeric racemate 1RS,4SR,9RS), (2.16) isopyrazam (syn-epimeric enantiomer 1R,4S,9R), (2.17) isopyrazam (syn-epimeric enantiomer 1S,4R,9S), (2.18) mepronil, (2.19) oxycarboxin, (2.20) penflufen, (2.21) penthiopyrad, (2.22) sedaxane, (2.23) thifluzamide, (2.24) 1-methyl-N-[2-(1,1,2,2-tetrafluoroethoxy)phenyl]-3-(trifluoromethyl)-1H-pyrazole-4-carboxamide, (2.25) 3-(difluoromethyl)-1-methyl-N-[2-(1,1,2,2-tetrafluoroethoxy)phenyl]-1H-pyrazole-4-carboxamide, (2.26) 3-(difluoromethyl)-N-[4-fluoro-2-(1,1,2,3,3,3-hexafluoropropoxy)phenyl]-1-methyl-1H-pyrazole-4-carboxamide, (2.27) N-[1-(2,4-dichlorophenyl)-1-methoxypropan-2-yl]-3-(difluoromethyl)-1-methyl-1H-pyrazole-4-carboxamide, (2.28) 5,8-difluoro-N-[2-(2-fluoro-4-{[4-(trifluoromethyl)pyridin-2-yl]oxy}phenyl)ethyl]quinazoline-4-amine, (2.29) benzovindiflupyr, (2.30) N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide and (2.31) N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide, (2.32) 3-(difluoromethyl)-1-methyl-N-(1,1,3-trimethyl-2,3-dihydro-1H-inden-4-yl)-1H-pyrazole-4-carboxamide, (2.33) 1,3,5-trimethyl-N-(1,1,3-trimethyl-2,3-dihydro-1H-inden-4-yl)-1H-pyrazole-4-carboxamide, (2.34) 1-methyl-3-(trifluoromethyl)-N-(1,1,3-trimethyl-2,3-dihydro-1H-inden-4-yl)-1H-pyrazole-4-carboxamide, (2.35) 1-methyl-3-(trifluoromethyl)-N-[(3R)-1,1,3-trimethyl-2,3-dihydro-1H-inden-4-yl]-1H-pyrazole-4-carboxamide, (2.36) 1-methyl-3-(trifluoromethyl)-N-[(3S)-1,1,3-trimethyl-2,3-dihydro-1H-inden-4-yl]-1H-pyrazole-4-carboxamide, (2.37) 3-(difluoromethyl)-1-methyl-N-[(3S)-1,1,3-trimethyl-2,3-dihydro-1H-inden-4-yl]-1H-pyrazole-4-carboxamide, (2.38) 3-(difluoromethyl)-1-methyl-N-[(3R)-1,1,3-trimethyl-2,3-dihydro-1H-inden-4-yl]-1H-pyrazole-4-carboxamide, (2.39) 1,3,5-trimethyl-N-[(3R)-1,1,3-trimethyl-2,3-dihydro-1H-inden-4-yl]-1H-pyrazole-4-carboxamide, (2.40) 1,3,5-trimethyl-N-[(3S)-1,1,3-trimethyl-2,3-dihydro-1H-inden-4-yl]-1H-pyrazole-4-carboxamide, (2.41) benodanil, (2.42) 2-chloro-N-(1,1,3-trimethyl-2,3-dihydro-1H-inden-4-yl)pyridine-3-carboxamide, (2.43) isofetamid (3) Respiration inhibitors (respiratory chain inhibitors) that act on complex III of the respiratory chain, for example (3.1) ametoctradin, (3.2) amisulbrom, (3.3) azoxystrobin, (3.4) cyazofamid, (3.5) coumethoxystrobin, (3.6) coumoxystrobin, (3.5) dimoxystrobin, (3.8) enestroburin, (3.9) famoxadone, (3.10) fenamidone, (3.11) flufenoxystrobin, (3.12) fluoxastrobin, (3.13) kresoxim-methyl, (3.14) metominostrobin, (3.15) orysastrobin, (3.16) picoxystrobin, (3.17) pyraclostrobin, (3.18) pyrametostrobin, (3.19) pyraoxystrobin, (3.20) pyribencarb, (3.21) triclopyricarb, (3.22) trifloxystrobin, (3.23) (2E)-2-(2-{[6-(3-chloro-2-methylphenoxy)-5-fluoropyrimidin-4-yl]oxy}phenyl)-2-(methoxyimino)-N-methylethanamide, (3.24) (2E)-2-(methoxyimino)-N-methyl-2-(2-{[({(1E)-1-[3-(trifluoromethyl)phenyl]ethylidene}amino)oxy]methyl}phenyl)ethanamide, (3.25) (2E)-2-(methoxyimino)-N-methyl-2-{2-[(E)-({1-[3-(trifluoromethyl)phenyl]ethoxy}imino)methyl]phenyl}ethanamide, (3.26) (2E)-2-{2-[({[(1E)-1-(3-{[(E)-1-fluoro-2-phenylethenyl]oxy}phenyl)ethylidene]amino}oxy)methyl]phenyl}-2-(methoxyimino)-N-methylethanamide, (3.27) (2E)-2-{2-[({[(2E,3E)-4-(2,6-dichlorophenyl)but-3-en-2-ylidene]amino}oxy)methyl]phenyl}-2-(methoxyimino)-N-methylethanamide, (3.28) 2-chloro-N-(1,1,3-trimethyl-2,3-dihydro-1H-inden-4-yl)pyridine-3-carboxamide, (3.29) 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, (3.30) methyl (2E)-2-{2-[({cyclopropyl[(4-methoxyphenyl)imino]methyl}sulphanyl)methyl]phenyl}-3-methoxyprop-2-enoate, (3.31) N-(3-ethyl-3,5,5-trimethylcyclohexyl)-3-(formylamino)-2-hydroxybenzamide, (3.32) 2-{2-[(2,5-dimethylphenoxy)methyl]phenyl}-2-methoxy-N-methylacetamide, (4) inhibitors of mitosis and cell division, for example (4.1) benomyl, (4.2) carbendazim, (4.3) chlorfenazole, (4.4) diethofencarb, (4.5) ethaboxam, (4.6) fluopicolid, (4.7) fuberidazole, (4.8) pencycuron, (4.9) thiabendazole, (4.10) thiophanate-methyl, (4.11) thiophanate, (4.12) zoxamide, (4.13) 5-chloro-7-(4-methylpiperidin-1-yl)-6-(2,4,6-trifluorophenyl)[1,2,4]triazolo[1,5-a]pyrimidine and (4.14) 3-chloro-5-(6-chloropyridin-3-yl)-6-methyl-4-(2,4,6-trifluorophenyl)pyridazine.

(5) Compounds having multisite activity, for example (5.1) Bordeaux mixture, (5.2) captafol, (5.3) captan, (5.4) chlorothalonil, (5.5) copper preparations such as copper hydroxide, (5.6) copper naphthenate, (5.7) copper oxide, (5.8) copper oxychloride, (5.9) copper sulphate, (5.10) dichlofluanid, (5.11) dithianon, (5.12) dodine, (5.13) dodine free base, (5.14) ferbam, (5.15) fluorfolpet, (5.16) folpet, (5.17) guazatine, (5.18) guazatine acetate, (5.19) iminoctadine, (5.20) iminoctadine albesilate, (5.21) iminoctadine triacetate, (5.22) mancopper, (5.23) mancozeb, (5.24) maneb, (5.25) metiram, (5.26) zinc metiram, (5.27) copper-oxine, (5.28) propamidine, (5.29) propineb, (5.30) sulphur and sulphur preparations, for example calcium polysulphide, (5.31) thiram, (5.32) tolylfluanid, (5.33) zineb, (5.34) ziram and (5.35) anilazine.

(6) Resistance inducers, for example (6.1) acibenzolar-S-methyl, (6.2) isotianil, (6.3) probenazole, (6.4) tiadinil and (6.5) laminarin.

(7) Amino acid and protein biosynthesis inhibitors, for example (7.1), (7.2) blasticidin-S, (7.3) cyprodinil, (7.4) kasugamycin, (7.5) kasugamycin hydrochloride hydrate, (7.6) mepanipyrim, (7.7) pyrimethanil, (7.8) 3-(5-fluoro-3,3,4,4-tetramethyl-3,4-dihydroisoquinolin-1-yl)quinoline and (7.9) oxytetracycline and (7.10) streptomycin.

(8) ATP production inhibitors, for example (8.1) fentin acetate, (8.2) fentin chloride, (8.3) fentin hydroxide and (8.4) silthiofam.

(9) Cell wall synthesis inhibitors, for example (9.1) benthiavalicarb, (9.2) dimethomorph, (9.3) flumorph, (9.4) iprovalicarb, (9.5) mandipropamid, (9.6) polyoxins, (9.7) polyoxorim, (9.8) validamycin A, (9.9) valifenalate and (9.10) polyoxin B.

(10) Lipid and membrane synthesis inhibitors, for example (10.1) biphenyl, (10.2) chlorneb, (10.3) dicloran, (10.4) edifenphos, (10.5) etridiazole, (10.6) iodocarb, (10.7) iprobenfos, (10.8) isoprothiolane, (10.9) propamocarb, (10.10) propamocarb hydrochloride, (10.11) prothiocarb, (10.12) pyrazophos, (10.13) quintozene, (10.14) tecnazene and (10.15) tolclofos-methyl.

(11) Melanin biosynthesis inhibitors, for example (11.1) carpropamid, (11.2) diclocymet, (11.3) fenoxanil, (11.4) fthalide, (11.5) pyroquilon, (11.6) tricyclazole and (11.7) 2,2,2-trifluoroethyl {3-methyl-1-[(4-methylbenzoyl)amino]butan-2-yl}carbamate.

(12) Nucleic acid synthesis inhibitors, for example (12.1) benalaxyl, (12.2) benalaxyl-M (kiralaxyl), (12.3) bupirimate, (12.4) clozylacon, (12.5) dimethirimol, (12.6) ethirimol, (12.7) furalaxyl, (12.8) hymexazole, (12.9) metalaxyl, (12.10) metalaxyl-M (mefenoxam), (12.11) ofurace, (12.12) oxadixyl, (12.13) oxolinic acid and (12.14) octhilinone.

(13) Signal transduction inhibitors, for example (13.1) chlozolinate, (13.2) fenpiclonil, (13.3) fludioxonil, (13.4) iprodione, (13.5) procymidone, (13.6) quinoxyfen, (13.7) vinclozolin and (13.8) proquinazid.

(14) Decouplers, for example (14.1) binapacryl, (14.2) dinocap, (14.3) ferimzone, (14.4) fluazinam and (14.5) mepthyldinocap.

(15) Further compounds, for example (15.1) benthiazole, (15.2) bethoxazine, (15.3) capsimycin, (15.4) carvone, (15.5) chinomethionat, (15.6) pyrifenone (chlazafenone), (15.7) cufraneb, (15.8) cyflufenamid, (15.9) cymoxanil, (15.10) cyprosulfamide, (15.11) dazomet, (15.12) debacarb, (15.13) dichlorophen, (15.14) diclomezine, (15.15) difenzoquat, (15.16) difenzoquat methylsulphate, (15.17) diphenylamine, (15.18) EcoMate, (15.19) fenpyrazamine, (15.20)

flumetover, (15.21) fluorimid, (15.22) flusulfamide, (15.23) flutianil, (15.24) fosetyl-aluminium, (15.25) fosetyl-calcium, (15.26) fosetyl-sodium, (15.27) hexachlorobenzene, (15.28) irumamycin, (15.29) methasulfocarb, (15.30) methyl isothiocyanate, (15.31) metrafenone, (15.32) mildiomycin, (15.33) natamycin, (15.34) nickel dimethyldithiocarbamate, (15.35) nitrothal-isopropyl, (15.36) octhilinone, (15.37) oxamocarb, (15.38) oxyfenthiin, (15.39) pentachlorophenol and its salts, (15.40) phenothrin, (15.41) phosphoric acid and its salts, (15.42) propamocarb-fosetylate, (15.43) propanosine-sodium, (15.44) pyrimorph, (15.45) (2E)-3-(4-tert-butylphenyl)-3-(2-chloropyridin-4-yl)-1-(morpholin-4-yl)prop-2-en-1-one, (15.46) (2Z)-3-(4-tert-butylphenyl)-3-(2-chloropyridin-4-yl)-1-(morpholin-4-yl)prop-2-en-1-one, (15.47) pyrrolnitrin, (15.48) tebufloquin, (15.49) tecloftalam, (15.50) tolnifanide, (15.51) triazoxide, (15.52) trichlamide, (15.53) zarilamid, (15.54) (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate, (15.55) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.56) 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.57) 1-(4-{4-[5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.58) 1-(4-methoxyphenoxy)-3,3-dimethylbutan-2-yl 1H-imidazole-1-carboxylate, (15.59) 2,3,5,6-tetrachloro-4-(methylsulphonyl)pyridine, (15.60) 2,3-dibutyl-6-chlorothieno[2,3-d]pyrimidin-4(3H)-one, (15.61) 2,6-dimethyl-1H,5H-[1,4]dithiino[2,3-c:5,6-c']dipyrrole-1,3,5,7(2H,6H)-tetrone, (15.62) 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone, (15.63) 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone, (15.64) 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone, (15.65) 2-butoxy-6-iodo-3-propyl-4H-chromen-4-one, (15.66) 2-chloro-5-[2-chloro-1-(2,6-difluoro-4-methoxyphenyl)-4-methyl-1H-imidazol-5-yl] pyridine, (15.67) 2-phenylphenol and salts, (15.68) 3-(4,4,5-trifluoro-3,3-dimethyl-3,4-dihydroisoquinolin-1-yl) quinoline, (15.69) 3,4,5-trichloropyridine-2,6-dicarbonitrile, (15.70) 3-chloro-5-(4-chlorophenyl)-4-(2,6-difluorophenyl)-6-methylpyridazine, (15.71) 4-(4-chlorophenyl)-5-(2,6-difluorophenyl)-3,6-dimethylpyridazine, (15.72) 5-amino-1,3,4-thiadiazole-2-thiol, (15.73) 5-chloro-N'-phenyl-N'-(prop-2-yn-1-yl)thiophene-2-sulphonohydrazide, (15.74) 5-fluoro-2-[(4-fluorobenzyl)oxy]pyrimidine-4-amine, (15.75) 5-fluoro-2-[(4-methylbenzyl)oxy]pyrimidine-4-amine, (15.76) 5-methyl-6-octyl[1,2,4]triazolo[1,5-a]pyrimidine-7-amine, (15.77) ethyl (2Z)-3-amino-2-cyano-3-phenylacrylate, (15.78) N'-(4-{[3-(4-chlorobenzyl)-1,2,4-thiadiazol-5-yl]oxy}-2,5-dimethylphenyl)-N-ethyl-N-methylimidoformamide, (15.79) N-(4-chlorobenzyl)-3-[3-methoxy-4-(prop-2-yn-1-yloxy)phenyl]propanamide, (15.80) N-[(4-chlorophenyl)(cyano)methyl]-3-[3-methoxy-4-(prop-2-yn-1-yloxy)phenyl]propanamide, (15.81) N-[(5-bromo-3-chloropyridin-2-yl)methyl]-2,4-dichlorobenzamide, (15.82) N-[1-(5-bromo-3-chloropyridin-2-yl)ethyl]-2,4-dichloronicotinamide, (15.83) N-[1-(5-bromo-3-chloropyridin-2-yl)ethyl]-2-fluoro-4-iodonicotinamide, (15.84) N-{(E)-[(cyclopropylmethoxy)imino][6-(difluoromethoxy)-2,3-difluorophenyl]methyl}-2-phenylacetamide, (15.85) N-{(Z)-[(cyclopropylmethoxy)imino][6-(difluoromethoxy)-2,3-difluorophenyl]methyl}-2-phenylacetamide, (15.86) N'-{4-[(3-tert-butyl-4-cyano-1,2-thiazol-5-yl)oxy]-2-chloro-5-methylphenyl}-N-ethyl-N-methylimidoformamide, (15.87) N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide, (15.88) N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide, (15.89) N-methyl-2-(1-{[5-methyl-3-(trifluoromethyl)-1H-pyrazol-1-yl]acetyl}piperidin-4-yl)-N-[(1 S)-1,2,3,4-tetrahydronaphthalen-1-yl]-1,3-thiazole-4-carboxamide, (15.90) pentyl {6-[({[(1-methyl-1H-tetrazol-5-yl)(phenyl)methylene]amino}oxy)methyl]pyridin-2-yl}carbamate, (15.91) phenazine-1-carboxylic acid, (15.92) quinolin-8-ol, (15.93) quinolin-8-ol sulphate (2:1), (15.94) tert-butyl {6-[({[(1-methyl-1H-tetrazol-5-yl)(phenyl)methylene]amino}oxy)methyl]pyridin-2-yl}carbamate, (15.95) 1-methyl-3-(trifluoromethyl)-N-[2'-(trifluoromethyl)biphenyl-2-yl]-1H-pyrazole-4-carboxamide, (15.96) N-(4'-chlorobiphenyl-2-yl)-3-(difluoromethyl)-1-methyl-1H-pyrazole-4-carboxamide, (15.97) N-(2',4'-dichlorobiphenyl-2-yl)-3-(difluoromethyl)-1-methyl-1H-pyrazole-4-carboxamide, (15.98) 3-(difluoromethyl)-1-methyl-N-[4'-(trifluoromethyl)biphenyl-2-yl]-1H-pyrazole-4-carboxamide, (15.99) N-(2',5'-difluorobiphenyl-2-yl)-1-methyl-3-(trifluoromethyl)-1H-pyrazole-4-carboxamide, (15.100) 3-(difluoromethyl)-1-methyl-N-[4'-(prop-1-yn-1-yl)biphenyl-2-yl]-1H-pyrazole-4-carboxamide, (15.101) 5-fluoro-1,3-dimethyl-N-[4'-(prop-1-yn-1-yl)biphenyl-2-yl]-1H-pyrazole-4-carboxamide, (15.102) 2-chloro-N-[4'-(prop-1-yn-1-yl)biphenyl-2-yl]nicotinamide, (15.103) 3-(difluoromethyl)-N-[4'-(3,3-dimethylbut-1-yn-1-yl)biphenyl-2-yl]-1-methyl-1H-pyrazole-4-carboxamide, (15.104) N-[4'-(3,3-dimethylbut-1-yn-1-yl)biphenyl-2-yl]-5-fluoro-1,3-dimethyl-1H-pyrazole-4-carboxamide, (15.105) 3-(difluoromethyl)-N-(4'-ethynylbiphenyl-2-yl)-1-methyl-1H-pyrazole-4-carboxamide, (15.106) N-(4'-ethynylbiphenyl-2-yl)-5-fluoro-1,3-dimethyl-1H-pyrazole-4-carboxamide, (15.107) 2-chloro-N-(4'-ethynylbiphenyl-2-yl)nicotinamide, (15.108) 2-chloro-N-[4'-(3,3-dimethylbut-1-yn-1-yl)biphenyl-2-yl]nicotinamide, (15.109) 4-(difluoromethyl)-2-methyl-N-[4'-(trifluoromethyl)biphenyl-2-yl]-1,3-thiazole-5-carboxamide, (15.110) 5-fluoro-N-[4'-(3-hydroxy-3-methylbut-1-yn-1-yl)biphenyl-2-yl]-1,3-dimethyl-1H-pyrazole-4-carboxamide, (15.111) 2-chloro-N-[4'-(3-hydroxy-3-methylbut-1-yn-1-yl)biphenyl-2-yl] nicotinamide, (15.112) 3-(difluoromethyl)-N-[4'-(3-methoxy-3-methylbut-1-yn-1-yl)biphenyl-2-yl]-1-methyl-1H-pyrazole-4-carboxamide, (15.113) 5-fluoro-N-[4'-(3-methoxy-3-methylbut-1-yn-1-yl)biphenyl-2-yl]-1,3-dimethyl-1H-pyrazole-4-carboxamide, (15.114) 2-chloro-N-[4'-(3-methoxy-3-methylbut-1-yn-1-yl)biphenyl-2-yl] nicotinamide, (15.115) (5-bromo-2-methoxy-4-methylpyridin-3-yl)(2,3,4-trimethoxy-6-methylphenyl) methanone, (15.116) N-[2-(4-{[3-(4-chlorophenyl)prop-2-yn-1-yl]oxy}-3-methoxyphenyl)ethyl]-N2-(methylsulphonyl)valinamide, (15.117) 4-oxo-4-[(2-phenylethyl)amino]butanoic acid, (15.118) but-3-yn-1-yl {6-[({[(Z)-(1-methyl-1H-tetrazol-5-yl)(phenyl)methylene] amino}oxy)methyl]pyridin-2-yl}carbamate, (15.119) 4-amino-5-fluoropyrimidin-2-ol (tautomeric form: 4-amino-5-fluoropyrimidin-2(1H)-one), (15.120) propyl 3,4,5-trihydroxybenzoate, (15.121) 1,3-dimethyl-N-(1,1,3-trimethyl-2, 3-dihydro-1H-inden-4-yl)-1H-pyrazole-4-carboxamide, (15.122) 1,3-dimethyl-N-[(3R)-1,1,3-trimethyl-2,3-dihydro-1H-inden-4-yl]-1H-pyrazole-4-carboxamide, (15.123) 1,3-dimethyl-N-[(3S)-1,1,3-trimethyl-2,3-dihydro-1H-inden-4-yl]-1H-pyrazole-4-carboxamide, (15.124) [3-(4-chloro-2-fluorophenyl)-5-(2,4-difluorophenyl)-1,2-oxazol-4-yl](pyridin-3-yl)methanol, (15.125) (S)-[3-(4-chloro-2-fluorophenyl)-5-(2,4-difluorophenyl)-1,2-oxazol-4-yl](pyridin-3-yl)methanol, (15.126) (R)-[3-(4-chloro-2-fluorophenyl)-5-(2,4-difluorophenyl)-1,2-oxazol-4-yl](pyridin-3-yl)methanol, (15.127) 2-{[3-(2-chlorophenyl)-2-(2,4-difluorophenyl)oxiran-2-yl]methyl}-2,4-dihydro-3H-1,2,4-triazole-3-thione, (15.128) 1-{[3-(2-chlorophenyl)-2-(2,4-difluorophenyl)oxiran-2-yl]methyl}-1H-1,2,4-triazol-5-yl thiocyanate, (15.129) 5-(allylsulphanyl)-1-{[3-(2-chlorophenyl)-2-(2,4-difluorophenyl)oxiran-2-yl]methyl}-1H-1,2,4-triazole, (15.130) 2-[1-(2,4-dichlorophenyl)-5-hydroxy-2,6,6-trimethylheptan-4-yl]-2,4-dihydro-3H-1,2,4-triazole-3-thione, (15.131) 2-{[rel(2R,3S)-3-(2-chlorophenyl)-2-(2,4-difluorophenyl)oxiran-2-yl]methyl}-2,4-dihydro-3H-1,2,4-triazole-3-thione, (15.132) 2-{[rel(2R,3R)-3-(2-chlorophenyl)-2-(2,4-difluorophenyl)oxiran-2-yl]methyl}-2,4-dihydro-3H-1,2,4-triazole-3-thione, (15.133) 1-{[rel(2R,3S)-3-(2-chlorophenyl)-2-(2,4-difluorophenyl)oxiran-2-yl]methyl}-1H-1,2,4-triazol-5-yl thiocyanate, (15.134) 1-{[rel(2R,3R)-3-(2-chlorophenyl)-2-(2,4-difluorophenyl)oxiran-2-yl]methyl}-1H-1,2,4-triazol-5-yl thiocyanate, (15.135) 5-(allylsulphanyl)-1-{[rel(2R,3S)-3-(2-chlorophenyl)-2-(2,4-difluorophenyl)oxiran-2-yl]methyl}-1H-,2,4-triazole, (15.136) 5-(allylsulphanyl)-1-{[rel(2R,3R)-3-(2-chlorophenyl)-2-(2,4-difluorophenyl)oxiran-2-yl]methyl}-1H-1,2,4-triazole, (15.137) 2-[(2S,4S,5S)-1-(2,4-dichlorophenyl)-5-hydroxy-2,6,6-trimethylheptan-4-yl]-2,4-dihydro-3H-1,2,4-triazole-3-thione, (15.138) 2-[(2R,4S,5S)-1-(2,4-dichlorophenyl)-5-hydroxy-2,6,6-trimethylheptan-4-yl]-2,4-dihydro-3H-1,2,4-triazole-3-thione, (15.139) 2-[(2R,4R,5R)-1-(2,4-dichlorophenyl)-5-hydroxy-2,6,6-trimethylheptan-4-yl]-2,4-dihydro-3H-1,2,4-triazole-3-thione, (15.140) 2-[(2S,4R,5R)-1-(2,4-dichlorophenyl)-5-hydroxy-2,6,6-trimethylheptan-4-yl]-2,4-dihydro-3H-1,2,4-triazole-3-thione, (15.141) 2-[(2S,4S,5R)-1-(2,4-dichlorophenyl)-5-hydroxy-2,6,6-trimethylheptan-4-yl]-2,4-dihydro-3H-1,2,4-triazole-3-thione, (15.142) 2-[(2R,4S,5R)-1-(2,4-dichlorophenyl)-5-hydroxy-2,6,6-trimethylheptan-4-yl]-2,4-dihydro-3H-1,2,4-triazole-3-thione, (15.143) 2-[(2R,4R,5S)-1-(2,4-dichlorophenyl)-5-hydroxy-2,6,6-trimethylheptan-4-yl]-2,4-dihydro-3H-1,2,4-triazole-3-thione, (15.144) 2-[(2S,4R,5S)-1-(2,4-dichlorophenyl)-5-hydroxy-2,6,6-trimethylheptan-4-yl]-2,4-dihydro-3H-1,2,4-triazole-3-thione, (15.145) 2-fluoro-6-(trifluoromethyl)-N-(1,1,3-trimethyl-2,3-dihydro-1H-inden-4-yl)benzamide, (15.146) 2-(6-benzylpyridin-2-yl)quinazoline, (15.147) 2-[6-(3-fluoro-4-methoxyphenyl)-5-methylpyridin-2-yl]quinazoline, (15.148) 3-(4,4-difluoro-3,3-dimethyl-3,4-dihydroisoquinolin-1-yl)quinoline, (15.149) abscisic acid, (15.150) 3-(difluoromethyl)-N-methoxy-1-methyl-N-[1-(2,4,6-trichlorophenyl)propan-2-yl]-1H-pyrazole-4-carboxamide, (15.151) N'-[5-bromo-6-(2,3-dihydro-1H-inden-2-yloxy)-2-methylpyridin-3-yl]-N-ethyl-N-methylimidoformamide, (15.152) N'-{5-bromo-6-[1-(3,5-difluorophenyl)ethoxy]-2-methylpyridin-3-yl}-N-ethyl-N-methylimidoformamide, (15.153) N'-{5-bromo-6-[(1R)-1-(3,5-difluorophenyl)ethoxy]-2-methylpyridin-3-yl}-N-ethyl-N-methylimidoformamide, (15.154) N'-{5-bromo-6-[(1S)-1-(3,5-difluorophenyl)ethoxy]-2-methylpyridin-3-yl}-N-ethyl-N-methylimidoformamide, (15.155) N'-{5-bromo-6-[(cis-4-isopropylcyclohexyl)oxy]-2-methylpyridin-3-yl}-N-ethyl-N-methylimidoformamide, (15.156) N'-{5-bromo-6-[(trans-4-isopropylcyclohexyl)oxy]-2-methylpyridin-3-yl}-N-ethyl-N-methylimidoformamide, (15.157) N-cyclopropyl-3-(difluoromethyl)-5-fluoro-N-(2-isopropylbenzyl)-1-methyl-1H-pyrazole-4-carboxamide, (15.158) N-cyclopropyl-N-(2-cyclopropylbenzyl)-3-(difluoromethyl)-5-fluoro-1-methyl-1H-pyrazole-4-carboxamide, (15.159) N-(2-tert-butylbenzyl)-N-cyclopropyl-3-(difluoromethyl)-5-fluoro-1-methyl-1H-pyrazole-4-carboxamide, (15.160) N-(5-chloro-2-ethylbenzyl)-N-cyclopropyl-3-(difluoromethyl)-5-fluoro-1-methyl-1H-pyrazole-4-carboxamide, (15.161) N-(5-chloro-2-isopropylbenzyl)-N-cyclopropyl-3-(difluoromethyl)-5-fluoro-1-methyl-1H-pyrazole-4-carboxamide, (15.162) N-cyclopropyl-3-(difluoromethyl)-N-(2-ethyl-5-fluorobenzyl)-5-fluoro-1-methyl-1H-pyrazole-4-carboxamide, (15.163) N-cyclopropyl-3-(difluoromethyl)-5-fluoro-N-(5-fluoro-2-isopropylbenzyl)-1-methyl-1H-pyrazole-4-carboxamide, (15.164) N-cyclopropyl-N-(2-cyclopropyl-5-fluorobenzyl)-3-(difluoromethyl)-5-fluoro-1-methyl-1H-pyrazole-4-carboxamide, (15.165) N-(2-cyclopentyl-5-fluorobenzyl)-N-cyclopropyl-3-(difluoromethyl)-5-fluoro-1-methyl-1H-pyrazole-4-carboxamide, (15.166) N-cyclopropyl-3-(difluoromethyl)-5-fluoro-N-(2-fluoro-6-isopropylbenzyl)-1-methyl-1H-pyrazole-4-carboxamide, (15.167) N-cyclopropyl-3-(difluoromethyl)-N-(2-ethyl-5-methylbenzyl)-5-fluoro-1-methyl-1H-pyrazole-4-carboxamide, (15.168) N-cyclopropyl-3-(difluoromethyl)-5-fluoro-N-(2-isopropyl-5-methylbenzyl)-1-methyl-1H-pyrazole-4-carboxamide, (15.169) N-cyclopropyl-N-(2-cyclopropyl-5-methylbenzyl)-3-(difluoromethyl)-5-fluoro-1-methyl-1H-pyrazole-4-carboxamide, (15.170) N-(2-tert-butyl-5-methylbenzyl)-N-cyclopropyl-3-(difluoromethyl)-5-fluoro-1-methyl-1H-pyrazole-4-carboxamide, (15.171) N-[5-chloro-2-(trifluoromethyl)benzyl]-N-cyclopropyl-3-(difluoromethyl)-5-fluoro-1-methyl-1H-pyrazole-4-carboxamide, (15.172) N-cyclopropyl-3-(difluoromethyl)-5-fluoro-1-methyl-N-[5-methyl-2-(trifluoromethyl)benzyl]-1H-pyrazole-4-carboxamide, (15.173) N-[2-chloro-6-(trifluoromethyl)benzyl]-N-cyclopropyl-3-(difluoromethyl)-5-fluoro-1-methyl-1H-pyrazole-4-carboxamide, (15.174) N-[3-chloro-2-fluoro-6-(trifluoromethyl)benzyl]-N-cyclopropyl-3-(difluoromethyl)-5-fluoro-1-methyl-1H-pyrazole-4-carboxamide, (15.175) N-cyclopropyl-3-(difluoromethyl)-N-(2-ethyl-4,5-dimethylbenzyl)-5-fluoro-1-methyl-1H-pyrazole-4-carboxamide, (15.176) N-cyclopropyl-3-(difluoromethyl)-5-fluoro-N-(2-isopropylbenzyl)-1-methyl-1H-pyrazol-4-carbothioamide, (15.177) 3-(difluoromethyl)-N-(7-fluoro-1,1,3-trimethyl-2,3-dihydro-1H-inden-4-yl)-1-methyl-1H-pyrazole-4-carboxamide, (15.178) 3-(difluoromethyl)-N-[(3R)-7-fluoro-1,1,3-trimethyl-2,3-dihydro-1H-inden-4-yl]-1-methyl-1H-pyrazole-4-carboxamide, (15.179) 3-(difluoromethyl)-N-[(3S)-7-fluoro-1,1,3-trimethyl-2,3-dihydro-1H-inden-4-yl]-1-methyl-1H-pyrazole-4-carboxamide, (15.180) N'-(2,5-dimethyl-4-phenoxyphenyl)-N-ethyl-N-methylimidoformamide, (15.181) N'-{4-[(4,5-dichloro-1,3-thiazol-2-yl)oxy]-2,5-dimethylphenyl}-N-ethyl-N-methylimidoformamide, (15.182) N-(4-chloro-2,6-difluorophenyl)-4-(2-chloro-4-fluorophenyl)-1,3-dimethyl-1H-pyrazol-5-amine. All the mixing partners mentioned in classes (1) to (15), as the case may be, may form salts with suitable bases or acids if they are capable of doing so on the basis of their functional groups.

Biological Pesticides as Mixing Components

The compounds of the formula (I) can be combined with biological pesticides.

Biological pesticides include especially bacteria, fungi, yeasts, plant extracts and products formed by microorganisms, including proteins and secondary metabolites.

Biological pesticides include bacteria such as spore-forming bacteria, root-colonizing bacteria and bacteria which act as biological insecticides, fungicides or nematicides.

Examples of such bacteria which are used or can be used as biological pesticides are:
*Bacillus amyloliquefaciens*, strain FZB42 (DSM 231179), or *Bacillus cereus*, especially *B. cereus* strain CNCM 1-1562 or *Bacillus firmus*, strain 1-1582 (Accession number CNCM 1-1582) or *Bacillus pumilus*, especially strain GB34 (Accession No. ATCC 700814) and strain QST2808 (Accession No. NRRL B-30087), or *Bacillus subtilis*, especially strain GB03 (Accession No. ATCC SD-1397), or *Bacillus subtilis* strain QST713 (Accession No. NRRL B-21661) or *Bacillus subtilis* strain OST 30002 (Accession No. NRRL B-50421) *Bacillus thuringiensis*, especially *B. thuringiensis* subspecies *israelensis* (serotype H-14), strain AM65-52 (Accession No. ATCC 1276), or *B. thuringiensis* subsp. *aizawai*, especially strain ABTS-1857 (SD-1372), or *B. thuringiensis* subsp. *kurstaki* strain HD-1, or *B. thuringiensis* subsp. *tenebrionis* strain NB 176 (SD-5428), *Pasteuria penetrans, Pasteuria* spp. (*Rotylenchulus reniformis* nematode)-PR3 (Accession Number ATCC SD-5834), *Streptomyces microflavus* strain AQ6121 (=QRD 31.013, NRRL B-50550), *Streptomyces galbus* strain AQ 6047 (Accession Number NRRL 30232).

Examples of fungi and yeasts which are used or can be used as biological pesticides are:
*Beauveria bassiana*, especially strain ATCC 74040, *Coniothyrium minitans*, especially strain CON/M/91-8 (Accession No. DSM-9660), *Lecanicillium* spp., especially strain HRO LEC 12, *Lecanicillium lecanii*, (formerly known as *Verticillium lecanii*), especially strain KV01, *Metarhizium anisopliae*, especially strain F52 (DSM3884/ATCC 90448), *Metschnikowia fructicola*, especially strain NRRL Y-30752, *Paecilomyces fumosoroseus* (now: *Isaria fumosorosea*), especially strain IFPC 200613, or strain Apopka 97 (Accesion No. ATCC 20874), *Paecilomyces lilacinus*, especially *P. lilacinus* strain 251 (AGAL 89/030550), *Talaromyces flavus*, especially strain V117b, *Trichoderma atroviride*, especially strain SC1 (Accession Number CBS 122089), *Trichoderma harzianum*, especially *T. harzianum rifai* T39 (Accession Number CNCM 1-952).

Examples of viruses which are used or can be used as biological pesticides are:
*Adoxophyes orana* (summer fruit *tortrix*) granulosis virus (GV), *Cydia pomonella* (codling moth) granulosis virus (GV), *Helicoverpa armigera* (cotton bollworm) nuclear polyhedrosis virus (NPV), *Spodoptera exigua* (beet armyworm) mNPV, *Spodoptera frugiperda* (fall armyworm) mNPV, *Spodoptera littoralis* (African cotton leafworm) NPV.

Also included are bacteria and fungi which are added as 'inoculant' to plants or plant parts or plant organs and which, by virtue of their particular properties, promote plant growth and plant health. Examples include:
*Agrobacterium* spp., *Azorhizobium caulinodans, Azospirillum* spp., *Azotobacter* spp., *Bradyrhizobium* spp., *Burkholderia* spp., especially *Burkholderia cepacia* (formerly known as *Pseudomonas cepacia*), *Gigaspora* spp., or *Gigaspora monosporum, Glomus* spp., *Laccaria* spp., *Lactobacillus buchneri, Paraglomus* spp., *Pisolithus tinctorus, Pseudomonas* spp., *Rhizobium* spp., especially *Rhizobium trifolii, Rhizopogon* spp., *Scleroderma* spp., *Suillus* spp., *Streptomyces* spp.

Safeners as Mixing Components

The compounds of the formula (I) can be combined with safeners, for example benoxacor, cloquintocet (-mexyl), cyometrinil, cyprosulfamide, dichlormid, fenchlorazole (-ethyl), fenclorim, flurazole, fluxofenim, furilazole, isoxadifen (-ethyl), mefenpyr (-diethyl), naphthalic anhydride, oxabetrinil, 2-methoxy-N-({4-[(methylcarbamoyl)amino]phenyl}sulphonyl)benzamide (CAS 129531-12-0), 4-(dichloroacetyl)-1-oxa-4-azaspiro[4.5]decane (CAS 71526-07-3), 2,2,5-trimethyl-3-(dichloroacetyl)-1,3-oxazolidine (CAS 52836-31-4).

Plants and Parts of Plants

All plants and parts of plants can be treated in accordance with the invention. Plants are understood here to mean all plants and populations of plants, such as desirable and undesirable wild plants or crop plants (including naturally occurring crop plants), for example cereals (wheat, rice, triticale, barley, rye, oats), maize, soya bean, potato, sugar beet, sugar cane, tomatoes, peas and other vegetable species, cotton, tobacco, oilseed rape, and also fruit plants (with the fruits apples, pears, citrus fruits and grapevines). Crop plants may be plants which can be obtained by conventional breeding and optimization methods or by biotechnological and genetic engineering methods or combinations of these methods, including the transgenic plants and including the plant cultivars which are protectable and non-protectable by plant breeders' rights. Parts of plants shall be understood to mean all parts and organs of the plants above and below ground, such as shoot, leaf, flower and root, examples given being leaves, needles, stalks, stems, flowers, fruit bodies, fruits and seeds, and also tubers, roots and rhizomes. Parts of plants also include harvested material and vegetative and generative propagation material, for example cuttings, tubers, rhizomes, slips and seeds.

The inventive treatment of the plants and parts of plants with the compounds of the formula (I) is effected directly or by allowing them to act on the surroundings, habitat or storage space thereof by the customary treatment methods, for example by dipping, spraying, evaporating, fogging, scattering, painting on, injecting, and, in the case of propagation material, especially in the case of seeds, also by applying one or more coats.

As already mentioned above, it is possible in accordance with the invention to treat all plants and parts thereof. In a preferred embodiment, wild plant species and plant cultivars, or those obtained by conventional biological breeding, such as crossing or protoplast fusion, and parts thereof, are treated. In a further preferred embodiment, transgenic plants and plant cultivars obtained by genetic engineering methods, if appropriate in combination with conventional methods (genetically modified organisms), and parts thereof are treated. The term "parts" or "parts of plants" or "plant parts" has been explained above. Particular preference is given in accordance with the invention to treating plants of the respective commercially customary cultivars or those that are in use. Plant cultivars are understood to mean plants having new properties ("traits") and which have been obtained by conventional breeding, by mutagenesis or by recombinant DNA techniques. They may be cultivars, varieties, biotypes or genotypes.

Transgenic Plants, Seed Treatment and Integration Events

The preferred transgenic plants or plant cultivars (those obtained by genetic engineering) which are to be treated in accordance with the invention include all plants which, through the genetic modification, received genetic material which imparts particular advantageous useful traits to these plants. Examples of such properties are better plant growth, increased tolerance to high or low temperatures, increased tolerance to drought or to levels of water or soil salinity, enhanced flowering performance, easier harvesting, accelerated ripening, higher yields, higher quality and/or higher nutritional value of the harvested products, better storage life and/or processibility of the harvested products. Further and particularly emphasized examples of such properties are increased resistance of the plants against animal and microbial pests, such as against insects, arachnids, nematodes, mites, slugs and snails owing, for example, to toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c Cry2Ab, Cry3Bb and CryIF and also combinations thereof), and also increased resistance of the plants against phytopathogenic fungi, bacteria and/or viruses caused, for example, by systemic acquired resistance (SAR), systemin, phytoalexins, elicitors and resistance genes and correspondingly expressed proteins and toxins, and also increased tolerance of the plants to certain active herbicidal ingredients, for example imidazolinones, sulphonylureas, glyphosate or phosphinothricin (for example the "PAT" gene). The genes which impart the desired traits in question may also be present in combinations with one another in the transgenic plants. Examples of transgenic plants include the important crop plants, such as cereals (wheat, rice, triticale, barley, rye, oats), maize, soya beans, potatoes, sugar beet, sugar cane, tomatoes, peas and other types of vegetable, cotton, tobacco, oilseed rape and also fruit plants (with the fruits apples, pears, citrus fruits and grapes), particular emphasis being given to maize, soya beans, wheat, rice, potatoes, cotton, sugar cane, tobacco and oilseed rape. Traits which are particularly emphasized are the increased resistance of the plants to insects, arachnids, nematodes and slugs and snails.

Crop Protection—Types of Treatment

The treatment of the plants and plant parts with the compounds of the formula (I) is effected directly or by action on their surroundings, habitat or storage space by the customary treatment methods, for example by dipping, spraying, atomizing, irrigating, evaporating, dusting, fogging, broadcasting, foaming, painting, spreading-on, injecting, watering (drenching), drip irrigating and, in the case of propagation material, especially in the case of seed, also by dry seed treatment, wet seed treatment, slurry treatment, incrustation, coating with one or more coats, etc. It is also possible to deploy the compounds of the formula (I) by the ultra-low volume method or to inject the use form or the compound of the formula (I) itself into the soil.

A preferred direct treatment of the plants is foliar application, meaning that the compounds of the formula (I) are applied to the foliage, where treatment frequency and application rate should be adjusted according to the level of infestation with the pest in question.

In the case of systemically active compounds, the compounds of the formula (I) also get into the plants via the root system. The plants are then treated by the action of the compounds of the formula (I) on the habitat of the plant. This can be accomplished, for example, by drenching, or by mixing into the soil or the nutrient solution, meaning that the locus of the plant (e.g. soil or hydroponic systems) is impregnated with a liquid form of the compounds of the formula (I), or by soil application, meaning that the compounds of the formula (I) are introduced in solid form (e.g. in the form of granules) into the locus of the plants. In the case of paddy rice crops, this can also be accomplished by metering the compound of the formula (I) in a solid application form (for example as granules) into a flooded paddy field.

Seed Treatment

The control of animal pests by the treatment of the seed of plants has long been known and is the subject of constant improvement. However, the treatment of seed entails a series of problems which cannot always be solved in a satisfactory manner. Thus, it is desirable to develop methods for protecting the seed and the germinating plant which dispense with, or at least reduce considerably, the additional application of pesticides during storage, after sowing or after emergence of the plants. It is additionally desirable to optimize the amount of active ingredient used so as to provide optimum protection for the seed and the germinating plant from attack by animal pests, but without damage to the plant itself by the active ingredient used. In particular, methods for the treatment of seed should also take account of the intrinsic insecticidal or nematicidal properties of pest-resistant or -tolerant transgenic plants in order to achieve optimal protection of the seed and the germinating plant with a minimum expenditure of crop protection products.

The present invention therefore also relates, more particularly, to a method for protection of seed and germinating plants from attack by pests, by treating the seed with one of the compounds of the formula (I). The inventive method for protecting seed and germinating plants against attack by pests further comprises a method in which the seed is treated simultaneously in one operation or sequentially with a compound of the formula (I) and a mixing component. It also comprises a method where the seed is treated at different times with a compound of the formula (I) and a mixing component.

The invention likewise relates to the use of the compounds of the formula (I) for treatment of seed for protection of the seed and the resulting plant from animal pests.

The invention further relates to seed which has been treated with a compound of the formula (I) for protection from animal pests. The invention also relates to seed which has been treated simultaneously with a compound of the formula (I) and a mixing component. The invention further relates to seed which has been treated at different times with a compound of the formula (I) and a mixing component. In the case of seed which has been treated at different times with a compound of the formula (I) and a mixing component, the individual substances may be present on the seed in different layers. In this case, the layers comprising a compound of the formula (I) and mixing components may optionally be separated by an intermediate layer. The invention also relates to seed in which a compound of the formula (I) and a mixing component have been applied as part of a coating or as a further layer or further layers in addition to a coating.

The invention further relates to seed which, after the treatment with a compound of the formula (I), is subjected to a film-coating process to prevent dust abrasion on the seed.

One of the advantages that occur when one of the compounds of the formula (I) acts systemically is that the treatment of the seed protects not only the seed itself but also the plants resulting therefrom, after emergence, from animal pests. In this way, the immediate treatment of the crop at the time of sowing or shortly thereafter can be dispensed with.

A further advantage is that the treatment of the seed with a compound of the formula (I) can enhance germination and emergence of the treated seed.

It is likewise considered to be advantageous that compounds of the formula (I) can especially also be used for transgenic seed.

Compounds of the formula (I) can also be used in combination with signalling technology compositions, which results, for example, in better colonization by symbionts, for example *rhizobia*, mycorrhizae and/or endophytic bacteria or fungi, and/or in optimized nitrogen fixation.

The compounds of the formula (I) are suitable for protection of seed of any plant variety which is used in agriculture, in the greenhouse, in forests or in horticulture. More particularly, this includes seed of cereals (for example wheat, barley, rye, millet and oats), corn, cotton, soya beans, rice, potatoes, sunflowers, coffee, tobacco, canola, oilseed rape, beets (for example sugarbeets and fodder beets), peanuts, vegetables (for example tomatoes, cucumbers, beans, cruciferous vegetables, onions and lettuce), fruit plants, lawns and ornamental plants. Of particular significance is the treatment of the seed of cereals (such as wheat, barley, rye and oats), maize, soya, cotton, canola, oilseed rape and rice.

As already mentioned above, the treatment of transgenic seed with a compound of the formula (I) is also of particular significance. This involves the seed of plants which generally contain at least one heterologous gene which controls the expression of a polypeptide having insecticidal and/or nematicidal properties in particular. The heterologous genes in transgenic seed may originate from microorganisms such as *Bacillus, Rhizobium, Pseudomonas, Serratia, Trichoderma,* Clavibacter, *Glomus* or *Gliocladium*. The present invention is particularly suitable for the treatment of transgenic seed containing at least one heterologous gene originating from *Bacillus* sp. The heterologous gene is more preferably derived from *Bacillus thuringiensis*.

In the context of the present invention, the compound of the formula (I) is applied to the seed. The seed is preferably treated in a state in which it is sufficiently stable for no damage to occur in the course of treatment. In general, the seed can be treated at any time between harvest and sowing. It is customary to use seed which has been separated from the plant and freed from cobs, shells, stalks, coats, hairs or the flesh of the fruits. For example, it is possible to use seed which has been harvested, cleaned and dried down to a moisture content which allows storage. Alternatively, it is also possible to use seed which, after drying, has been treated with, for example, water and then dried again, for example priming.

In general, in the treatment of the seed, it has to be ensured that the amount of the compound of the formula (I) and/or further additives applied to the seed is chosen such that the germination of the seed is not impaired and the plant which arises therefrom is not damaged. This has to be ensured particularly in the case of active ingredients which can exhibit phytotoxic effects at certain application rates.

The compounds of the formula (I) are generally applied to the seed in a suitable formulation. Suitable formulations and processes for seed treatment are known to the person skilled in the art.

The compounds of the formula (I) can be converted to the customary seed dressing formulations, such as solutions, emulsions, suspensions, powders, foams, slurries or other coating compositions for seed, and also ULV formulations.

These formulations are produced in a known manner, by mixing the compounds of the formula (I) with customary additives, for example customary extenders and solvents or diluents, dyes, wetters, dispersants, emulsifiers, antifoams, preservatives, secondary thickeners, stickers, gibberellins and also water.

Useful dyes which may be present in the seed dressing formulations usable in accordance with the invention are all dyes which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Useful wetters which may be present in the seed dressing formulations usable in accordance with the invention are all substances which promote wetting and which are conventionally used for the formulation of active agrochemical ingredients. Preference is given to using alkyl naphthalenesulphonates, such as diisopropyl or diisobutyl naphthalenesulphonates.

Useful dispersants and/or emulsifiers which may be present in the seed dressing formulations usable in accordance with the invention are all nonionic, anionic and cationic dispersants conventionally used for the formulation of active agrochemical ingredients. Preference is given to using nonionic or anionic dispersants or mixtures of nonionic or anionic dispersants. Suitable nonionic dispersants include in particular ethylene oxide/propylene oxide block polymers, alkylphenol polyglycol ethers and tristryrylphenol polyglycol ethers, and the phosphated or sulphated derivatives thereof. Suitable anionic dispersants are especially lignosulphonates, polyacrylic acid salts and arylsulphonate/formaldehyde condensates.

Antifoams which may be present in the seed dressing formulations usable in accordance with the invention are all foam-inhibiting substances conventionally used for formulation of active agrochemical ingredients. Silicone antifoams and magnesium stearate can be used with preference.

Preservatives which may be present in the seed dressing formulations usable in accordance with the invention are all substances usable for such purposes in agrochemical compositions. Examples include dichlorophene and benzyl alcohol hemiformal.

Secondary thickeners which may be present in the seed dressing formulations usable in accordance with the invention are all substances which can be used for such purposes in agrochemical compositions. Preferred examples include cellulose derivatives, acrylic acid derivatives, xanthan, modified clays and finely divided silica.

Useful stickers which may be present in the seed dressing formulations usable in accordance with the invention are all customary binders usable in seed dressing products. Preferred examples include polyvinylpyrrolidone, polyvinyl acetate, polyvinyl alcohol and tylose.

Gibberellins which may be present in the seed dressing formulations usable in accordance with the invention are preferably the gibberellins A1, A3 (=gibberellic acid), A4 and A7; particular preference is given to using gibberellic acid. The gibberellins are known (cf. R. Wegler "Chemie der Pflanzenschutz- und Schädlingsbekämpfungsmittel" [Chemistry of the Crop Protection Compositions and Pesticides], vol. 2, Springer Verlag, 1970, p. 401-412).

The seed dressing formulations usable in accordance with the invention can be used to treat a wide variety of different kinds of seed, either directly or after prior dilution with water. For instance, the concentrates or the preparations obtainable therefrom by dilution with water can be used to dress the seed of cereals, such as wheat, barley, rye, oats, and triticale, and also the seed of maize, rice, oilseed rape, peas, beans, cotton, sunflowers, soya beans and beets, or else a wide variety of different vegetable seed. The seed dressing formulations usable in accordance with the invention, or the dilute use forms thereof, can also be used to dress seed of transgenic plants.

For treatment of seed with the seed dressing formulations usable in accordance with the invention, or the use forms prepared therefrom, all mixing units usable customarily for the seed dressing are useful. Specifically, the procedure in seed dressing is to place the seed into a mixer in batchwise or continuous operation, to add the particular desired amount of seed dressing formulations, either as such or after prior dilution with water, and to mix until the formulation is distributed homogeneously on the seed. If appropriate, this is followed by a drying operation.

The application rate of the seed dressing formulations usable in accordance with the invention can be varied within a relatively wide range. It is guided by the particular content of the compounds of the formula (I) in the formulations and by the seed. The application rates of the compound of the formula (I) are generally between 0.001 and 50 g per kilogram of seed, preferably between 0.01 and 15 g per kilogram of seed.

Use in Animal Health

In the animal health sector, i.e. in the field of veterinary medicine, the active ingredients according to the present invention act against animal parasites, especially ectoparasites or else, in a further embodiment, endoparasites. The term "endoparasites" includes especially helminths such as cestodes, nematodes or trematodes, and protozoa such as coccidia. Ectoparasites are typically and preferably arthropods, especially insects such as flies (biting and licking), parasitic fly larvae, lice, hair lice, bird lice, fleas and the like; or acarids such as ticks, for example hard ticks or soft ticks, or mites such as scab mites, harvest mites, bird mites and the like, and also aquatic ectoparasites such as copepods.

In the field of veterinary medicine, the compounds of the formula (I) having favourable homeotherm toxicity are suitable for controlling parasites which occur in animal breeding and animal husbandry in livestock, breeding animals, zoo animals, laboratory animals, experimental animals and domestic animals. They are active against all or specific stages of development of the parasites.

Agricultural livestock include, for example, mammals such as sheep, goats, horses, donkeys, camels, buffalo, rabbits, reindeer, fallow deer, and particularly cattle and pigs; poultry such as turkeys, ducks, geese, and particularly chickens; fish and crustaceans, for example in aquaculture, and also insects such as bees.

Domestic animals include, for example, mammals, such as hamsters, guinea pigs, rats, mice, chinchillas, ferrets, and particularly dogs, cats, cage birds, reptiles, amphibians and aquarium fish.

In a preferred embodiment, the compounds of the formula (I) are administered to mammals.

In another preferred embodiment, the compounds of the formula (I) are administered to birds, namely caged birds and particularly poultry.

Use of the compounds of the formula (I) for the control of animal parasites is intended to reduce or prevent illness, cases of deaths and reductions in performance (in the case of meat, milk, wool, hides, eggs, honey and the like), such that more economical and simpler animal keeping is enabled and better animal well-being is achievable.

In relation to the animal health field, the term "control" or "controlling" means that the compounds of the formula (I) are effective in reducing the incidence of the particular parasite in an animal infected with such parasites to an innocuous degree. More specifically, "controlling" in the present context means that the compound of the formula (I) can kill the respective parasite, inhibit its growth, or inhibit its proliferation.

These parasites include:

From the order of the Anoplurida, for example, *Haematopinus* spp., *Linognathus* spp., *Pediculus* spp., *Phthirus* spp., *Solenopotes* spp.; specific examples are: *Linognathus setosus, Linognathus vituli, Linognathus ovillus, Linognathus oviformis, Linognathus pedalis, Linognathus stenopsis, Haematopinus asini macrocephalus, Haematopinus eurysternus, Haematopinus suis, Pediculus humanus capitis, Pediculus humanus corporis, Phylloera vastatrix, Phthirus pubis, Solenopotes capillatus;*

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.; specific examples are: *Bovicola bovis, Bovicola ovis, Bovicola limbata, Damalina bovis, Trichodectes canis, Felicola subrostratus, Bovicola caprae, Lepikentron ovis, Werneckiella equi;*

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Odagmia* spp., *Wilhelmia* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp., *Rhinoestrus* spp., *Tipula* spp.; specific examples are: *Aedes aegypti, Aedes albopictus, Aedes taeniorhynchus, Anopheles gambiae, Anopheles maculipennis, Calliphora erythrocephala, Chrysozona pluvialis, Culex quinquefasciatus, Culex pipiens, Culex tarsalis, Fannia canicularis, Sarcophaga carnaria, Stomoxys calcitrans, Tipula paludosa, Lucilia cuprina, Lucilia sericata, Simulium reptans, Phlebotomus papatasi, Phlebotomus longipalpis, Odagmia ornata, Wilhelmia equina, Boophthora erythrocephala, Tabanus bromius, Tabanus spodopterus, Tabanus atratus, Tabanus sudeticus, Hybomitra ciurea, Chrysops caecutiens, Chrysops relictus, Haematopota pluvialis, Haematopota italica, Musca autumnalis, Musca domestica, Haematobia irritans irritans, Haematobia irritans exigua, Haematobia stimulans, Hydrotaea irritans, Hydrotaea albipuncta, Chrysomya chloropyga, Chrysomya bezziana, Oestrus ovis, Hypoderma bovis, Hypoderma lineatum, Przhevalskiana silenus, Dermatobia hominis, Melophagus ovinus, Lipoptena capreoli, Lipoptena cervi, Hippobosca variegata, Hippobosca equina, Gasterophilus intestinalis, Gasterophilus haemorrhoidalis, Gasterophilus inermis, Gasterophilus nasalis, Gasterophilus nigricomis, Gasterophilus pecorum, Braula coeca;*

From the order of the Siphonapterida, for example, *Pulex* spp., *Ctenocephalides* spp., *Tunga* spp., *Xenopsylla* spp., *Ceratophyllus* spp.; specific examples are: *Ctenocephalides canis, Ctenocephalides felis, Pulex irritans, Tunga penetrans, Xenopsylla cheopis;*

From the order of the Heteropterida, for example, *Cimex* spp., *Triatoma* spp., *Rhodnius* spp., *Panstrongylus* spp.

From the order of the Blattarida, for example, *Blatta orientalis, Periplaneta americana*, Blattela *germanica* and *Supella* spp. (e.g. *Suppella longipalpa*);

From the subclass of the Acari (Acarina) and the orders of the Meta- and Mesostigmata, for example, *Argas* spp., *Ornithodorus* spp., *Otobius* spp., *Ixodes* spp., *Amblyomma* spp., *Rhipicephalus* (*Boophilus*) spp., *Dermacentor* spp., *Haemophysalis* spp., *Hyalomma* spp., *Dermanyssus* spp., *Rhipicephalus* spp. (the original genus of multihost ticks), *Ornithonyssus* spp., *Pneumonyssus* spp., *Raillietia* spp., *Pneumonyssus* spp., *Sternostoma* spp., *Varroa* spp., *Acarapis* spp.; specific examples are: *Argas persicus, Argas reflexus, Omithodorus moubata, Otobius megnini, Rhipicephalus* (*Boophilus*) *microplus, Rhipicephalus* (*Boophilus*) *decoloratus, Rhipicephalus* (*Boophilus*) *annulatus, Rhipicephalus* (*Boophilus*) *calceratus, Hyalomma anatolicum, Hyalomma aegypticum, Hyalomma marginatum, Hyalomma transiens, Rhipicephalus evertsi, Ixodes ricinus, Ixodes hexagonus, Ixodes canisuga, Ixodes pilosus, Ixodes rubicundus, Ixodes scapularis, Ixodes holocyclus, Haemaphysalis concinna, Haemaphysalis punctata, Haemaphysalis cinnabarina, Haemaphysalis otophila, Haemaphysalis leachi, Haemaphysalis longicomi, Dermacentor marginatus, Dermacentor reticulatus, Dermacentor pictus, Dermacentor albipictus, Dermacentor andersoni, Dermacentor variabilis, Hyalomma mauritanicum, Rhipicephalus sanguineus, Rhipicephalus bursa, Rhipicephalus appendiculatus, Rhipicephalus capensis, Rhipicephalus turanicus, Rhipicephalus zambeziensis, Amblyomma americanum, Amblyomma variegatum, Amblyomma maculatum, Amblyomma hebraeum, Amblyomma cajennense, Dermanyssus gallinae, Omithonyssus bursa, Omithonyssus sylviarum, Varroa jacobsoni;*
From the order of the Actinedida (Prostigmata) and Acaridida (Astigmata), for example, *Acarapis* spp., *Cheyletiella* spp., *Omithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.; specific examples are: *Cheyletiella yasguri, Cheyletiella blakei, Demodex canis, Demodex bovis, Demodex ovis, Demodex caprae, Demodex equi, Demodex caballi, Demodex suis, Neotrombicula autumnalis, Neotrombicula desaleri, Neoschongastia xerothermobia, Trombicula akamushi, Otodectes cynotis, Notoedres cati, Sarcoptis canis, Sarcoptes bovis, Sarcoptes ovis, Sarcoptes rupicaprae (=S. caprae), Sarcoptes equi, Sarcoptes suis, Psoroptes ovis, Psoroptes cuniculi, Psoroptes equi, Chorioptes bovis, Psoergates ovis, Pneumonyssoidic mange, Pneumonyssoides caninum, Acarapis woodi.*
From the subclass of the copepods with the order of the Siphonostomatoida in particular the genera *Lepeophtheirus* and *Caligus*; the species *Lepeophtheirus salmonis, Caligus elongatus* and *Caligus clemensi* may be mentioned by way of example and with particular preference.

In general, the inventive active ingredients can be employed directly when they are used for the treatment of animals. They are preferably employed (administered) in the form of pharmaceutical compositions which may comprise pharmaceutically acceptable excipients and/or auxiliaries known in the prior art.

In the sector of animal health and in animal husbandry, the active ingredients are employed (=administered) in a known manner, by enteral administration in the form of, for example, tablets, capsules, potions, drenches, granules, pastes, boluses, the feed-through process and suppositories, by parenteral administration, for example by injection (intramuscular, subcutaneous, intravenous, intraperitoneal inter alia), implants, by nasal administration, by dermal administration in the form, for example, of dipping or bathing, spraying, pouring on and spotting on, washing and powdering, and also with the aid of moulded articles containing the active ingredient, such as collars, earmarks, tailmarks, limb bands, halters, marking devices, etc. The active ingredients can be formulated as a shampoo or as suitable formulations applicable in aerosols or unpressurized sprays, for example pump sprays and atomizer sprays, In the case of employment for livestock, poultry, domestic pets, etc., the inventive active ingredients can be employed as formulations (for example powders, wettable powders ["WP"], emulsions, emulsifiable concentrates ["EC"], free-flowing compositions, homogeneous solutions and suspension concentrates ["SC"]), which contain the active ingredients in an amount of 1% to 80% by weight, directly or after dilution (e.g. 100- to 10 000-fold dilution), or they can be used as a chemical bath.

In the case of use in the animal health sector, the inventive active ingredients, in order to broaden the spectrum of activity, can be used in combination with suitable synergists, repellents or other active ingredients, for example acaricides, insecticides, anthelmintics, anti-protozoal agents. Potential mixing components for inventive compounds of the formula (I) may, in the case of applications in animal health, be one or more compounds from groups (In-1) to (In-25).

(In-1) Acetylcholinesterase (AChE) inhibitors, for example carbamates, e.g. alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; particular preference is given here, for applications against ectoparasites, to bendiocarb, carbaryl, methomyl, promacyl and propoxur; or organophosphates, e.g. acephate, azamethiphos, azinphos (-methyl, -ethyl), cadusafos, chlorethoxyfos, chlorfenvinphos, chlormephos, chlorpyrifos (-methyl), coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, isofenphos, isopropyl O-(methoxyaminothiophosphoryl) salicylate, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos (-methyl), profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion; particular preference is given here, for applications against ectoparasites, to azamethiphos, chlorfenvinphos, chlorpyrifos, coumaphos, cythioate, diazinon (dimpylate), dichlorvos (DDVP), dicrotophos, dimethoate, ethion (diethion), famphur (famophos), fenitrothion, fenthion (MPP), heptenophos, malathion, naled, phosmet (PMP, phtalofos) phoxim, propetamphos, temephos, tetrachlorvinphos (CVMP) and triclorfon/metrifonate.

(In-2) GABA-gated chloride channel antagonists, for example organochlorines, e.g. bromocyclene, chlordane and endosulfan (alpha-), heptachlor, lindane and toxaphene; particular preference is given here, for applications against ectoparasites, to endosulfan (alpha-) and lindane; or fiproles (phenylpyrazoles), e.g. acetoprole, ethiprole, fipronil, pyrafluprole, pyriprole, rizazole; particular preference is given here, for applications against ectoparasites, to fipronil and pyriprole; or arylisoxazolines, arylpyrrolines, arylpyrrolidines, e.g. fluralaner (known from WO2009/2024541, ex. 11-1; but also compounds from WO2012007426, WO2012042006, WO2012042007, WO2012107533, WO2012120135, WO2012165186, WO2012155676, WO2012017359, WO2012127347, WO2012038851, WO2012120399, WO2012156400, WO2012163959, WO2011161130, WO2011073444, WO2011092287, WO2011075591, WO2011157748, WO 2007/075459, WO 2007/125984, WO 2005/085216, WO 2009/002809), afoxolaner (e.g. in WO2011149749) and structurally related arylpyrrolines (known, for example, from WO2009/072621, WO 2010020522, WO 2009112275, WO 2009097992, WO 2009072621, JP 2008133273, JP 2007091708), or arylpyrrolidines (e.g. in WO2012004326, WO2012035011, WO2012045700, WO 2010090344, WO 2010043315, WO 2008128711, JP 2008110971), and compounds from the group of the so-called metadiamides (known, for example, from WO2012020483, WO2012020484, WO2012077221, WO2012069366, WO2012175474, WO2011095462, WO2011113756, WO2011093415, WO2005073165); particular preference is given here, for applications against ectoparasites, to afoxolaner and fluaralaner.

(In-3) Sodium channel modulators/voltage-gated sodium channel blockers, for example pyrethroids, e.g. acrinathrin, allethrin (d-cis-trans, d-trans), bifenthrin, bioallethrin, bioallethrin S-cyclopentenyl, bioresmethrin, cyclopyrothrin, cyfluthrin (beta-), cyhalothrin (gamma-, lambda-), cypermethrin (alpha-, beta-, theta-, zeta-), cyphenothrin [(1R)-trans isomer], deltamethrin, dimefluthrin, empenthrin [(EZ)-(1R) isomer], esfenvalerate, etofenprox, fenpropathrin, fenvalerate, flucythrinate, flumethrin, fluvalinate (tau-), halfenprox, imiprothrin, metofluthrin, permethrin, phenothrin [(1R)-trans isomer], prallethrin, profluthrin, pyrethrins (pyrethrum), resmethrin, RU 15525, silafluofen, tefluthrin, tetramethrin [(1R) isomer)], tralomethrin, transfluthrin and ZXI 8901; particular preference is given here, for applications against ectoparasites, to the type I pyrethroids allethrin, bioallethrin, permethrin, phenothrin, resmethrin, tetramethrin and the type II pyrethroids (alphacyanopyrethroids) alpha-cypermethrin, cyfluthrin (beta-), cyhalothrin (lambda-), cypermethrin (alpha-, zeta-), deltamethrin, fenvalerate, flucythrinate, flumethrin, fluvalinate (tau-), and the ester-free pyrethroids etofenprox and silafluofen; or organochlorine compounds, e.g. DDT or methoxychlor. Active ingredients from this class are very particularly suitable as mixing components, since they have a longer-lasting contact-repelling action and therefore extend the activity spectrum to include this component.

(In-4) Nicotinergic acetylcholine receptor agonists, for example neonicotinoids, e.g. acetamiprid, clothianidin, dinotefuran, imidacloprid, imidaclothin, nitenpyram, thiacloprid, thiamethoxam; particular preference is given here, for applications against ectoparasites, to clothianidin, dinotefuran, imidacloprid, nitenpyram and thiacloprid; or nicotine.

(In-5) Allosteric acetylcholine receptor modulators (agonists), for example spinosyns, e.g. spinetoram and spinosad; particular preference is given here, for applications against ectoparasites, to spinosad and spinetoram.

(In-6) Chloride channel activators, for example avermectins/milbemycins, e.g. abamectin, doramectin, emamectin benzoate, eprinomectin, ivermectin, latidectin, lepimectin, milbemycin oxime, milbemectin, moxidectin and selamectin; indole terpenoids, for example nodulisporic acid derivatives, especially nodulisporic acid A; particular preference is given here, for applications against ectoparasites, to doramectin, eprinomectin, ivermectin, milbemycin oxime, moxidectin, selamectin and nodulisporic acid A.

(In-7) Juvenile hormone analogues, for example hydroprene (S—), kinoprene, methoprene (S—); or fenoxycarb; pyriproxyfen; particular preference is given here, for applications against ectoparasites, to methoprene (S—) and pyriproxyfen.

(In-8) Mite growth inhibitors, e.g. clofentezine, diflovidazin, hexythiazox, etoxazole; particular preference is given here, for applications against ectoparasites, to etoxazole.

(In-9) Slo-1 and latrophilin receptor agonists, for example cyclic depsipeptides, e.g. emodepside and its precursor PF1022A (known from EP 382173, compound I); particular preference is given here, for applications against ectoparasites, to emodepside.

(In-10) Oxidative phosphorylation inhibitors, ATP disruptors, for example diafenthiuron.

(In-12) Nicotinergic acetylcholine receptor antagonists, for example bensultap, cartap (hydrochloride), thiocylam, and thiosultap (sodium).

(In-13) Chitin biosynthesis inhibitors, type 0, for example benzoylureas, e.g. bistrifluron, chlorfluazuron, diflubenzuron, flucycloxuron, flufenoxuron, hexaflumuron, lufenuron, novaluron, noviflumuron, teflubenzuron and triflumuron; particular preference is given here, for applications against ectoparasites, to diflubenzuron, fluazuron, lufenuron and triflumuron.

(In-14) Chitin biosynthesis inhibitors, type 1, for example buprofezin.

(In-15) Moulting inhibitors, for example cyromazine and dicyclanil; particular preference is given here, for applications against ectoparasites, to cyromazine and dicyclanil.

(In-16) Ecdysone agonists/disruptors, for example diacylhydrazines, e.g. chromafenozide, halofenozide, methoxyfenozide and tebufenozide.

(In-17) Octopaminergic agonists, for example amitraz, cymiazole, chlordimeform and demiditraz; particular preference is given here, for applications against ectoparasites, to amitraz, cymiazole and demiditraz.

(In-18) Complex-III electron transport inhibitors, for example hydramethylnone; acequinocyl; fluacrypyrim.

(In-19) Complex-I electron transport inhibitors, for example from the group of the METI acaricides, e.g. fenazaquin, fenpyroximate, pyrimidifen, pyridaben, tebufenpyrad, tolfenpyrad; particular preference is given here, for applications against ectoparasites, to fenpyroximate, pyrimidifen and tolfenpyrad;

(In-20) Voltage-gated sodium channel blockers, for example indoxacarb and metaflumizone; particular preference is given here, for applications against ectoparasites, to indoxacarb and metaflumizone.

(In-21) Inhibitors of acetyl-CoA carboxylase, for example tetronic acid derivatives, e.g. spirodiclofen and spiromesifen; or tetramic acid derivatives, e.g. spirotetramat.

(In-22) Complex-II electron transport inhibitors, for example cyenopyrafen.

(In-23) Ryanodine receptor effectors, for example diamides, e.g. flubendiamide, chlorantraniliprole (Rynaxypyr), cyantraniliprole (Cyazypyr) and also 3-bromo-N-{2-bromo-4-chloro-6-[(1-cyclopropylethyl)carbamoyl]phenyl}-1-(3-chloropyridin-2-yl)-1H-pyrazole-5-carboxamide (known from WO2005/077934) or methyl 2-[3,5-dibromo-2-({[3-bromo-1-(3-chloropyridin-2-yl)-1H-pyrazol-5-yl]carbonyl}amino)benzoyl]-1,2-dimethylhydrazinecarboxylate (known from WO2007/043677).

(In-24) Further active ingredients with unknown mechanism of action, for example azadirachtin, amidoflumet, benzoximate, bifenazate, chinomethionat, cryolite, cyflumetofen, dicofol, fluensulfone (5-chloro-2-[(3,4,4-trifluorobut-3-en-1-yl)sulphonyl]-1,3-thiazole), flufenerim, pyridalyl and pyrifluquinazon; and additionally preparations based on *Bacillus firmus* (1-1582, BioNeem, Votivo) and the following known active compounds: 4-{[(6-bromopyrid-3-yl)methyl](2-fluoroethyl)amino}furan-2(5H)-one (known from WO 2007/115644), 4-{[(6-fluoropyrid-3-yl)methyl](2,2-difluoroethyl)amino}furan-2(5H)-one (known from WO 2007/115644), 4-{[(2-chloro-1,3-thiazol-5-yl)methyl](2-fluoroethyl)amino}furan-2(5H)-one (known from WO 2007/115644), 4-{[(6-chloropyrid-3-yl)methyl](2-fluoroethyl)amino}furan-2(5H)-one (known from WO 2007/115644), 4-{[(6-chloropyrid-3-yl)methyl](2,2-difluoroethyl)amino}furan-2(5H)-one (known from WO 2007/115644), 4-{[(6-chloro-5-fluoropyrid-3-yl)methyl](methyl)amino}furan-2(5H)-one (known from WO 2007/115643), 4-{[(5,6-dichloropyrid-3-yl)methyl](2-fluoroethyl)amino}furan-2(5H)-one (known from WO 2007/115646), 4-{[(6-chloro-5-fluoropyrid-3-yl)methyl](cyclopropyl)amino}furan-2(5H)-one (known from WO 2007/115643), 4-{[(6-chloropyrid-3-yl)methyl](cyclopropyl)amino}furan-2(5H)-one (known from EP-A-0 539 588), 4-{[(6-chloropyrid-3-yl)methyl](methyl)amino}furan-2(5H)-one (known from EP-A-0 539 588), [(6-chloropyridin-3-yl)methyl](methyl)oxido-$\lambda^4$-sulphanylidenecyanamide (known from WO 2007/149134), [1-(6-chloropyridin-3-yl)ethyl](methyl)oxido-$\lambda^4$-sulphanylidenecyanamide (known from WO 2007/149134), [(6-trifluoromethylpyridin-3-yl)methyl](methyl)oxido-$\lambda^4$-sulphanylidenecyanamide (known from WO 2007/095229), sulfoxaflor (likewise known from WO 2007/149134), 11-(4-chloro-2,6-dimethylphenyl)-12-hydroxy-1,4-dioxa-9-azadispiro[4.2.4.2]tetradec-11-en-10-one (known from WO 2006/089633), 3-(4'-fluoro-2,4-dimethylbiphenyl-3-yl)-4-hydroxy-8-oxa-1-azaspiro[4.5]dec-3-en-2-one (known from WO 2008/067911), 1-[2-fluoro-4-methyl-5-[(2,2,2-trifluoroethyl)sulphinyl]phenyl]-3-(trifluoromethyl)-1H-1,2,4-triazol-5-amine (known from WO 2006/043635), [(3 S,4aR,12R,12aS,12bS)-3-[(cyclopropylcarbonyl)oxy]-6,12-dihydroxy-4,12b-dimethyl-11-oxo-9-(pyridin-3-yl)-1,3,4,4a,5,6,6a, 12,12a, 12b-decahydro-2H,11H-benzo[f]pyrano[4,3-b]chromen-4-yl]methyl cyclopropanecarboxylate (known from WO 2006/129714), 2-cyano-3-(difluoromethoxy)-N-ethyl-benzenesulphonamide (known from WO 2005/035486), N-[1-(2,3-dimethylphenyl)-2-(3,5-dimethylphenyl)ethyl]-4,5-dihydro-2-thiazolamine (known from WO 2008/104503); penigequinolone A (known from EP 2248422 (compound I) and WO 2009/060015 (compound No. 11).

(In-25) Suitable synergists in the case of use together with ectoparasiticides here include MGK264 (N-octylbicycloheptenecarboxamide), piperonyl butoxide (PBO) and verbutin; particular preference is given here to piperonyl butoxide and MGK264.

In addition to these groups, it is also possible to use short-term repellents in mixtures or a combined application. Examples are DEET (N,N-diethyl-3-methylbenzamide), icaridin (1-piperidinecarboxylic acid), (1S,2OS)-2-methylpiperidinyl-3-cyclohexene-1-carboxamide (SS220), indalone (butyl 3,4-dihydro-2, 2-dimethyl-4-oxo-2H-pyran-6-carboxylate), dihydronepetalactones, nootkatone, IR3535 (3-[N-butyl-N-acetyl]-aminopropionic acid ethyl ester), 2-ethylhexane-1,3-diol, (1R,2R,5R)-2-(2-hydroxypropan-2-yl)-5-methyl-cyclohexan-1-ol, dimethyl benzene-1,2-dicarboxylate, dodecanoic acid, undecan-2-one, N,N-diethyl-2-phenylacetamide and essential oils or other plant ingredients with known repellent action, for example borneol, callicarpenal, 1,8-cineol (eucalyptol), carvacrol, b-citronellol, a-copaene, coumarin (or its synthetic derivatives known from US20120329832). Icaridin, indalone and IR3535 (3-[N-butyl-N-acetyl]-aminopropionic acid ethyl ester) are particularly preferred for use against ectoparasites.

From the aforementioned groups (I-1) to (1-25), preference is given to the following groups as mixing components: (In-2), (In-3), (In-4), (In-5), (In-6), (In-17), (In-25).

Particularly preferred examples of insecticidally or acaricidally active compounds, synergists or repellents as mixing components for the inventive compounds of the formula (I) are afoxolaner, allethrin, amitraz, bioallethrin, chlothianidin, cyfluthrin (beta-), cyhalothrin (lambda-), cymiazole, cypermethrin (alpha-, zeta-), cyphenothrin, deltamethrin, demiditraz, dinotefuran, doramectin, eprinomectin, etofenprox, fenvalerate, fipronil, fluazuron, flucythrinate, flumethrin, fluralaner, fluvalinate (tau-), icaridin, imidacloprid, ivermectin, MGK264, milbemycin oxime, moxidectin, nitenpyram, permethrin, phenothrin, piperonyl butoxide, pyriprole, resmethrin, selamectin, silafluofen, spinetoram, spinosad, tetramethrin, thiacloprid.

Vector Control

The compounds of the formula (I) can also be used in vector control. In the context of the present invention, a vector is an arthropod, especially an insect or arachnid, capable of transmitting pathogens, for example, viruses, worms, single-cell organisms and bacteria, from a reservoir (plant, animal, human, etc.) to a host. The pathogens can be transmitted either mechanically (for example trachoma by non-stinging flies) to a host or after injection (for example malaria parasites by mosquitoes) into a host.

Examples of vectors and the diseases or pathogens they transmit are:

1) Mosquitoes
   *Anopheles*: malaria, filariasis;
   *Culex*: Japanese encephalitis, filariasis, other viral diseases, transmission of worms;
   *Aedes*: yellow fever, dengue fever, filariasis, other viral diseases;
   Simuliidae: transmission of worms, in particular *Onchocerca volvulus;*
2) Lice: skin infections, epidemic typhus;
3) Fleas: plague, endemic typhus;
4) Flies: sleeping sickness (trypanosomiasis); cholera, other bacterial diseases;
5) Mites: acariosis, epidemic typhus, rickettsialpox, tularaemia, Saint Louis encephalitis, tick-bornme encephalitis (TBE), Crimean-Congo haemorrhagic fever, borreliosis;
6) Ticks: borellioses such as *Borrelia* duttoni, tick-borne encephalitis, Q fever (*Coxiella burnetii*), babesioses (*Babesia canis canis*).

Examples of vectors in the context of the present invention are insects, for example aphids, flies, leafhoppers or *thrips*, which can transmit plant viruses to plants. Other vectors capable of transmitting plant viruses are spider mites, lice, beetles and nematodes.

Further examples of vectors in the context of the present invention are insects and arachnids such as mosquitoes, especially of the genera *Aedes, Anopheles*, for example *A. gambiae, A. arabiensis, A. funestus, A. dirus* (malaria) and *Culex*, lice, fleas, flies, mites and ticks, which can transmit pathogens to animals and/or humans.

Vector control is also possible if the compounds of the formula (I) are resistance-breaking.

Compounds of the formula (I) are suitable for use in the prevention of diseases and/or pathogens transmitted by vectors. Thus, a further aspect of the present invention is the use of compounds of the formula (I) for vector control, for example in agriculture, in horticulture, in forestry, in gardens and in leisure facilities, and also in the protection of materials and stored products.

Protection of Industrial Materials

The compounds of the formula (I) are suitable for protecting industrial materials against attack or destruction by insects, for example from the orders Coleoptera, Hymenoptera, Isoptera, Lepidoptera, Psocoptera and Zygentoma.

Industrial materials in the present context are understood to mean inanimate materials, such as preferably plastics, adhesives, sizes, papers and cards, leather, wood, processed wood products and coating compositions. The use of the invention for protection of wood is particularly preferred.

In a further embodiment, the compounds of the formula (I) are used together with at least one further insecticide and/or at least one fungicide.

In a further embodiment, the compounds of the formula (I) are in the form of a ready-to-use pesticide, meaning that they can be applied to the material in question without further modifications. Suitable further insecticides or fungicides are in particular those mentioned above.

It has also been found that, surprisingly, the compounds of the formula (I) can be used to protect objects which come into contact with saltwater or brackish water, especially hulls, screens, nets, buildings, moorings and signalling systems, against fouling. It is equally possible to use the compounds of the formula (I), alone or in combinations with other active ingredients, as antifouling agents.

Control of Animal Pests in the Hygiene Sector

The compounds of the formula (I) are suitable for controlling animal pests in the hygiene sector. More particularly, the invention can be used in the domestic sector, in the hygiene sector and in the protection of stored products, particularly for control of insects, arachnids and mites encountered in enclosed spaces, for example dwellings, factory halls, offices, vehicle cabins. For controlling animal pests, the compounds of the formula (I) are used alone or in combination with other active ingredients and/or auxiliaries. They are preferably used in domestic insecticide products. The compounds of the formula (I) are effective against sensitive and resistant species, and against all developmental stages.

These pests include, for example, pests from the class Arachnida, from the orders Scorpiones, Araneae and Opiliones, from the classes Chilopoda and Diplopoda, from the class Insecta the order Blattodea, from the orders Coleoptera, Dermaptera, Diptera, Heteroptera, Hymenoptera, Isoptera, Lepidoptera, Phthiraptera, Psocoptera, Saltatoria or Orthoptera, Siphonaptera and Zygentoma and from the class Malacostraca the order Isopoda.

Application is effected, for example, in aerosols, unpressurized spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free, or passive, evaporation systems, moth papers, moth bags and moth gels, as granules or dusts, in baits for spreading or in bait stations.

Preparation Processes

The inventive compounds can be prepared by customary methods known to those skilled in the art.

The compounds of the structure (I-T1) and (I-T2) can be prepared by the methods already described in the literature for analogous compounds:

Process I-T1

The compounds of the structure (I-T1) can be prepared by the process specified in Reaction Scheme 1.

Reaction Scheme 1:

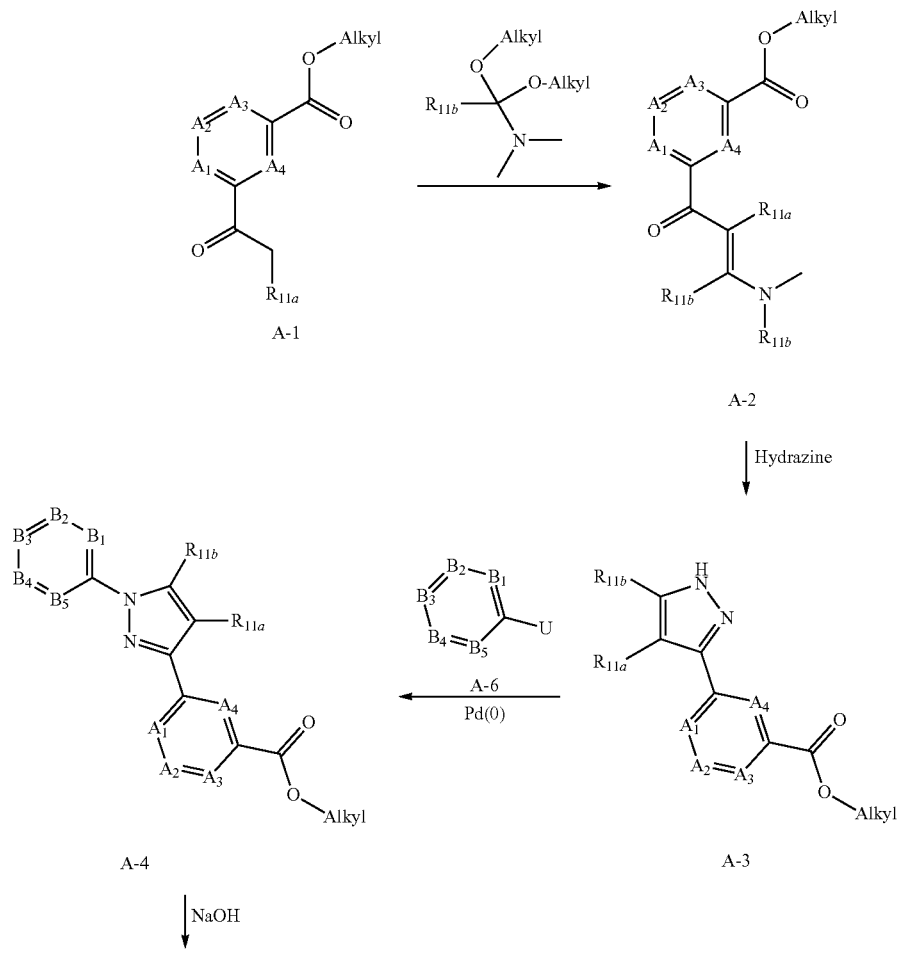

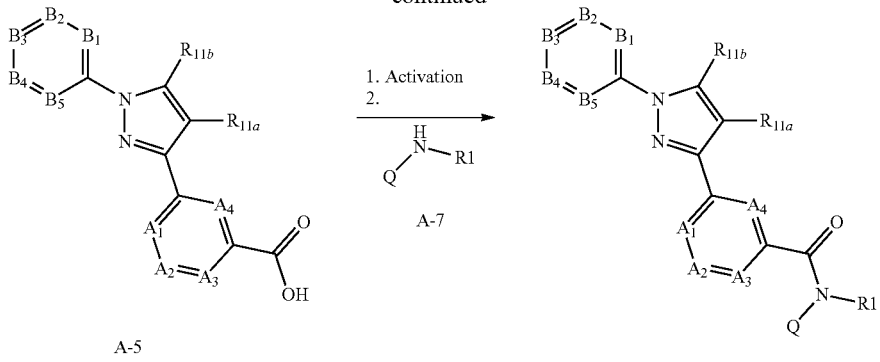

The $A_1$-$A_4$, $B_1$-$B_5$, alkyl, Q, $R^1$ and $R^{11}$ radicals are each as defined above. U is, for example, bromine, iodine or triflate. Starting compounds of the structure (A-1) (e.g. WO 2004/099146, p. 75-76) and (A-7) (e.g. U.S. Pat. No. 5,739,083 page 10, US 2003/187233A1, p. 6) are known or can be prepared by known methods.

Compounds of the general structure (A-2) can be prepared in analogy to methods known from the literature from the compounds of the general structure (A-1) and carboxamide acetals (B-8) (e.g. WO 2013/009791, p. 50, Example 43; WO 2004/099146, p. 75-76). Compounds of the general structure (A-3) can be prepared in analogy to methods known from the literature from the compounds of the general structure (A-2) and hydrazine (e.g. WO 2013/009791, p. 50, Example 43; WO 2004/099146, p. 75-76).

Compounds of the general structure (A-4) can be prepared in analogy to methods known from the literature from the compounds of the general structure (A-3) and (A-6) (e.g. WO 2013/009791, p. 50, Example 44). Compounds of the general structure (A-5) can be prepared in analogy to processes known from the literature by ester hydrolysis from compounds of the general structure (A-4) (see, for example, WO 2010/051926 or WO 2010/133312). Inventive compounds of the general structure (I-T1) can be prepared in analogy to peptide coupling methods known from the literature from the starting materials (A-5) and (A-7) (e.g. WO 2010/051926 or WO 2010/133312).

Process I-T2

The compounds of the structure (I-T2) can be prepared by the process specified in Reaction Scheme 2.

Reaction Scheme 2:

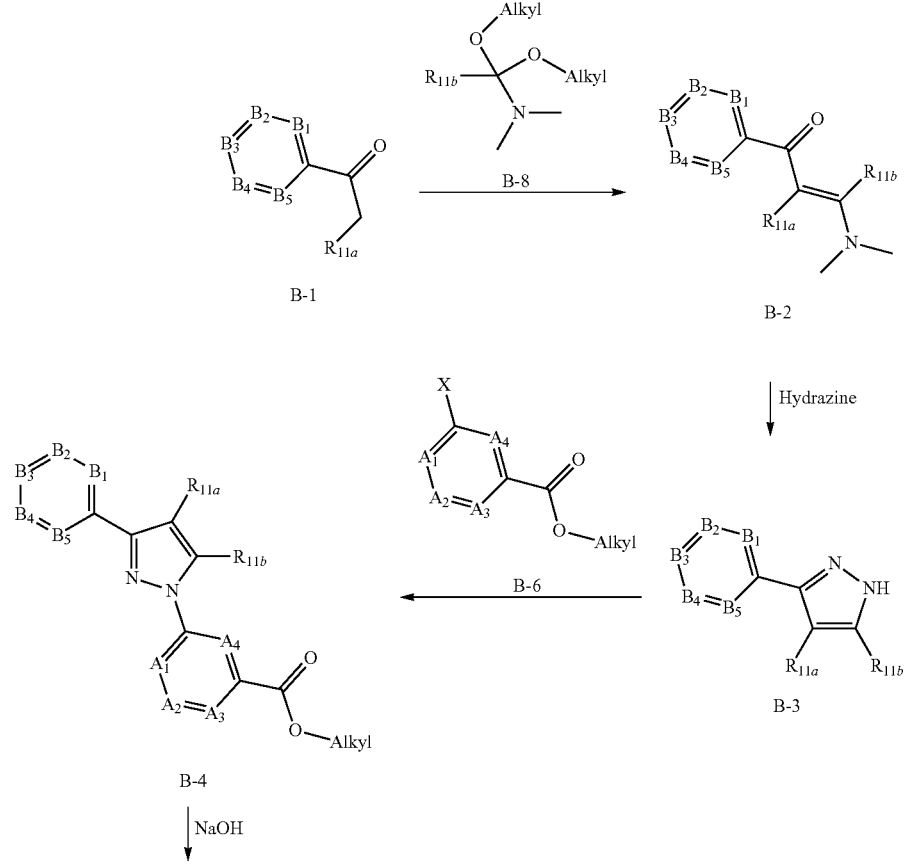

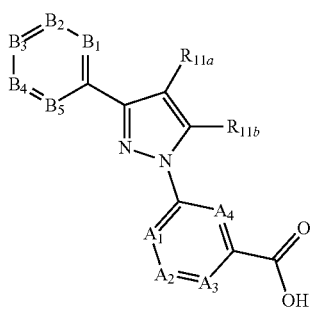

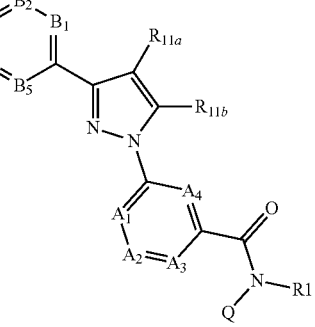

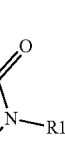

B-7

B-5

1-T2

The $A_1$ to $A_4$, $B_1$ to $B_5$, alkyl, Q, $R^1$ and $R^{11}$ radicals are each as defined above. X is, for example, Cl, Br, I or a boronic acid or boronic ester radical. Starting compounds of the structure (B-1) (e.g. Filler, Robert; Kong, Zhengrong; Zhang, Zhaoxu; Sinha, Arun Kr.; Li, Xiaofang Journal of Fluorine Chemistry, 80 (1996) p. 71-76; US2003/187233, p. 14, Example 21) and (B-6) are known or can be prepared by known methods.

Compounds of the general structure (B-2) can be prepared in analogy to methods known from the literature from the compounds of the general structure (B-1) and carboxamide acetals (B-8) (e.g. WO 2006/044505, Compound 60, Part A; WO 2012/4604, Intermediate 2). Compounds of the general structure (B-3) can be prepared in analogy to methods known from the literature from the compounds of the general structure (B-2) and hydrazine (e.g. WO 2013/009791, p. 50, Example 43; WO 2004/099146, p. 75-76). Compounds of the general structure (B-4) can be prepared in analogy to methods known from the literature from the compounds of the general structure (B-3) and (B-6) (e.g. WO 2013/009791, p. 50, Example 44, X=Br). Compounds of the general structure (B-5) can be prepared in analogy to processes known from the literature by ester hydrolysis from compounds of the general structure (B-4) (e.g. WO 2010/051926 or WO 2010/133312). Inventive compounds of the general structure (I-T1) can be prepared in analogy to peptide coupling methods known from the literature from the starting materials (B-5) and (B-7) (e.g. WO 2010/051926 or WO 2010/133312).

Stage 1 Dialkylaminoalkenylation

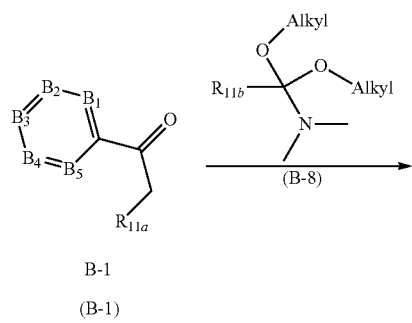

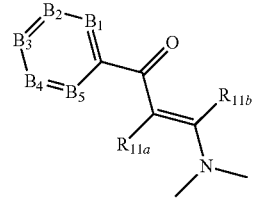

(B-2)

Compounds of the general structure (B-2) can be prepared in analogy to methods known from the literature from the starting materials of the structure (B-1) and (B-8). The $B^1$-$B^5$, alkyl and $R^{11}$ radicals are each as defined above. Starting compounds of the structure (B-1) (e.g. Filler, Robert; Kong, Zhengrong; Zhang, Zhaoxu; Sinha, Arun Kr.; Li, Xiaofang Journal of Fluorine Chemistry, 80 (1996) p. 71-76; US2003/187233, p. 14, Example 21 [0294], U.S. Pat. No. 5,739,083, Example 6) are known or can be prepared by known methods. The reaction is conducted by reacting the compounds (B-1) with the compounds (B-8) under the conditions known in the literature for analogous reactions (e.g. EP1204323, p. 25, Example 13).

Stage 2 Pyrazole Ring Closure

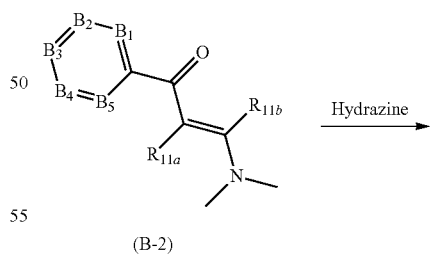

(B-2)

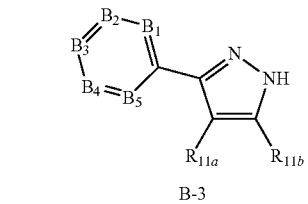

B-3

(B-3)

Compounds of the general structure (B-2) can be prepared in analogy to methods known from the literature from the starting materials of the structure (B-2) and hydrazine. The $B^1$-$B^5$ and $R^{11}$ radicals are each as defined above. The preparation of the starting compounds of the structure (B-2) is described above. The reaction is conducted by reacting the compounds (B-2) with hydrazine under the conditions known in the literature for analogous reactions (EP1382603, Example 3, p. 43)

Stage 3 Aryl Coupling

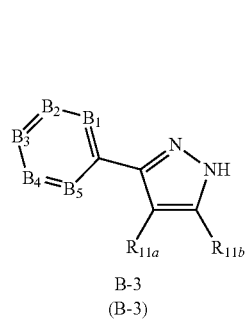

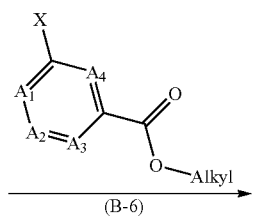

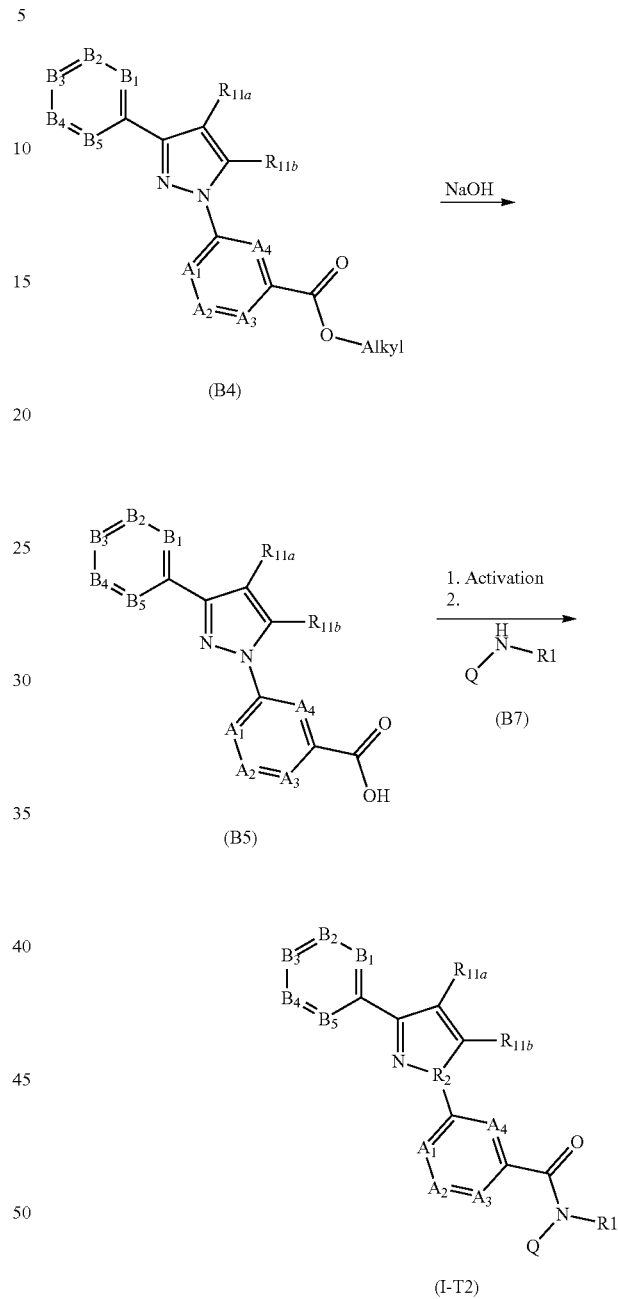

Compounds of the general structure (B-4) can be prepared in analogy to methods known from the literature from the starting materials of the structure (B-3) and (B-6). The $A^1$-$A^4$, $B^1$-$B^5$, alkyl, $R^1$ and $R^{11}$ radicals are each as defined above. X is a boronic acid or a boronic ester radical. The preparation of the starting compounds of the structure (B-3) is described above. The compounds of the general structure (B-6) are either commercially available or can be prepared by processes known to those skilled in the art. The reaction is conducted under the conditions known in the literature for analogous reactions (WO2009140342, p. 96).

Stages 4, 5 Hydrolysis, Amidation

Inventive compounds of the general structure (I-T2) can be prepared in analogy to peptide coupling methods known from the literature from the starting materials (B5) and (B7) [WO2010-051926; WO2010-133312]. Compounds of the general structure (B5) can be prepared analogously to processes known from the literature by ester hydrolysis from compounds of the general structure (B4) [WO2010-051926; WO2010-133312]. The $A^1$-$A^4$, $B^1$-$B^5$, alkyl, Q, $R^1$ and $R^{11}$ radicals are each as defined above. The preparation of the compounds of the structure (B-7) is described above.

Process I-T3

The compounds of the structure (I-T3) can be prepared by the process specified in Reaction Scheme 3a.

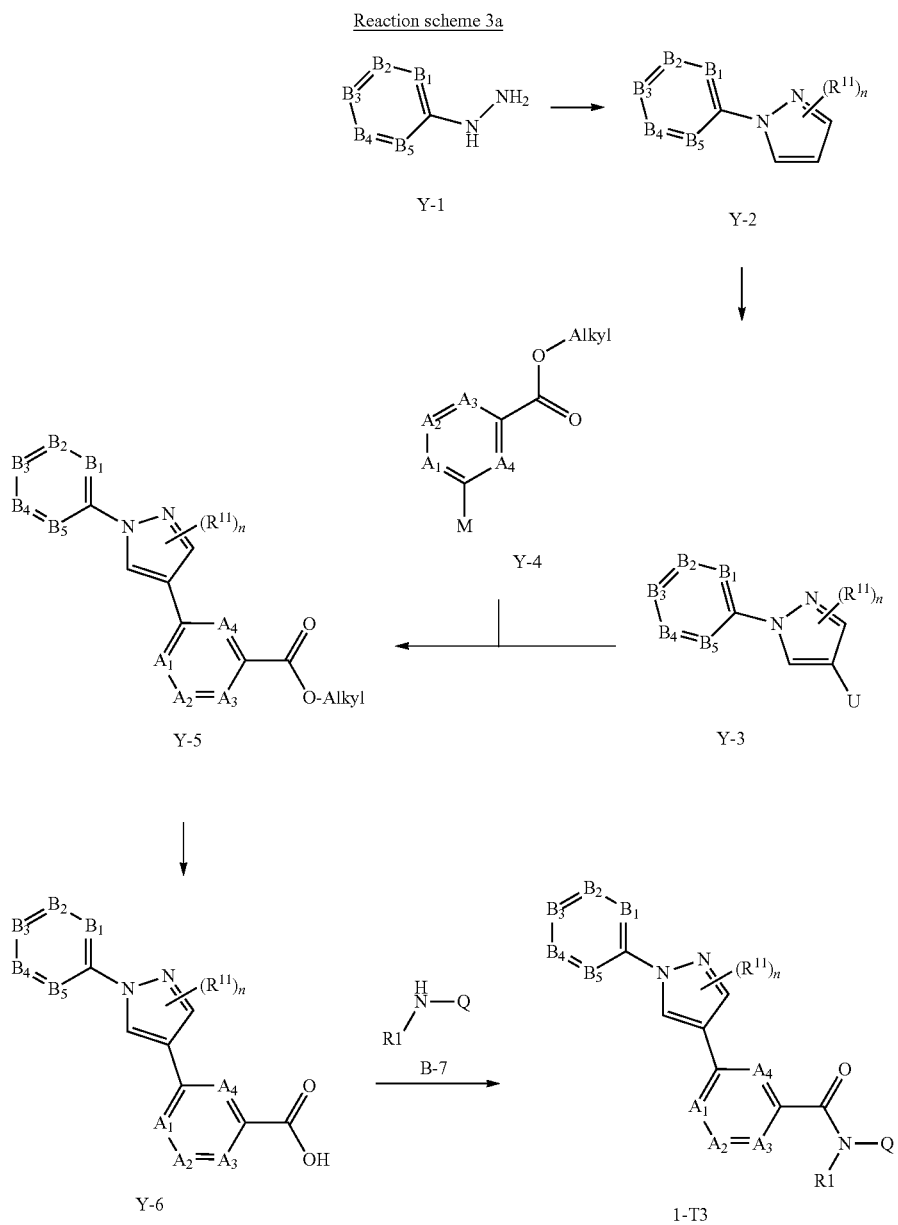

The $A_1$ to $A_4$, $B_1$ to $B_5$, alkyl, Q, $R^1$, n and $R^{11}$ radicals are each as defined above. M is, for example, a boronic acid, boronic ester or trifluoroboronate. U is, for example, bromine, iodine or triflate. X is, for example, Cl, Br, I.

Stage 1 Pyrazole

Stage 1 of the preparation process for the inventive compounds (I-T3):

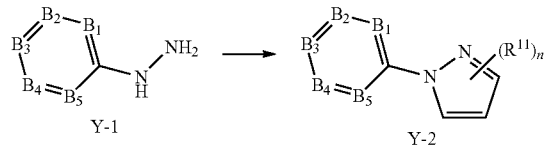

Inventive compounds of the general structure (Y-2) can be prepared in analogy to methods known from the literature from the starting materials of the structure (Y-1). The $B_1$-$B_5$ and $R^{11}$ radicals are each as defined above. Starting compounds of the structure (Y1) are known or can be prepared by known methods. Examples include [2,6-dichloro-4-(trifluoromethyl)phenyl]hydrazine, [3-chloro-5-(trifluoromethyl)-2-pyridyl]hydrazine, [2,6-dichloro-4-[1,2,2,2-tetrafluoro-1-(trifluoromethyl)ethyl]phenyl]hydrazine, [2,6-dimethyl-4-[1,2,2,2-tetrafluoro-1-(trifluoromethyl)ethyl]phenyl]hydrazine, [2-methyl-4-[1,2,2,2-tetrafluoro-1-(trifluoromethyl)ethyl]-6-(trifluoromethyl)phenyl]hydrazine or [2-chloro-4-[1,2,2,2-tetrafluoro-1-(trifluoromethyl)ethyl]-6-(trifluoromethyl)phenyl]hydrazine. They can be prepared, for example, by methods described in US 2003/187233, p. 13; Haga, Takahiro et al., Heterocycles, 22 (1984), p. 117-124.

Stage 2 Iodopyrazole

Stage 2 of the preparation process for the inventive compounds (1-T3):

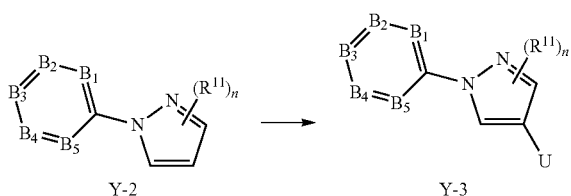

The $B_1$-$B_5$, n and $R^{11}$ radicals are each as defined above. U is, for example, bromine or iodine.

The compounds of the structural formula (Y-3) are, for example, 1-(2,6-dichloro-4-trifluoromethylphenyl)-4-iodopyrazole, 3-chloro-2-(4-iodopyrazol-1-yl)-5-(trifluoromethyl)pyridine (CAS RN: 8611-89-2), 1-(2,6-dichloro-4-heptafluoroisopropylphenyl)-4-iodopyrazole, 1-(2,6-dimethyl-4-heptafluoroisopropylphenyl)-4-iodopyrazole, 1-[2-methyl-4-[1,2,2,2-tetrafluoro-1-(trifluoromethyl)ethyl]-6-(trifluoromethyl)phenyl]-4-iodopyrazole, 1-[2-chloro-4-[1,2,2,2-tetrafluoro-1-(trifluoromethyl)ethyl]-6-(trifluoromethyl)phenyl]-4-iodopyrazole or 1-[2-ethyl-6-methyl-4-[1,2,2,2-tetrafluoro-1-(trifluoromethyl)ethyl]phenyl]-4-iodopyrazole.

Inventive compounds of the general structure (Y-3) are prepared by reacting pyrazoles of the structure (Y-2) with halogenating agents. The $B^1$ to $B^5$ and $R^{11}$ radicals are each as defined above. Suitable halogenating compounds are known to those skilled in the art, for example chlorine, bromine, iodine N-chlorosuccinimide, N-bromosuccinimide, N-iodosuccinimide, 1,3-dichloro-5,5-dimethylhydantoin, 1,3-dibromo-5,5-dimethylhydantoin, sodium hypochlorite and iodine monochloride. Preference is given to using bromine, iodine and iodosuccinimide. It may be advantageous to conduct the reaction in the presence of an oxidizing agent, e.g. hydrogen peroxide. The reaction follows the conditions known from the literature, for example Guo Li et al., Tetrahedron Letters 48 (2007), 4595-4599; Mary M. Kim et al., Tetrahedron Letters 49 (2008), 4026-4028.

Alternative Coupling with Pyrazole

Alternatively, the compounds of the structure Y-3 can also be prepared by methods known from the literature through direct coupling of iodopyrazoles with appropriate aryl halides (e.g. Sammelson, Robert E. et al., J. of Organic Chemistry, 68 (2003), 8075-8079).

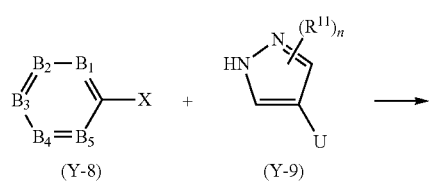

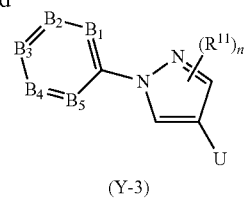

The $B_1$ to $B_5$, n and $R^{11}$ radicals are each as defined above. X is, for example, a halogen. U is, for example, bromine, iodine or triflate.

Starting compounds of the structure (Y-8) are known or can be prepared by known methods. Examples include 2-bromo-1,3-dichloro-5-[1,2,2,2-tetrafluoro-1-(trifluoromethyl)ethyl]benzene, 2-bromo-1,3-dimethyl-5-[1,2,2,2-tetrafluoro-1-(trifluoromethyl)ethyl]benzene, 2-bromo-1-ethyl-3-methyl-5-[1,2,2,2-tetrafluoro-1-(trifluoromethyl)ethyl]benzene, 2-bromo-1-chloro-5-[1,2,2,2-tetrafluoro-1-(trifluoromethyl)ethyl]-3-(trifluoromethyl)benzene, 2-bromo-1-methyl-5-[1,2,2,2-tetrafluoro-1-(trifluoromethyl)ethyl]-3-(trifluoromethyl)benzene, 2-bromo-1-chloro-5-[1,2,2,2-tetrafluoro-1-(trifluoromethyl)ethyl]-3-(trifluoromethoxy)benzene, 2-bromo-1-methyl-5-[1,2,2,2-tetrafluoro-1-(trifluoromethyl)ethyl]-3-(trifluoromethoxy)benzene. They can be prepared, for example, by the methods described in EP1253128, pages 8-10.

Stage 3 Boronic Acid Coupling

Stage 3 of the preparation process for the inventive compounds (1-T3):

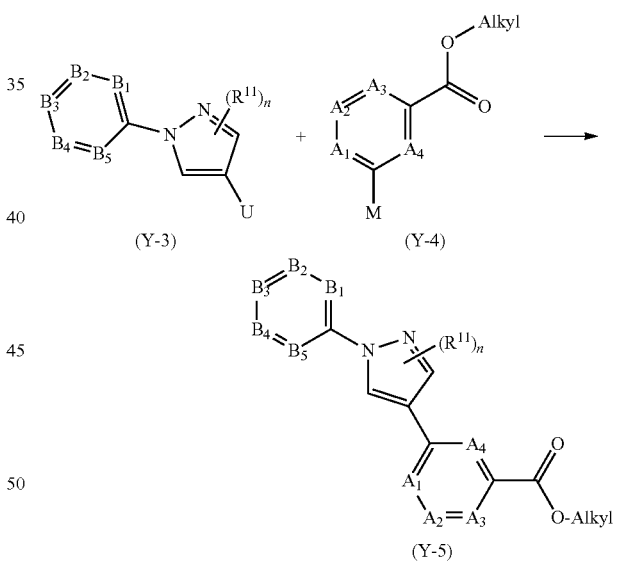

The $A_1$ to $A_4$, $B_1$ to $B_5$, alkyl, n and $R^{11}$ radicals are each as defined above. U is, for example, bromine, iodine or triflate when M is a boronic acid, boronic ester or trifluoroboronate; or U is, for example, a boronic acid, boronic ester or trifluoroboronate when M is bromine, iodine or triflate.

Inventive compounds of the general structure (Y-5) can be prepared by methods known from the literature, by means of palladium-catalysed reactions from the co-reactants (Y-3) and (Y-4) (e.g. WO 2005/040110 or WO 2009/089508). The compounds of the general structure (Y-4) are either commercially available or can be prepared by processes known to those skilled in the art.

Stages 4, 5 Hydrolysis, Amidation

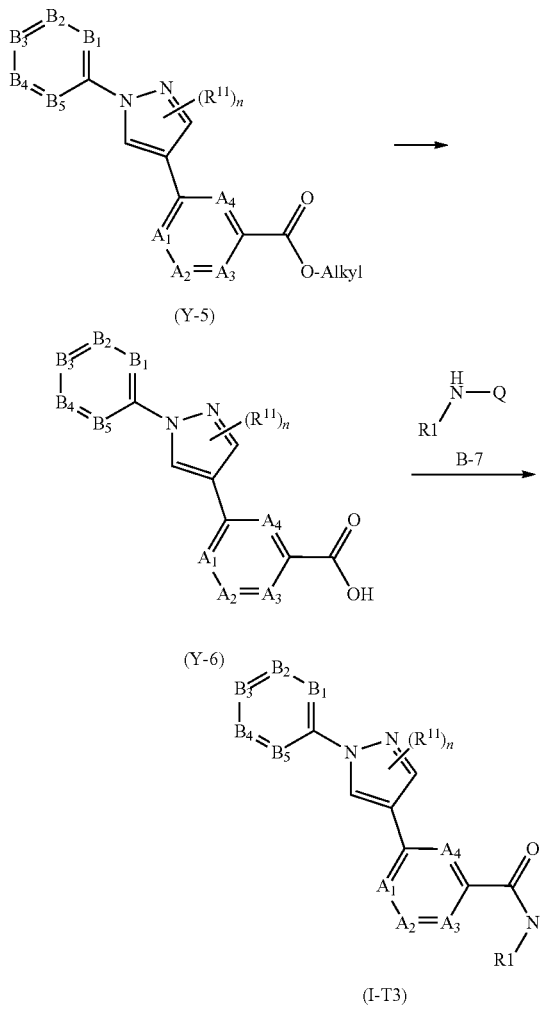

Inventive compounds of the general structure (I-T3) can be prepared in analogy to peptide coupling methods known from the literature from the starting materials (Y-6) and (Y-7) (e.g. WO 2010/051926 or WO 2010/133312). Compounds of the general structure (Y-6) can be prepared in analogy to processes known from the literature by ester hydrolysis from compounds of the general structure (Y-5) (e.g. WO 2010/051926 or WO 2010/133312). The $A_1$ to $A_4$, $B_1$ to $B_5$, alkyl, Q, $R^1$ and $R^{11}$ radicals are each as defined above.

Stage 3 Alternative: Coupling with Amides

Alternatively, the inventive compounds (I-T3) can be prepared by general preparation process 3b.

Reaction Scheme 3b

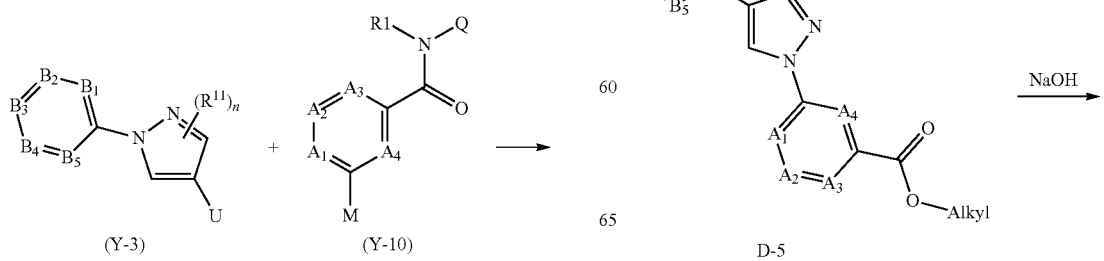

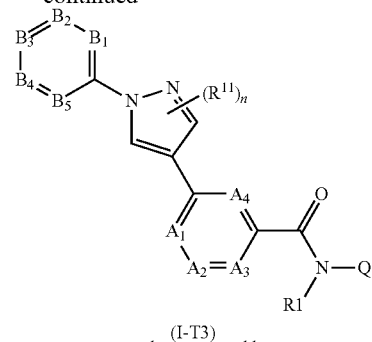

The $A_1$ to $A_4$, $B_1$ to $B_5$, alkyl, Q, $R^1$, n and $R^{11}$ radicals are each as defined above. U is bromine, iodine or triflate when M is a boronic acid, boronic ester or trifluoroboronate. U is a boronic acid, boronic ester or trifluoroboronate when M is bromine, iodine or triflate.

Inventive compounds of the general structure (I-T3) can be prepared by methods known from the literature, by means of palladium-catalysed reactions from the co-reactants (Y-3) and (Y-10) (e.g. WO 2005/040110 or WO 2009/089508). The compounds of the general structure (Y-10) are either commercially available or can be prepared by processes known to those skilled in the art. The preparation of compounds of the structure (Y-3) has already been described above.

Process I-T4

The compounds of the structure (I-T4) can be prepared by the process specified in Reaction Scheme 4.

Reaction Scheme 4

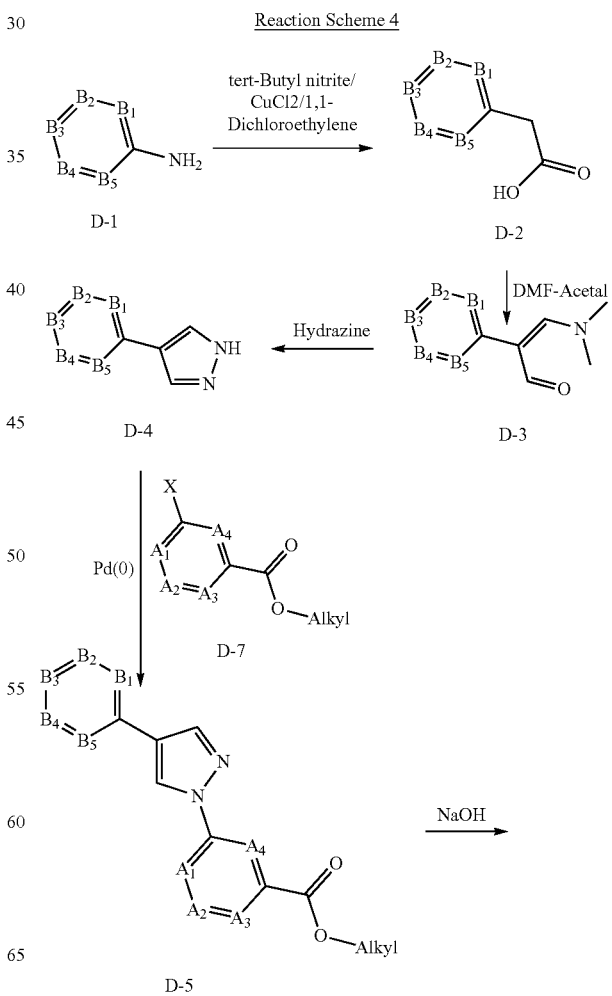

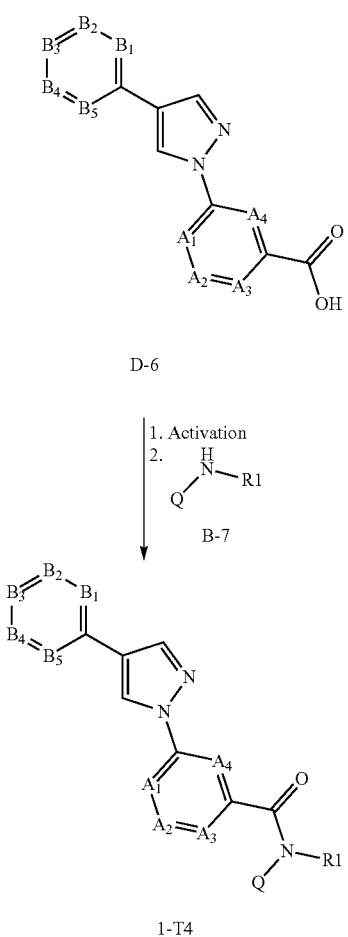

The $A_1$ to $A_4$, $B_1$ to $B_5$, alkyl, Q and $R^1$ radicals are each as defined above. X is Cl, Br, I. Starting compounds of the structure (D-1) (e.g. EP2319830, p. 330) and (D-7) are known or can be prepared by known methods.

The reactions can be conducted by the processes described in the literature, for example WO 2012/149236, Majumder, Supriyo et al., Advanced Synthesis and Catalysis, 351 (2009), 2013-2023, or U.S. Pat. No. 5,061,705.

Compounds of the general structure (D2) can be prepared in analogy to methods known from the literature from the compounds of the general structure (D1) (e.g. WO2008148868A1, p. 87). Compounds of the general structure (D3) can be prepared in analogy to reactions known from the literature from the compounds of the general structure (D2) and an iminium salt (e.g. Knorr, Rudolf; Loew, Peter; Hassel, Petra; Bronberger, Hildegard Journal of Organic Chemistry, 49 (1984) p. 1288-1290). Compounds of the general structure (D4) can be prepared in analogy to methods known from the literature from the compounds of the general structure (D3) and hydrazine (e.g. WO2008080969 A1, p. 102-103, Example 104). Compounds of the general structure (D5) can be prepared in analogy to methods known from the literature from the compounds of the general structure (D4) and (D7) (e.g. WO2013009791, p. 50, Example 44). Compounds of the general structure (D6) can be prepared analogously to processes known from the literature by ester hydrolysis from compounds of the general structure (D5) [WO2010-051926; WO2010-133312]. Inventive compounds of the general structure (I-T4) can be prepared in analogy to peptide coupling methods known from the literature from the starting materials (D6) and (D8) [WO2010-051926; WO2010-133312].

The compounds of the structure (I-T4) can alternatively be prepared by the process specified in Reaction Scheme 5.

Reaction Scheme 5:

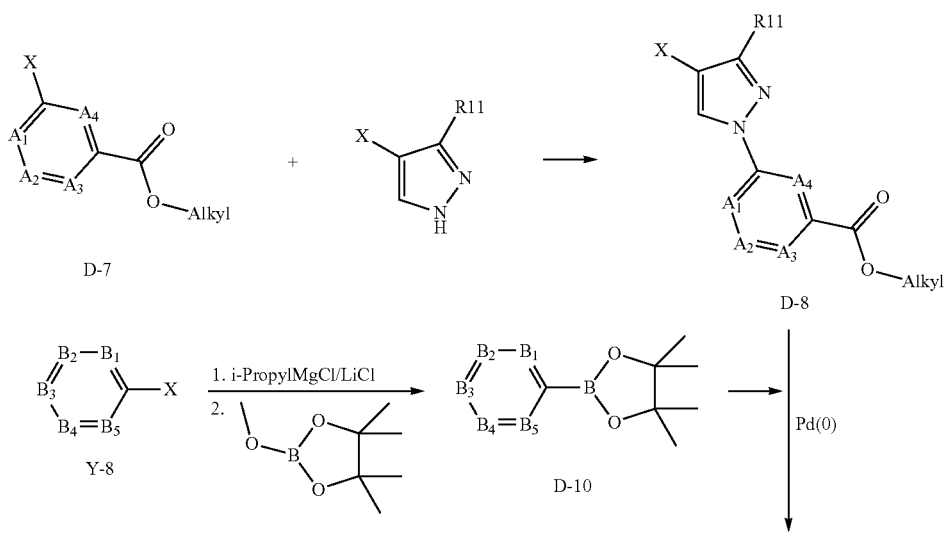

-continued

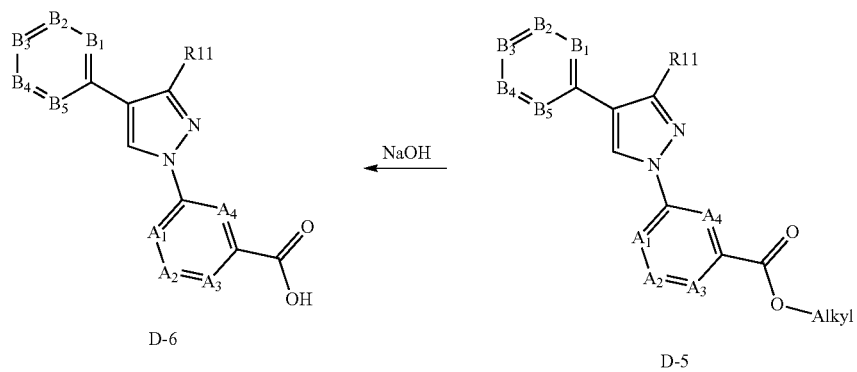

D-6

NaOH ←

D-5

1. Activation
2. 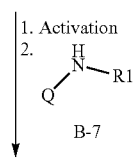
B-7

↓

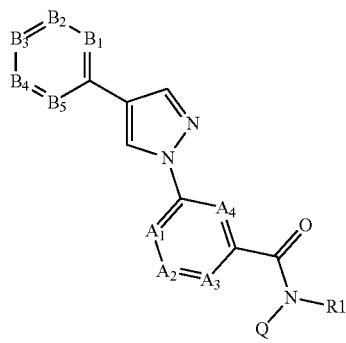

1-T4

The $A_1$ to $A_4$, $B_1$ to $B_5$, alkyl, Q, $R^1$ and $R^{11}$ radicals are each as defined herein. X is Cl, Br, I. Starting compounds of the structure (D-7), (D-9) and (D-11) (e.g. EP1253128, p. 8-10) are known, and some are commercially available or can be prepared by known methods.

The reactions can be conducted by the processes described in the literature:

Stage 1 Pyrazole Coupling

Stage 1 of the preparation process for the inventive compounds (I-T4):

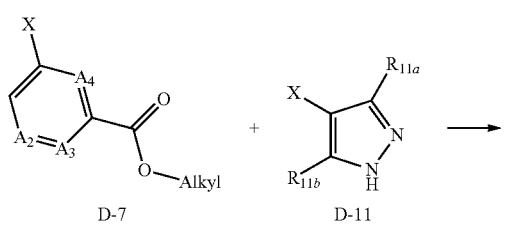

-continued

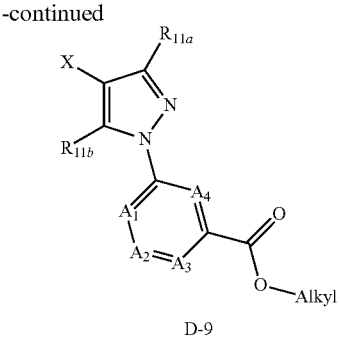

D-9

Compounds of the general structure (D-9) can be prepared in analogy to methods known from the literature from the starting materials of the structure (D-7) and (D-11). The $A^1$-$A^4$, alkyl and X radicals are each as defined above. Starting compounds of the structure (D-7) are known (e.g. WO2004099146A1, p. 68-69) or can be prepared by known methods. Examples include: methyl 2-chloro-5-iodobenzoate, ethyl 2-bromo-5-iodobenzoate, methyl 5-bromo-2-chloro-3-fluorobenzoate, ethyl 5-bromo-2-chloronicotinate. The starting compounds of the structure (D-11) are known, and some of them are commercially available or can be prepared by known methods. Examples include 4-bromopyrazole, 4-bromo-3-methylpyrazole, 4-bromo-3,5-dimethylpyrazole and 4-bromo-3-(trifluoromethyl)pyrazole.

The as yet unknown compounds (D-9) can be prepared in analogy to known processes for joining pyrazoles to aromatic systems (e.g. WO2013009791, p. 50, Example 44).

Pyrazole Alternative Preparation

Alternatively, the inventive compounds of the general structure (D9) can be obtained via the route specified in Reaction Scheme 6.

each as defined above. Preferred compounds of the structure (D15) include methyl 2-chloro-5-(pyrazol-1-yl)benzoate, ethyl 2-chloro-5-(pyrazol-1-yl)benzoate, methyl 2-chloro-3-fluoro-5-(pyrazol-1-yl)benzoate, ethyl 2-chloro-5-(pyrazol-1-yl)-nicotinate.

Suitable halogenating compounds are known to those skilled in the art, for example e.g. chlorine, bromine, iodine, N-chlorosuccinimide, N-bromosuccinimide, N-iodosuccinimide, 1,3-dichloro-5,5-dimethylhydantoin, 1,3-dibromo-5,5-dimethylhydantoin, sodium hypochlorite and iodine Reaction Scheme 6:

The $A_1$ to $A_4$, alkyl and $R_{11}$ radicals are each as defined above. X is Cl, Br, I. Starting compounds of the structure (D-13) are known (e.g. WO2004099146A1, p. 68-69) or can be prepared by known methods. Examples include: methyl 5-amino-2-chlorobenzoate, ethyl 5-amino-2-chlorobenzoate, methyl 5-amino-2-chloro-3-fluorobenzoate, ethyl 5-amino-2-chloronicotinate.

The as yet unknown compounds (D-14) can be prepared in analogy to known processes for preparing aryl hydrazines (e.g. WO 2004058731, p. 65).

Inventive compounds of the general structure (D-15) can be prepared in analogy to methods known from the literature from the starting materials of the structure (D-14). The $A_1$ to $A_4$, alkyl and R1 radicals are each as defined above. Starting compounds of the structure (D-14) are known or can be prepared by known methods. Examples include methyl 2-chloro-5-hydrazinobenzoate, ethyl 2-chloro-5-hydrazinobenzoate, methyl 2-chloro-3-fluoro-5-hydrazinobenzoate, ethyl 2-chloro-5-hydrazinonicotinate. The reaction can be conducted analogously to the conditions for pyrazole ring closure known in the literature (e.g. Sachweh, Volker; Langhals, Heinz Chemische Berichte, 119 (1986) 1627-1639).

Inventive compounds of the general structure (D9) are prepared by reacting pyrazoles of the structure (D-15) with halogenating agents. The $A_1$ to $A_4$, alkyl and $R_{11}$ radicals are monochloride. Preference is given to using bromine, iodine, bromosuccinimide and iodosuccinimide. It may be advantageous to conduct the reaction in the presence of an oxidizing agent, e.g. hydrogen peroxide. The reaction follows the conditions known from the literature, for example Guo Li et al., Tetrahedron Letters 48 (2007), 4595-4599; Mary M. Kim et al., Tetrahedron Letters 49 (2008), 4026-4028.

Stage 2 Boronic Ester

Stage 2: Preparation of the starting compounds of the structure (D12)

-continued

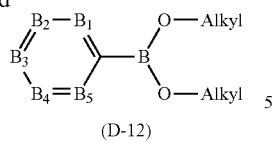

(D-12)

Inventive compounds of the general structure (D-12) can be prepared in analogy to methods known from the literature (Chien, Yuh-Yih; Chou, Meng-Yen; Leung, Man-Kit; Liao, Yuan-Li; Lin, Chang-Chih; Wong, Ken-Tsung; Journal of Organic Chemistry, 67 (2002) p. 1041-1044) from the starting materials of the structure (D-10) through reaction with magnesium and subsequent reaction with boric esters of the structure (D-16).

The $B^1$-$B^5$ and alkyl radicals are each as defined above.

The boric esters of the structure (D-13) used in the reaction are known or can be prepared by known methods. Examples include trimethyl borate, triethyl borate and 2-methoxy-4,4,5,5-tetramethyl-1,3,2-dioxaborolane.

Alternatively, the inventive compounds of the general structure (D-12) can be prepared in analogy to methods known from the literature (Tang, Wenjun; Keshipeddy, Santosh; Zhang, Yongda; Wei, Xudong; Savoie, Jolaine; Patel, Nitinchandra D.; Yee, Nathan K.; Senanayake, Chris H.; Organic Letters, 13 (2011) S. 1366-1369) from the starting materials of the structure (D-10) through reaction with diboranes of the structure (D-14) in the presence of catalysts.

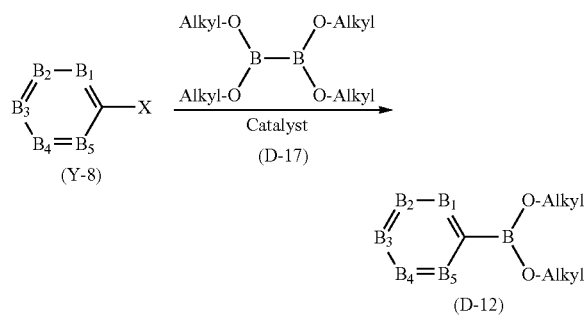

The boric esters of the structure (D-17) used in the reaction are known or can be prepared by known methods. Examples include 4,4,5,5-tetramethyl-2-(4,4,5,5-tetramethyl-1,3,2-dioxaborolan-2-yl)-1,3,2-dioxaborolane (bis(pinacolato)diboron).

Catalysts used may, in particular, be compounds and complexes of palladium and Cu(I).

Stage 3 Aryl Coupling

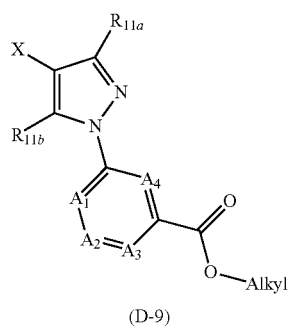

(D-9)

+

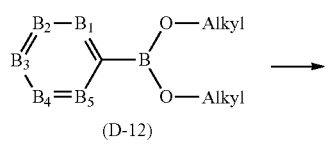

(D-12)

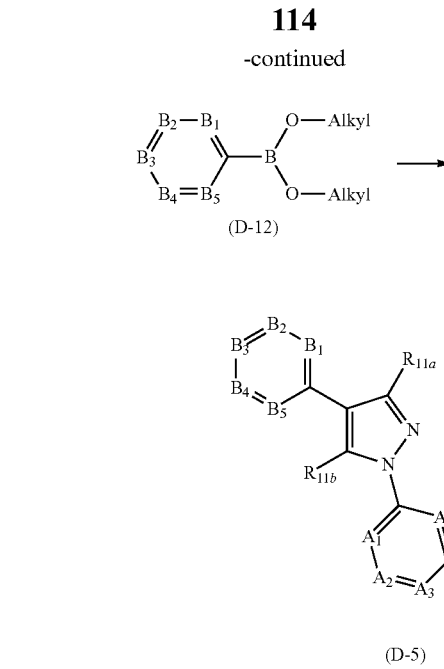

(D-5)

Inventive compounds of the general structure (D-5) are prepared by reacting the compounds of the structure (D-9) with boronic esters of the structure (D-12).

The $A^1$-$A^4$, $B^1$-$B^5$, $R^{11}$, alkyl and X radicals are each as defined above.

The preparation of the compounds of the structures (D-9) and (D-12) is described above.

Examples of compounds of the structure (D-9) include: methyl 5-(4-bromopyrazol-1-yl)-2-chlorobenzoate, methyl 5-(4-iodopyrazol-1-yl)-2-chlorobenzoate, ethyl 5-(4-bromo-3-methylpyrazol-1-yl)-2-chlorobenzoate, methyl 5-(4-bromo-3-(trifluoromethyl)pyrazol-1-yl)-2-chlorobenzoate, methyl 5-(4-bromo-3-(trifluoromethyl)pyrazol-1-yl)-2-chlorobenzoate, methyl 5-(4-bromo-3,5-dimethylpyrazol-1-yl)-2-chlorobenzoate and ethyl 5-(4-bromo-3-methylpyrazol-1-yl)-2-chloronicotinate.

The reaction is conducted under the conditions described in the literature, for example WO 2005040110 or WO 2009089508.

Stages 4, 5 Hydrolysis, Amidation

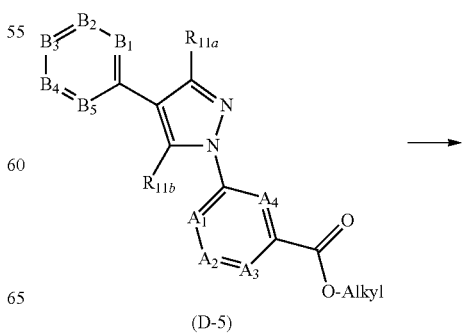

(D-5)

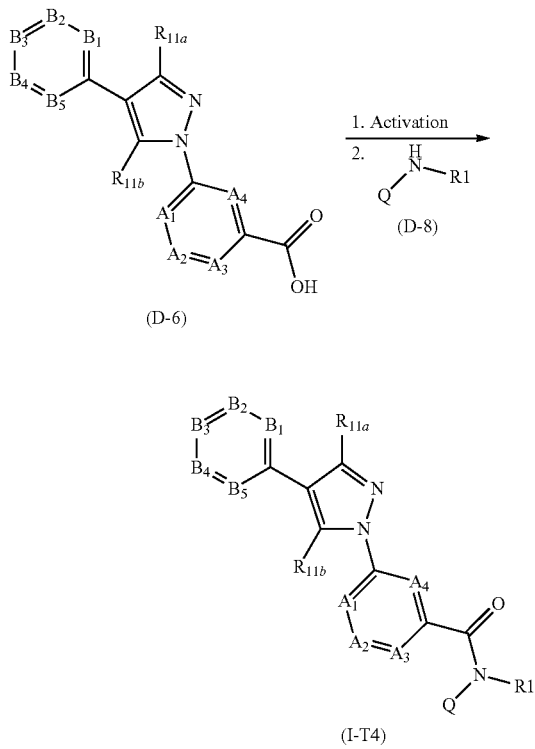

Inventive compounds of the general structure (I-T4) can be prepared in analogy to peptide coupling methods known from the literature from the starting materials (D-6) and (D-8) [WO2010051926; WO2010133312]. Compounds of the general structure (D-6) can be prepared analogously to processes known from the literature by ester hydrolysis from compounds of the general structure (D-5) [WO2010-051926; WO2010133312]. The $A_1$-$A_4$, $B_1$-$B_5$, alkyl, Q, $R^1$ and $R^{11}$ radicals are each as defined above. The preparation of the compounds of the structure (D5) is described above.

(I-T5): Compounds of the formula (I-T5) can be prepared, for example, analogously to Friedrich, L. E. et al. Journal of Organic Chemistry, 43 (1978), 34-38; or Huettel, R. et al. Chemische Berichte, 93 (1960), p. 1425-1432; or Sato, T et al., Bulletin of the Chemical Society of Japan, 41 (1968), p. 3017-3018.

(I-T8): Compounds of the formula (I-T8) can be prepared, for example, analogously to EP 1 405 636, Example 5; or EP 2 301 538, p. 162; or Schmidt, Bernd et al., European Journal of Organic Chemistry, (2011), p. 4814-4822.

(I-T9): Compounds of the formula (I-T9) can be prepared, for example, analogously to Ma, Shengming et al., Chemistry-A European Journal, 9 (2003), p. 2447-2456.

(I-T10): Compounds of the formula (I-T10) can be prepared, for example, analogously to EP 2 301 538, p. 162.

(I-T11): Compounds of the formula (I-T11) can be prepared, for example, analogously to EP 2 301 538, p. 165.

(I-T12): Compounds of the formula (I-T12) can be prepared, for example, analogously to EP 2 301 538, p. 164.

(I-T13): Compounds of the formula (I-T13) can be prepared, for example, analogously to EP 2 301 538, p. 164.

(I-T14): Compounds of the formula (I-T14) can be prepared, for example, analogously to Hibi, Shigeki et al., Bioorganic & Medicinal Chemistry Letters, 10 (2000), p. 623-626 or Wang, Xiang et al. Journal of Organic Chemistry, 72 (2007), 1476-1479; EP1405636, page 31.

(I-T15): Compounds of the formula (I-T15) can be prepared, for example, analogously to Chattopadhyay, Buddhadeb et al., Organic Letters, 13 (2011), p. 3746-3749.

(I-T16): Compounds of the formula (I-T16) can be prepared, for example, analogously to Campi, Eva M. et al. Tetrahedron Letters, 32 (1991), p. 1093-1094; or Thompson, Benjamin B. et al., Organic Letters, 13 (2011), p. 3289-3291; or Kloetzel et al. Journal of the American Chemical Society, 79 (1957), p. 4222; or Chi, Yonggui Robin et al., Journal of the American Chemical Society, 135 (2013), p. 8113-8116.

(I-T18): Compounds of the formula (I-T18) can be prepared, for example, analogously to EP 2 311 455, p. 150; or Balaban, A. T. et al. Tetrahedron, 19 (1963), p. 2199-2207.

(I-T19): Compounds of the formula (I-T19) can be prepared, for example, analogously to WO 2004/14366, p. 108.

(I-T20): Compounds of the formula (I-T20) can be prepared, for example, analogously to Araki, Hiroshi; Katoh, Tadashi; Inoue, Munenori; Synlett, (2006), p. 555-558; U.S. Pat. No. 6,545,009, p. 27, Example 1.

(I-T21): Compounds of the formula (I-T21) can be prepared, for example, analogously to WO 2004/72050, p. 13; or U.S. Pat. No. 6,545,009, p. 27.

Process I-T22

The compounds of the structure (I-T22) can be prepared by the process specified in Scheme 7.

Reaction Scheme 7:

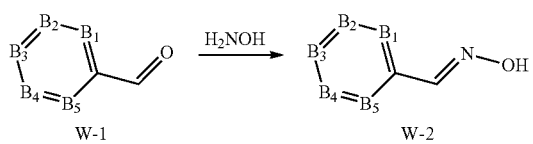

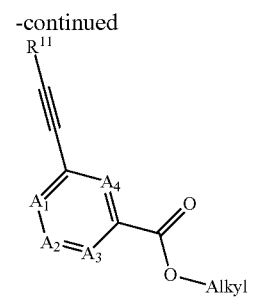
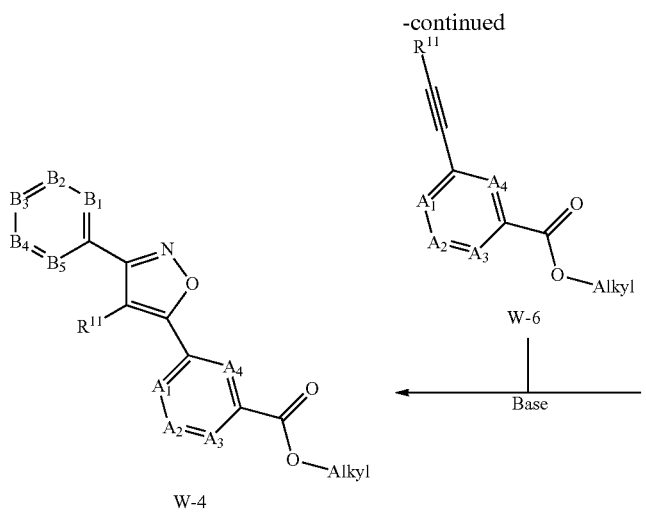
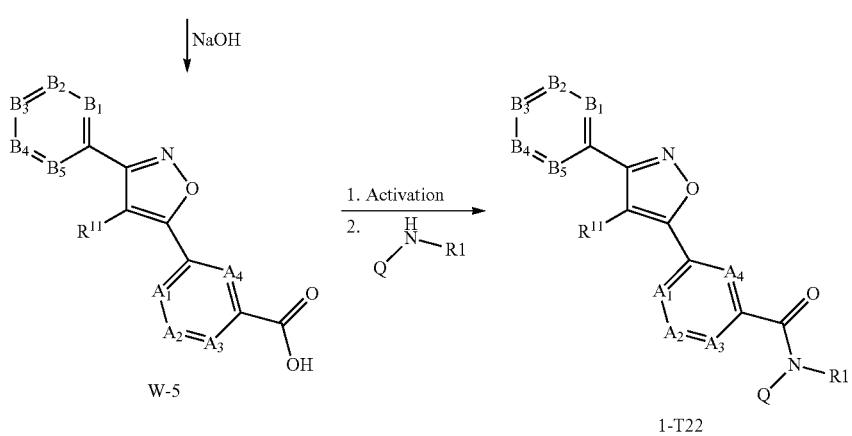

The $A_1$-$A_4$, $B_1$-$B_5$, alkyl, Q, $R^1$ and $R^{11}$ radicals are each as defined above. X is Cl, Br, I. Starting compounds of the structure (W-1) and (W-6) are known (W1 e.g. US 2011/53904 p. 19, W6 e.g. WO 2012/175474, p. 117-118) or can be prepared by known methods. The reactions are conducted analogously to the conditions specified for preparation of the compounds (I-T23).

Stage 1 Aldehyde

Stage 1 of the preparation process for the inventive compounds (I-T22):

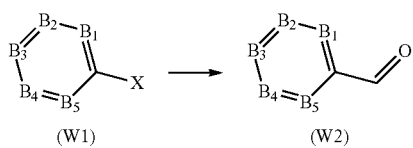

Inventive compounds of the general structure (W2) can be prepared in analogy to methods known from the literature (U.S. Pat. No. 5,739,083, Example 2; WO2011/23667, p. 34) from the starting materials of the structure (W1).

The $B^1$-$B^5$ and X radicals are each as defined above. X is, for example, chlorine, bromine or iodine.

Starting compounds of the structure (B1) are known or can be prepared by known methods. Examples include 2-bromo-1,3-dichloro-5-[1,2,2,2-tetrafluoro-1-(trifluoromethyl)ethyl]benzene, 2-bromo-1,3-dimethyl-5-[1,2,2,2-tetrafluoro-1-(trifluoromethyl)ethyl]benzene, 2-bromo-1-ethyl-3-methyl-5-[1,2,2,2-tetrafluoro-1-(trifluoromethyl)ethyl]benzene, 2-bromo-1-chloro-5-[1,2,2,2-tetrafluoro-1-(trifluoromethyl)ethyl]-3-(trifluoromethyl)benzene, 2-bromo-1-methyl-5-[1,2,2,2-tetrafluoro-1-(trifluoromethyl)ethyl]-3-(trifluoromethyl)benzene, 2-bromo-1-chloro-5-[1,2,2,2-tetrafluoro-1-(trifluoromethyl)ethyl]-3-(trifluoromethoxy)benzene, 2-bromo-1-methyl-5-[1,2,2,2-tetrafluoro-1-(trifluoromethyl)ethyl]-3-(trifluoromethoxy)benzene, 1,3-dimethyl-2-iodo-5-[1,2,2,2-tetrafluoro-1-(trifluoromethyl)ethyl]benzene, 2-iodo-1-methyl-5-[1,2,2,2-tetrafluoro-1-(trifluoromethyl)ethyl]-3-(trifluoromethyl)benzene. They can be prepared, for example, by the methods described in EP1253128, pages 8-10.

Stage 2 Oxime

Stage 2 of the preparation process for the inventive compounds (1-T22):

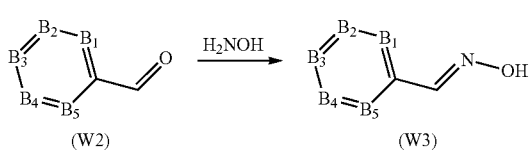

Inventive compounds of the general structure (W3) can be prepared in analogy to methods known from the literature from the starting materials of the structure (W2). The $B_1$-$B_5$ radicals are each as defined above. The preparation of the starting compounds of the structure (W2) is described above. Examples include 2,6-dichloro-4-[1,2,2,2-tetrafluoro-1-(trifluoromethyl)ethyl]benzaldehyde, 2,6-dimethyl-4-[1,2,2,2-tetrafluoro-1-(trifluoromethyl)ethyl]benzaldehyde, 2-ethyl-6-methyl-5-[1,2,2,2-tetrafluoro-1-(trifluoromethyl)ethyl]benzaldehyde, 2-chloro-4-[1,2,2,2-tetrafluoro-1-(trifluoromethyl)ethyl]-6-(trifluoromethyl)benzaldehyde, 2-methyl-4-[1,2,2,2-tetrafluoro-1-(trifluoromethyl)ethyl]-6-(trifluoromethyl)benzaldehyde, 2-chloro-4-[1,2,2,2-tetrafluoro-1-(trifluoromethyl)ethyl]-6-(trifluoromethoxy)benzaldehyde, 2-methyl-4-[1,2,2,2-tetrafluoro-1-(trifluoromethyl)ethyl]-6-(trifluoromethoxy)benzaldehyde. The preparation thereof is described above.

The compounds of the structural formula (W3) are novel. The as yet unknown compounds (W3) can be prepared in analogy to the known processes for preparing oximes from aldehydes (H. Metzger in Houben-Weyl, volume X/4, page 55 ff., Georg Thieme Verlag Stuttgart 1968). The compounds of the structural formula (W3) may be in the form of pure stereoisomers, but also in the form of mixtures of the stereoisomers.

Stage 3 Hydroxamyl Chloride

Stage 3 of the preparation process for the inventive compounds (1-T22):

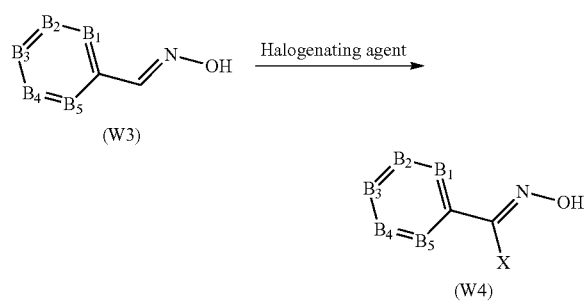

Inventive compounds of the general structure (W4) are prepared by reacting the oximes of the structure (W3) with halogenating agents.

The B1-B5 radicals are each as defined above. X is chlorine, bromine or iodine.

Typical compounds of the structure (W4) are, for example, 2,6-dichloro-4-[1,2,2,2-tetrafluoro-1-(trifluoromethyl)ethyl]-N-hydroxybenzimidoyl chloride, 2,6-dimethyl-4-[1,2,2,2-tetrafluoro-1-(trifluoromethyl)ethyl]-N-hydroxybenzimidoyl chloride, 2-ethyl-6-methyl-5-[1,2,2,2-tetrafluoro-1-(trifluoromethyl)ethyl]-N-hydroxybenzimidoyl chloride, 2-chloro-4-[1,2,2,2-tetrafluoro-1-(trifluoromethyl)ethyl]-6-(trifluoromethyl)-N-hydroxybenzimidoyl chloride, 2-methyl-4-[1,2,2,2-tetrafluoro-1-(trifluoromethyl)ethyl]-6-(trifluoromethyl)-N-hydroxybenzimidoyl chloride, 2-chloro-4-[1,2,2,2-tetrafluoro-1-(trifluoromethyl)ethyl]-6-(trifluoromethoxy)-N-hydroxybenzimidoyl chloride, 2-methyl-4-[1,2,2,2-tetrafluoro-1-(trifluoromethyl)ethyl]-6-(trifluoromethoxy)-N-hydroxybenzimidoyl chloride, 2-methyl-4-[1,2,2,2-tetrafluoro-1-(trifluoromethyl)ethyl]-6-(trifluoromethyl)-N-hydroxybenzimidoyl bromide.

Suitable halogenating compounds are known to those skilled in the art, for example chlorine, bromine, iodine, N-chlorosuccinimide, N-bromosuccinimide, N-iodosuccinimide, 1,3-dichloro-5,5-dimethylhydantoin, 1,3-dibromo-5,5-dimethylhydantoin, benzyltrimethylammonium tetrachloroiodate and sodium hypochlorite. Preference is given to using chlorinating reagents.

The reaction can be conducted using suitable solvents.

Useful diluents or solvents for conducting the processes according to the invention in principle include all organic solvents which are inert under the specific reaction conditions. Examples include: hydrohalocarbons (e.g. hydrochlorocarbons, such as tetraethylene, tetrachloroethane, dichloropropane, methylene chloride, dichlorobutane, chloroform, carbon tetrachloride, trichloroethane, trichloroethylene, pentachloroethane, difluorobenzene, 1,2-dichloroethane, chlorobenzene, bromobenzene, dichlorobenzene, chlorotoluene, trichlorobenzene), alcohols (e.g. methanol, ethanol, isopropanol, butanol), ethers (e.g. ethyl propyl ether, methyl tert-butyl ether, n-butyl ether, anisole, phenetole, cyclohexyl methyl ether, dimethyl ether, diethyl ether, dipropyl ether, diisopropyl ether, di-n-butyl ether, diisobutyl ether, diisoamyl ether, ethylene glycol dimethyl ether, tetrahydrofuran, dioxane, dichlorodiethyl ether and polyethers of ethylene oxide and/or propylene oxide), amines (e.g. trimethyl-, triethyl-, tripropyl-, tributylamine, N-methylmorpholine, pyridine and tetramethylenediamine), nitrohydrocarbons (e.g. nitromethane, nitroethane, nitropropane, nitrobenzene, chloronitrobenzene, o-nitrotoluene; nitriles such as acetonitrile, propionitrile, butyronitrile, isobutyronitrile, benzonitrile, m-chlorobenzonitrile), tetrahydrothiophene dioxide, dimethyl sulphoxide, tetramethylene sulphoxide, dipropyl sulphoxide, benzyl methyl sulphoxide, diisobutyl sulphoxide, dibutyl sulphoxide, diisoamyl sulphoxide, sulphones (e.g. dimethyl, diethyl, dipropyl, dibutyl, diphenyl, dihexyl, methyl ethyl, ethyl propyl, ethyl isobutyl and pentamethylene sulphone), aliphatic, cycloaliphatic or aromatic hydrocarbons (e.g. pentane, hexane, heptane, octane, nonane and technical hydrocarbons), and also what are called "white spirits" with components having boiling points in the range from, for example, 40° C. to 250° C., cymene, petroleum fractions within a boiling range from 70° C. to 190° C., cyclohexane, methylcyclohexane, petroleum ether, ligroin, octane, benzene, toluene, chlorobenzene, bromobenzene, nitrobenzene, xylene, esters (e.g. methyl, ethyl, butyl and isobutyl acetate, dimethyl, dibutyl and ethylene carbonate); amides (e.g. hexamethylenephosphoramide, formamide, N-methylformamide, N,N-dimethylformamide, N,N-dipropylformamide, N,N-dibutylformamide, N-methylpyrrolidine, N-methylcaprolactam, 1,3-dimethyl-3,4,5,6-tetrahydro-2(1H)-pyrimidine, octylpyrrolidone, octylcaprolactam, 1,3-dimethyl-2-imidazolinedione, N-formylpiperidine, N,N'-1,4-diformylpiperazine) and ketones (e.g. acetone, acetophenone, methyl ethyl ketone, methyl butyl ketone).

Preferred diluents used may be any solvent that does not impair the reaction, for example water. Useful examples are aromatic hydrocarbons such as benzene, toluene, xylene or chlorobenzene; halogenated hydrocarbons such as dichloromethane, chloroform, 1,2-dichloroethane or carbon tetrachloride, open-chain or cyclic ethers such as diethyl ether, dioxane, tetrahydrofuran or 1,2-dimethoxyethane; esters such as ethyl acetate and butyl acetate; ketones, for example acetone, methyl isobutyl ketone and cyclohexanone; amides such as dimethylformamide and dimethylacetamide, N-methylpyrrolidone; nitriles such as acetonitrile or propionitrile; and other inert solvents such as 1,3-dimethyl-2-imidazolidinone; the solvents may be used alone or in a combination of 2 or more.

The reaction can be executed within a wide temperature range. Usually, it is conducted within a temperature range from −78° C. to 200° C., preferably at temperatures between −10 and 150° C. The reaction can be executed under elevated or else reduced pressure. But it is preferably conducted under standard pressure. The reaction times are between 0.1 and 72 hours, preferably between 1 and 24 hours.

To perform the reaction, 1 to 3 mol, preferably 1 to 1.5 mol, of halogenating agent are used per mole of the compound of the structure (W3) in a solvent, for example dimethylformamide (DMF).

Stage 4 Ring Closure

Stage 4 of the preparation process for the inventive compounds (1-T22):

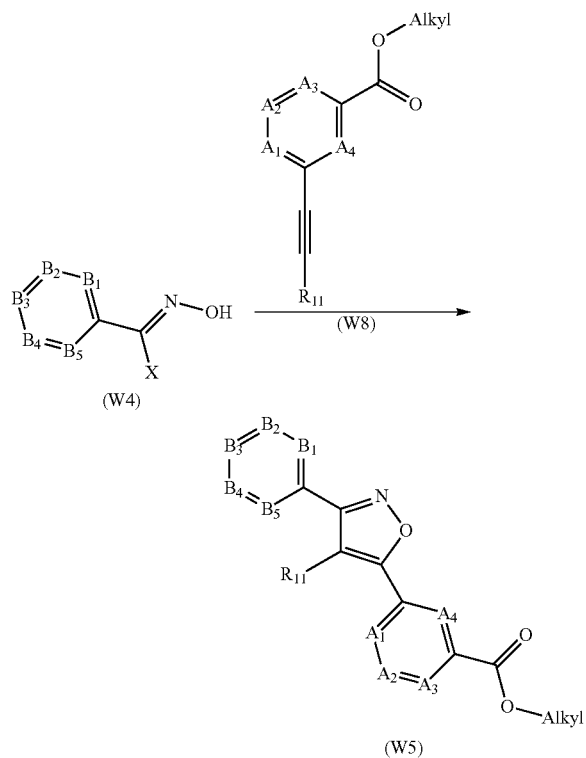

Inventive compounds of the general structure (W5) are prepared by reacting the hydroxamyl chlorides of the structure (W4) with acetylenes of the structure (W8).

The $A_1$-$A_4$, $B_1$-$B_5$, $R^{11}$ and alkyl radicals are each as defined above. X is halogen, such as chlorine, bromine, iodine.

The preparation of the compounds of the structure (W4) is described above. Typical compounds of the structure (W4) are, for example, 2,6-dichloro-4-[1,2,2,2-tetrafluoro-1-(trifluoromethyl)ethyl]-N-hydroxybenzimidoyl chloride, 2,6-dimethyl-4-[1,2,2,2-tetrafluoro-1-(trifluoromethyl)ethyl]-N-hydroxybenzimidoyl chloride, 2-ethyl-6-methyl-5-[1,2,2,2-tetrafluoro-1-(trifluoromethyl)ethyl]-N-hydroxybenzimidoyl chloride, 2-chloro-4-[1,2,2,2-tetrafluoro-1-(trifluoromethyl)ethyl]-6-(trifluoromethyl)-N-hydroxybenzimidoyl chloride, 2-methyl-4-[1,2,2,2-tetrafluoro-1-(trifluoromethyl)ethyl]-6-(trifluoromethyl)-N-hydroxybenzimidoyl chloride, 2-chloro-4-[1,2,2,2-tetrafluoro-1-(trifluoromethyl)ethyl]-6-(trifluoromethoxy)-N-hydroxybenzimidoyl chloride, 2-methyl-4-[1,2,2,2-tetrafluoro-1-(trifluoromethyl)ethyl]-6-(trifluoromethoxy)-N-hydroxybenzimidoyl chloride, 2-methyl-4-[1,2,2,2-tetrafluoro-1-(trifluoromethyl)ethyl]-6-(trifluoromethyl)-N-hydroxybenzimidoyl bromide.

The compounds of the structure (W8) are known (WO2012107434, p. 103) or can be prepared by methods known from the literature (Chinchilla, Rafael; Najera, Carmen, Chemical Society Reviews (2011), 40(10), 5084-5121, Chinchilla, Rafael; Najera, Carmen, Chemical Reviews (Washington, D.C., United States) (2007), 107(3), 874-922). Typical compounds of the structure (W8) are, for example, methyl 2-chloro-5-ethynylbenzoate, ethyl 2-bromo-5-ethynylbenzoate, methyl 2-chloro-5-ethynyl-3-fluorobenzoate, ethyl 2-chloro-5-ethynylnicotinate, ethyl 5-ethynyl-2-methylnicotinate.

The reaction can be conducted using suitable solvents.

Useful diluents or solvents for conducting the processes according to the invention in principle include all organic solvents which are inert under the specific reaction conditions. Examples include: hydrohalocarbons (e.g. hydrochlorocarbons, such as tetraethylene, tetrachloroethane, dichloropropane, methylene chloride, dichlorobutane, chloroform, carbon tetrachloride, trichloroethane, trichloroethylene, pentachloroethane, difluorobenzene, 1,2-dichloroethane, chlorobenzene, bromobenzene, dichlorobenzene, chlorotoluene, trichlorobenzene), alcohols (e.g. methanol, ethanol, isopropanol, butanol), ethers (e.g. ethyl propyl ether, methyl tert-butyl ether, n-butyl ether, anisole, phenetole, cyclohexyl methyl ether, dimethyl ether, diethyl ether, dipropyl ether, diisopropyl ether, di-n-butyl ether, diisobutyl ether, diisoamyl ether, ethylene glycol dimethyl ether, tetrahydrofuran, dioxane, dichlorodiethyl ether and polyethers of ethylene oxide and/or propylene oxide), amines (e.g. trimethyl-, triethyl-, tripropyl-, tributylamine, N-methylmorpholine, pyridine and tetramethylenediamine), nitrohydrocarbons (e.g. nitromethane, nitroethane, nitropropane, nitrobenzene, chloronitrobenzene, o-nitrotoluene; nitriles such as acetonitrile, propionitrile, butyronitrile, isobutyronitrile, benzonitrile, m-chlorobenzonitrile), tetrahydrothiophene dioxide, dimethyl sulphoxide, tetramethylene sulphoxide, dipropyl sulphoxide, benzyl methyl sulphoxide, diisobutyl sulphoxide, dibutyl sulphoxide, diisoamyl sulphoxide, sulphones (e.g. dimethyl, diethyl, dipropyl, dibutyl, diphenyl, dihexyl, methyl ethyl, ethyl propyl, ethyl isobutyl and pentamethylene sulphone), aliphatic, cycloaliphatic or aromatic hydrocarbons (e.g. pentane, hexane, heptane, octane, nonane and technical hydrocarbons), and also what are called "white spirits" with components having boiling points in the range from, for example, 40° C. to 250° C., cymene, petroleum fractions within a boiling range from 70° C. to 190° C., cyclohexane, methylcyclohexane, petroleum ether, ligroin, octane, benzene, toluene, chlorobenzene, bromobenzene, nitrobenzene, xylene, esters (e.g. methyl, ethyl, butyl and isobutyl acetate, dimethyl, dibutyl and ethylene carbonate); amides (e.g. hexamethylenephosphoramide, formamide, N-methylformamide, N,N-dimethylformamide, N,N-dipropylformamide, N,N-dibutylformamide, N-methylpyrrolidine, N-methylcaprolactam, 1,3-dimethyl-3,4,5,6-tetrahydro-2(1H)-pyrimidine, octylpyrrolidone, octylcaprolactam, 1,3-dimethyl-2-imidazolinedione, N-formylpiperidine, N,N'-1,4-diformylpiperazine) and ketones (e.g. acetone, acetophenone, methyl ethyl ketone, methyl butyl ketone).

Preferred diluents used may be any solvent that does not impair the reaction, for example water. Useful examples are aromatic hydrocarbons such as benzene, toluene, xylene or chlorobenzene; halogenated hydrocarbons such as dichloromethane, chloroform, 1,2-dichloroethane or carbon tetrachloride, open-chain or cyclic ethers such as diethyl ether, dioxane, tetrahydrofuran or 1,2-dimethoxyethane; esters such as ethyl acetate and butyl acetate; ketones, for example acetone, methyl isobutyl ketone and cyclohexanone; amides such as dimethylformamide and dimethylacetamide, N-methylpyrrolidone; nitriles such as acetonitrile or propionitrile; and other inert solvents such as 1,3-dimethyl-2-imidazolidinone; the solvents may be used alone or in a combination of 2 or more.

In the reactions of the compounds of the structure (W4) with the acetylenes of the structure (W8), it is possible to add bases. Examples include alkaline earth metal or alkali metal compounds (e.g. hydroxides, hydrides, oxides and carbonates of lithium, sodium, potassium, magnesium, calcium and barium), amidine bases or guanidine bases (e.g. 7-methyl-1,5,7-triazabicyclo[4.4.0]dec-5-ene (MTBD); diazabicyclo[4.3.0]nonene (DBN), diazabicyclo[2.2.2]octane (DABCO), 1,8-diazabicyclo[5.4.0]undecene (DBU), cyclohexyltetrabutylguanidine (CyTBG), cyclohexyltetramethylguanidine (CyTMG), N,N,N,N-tetramethyl-1,8-naphthalenediamine, pentamethylpiperidine) and amines, especially tertiary amines (e.g. triethylamine, trimethylamine, tribenzylamine, triisopropylamine, tributylamine, tricyclohexylamine, triamylamine, trihexylamine, N,N-dimethylaniline, N,N-dimethyltoluidine, N,N-dimethyl-p-aminopyridine, N-methylpyrrolidine, N-methylpiperidine, N-methylimidazole, N-methylpyrazole, N-methylmorpholine, N-methylhexamethylenediamine, pyridine, 4-pyrrolidinopyridine, 4-dimethylaminopyridine, quinoline, α-picoline, β-picoline, isoquinoline, pyrimidine, acridine, N,N,N',N'-tetramethylenediamine, N,N,N',N'-tetraethylenediamine, quinoxaline, N-propyldiisopropylamine, N-ethyldiisopropylamine, N,N'-dimethylcyclohexylamine, 2,6-lutidine, 2,4-lutidine or triethylenediamine).

A preferred basic reaction auxiliary used may be an organic base such as triethylamine, ethyldiisopropylamine, tri-n-butylamine, pyridine and 4-dimethylaminopyridine; in addition, it is possible to use, for example, the following bases: alkali metal hydroxides, for example sodium hydroxide and potassium hydroxide; carbonates such as sodium hydrogencarbonate and potassium carbonate; phosphates such as dipotassium hydrogenphosphate and trisodium phosphate.

The reaction can be executed within a wide temperature range. Usually, it is conducted within a temperature range from −78° C. to 200° C., preferably at temperatures between −10 and 150° C. The reaction can be executed under elevated or else reduced pressure. But it is preferably conducted under standard pressure. The reaction times are between 0.1 and 72 hours, preferably between 1 and 24 hours.

To conduct the reaction, for example, 1-2 molar equivalents of the compounds of the structure (W8) and 1 molar equivalent up to a slight excess of base per mole of the compound of the structure (W4) are reacted in a solvent, for example dimethylformamide (DMF).

Stages 3 and 4 for preparation of the compounds of the structure (W5) can be conducted in individual steps or else as a one-pot reaction.

Stages 5, 6 Hydrolysis, Amidation

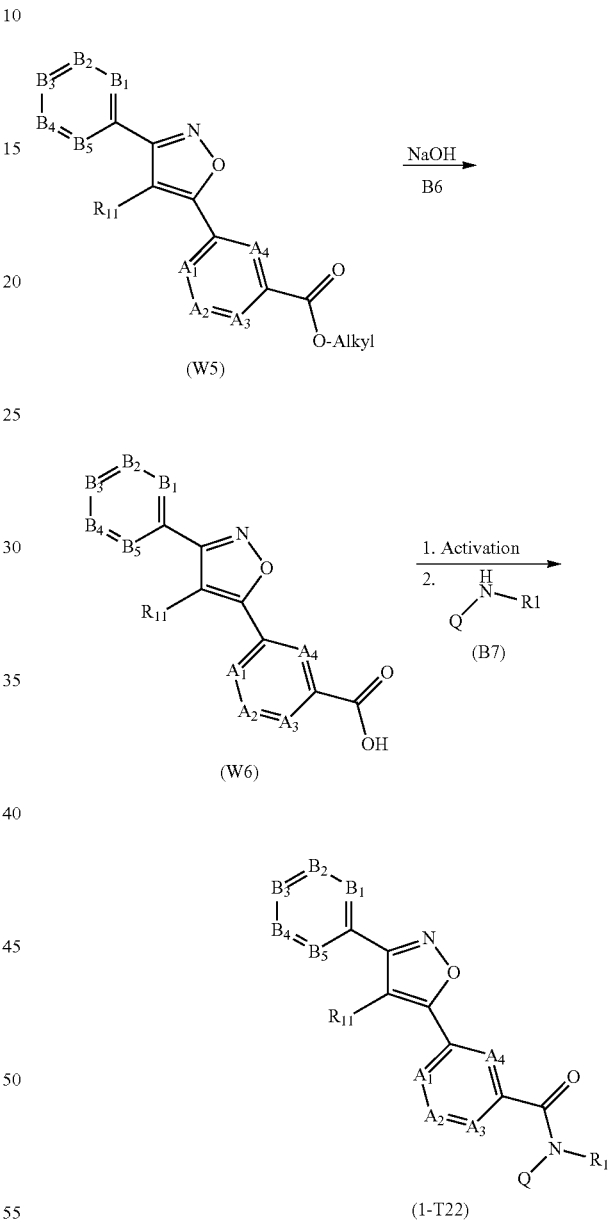

Inventive compounds of the general structure (I-T22) can be prepared in analogy to peptide coupling methods known from the literature from the starting materials (W6) and (W9) (WO2010051926; WO2010133312). Compounds of the general structure (W6) can be prepared analogously to processes known from the literature by ester hydrolysis from compounds of the general structure (W5) (WO2010051926; WO2010133312). The $A_1$-$A_4$, $B_1$-$B_5$, alkyl, Q, $R^1$ and $R^{11}$ radicals are each as defined above.

Process I-T23
The compounds of the structure (I-T23) can be prepared by the process specified in Reaction Scheme 8.
Reaction Scheme 8:
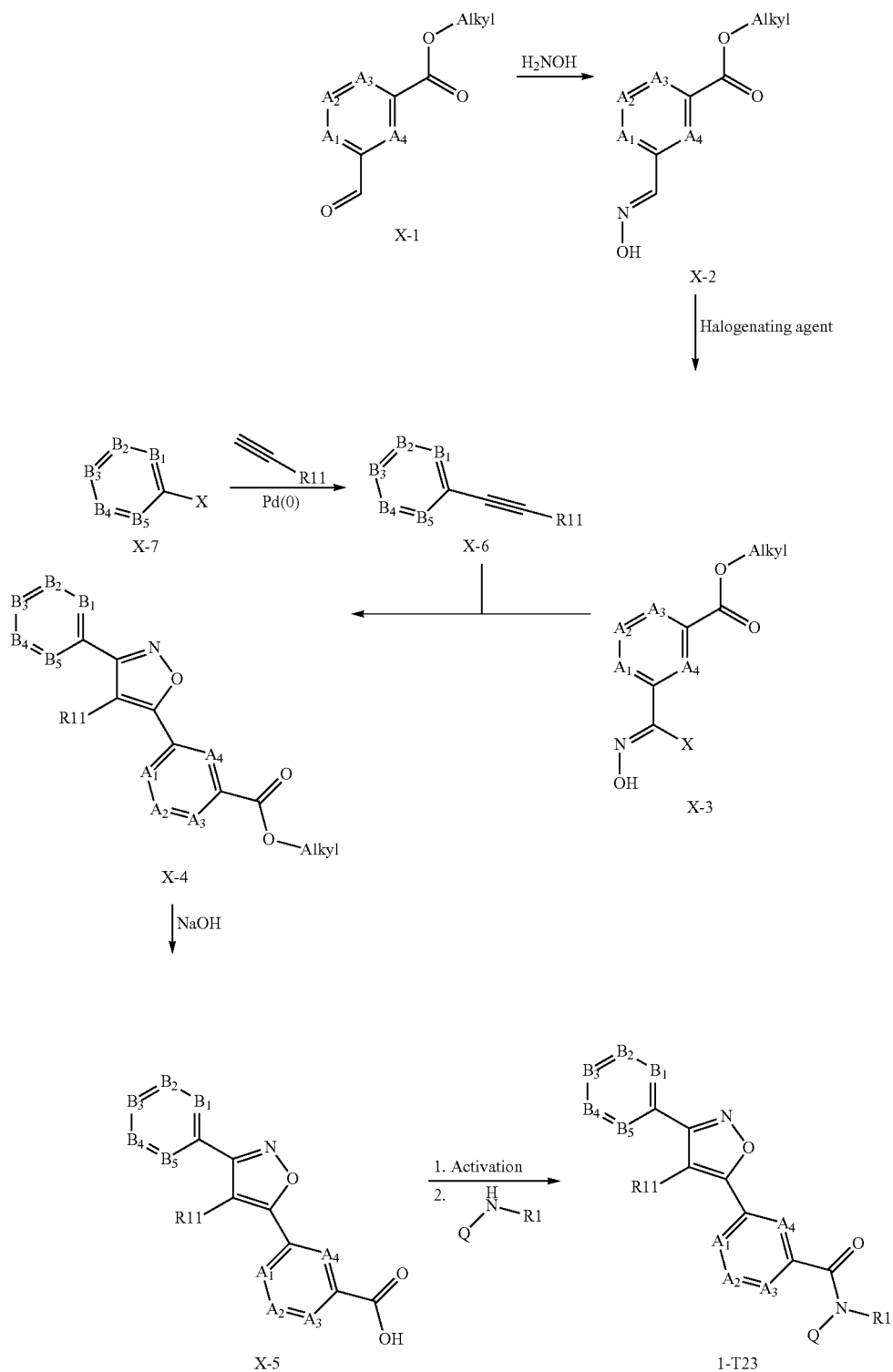

The $A_1$-$A_4$, $B_1$-$B_5$, alkyl, Q, $R^1$ and $R^{11}$ radicals are each as defined above. X is, for example, Cl, Br, I.

Stage 1 Oxime

Stage 1 of the preparation process for the inventive compounds (I-T23):

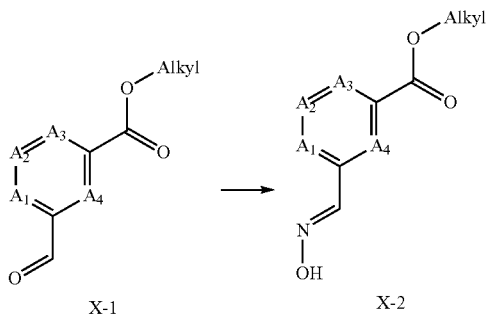

Inventive compounds of the general structure (X-2) can be prepared in analogy to methods known from the literature from the starting materials of the structure (X-1). The $A^1$-$A^4$ and alkyl radicals are each as defined above. Starting compounds of the structure (X-1) are known or can be prepared by known methods. Examples include 3-carbomethoxybenzaldehyde, 3-carbomethoxy-4-chlorobenzaldehyde, 3-carbomethoxy-4-bromobenzaldehyde, 3-carbomethoxy-4-fluorobenzaldehyde, 3-carbomethoxy-4-chloro-5-fluorobenzaldehyde and the corresponding ethyl esters. They can be prepared, for example, by the methods described in WO 2010/011584, p. 19-20; Journal of Organic Chemistry, 76 (2011), p. 1062-1071; WO 2012/114268, p. 137; Journal of the American Chemical Society, 108 (1986), p. 452-461.

The as yet unknown compounds (X-2) can be prepared in analogy to the known processes for preparing oximes from aldehydes (H. Metzger in Houben-Weyl, volume X/4, p. 55 ff., Georg Thieme Verlag Stuttgart 1968). The compounds of the structural formula (X-2) may be in the form of pure stereoisomers, but also in the form of mixtures of the stereoisomers.

Stage 2 Hydroxamyl Chloride

Stage 2 of the preparation process for the inventive compounds (I-T23):

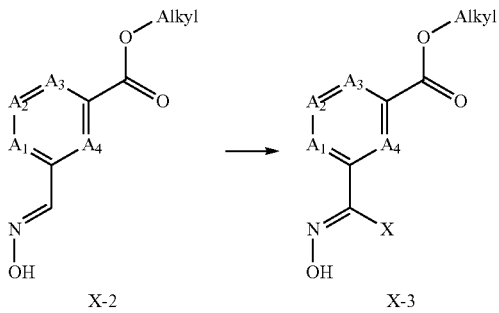

Inventive compounds of the general structure (X-3) are prepared by reacting the oximes of the structure (X-2) with halogenating agents.

The $A_1$-$A_4$ and alkyl radicals are each as defined above.

Typical compounds of the structure (X-3) are, for example, carbomethoxy-4-chloro-N-hydroxybenzimidoyl chloride, 3-carbomethoxy-4-fluoro-N-hydroxybenzimidoyl chloride, 3-carbomethoxy-4-chloro-5-fluoro-N-hydroxybenzimidoyl chloride, 3-carbomethoxy-4-bromo-N-hydroxybenzimidoyl chloride.

Suitable halogenating compounds are known to those skilled in the art, for example chlorine, bromine, iodine, N-chlorosuccinimide, N-bromosuccinimide, N-iodosuccinimide, 1,3-dichloro-5,5-dimethylhydantoin, 1,3-dibromo-5,5-dimethylhydantoin, benzyltrimethylammonium tetrachloroiodate and sodium hypochlorite. Preference is given to using chlorinating reagents.

Useful diluents or solvents for conducting the processes according to the invention in principle include all organic solvents which are inert under the specific reaction conditions. Examples include: hydrohalocarbons (e.g. hydrochlorocarbons, such as tetraethylene, tetrachloroethane, dichloropropane, methylene chloride, dichlorobutane, chloroform, carbon tetrachloride, trichloroethane, trichloroethylene, pentachloroethane, difluorobenzene, 1,2-dichloroethane, chlorobenzene, bromobenzene, dichlorobenzene, chlorotoluene, trichlorobenzene), alcohols (e.g. methanol, ethanol, isopropanol, butanol), ethers (e.g. ethyl propyl ether, methyl tert-butyl ether, n-butyl ether, anisole, phenetole, cyclohexyl methyl ether, dimethyl ether, diethyl ether, dipropyl ether, diisopropyl ether, di-n-butyl ether, diisobutyl ether, diisoamyl ether, ethylene glycol dimethyl ether, tetrahydrofuran, dioxane, dichlorodiethyl ether and polyethers of ethylene oxide and/or propylene oxide), amines (e.g. trimethyl-, triethyl-, tripropyl-, tributylamine, N-methylmorpholine, pyridine and tetramethylenediamine), nitrohydrocarbons (e.g. nitromethane, nitroethane, nitropropane, nitrobenzene, chloronitrobenzene, o-nitrotoluene; nitriles such as acetonitrile, propionitrile, butyronitrile, isobutyronitrile, benzonitrile, m-chlorobenzonitrile), tetrahydrothiophene dioxide, dimethyl sulphoxide, tetramethylene sulphoxide, dipropyl sulphoxide, benzyl methyl sulphoxide, diisobutyl sulphoxide, dibutyl sulphoxide, diisoamyl sulphoxide, sulphones (e.g. dimethyl, diethyl, dipropyl, dibutyl, diphenyl, dihexyl, methyl ethyl, ethyl propyl, ethyl isobutyl and pentamethylene sulphone), aliphatic, cycloaliphatic or aromatic hydrocarbons (e.g. pentane, hexane, heptane, octane, nonane and technical hydrocarbons), and also what are called "white spirits" with components having boiling points in the range from, for example, 40° C. to 250° C., cymene, petroleum fractions within a boiling range from 70° C. to 190° C., cyclohexane, methylcyclohexane, petroleum ether, ligroin, octane, benzene, toluene, chlorobenzene, bromobenzene, nitrobenzene, xylene, esters (e.g. methyl, ethyl, butyl and isobutyl acetate, dimethyl, dibutyl and ethylene carbonate); amides (e.g. hexamethylenephosphoramide, formamide, N-methylformamide, N,N-dimethylformamide, N,N-dipropylformamide, N,N-dibutylformamide, N-methylpyrrolidine, N-methylcaprolactam, 1,3-dimethyl-3,4,5,6-tetrahydro-2(1H)-pyrimidine, octylpyrrolidone, octylcaprolactam, 1,3-dimethyl-2-imidazolinedione, N-formylpiperidine, N,N'-1,4-diformylpiperazine) and ketones (e.g. acetone, acetophenone, methyl ethyl ketone, methyl butyl ketone).

Preferred diluents used may be any solvent that does not impair the reaction, for example water. Useful examples are aromatic hydrocarbons such as benzene, toluene, xylene or chlorobenzene; halogenated hydrocarbons such as dichloromethane, chloroform, 1,2-dichloroethane or carbon tetrachloride, open-chain or cyclic ethers such as diethyl ether, dioxane, tetrahydrofuran or 1,2-dimethoxyethane; esters such as ethyl acetate and butyl acetate; ketones, for example acetone, methyl isobutyl ketone and cyclohexanone; amides such as dimethylformamide and dimethylacetamide, N-methylpyrrolidone; nitriles such as acetonitrile or propionitrile; and other inert solvents such as 1,3-dimethyl-2-imidazolidinone; the solvents may be used alone or in a combination of 2 or more.

The reaction can be executed within a wide temperature range. Usually, it is conducted within a temperature range from −78° C. to 200° C., preferably at temperatures between −10 and 150° C. The reaction can be executed under elevated or else reduced pressure. But it is preferably conducted under standard pressure. The reaction times are between 0.1 and 72 hours, preferably between 1 and 24 hours.

To perform the reaction, 1 to 3 mol, preferably 1 to 1.5 mol, of halogenating agent are used per mole of the compound of the structure (X-2) in a solvent, for example dimethylformamide (DMF).

Stage 3 Ring Closure

Stage 3 of the preparation process for the inventive compounds (1-T23):

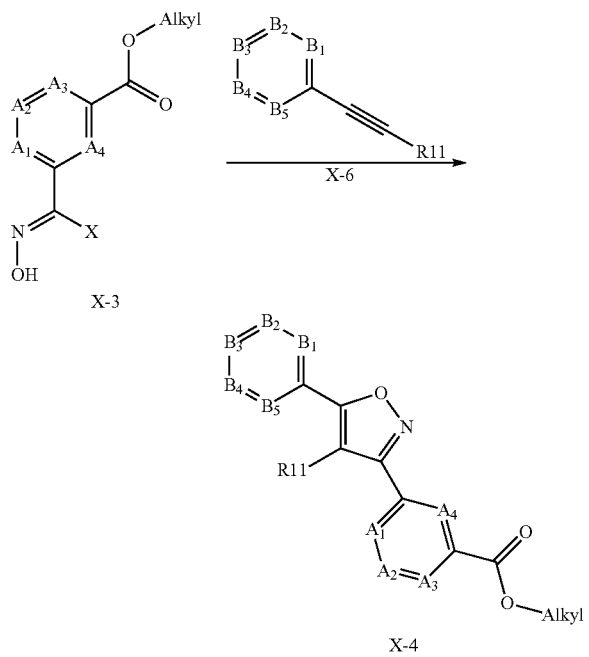

Inventive compounds of the general structure (X-4) are prepared by reacting the hydroxamyl chlorides of the structure (X-3) with acetylenes of the structure (X-6).

The $A^1$-$A^4$, $B^1$-$B^5$, $R^{11}$ and alkyl radicals are each as defined above.

Typical compounds of the structure (X-3) are, for example, carbomethoxy-4-chloro-N-hydroxybenzimidoyl chloride, 3-carbomethoxy-4-fluoro-N-hydroxybenzimidoyl chloride, 3-carbomethoxy-4-chloro-5-fluoro-N-hydroxybenzimidoyl chloride, 3-carbomethoxy-4-bromo-N-hydroxybenzimidoyl chloride.

Useful diluents or solvents for conducting the processes according to the invention in principle include all organic solvents which are inert under the specific reaction conditions. Examples include: hydrohalocarbons (e.g. hydrochlorocarbons, such as tetraethylene, tetrachloroethane, dichloropropane, methylene chloride, dichlorobutane, chloroform, carbon tetrachloride, trichloroethane, trichloroethylene, pentachloroethane, difluorobenzene, 1,2-dichloroethane, chlorobenzene, bromobenzene, dichlorobenzene, chlorotoluene, trichlorobenzene), alcohols (e.g. methanol, ethanol, isopropanol, butanol), ethers (e.g. ethyl propyl ether, methyl tert-butyl ether, n-butyl ether, anisole, phenetole, cyclohexyl methyl ether, dimethyl ether, diethyl ether, dipropyl ether, diisopropyl ether, di-n-butyl ether, diisobutyl ether, diisoamyl ether, ethylene glycol dimethyl ether, tetrahydrofuran, dioxane, dichlorodiethyl ether and polyethers of ethylene oxide and/or propylene oxide), amines (e.g. trimethyl-, triethyl-, tripropyl-, tributylamine, N-methylmorpholine, pyridine and tetramethylenediamine), nitrohydrocarbons (e.g. nitromethane, nitroethane, nitropropane, nitrobenzene, chloronitrobenzene, o-nitrotoluene; nitriles such as acetonitrile, propionitrile, butyronitrile, isobutyronitrile, benzonitrile, m-chlorobenzonitrile), tetrahydrothiophene dioxide, dimethyl sulphoxide, tetramethylene sulphoxide, dipropyl sulphoxide, benzyl methyl sulphoxide, diisobutyl sulphoxide, dibutyl sulphoxide, diisoamyl sulphoxide, sulphones (e.g. dimethyl, diethyl, dipropyl, dibutyl, diphenyl, dihexyl, methyl ethyl, ethyl propyl, ethyl isobutyl and pentamethylene sulphone), aliphatic, cycloaliphatic or aromatic hydrocarbons (e.g. pentane, hexane, heptane, octane, nonane and technical hydrocarbons), and also what are called "white spirits" with components having boiling points in the range from, for example, 40° C. to 250° C., cymene, petroleum fractions within a boiling range from 70° C. to 190° C., cyclohexane, methylcyclohexane, petroleum ether, ligroin, octane, benzene, toluene, chlorobenzene, bromobenzene, nitrobenzene, xylene, esters (e.g. methyl, ethyl, butyl and isobutyl acetate, dimethyl, dibutyl and ethylene carbonate); amides (e.g. hexamethylenephosphoramide, formamide, N-methylformamide, N,N-dimethylformamide, N,N-dipropylformamide, N,N-dibutylformamide, N-methylpyrrolidine, N-methylcaprolactam, 1,3-dimethyl-3,4,5,6-tetrahydro-2(1H)-pyrimidine, octylpyrrolidone, octylcaprolactam, 1,3-dimethyl-2-imidazolinedione, N-formylpiperidine, N,N'-1,4-diformylpiperazine) and ketones (e.g. acetone, acetophenone, methyl ethyl ketone, methyl butyl ketone).

Preferred diluents used may be any solvent that does not impair the reaction, for example water. Useful examples are aromatic hydrocarbons such as benzene, toluene, xylene or chlorobenzene; halogenated hydrocarbons such as dichloromethane, chloroform, 1,2-dichloroethane or carbon tetrachloride, open-chain or cyclic ethers such as diethyl ether, dioxane, tetrahydrofuran or 1,2-dimethoxyethane; esters such as ethyl acetate and butyl acetate; ketones, for example acetone, methyl isobutyl ketone and cyclohexanone; amides such as dimethylformamide and dimethylacetamide, N-methylpyrrolidone; nitriles such as acetonitrile or propionitrile; and other inert solvents such as 1,3-dimethyl-2-imidazolidinone; the solvents may be used alone or in a combination of 2 or more.

In the reactions of the compounds of the structure (X-3) with the acetylenes of the structure (X-6), it is possible to add bases. Examples include alkaline earth metal or alkali metal compounds (e.g. hydroxides, hydrides, oxides and carbonates of lithium, sodium, potassium, magnesium, calcium and barium), amidine bases or guanidine bases (e.g. 7-methyl-1,5,7-triazabicyclo[4.4.0]dec-5-ene (MTBD); diazabicyclo[4.3.0]nonene (DBN), diazabicyclo[2.2.2]octane (DABCO), 1,8-diazabicyclo[5.4.0]undecene (DBU), cyclohexyltetrabutylguanidine (CyTBG), cyclohexyltetramethylguanidine (CyTMG), N,N,N,N-tetramethyl-1,8-naphthalenediamine, pentamethylpiperidine) and amines, especially tertiary amines (e.g. triethylamine, trimethylamine, tribenzylamine, triisopropylamine, tributylamine, tricyclohexylamine, triamylamine, trihexylamine, N,N-dimethylaniline, N,N-dimethyltoluidine, N,N-dimethyl-p-aminopyridine, N-methylpyrrolidine, N-methylpiperidine, N-methylimidazole, N-methylpyrazole, N-methylmorpholine, N-methylhexamethylenediamine, pyridine, 4-pyrrolidinopyridine, 4-dimethylaminopyridine, quinoline, α-picoline, β-picoline, isoquinoline, pyrimidine, acridine, N,N,N',N'-tetramethylenediamine, N,N,N',N'-tetraethylenediamine, quinoxaline, N-propyldiisopropylamine, N-ethyldiisopropylamine, N,N'-dimethylcyclohexylamine, 2,6-lutidine, 2,4-lutidine or triethylenediamine).

A preferred basic reaction auxiliary used may be an organic base such as triethylamine, ethyldiisopropylamine, tri-n-butylamine, pyridine and 4-dimethylaminopyridine; in addition, it is possible to use, for example, the following bases: alkali metal hydroxides, for example sodium hydroxide and potassium hydroxide; carbonates such as sodium hydrogencarbonate and potassium carbonate; phosphates such as dipotassium hydrogenphosphate and trisodium phosphate.

The reaction can be executed within a wide temperature range. Usually, it is conducted within a temperature range from −78° C. to 200° C., preferably at temperatures between −10 and 150° C. The reaction can be executed under elevated or else reduced pressure. But it is preferably conducted under standard pressure. The reaction times are between 0.1 and 72 hours, preferably between 1 and 24 hours.

To conduct the reaction, for example, 1-2 molar equivalents of the compounds of the structure (X-6) and 1 molar equivalent up to a slight excess of base per mole of the compound of the structure (X-3) are reacted in a solvent, for example dimethylformamide (DMF).

Stages 2 and 3 for preparation of the compounds of the structure (X-4) can be conducted in individual steps or else as a one-pot reaction.

Stages 4, 5 Hydrolysis, Amidation

The last stages (stages 4 and 5) for preparation of the inventive compounds (1-T23), hydrolysis of the carboxylic ester (X-4) and amidation of the carboxylic acid X-5, can be conducted by the general processes described above (Reaction Scheme) for ester hydrolysis and amidation of the carboxylic acid.

Stage 6 Preparation of the Acetylenes

Stage 6 Preparation of the starting compounds of the structure (X-6)

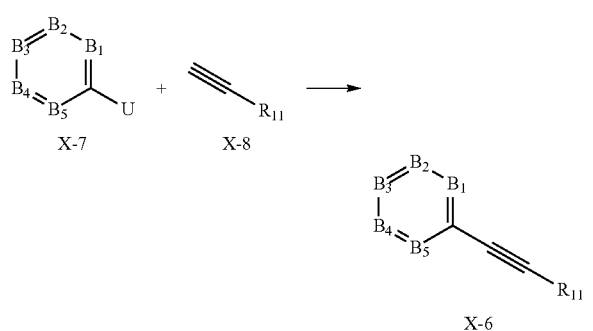

The $B_1$-$B_5$, $R^{11}$ and U radicals are each as defined above. U is, for example, bromine, iodine or triflate.

Inventive compounds of the general structure (X-6) can be prepared in analogy to methods known from the literature (Chinchilla, Rafael et al., Chemical Society Reviews (2011), 40(10), p. 5084-5121, Chinchilla, Rafael et al., Chemical Reviews (Washington, D.C., United States) (2007), 107(3), p. 874-922) from the starting materials of the structure (X-7) with catalysis by means of transition metal catalysts comprising palladium and copper.

Starting compounds of the structure (X-7) are known or can be prepared by known methods. Examples include 2-bromo-1,3-dichloro-5-[1,2,2,2-tetrafluoro-1-(trifluoromethyl)ethyl]benzene, 2-bromo-1,3-dimethyl-5-[1,2,2,2-tetrafluoro-1-(trifluoromethyl)ethyl]benzene, 2-bromo-1-ethyl-3-methyl-5-[1,2,2,2-tetrafluoro-1-(trifluoromethyl)ethyl]benzene, 2-bromo-1-chloro-5-[1,2,2,2-tetrafluoro-1-(trifluoromethyl)ethyl]-3-(trifluoromethyl)benzene, 2-bromo-1-methyl-5-[1,2,2,2-tetrafluoro-1-(trifluoromethyl)ethyl]-3-(trifluoromethyl)benzene, 2-bromo-1-chloro-5-[1,2,2,2-tetrafluoro-1-(trifluoromethyl)ethyl]-3-(trifluoromethoxy)benzene, 2-bromo-1-methyl-5-[1,2,2,2-tetrafluoro-1-(trifluoromethyl)ethyl]-3-(trifluoromethoxy)benzene. They can be prepared, for example, by the methods described in EP 1 253 128, pages 8-10.

Starting compounds of the structure (X-8) are known or can be prepared by known methods. If $R^6$=H, it is possible in this process to use a protecting group rather than $R^6$. Suitable protecting groups are, for example, trimethylsilyl, triethylsilyl and dimethylhydroxymethyl. Further suitable protecting groups for introduction and detachment are described in the literature [see lists in Greene's protective groups in organic synthesis, 4th edition, P. G. M. Wuts, T. W. Greene, John Wiley & Sons, Inc., Hoboken, N.J., 2007, pages 927-933.]

Stage 3 Alternative: Coupling with Amides

Alternatively, the inventive compounds (I-T23) can be prepared by the general Preparation Process B (Reaction Scheme 9).

Reaction Scheme 9:

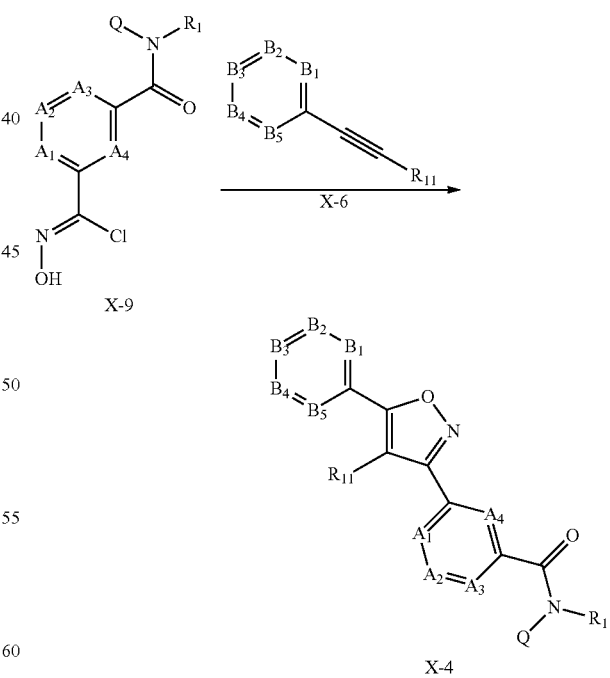

The $A_1$-$A_4$, $B_1$-$B_5$, Q, $R^1$ and $R^{11}$ radicals are each as defined above.

Inventive compounds of the general structure (X-4) are prepared by reacting the hydroxamyl chlorides of the structure (X-9) with acetylenes of the structure (X-6).

The preparation of the compounds of the structure (X-6) is described above. The compounds of the structure (X-9) are prepared analogously to the above-described preparation of the compounds of the structure (X-3).

Typical compounds of the structure (X-3) are, for example, 4-chloro-3-(cyclopropylcarbamoyl)-N-hydroxybenzimidoyl chloride, 3-(cyclopropylcarbamoyl)-4-fluoro-N-hydroxybenzimidoyl chloride, 4-chloro-3-(cyclopropylcarbamoyl)-5-fluoro-N-hydroxybenzimidoyl chloride, 4-bromo-3-(cyclopropylcarbamoyl)-N-hydroxybenzimidoyl chloride.

(I-T24): Compounds of the formula (I-24) can be prepared, for example, analogously to Furukawa, Hirotoshi et al. Heterocycles, 79 (2009), p. 303-309; U.S. Pat. No. 6,545,009, p. 34, Example 111.

(I-T25): Compounds of the formula (I-25) can be prepared, for example, analogously to WO 2004/14366, p. 113.

(I-T26): Compounds of the formula (I-26) can be prepared, for example, analogously to Chihiro, Masatoshi et al., Journal of Medicinal Chemistry, 38 (1995), p. 353-358.

(I-T27): Compounds of the formula (I-27) can be prepared, for example, analogously to U.S. Pat. No. 6,545,009, p. 31, Example 74.

The compounds of the structure (I-T28) can be prepared by the process specified in Reaction Scheme 10.

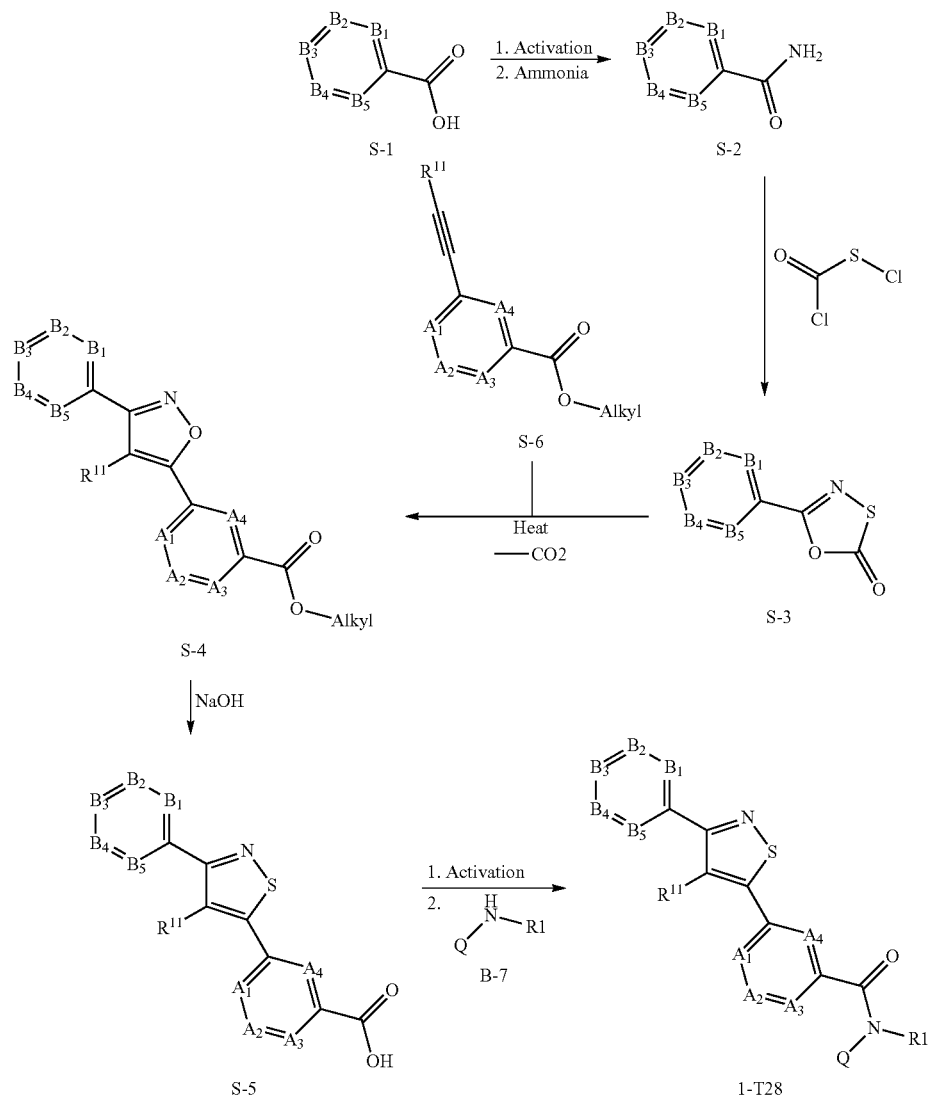

Reaction Scheme 10

The $A^1$-$A^4$, $B^1$-$B^5$, alkyl, Q, $R^1$ and $R^{11}$ radicals are each as defined above. Starting compounds of the structure (S-1) are known (e.g. U.S. Pat. No. 5,739,083 p. 10, or WO 2012/175474, p. 117-118) or can be prepared by known methods. The reactions are conducted under the conditions specified in the literature (e.g. Abdelrahman S. Mayhoub et al., Bioorg. Med. Chem. 20 (2012) p. 2427-2434 or WO 2009/023372).

Process I-T29

The compounds of the structure (I-T29) can be prepared by the process specified in Reaction Scheme 11.

Reaction Scheme 3:

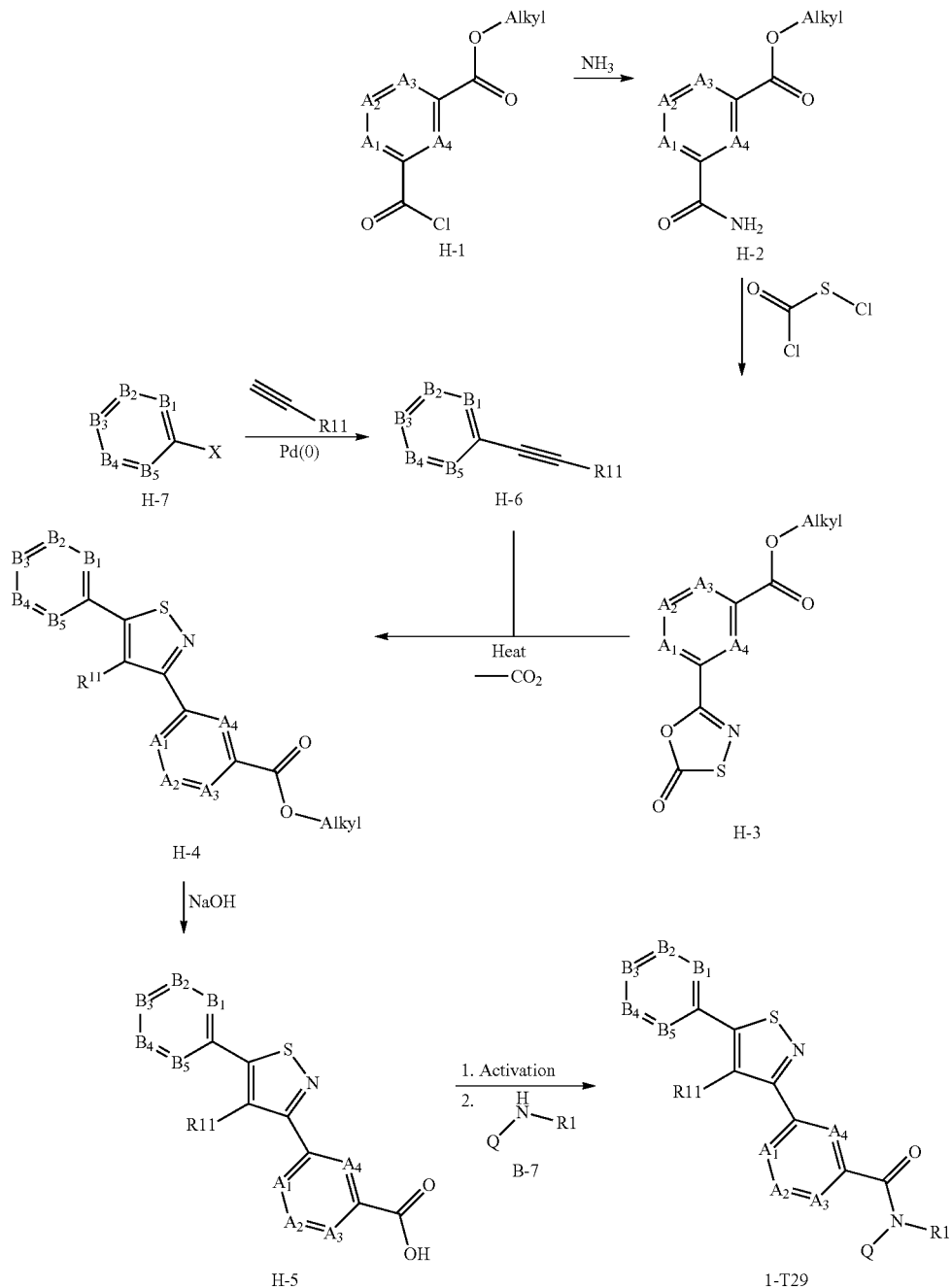

The $A^1$-$A^4$, $B^1$-$B^5$, alkyl, Q, $R^1$ and $R^{11}$ radicals are each as defined above. Starting compounds of the structure (H-1) and (H-7) are known (e.g. U.S. Pat. No. 3,725,417 p. 7 or WO 2012/175474, p. 117-118) or can be prepared by known methods. The reactions are conducted under the conditions specified in the literature (e.g. Abdelrahman S. Mayhoub et al., Bioorg. Med. Chem. 20 (2012) p. 2427-2434 or WO 2009/023372).

Process I-T30

(I-T30): Compounds of the formula (I-T30) can be prepared, for example, analogously to WO 2011/9484, p. 104; or Gamber, Gabriel G. et al., Bioorganic and Medicinal Chemistry Letters, 21 (2011), p. 1447-1451.

(I-T31): Compounds of the formula (I-T31) can be prepared, for example, analogously to Bishop, Brian C. et al., Synthesis, (2004), p. 43-52; or Heller, Stephen T. et al., Organic Letters, 8 (2006), p. 2675-2678; or Baddar, F. G. et al. Journal of Heterocyclic Chemistry, 15 (1978), p. 385-393.

(I-T32): Compounds of the formula (I-T32) can be prepared, for example, analogously to Joo, Jung Min et al., Journal of Organic Chemistry, 75 (2010), p. 4911-4920.

(I-T33): Compounds of the formula (I-T33) can be prepared, for example, analogously to Joo, Jung Min et al., Journal of Organic Chemistry, 75 (2010), p. 4911-4920; or WO 2004/91610, p. 70.

(I-T34): Compounds of the formula (I-T34) can be prepared, for example, analogously to Al-Tel, Taleb et al., Journal of Medicinal Chemistry, 54 (2011), p. 8373-8385.

(I-T35): Compounds of the formula (I-T35) can be prepared, for example, analogously to Yang, Shu-wie et al., Bioorganic and Medicinal Chemistry Letters, 21 (2011), p. 182-185; or Kennedy, Andrew J. et al, Journal of Medicinal Chemistry, 54 (2011), p. 3524-3548.

The compounds of the structure (I-T45) can be prepared by the process specified in Reaction Scheme 12.

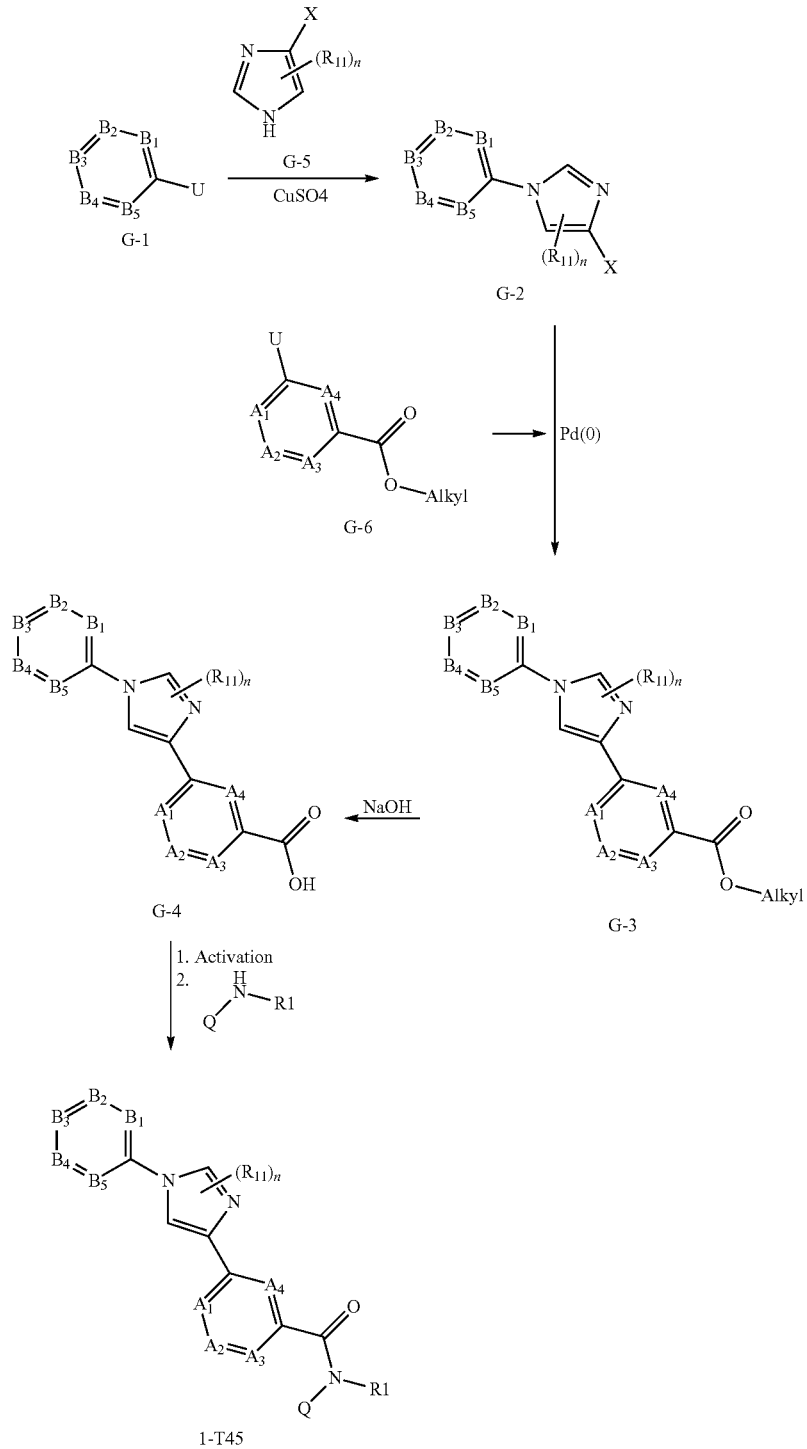

The $A_1$-$A_4$, $B_1$-$B_5$, alkyl, Q, $R^1$ and $R^{11}$ radicals are each as defined above. U is a boronic acid, boronic ester or trifluoroboronate. X is bromine, iodine or triflate. Starting compounds of the structure (G-1), (G-5) and (G6) are known or can be prepared by known methods.

The reactions can be conducted by the processes described in the literature (see, for example Stage G1→G2 US 2013/0012532, p. 29).

Process I-T46

The compounds of the structure (I-T46) can be prepared by the process specified in Reaction Scheme 13.

The $A_1$-$A_4$, $B_1$-$B_5$, alkyl, Q, $R^1$ and $R^{11}$ radicals are each as defined above. U is a boronic acid, boronic ester or trifluoroboronate. X is bromine, iodine or triflate. Starting compounds of the structure (F-1) and (F-5) are known (e.g. F-1: Hulcoop, David G. et al., Organic Letters, 9 (2007), p. 1761-1764) or can be prepared by known methods.

The reactions can be conducted by the processes described in the literature, for example US 2009/209476, p. 18-19.

Reaction Scheme 13

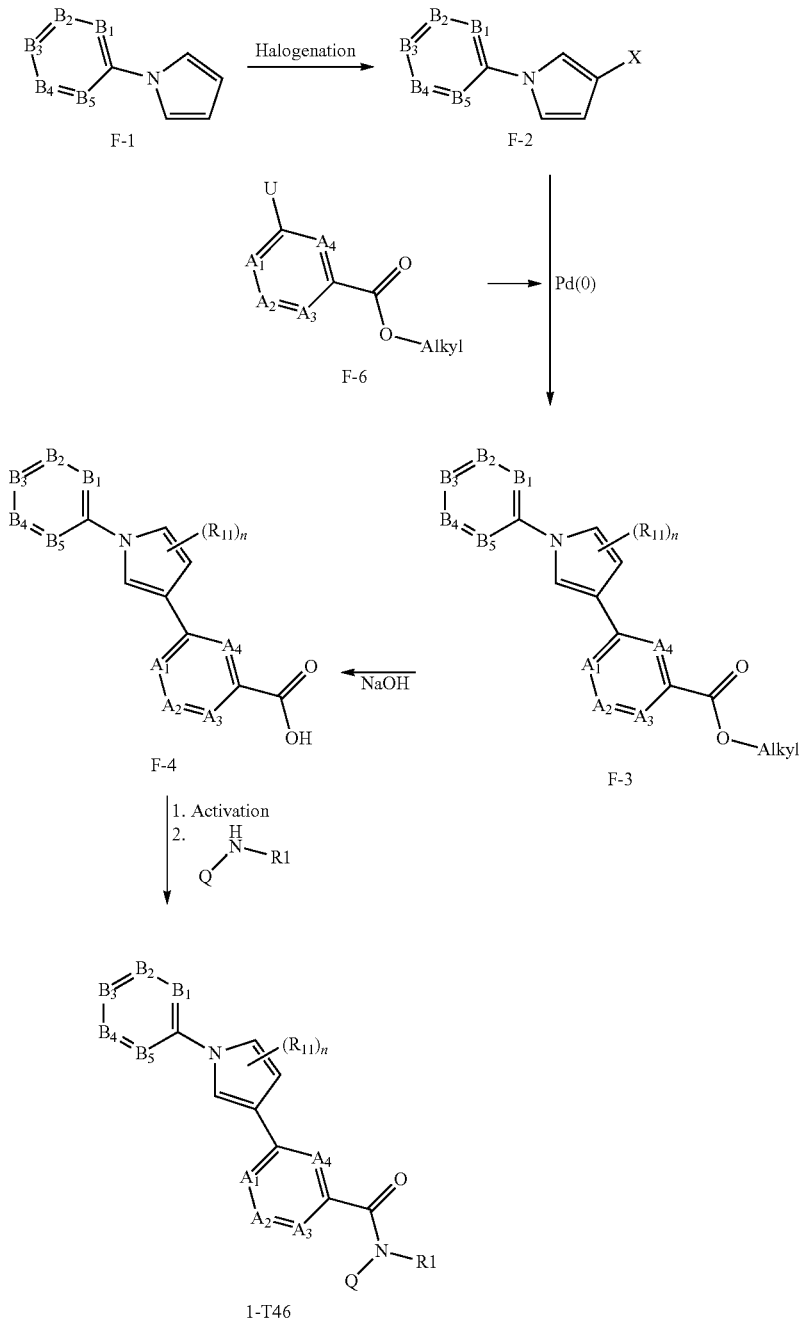

Process I-T47

The compounds of the structure (I-T47) can be prepared by the process specified in Reaction Scheme 14.

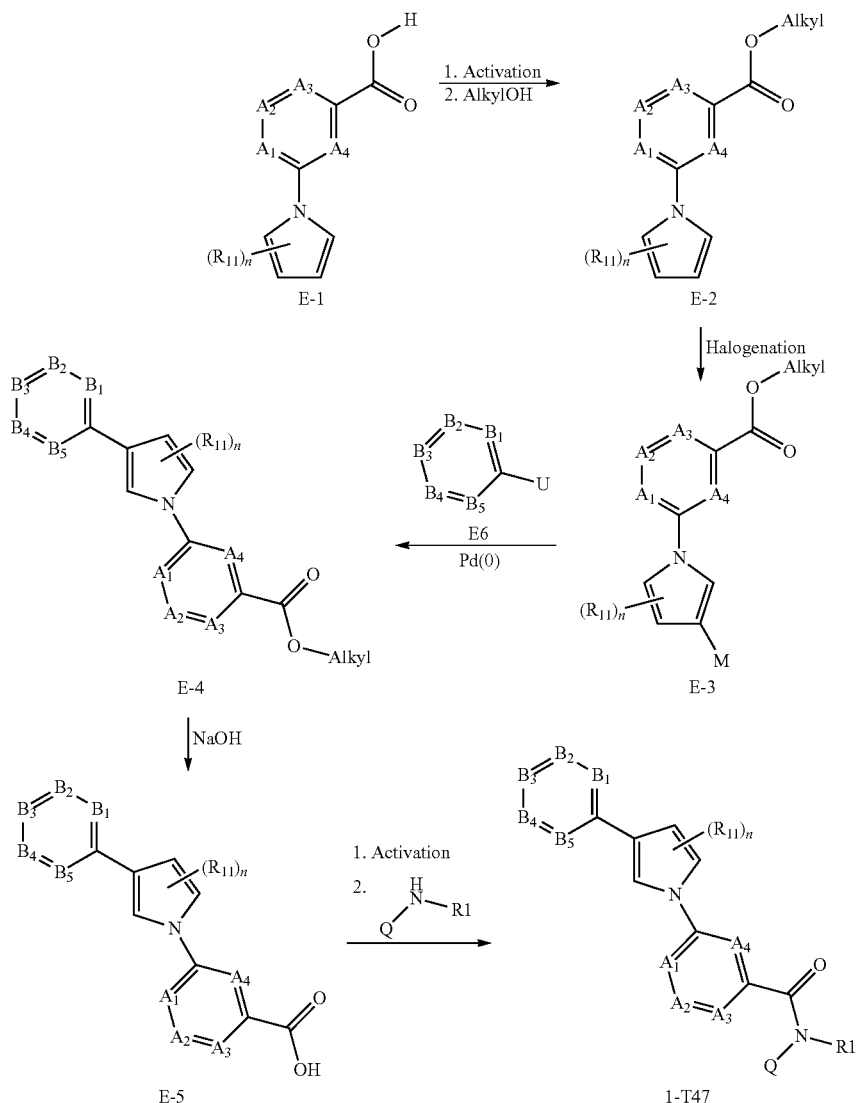

The $A_1$-$A_4$, $B_1$-$B_5$, alkyl, Q, $R^1$ and $R^{11}$ radicals are each as defined above. U is bromine, iodine or triflate when M is a boronic acid, boronic ester or trifluoroboronate. U is a boronic acid, boronic ester or trifluoroboronate when M is bromine, iodine or triflate. Starting compounds of the structure (E-1) and (E-6) are known (e.g. Liu, Kun et al., Journal of Medicinal Chemistry, 51 (2008), p. 7843-7854; or Cornet, Stephanie M. et al., Transactions, (2003), p. 4395-4405), or can be prepared by known methods.

The reactions can be conducted by the processes described in the literature, for example US 2009/209476, p. 18-19.

Process for Preparing Thioamides

The compounds of the structure (Ii) can be prepared by the process specified in Reaction Scheme 15 from compounds of the structure (Ih) through reaction with sulphur-transferring reagents.

Reaction Scheme 15:

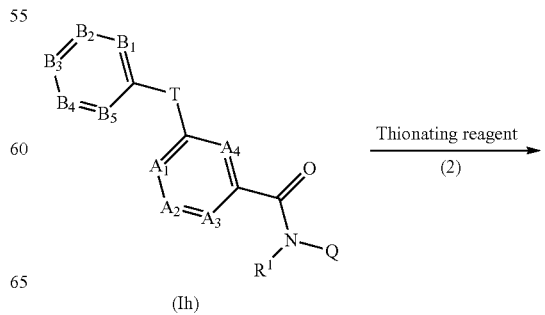

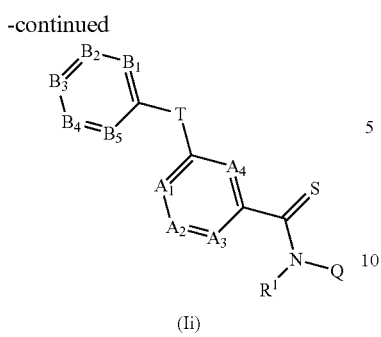

(Ii)

The $A_1$-$A_4$, $B_1$-$B_5$, alkyl, Q, T and $R^1$ radicals are each as defined above. The thionating reagent (2) used may, for example, be $P_4S_{10}$ or Lawesson's reagent (2,4-bis(4-methoxyphenyl)-1,3,2,4-dithiadiphosphetane 2,4-disulphide).

The preparation of the compounds (Ih) is described above.

The thionating reagents are commercially available or can be prepared by processes known to those skilled in the art or in analogy to these processes.

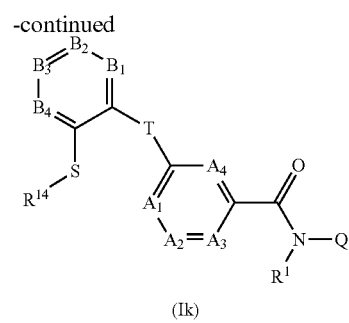

(Ik)

The $A_1$ to $A_4$, $B_1$ to B4, alkyl, Q, $R^1$, n and $R^{11}$ radicals are each as defined above. X is a suitable leaving group, for example fluorine, chlorine, bromine or iodine. $R^{14}$ is optionally substituted $C_1$-$C_6$-alkyl. Y is hydrogen or an alkali metal, for example sodium or lithium.

The reaction is conducted in analogy to methods known from the literature for introduction of alkylthio radicals into aromatic systems [e.g. Organometallics 1989, 8(5), 1303-1308; WO1998056761, Example 63, p. 97].

Process for Preparing (Ika) and (Ikb)

The inventive compounds (Ika) and (Ikb) can be prepared by the process specified in Reaction Scheme 17 from the compounds of the structure (Ik) through reaction with oxidizing reagents.

Reaction Scheme 17

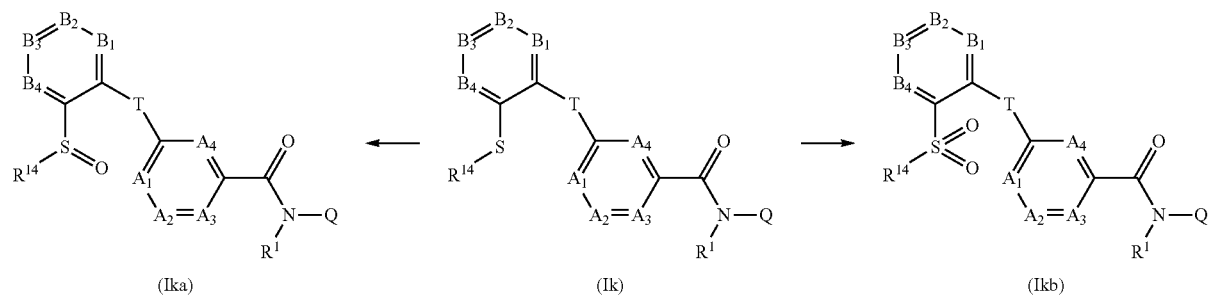

The reaction is conducted in analogy to methods known from the literature for thionating carbonamides (e.g. WO2012056372, p. 77; WO2003066050, p. 31).

Process for Preparing (Ik)

The inventive compounds (Ik) can be prepared by the process specified in Reaction Scheme 16 from the compounds (Ij) through reaction with sulphur compounds of the structure (Y-3).

Reaction Scheme 16

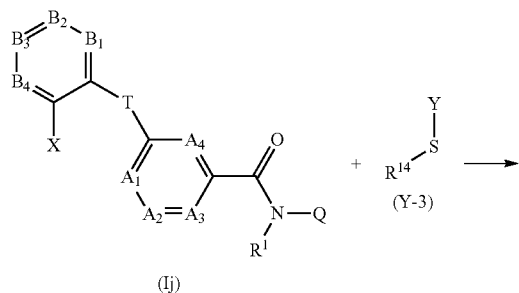

The $A_1$ to $A_4$, $B_1$ to B4, alkyl, Q, $R^1$, n and $R^{11}$ radicals are each as defined above. $R^{14}$ is optionally substituted $C_1$-$C_6$-alkyl.

The preparation of the compounds of the structure (Ik) is described above.

The oxidizing agents used may be the reagents known to those skilled in the art from the literature for preparation of sulphoxides and sulphones. They are commercially available or can be prepared by processes known to those skilled in the art or in analogy to these processes. Examples include: hydrogen peroxide, peroxyacetic acid, 3-chloroperbenzoic acid and trifluoroperoxyacetic acid.

The reaction is conducted in analogy to methods known from the literature for preparation of sulphoxides and sulphones [sulphoxide derivatives: WO2006/097766; WO2005/019151; sulphone derivatives: WO2008/125214; WO2005/121087].

Process for Preparing N-Alkyl Compounds

The compounds of the structure (I) can be prepared by the process specified in Reaction Scheme 18 from compounds of the structure (Im) through reaction with alkylating agents.

Reaction Scheme 18:

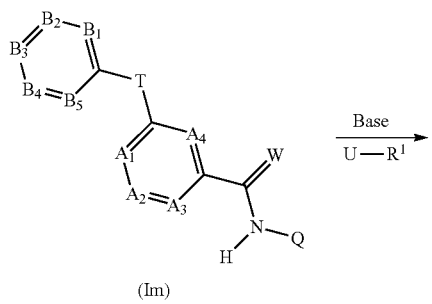

(Im)

$\xrightarrow{\text{Base}}$ U—R$^1$

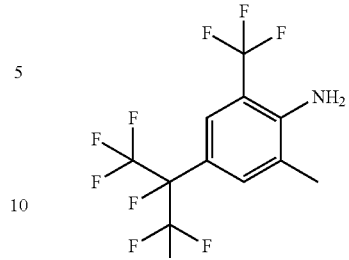

(I)

The A$_1$-A$_4$, B$_1$-B$_5$, alkyl and Q radicals are each as defined above. U is, for example, bromine, iodine or triflate. R$^1$ is in each case primary or secondary, optionally substituted C$_1$-C$_6$-alkyl, C$_3$-C$_6$-alkenyl, C$_3$-C$_6$-alkynyl, C$_4$-C$_7$-cycloalkyl, C$_1$-C$_6$-alkylcarbonyl, C$_1$-C$_6$-alkoxycarbonyl, aryl-(C$_1$-C$_3$)-alkyl, heteroaryl-(C$_1$-C$_3$)-alkyl. W is oxygen.

Compounds of the structure U-R$^1$ are commercially available or known from the literature, or can be prepared in analogy to methods known from the literature. Examples include: methyl chloride, methyl bromide, methyl iodide, dimethyl sulphate, methyl triflate, ethyl bromide, ethyl iodide, diethyl sulphate and ethyl triflate.

The bases used for the reaction are commercially available. Examples include alkaline earth metal and alkali metal compounds (e.g. hydroxides, hydrides, oxides and carbonates of lithium, sodium, potassium, magnesium, calcium and barium), for example sodium hydride, sodium hydroxide and potassium hydroxide; carbonates such as sodium hydrogencarbonate and potassium carbonate.

The reaction is conducted in analogy to methods known from the literature for N-alkylation of secondary amides (e.g. G. L. Gisele, A. Liittringhaus, Synthesis (1971) p. 266, for an overview see: B. C. Challis, J. A. Challis in: The Chemistry of Functional Groups, The Chemistry of Amides, S. Patai, J. Zabicky, editors, Interscience Publishers, London, 1970, p. 734 ff).

Preparation of the 4-heptafluoroisopropyl-2-methyl-6-trifluoromethylaniline Starting Material The 4-heptafluoroisopropyl-2-methyl-6-trifluoromethylaniline starting material of the structure (D-1a) has not been described to date in the literature. The preparation can be conducted by 2 different processes.

D-1a

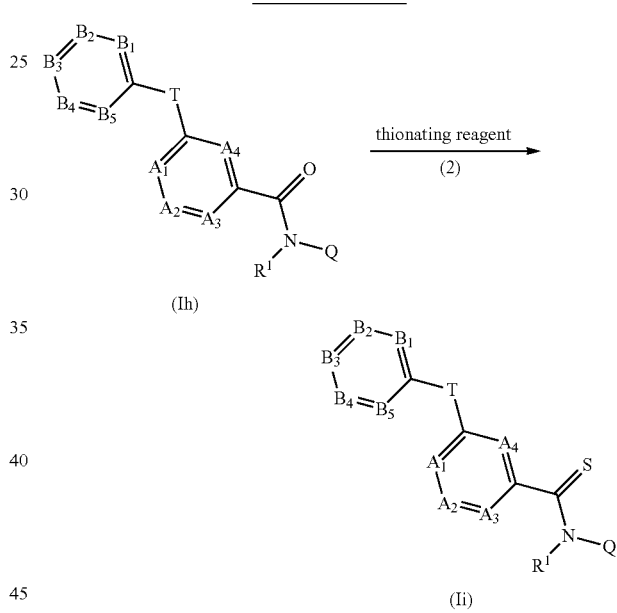

Process for Preparing Thioamides

The compounds of the structure (Ii) can be prepared by the process described in Reaction Scheme 15 from compounds of the structure (Ih) by reaction with sulphur-transferring reagents.

Reaction Scheme 15

The A$_1$-A$_4$, B$_1$-B$_5$, alkyl, Q, T, and R$^1$ radicals are each as defined above. Thionating reagents (2) used may, for example, be P$_4$S$_{10}$ or Lawesson's reagent (2,4-bis(4-methoxyphenyl)-1,3,2,4-dithiadiphosphetane 2,4-disulphide).

The preparation of the compounds (Ih) is described above.

The thionating reagents are commercially available or can be prepared by processes known to those skilled in the art or in analogy to these processes.

The reaction is conducted in analogy to methods known from literature for thionation of carbonamides (e.g. WO2012056372, p. 77; WO2003066050, p. 31).

Process for Preparing (Ik)

The inventive compounds (Ik) can be prepared by the process specified in Reaction Scheme 16 from the compounds (Ij) by reaction with sulphur compounds of the structure (Y-3).

Reaction Scheme 16

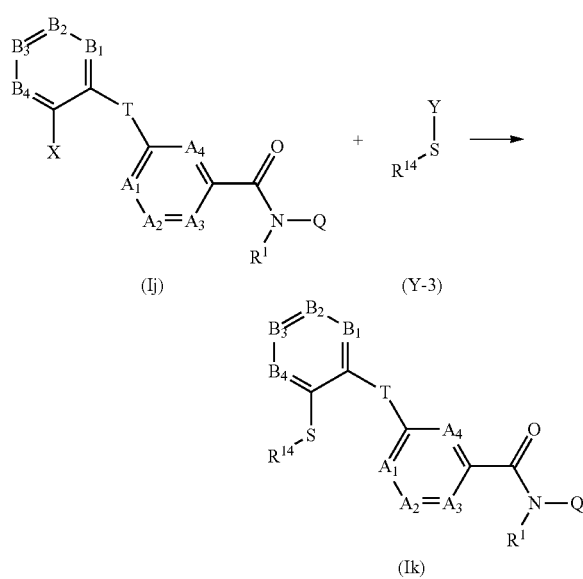

The $A_1$ to $A_4$, $B_1$ to B4, alkyl, Q, $R^1$, n and $R^{11}$ radicals are each as defined above. X is a suitable leaving group, for example fluorine, chlorine, bromine or iodine. $R^{14}$ is optionally substituted $C_1$-$C_6$-alkyl. Y is hydrogen or an alkali metal, for example sodium or lithium.

The reaction is conducted in analogy to methods known from the literature for introduction of alkylthio radicals into aromatics [e.g. Organometallics 1989, 8(5), 1303-1308; WO1998056761, Example 63, p. 97].

Process 1:

4-Heptafluoroisopropyl-2-methyl-6-trifluoromethylaniline of the structure (K-1) can be prepared proceeding from 2-methyl-6-trifluoromethylaniline by the process specified in Reaction Scheme 1, by reaction with heptafluoroisopropyl iodide in the presence of hydrogen peroxide.

Reaction Scheme 4

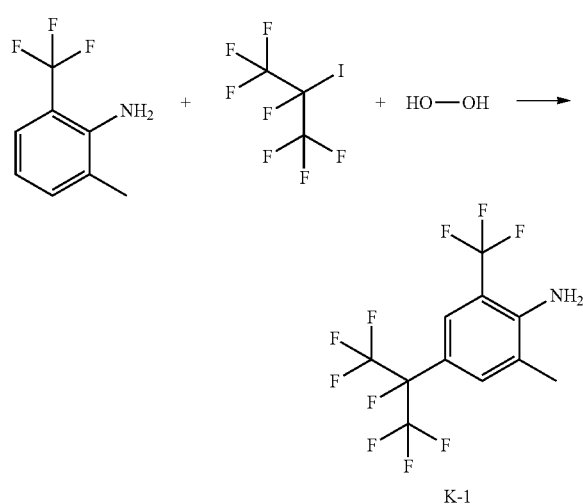

2-methyl-6-trifluoromethylaniline is known from literature (John P. Chupp, Terry M. Balthazor, Michael J. Miller, and Mark J. Pozzo, J. Org. Chem. 49 (1984),4711-4716 or Thomas E. Nickson J. Org. Chem. 51 (1986) 3903-3904), and heptafluoroisopropyl iodide is commercially available.

The reaction is conducted in analogy to known processes for trifluoromethylation of aromatics (Tatsuhito Kino, Yu Nagase, Yuhki Ohtsuka, Kyoko Yamamoto, Daisuke Uraguchi, Kenji Tokuhisa and Tetsu Yamakawa, Journal of Fluorine Chemistry 131 (2010) 98-105).

Process 2

In addition, 4-heptafluoroisopropyl-2-methyl-6-trifluoromethylaniline of the structure (K-1) can be prepared proceeding from 4-heptafluoroisopropyl-2-methylaniline by the process specified in Scheme 2, by reaction with sodium trifluoromethylsulphinate in the presence of oxidizing agents and transition metal catalysts.

Reaction Scheme 5

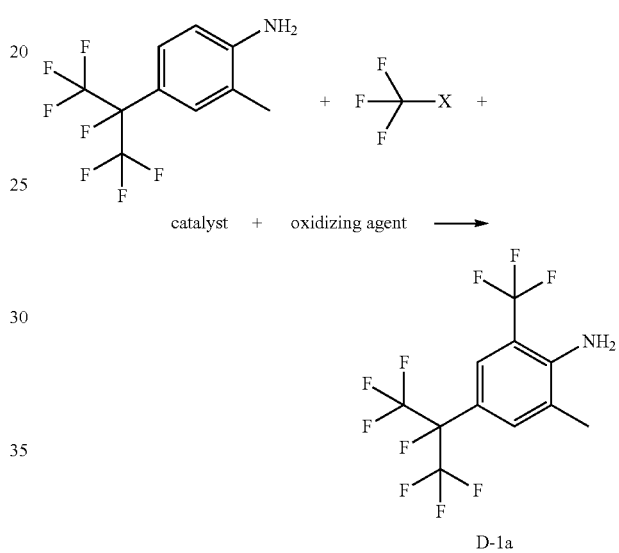

X is Br, I, $NaSO_2^-$ (sodium trifluoromethylsulphinate), $KSO_2^-$ (potassium trifluoromethylsulphinate). Particular preference is given to sodium trifluoromethylsulphinate.

4-Heptafluoroisopropyl-2-methylaniline is known (US2004/92762).

Suitable catalysts are transition metals such as iron(II) sulphate, iron(III) nitrate, copper(II) triflate or ferrocene. Particular preference is given to iron(II) sulphate.

Suitable oxidizing agents are, in particular, peroxides such as hydrogen peroxide, tert-butyl hydroperoxide or sodium peroxodisulphate, potassium peroxodisulphate, sodium peroxomonosulphate or potassium peroxomonosulphate. Particular preference is given to tert-butyl hydroperoxide.

In the performance of the reaction, suitable solvents may be used.

Useful diluents or solvents for performance of the processes according to the invention in principle include all organic solvents that are inert under the specific reaction conditions. Examples include: nitriles such as acetonitrile, propionitrile, butyronitrile, isobutyronitrile; water, tetrahydrothiophene dioxide, dimethyl sulphoxide, tetramethylene sulphoxide, dipropyl sulphoxide, diisobutyl sulphoxide, dibutyl sulphoxide, diisoamyl sulphoxide, sulphones (e.g. dimethyl, diethyl, dipropyl, dibutyl, dihexyl, methyl ethyl, ethyl propyl, ethyl isobutyl and pentamethylene sulphone); aliphatic, cycloaliphatic (e.g. pentane, hexane, heptane, octane, nonane and technical hydrocarbons), and also what are called "white spirits" having components having boiling points in the range from, for example, 40° C. to 250° C., petroleum fractions within a boiling range from 70° C. to 190° C., cyclohexane, methylcyclohexane, petroleum ether, ligroin, octane.

Preferred diluents used may be any solvent that does not impair the reaction, for example water; nitriles such as acetonitrile, propionitrile, butyronitrile, isobutyronitrile. The solvents can be used alone or in a combination of 2 or more.

Bases may be used in the reactions. Examples include alkaline earth metal or alkali metal compounds (e.g. hydroxide, hydrides, oxides and carbonates of lithium, sodium, potassium, magnesium, calcium and barium).

A preferred basic reaction auxiliary used may be sodium hydrogencarbonate; in addition, it is possible, for example, to use the following bases: alkali metal hydroxides, for example sodium hydroxide and potassium hydroxide; carbonates such as sodium hydrogencarbonate and potassium carbonate; phosphates such as sodium dihydrogenphosphate, dipotassium hydrogenphosphate and trisodium phosphate.

The reaction can be conducted within a wide temperature range. It is usually conducted within a temperature range from −78 to 200° C., preferably at temperatures between −10 and 150° C. The reaction can be executed under elevated or else reduced pressure. But it is preferably conducted under standard pressure. The reaction times are between 0.1 and 72 hours, preferably between 1 and 24 hours.

To conduct the reaction, 1 to 10 mol, preferably 1 to 4 mol, of trifluoromethylating agent; 1 to 20 mol, preferably 1 to 8 mol, of oxidizing agent and 0.01 to 1 mol, preferably 0.05 to 0.4 mol, of catalyst per mole of 4-heptafluoroisopropyl-2-methyl-6-trifluoromethylaniline are used in a solvent or solvent mixture, for example in a mixture of acetonitrile and water.

Process I-T46 Extended

The compounds of the structure (I-T46) can be prepared by the process specified in the Reaction Scheme.

Reaction Scheme 6

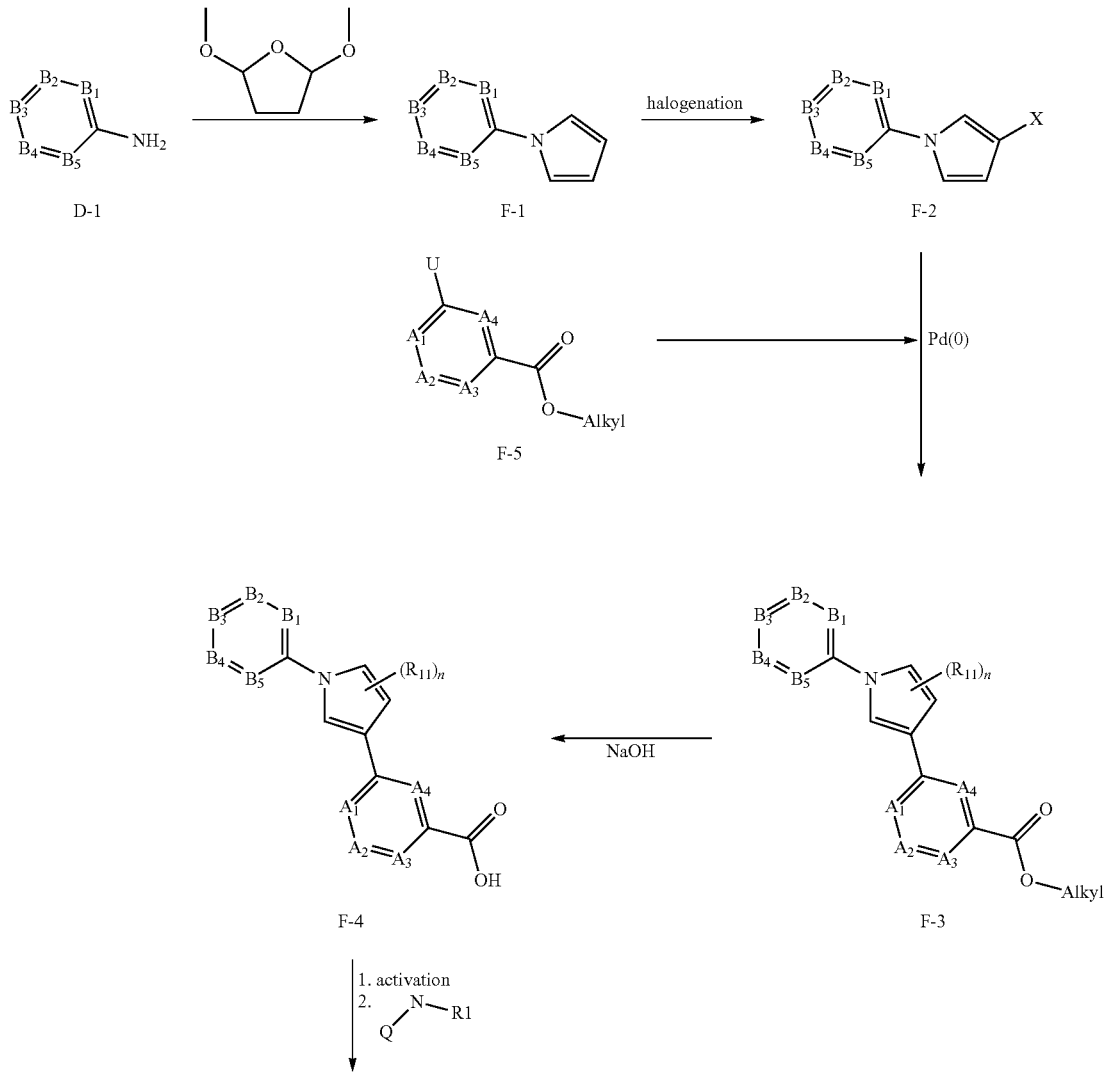

-continued

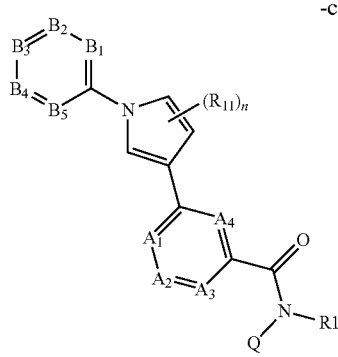

1-T46

The $A_1$-$A_4$, $B_1$-$B_5$, alkyl, Q, $R^1$ and $R^{11}$ radicals are each as defined above. U is a boronic acid, boronic ester or trifluoroboronate. X is bromine, iodine or triflate. Starting compounds of the structure (F-1) and (F-5) are known (e.g. F-1: Hulcoop, David G. et al., Organic Letters, 9 (2007), p. 1761-1764, Supporting information pages 1 ff.), or can be prepared by known methods (for example from D-1).

The reactions can be conducted by the processes described in the literature, e.g. US2009/209476, p. 18-19.

Stage 1 Pyrrole Ring Closure
Stage 1 for the Preparation Process for the Inventive Compounds (I-T46):

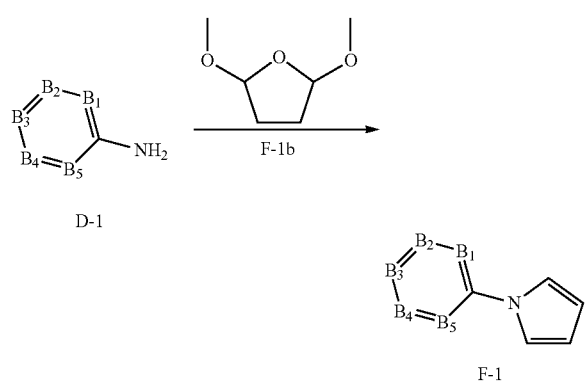

Inventive compounds of the general structure (F-1) can be prepared in analogy to methods known from the literature from the starting materials of the structure (D-1) and (F-1b). The $B^1$-$B^5$ radicals are each as defined above. The compounds of the structures (D-1) are known from the literature (e.g. US2002/198399, WO2009/30457, page 28) or can be prepared by methods known from the literature. The compound (F1-b) is commercially available. Typical representatives of the compounds of the structure (D-1) include 2-amino-1,3-dichloro-5-[1,2,2,2-tetrafluoro-1-(trifluoromethyl)ethyl]benzene, 2-amino-1,3-dimethyl-5-[1,2,2,2-tetrafluoro-1-(trifluoromethyl)-ethyl]benzene, 2-amino-1-ethyl-3-methyl-5-[1,2,2,2-tetrafluoro-1-(trifluoromethyl)ethyl]benzene, 2-amino-1-chloro-5-[1,2,2,2-tetrafluoro-1-(trifluoromethyl)ethyl]-3-(trifluoromethyl)benzene, 2-amino-1-methyl-5-[1,2,2,2-tetrafluoro-1-(trifluoromethyl)ethyl]3-(trifluoromethyl)benzene, 2-amino-1-chloro-5-[1,2,2,2-tetrafluoro-1-(trifluoromethyl)ethyl]-3-(trifluoromethoxy)benzene, 2-amino-1-methyl-5-[1,2,2,2-tetrafluoro-1-(trifluoromethyl)ethyl]-3-(trifluoromethoxy)

benzene. The reaction is conducted under the conditions known for analogous compounds in the literature (e.g. Hulcoop, David G. et al., Organic Letters, 9 (2007), p. 1761-1764, Supporting information pages 1 ff.)

Stage 2 Halogenation
Stage 1 for the Preparation Process for the Inventive Compounds (I-T46):

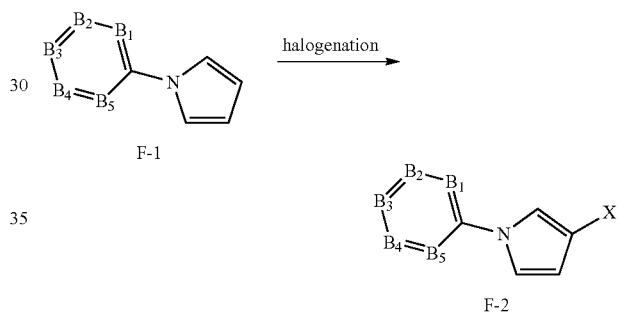

Inventive compounds of the general structure (F-2) can be prepared in analogy to methods known from literature from the starting materials of the structure (F-1) by halogenation. The $B^1$-$B^5$ radicals are each as defined above. The compounds of the structures (F-1) are known from the literature (e.g. F-1: Hulcoop, David G. et al., Organic Letters, 9 (2007), p. 1761-1764, Supporting information page 1 ff.) or can be prepared by the method described above. Typical representatives of the compounds of the structure (F-1) include 1-[2,6-dichloro-4-[1,2,2,2-tetrafluoro-1-(trifluoromethyl)ethyl]phenyl]pyrrole, 1-[2,6-dimethyl-4-[1,2,2,2-tetrafluoro-1-(trifluoromethyl)ethyl]phenyl]pyrrole, 1-[2-ethyl-6-methyl-4-[1,2,2,2-tetrafluoro-1-(trifluoromethyl)ethyl]phenyl]pyrrole, 1-[2-chloro-4-[1,2,2,2-tetrafluoro-1-(trifluoromethyl)ethyl]-6-(trifluoromethyl)phenyl]pyrrole, 1-[2-methyl-4-[1,2,2,2-tetrafluoro-1-(trifluoromethyl)ethyl]-6-(trifluoromethyl)phenyl]pyrrole, 1-[1-chloro-5-[1,2,2,2-tetrafluoro-1-(trifluoromethyl)ethyl]-6-(trifluoromethoxy)phenyl]pyrrole, 1-[1-methyl-5-[1,2,2,2-tetrafluoro-1-(trifluoromethyl)ethyl]-6-(trifluoromethoxy)phenyl]pyrrole.

Suitable halogenating compounds are known to those skilled in the art, for example bromine, iodine, N-bromosuccinimide, N-iodosuccinimide, 1,3-dibromo-5,5-dimethylhydantoin and benzyltrimethylammonium tetrachloroiodate. Preference is given to using bromine, iodine and iodosuccinimide. The reaction follows the conditions known from literature (e.g. Tatsuta; Itoh Bulletin of the Chemical Society of Japan, 67 (1994) 1449-1455).

Stage 3 Boronic Acid Coupling

Stage 3 of the Preparation Process for the Inventive Compounds (I-T46):

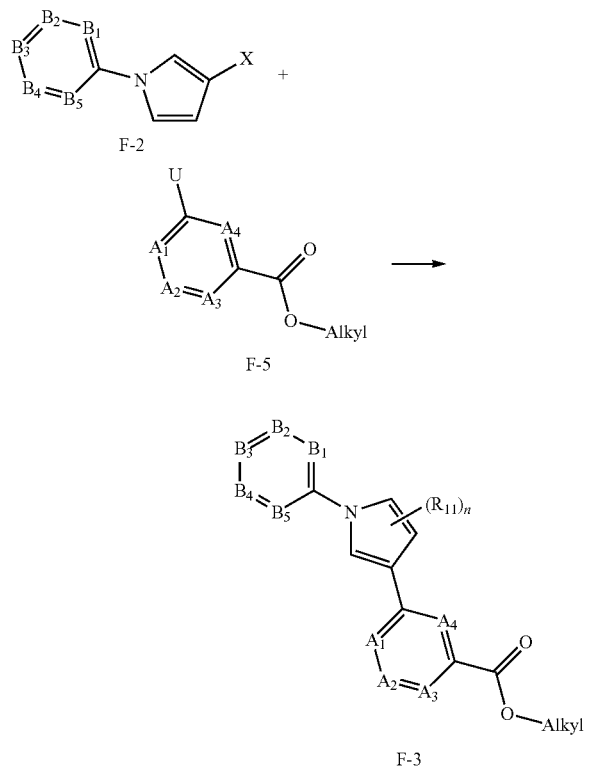

The $A_1$ to $A_4$, $B_1$ to $B_5$, alkyl, n and $R^{11}$ radicals are each as defined above. U is, for example, a boronic acid, boronic ester or trifluoroboronate, X is bromine, iodine or triflate.

Inventive compounds of the general structure (F-3) can be prepared by processes known from the literature by means of palladium-catalysed reactions from the co-reactants of the general structure (F-2) and (F-5) (e.g. WO 2005/040110 or WO 2009/089508). The compounds of the general structure (F-5) are either commercially available or can be prepared by processes known to those skilled in the art.

Stages 4, 5 Hydrolysis, Amidation

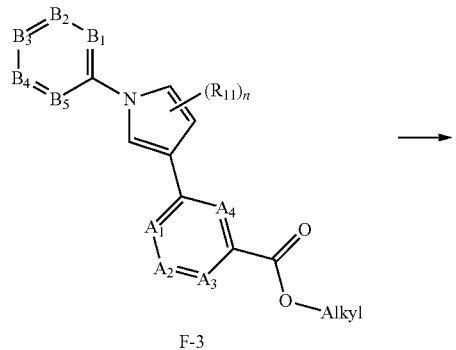

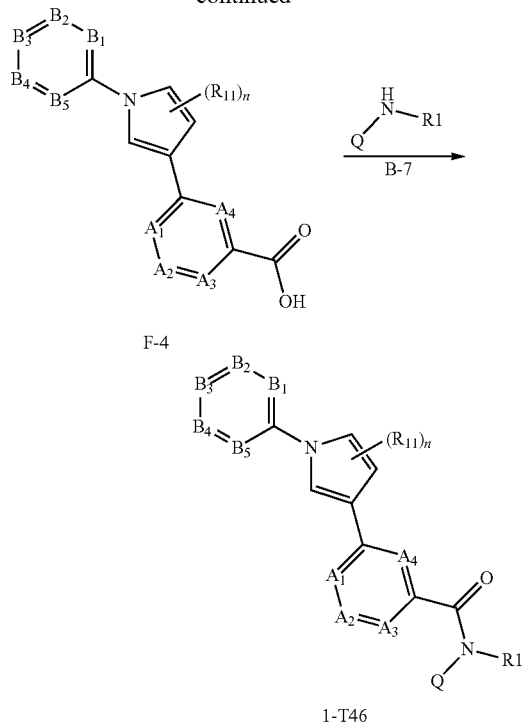

Inventive compounds of the general structure (I-T46) can be prepared in analogy to peptide coupling methods known from literature from the starting materials (F-4) and (B-7) (e.g. WO 2010/051926 or WO 2010/133312). Compounds of the general structure (F-4) can be prepared in analogy to processes known from the literature by ester hydrolysis from compounds of the general structure (F-3) (e.g. WO 2010/051926 or WO 2010/133312). The $A_1$ to $A_4$, $B_1$ to $B_5$, alkyl, Q, $R^1$ and $R^{11}$ radicals are each as defined above.

Q

In a more preferred embodiment Q in a compound of the formula (I) or (Ia") or (IT-2) or (I-T3) or (I-T4) or (I-T22) or (I-T23) or (I-T46) is $C_1$-$C_4$-alkyl, 2-oxo-2-(2,2,2-trifluoroethylamino)ethyl, fluorine- or 1-cyanopropyl- or pyridine-substituted $C_1$-$C_4$-alkyl such as 2,2,2-trifluoroethyl, 2,2-difluoroethyl, 3,3,3-trifluoropropyl, pyridin-2-ylmethyl or (1-cyanocyclopropyl)methyl; $C_3$-$C_4$-cycloalkyl such as cyclopropyl or cyclobutyl; optionally substituted $C_3$-$C_4$-cycloalkyl such as optionally fluorine-substituted $C_1$-$C_4$-alkyl-substituted cyclopropyl (e.g. 1-trifluoromethyl-cyclopropyl, 1-tert-butylcyclopropyl), 1-thiocarbamoylcyclopropyl, 1-carbamoylcyclopropyl, 1-cyanocyclopropyl, trans-2-fluorocyclopropyl, cis-2-fluorocyclopropyl; $C_4$-$C_6$-heterocycloalkyl such as oxetan-3-yl, thietan-3-yl, 1-oxidothietan-3-yl, or 1,1-dioxidothietan-3-yl; or each case optionally $C_1$-$C_4$-alkyl-substituted benzyl; pyrazole (such as N-methylpyrazol-3-yl), pyridine; methylsulphonyl; or 2-oxo-2-(2,2,2-trifluoroethylamino)ethyl.

In a particularly preferred embodiment Q in a compound of the formula (I) or (Ia") or (IT-2) or (I-T3) or (I-T4) or (I-T22) or (I-T23) or (I-T46) is fluorine-substituted $C_1$-$C_3$-alkyl such as 2,2,2-trifluoroethyl or 3,3,3-trifluoropropyl; cyclopropyl; optionally cyano-, $C_1$-$C_4$-alkyl-substituted cyclopropyl such as 1-cyanocyclopropyl or 1-trifluoromethylcyclopropyl; thietan-3-yl; or 2-oxo-2-(2,2,2-trifluoroethyl)aminoethyl.

Formula (I)

A further preferred embodiment relates to compounds of the formula (I) in which T is T2, T3, T4, T22, T23 or T46 and all the other parameters are as defined above.

A further preferred embodiment relates to compounds of the formula (I) in which T is T2, T3, T4, T22, T23 or T46 and all the other parameters are as defined above.

A further preferred embodiment relates to compounds of the formula (I) in which T is T2 or T4 and all the other parameters are as defined above.

A further preferred embodiment relates to compounds of the formula (I) in which T is T3 or T46 and all the other parameters are as defined above.

A further preferred embodiment relates to compounds of the formula (I) in which T is T22 or T23 and all the other parameters are as defined above.

A further preferred embodiment relates to compounds of the formula (I) in which T is T2, T3, T4, T22, T23 or T46, B3 is C—R8 and R8 is a (C1-C6)-alkyl, (C1-C6)-alkoxy or alkylsulphanyl, each of which is substituted, where the substituents are selected from halogen and hydroxyl, where at least one substituent is halogen and all the other parameters are as defined above.

A further preferred embodiment relates to compounds of the formula (I) in which T is T2, T3, T4, T22, T23 or T46, B3 is C—R8 and R8 is a (C1-C6)-alkyl, (C1-C6)-alkoxy or alkylsulphanyl, each of which is substituted, where the substituents are selected from halogen and hydroxyl, where at least one substituent is halogen and all the other parameters are as defined above.

A further preferred embodiment relates to compounds of the formula (I) in which T is T2 or T4, B3 is C—R8 and R8 is a (C1-C6)-alkyl, (C1-C6)-alkoxy or alkylsulphanyl, each of which is substituted, where the substituents are selected from halogen and hydroxyl, where at least one substituent is halogen and all the other parameters are as defined above.

A further preferred embodiment relates to compounds of the formula (I) in which T is T3 or T46, B3 is C—R8 and R8 is a (C1-C6)-alkyl, (C1-C6)-alkoxy or alkylsulphanyl, each of which is substituted, where the substituents are selected from halogen and hydroxyl, where at least one substituent is halogen and all the other parameters are as defined above.

A further preferred embodiment relates to compounds of the formula (I) in which T is T22 or T23, B3 is C—R8 and R8 is a (C1-C6)-alkyl, (C1-C6)-alkoxy or alkylsulphanyl, each of which is substituted, where the substituents are selected from halogen and hydroxyl, where at least one substituent is halogen and all the other parameters are as defined above. In this context, a particularly preferred embodiment relates to compounds in which $R^8$ is perfluorinated (C1-C6)-alkyl, (C1-C6)-alkoxy or alkylsulphanyl, most preferably perfluorinated (C1-C4)-alkyl, (C1-C4)-alkoxy.

A further preferred embodiment relates to compounds of the formula (I) in which T is T2, T3, T4, T22, T23 or T46, B3 is C—R8 and R8 is a (C1-C6)-alkyl, (C1-C6)-alkoxy or alkylsulphanyl, each of which is substituted, where the substituents are selected from halogen and hydroxyl, where at least one substituent is halogen, more preferably in which R8 is perfluorinated (C1-C6)-alkyl, (C1-C6)-alkoxy or alkylsulphanyl, most preferably perfluorinated (C1-C4)-alkyl, (C1-C4)-alkoxy, in which $B_1$, $B_2$, $B_4$ and $B_5$ are, respectively, $CR^6$, $CR^7$, $CR^9$ and $CR^{10}$ in which $R^6$, $R^7$, $R^9$ and $R^{10}$ are each independently H, halogen, cyano, nitro, or $C_1$-$C_4$-alkyl, $C_3$-$C_4$-cycloalkyl, $C_1$-$C_4$-alkoxy, N-alkoxyiminoalkyl, $C_1$-$C_4$-alkylsulphanyl, $C_1$-$C_4$-alkylsulphinyl, $C_1$-$C_4$-alkylsulphonyl, N—$C_1$-$C_4$-alkylamino, N,N-di-$C_1$-$C_4$-alkylamino, each of which is substituted by at least one substituent selected from halogen and hydroxyl, where at least one substituent is a halogen, and all the other parameters are as defined above. In a further preferred embodiment, $R^6$ and $R^{10}$ are each halogen (such as Cl, Br or F), each $C_1$-$C_3$-alkyl, or each halogen-substituted $C_1$-$C_3$-alkyl, for example perfluorinated $C_1$-$C_3$-alkyl (perfluoromethyl, perfluoroethyl or perfluoropropyl).

A further preferred embodiment relates to compounds of the formula (I) in which T is T2, T3, T4, T22, T23 or T46, B3 is C—R8 and R8 is a (C1-C6)-alkyl, (C1-C6)-alkoxy or alkylsulphanyl, each of which is substituted, where the substituents are selected from halogen and hydroxyl, where at least one substituent is halogen, more preferably in which R8 is perfluorinated (C1-C6)-alkyl, (C1-C6)-alkoxy or alkylsulphanyl, most preferably perfluorinated (C1-C4)-alkyl, (C1-C4)-alkoxy, in which $B_1$, $B_2$ and $B_4$ are, respectively, $CR^6$, $CR^7$ and $CR^9$ and $B^5$ is N, in which $R^6$, $R^7$ and $R^9$ are each independently H, halogen, cyano, nitro, or $C_1$-$C_4$-alkyl, $C_3$-$C_4$-cycloalkyl, $C_1$-$C_4$-alkoxy, N-alkoxyiminoalkyl, $C_1$-$C_4$-alkylsulphanyl, $C_1$-$C_4$-alkylsulphinyl, $C_1$-$C_4$-alkylsulphonyl, N—$C_1$-$C_4$-alkylamino, N,N-di-$C_1$-$C_4$-alkylamino, each of which is substituted by at least one substituent selected from halogen and hydroxyl, where at least one substituent is a halogen, and all the other parameters are as defined above.

A further preferred embodiment relates to compounds of the formula (I) in which T is T2, T3, T4, T22, T23 or T46, B3 is C—R8 and R8 is a (C1-C6)-alkyl, (C1-C6)-alkoxy or alkylsulphanyl, each of which is substituted, where the substituents are selected from halogen and hydroxyl, where at least one substituent is halogen, more preferably in which R8 is perfluorinated (C1-C6)-alkyl, (C1-C6)-alkoxy or alkylsulphanyl, most preferably perfluorinated (C1-C4)-alkyl, (C1-C4)-alkoxy, in which $B_1$, $B_2$, $B_4$ and $B_5$ are, respectively, $CR^6$, $CR^7$, $CR^9$ and $CR^{10}$ in which $R^6$, $R^7$, $R^9$ and $R^{10}$ are each independently H, halogen, cyano, nitro, or $C_1$-$C_4$-alkyl, $C_3$-$C_4$-cycloalkyl, $C_1$-$C_4$-alkoxy, N-alkoxyiminoalkyl, $C_1$-$C_4$-alkylsulphanyl, $C_1$-$C_4$-alkylsulphinyl, $C_1$-$C_4$-alkylsulphonyl, N—$C_1$-$C_4$-alkylamino, N,N-di-$C_1$-$C_4$-alkylamino, each of which is substituted by at least one substituent selected from halogen and hydroxyl, where at least one substituent is a halogen, each $R^{11}$ is independently H, amino (NH$_2$) or cyano, preferably H, W is O, $R^1$ is H, methyl, ethyl, n-propyl, isopropyl, n-butyl, isobutyl, s-butyl, t-butyl, preferably H or methyl, and all the other parameters are as defined above. In a further preferred embodiment, $R^6$ and $R^{10}$ are each halogen (such as Cl, Br or F), each $C_1$-$C_3$-alkyl, or each halogen-substituted $C_1$-$C_3$-alkyl, for example perfluorinated $C_1$-$C_3$-alkyl (perfluoromethyl, perfluoroethyl or perfluoropropyl).

A further preferred embodiment relates to compounds of the formula (I) in which T is T2, T3, T4, T22, T23 or T46, B3 is C—R8 and R8 is a (C1-C6)-alkyl, (C1-C6)-alkoxy or alkylsulphanyl, each of which is substituted, where the substituents are selected from halogen and hydroxyl, where at least one substituent is halogen, more preferably in which R8 is perfluorinated (C1-C6)-alkyl, (C1-C6)-alkoxy or alkylsulphanyl, most preferably perfluorinated (C1-C4)-alkyl, (C1-C4)-alkoxy, in which $B_1$, $B_2$ and $B_4$ are, respectively, $CR^6$, $CR^7$ and $CR^9$ and $B^5$ is N, in which $R^6$, $R^7$ and $R^9$ are each independently H, halogen, cyano, nitro, or $C_1$-$C_4$-alkyl, $C_3$-$C_4$-cycloalkyl, $C_1$-$C_4$-alkoxy, N-alkoxyiminoalkyl, $C_1$-$C_4$-alkylsulphanyl, $C_1$-$C_4$-alkylsulphinyl, $C_1$-$C_4$-alkylsulphonyl, N—$C_1$-$C_4$-alkylamino, N,N-di-$C_1$-$C_4$-alkylamino, each of which is substituted by at least one substituent selected from halogen and hydroxyl, where at least one substituent is a halogen, each $R^{11}$ is independently H, amino ($NH_2$) or cyano, preferably H, W is O, $R^1$ is H, methyl, ethyl, n-propyl, isopropyl, n-butyl, isobutyl, s-butyl, t-butyl, preferably H or methyl, and all the other parameters are as defined above.

A further preferred embodiment relates to compounds of the formula (I) in which T is T2, T3, T4, T22, T23 or T46, B3 is C—R8 and R8 is a (C1-C6)-alkyl, (C1-C6)-alkoxy or alkylsulphanyl, each of which is substituted, where the substituents are selected from halogen and hydroxyl, where at least one substituent is halogen, more preferably in which R8 is perfluorinated (C1-C6)-alkyl, (C1-C6)-alkoxy or alkylsulphanyl, most preferably perfluorinated (C1-C4)-alkyl, (C1-C4)-alkoxy, in which $B_1$, $B_2$, $B_4$ and $B_5$ are, respectively, $CR^6$, $CR^7$, $CR^9$ and $CR^{10}$ in which $R^6$, $R^7$, $R^9$ and $R^{10}$ are each independently H, halogen, cyano, nitro, or $C_1$-$C_4$-alkyl, $C_3$-$C_4$-cycloalkyl, $C_1$-$C_4$-alkoxy, N-alkoxyiminoalkyl, $C_1$-$C_4$-alkylsulphanyl, $C_1$-$C_4$-alkylsulphinyl, $C_1$-$C_4$-alkylsulphonyl, N—$C_1$-$C_4$-alkylamino, N,N-di-$C_1$-$C_4$-alkylamino, each of which is substituted by at least one substituent selected from halogen and hydroxyl, where at least one substituent is a halogen, each $R^{11}$ is independently H, amino ($NH_2$) or cyano, preferably H, W is O, $R^1$ is H, methyl, ethyl, n-propyl, isopropyl, n-butyl, isobutyl, s-butyl, t-butyl, preferably H or methyl, Q is $C_1$-$C_4$-alkyl, 2-oxo-2-(2,2,2-trifluoroethylamino)ethyl, fluorine- or 1-cyanopropyl- or pyridine-substituted $C_1$-$C_4$-alkyl such as 2,2,2-trifluoroethyl, 2,2-difluoroethyl, 3,3,3-trifluoropropyl, pyridin-2-ylmethyl or (1-cyanocyclopropyl)methyl; $C_3$-$C_4$-cycloalkyl such as cyclopropyl or cyclobutyl; optionally substituted $C_3$-$C_4$-cycloalkyl such as optionally fluorine-substituted $C_1$-$C_4$-alkyl-substituted cyclopropyl (e.g. 1-trifluoromethylcyclopropyl, 1-tert-butylcyclopropyl), 1-thiocarbamoylcyclopropyl, 1-carbamoylcyclopropyl, 1-cyanocyclopropyl, trans-2-fluorocyclopropyl, cis-2-fluorocyclopropyl; $C_4$-$C_6$-heterocycloalkyl such as oxetan-3-yl, thietan-3-yl, 1-oxidothietan-3-yl, or 1,1-dioxidothietan-3-yl; or in each case optionally $C_1$-$C_4$-alkyl-substituted benzyl; pyrazole (such as N-methylpyrazol-3-yl), pyridine; methylsulphonyl; or 2-oxo-2-(2,2,2-trifluoroethylamino)ethyl, preferably fluorine-substituted $C_1$-$C_3$-alkyl such as 2,2,2-trifluoroethyl or 3,3,3-trifluoropropyl; cyclopropyl; optionally substituted cyclopropyl such as 1-cyanocyclopropyl or 1-trifluoromethylcyclopropyl, thietan-3-yl; or 2-oxo-2-(2,2,2-trifluoroethyl)aminoethyl, and all the other parameters are as defined above. In a further preferred embodiment, $R^6$ and $R^{10}$ are each halogen (such as Cl, Br or F), each $C_1$-$C_3$-alkyl, or each halogen-substituted $C_1$-$C_3$-alkyl, for example perfluorinated $C_1$-$C_3$-alkyl (perfluoromethyl, perfluoroethyl or perfluoropropyl).

A further preferred embodiment relates to compounds of the formula (I) in which T is T2, T3, T4, T22, T23 or T46, B3 is C—R8 and R8 is a (C1-C6)-alkyl, (C1-C6)-alkoxy or alkylsulphanyl, each of which is substituted, where the substituents are selected from halogen and hydroxyl, where at least one substituent is halogen, more preferably in which R8 is perfluorinated (C1-C6)-alkyl, (C1-C6)-alkoxy or alkylsulphanyl, most preferably perfluorinated (C1-C4)-alkyl, (C1-C4)-alkoxy, in which $B_1$, $B_2$ and $B_4$ are, respectively, $CR^6$, $CR^7$ and $CR^9$ and $B^5$ is N, in which $R^6$, $R^7$ and $R^9$ are each independently H, halogen, cyano, nitro, or $C_1$-$C_4$-alkyl, $C_3$-$C_4$-cycloalkyl, $C_1$-$C_4$-alkoxy, N-alkoxyiminoalkyl, $C_1$-$C_4$-alkylsulphanyl, $C_1$-$C_4$-alkylsulphinyl, $C_1$-$C_4$-alkylsulphonyl, N—$C_1$-$C_4$-alkylamino, N,N-di-$C_1$-$C_4$-alkylamino, each of which is substituted by at least one substituent selected from halogen and hydroxyl, where at least one substituent is a halogen, each $R^{11}$ is independently H, amino ($NH_2$) or cyano, preferably H, W is O, $R^1$ is H, methyl, ethyl, n-propyl, isopropyl, n-butyl, isobutyl, s-butyl, t-butyl, preferably H or methyl, Q is $C_1$-$C_4$-alkyl, 2-oxo-2-(2,2,2-trifluoroethylamino)ethyl, fluorine- or 1-cyanopropyl- or pyridine-substituted $C_1$-$C_4$-alkyl such as 2,2,2-trifluoroethyl, 2,2-difluoroethyl, 3,3,3-trifluoropropyl, pyridin-2-ylmethyl or (1-cyanocyclopropyl)methyl; $C_3$-$C_4$-cycloalkyl such as cyclopropyl or cyclobutyl; optionally substituted $C_3$-$C_4$-cycloalkyl such as optionally fluorine-substituted $C_1$-$C_4$-alkyl-substituted cyclopropyl (e.g. 1-trifluoromethylcyclopropyl, 1-tert-butylcyclopropyl), 1-thiocarbamoylcyclopropyl, 1-carbamoylcyclopropyl, 1-cyanocyclopropyl, trans-2-fluorocyclopropyl, cis-2-fluorocyclopropyl; $C_4$-$C_6$-heterocycloalkyl such as oxetan-3-yl, thietan-3-yl, 1-oxidothietan-3-yl, or 1,1-dioxidothietan-3-yl; or in each case optionally $C_1$-$C_4$-alkyl-substituted benzyl; pyrazole (such as N-methylpyrazol-3-yl), pyridine; methylsulphonyl; or 2-oxo-2-(2,2,2-trifluoroethylamino)ethyl, preferably fluorine-substituted $C_1$-$C_3$-alkyl such as 2,2,2-trifluoroethyl or 3,3,3-trifluoropropyl; cyclopropyl; optionally substituted cyclopropyl such as 1-cyanocyclopropyl or 1-trifluoromethylcyclopropyl, thietan-3-yl; or 2-oxo-2-(2,2,2-trifluoroethyl)-aminoethyl, $A_1$ is $CR^2$ or N, $A_2$ is $CR^3$ or N, $A_3$ is $CR^4$ and $A_4$ is $CR^5$ or N, where $R^2$ is H, C1-C4-alkyl or halogen (such as methyl, F, Cl or H), $R^3$ is H or halogenated C1-C4-alkyl (such as H or —$CF_3$), $R^4$ is H, C1-C4-alkyl, C1-C4-alkylamine (such as —NH—$CH_3$), cyclopropylamine, C1-C4-alkoxy (such as —O—$CH_3$), C1-C4-alkoxy-C1-C4-alkylamine (such as NH—$CH_2$—$CH_2$—O—$CH_3$) or halogen (such as F or Cl). In a further preferred embodiment, $R^6$ and $R^{10}$ are each halogen (such as Cl, Br or F), each $C_1$-$C_3$-alkyl, or each halogen-substituted $C_1$-$C_3$-alkyl, for example perfluorinated $C_1$-$C_3$-alkyl (perfluoromethyl, perfluoroethyl or perfluoropropyl).

A further preferred embodiment relates to compounds of the formula (I) in which T is T2, T3, T4, T22, T23 or T46, B3 is C—R8 and R8 is a (C1-C6)-alkyl, (C1-C6)-alkoxy or alkylsulphanyl, each of which is substituted, where the substituents are selected from halogen and hydroxyl, where at least one substituent is halogen, more preferably in which R8 is perfluorinated (C1-C6)-alkyl, (C1-C6)-alkoxy or alkylsulphanyl, most preferably perfluorinated (C1-C4)-alkyl, (C1-C4)-alkoxy, in which $B_1$, $B_2$ and $B_4$ are, respectively, $CR^6$, $CR^7$ and $CR^9$ and $B^5$ is N, in which $R^6$, $R^7$ and $R^9$ are each independently H, halogen, cyano, nitro, or $C_1$-$C_4$-alkyl, $C_3$-$C_4$-cycloalkyl, $C_1$-$C_4$-alkoxy, N-alkoxyiminoalkyl, $C_1$-$C_4$-alkylsulphanyl, $C_1$-$C_4$-alkylsulphinyl, $C_1$-$C_4$-alkylsulphonyl, N—$C_1$-$C_4$-alkylamino, N,N-di-$C_1$-$C_4$-alkylamino, each of which is substituted by at least one substituent selected from halogen and hydroxyl, where at least one substituent is a halogen, each $R^{11}$ is independently H, amino ($NH_2$) or cyano, preferably H, W is O, $R^1$ is H, methyl, ethyl, n-propyl, isopropyl, n-butyl, isobutyl, s-butyl, t-butyl, preferably H or methyl, Q is $C_1$-$C_4$-alkyl, 2-oxo-2-(2,2,2-trifluoroethylamino)ethyl, fluorine- or 1-cyanopropyl- or pyridine-substituted $C_1$-$C_4$-alkyl such as 2,2,2-trifluoroethyl, 2,2-difluoroethyl, 3,3,3-trifluoropropyl, pyridin-2-ylmethyl or (1-cyano-cyclopropyl)methyl; $C_3$-$C_4$-cycloalkyl such as cyclopropyl or cyclobutyl; optionally substituted $C_3$-$C_4$-cycloalkyl such as optionally fluorine-substituted $C_1$-$C_4$-alkyl-substituted cyclopropyl (e.g. 1-trifluoromethylcyclopropyl, 1-tert-butylcyclopropyl), 1-thiocarbamoylcyclopropyl, 1-carbamoyl-cyclopropyl, 1-cyanocyclopropyl, trans-2-fluorocyclopropyl, cis-2-fluorocyclopropyl; $C_4$-$C_6$-hetero-cycloalkyl such as oxetan-3-yl, thietan-3-yl, 1-oxidothietan-3-yl, or 1,1-dioxidothietan-3-yl; or in each case optionally $C_1$-$C_4$-alkyl-substituted benzyl; pyrazole (such as N-methylpyrazol-3-yl), pyridine; methylsulphonyl; or 2-oxo-2-(2,2,2-trifluoroethylamino)ethyl, preferably fluorine-substituted $C_1$-$C_3$-alkyl such as 2,2,2-trifluoroethyl or 3,3,3-trifluoropropyl; cyclopropyl; optionally substituted cyclopropyl such as 1-cyanocyclopropyl or 1-trifluoromethylcyclopropyl, thietan-3-yl; or 2-oxo-2-(2,2,2-trifluoroethyl)aminoethyl, $A_1$ is $CR^2$ or N, $A_2$ is $CR^3$ or N, $A_3$ is $CR^4$ and $A_4$ is $CR^5$ or N, where $R^2$ is H, C1-C4-alkyl or halogen (such as methyl, F, Cl or H), $R^3$ is H or halogenated C1-C4-alkyl (such as H or —$CF_3$), $R^4$ is H, C1-C4-alkyl, C1-C4-alkylamine (such as —NH—$CH_3$), cyclopropylamine, C1-C4-alkoxy (such as —O—$CH_3$), C1-C4-alkoxy-C1-C4-alkylamine (such as NH—$CH_2$—$CH_2$—O—$CH_3$) or halogen (such as F or Cl).

In a further preferred embodiment, $R^6$ is perfluorinated $C_1$-$C_3$-alkyl (e.g. perfluoromethyl) and $R^{10}$ is Cl, Br or F, more preferably Cl or Br.

Formula (Ia″)

A further preferred embodiment relates to compounds of the formula (Ia″)

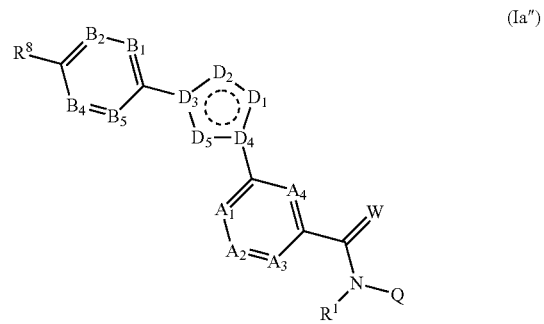

(Ia″)

in which one D selected from D1 and D2 is N and the respective other D selected from D1 and D2 is O; or D4 is N and one D selected from D1 and D5 is N; or D3 is N and D1, D2 and D5 are each C—R11 and D4 is C, and all other parameters are as defined above.

A further preferred embodiment relates to compounds of the formula (Ia″) in which R8 is a (C1-C6)-alkyl, (C1-C6)-alkoxy or alkylsulphanyl, each of which is substituted, where the substituents are selected from halogen and hydroxyl, where at least one substituent is halogen, and one D selected from D1 and D2 is N and the respective other D selected from D1 and D2 is O; or D4 is N and one D selected from D1 and D5 is N; or D3 is N and D1, D2 and D5 are each C—R11 and D4 is C, and all other parameters are as defined above.

In a preferred embodiment, not more than one (1) $B_1$ to $B_5$ moiety is N (in other words: one (1) $B_1$ to $B_5$ is N); or no (0) $B_1$ to $B_5$ is N ($B_1$ to $B_5$ are $CR^6$, $CR^7$, $CR^8$, $CR^9$ and $CR^{10}$).

In a further preferred embodiment, $R^6$, $R^7$, $R^9$ and $R^{10}$ (if the corresponding B moiety is CR) are each independently H, halogen, cyano, nitro, in each case optionally substituted $C_1$-$C_4$-alkyl, $C_3$-$C_4$-cycloalkyl, $C_1$-$C_4$-alkoxy, N-alkoxyiminoalkyl, $C_1$-$C_4$-alkylsulphanyl, $C_1$-$C_4$-alkylsulphinyl, $C_1$-$C_4$-alkylsulphonyl, N—$C_1$-$C_4$-alkylamino, N,N-di-$C_1$-$C_4$-alkylamino.

In a further preferred embodiment, $R^6$, $R^7$, $R^9$ and $R^{10}$ are each independently H, halogen, cyano, nitro, methyl, ethyl, fluoromethyl, difluoromethyl, chlorodifluoromethyl, trifluoromethyl, 2,2,2-trifluoroethyl, methoxy, ethoxy, n-propoxy, 1-methylethoxy, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, N-methoxyiminomethyl, 1-(N-methoxyimino)ethyl, methylsulphanyl, trifluoromethylsulphanyl, methylsulphonyl, methylsulphinyl, trifluoromethylsulphonyl, trifluoromethylsulphinyl.

In a further preferred embodiment, $R^6$ and $R^{10}$ are each independently H, halogen (especially chlorine, bromine, fluorine), cyano, nitro, methyl, ethyl, difluoromethyl, chlorodifluoromethyl, trifluoromethyl, methoxy, ethoxy, 1-methylethoxy, difluoromethoxy, chlorodifluoromethoxy, dichlorofluoromethoxy, trifluoromethoxy, 2,2,2-trifluoroethoxy, 2-chloro-2,2-difluoroethoxy, methylsulphanyl, trifluoromethylsulphanyl, methylsulphonyl, methylsulphinyl, trifluoromethylsulphonyl, trifluoromethylsulphinyl.

In a further preferred embodiment, $R^6$ and $R^{10}$ are the substituents described herein, but $R^6$ and $R^{10}$ in one compound are not both H. In other words, if $R^6$ in a compound is H, $R^{10}$ is one of the other substituents described herein, and vice versa.

In a further preferred embodiment, $R^6$ and $R^{10}$ are each a substituent selected from halogen (preferably Cl, Br or F), $C_1$-$C_3$-alkyl, halogen-substituted $C_1$-$C_3$-alkyl, $C_1$-$C_3$-alkoxy or halogen-substituted $C_1$-$C_3$-alkoxy.

In a further preferred embodiment, $R^6$ and $R^{10}$ are each halogen (such as Cl, Br or F), each $C_1$-$C_3$-alkyl, or each halogen-substituted $C_1$-$C_3$-alkyl, for example perfluorinated $C_1$-$C_3$-alkyl (perfluoromethyl, perfluoroethyl or perfluoropropyl).

In a further preferred embodiment, $R^6$ is perfluorinated $C_1$-$C_3$-alkyl (e.g. perfluoromethyl) and $R^{10}$ is Cl, Br or F, more preferably Cl or Br.

T46—Methyl

A further preferred embodiment relates to compounds of the formula (I) in which $R^1$ is methyl, T is T46, $R^{11}$ in T46 is H, W is O and all the other parameters are as defined above.

A further preferred embodiment relates to compounds of the formula (I) in which $R^1$ is methyl, T is T46, $R^{11}$ in T46 is H, W is O, $A_1$ is $CR^2$, $A_2$ is $CR^3$ or N, $A_3$ is $CR^4$, $A_4$ is $CR^5$, $B_1$ is $CR^6$, $B_2$ is $CR^7$, $B_3$ is $CR^8$, $B_4$ is $CR^9$, $B_5$ is $CR^{10}$ and all the other parameters are as defined above.

A further preferred embodiment relates to compounds of the formula (I) in which $R^1$ is methyl, T is T46, $R^{11}$ in T46 is H, W is O, $A_1$ is CH, $A_2$ is CH or N, $A_3$ is $CR^4$, $A_4$ is CH, $B_1$ is $CR^6$, $B_2$ is CH, $B_3$ is $CR^8$, $B_4$ is CH, $B_5$ is $CR^{10}$, where $R^6$ and $R^{10}$ are each a substituent selected from halogen (preferably chlorine, bromine or fluorine), $C_1$-$C_3$-alkyl, halogen-substituted $C_1$-$C_3$-alkyl, $C_1$-$C_3$-alkoxy or halogen-substituted $C_1$-$C_3$-alkoxy and all the other parameters are as defined above.

A further preferred embodiment relates to compounds of the formula (I) in which $R^1$ is methyl, T is T46, $R^{11}$ in T46 is H, W is O, $A_1$ is CH, $A_2$ is CH or N, $A_3$ is $CR^4$, $A_4$ is CH, $B_1$ is $CR^6$, $B_2$ is CH, $B_3$ is $CR^8$, $B_4$ is CH, $B_5$ is $CR^{10}$, where $R^6$ and $R^{10}$ are each a substituent selected from halogen (preferably chlorine, bromine or fluorine), $C_1$-$C_3$-alkyl, halogen-substituted $C_1$-$C_3$-alkyl, $C_1$-$C_3$-alkoxy or halogen-substituted $C_1$-$C_3$-alkoxy and all the other parameters are as defined above.

T46—H

A further preferred embodiment relates to compounds of the formula (I) in which $R^1$ is H, T is T46, $R^{11}$ in T46 is H, W is O and all the other parameters are as defined above.

A further preferred embodiment relates to compounds of the formula (I) in which $R^1$ is H, T is T46, $R^{11}$ in T46 is H, W is O, $A_1$ is $CR^2$, $A_2$ is $CR^3$ or N, $A_3$ is $CR^4$, $A_4$ is $CR^5$, $B_1$ is $CR^6$, $B_2$ is $CR^7$, $B_3$ is $CR^8$, $B_4$ is $CR^9$, $B_5$ is $CR^{10}$ and all the other parameters are as defined above.

A further preferred embodiment relates to compounds of the formula (I) in which $R^1$ is H, T is T46, $R^{11}$ in T46 is H, W is O, $A_1$ is CH, $A_2$ is CH or N, $A_3$ is $CR^4$, $A_4$ is CH, $B_1$ is $CR^6$, $B_2$ is CH, $B_3$ is $CR^8$, $B_4$ is CH, $B_5$ is $CR^{10}$, where $R^6$ and $R^{10}$ are each a substituent selected from halogen (preferably chlorine, bromine or fluorine), $C_1$-$C_3$-alkyl, halogen-substituted $C_1$-$C_3$-alkyl, $C_1$-$C_3$-alkoxy or halogen-substituted $C_1$-$C_3$-alkoxy and all the other parameters are as defined above.

A further preferred embodiment relates to compounds of the formula (I) in which $R^1$ is H, T is T46, $R^{11}$ in T46 is H, W is O, $A_1$ is CH, $A_2$ is CH or N, $A_3$ is $CR^4$, $A_4$ is CH, $B_1$ is $CR^6$, $B_2$ is CH, $B_3$ is $CR^8$, $B_4$ is CH, $B_5$ is $CR^{10}$, where $R^6$ and $R^{10}$ are each a substituent selected from halogen (preferably chlorine, bromine or fluorine), $C_1$-$C_3$-alkyl, halogen-substituted $C_1$-$C_3$-alkyl, $C_1$-$C_3$-alkoxy or halogen-substituted $C_1$-$C_3$-alkoxy and all the other parameters are as defined above.

A further embodiment is directed to compounds of the formula (I-T46):

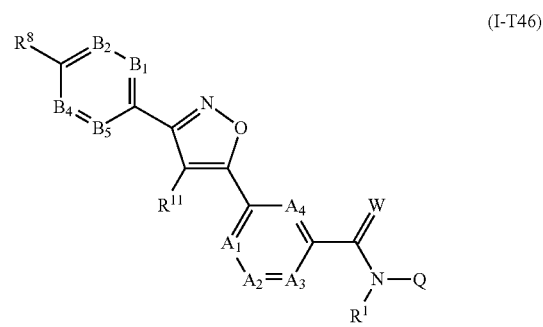

(I-T46)

in which $R^1$, $A_1$, $A_2$, $A_3$, $A_4$, $R^{11}$, $B_1$, $B_2$, $B_4$, $B_5$, $R^8$, $R^{11}$ Q and W are each defined as described herein, where not more than one moiety selected from $A_1$, $A_2$, $A_3$, $A_4$ is N and not more than one moiety selected from $B_1$, $B_2$, $B_3$, $B_4$ and $B_5$ is N; or where one or two moieties selected from $A_1$, $A_2$, $A_3$, $A_4$ can be N and not more than one moiety selected from $B_1$, $B_2$, $B_3$, $B_4$, and $B_5$ is N.

A further embodiment is directed to compounds of the formula (I-T2), (I-T3), (I-T4), (I-T22), (I-T23) or (I-T46) in which $R^1$, $A_1$, $A_2$, $A_3$, $A_4$, $R^{11}$, $B_1$, $B_2$, $B_4$, $B_5$, $R^8$, Q and W are each as described above.

A further embodiment is directed to compounds of the formula (I-T2), (I-T3), (I-T4), (I-T22), (I-T23) or (I-T46) in which $R^1$, $A_1$, $A_2$, $A_3$, $A_4$, $R^{11}$, $B_1$, $B_2$, $B_4$, $B_5$, $R^8$, Q and W are each as described above.

A further preferred embodiment is directed to compound D-1a

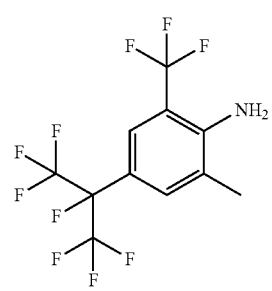 [SMILES: Cc1cc(C(F)(C(F)(F)F)C(F)(F)F)cc(C(F)(F)F)c1N]

D-1a

A further embodiment is directed to the use of the compound D-1a for preparation of compounds of the formula (I).

A further embodiment is directed to a process for preparing a compound of the formula (I), preferably in which T=T4, comprising the use of the compound D-1a, preferably in a reaction sequence according to Reaction Scheme 4.

163

A further embodiment is directed to compound D-1b

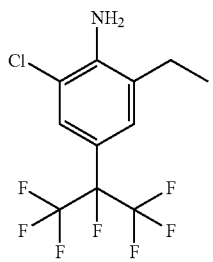

D-1b

A further embodiment is directed to the use of the compound D-1b for preparation of compounds of the formula (I).

A further embodiment is directed to a process for preparing a compound of the formula (I), preferably in which T=T4, comprising the use of the compound D-1b, preferably in a reaction sequence according to Reaction Scheme 4.

A further embodiment is directed to compound D-1c

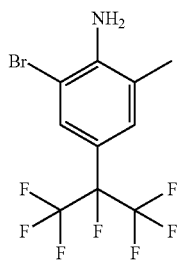

D-1c

A further embodiment is directed to the use of the compound D-1c for preparation of compounds of the formula (I).

A further embodiment is directed to a process for preparing a compound of the formula (I), preferably in which T=T4, comprising the use of the compound D-1c, preferably in a reaction sequence according to Reaction Scheme 4.

A further embodiment is directed to the compound 2-(3,5-dichloro-4-hydrazinophenyl)-1,1,1,3,3,3-hexafluoropropan-2-ol.

A further embodiment is directed to the use of the compound 2-(3,5-dichloro-4-hydrazino-phenyl)-1,1,1,3,3,3-hexafluoropropan-2-ol for preparation of compounds of the formula (I).

A further embodiment is directed to a process for preparing a compound of the formula (I), preferably in which T=T4, comprising the use of the compound 2-(3,5-dichloro-4-hydrazino-phenyl)-1,1,1,3,3,3-hexafluoropropan-2-ol, preferably in a reaction sequence according to Reaction Scheme 4.

164

EXPERIMENTAL

Preparation Process I-T2

Example I-T2-1

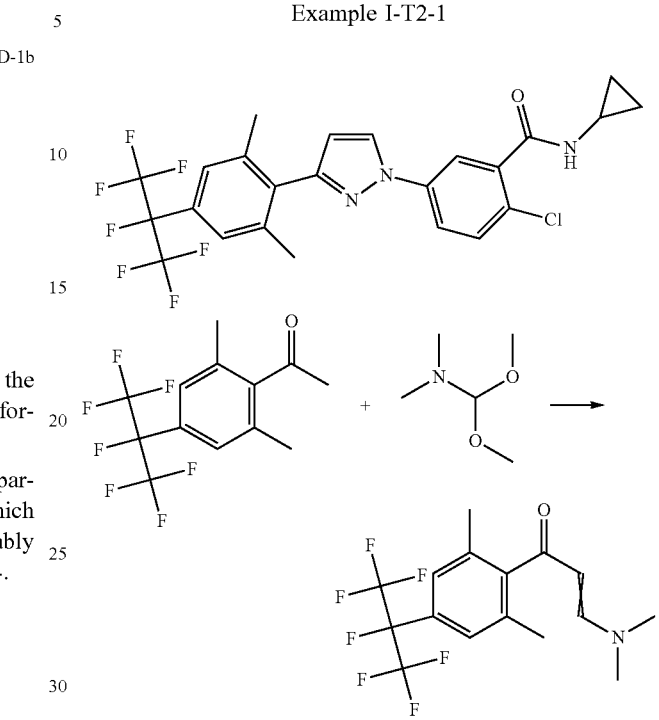

710 mg (2.24 mmol) of 1-[2,6-dimethyl-4-[1,2,2,2-tetrafluoro-1-(trifluoromethyl)ethyl]phenyl]ethanone were added to 401 mg (3.36 mmol) of N,N-dimethylformamide dimethyl acetal, and the mixture was heated to reflux for 5 hours. For workup, the mixture was cooled a little and all the volatile constituents were evaporated off on a rotary evaporator under reduced pressure. The residue was chromatographed using a cartridge containing 40 g of silica gel with a gradient in cyclohexane/ethyl acetate of 90:10 to 50:50 (v/v). 675 mg of 3-(dimethylamino)-1-[2,6-dimethyl-4-[1,2,2,2-tetrafluoro-1-(trifluoromethyl)ethyl]phenyl]prop-2-en-1-one were obtained.

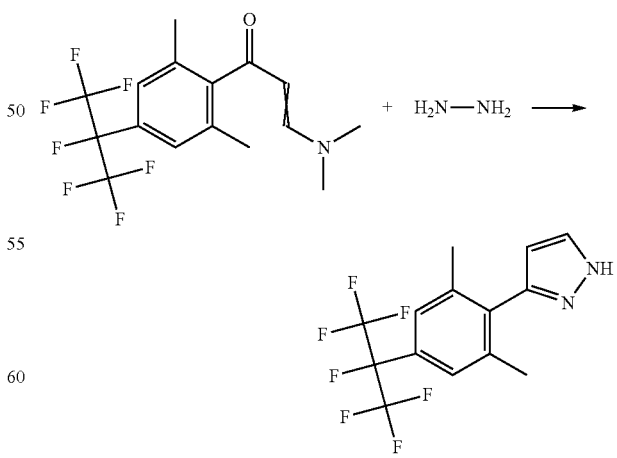

1.2 g (3.23 mmol) of 3-(dimethylamino)-1-[2,6-dimethyl-4-[1,2,2,2-tetrafluoro-1-(trifluoromethyl)ethyl]phenyl]prop-2-en-1-one were added to 15.5 ml of ethanol, and 170 mg (3.39 mmol) of hydrazine hydrate and 192 mg (3.2 mmol) of glacial acetic acid were added. The mixture was stirred at room temperature for 7 hours. Then a further 170 mg (3.39 mmol) of hydrazine hydrate were added and the mixture was stirred at room temperature for a further 4 hours. Since the conversion was still incomplete, another 190 mg (3.2 mmol) of glacial acetic acid were added and the mixture was stirred at 60° C. for 17 hours. For workup, the mixture was concentrated on a rotary evaporator under reduced pressure and the residue was partitioned between ethyl acetate and water. The organic phase was removed, washed with water, dried with sodium sulphate and concentrated on a rotary evaporator under reduced pressure. As residue, 1.04 g of (3-[2,6-dimethyl-4-[1,2,2,2-tetrafluoro-1-(trifluoromethyl) ethyl]phenyl]-1H-pyrazole remained.

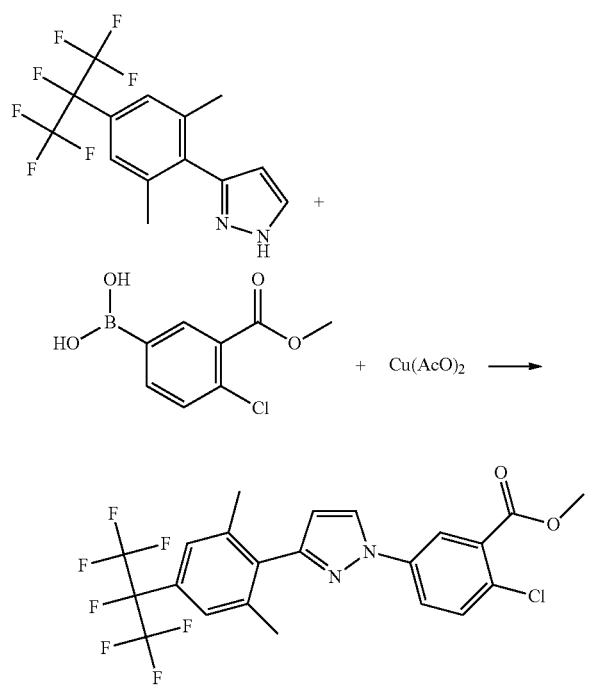

23 ml of dichloromethane, 353 mg (4.46 mmol) of pyridine, 609 mg (3.35 mmol) of copper(II) acetate, 958 mg (4.46 mmol) of 3-carboxymethyl-4-chlorophenylboronic acid and 760 mg (2.23 mmol) of (3-[2,6-dimethyl-4-[1,2,2,2-tetrafluoro-1-(trifluoromethyl)ethyl]phenyl]-1H-pyrazole were initially charged and then 1.1 g of freshly ground 3 Å molecular sieve were added. The mixture was then stirred at room temperature for 20 hours. For workup, the mixture was filtered through a layer of kieselguhr and washed through with dichloromethane. The filtrate was concentrated on a rotary evaporator under reduced pressure. For purification, chromatography was effected first using a cartridge containing 40 g of silica gel with a gradient in cyclohexane/ethyl acetate of 95:5 to 75:25 (v/v). The product-containing fractions were concentrated and chromatographed using a second cartridge containing 40 g of silica gel with toluene as eluent. After concentration, 628 mg of methyl 2-chloro-5-[3-[2,6-dimethyl-4-[1,2,2,2-tetrafluoro-1-(trifluoromethyl) ethyl]phenyl]pyrazol-1-yl]benzoate were obtained.

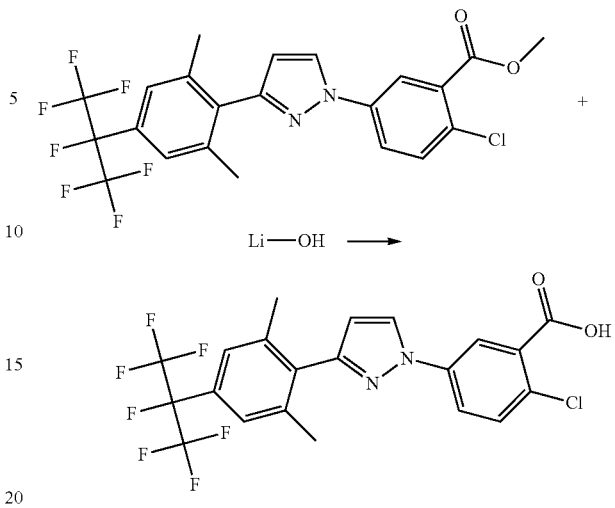

609 mg (1.19 mmol) of methyl 2-chloro-5-[3-[2,6-dimethyl-4-[1,2,2,2-tetrafluoro-1-(trifluoromethyl)ethyl]phenyl]pyrazol-1-yl]benzoate were initially charged in a mixture of 14 ml of dioxane and 5 ml of water, 53 mg (1.25 mmol) of lithium hydroxide hydrate were added and the mixture was stirred at room temperature. After 2 hours, a further 25 mg (0.6 mmol) of lithium hydroxide hydrate were added and the mixture was stirred at room temperature for a further hour. Thereafter, the volatile constituents were removed on a rotary evaporator under reduced pressure. The residue was partitioned between dilute hydrochloric acid and dichloromethane. The organic phase was removed and the aqueous phase was extracted twice with dichloromethane. The combined organic phases were then washed with saturated aqueous sodium chloride solution, dried with sodium sulphate and concentrated on a rotary evaporator under reduced pressure. As residue, 554 mg of 2-chloro-5-[3-[2,6-dimethyl-4-[1,2,2,2-tetrafluoro-1-(trifluoromethyl)ethyl]phenyl]pyrazol-1-yl]benzoic acid were obtained.

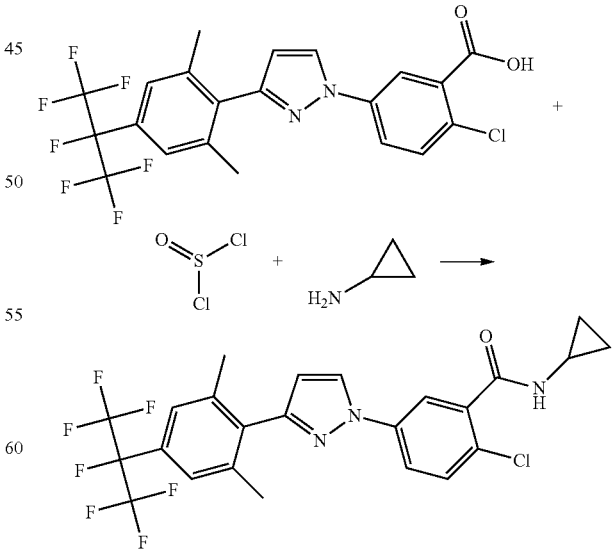

100 mg (0.2 mmol) of 2-chloro-5-[3-[2,6-dimethyl-4-[1,2,2,2-tetrafluoro-1-(trifluoromethyl)ethyl]phenyl]pyrazol- 1-yl]benzoic acid were initially charged in 2 ml of dry toluene, then 120 mg (1 mmol) of thionyl chloride (SOCl2) and 1 drop of dimethylformamide (DMF) were added, and the mixture was heated to reflux. After the evolution of gas had ended, the mixture was stirred under reflux for another 30 minutes and then concentrated on a rotary evaporator under reduced pressure. The residue was dissolved in 1 ml of dry dichloromethane and added dropwise to a solution of 29 mg (0.5 mmol) of cyclopropylamine in 1 ml of dichloromethane at 0° C. The mixture was then stirred at room temperature for 2 hours. For workup, the mixture was poured onto 5% aqueous sodium hydrogencarbonate solution, and the organic phase was removed, washed with saturated aqueous sodium chloride solution, dried with sodium sulphate and concentrated on a rotary evaporator under reduced pressure. For purification, chromatography was effected using a cartridge containing 40 g of silica gel with a gradient in cyclohexane/ethyl acetate of 90:10 to 50:50 (v/v). 159.5 mg of 2-chloro-N-cyclopropyl-5-[3-[2,6-dimethyl-4-[1,2,2,2-tetrafluoro-1-(trifluoromethyl)ethyl]phenyl]pyrazol-1-yl]benzamide (compound I-T2-1) were obtained.

HPLC-MS[a]: log P=4.9, mass (m/z)=534 [M+H]+.

$^1$H NMR (400 MHz, d$_3$-acetonitrile): δ (ppm)=8.29 (d, J=2.5 Hz, 1H), 7.82-7.85 (m, 2H), 7.52 (d, J=8.8 Hz, 1H), 7.44 (s, 2H), 6.97 (s (broad), 1H (N—H)), 6.54 (d, J=2.5 Hz, 1H), 2.82-2.86 (m, 1H), 0.74-0.79 (m, 2H), 0.59-0.61 (m, 2H).

Preparation of the Starting Compounds:

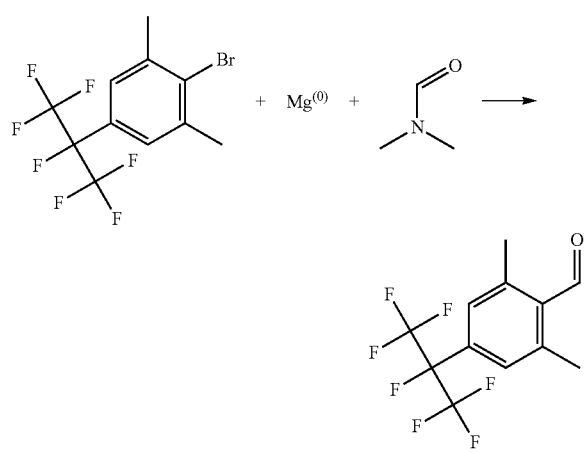

271 mg (11.1 mg atom) of magnesium turnings were initially charged, covered with a little dry tetrahydrofuran and, after addition of a few drops of a solution of 3 g (8.49 mmol) of 2-bromo-1,3-dimethyl-5-[1,2,2,2-tetrafluoro-1-(trifluoromethyl)ethyl]benzene (prepared according to US2003/187233, p. 6, Example 2/4 [0080]) in 10 ml of dry tetrahydrofuran, a crumb of iodine was added. To start the reaction, the mixture was heated to 60° C. After the reaction had started up, the rest of the solution containing the 2-bromo-1,3-dimethyl-5-[1,2,2,2-tetrafluoro-1-(trifluoromethyl)ethyl]benzene was added dropwise at 60° C. After the addition had ended, the mixture was stirred at 60° C. for another hour. Thereafter, the mixture was cooled to 0° C. with an ice bath, and 1.86 g (25.4 mmol) of N,N-dimethylformamide, dissolved in 5 ml of dry tetrahydrofuran, were added dropwise. Then the mixture was stirred without cooling until the mixture had reached room temperature. For workup, the mixture was poured onto saturated aqueous ammonium chloride solution. The phases were separated; the aqueous phase was extracted with ethyl acetate. The combined organic phases were washed with saturated aqueous sodium chloride solution, dried with sodium sulphate and concentrated on a rotary evaporator under reduced pressure. As residue, 2.34 g of 2,6-dimethyl-4-[1,2,2,2-tetrafluoro-1-(trifluoromethyl)ethyl]benzaldehyde remained, which was used without purification in the next stage.

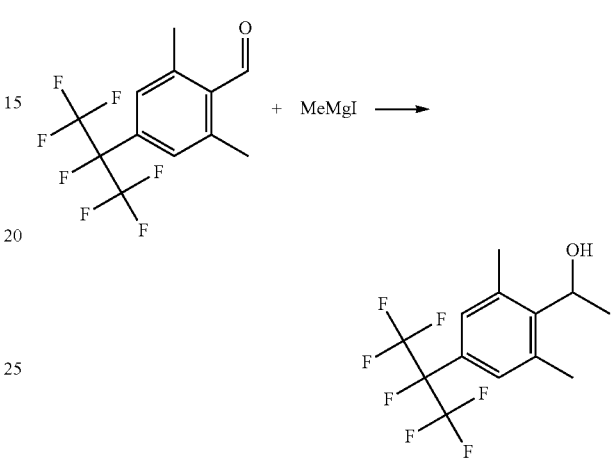

2.34 g (7.74 mmol) of 2,6-dimethyl-4-[1,2,2,2-tetrafluoro-1-(trifluoromethyl)ethyl]benzaldehyde were initially charged in 15.5 ml of dry tetrahydrofuran, and 2.58 ml (7.74 mmol) of a 3 M solution of methylmagnesium iodide in diethyl ether were added dropwise while cooling with an ice bath. Subsequently, the mixture was stirred without cooling for a further hour. For workup, the mixture was poured onto 100 ml of saturated aqueous ammonium chloride solution. The mixture was extracted twice with ethyl acetate. The combined organic phases were washed with saturated aqueous sodium chloride solution, dried with sodium sulphate and concentrated on a rotary evaporator under reduced pressure. The residue was chromatographed using a 40 g cartridge containing silica gel with a gradient in cyclohexane/ethyl acetate of 90:10 to 70:30 (v/v), and gave 1.0 g of 1-[2,6-dimethyl-4-[1,2,2,2-tetrafluoro-1-(trifluoromethyl)ethyl]phenyl]ethanol.

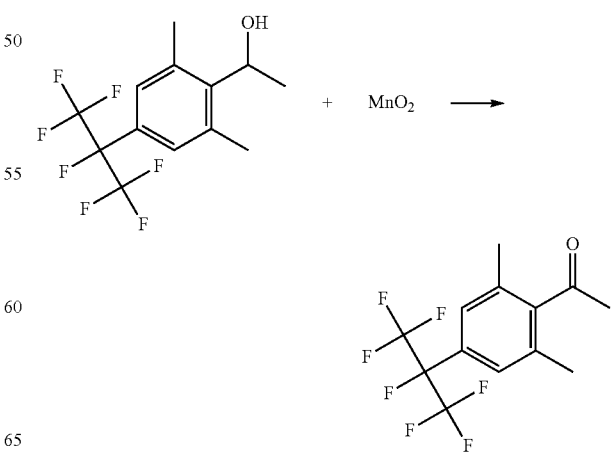

1.49 g (4.68 mmol) of 1-[2,6-dimethyl-4-[1,2,2,2-tetrafluoro-1-(trifluoromethyl)ethyl]phenyl]ethanol were initially charged in 84 ml of toluene, and 10.8 g (124 mmol) of manganese(IV) oxide were added. The mixture was heated to reflux while stirring for one hour. This was followed by cooling, filtering through a layer of kieselguhr and washing through with ethyl acetate. The filtrate was concentrated on a rotary evaporator under reduced pressure. The residue was chromatographed using a cartridge containing 50 g of silica gel with a gradient in cyclohexane/ethyl acetate of 95:5 to 70:30 (v/v). 1.03 g of 1-[2,6-dimethyl-4-[1,2,2,2-tetrafluoro-1-(trifluoromethyl)ethyl]phenyl]ethanone were obtained.

Preparation Process I-T3

Example I-T3-1

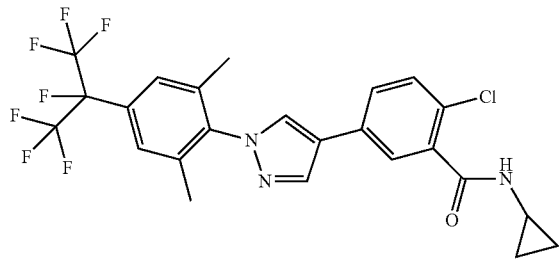 [SMILES: Cc1cc(C(F)(C(F)(F)F)C(F)(F)F)cc(C)c1-n1cc(-c2ccc(Cl)c(C(=O)NC3CC3)c2)cn1]

The preparation of the precursor [2,6-dimethyl-4-[1,2,2,2-tetrafluoro-1-(trifluoromethyl)ethyl]phenyl]hydrazine is described in the literature (US 2003/187233).

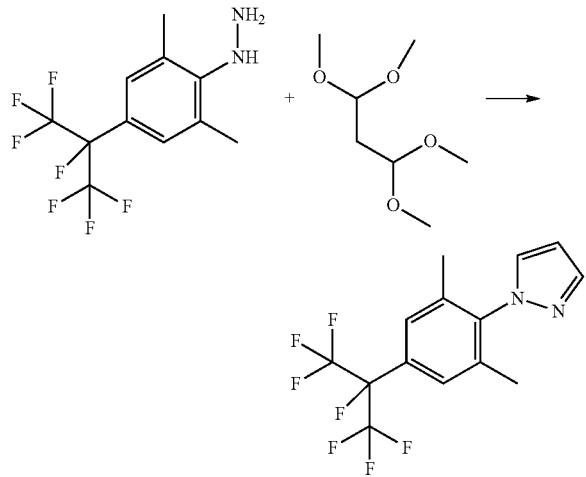

A 25 ml flask was initially charged with 3.41 g (11.2 mmol) of [2,6-dimethyl-4-[1,2,2,2-tetrafluoro-1-(trifluoromethyl)ethyl]phenyl]hydrazine (free base) in 13 ml of ethanol. Then 1.84 g (11.2 mmol) of tetramethoxypropane and subsequently 0.55 g (5.6 mmol) of 96% sulphuric acid were added. The reaction mixture was heated to reflux for 2 h. Ethanol was evaporated off on a rotary evaporator under reduced pressure. The residue was partitioned between ethyl acetate and saturated aqueous sodium hydrogencarbonate solution. The organic phase was removed, dried with sodium sulphate and concentrated on a rotary evaporator under reduced pressure. The residue was distilled in a Kugelrohr under reduced pressure at 1 mbar and 150° C., and gave 2.5 g of 1-[2,6-dimethyl-4-[1,2,2,2-tetrafluoro-1-(trifluoromethyl)ethyl]phenyl]pyrazole.

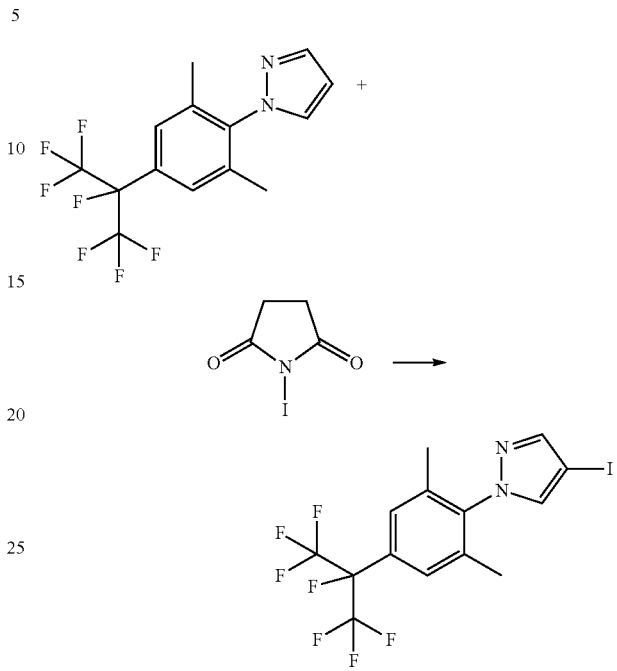

A 250 ml flask was initially charged with 2.5 g (7.34 mmol) of 1-[2,6-dimethyl-4-[1,2,2,2-tetrafluoro-1-(trifluoromethyl)ethyl]phenyl]pyrazole in 30 ml of acetonitrile, and 8.3 g (36.9 mmol) of N-iodosuccinimide in 50 ml of acetonitrile were added dropwise. Subsequently, the mixture was heated to reflux. For workup, the mixture was concentrated, and the residue was partitioned between water and ethyl acetate. The organic phase was removed, washed first with saturated aqueous sodium hydrogensulphite solution, then with saturated sodium chloride solution, dried with sodium sulphate and concentrated. The residue was purified by chromatography with silica gel by means of a gradient from 90:10 to 70:30 (v/v) in cyclohexane/ethyl acetate. After concentration of the fractions containing the product, 2.5 g of a residue were obtained, which consisted of 1-[2,6-dimethyl-4-[1,2,2,2-tetrafluoro-1-(trifluoromethyl)ethyl]phenyl]-4-iodopyrazole and some toluene.

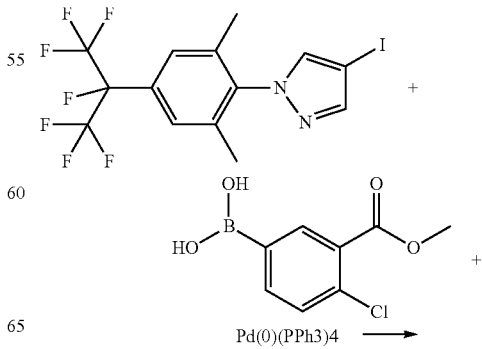

-continued

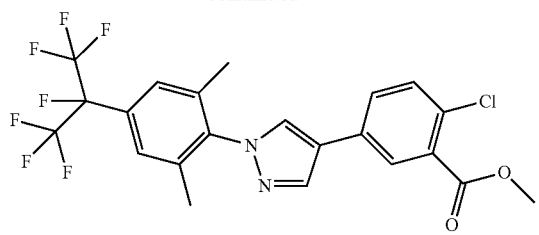

A 100 ml flask was initially charged with 280 mg (0.6 mmol) of 1-[2,6-dimethyl-4-[1,2,2,2-tetrafluoro-1-(trifluoromethyl)ethyl]phenyl]-4-iodopyrazole and 0.129 g (0.60 mmol) of [4-chloro-3-(methoxycarbonyl)phenyl]boronic acid in 21 ml of isopropanol, and lastly 1.84 ml (1.84 mmol) of degassed 1 molar sodium hydrogencarbonate solution were added. 0.035 g (0.03 mmol) of tetrakis(triphenylphosphine)palladium(0) was added. Then the mixture was heated to reflux. For workup, the mixture was concentrated on a rotary evaporator, and the residue was partitioned between water and ethyl acetate. The organic phase was removed, washed once with saturated sodium chloride solution and concentrated on a rotary evaporator under reduced pressure. The residue was purified by chromatography with silica gel by means of a gradient from 90:10 to 70:30 (v/v) in cyclohexane/ethyl acetate, and gave 151 mg of methyl 2-chloro-5-[1-[2,6-dimethyl-4-[1,2,2,2-tetrafluoro-1-(trifluoromethyl)ethyl]phenyl]pyrazol-4-yl]benzoate.

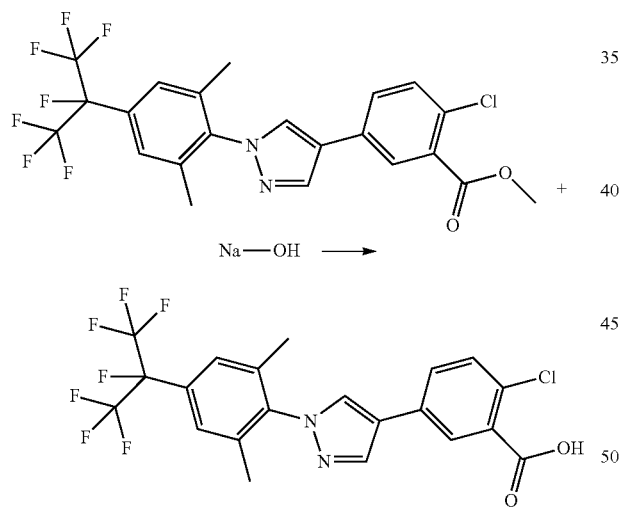

0.151 g (0.29 mmol) of methyl 2-chloro-5-[1-[2,6-dimethyl-4-[1,2,2,2-tetrafluoro-1-(trifluoromethyl)ethyl]phenyl]pyrazol-4-yl]benzoate were initially charged in 11 ml of methanol, and 0.3 ml (0.3 mmol) of 1M sodium hydroxide solution were added. Subsequently, the mixture was heated to reflux for 6 hours, excess solvent was evaporated off under reduced pressure, and the residue was taken up with dilute hydrochloric acid and extracted three times with ethyl acetate. The combined extracts were washed with saturated sodium chloride solution, dried with sodium sulphate and concentrated, and gave 130 mg of 2-chloro-5-[1-[2,6-dimethyl-4-[1,2,2,2-tetrafluoro-1-(trifluoromethyl)ethyl]phenyl]pyrazol-4-yl]benzoic acid.

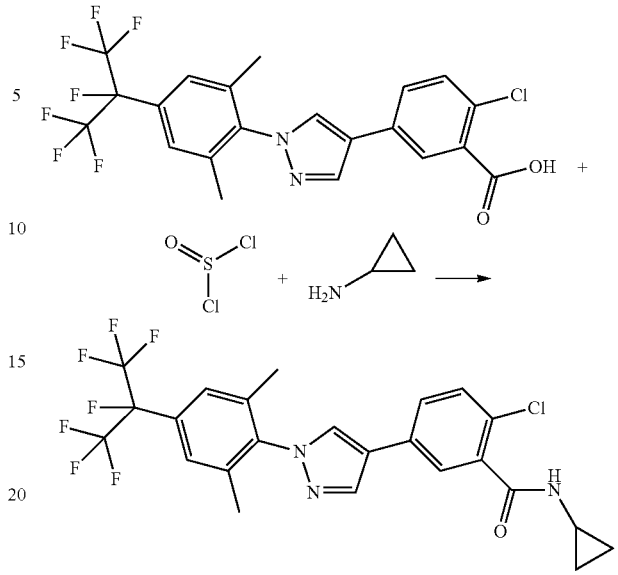

0.134 g (0.27 mmol) of 2-chloro-5-[1-[2,6-dimethyl-4-[1,2,2,2-tetrafluoro-1-(trifluoromethyl)ethyl]phenyl]pyrazol-4-yl]benzoic acid were dissolved in 1.26 ml of toluene, and 0.161 g (1.35 mmol) of thionyl chloride were added. The mixture was heated to 80° C. for 2 hours. This was followed by concentration under reduced pressure. The residue was dissolved in 1.26 ml of dichloromethane and added dropwise to a solution of 39 mg (0.67 mmol) of cyclopropylamine in 0.63 ml of dichloromethane at 0° C. while cooling, and the solution was cooled. For workup, 5% aqueous sodium dihydrogenphosphate solution was added, and the organic phase was removed, dried with sodium sulphate and concentrated on a rotary evaporator under reduced pressure. The residue was separated with silica gel with a gradient of cyclohexane/ethyl acetate of 9:1 to 7:3 (v/v), and gave 46 mg of 2-chloro-N-cyclopropyl-5-[1-[2,6-dimethyl-4-[1,2,2,2-tetrafluoro-1-(trifluoromethyl)ethyl]phenyl]pyrazol-4-yl]benzamide (compound I-T3-1).

HPLC-MS[a]: log P=4.36, mass (m/z)=534 [M+H]+.
$^1$H NMR (400 MHz, d$_3$-acetonitrile): δ=8.11 (s, 1H), 8.06 (s, 1H), 7.68 (d, J1=2.2 Hz, 1H), 7.62-7.65 (dd, J1=8.4 Hz, J2=2.2 Hz, 1H), 7.45 (d, J=8.4 Hz, 1H), 6.9 (s (broad), 1H (N—H)), 3.97 (s, 3H), 2.82-2.88 (m, 1H), 0.76-0.8 (m, 2H), 0.57-0.61 (m, 2H).

Examples I-T3-48 and IT-T3-50

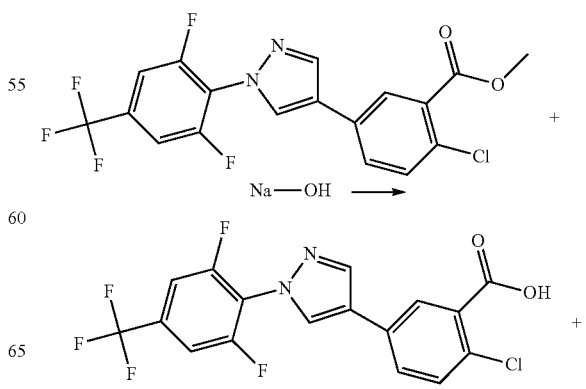

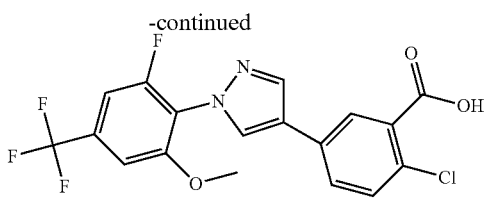

2.46 g (5.9 mmol) of methyl 2-chloro-5-[1-[2,6-difluoro-4-(trifluoromethyl)phenyl]pyrazol-4-yl]benzoate were initially charged in 127 ml of methanol, and 5.9 mg (5.9 mmol) of 1 molar sodium hydroxide solution were added. The mixture was heated to reflux for 2 hours. Thereafter, the mixture was cooled, and the majority of the methanol was removed on a rotary evaporator under reduced pressure. The aqueous residue was extracted with dichloromethane. The extract was discarded. The aqueous phase was set to pH 1 with 33% hydrochloric acid and extracted twice with dichloromethane. The combined extracts were washed with saturated aqueous sodium chloride solution, dried with sodium sulphate and concentrated. 1.41 g of residue were obtained as a 45:55 (LC-MS areas) mixture of 2-chloro-5-[1-[2,6-difluoro-4-(trifluoromethyl)phenyl]pyrazol-4-yl]benzoic acid and 2-chloro-5-[1-[2-fluoro-6-methoxy-4-(trifluoromethyl)phenyl]pyrazol-4-yl]benzoic acid.

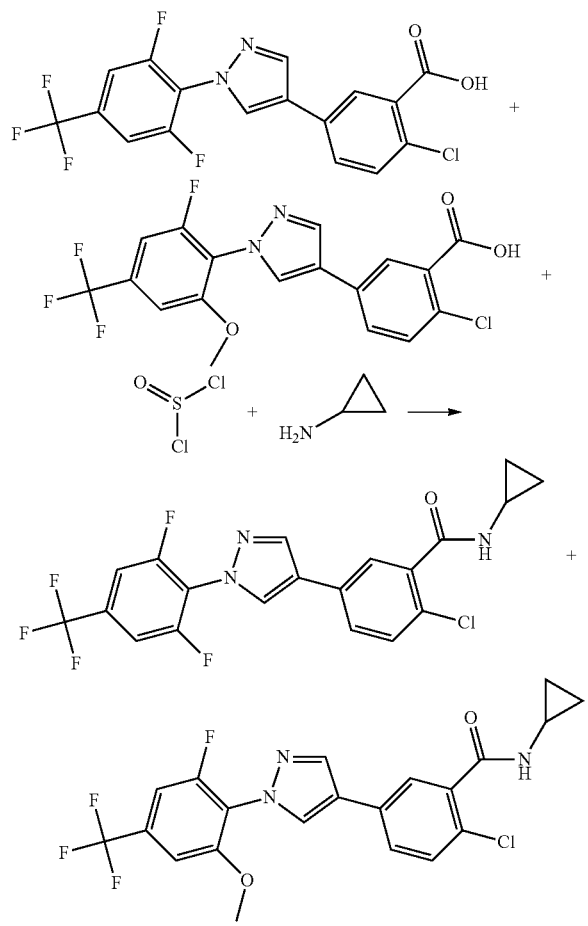

700 mg (about 1.7 mmol) of a 45:55 (LC-MS areas) mixture of 2-chloro-5-[1-[2,6-difluoro-4-(trifluoromethyl)phenyl]pyrazol-4-yl]benzoic acid and 2-chloro-5-[1-[2-fluoro-6-methoxy-4-(trifluoromethyl)phenyl]pyrazol-4-yl]benzoic acid were dissolved in 6.6 ml of toluene, and 1.34 g (8.7 mmol) of thionyl chloride were added. The mixture was heated to 80° C. for 2 hours. Thereafter, all the volatile constituents were drawn off on a rotary evaporator under reduced pressure. The residue was dissolved in 3.3 ml of dichloromethane and added dropwise to a solution of 248 mg (4.34 mmol) of cyclopropylamine in 3.3 ml of dichloromethane at 0° C. The mixture was then stirred without cooling for 2 hours. Thereafter, the solution was washed with 5% aqueous sodium dihydrogenphosphate solution, dried with sodium sulphate and concentrated. The residue was chromatographed using a cartridge containing 40 g of silica gel with a gradient in cyclohexane/ethyl acetate of 90:10 to 50:50 (v/v). 240 mg of 2-chloro-N-cyclopropyl-5-[1-[2,6-difluoro-4-(trifluoromethyl)phenyl]pyrazol-4-yl]benzamide Example I-T3-48

HPLC-MS$^{a)}$: log P=3.2, mass (m/z)=442 [M+H]+.
$^1$H NMR (400 MHz, d$_3$-acetonitrile): δ (ppm)=8.26 (s, 1H), 8.19 (s, 1H), 7.61-7.69 (m, 4H), 7.46 (d, J=8.3 Hz, 1H), 6.94 (s, 1H (broad)), 2.82-2.88 (m, 1H), 0.75-0.80 (m, 2H), 0.58-0.62 (m, 2H).

and 2-chloro-N-cyclopropyl-5-[1-[2-fluoro-6-methoxy-4-(trifluoromethyl)phenyl]pyrazol-4-yl]benzamide (Example I-T3-50) were obtained.
HPLC-MS$^{a)}$: log P=3.1, mass (m/z)=454 [M+H]+.
$^1$H NMR (400 MHz, d$_3$-acetonitrile): δ (ppm)=8.13 (s, 1H), 8.11 (s, 1H), 7.67 (d, J=2.2 Hz, 1H), 7.62 (dd, J$_1$=8.3 Hz, J$_2$=2.2 Hz, 1H), 7.45 (d, J=8.3 Hz, 1H), 7.32 (s, 1H), 7.30 (s, 1H), 6.91 (s, 1H (broad)), 3.90 (s, 3H), 2.83-2.87 (m, 1H), 0.75-0.79 (m, 2H), 0.57-0.61 (m, 2H).

Example I-T3-121

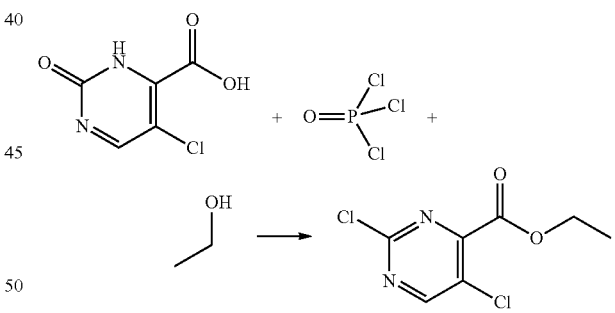

4.6 ml (49.6 mmol) of phosphorus oxychloride were initially charged and 1.3 g (7.44 mmol) of 5-chloro-2-oxo-1H-pyrimidine-6-carboxylic acid (commercially available, or can be prepared by methods known from the literature (e.g. Gacek, Michel; Ongstad, Leif; Undheim, Kjell; Acta Chemica Scandinavica, Series B: Organic Chemistry and Biochemistry B33(2), (1979), p. 150-1)) were introduced. The mixture was heated gradually and kept under reflux for 2 hours. Thereafter, the mixture was cooled a little and the excess phosphorus oxychloride was drawn off on a rotary evaporator under reduced pressure. 20 ml of dry ethanol were added to the residue, and the mixture was then stirred at room temperature overnight. Thereafter, excess ethanol was drawn off on a rotary evaporator under reduced pressure. The residue was taken up in dichloromethane and washed three times with saturated aqueous sodium hydrogencarbonate solution. The aqueous phases were re-extracted with dichloromethane, then the combined organic phases were washed with saturated aqueous sodium chloride solution, dried with sodium sulphate and concentrated on a rotary evaporator under reduced pressure. The residue was chromatographed using a cartridge containing 15 g of silica gel with a gradient from pure cyclohexane to 50:50 (v/v) cyclohexane/ethyl acetate, and gave 115 mg of ethyl 2,5-dichloropyrimidine-4-carboxylate.

cartridge containing silica gel with a gradient proceeding from pure cyclohexane up to 80:20 (v/v) cyclohexane/ethyl acetate, 0.6 g of 1-[2,6-dimethyl-4-[1,2,2,2-tetrafluoro-1-(trifluoromethyl)ethyl]phenyl]-4-(4,4,5,5-tetramethyl-1,3,2-dioxaborolan-2-yl)pyrazole was obtained.

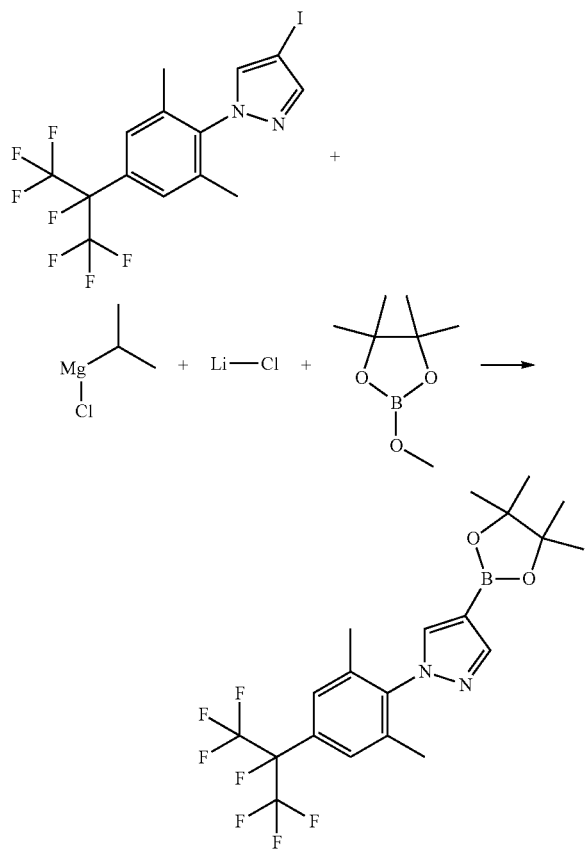

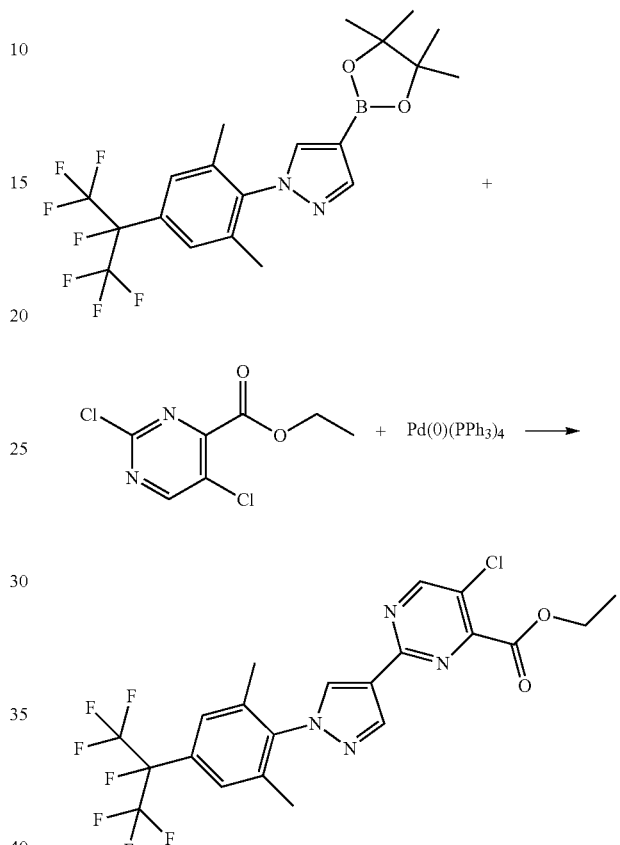

A baked-out 25 ml three-neck flask was initially charged with 5.94 ml (7.72 mmol) of a 1.3 molar solution of i-propylmagnesium chloride/lithium chloride complex, and a solution of 4-iodo-1-[2-methyl-4-[1,2,2,2-tetrafluoro-1-(trifluoromethyl)ethyl]-6-(trifluoromethyl)phenyl]pyrazole (for preparation see Example I-T3-1) in 3.4 ml of dry tetrahydrofuran was added dropwise. Stirring of the mixture at room temperature continued overnight, and then the mixture was cooled to −20° C. and 1.63 g (10.2 mmol) of 2-methoxy-4,4,5,5-tetramethyl-1,3,2-dioxaborolane were added dropwise. The mixture was stirred at 0-10° C. for a further 1 hour. For workup, the mixture was poured onto 30 ml of saturated aqueous ammonium chloride solution and diluted with cyclohexane. The phases were separated; the aqueous phase was re-extracted with cyclohexane. The combined organic phases were washed first with saturated aqueous sodium hydrogencarbonate solution and then with saturated aqueous sodium chloride solution, dried with sodium sulphate and concentrated on a rotary evaporator under reduced pressure. After chromatography using a 40 g 155 mg (0.7 mmol) of ethyl 2,5-dichloropyrimidine-4-carboxylate and 327 mg (0.7 mmol) of 1-[2,6-dimethyl-4-[1,2,2,2-tetrafluoro-1-(trifluoromethyl)ethyl]phenyl]-4-(4,4,5,5-tetramethyl-1,3,2-dioxaborolan-2-yl)pyrazole were initially charged in 25 ml of dioxane, and 234 mg (2.2 mmol) of sodium carbonate and 1.25 ml of water were added. The mixture was degassed with argon and then 81 mg (0.07 mmol) of tetrakis(triphenylphosphine)palladium(0) were added. The mixture was degassed once again with argon and stirred at 100° C. overnight. The next morning, the mixture was cooled and the solvent was drawn off on a rotary evaporator under reduced pressure. The residue was partitioned between water and ethyl acetate. The organic phase was removed, washed once with saturated aqueous sodium chloride solution and then concentrated on a rotary evaporator under reduced pressure. For purification, chromatography was effected using a cartridge containing 15 g of silica gel and a gradient proceeding from pure cyclohexane as far as a mixture of 70:30 (v/v) cyclohexane/ethyl acetate. 120 mg of ethyl 5-chloro-2-[1-[2,6-dimethyl-4-[1,2,2,2-tetrafluoro-1-(trifluoromethyl)ethyl]phenyl]pyrazol-4-yl]pyrimidine-4-carboxylate were obtained.

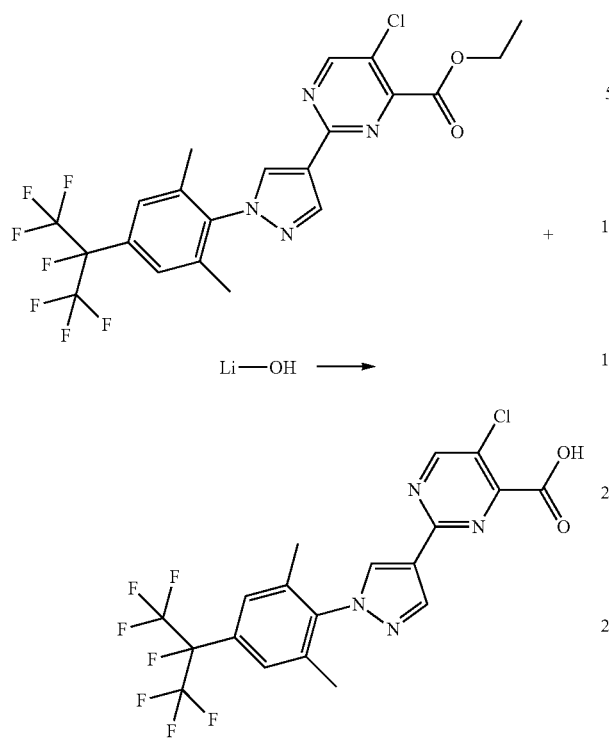

0.120 g (0.23 mmol) of ethyl 5-chloro-2-[1-[2,6-dimethyl-4-[1,2,2,2-tetrafluoro-1-(trifluoromethyl)ethyl]phenyl]pyrazol-4-yl]pyrimidine-4-carboxylate were initially charged in a mixture of 4.1 ml of dioxane and 1.44 ml of water, and 31 mg (0.74 mmol) of lithium hydroxide monohydrate were added. Subsequently, the mixture was stirred at room temperature for 4 hours, then excess solvent was evaporated off under reduced pressure, and the residue was taken up with dilute hydrochloric acid and extracted three times with dichloromethane. The combined extracts were washed with saturated aqueous sodium chloride solution, dried with sodium sulphate and concentrated, and gave 115 mg of crude 5-chloro-2-[1-[2,6-dimethyl-4-[1,2,2,2-tetrafluoro-1-(trifluoromethyl)ethyl]phenyl]pyrazol-4-yl]pyrimidine-4-carboxylic acid.

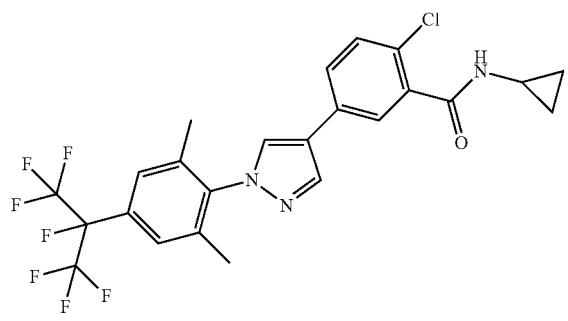

0.110 g (0.22 mmol) of crude 5-chloro-2-[1-[2,6-dimethyl-4-[1,2,2,2-tetrafluoro-1-(trifluoromethyl)ethyl]phenyl]pyrazol-4-yl]pyrimidine-4-carboxylic acid were dissolved in 2 ml of toluene, and 0.132 g (1.1 mmol) of thionyl chloride and one drop of dimethylformamide were added. The mixture was heated to 80° C. for 2 hours. This was followed by concentration under reduced pressure. The residue was dissolved in 1 ml of dichloromethane and added dropwise to a solution of 32 mg (0.55 mmol) of cyclopropylamine in 1 ml of dichloromethane at 0° C. while cooling, and the mixture was then stirred without cooling for 2 hours. For workup, 5% aqueous sodium dihydrogenphosphate solution was added, and the organic phase was removed, dried with sodium sulphate and concentrated on a rotary evaporator under reduced pressure. The residue was separated using a cartridge containing 15 g of silica gel with a gradient of cyclohexane/ethyl acetate of 9:1 to 7:3 (v/v), and gave 49 mg of 5-chloro-N-cyclopropyl-2-[1-[2,6-dimethyl-4-[1,2,2,2-tetrafluoro-1-(trifluoromethyl)ethyl]phenyl]pyrazol-4-yl]pyrimidine-4-carboxamide (compound I-T3-121).

HPLC-MS[a)]: log P=4.5, mass (m/z)=536 [M+H]+.

$^1$H NMR (400 MHz, d$_3$-acetonitrile): δ (ppm)=8.84 (s, 1H), 8.46 (s, 1H), 8.44 (s, 1H), 7.87 (s, 1H (broad)), 7.55 (s, 2H), 2.84-2.91 (m, 1H), 2.2 (s, 6H), 0.79-0.83 (m, 2H), 0.64-0.68 (m, 2H).

Example I-T3-134

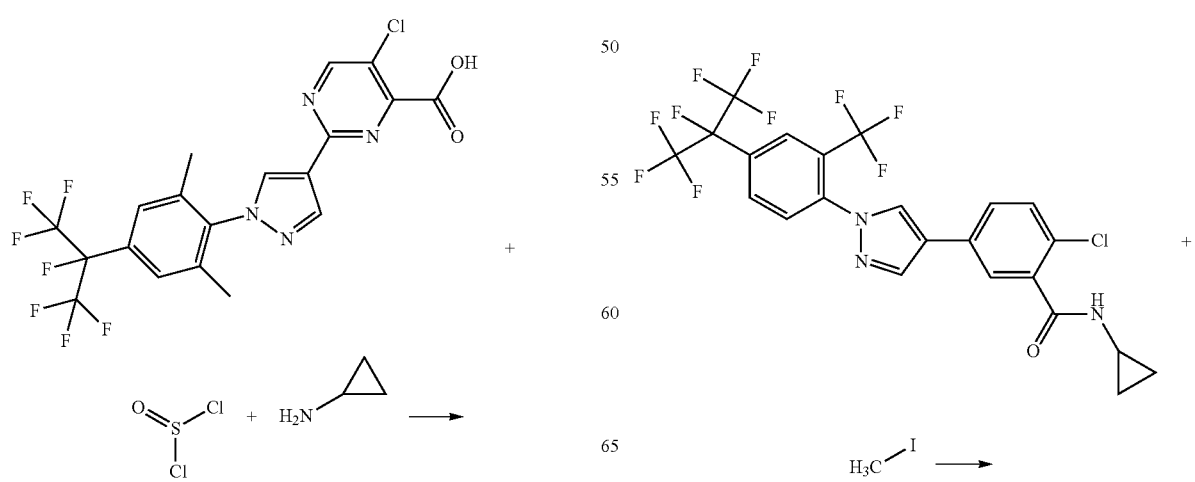

-continued

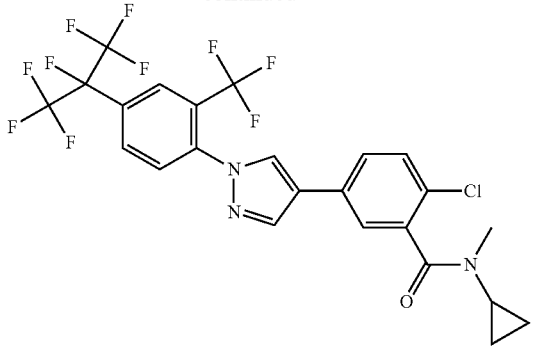

To a mixture, cooled to 0° C., of 6.5 mg (0.163 mmol) of sodium hydride (60% in mineral oil) in 2 ml of dry tetrahydrofuran were added 49.3 mg (0.08 mmol) of 2-chloro-N-cyclopropyl-5-{1-[4-(1,1,1,2,3,3,3-heptafluoropropan-2-yl)-2-(trifluoromethyl)phenyl]-1H-pyrazol-4-yl}benzamide. After 30 minutes, 35 mg (0.24 mmol) of methyl iodide were added, and the mixture was stirred at 0° C. and for 1 hour, then warmed up to room temperature over the course of 1 hour and stirred at room temperature for a further 14 hours. Thereafter, the mixture was added to water and extracted with ethyl acetate, the organic phase was dried over sodium sulphate and the solvent was removed under reduced pressure. The residue was purified by chromatography on reversed-phase silica gel (C18) with water/acetonitrile (gradient) as eluent. 40.0 mg (0.068 mmol, 78%) of 2-chloro-N-cyclopropyl-5-[5-[2,6-dichloro-4-[1,2,2,2-tetrafluoro-1-(trifluoromethyl)ethyl]phenyl]isoxazol-3-yl]benzamide (compound I-T3-134) were obtained.

HPLC-MS[a)]: log P=4.88, mass (m/z)=588 [M+H]+.

$^1$H NMR (400 MHz, d$_6$-DMSO): δ (ppm)=8.82 (s, 1H), 8.43 (s, 1H), 8.25 (d, 1H), 8.11 (d, 1H), 8.06 (d, 1H), 7.81 (d, 1H), 7.75 (m, 1H), 7.54 (d, 1H), 3.02 (s, 3H), 2.72 (m, 1H), 0.55 (m, 2H), 0.46 (m, 2H).

Example I-T3-156

2-Chloro-N-cyclopropyl-5-{1-[3-(ethylsulphanyl)-5-(1,1,1,2,3,3,3-heptafluoropropan-2-yl)pyridin-2-yl]-1H-pyrazol-4-yl}benzamide

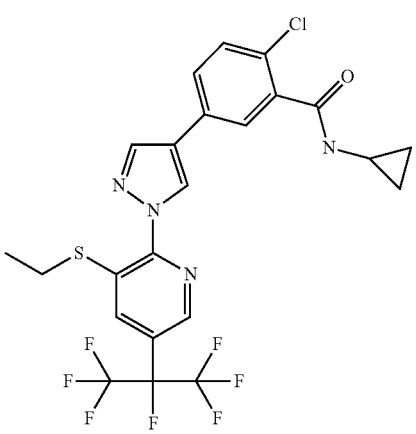 [SMILES: CCSc1cc(C(F)(C(F)(F)F)C(F)(F)F)cnc1-n1cc(-c2ccc(Cl)c(C(=O)NC3CC3)c2)cn1]

2-(4-Bromo-1H-pyrazol-1-yl)-3-chloro-5-(1,1,1,2,3,3,3-heptafluoropropan-2-yl)pyridine 1.0 g (3.16 mmol) of 2,3-dichloro-5-(1,1,1,2,3,3,3-heptafluoropropan-2-yl)pyridine were added dropwise to a suspension of 0.51 g (3.48 mmol) of 4-bromo-1H-pyrazole and 2.58 g (7.91 mmol) of caesium carbonate in 10.0 ml of dimethylformamide p.a. The reaction was stirred at room temperature for 3 h. The reaction mixture was then diluted with ethyl acetate and then washed with semisaturated aqueous ammonium chloride solution. The aqueous phase was then extracted repeatedly with ethyl acetate, and the combined organic phases were subsequently washed with distilled water and saturated sodium chloride solution. The organic phase was dried over magnesium sulphate, filtered and concentrated on a rotary evaporator under reduced pressure. The crude product was purified by column chromatography on silica gel.

This gives 1.34 g (3.14 mmol) of 2-(4-bromo-1H-pyrazol-1-yl)-3-chloro-5-(1,1,1,2,3,3,3-heptafluoropropan-2-yl)pyridine as a colourless oil.

HPLC-MS[a)]: log P=4.74, mass (m/z)=428 [M+H]+.

$^1$H NMR (400 MHz, D6-DMSO): 8.90 (s, 1H), 8.67 (s, 1H), 8.63 (d, 1H), 8.06 (s, 1H).

2-Chloro-5-{1-[3-chloro-5-(1,1,1,2,3,3,3-heptafluoropropan-2-yl)pyridin-2-yl]-1H-pyrazol-4-yl}-N-cyclopropylbenzamide 150 mg (0.35 mmol) of 2-(4-bromo-1H-pyrazol-1-yl)-3-chloro-5-(1,1,1,2,3,3,3-heptafluoropropan-2-yl)pyridine, 136 mg (0.42 mmol) of 2-chloro-N-cyclopropyl-5-(4,4,5,5-tetramethyl-1,3,2-dioxaborolan-2-yl)benzamide, 59 mg (0.70 mmol) of sodium hydrogencarbonate and 20 mg of tetrakis(triphenylphosphine)palladium (0.01 mmol) were dissolved in a mixture of 1.5 ml of dioxane and 0.5 ml of distilled water. The solvents were saturated with argon for about 30 minutes prior to use, by passing argon gas through the solvents. The reaction mixture was heated in an oil bath to 100° C. for 16 hours. After the reaction mixture had been cooled to room temperature, the mixture was admixed with water and the crude product was extracted repeatedly with ethyl acetate. The combined organic phases were dried over magnesium sulphate and filtered through silica gel. The solvents were removed on a rotary evaporator under reduced pressure. The crude product was purified by column chromatography on silica gel.

This gave 25 mg (0.05 mmol) of 2-chloro-5-{1-[3-chloro-5-(1,1,1,2,3,3,3-heptafluoropropan-2-yl)pyridin-2-yl]-1H-pyrazol-4-yl}-N-cyclopropylbenzamide as a colourless solid.

HPLC-MS[a)]: log P=4.08, mass (m/z)=541 [M+H]+.

1H NMR (400 MHz, D6-DMSO): 9.02 (s, 1H), 8.89 (s, 1H), 8.61 (d, 1H), 8.54-8.52 (m, 1H), 8.50 (s, 1H), 7.83-7.81 (m, 2H), 7.52 (d, 1H), 2.87-2.81 (m, 1H), 0.74-0.65 (m, 2H), 0.60-0.50 (m, 2H)

2-Chloro-N-cyclopropyl-5-{1-[3-(ethylsulphanyl)-5-(1,1,1,2,3,3,3-heptafluoropropan-2-yl)pyridin-2-yl]-1H-pyrazol-4-yl}benzamide 300 mg (0.55 mmol) of 2-chloro-5-{1-[3-chloro-5-(1,1,1,2,3,3,3-heptafluoropropan-2-yl)pyridin-2-yl]-1H-pyrazol-4-yl}-N-cyclopropylbenzamide were dissolved in 5.0 ml of DMF abs. and cooled with a dry ice/acetone bath. To the cooled reaction mixture was added dropwise a solution of 81.6 mg (0.97 mmol) of sodium ethanethiolate in 5 ml of DMF abs. After 3 hours, the reaction mixture was warmed up to room temperature and poured cautiously onto water. The crude product was extracted repeatedly with ethyl acetate. The combined organic phases were washed with saturated aqueous sodium chloride solution, dried over magnesium sulphate and filtered, and concentrated on a rotary evaporator under reduced pressure. The crude product was purified by column chromatography on silica gel.

This gives 226 mg (0.40 mmol) of 2-chloro-N-cyclopropyl-5-{1-[3-(ethylsulphanyl)-5-(1,1,1,2,3,3,3-heptafluoropropan-2-yl)pyridin-2-yl]-1H-pyrazol-4-yl}benzamide as a colourless solid.

HPLC-MS[a)]: log P=4.69, mass (m/z)=567 [M+H]$^+$.

1H NMR (400 MHz, D6-DMSO): 9.08 (d, 1H), 8.59 (d, 1H), 8.53 (d, 1H), 8.47 (s, 1H), 8.02 (d, 1H), 7.85-7.82 (m, 2H), 7.53-7.50 (m, 1H), 3.08 (q, 2H), 2.87-2.81 (m, 1H), 1.22 (t, 3H), 0.74-0.69 (m, 2H), 0.58-0.54 (m, 2H).

Example I-T3-157

2-Chloro-N-cyclopropyl-5-{1-[3-(ethylsulphinyl)-5-(1,1,2,3,3-heptafluoropropan-2-yl)pyridin-2-yl]-1H-pyrazol-4-yl}benzamide

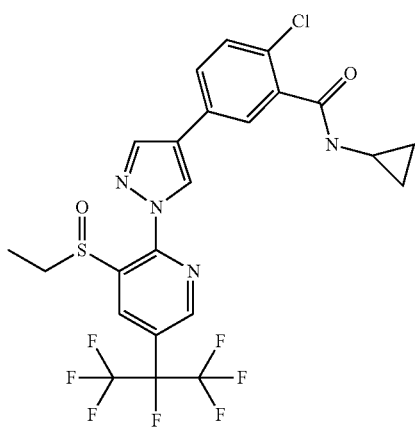 [SMILES: CCS(=O)c1cc(C(F)(C(F)(F)F)C(F)(F)F)cnc1-n1cc(-c2ccc(Cl)c(C(=O)NC3CC3)c2)cn1]

100 mg (0.17 mmol) of 2-chloro-N-cyclopropyl-5-{1-[3-(ethylsulphanyl)-5-(1,1,1,2,3,3,3-heptafluoropropan-2-yl)pyridin-2-yl]-1H-pyrazol-4-yl}benzamide were dissolved in 10.0 ml of dichloromethane and cooled with an ice bath. 43.5 mg of 3-chloroperbenzoic acid were added in portions. The reaction mixture was stirred while cooling with ice for 2 hours. The reaction mixture was admixed with 5 ml of 1N sodium hydroxide solution. After 5 minutes, the aqueous phase was removed. After checking for peroxides, the organic phase was concentrated on a rotary evaporator under reduced pressure. The crude product was purified by column chromatography on silica gel.

This gave 61 mg of 2-Chloro-N-cyclopropyl-5-{1-[3-(ethylsulphinyl)-5-(1,1,1,2,3,3,3-heptafluoropropan-2-yl)pyridin-2-yl]-1H-pyrazol-4-yl}benzamide as a colourless solid.

HPLC-MS[a)]: log P=3.79, mass (m/z)=583 [M+H]$^+$.

1H NMR (400 MHz, D6-DMSO): 9.36 (s, 1H), 8.96 (d, 1H), 8.63 (s, 1H), 8.58 (s, 1H), 8.53 (d, 1H), 7.91 (s, 1H), 7.89 (d, 1H), 7.53 (d, 1H), 3.45-3.30 (m, 1H beneath water), 2.95-2.88 (m, 1H), 2.86-2.81 (m, 1H), 1.08 (t, 3H), 0.74-0.69 (m, 2H), 0.60-0.50 (m, 2H).

Preparation of the Starting Compounds 2,3-Dichloro-5-(1,1,1,2,3,3,3-heptafluoropropan-2-yl)pyridine

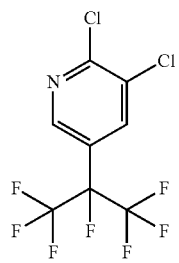

1st Stage: 3-Chloro-5-(1,1,1,2,3,3,3-heptafluoropropan-2-yl)pyridin-2-amine 130.6 g (750 mmol) of sodium dithionite were added to a mixture, cooled to 0-5° C., of 64.3 g (500 mmol) of 3-chloropyridin-2-amine, 222 g (750 mmol) of 1,1,1,2,3,3,3-heptafluoro-2-iodopropane and 126 g (1500 mmol) of sodium hydrogencarbonate in 2000 ml of a 3:1 mixture of acetonitrile/water (v/v) under protective gas. The reaction mixture was stirred at room temperature for 48 hours. The acetonitrile was then removed on a rotary evaporator under reduced pressure. The residue was diluted with 500 ml of water. The crude product was extracted repeatedly from the aqueous phase with ethyl acetate. The combined organic phases were dried over sodium sulphate, filtered and then concentrated on a rotary evaporator under reduced pressure. The crude product was purified by column chromatography on silica gel.

2nd Stage: 3-Chloro-5-(1,1,1,2,3,3,3-heptafluoropropan-2-yl)pyridin-2(1H)-one 5.8 g (19.5 mmol) of 3-chloro-5-(1,1,1,2,3,3,3-heptafluoropropan-2-yl)pyridin-2-amine were dissolved in 150 ml of sulphuric acid (20%, w/w) and cooled to 0-5° C. The solution was admixed with 2.7 g (40 mmol) of sodium nitrite in portions. The reaction mixture was stirred at room temperature for 16 hours. The crude product was extracted repeatedly from the reaction mixture with dichloromethane (DCM). The combined organic phases were dried over sodium sulphate, filtered and then concentrated on a rotary evaporator under reduced pressure. The crude product was used in the next stage without purification.

3rd Stage: 2,3-Dichloro-5-(1,1,1,2,3,3,3-heptafluoropropan-2-yl)pyridine 15.4 g (51.7 mmol) of 3-chloro-5-(1,1,1,2,3,3,3-heptafluoropropan-2-yl)pyridin-2(1H)-one and 150 ml of phosphoryl chloride were heated to 105° C. for 5 hours. The reaction mixture was neutralized cautiously with sodium hydrogencarbonate solution. The crude product was extracted repeatedly from the reaction mixture with DCM. The combined organic phases were washed with saturated aqueous sodium chloride solution, dried over sodium sulphate and filtered, and then concentrated on a rotary evaporator under reduced pressure. The product was provided by vacuum distillation (b.p. 40° C. at 1 mbar).

This gave 14.8 g of 2,3-dichloro-5-(1,1,1,2,3,3,3-heptafluoropropan-2-yl)pyridine as a colourless liquid.

MS: mass (m/z)=315 [M]+.

1H NMR (400 MHz, d1-chloroform): 8.48 (s, 1H), 7.95 (s, 1H).

Example I-T3-161

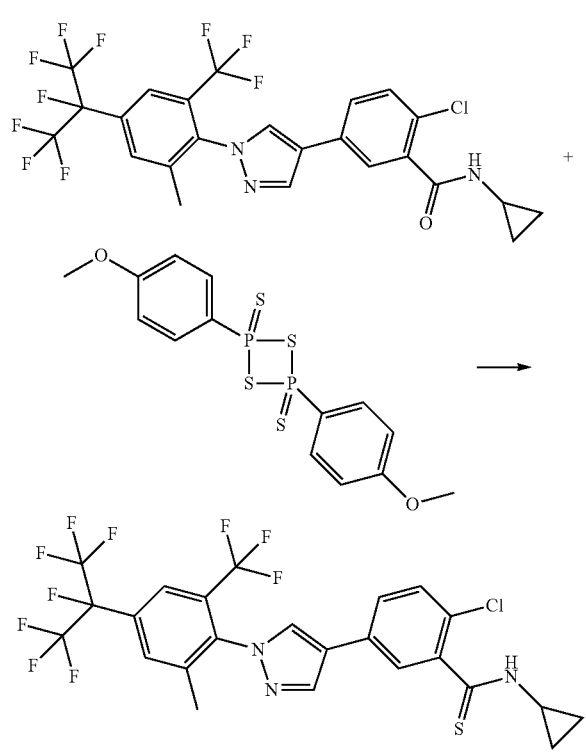

294 mg (0.5 mmol) of 2-chloro-N-cyclopropyl-5-[1-[2-methyl-4-[1,2,2,2-tetrafluoro-1-(trifluoromethyl)ethyl]-6-(trifluoromethyl)phenyl]pyrazol-4-yl]benzamide were initially charged in a mixture of 0.5 ml of ethanol-free trichloromethane and 1.5 ml of 1,2-dimethoxyethane, and 101 mg (0.25 mmol) of Lawesson's reagent (2,4-bis(4-methoxyphenyl)-1,3,2,4-dithiadiphosphetane 2,4-disulphide) were added. The mixture was heated to 50° C. for 4 hours. Thereafter, the mixture was cooled and the solvent was drawn off on a rotary evaporator under reduced pressure. The residue was partitioned between ethyl acetate and saturated aqueous sodium hydrogencarbonate solution; the aqueous phase was re-extracted once with ethyl acetate. The combined organic phases were dried with sodium sulphate and concentrated on a rotary evaporator under reduced pressure. For purification, chromatography was effected using a cartridge containing 40 g of silica gel with a gradient in cyclohexane/ethyl acetate of 90:10 to 50:50 (v/v). 248 mg of 2-chloro-N-cyclopropyl-5-[1-[2-methyl-4-[1,2,2,2-tetrafluoro-1-(trifluoromethyl)ethyl]-6-(trifluoromethyl)phenyl]pyrazol-4-yl]benzenecarbothioamide (compound I-T3-161) were obtained.

HPLC-MS[a)]: log P=5.0, mass (m/z)=604 [M+H]+.

1H-NMR (400 MHz, d3-acetonitrile): δ (ppm)=8.62 (s, 1H (broad)), 8.14 (s, 1H), 8.10 (s, 1H), 8.0 (s, 1H), 7.95 (s, 1H), 7.63 (d, J=2.2 Hz, 1H), 7.57-7.60 (m, 1H), 7.42 (d, J=8.4 Hz, 1H), 3.02 (s, 3H), 3.37-3.44 (m, 1H), 0.92-0.95 (m, 2H), 0.74-0.78 (m, 2H).

Preparation Process I-T4

Example I-T4-1

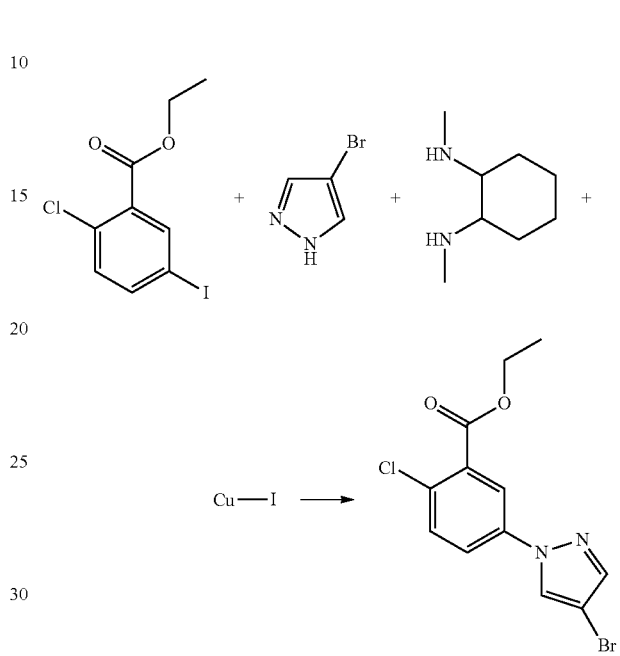

3.81 g (12.2 mmol) of ethyl 2-chloro-5-iodobenzoate were initially charged in 37 ml of dimethylformamide, and 2.885 g (19.6 mmol) of 4-bromopyrazole, 5.09 g (36.8 mmol) of freshly ground potassium carbonate, 0.349 g (2.4 mmol) of 1,2-bis(methylamino)cyclohexane (racemic, trans) and 0.234 g (1.22 mmol) of copper(I) iodide were added. The mixture was degassed with argon and then heated to reflux for one hour. For workup, the mixture was cooled, poured onto 100 ml of water and extracted twice with 100 ml each time of ethyl acetate. The combined organic phases were washed twice with 100 ml of water and then with saturated sodium chloride solution, dried with sodium sulphate and concentrated on a rotary evaporator under reduced pressure. For purification, the residue was chromatographed using a 120 g cartridge containing silica gel with a gradient of cyclohexane/ethyl acetate of 90:10 to 70:30 (v/v). 1.41 g of ethyl 5-(4-bromopyrazol-1-yl)-2-chlorobenzoate were obtained.

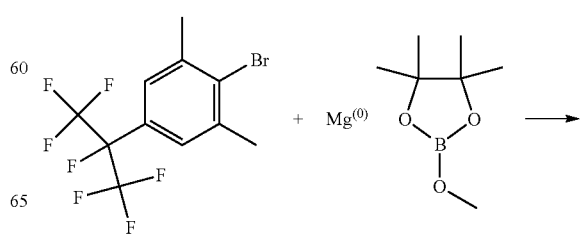

-continued

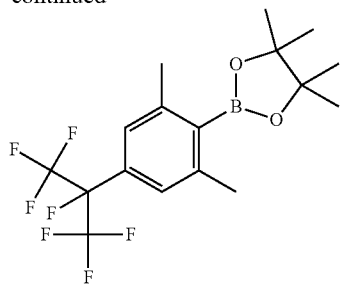

0.158 g (6.49 mg) of magnesium turnings were covered with 1.5 ml of dry tetrahydrofuran. A few drops of a solution of 1.75 g (4.95 mmol) of 2-bromo-1,3-dimethyl-5-[1,2,2,2-tetrafluoro-1-(trifluoromethyl)ethyl]benzene (prepared according to US2003/187233, p. 6) in 2.5 ml of dry tetrahydrofuran were added. To start the reaction, a crumb of iodine was added and the mixture was heated to about 55° C. After the reaction had started, the remaining solution of the 2-bromo-1,3-dimethyl-5-[1,2,2,2-tetrafluoro-1-(trifluoromethyl)ethyl]benzene was added dropwise at a temperature of 55° C. After the addition had ended, stirring was continued at 55° C. for another 1 hour, then the mixture was cooled to 0° C. and a solution of 2-methoxy-4,4,5,5-tetramethyl-1,3,2-dioxaborolane in 2.5 ml of dry tetrahydrofuran was added dropwise. Then the mixture was allowed to come to room temperature. For workup, the mixture was poured onto saturated aqueous ammonium chloride solution. The phases were separated, the aqueous phase was re-extracted with ethyl acetate, then the combined organic phases were washed with saturated aqueous sodium chloride solution, dried with sodium sulphate and concentrated on a rotary evaporator under reduced pressure. The residue was distilled in a Kugelrohr at a vacuum of 1 mbar and 220° C. 1.85 g of 2-[2,6-dimethyl-4-[1,2,2,2-tetrafluoro-1-(trifluoromethyl)ethyl]phenyl]-4,4,5,5-tetramethyl-1,3,2-dioxaborolane were obtained.

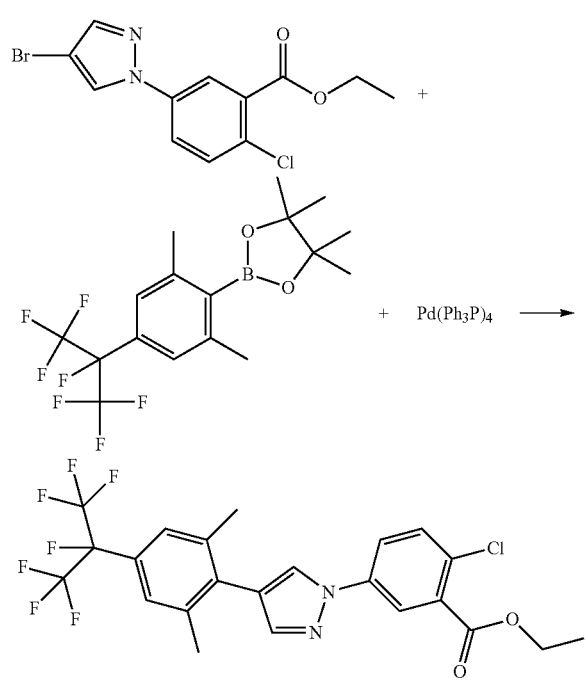

0.947 g (2.87 mmol) of ethyl 5-(4-bromopyrazol-1-yl)-2-chlorobenzoate and 1.15 g (2.87 mmol) of 2-[2,6-dimethyl-4-[1,2,2,2-tetrafluoro-1-(trifluoromethyl)ethyl]phenyl]-4,4,5,5-tetramethyl-1,3,2-dioxaborolane were initially charged in 62 ml of isopropanol, and 8.7 ml (8.7 mmol) of degassed 1 molar aqueous sodium hydrogencarbonate solution were added. The mixture was degassed with argon and 0.166 g (0.14 mmol) of tetrakis(triphenylphosphine)palladium(0) were added and the mixture was heated to reflux overnight.

For workup, the mixture was concentrated on a rotary evaporator under reduced pressure, and the residue was partitioned between water and ethyl acetate. The organic phase was removed; the aqueous phase was re-extracted with ethyl acetate. The combined organic phases were then washed once with saturated aqueous sodium chloride solution and concentrated on a rotary evaporator under reduced pressure. As residue, 1.17 g of crude ethyl 2-chloro-5-[4-[2,6-dimethyl-4-[1,2,2,2-tetrafluoro-1-(trifluoromethyl)ethyl]phenyl]pyrazol-1-yl]benzoate were obtained.

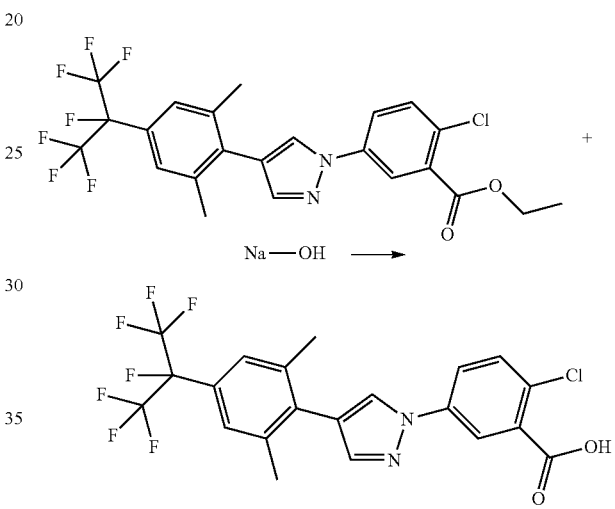

1.76 g (3.36 mmol) of ethyl 2-chloro-5-[4-[2,6-dimethyl-4-[1,2,2,2-tetrafluoro-1-(trifluoromethyl)ethyl]phenyl]pyrazol-1-yl]benzoate were initially charged in 72 ml of methanol, and 4.03 ml (4.03 mmol) of 1 molar sodium hydroxide solution were added. The mixture was then heated to reflux for 3 hours. For workup, the mixture was concentrated on a rotary evaporator under reduced pressure, and the residue was taken up with dilute hydrochloric acid and extracted three times with ethyl acetate. The combined extracts were washed with saturated sodium chloride solution, dried with sodium sulphate and concentrated, and gave 1.36 g of crude 2-chloro-5-[4-[2,6-dimethyl-4-[1,2,2,2-tetrafluoro-1-(trifluoromethyl)ethyl]phenyl]pyrazol-1-yl]benzoic acid.

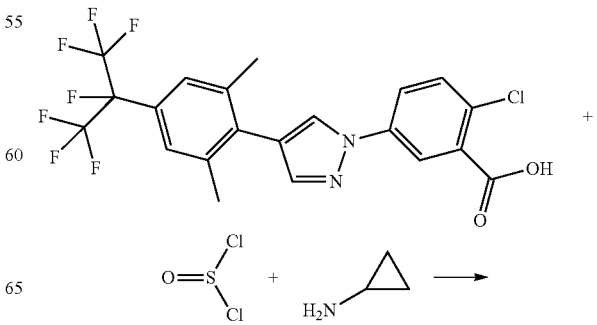

-continued

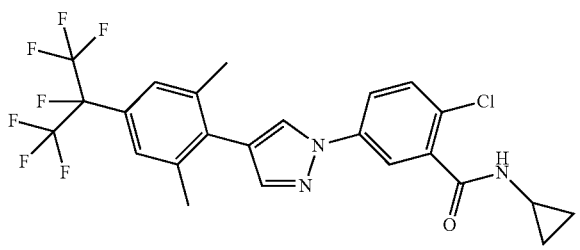

1.36 g (2.76 mmol) of crude 2-chloro-5-[4-[2,6-dimethyl-4-[1,2,2,2-tetrafluoro-1-(trifluoromethyl)ethyl]phenyl]pyrazol-1-yl]benzoic acid were dissolved in 14 ml of dry toluene, 1 ml (13.8 mmol) of thionyl chloride was added and then the mixture was heated to 80° C. for 2 hours. Thereafter, the mixture was concentrated on a rotary evaporator under reduced pressure, 1 ml of dry toluene was added and the mixture was concentrated again. 1.4 g of crude acid chloride were obtained as residue. 0.7 g of the residue was dissolved in 5 ml of dichloromethane and added dropwise to a solution of 0.195 g (3.41 mmol) of cyclopropylamine in 2 ml of dichloromethane at room temperature. The mixture was stirred at room temperature for a further 2 hours, then poured onto 20 ml of 5% aqueous sodium dihydrogenphosphate solution. The organic phase was removed and washed with saturated sodium chloride solution, dried with sodium sulphate and concentrated on a rotary evaporator under reduced pressure. The residue was purified by two chromatography runs using a cartridge containing 15 g of silica gel with a gradient of cyclohexane/ethyl acetate of 90:10 to 50:50 (v/v). 91 mg (1.36 mmol) of N-cyclopropyl-2-chloro-5-[4-[2,6-dimethyl-4-[1,2,2,2-tetrafluoro-1-(trifluoromethyl)ethyl]phenyl]pyrazol-1-yl]benzamide (compound I-T4-1) were obtained.

HPLC-MS$_{a)}$: log P=4.74, mass (m/z)=534 [M+H]+.

$^1$H NMR (400 MHz, d3-acetonitrile): δ=(ppm) 8.17 (s, 1H), 7.86 (s, 1H), 7.84 (d, J1=2.7 Hz, 1H), 7.69 (s, 1H), 7.54 (d, J1=8.8 Hz, 1H), 7.44 (s, 2H), 6.97 (s (broad), 1H (N—H)), 2.83-2.87 (m, 1H), 2.25 (s, 6H), 0.76-0.8 (m, 2H), 0.58-0.62 (m, 2H).

Example I-T4-3

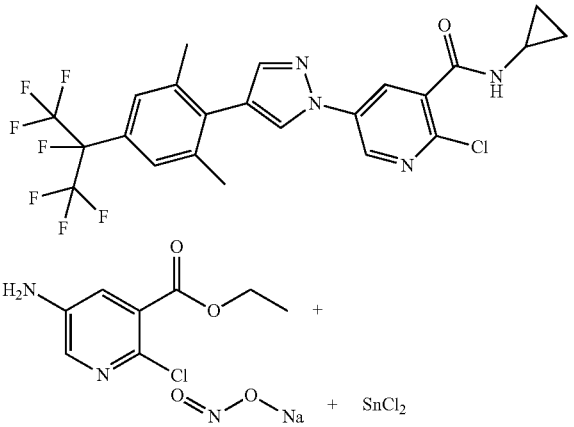

-continued

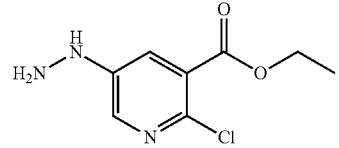

2 g (9.96 mmol) of ethyl 5-amino-2-chloronicotinate (commercially available) were initially charged in 8.6 ml of 33% aqueous hydrochloric acid, and the mixture was stirred at room temperature for 30 minutes. Thereafter, 7 ml of water were added and the mixture was cooled to 0° C. with an ice bath. To this mixture was added dropwise a solution of 750 mg (10.8 mmol) of sodium nitrite in 6.92 ml of water within 30 minutes. The temperature was kept below +5° C. with an ice bath. Stirring was continued at 0° C. for 15 minutes.

A second flask was initially charged with 5.77 g (25.5 mmol) of tin(II) chloride dihydrate in 24 ml of 16% aqueous hydrochloric acid, and the diazonium salt suspension prepared above was slowly added dropwise at 0° C. Stirring was continued at 0° C. for 1 hour. Thereafter, 50 ml of acetonitrile and 40 ml of saturated aqueous sodium chloride solution were added. The phases formed were separated. The aqueous phase was extracted twice with 50 ml each time of acetonitrile. The combined organic phases were dried with sodium sulphate and concentrated on a rotary evaporator under reduced pressure. The residue obtained was 10.7 g of crude ethyl 2-chloro-5-hydrazinonicotinate.

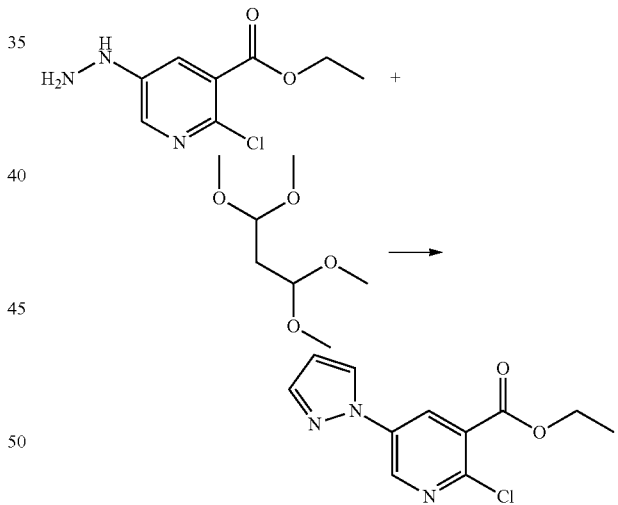

10.7 g of crude ethyl 2-chloro-5-hydrazinonicotinate were initially charged in 50 ml of ethanol, then 1.63 g (9.92 mmol) of 1,1,3,3-tetramethoxypropane and 487 mg of 96% sulphuric acid were added. The mixture was subsequently heated to reflux for 2 hours. The majority of the ethanol was removed on a rotary evaporator under reduced pressure, and the residue was partitioned between saturated aqueous sodium hydrogencarbonate solution and ethyl acetate. The organic phase was removed, washed with saturated aqueous sodium chloride solution, dried over sodium sulphate and concentrated on a rotary evaporator under reduced pressure. The residue was chromatographed using a cartridge containing 15 g of silica gel and a gradient proceeding from pure cyclohexane to 50:50 (v/v) cyclohexane/ethyl acetate. 396 mg of ethyl 2-chloro-5-(pyrazol-1-yl)nicotinate were obtained.

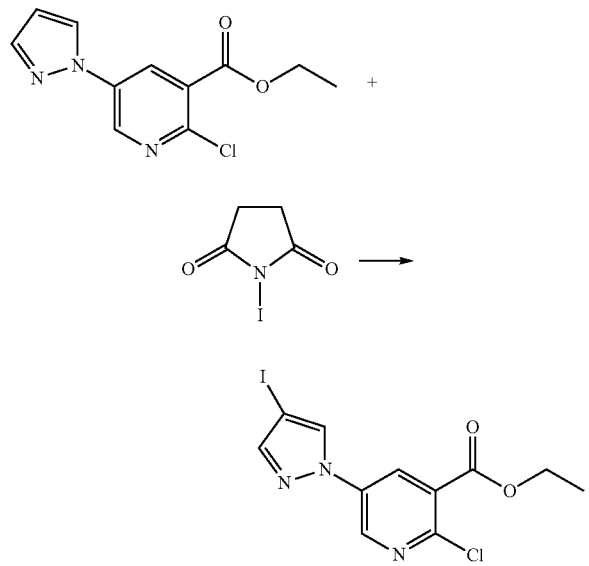

396 mg (1.57 mmol) of ethyl 2-chloro-5-(pyrazol-1-yl)-nicotinate were initially charged in 10 ml of acetonitrile, and 1.062 g (4.72 mmol) of N-iodosuccinimide were added. Subsequently, the mixture was heated under reflux under argon for 3 hours. The mixture was cooled a little and the solvent was removed on a rotary evaporator under reduced pressure. The residue was partitioned between water and ethyl acetate. The organic phase was removed, washed first with saturated aqueous sodium hydrogensulphite solution then with saturated aqueous sodium hydrogencarbonate solution and lastly with saturated aqueous sodium chloride solution, dried with sodium sulphate and concentrated on a rotary evaporator under reduced pressure. The residue was chromatographed using a cartridge containing 15 g of silica gel and a gradient proceeding from pure cyclohexane to 50:50 (v/v) cyclohexane/ethyl acetate.

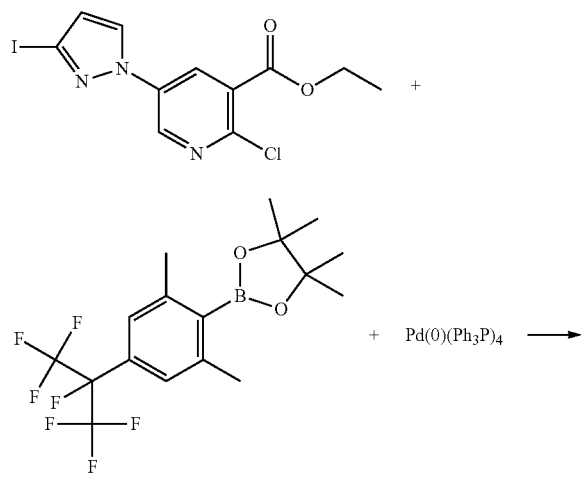

-continued

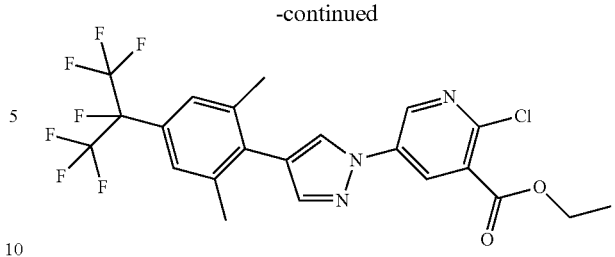

401 mg (1.06 mmol) of ethyl 2-chloro-5-(4-iodopyrazol-1-yl)pyridin-3-carboxylate and 425 mg (1.06 mmol) of 2-[2,6-dimethyl-4-[1,2,2,2-tetrafluoro-1-(trifluoromethyl) ethyl]phenyl]-4,4,5,5-tetramethyl-1,3,2-dioxaborolane were initially charged in 23 ml of isopropanol, and 3.24 ml (3.24 mmol) of degassed 1 molar aqueous sodium hydrogencarbonate solution and 61 mg (0.05 mmol) of tetrakis(triphenylphosphine)palladium(0) were added. The mixture was degassed once again with argon and heated to reflux overnight. Thereafter, the mixture was cooled and the volatile constituents were drawn off on a rotary evaporator under reduced pressure. The residue was partitioned between water and ethyl acetate. The organic phase was removed, washed once with saturated aqueous sodium chloride solution and concentrated on a rotary evaporator under reduced pressure. 415 mg of crude ethyl 2-chloro-5-[4-[2,6-dimethyl-4-[1,2,2,2-tetrafluoro-1-(trifluoromethyl)ethyl]phenyl]pyrazol-1-yl]pyridine-3-carboxylate were obtained.

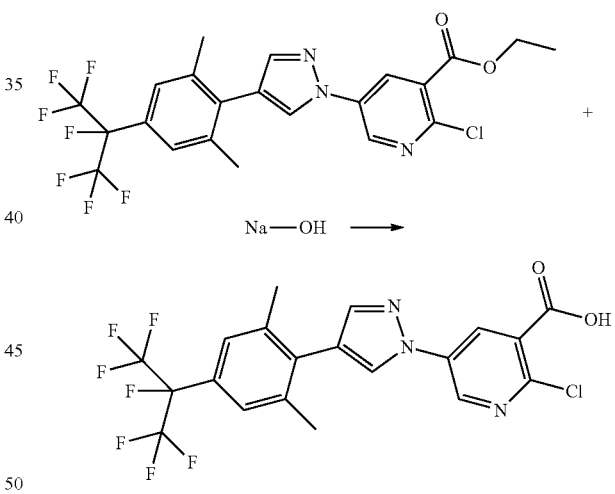

416 mg (0.79 mmol) of crude ethyl 2-chloro-5-[4-[2,6-dimethyl-4-[1,2,2,2-tetrafluoro-1-(trifluoromethyl)ethyl] phenyl]pyrazol-1-yl]pyridine-3-carboxylate were dissolved in 16.9 ml of methanol, and 0.952 ml (0.95 mmol) of 1 M sodium hydroxide solution was added. The mixture was heated under reflux for 6 hours, then cooled and concentrated on a rotary evaporator under reduced pressure. The residue was partitioned between ethyl acetate and dilute hydrochloric acid. The aqueous phase was re-extracted twice with ethyl acetate. The combined organic phases were washed with saturated aqueous sodium chloride solution, dried with sodium sulphate and concentrated on a rotary evaporator under reduced pressure. 380 mg of crude 2-chloro-5-[4-[2,6-dimethyl-4-[1,2,2,2-tetrafluoro-1-(trifluoromethyl)ethyl]phenyl]pyrazol-1-yl]pyridine-3-carboxylic acid were obtained.

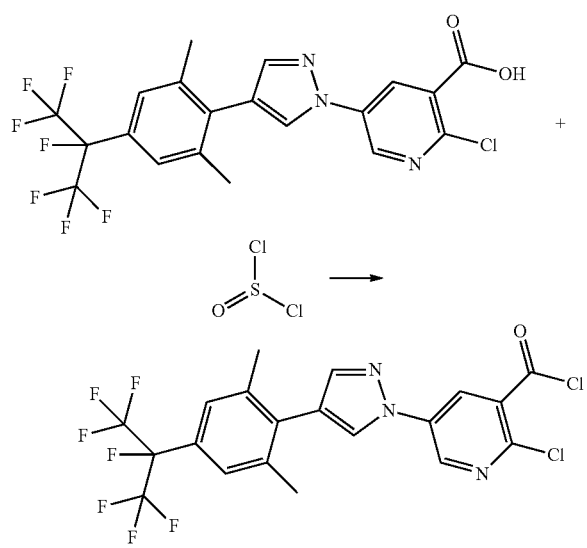

380 mg (0.76 mmol) of crude 2-chloro-5-[4-[2,6-dimethyl-4-[1,2,2,2-tetrafluoro-1-(trifluoromethyl)ethyl]phenyl]pyrazol-1-yl]pyridine-3-carboxylic acid were dissolved in toluene, and 456 mg (3.83 mmol) of thionyl chloride were added. The mixture was heated to 80° C. for 2 hours and then concentrated on a rotary evaporator under reduced pressure. 400 mg of crude 2-chloro-5-[4-[2,6-dimethyl-4-[1,2,2,2-tetrafluoro-1-(trifluoromethyl)ethyl]phenyl]pyrazol-1-yl]pyridine-3-carbonyl chloride were obtained.

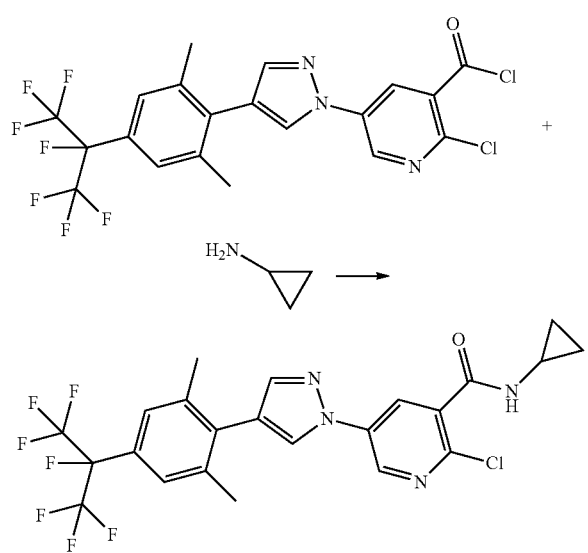

138 mg (0.26 mmol) of 2-chloro-5-[4-[2,6-dimethyl-4-[1,2,2,2-tetrafluoro-1-(trifluoromethyl)ethyl]phenyl]pyrazol-1-yl]pyridine-3-carbonyl chloride were dissolved in 1 ml of dichloromethane and added dropwise to a solution of 38 mg of cyclopropylamine in 1 ml of dichloromethane at room temperature. The mixture was stirred at room temperature for a further 2 hours. Then the mixture was washed with 5% sodium dihydrogenphosphate solution and then with saturated aqueous sodium chloride solution, dried with sodium sulphate and concentrated on a rotary evaporator under reduced pressure. For purification, chromatography was effected using a cartridge containing 15 g of silica gel with a gradient in cyclohexane/ethyl acetate of 90:10 to 50:50 (v/v). 30 mg of 2-chloro-N-cyclopropyl-5-[4-[2,6-dimethyl-4-[1,2,2,2-tetrafluoro-1-(trifluoromethyl)ethyl]phenyl]pyrazol-1-yl]pyridine-3-carboxamide were obtained.

HPLC-MS$_{a)}$: log P=4.42, mass (m/z)=534 [M+H]+.

$^1$H NMR (400 MHz, d3-acetonitrile): δ (ppm)=8.92 (d, J=2.8 Hz, 1H), 8.22 (d, J1=2.8 Hz, 1H), 8.20 (s, 1H), 7.75 (s, 1H), 7.44 (s, 2H), 5.1 (s (broad), 1H (N—H)), 2.84-2.88 (m, 1H), 2.25 (s, 6H), 0.78-0.81 (m, 2H), 0.59-0.63 (m, 2H).

Preparation Process I-T22

Example I-T22-1

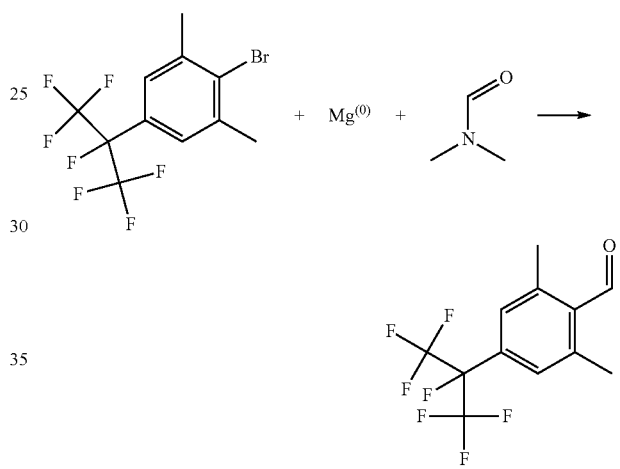

The preparation of 2,6-dimethyl-4-heptafluoroisopropylbromobenzene is described in US2003/187233, p. 6 [0080].

In a 25 ml three-neck flask, 158 mg (6.5 mg atom) of magnesium turnings were covered with dry tetrahydrofuran (THF). Then a few drops of a solution of 1.75 g (4.95 mmol) of 2,6-dimethyl-4-heptafluoroisopropylbromobenzene in 2.5 ml of dry THF were added. To start the reaction, a crumb of iodine was added and the mixture was heated to about 60° C. After the reaction had started, the rest of the solution of the 2,6-dimethyl-4-heptafluoroisopropylbromobenzene was added dropwise at about 60° C. After the addition had ended, stirring was continued at 60° C. for another hour, then the mixture was cooled to 0° C. and a solution of 1.09 g (14.8 mmol) of dimethylformamide in 2.5 ml of dry THF was added dropwise. Then the mixture was allowed to come to room temperature. For workup, excess saturated aqueous ammonium chloride solution was added, the phases were separated, and the aqueous phase was re-extracted with ethyl acetate. The combined organic phases were washed with saturated sodium chloride solution, dried with sodium sulphate and concentrated on a rotary evaporator under reduced pressure. As residue, 1.3 g of crude 2,6-dimethyl-4-heptafluoroisopropylbenzaldehyde (purity about 80%) remained, which were used further without purification.

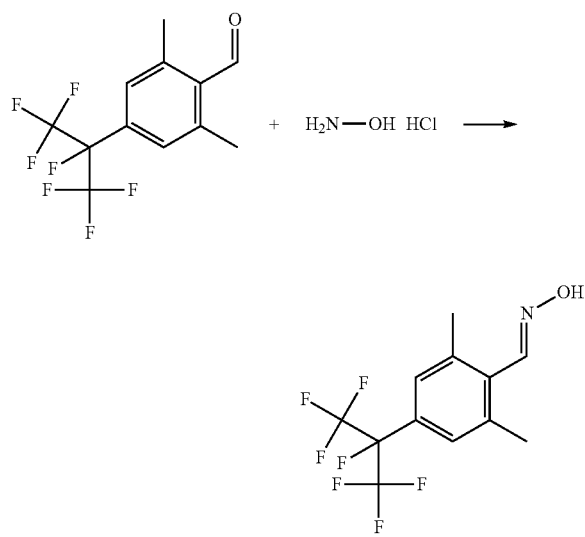

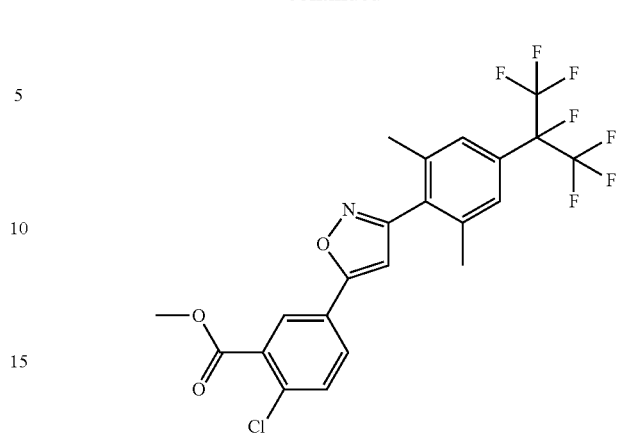

1.3 g (about 3.44 mmol) of crude 2,6-dimethyl-4-heptafluoroisopropylbenzaldehyde were dissolved in 26 ml of methanol, 361 mg (4.3 mmol) of sodium hydrogencarbonate were added and the mixture was cooled to 0° C. Thereafter, 1.2 g (17.2 mmol) of hydroxylammonium chloride were added and the mixture was stirred at room temperature overnight. For workup, the mixture was concentrated on a rotary evaporator under reduced pressure, and the residue was taken up in 100 ml of ethyl acetate. Undissolved constituents were filtered off and the filtrate was concentrated on a rotary evaporator under reduced pressure. The residue was then purified by chromatography using a 40 g cartridge containing silica and a gradient proceeding from pure cyclohexane to 70:30 (v/v) cyclohexane/ethyl acetate. 0.5 g of 2,6-dimethyl-4-heptafluoroisopropylbenzaldehyde oxime was obtained.

505 mg (1.59 mmol) of 2,6-dimethyl-4-heptafluoroisopropylbenzaldehyde oxime were initially charged in 3.5 ml of dimethylformamide (DMF), and 234 mg (1.75 mmol) of N-chlorosuccinimide were added. The mixture was stirred at room temperature for 3.5 hours. Then the mixture was cooled to 0° C. and a solution of 310 mg (1.59 mmol) of methyl 2-chloro-5-ethynylbenzoate (prepared according to WO2012/107434, p. 103) in 1.5 ml of DMF was added dropwise, followed by 355 mg (3.5 mmol) of triethylamine. The reaction mixture was then stirred at room temperature overnight. For workup, the mixture was poured onto water and extracted twice with dichloromethane, and the combined extracts were washed with water, dried with sodium sulphate and concentrated on a rotary evaporator under reduced pressure. For purification, purification was effected using a 40 g cartridge containing silica gel and a gradient proceeding from pure cyclohexane to 80:20 (v/v) cyclohexane/ethyl acetate. 488 mg of methyl 2-chloro-5-[3-[2,6-dimethyl-4-[1,2,2,2-tetrafluoro-1-(trifluoromethyl)ethyl]phenyl]isoxazol-5-yl]benzoate were obtained.

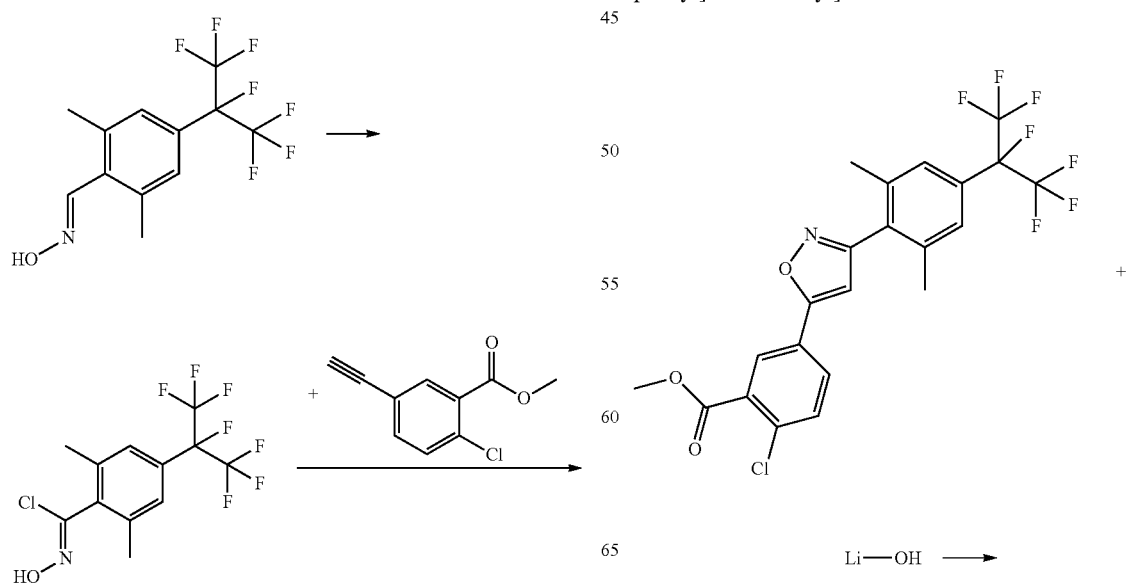

Li—OH ⟶

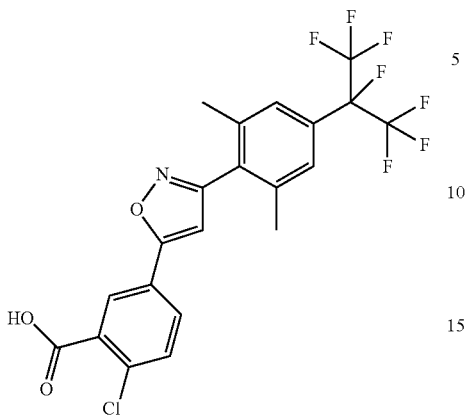

0.8 g (1.56 mmol) of methyl 2-chloro-5-[3-[2,6-dimethyl-4-[1,2,2,2-tetrafluoro-1-(trifluoromethyl)ethyl]phenyl]isoxazol-5-yl]benzoate were initially charged in a mixture of 18 ml of dioxane and 6.5 ml of water, 86 mg (2.04 mmol) of lithium hydroxide monohydrate were added and the mixture was stirred at room temperature overnight. For workup, the mixture was concentrated under reduced pressure and the residue was partitioned between a mixture of dilute hydrochloric acid and dichloromethane. The organic phase was removed; the aqueous phase was extracted first with dichloromethane, then with ethyl acetate. The combined organic phases were washed with saturated aqueous sodium chloride solution, dried with sodium sulphate and concentrated on a rotary evaporator under reduced pressure. 680 mg of 2-chloro-5-[3-[2,6-dimethyl-4-[1,2,2,2-tetrafluoro-1-(trifluoromethyl)ethyl]phenyl]isoxazol-5-yl]benzoic acid were obtained.

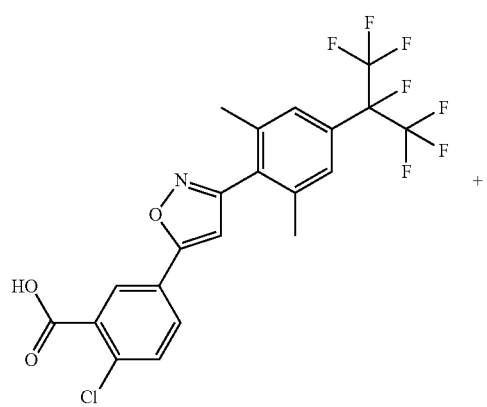

+

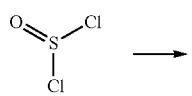

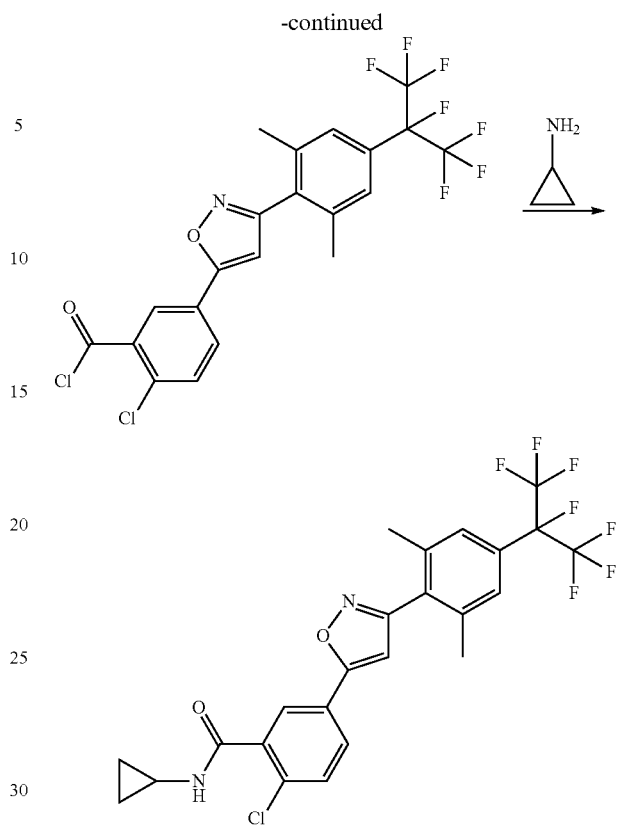

680 mg (1.37 mmol) of 2-chloro-5-[3-[2,6-dimethyl-4-[1,2,2,2-tetrafluoro-1-(trifluoromethyl)ethyl]phenyl]isoxazol-5-yl]benzoic acid were dissolved in 7 ml of toluene, and 0.5 ml (6.89 mmol) of thionyl chloride were added. The mixture was heated to 80° C. for two hours and then concentrated on a rotary evaporator under reduced pressure. 200 mg (0.38 mmol) of the crude acid chloride thus obtained were dissolved in 1 ml of dichloromethane and added dropwise to a solution of 56 mg (0.97 mmol) of cyclopropylamine in 0.95 ml of dichloromethane at room temperature. The mixture was then stirred at room temperature overnight. For workup, the mixture was poured onto 5% aqueous sodium dihydrogenphosphate solution, and the organic phase was removed, dried with sodium sulphate and concentrated on a rotary evaporator under reduced pressure. For purification, the residue was chromatographed using a cartridge containing 15 g of silica gel and a gradient from pure cyclohexane to 80:20 (v/v) cyclohexane/ethyl acetate. 165 mg of 2-chloro-N-cyclopropyl-5-[3-[2,6-dimethyl-4-[1,2,2,2-tetrafluoro-1-(trifluoromethyl)ethyl]phenyl]isoxazol-5-yl]benzamide (compound I-T22-1) were obtained.

HPLC-MS[a)]: log P=4.75, mass (m/z)=535 [M+H]+.

$^1$H NMR (400 MHz, d$_3$-acetonitrile): δ (ppm)=7.93 (d, J=2.2 Hz, 1H), 7.89 (dd, J1=8.4 Hz, J2=2.2 Hz, 1H), 7.6 (d, J=8.4 Hz, 1H), 7.49 (s, 2H), 7.03 (s, broad), 1H (N—H)), 6.86 (s, 1H), 2.83-2.88 (m, 1H), 0.75-0.79 (m, 2H), 0.59-0.62 (m, 2H).

Preparation Process I-T23

Example I-T23-1

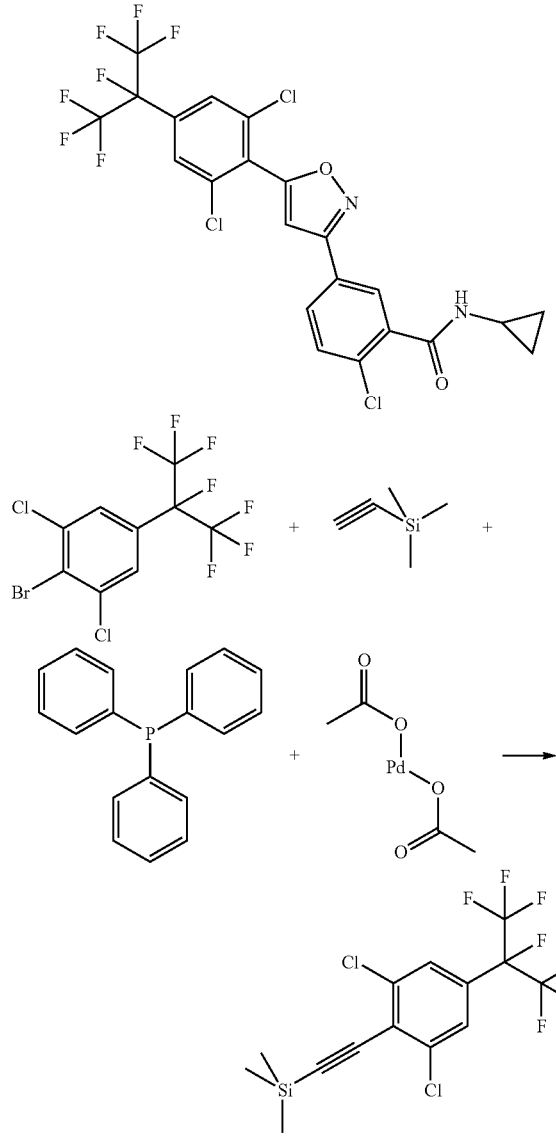

3 g (7.61 mmol) of 2-bromo-1,3-dichloro-5-[1,2,2,2-tetrafluoro-1-(trifluoromethyl)ethyl]benzene (for preparation see EP 1 253 128, page 10), 1.21 g (12.3 mmol) of ethynyltrimethylsilane, 86 mg (0.38 mmol) of palladium(II) acetate and 260 mg (1.0 mmol) of triphenylphosphine were initially charged in 20 ml of dry triethylamine and heated to reflux. After concentrating the volume on a rotary evaporator at 30° C., the residue was admixed with 20 ml of saturated sodium hydrogencarbonate solution and extracted three times with dichloromethane. The combined extracts were washed with 5% aqueous NaH$_2$PO4 solution and then with saturated sodium chloride solution. After drying the solution with sodium sulphate and concentrating the volume on a rotary evaporator at 30° C., purification was effected by means of chromatography on silica gel with cyclohexane as eluent. Yield: 1.4 g of 2-[2,6-dichloro-4-[1,2,2,2-tetrafluoro-1-(trifluoromethyl)ethyl]phenyl]ethynyltrimethylsilane in a purity of about 50% (LC-MS area).

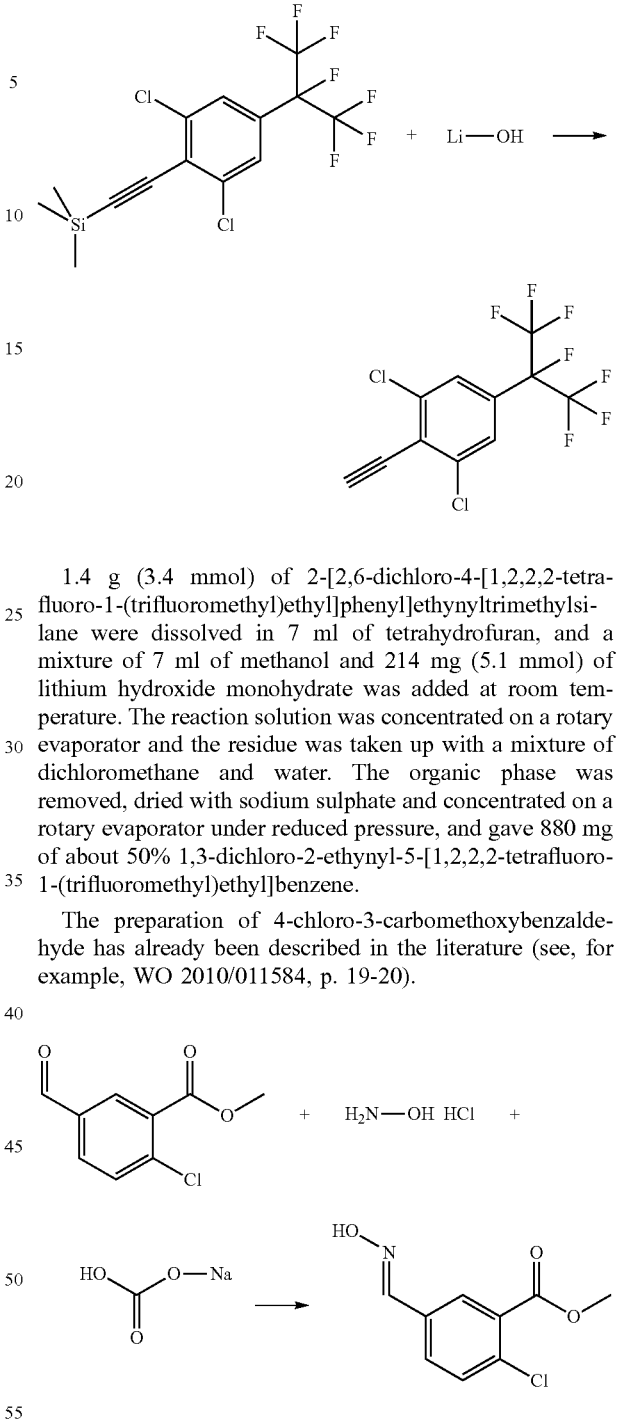

1.4 g (3.4 mmol) of 2-[2,6-dichloro-4-[1,2,2,2-tetrafluoro-1-(trifluoromethyl)ethyl]phenyl]ethynyltrimethylsilane were dissolved in 7 ml of tetrahydrofuran, and a mixture of 7 ml of methanol and 214 mg (5.1 mmol) of lithium hydroxide monohydrate was added at room temperature. The reaction solution was concentrated on a rotary evaporator and the residue was taken up with a mixture of dichloromethane and water. The organic phase was removed, dried with sodium sulphate and concentrated on a rotary evaporator under reduced pressure, and gave 880 mg of about 50% 1,3-dichloro-2-ethynyl-5-[1,2,2,2-tetrafluoro-1-(trifluoromethyl)ethyl]benzene.

The preparation of 4-chloro-3-carbomethoxybenzaldehyde has already been described in the literature (see, for example, WO 2010/011584, p. 19-20).

4.1 g (20.6 mmol) of 4-chloro-3-carbomethoxybenzaldehyde were dissolved in 82 ml of methanol, 1.734 mg (20.6 mmol) of sodium hydrogencarbonate were added and the mixture was cooled to 0° C. Then 5.738 g (82.5 mmol) of hydroxylamine hydrochloride were added and the mixture was stirred. For workup, the mixture was concentrated on a rotary evaporator, and the residue was taken up in 100 ml of ethyl acetate. The solids were filtered off and the filtrate was concentrated on a rotary evaporator under reduced pressure. For purification, the residue was chromatographed with silica gel by means of a gradient in 9:1 to 7:3 (v/v)

cyclohexane/ethyl acetate, and gave 2.68 g of ethyl 2-chloro-5-[(E)-hydroxyiminomethyl]benzoate.

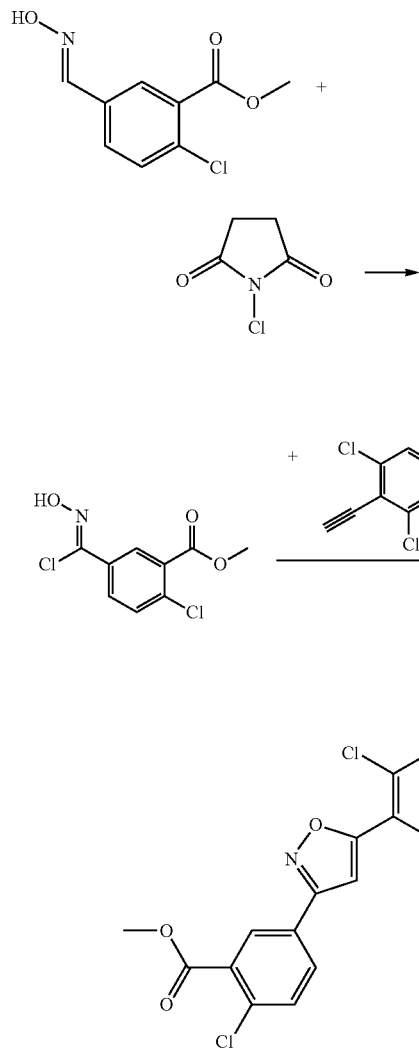

277 mg (1.29 mmol) of ethyl 2-chloro-5-[(E)-hydroxyiminomethyl]benzoate were initially charged in 4.6 ml of dimethylformamide, 381 mg (2.84 mmol) of N-chlorosuccinimide were added, and the mixture was stirred at room temperature. The mixture was then cooled to 0° C. with an ice bath, and a solution of 880 mg (about 50% strength, 1.29 mmol) of 1,3-dichloro-2-ethynyl-5-[1,2,2,2-tetrafluoro-1-(trifluoromethyl)ethyl]benzene in 1.5 ml of dimethylformamide was added dropwise, followed by 289 mg (2.85 mmol) of triethylamine. The mixture was stirred at room temperature. For workup, the reaction was diluted with water and extracted twice with dichloromethane. The combined extracts were washed with water, dried with sodium sulphate and concentrated on a rotary evaporator. The residue was purified by two chromatography runs on silica with a gradient proceeding from pure cyclohexane to 80:20 (v/v) cyclohexane/ethyl acetate as eluent, and gave 410 mg of methyl 2-chloro-5-[5-[2,6-dichloro-4-[1,2,2,2-tetrafluoro-1-(trifluoromethyl)ethyl]phenyl]isoxazol-3-yl]benzoate.

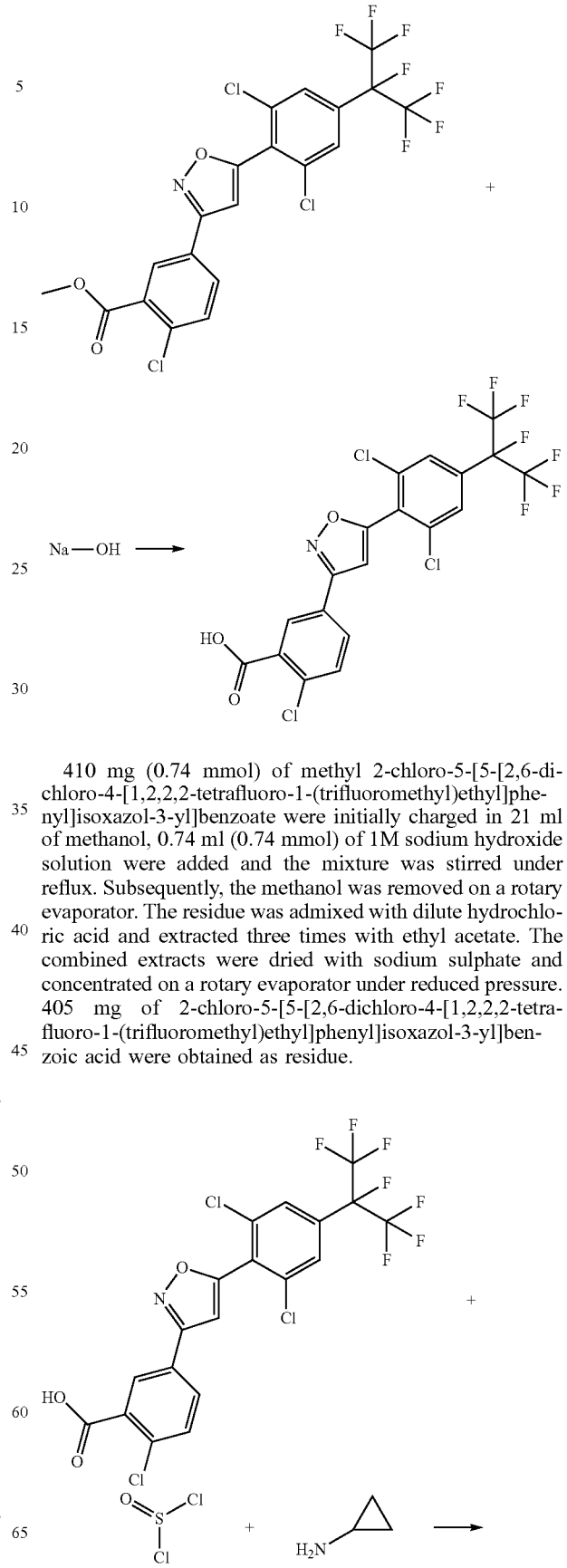

410 mg (0.74 mmol) of methyl 2-chloro-5-[5-[2,6-dichloro-4-[1,2,2,2-tetrafluoro-1-(trifluoromethyl)ethyl]phenyl]isoxazol-3-yl]benzoate were initially charged in 21 ml of methanol, 0.74 ml (0.74 mmol) of 1M sodium hydroxide solution were added and the mixture was stirred under reflux. Subsequently, the methanol was removed on a rotary evaporator. The residue was admixed with dilute hydrochloric acid and extracted three times with ethyl acetate. The combined extracts were dried with sodium sulphate and concentrated on a rotary evaporator under reduced pressure. 405 mg of 2-chloro-5-[5-[2,6-dichloro-4-[1,2,2,2-tetrafluoro-1-(trifluoromethyl)ethyl]phenyl]isoxazol-3-yl]benzoic acid were obtained as residue.

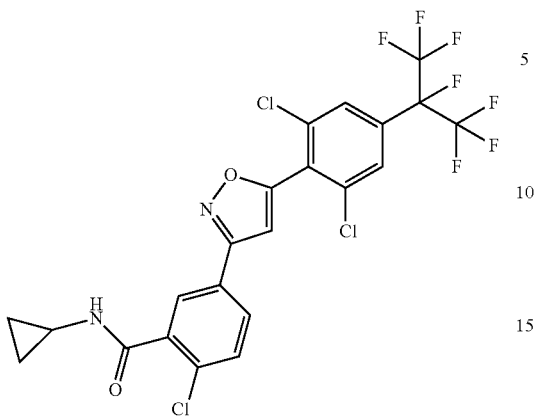

125 mg (0.23 mmol) of 2-chloro-5-[5-[2,6-dichloro-4-[1,2,2,2-tetrafluoro-1-(trifluoromethyl)ethyl]phenyl]isoxazol-3-yl]benzoic acid were dissolved in 1.1 ml of dry toluene, and 0.14 g (1.16 mmol) of thionyl chloride was added. The mixture was heated to 80° C. and then concentrated on a rotary evaporator. The residue was dissolved in 0.25 ml of dichloromethane and added dropwise to a solution of 33 mg (0.58 mmol) of cyclopropylamine in 0.75 ml of dichloromethane at 0° C., and the mixture was stirred at room temperature for 2 hours. For workup, 5% aqueous sodium dihydrogenphosphate solution was added and then the organic phase was removed. The organic phase was dried with sodium sulphate and concentrated on a rotary evaporator. The residue was purified by chromatography with silica gel and 70:30 (v/v) cyclohexane/ethyl acetate as eluent. 49 mg of 2-chloro-N-cyclopropyl-5-[5-[2,6-dichloro-4-[1,2,2,2-tetrafluoro-1-(trifluoromethyl)ethyl]phenyl]isoxazol-3-yl]benzamide (compound I-T23-1) were obtained.

HPLC-MS[a)]: log P=4.96, mass (m/z)=575 [M+H]+.

$^1$H NMR (400 MHz, d$_3$-acetonitrile): δ=7.96 (s, 1H), 7.94-7.96 (dd, J1=8.4 Hz, J2=2.2 Hz, 1H), 7.86 (s, 2H), 7.6 (d, J1=7.6 Hz, J2=1.2, 1H), 7.15 (s, 1H), 6.9 (s (broad), 1H (N—H)), 3.97 (s, 3H), 2.83-2.88 (m, 1H), 0.75-0.79 (m, 2H), 0.58-0.62 (m, 2H).

Process 1 Example 4-heptafluoroisopropyl-2-methyl-6-trifluoromethylaniline

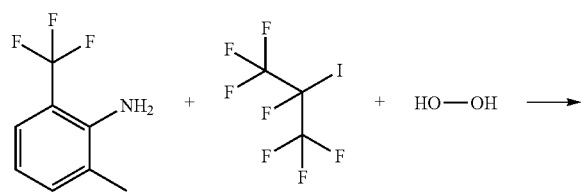

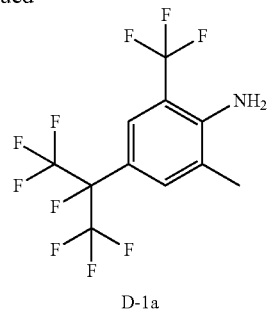

D-1a

A three-neck flask was initially charged with 17.48 g (100 mmol) of 2-methyl-6-trifluoromethylaniline in 498 ml of dimethyl sulphoxide, and then 44.3 g (21.095 ml, 150 mmol) of 2-iodoheptafluoropropane, 29.9 ml (29.9 mmol) of 1 molar iron(II) sulphate solution in water and 5.43 ml (104 mmol) of 96% sulphuric acid were added. The mixture was then degassed with argon and then a syringe pump was used to add 20.4 ml of 30% aqueous hydrogen peroxide solution dropwise within 15 minutes. The temperature rose to 54° C. Towards the end of the dropwise addition, the mixture was heated briefly to 60° C. The mixture was stirred for a further 20 minutes without heating, in the course of which the temperature fell to 36° C. For workup, the mixture was poured onto saturated aqueous sodium hydrogencarbonate solution and the product was extracted with ethyl acetate. The combined extracts were washed first with water and then with saturated aqueous sodium chloride solution, dried with sodium sulphate and concentrated on a rotary evaporator under reduced pressure. For purification, chromatography was effected in two portions through a column containing 120 g of silica gel and a gradient from pure cyclohexane to 95:5 cyclohexane/ethyl acetate (v/v). 18.9 g of 4-heptafluoroisopropyl-2-methyl-6-trifluoromethylaniline were obtained.

Analogously, 2-chloro-4-heptafluoroisopropyl-6-trifluoromethylaniline was also obtained proceeding from 2-chloro-6-trifluoromethylaniline and 2-iodoheptafluoropropane:

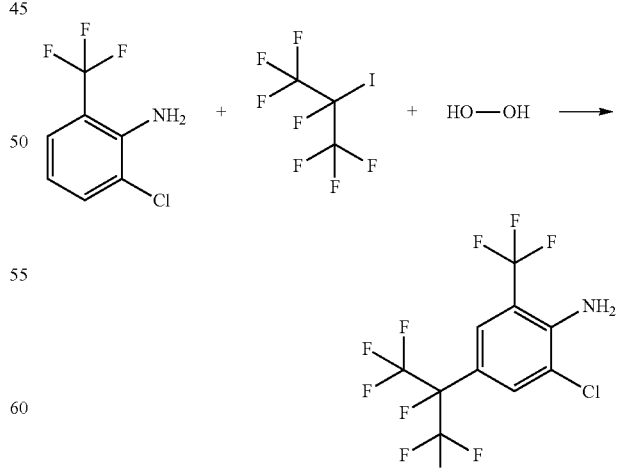

A three-neck flask was initially charged with 30 g (0.153 mol) of 2-chloro-6-trifluoromethylaniline (commercially available) in 765 ml of dimethyl sulphoxide (DMSO), and then 68.1 g (0.23 mol) of 2-iodoheptafluoropropane, 46 ml of a 1 molar aqueous iron(II) sulphate solution and 15.4 g of 98% sulphuric acid were added. The mixture was degassed with argon and then a syringe pump was used to add 34.8 g of 30% aqueous hydrogen peroxide solution dropwise within 30 minutes. In the course of this, the temperature rose to 70° C. The mixture was stirred for a further 20 minutes, in the course of which the temperature fell to 30° C. The reaction mixture was then poured onto saturated aqueous sodium hydrogencarbonate solution and extracted with ethyl acetate. The combined extracts were washed first with water, then with saturated aqueous bisulphite solution and saturated aqueous sodium chloride solution, dried with sodium sulphate and concentrated on a rotary evaporator under reduced pressure. For purification, chromatography was effected using a cartridge containing 330 g of silica gel and a gradient proceeding from pure cyclohexane to 90:10 (v/v) cyclohexane/ethyl acetate. 46.1 g of 2-chloro-4-heptafluoroisopropyl-6-trifluoromethylaniline were obtained.

Process 2 Example 4-heptafluoroisopropyl-2-methyl-6-trifluoromethylaniline

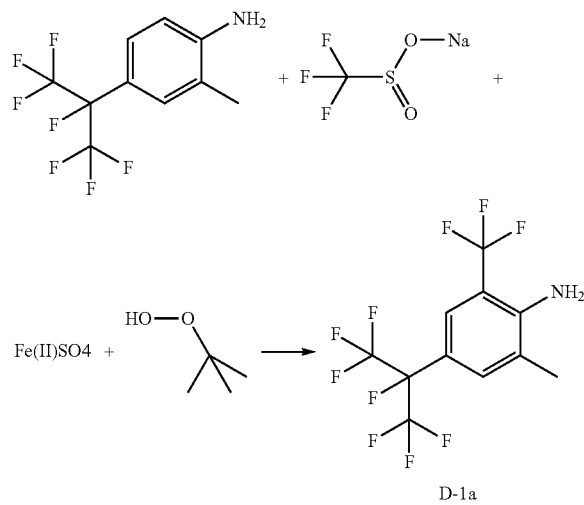

D-1a

In a 1000 ml three-neck flask, 25 g (91 mmol) of 4-heptafluoroisopropyl-2-methylaniline were added to a mixture of 363.4 ml of water and 181.7 ml of acetonitrile. Then 27.3 ml (27.3 mmol) of aqueous 1 molar iron(II) sulphate solution and 31.19 g (200 mmol) of sodium trifluoromethylsulphinate were added. The mixture was blanketed with argon and then 35.1 g (273 mmol) of a 70% aqueous tert-butyl hydroperoxide solution were metered in with a syringe pump within 4.5 hours without cooling. The temperature rose to 34° C. After the addition had ended, stirring was continued for another 1 hour. For workup, the mixture was poured onto 425 ml of saturated aqueous sodium hydrogensulphite solution and stirred for 15 minutes. Then 425 ml of saturated sodium hydrogen carbonate solution were added and the mixture was extracted three times with ethyl acetate. The combined organic phases were washed first with water and then with saturated aqueous sodium chloride solution, dried with sodium sulphate and concentrated on a rotary evaporator under reduced pressure. The crude product was chromatographed in two portions using a cartridge containing 120 g of silica gel and a cyclohexane/ethyl acetate gradient of 95:5 to 85:15 (v/v). 19.5 g of 4-heptafluoroisopropyl-2-methyl-6-trifluoromethylaniline were obtained.

HPLC-MS$^{a)}$: log P=4.67

GC/MS: mass (m/z)=343, retention time: 2.98 min, Kovats index: 1089

(Agilent 6890 GC, HP5979 MSD, 10 m DB-1, iD=0.18 mm, FILM=0.4 μm, Inj.:250° C., const. flow: 1.6 mm/min He, Det.:MSD:280° C., FID: 320° C., Oven:50° C. (1 min)-40° C./min-320° C. (3.25 min))

$^1$H NMR (AV400, 400 MHz, d$_3$-acetonitrile): δ (ppm)=7.50 (s, 1H), 7.48 (s, 1H), 5.03 (s, 2H, broad), 2.23 (s, 3H).

Preparation of the 2-chloro-6-ethyl-4-heptafluoroisopropylaniline Starting Material The 2-chloro-6-ethyl-4-heptafluoroisopropylaniline starting material of the structure (D-1b) has not yet been described in the literature. It can be prepared by means of known chlorinating methods from 2-ethyl-4-heptafluoroisopropylaniline, which is known from literature (e.g. US2002/198399).

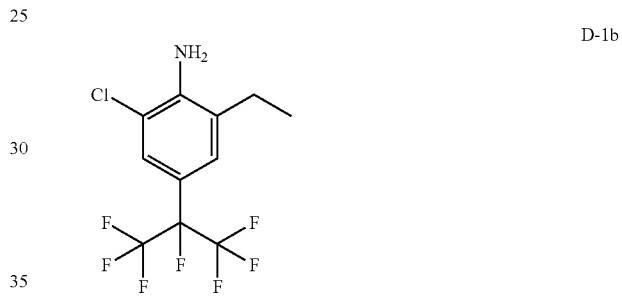

D-1b 4.9 g (16.9 mmol) of 2-ethyl-4-heptafluoroisopropylaniline (prepared according to US2002/198399) were initially charged in 100 ml of chloroform, the mixture was heated to 45-50° C., and then 2.18 ml (26.7 mmol) of sulphuryl chloride, dissolved in 400 ml of chloroform, were slowly added dropwise. The mixture was stirred at 50° C. overnight, then a further 0.34 ml (4.2 mmol) of sulphuryl chloride dissolved in 2 ml of chloroform was added dropwise and the mixture was stirred at 50° C. for a further 3 hours. Thereafter, the mixture was cooled and the solvent was drawn off on a rotary evaporator under reduced pressure. The residue was taken up in dichloromethane, washed first with sodium hydrogensulphite and then with dilute sodium hydroxide solution, and dried with sodium sulphate, and the solvent was distilled off on a rotary evaporator under reduced pressure. For purification, chromatography was effected using a cartridge containing 120 g of silica gel with a gradient proceeding from pure cyclohexane to 90:10 cyclohexane/ethyl acetate (v/v). 4.25 g of 2-chloro-6-ethyl-4-heptafluoroisopropylaniline were obtained.

HPLC-MS$^{a)}$: log P=4.67, mass (m/z)=324 [M+H]+.

$^1$H NMR (AV400, 400 MHz, d$_3$-acetonitrile): δ (ppm)=7.84 (s, 1H), 7.82 (s, 1H), 7.53-7.56 (s, 2H, broad), 2.37 (q, J=7.6 Hz, 2H), 1.06 (t, J=7.6 Hz, 3H).

Preparation of the 2-bromo-6-methyl-4-heptafluoroisopropylaniline Starting Material The 2-bromo-6-methyl-4-heptafluoroisopropylaniline starting material of the structure (D-1c) has not yet been described in literature. It can be prepared by means of known brominating methods (e.g. EP2319830, p. 327) from 2-methyl-4-heptafluoroisopropylaniline, which is known from literature (e.g. US2004/92762).

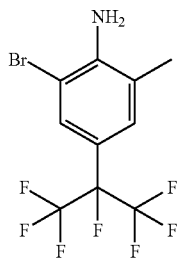
D-1c 3.4 g (12.356 mmol) of 2-methyl-4-heptafluoroisopropylaniline were dissolved in 27 ml of dimethylformamide, then 2.44 g (13.6 mmol) of N-bromosuccinimide were added and the mixture was stirred at 60° C. for 1 hour. The mixture was cooled, admixed with water and extracted three times with 15 ml each time of n-hexane. The combined organic phases were washed with water, dried with sodium sulphate and concentrated on a rotary evaporator under reduced pressure. Chromatography using a 120 g cartridge containing silica gel with a gradient beginning with pure cyclohexane to 90:10 cyclohexane/ethyl acetate (v/v) gave 2.44 g of 2-bromo-6-ethyl-4-heptafluoroisopropylaniline.

HPLC-MS[a]: log P=4.38, mass (m/z)=354 [M+H]+.

$^1$H NMR (AV400, 400 MHz, $d_3$-acetonitrile): δ (ppm)=7.51 (s, 1H), 7.23 (s, 1H), 4.86 (s, 2H, broad), 2.23 (s, 3H).

Preparation of the starting compound 2-(3,5-dichloro-4-hydrazinophenyl)-1,1,1,3,3,3-hexafluoropropan-2-ol

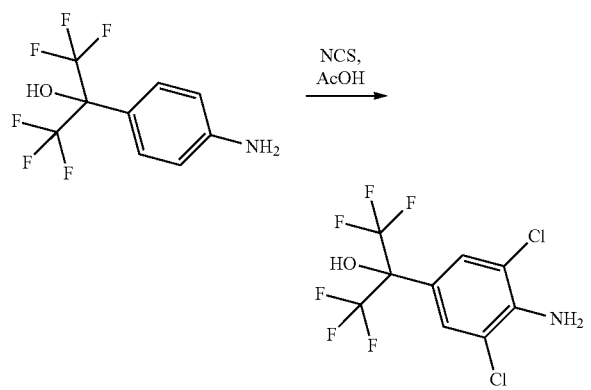

To a solution of 2-(4-aminophenyl)-1,1,1,3,3,3-hexafluoropropan-2-ol (2.50 g, 9.64 mmol) (preparation, for example, W. A. Sheppard, J. Am. Chem. Soc. 1965, 87, 2410-2420) in glacial acetic acid (40 ml) was added, at RT, N-chlorosuccinimide (2.71 g, 20.2 mmol). The mixture was stirred at 75° C. for 3 h and then at RT for 14 h. Subsequently, the mixture was added to water and extracted with EtOAc. The organic phase was washed with water and saturated aqueous $NaHCO_3$ solution and dried over magnesium sulphate. After solvent had been removed, the residue was taken up in MTBE and the solids were filtered off. The filtrate was concentrated under reduced pressure and the crude product was purified by means of column chromatography on $SiO_2$ (n-hexane/EtOAc gradient). 2.89 g (91%) of 2-(4-amino-3,5-dichlorphenyl)-1,1,1,3,3,3-hexafluoropropan-2-ol were obtained.

HPLC-MS[a]: log P=3.04, mass (m/z)=328 [M+H]+.

$^1$H NMR (400 MHz, $d_3$-acetonitrile): δ=5.13 (br s, 2H), 6.02 (br s, 1H), 7.51 (s, 2H).

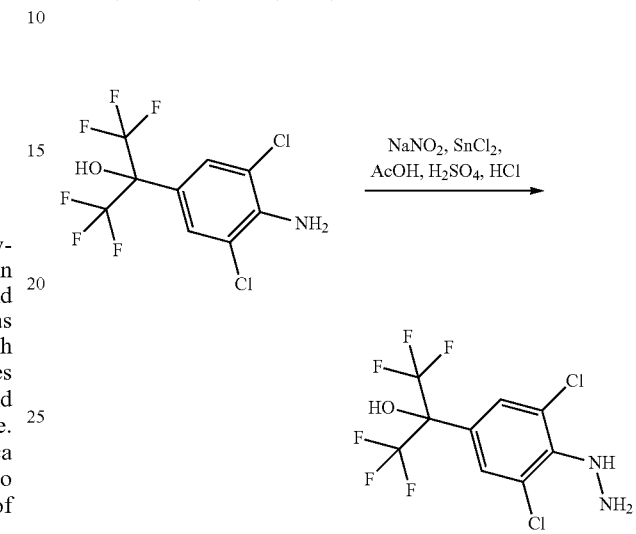

To a solution, heated to 55° C., of 2-(4-amino-3,5-dichlorphenyl)-1,1,1,3,3,3-hexafluoropropan-2-ol (1.88 g, 5.73 mmol) in 5 ml of glacial acetic acid was added dropwise a solution of sodium nitrite (455 mg, 6.59 mmol) in 2.5 ml of sulphuric acid, and the mixture was stirred at this temperature for a further hour. Subsequently, the mixture was cooled to 0° C. and a solution of tin(II) chloride (3.37 g, 17.7 mmol) in conc. HCl (10 ml) was added dropwise. The mixture was stirred at 0° C. for a further hour, then added to ice, alkalized with sodium hydroxide solution and extracted with EtOAc. The organic phase was washed with saturated sodium chloride solution and dried over magnesium sulphate, and the solvent was removed under reduced pressure. 1.41 g (90% pure, 64% of theory) of 2-(3,5-dichloro-4-hydrazinophenyl)-1,1,1,3,3,3-hexafluoropropan-2-ol were obtained.

HPLC-MS[a]: log P=1.92, mass (m/z)=343 [M+H]+.

$^1$H NMR (600 MHz, $d_3$-acetonitrile): δ=4.14 (br s, 2H), 5.90 (br s, 1H), 6.50 (br s, 1H), 7.58 (s, 2H).

Examples I-T46-1

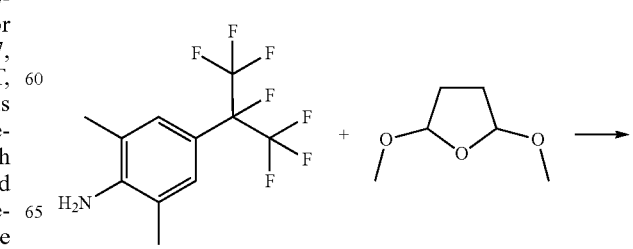

-continued

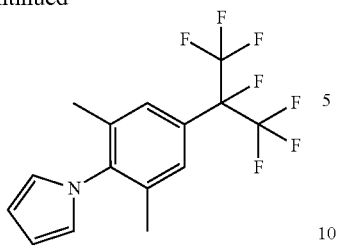

10 g (34.6 mmol) of 2,6-Dimethyl-4-[1,2,2,2-tetrafluoro-1-(trifluoromethyl)ethyl]aniline were initially charged in 60 ml of glacial acetic acid, and 5.02 g (38.04 mmol) of 2,6-dimethoxy-tetrahydrofuran were added. The resultant solution was heated at 120° C. for two hours. Subsequently, it was cooled a little and the volatile constituents were evaporated off on a rotary evaporator under reduced pressure. The residue was stirred with water and the solids were filtered off with suction. The filtercake was then dissolved in dichloromethane, and the solution was dried with sodium sulphate and concentrated on a rotary evaporator under reduced pressure. 10.38 g of 1-[2,6-dimethyl-4-[1,2,2,2-tetrafluoro-1-(trifluoromethyl)ethyl]phenyl]pyrrole were obtained.

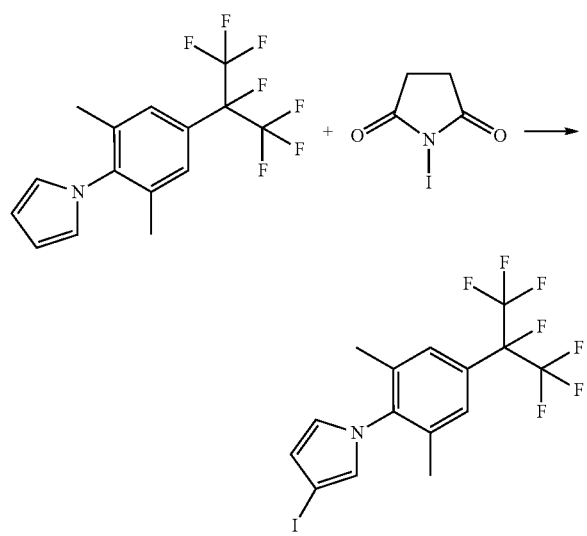

1.5 g (4.293 mmol) 1-[2,6-dimethyl-4-[1,2,2,2-tetrafluoro-1-(trifluoromethyl)ethyl]phenyl]-pyrrole were dissolved in 60 ml of n-hexane, and 966 mg (4.3 mmol) of N-iodosuccinimide were added. Subsequently, the mixture was allowed to come to room temperature and stirred at room temperature for 6 days. Then a further 242 mg (1.1 mmol) of N-iodosuccinimide were added and the mixture was stirred at room temperature overnight. Subsequently, excess aqueous sodium hydrogen-sulphite solution and a little ethyl acetate were added. The organic phase was removed and first washed twice with aqueous sodium hydrogensulphite solution, then with saturated sodium chloride solution, dried with sodium sulphate and concentrated. For purification, chromatography was effected using a cartridge containing 120 g of silica gel and a gradient proceeding from pure cyclohexane to 95:5 cyclohexane/ethyl acetate (v/v). 453 mg of a mixture of 80% 1-[2,6-dimethyl-4-[1,2,2,2-tetrafluoro-1-(trifluoromethyl)ethyl]phenyl]-3-iodopyrrole and 16% 1-[2,6-dimethyl-4-[1,2,2,2-tetrafluoro-1-(trifluoromethyl)ethyl]phenyl]-2-iodopyrrole were obtained.

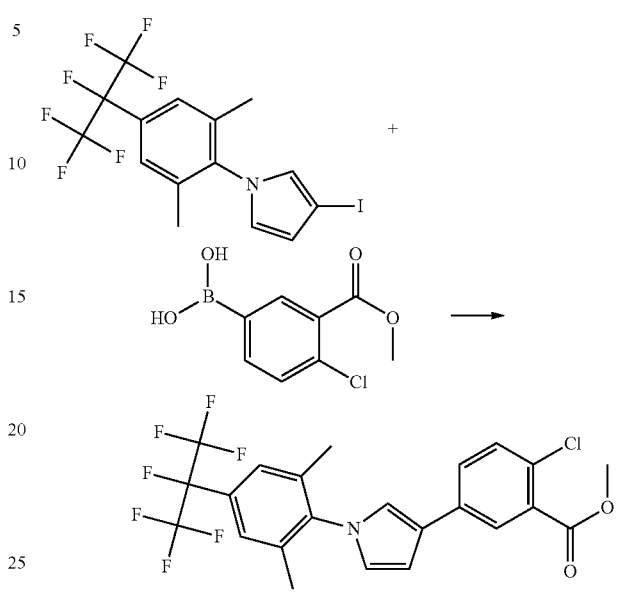

998 mg (1.696 mmol) of a mixture of 80% 1-[2,6-dimethyl-4-[1,2,2,2-tetrafluoro-1-(trifluoromethyl)ethyl]phenyl]-3-iodopyrrole and 16% 1-[2,6-dimethyl-4-[1,2,2,2-tetrafluoro-1-(trifluoromethyl)ethyl]phenyl]-2-iodopyrrole and 364 mg (1.7 mmol) of 4-chloro-3-(methoxy-carbonyl)phenylboronic acid were initially charged in 10 ml of 2-propanol. Thereafter, the air was displaced by argon, and 5.2 ml of 1 molar aqueous sodium hydrogencarbonate solution and 98 mg (0.085 mmol) of tetrakis(triphenylphosphine)palladium(0) were added under argon. Subsequently, the mixture was heated to reflux for 3 hours. For workup, the mixture was cooled a little, then concentrated on a rotary evaporator under reduced pressure. The residue was partitioned between ethyl acetate and water. The organic phase was removed, washed with saturated sodium chloride solution and concentrated on a rotary evaporator under reduced pressure. 1.57 g of crude methyl 2-chloro-5-[1-[2,6-dimethyl-4-[1,2,2,2-tetrafluoro-1-(trifluoromethyl)ethyl]phenyl]pyrrol-3-yl]benzoate were obtained.

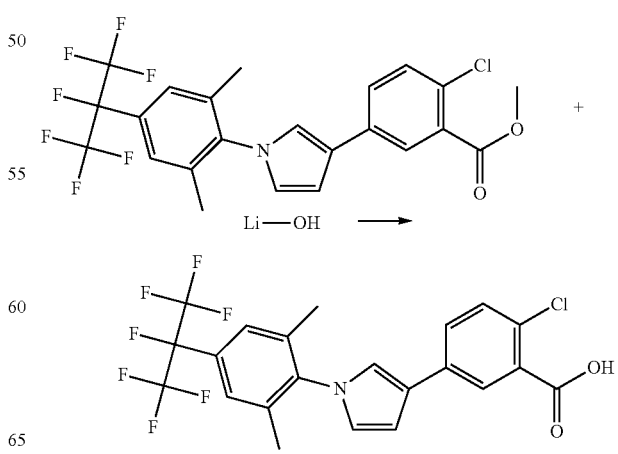

416 mg (0.33 mmol, about 40% pure) of crude methyl 2-chloro-5-[1-[2,6-dimethyl-4-[1,2,2,2-tetrafluoro-1-(trifluoromethyl)ethyl]phenyl]pyrrol-3-yl]benzoate are initially charged in a mixture of 18 ml of dioxane and 6 ml of water, and 61 mg (1.46 mmol) of lithium hydroxide hydrate are added. The mixture was stirred at room temperature until dissolution was complete, then heated under reflux for 2 hours. The mixture was then concentrated on a rotary evaporator under reduced pressure, and the residue was admixed with a little water and adjusted to pH 1 with concentrated hydrochloric acid. The mixture was then extracted twice with ethyl acetate, and the combined extracts were washed with saturated sodium chloride solution, dried with sodium sulphate and concentrated. As residue, there remained 207 mg of crude 2-chloro-5-[1-[2,6-dimethyl-4-[1,2,2,2-tetrafluoro-1-(trifluoromethyl)ethyl]phenyl]pyrrol-3-yl]-benzoic acid.

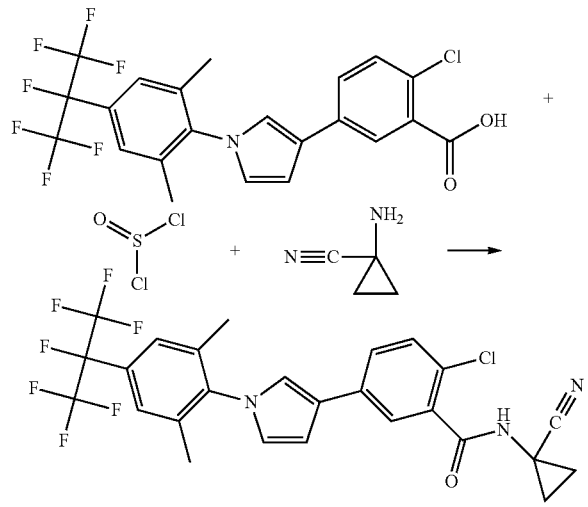

137 mg (0.11 mmol, purity about 38%) of crude 2-chloro-5-[1-[2,6-dimethyl-4-[1,2,2,2-tetrafluoro-1-(trifluoromethyl)ethyl]phenyl]pyrrol-3-yl]benzoic acid were dissolved in 15 ml of toluene, and 230 mg (1.93 mmol) of thionyl chloride were added. The mixture was heated to reflux for 3 hours. Thereafter, all the volatile components were drawn off on a rotary evaporator under reduced pressure. The residue was taken up in 4 ml of dichloromethane and added dropwise to a mixture of 82 mg (0.69 mmol) of 1-cyanocyclopropylamine hydrochloride and 98 mg (0.96 mmol) of triethylamine in 2 ml of dichloromethane at 0° C. Subsequently, the mixture was stirred at room temperature overnight. For workup, the mixture was washed with 5% aqueous sodium dihydrogenphosphate solution, then with saturated sodium chloride solution, and the organic phase was dried with sodium sulphate and concentrated. The residue was chromatographed using a cartridge containing 15 g of silica gel and 85:15 cyclohexane/ethyl acetate (v/v). The fractions containing the product were concentrated and purified by means of preparative HPLC (Zorbax Eclipse Plus C18 1.8 μm, 50×4.6 mm in a gradient in acetonitrile/ 0.1% aqueous $H_3PO_4$. 13 mg of 2-chloro-N-cyclopropyl-5-[1-[2,6-dimethyl-4-[1,2,2,2-tetrafluoro-1-(trifluoromethyl) ethyl]phenyl]pyrrol-3-yl]benzamide (compound I-T46-1) were obtained.

HPLC-MS[a]: log P=4.90, mass (m/z)=558 [M+H]+.

$^1$H NMR (400 MHz, $d_3$-acetonitrile): δ=7.63-7.67 (m, 2H), 7.56 (s, broad), 1H (N—H)), 7.51 (s, 2H), 7.41 (d, J=8.3 Hz, 1H), 7.16-7.17 (m, 1H), 6.75-6.77 (m, 1H), 6.72-6.73 (m, 1H), 2.14 (s, 6H), 1.55-1.59 (m, 2H), 1.32-1.39 (m, 2H).

TABLE I-T2

Structure: pyrazole-pyrimidine with substituents $B_1, B_2, B_3, B_4, B_5, R_{11a}, R_{11b}, A_1, A_2, A_3, A_4, W, Q, R_1$ $B_2$ and $B_4$ = C—H, W = O

| Ex. No. | $B_1$ | $B_3$ | $B_5$ | $R_1$ | $R_{11a}$ | $R_{11b}$ | $A_1$ | $A_2$ | $A_3$ | $A_4$ | Q | logP[a)] | Mass [m/z][a)1)] |
|---|---|---|---|---|---|---|---|---|---|---|---|---|---|
| I-T2-1 | C—CH$_3$ | C-i-C$_3$F$_7$ | C—CH$_3$ | H | H | H | C—H | C—H | C—Cl | C—H | cyclopropyl | 4.9 | 534 |
| I-T2-2 | C—CH$_3$ | C-i-C$_3$F$_7$ | C—CH$_3$ | H | H | H | C—H | C—H | C—Cl | C—H | 1-(cyano)cyclopropyl | 4.8 | 559 |

| Ex. No. | $B_1$ | $B_3$ | $B_5$ | $R^{11a}$ | $R^{11b}$ | $A_1$ | $A_2$ | $A_3$ | $A_4$ | W | Q | $R_1$ | logP[a)] | Mass [m/z][a)1)] |
|---|---|---|---|---|---|---|---|---|---|---|---|---|---|---|
| I-T3-1 | C—CH$_3$ | C-i-C$_3$F$_7$ | C—CH$_3$ | H | H | C—H | C—Cl | C—H | C—H | O | cyclopropyl | H | 4.4 | 534 |
| I-T3-2 | C—CH$_3$ | C-i-C$_3$F$_7$ | C—CH$_3$ | H | H | C—H | C—Cl | C—H | C—H | O | CH$_2$CF$_3$ | H | 4.7 | 577 |
| I-T3-3 | C—CH$_3$ | C-i-C$_3$F$_7$ | C—CH$_3$ | H | H | C—H | C—Cl | C—H | C—H | O | 1-(cyano)cyclopropyl | H | 4.2 | 559 |
| I-T3-4 | C—CH$_3$ | C-i-C$_3$F$_7$ | C—CH$_3$ | H | H | C—H | C—Cl | C—H | C—H | O | thietan-3-yl | H | 4.7 | 566 |
| I-T3-5 | C—CH$_3$ | C-i-C$_3$F$_7$ | C—CH$_3$ | H | H | C—H | C—Cl | C—H | C—H | O | 1-(trifluoromethyl)cyclopropyl | H | 4.6 | 602 |
| I-T3-6 | C—CH$_3$ | C-i-C$_3$F$_7$ | C—CH$_3$ | H | H | C—H | C—Cl | C—H | C—H | O | 2-oxo-2-(2,2,2-trifluoroethylamino)-ethyl | H | 4.1 | 633 |
| I-T3-7 | C—CH$_3$ | C-i-C$_3$F$_7$ | C—CH$_3$ | H | H | N | C—H | C—H | C—H | O | cyclopropyl | H | 3.4 | 501 |
| I-T3-8 | C—CH$_3$ | C-i-C$_3$F$_7$ | C—CH$_3$ | H | H | N | C—H | C—H | C—H | O | 1-(cyano)cyclopropyl | H | 3.4 | 526 |
| I-T3-9 | C—CH$_3$ | C-i-C$_3$F$_7$ | C—CH$_3$ | H | H | CF | C—H | C—H | C—H | O | cyclopropyl | H | 4.3 | 518 |
| I-T3-10 | C—CH$_3$ | C-i-C$_3$F$_7$ | C—CH$_3$ | H | H | CF | C—H | C—H | C—H | O | 1-(cyano)cyclopropyl | H | 4.2 | 543 |
| I-T3-11 | C—CH$_3$ | C-i-C$_3$F$_7$ | C—CH$_3$ | H | H | C—H | C—F | C—H | C—H | O | 1-(cyano)cyclopropyl | H | 4.9 | 552 |
| I-T3-12 | C—CH$_3$ | C-i-C$_3$F$_7$ | C—CH$_3$ | H | H | C—Cl | C—H | C—H | C—H | O | 1-(cyano)cyclopropyl | H | 4.7 | 577 |
| I-T3-13 | C—CH$_3$ | C-i-C$_3$F$_7$ | C—CH$_3$ | H | H | C—CF$_3$ | C—H | C—H | C—H | O | cyclopropyl | H | 4.5 | 518 |
| I-T3-14 | C—CH$_3$ | C-i-C$_3$F$_7$ | C—CH$_3$ | H | H | C—CF$_3$ | C—H | C—H | C—H | O | cyclopropyl | H | 4.5 | 552 |
| I-T3-15 | C—CH$_3$ | C-i-C$_3$F$_7$ | C—CH$_3$ | H | H | C—CH$_3$ | C—H | C—H | C—H | O | cyclopropyl | H | 4.9 | 568 |
| I-T3-16 | C—CH$_3$ | C-i-C$_3$F$_7$ | C—CH$_3$ | H | H | CF | C—H | C—H | C—H | O | cyclopropyl | H | 4.4 | 514 |
| I-T3-17 | C—CH$_3$ | C-i-C$_3$F$_7$ | C—CH$_3$ | H | H | CF | C—H | C—H | C—H | O | 1-(cyano)cyclopropyl | H | 4.4 | 577 |
| I-T3-18 | C—CH$_3$ | C-i-C$_3$F$_7$ | C—CH$_3$ | H | H | C—CH$_3$ | C—H | C—H | C—H | O | 1-(cyano)cyclopropyl | H | 4.7 | 593 |
| I-T3-19 | C—CH$_3$ | C-i-C$_3$F$_7$ | C—CH$_3$ | H | H | C—H | C—H | C—H | C—H | O | 1-(cyano)cyclopropyl | H | 4.3 | 543 |
| I-T3-20 | C—CH$_3$ | C-i-C$_3$F$_7$ | C—CH$_3$ | H | H | N | C—H | C—H | C—H | O | cyclopropyl | H | 3.8 | 535 |
| I-T3-21 | C—CH$_3$ | C-i-C$_3$F$_7$ | C—CH$_3$ | H | H | N | C—H | C—H | C—H | O | 1-(cyano)cyclopropyl | H | 3.7 | 560 |
| I-T3-22 | C—Cl | C-i-C$_3$F$_7$ | C—Cl | H | H | C—H | C—Cl | C—H | C—H | O | 1-(cyano)cyclopropyl | H | 4.1 | 583 |
| I-T3-23 | C—CH$_3$ | C-i-C$_3$F$_7$ | C—CH$_3$ | H | H | C—H | C—Cl | C—F | C—H | O | 1-(cyano)cyclopropyl | H | 4.2 | 599 |
| I-T3-24 | C—CH$_3$ | C-i-C$_3$F$_7$ | C—CH$_3$ | H | H | C—H | C—Cl | C—H | C—H | O | cyclopropyl | H | 4.3 | 574 |
| I-T3-25 | C—CH$_3$ | C-i-C$_3$F$_7$ | C—CH$_3$ | H | H | C—H | C—Cl | C—H | C—H | O | CH$_2$CF$_3$ | H | 4.7 | 616 |

TABLE I-T2-continued

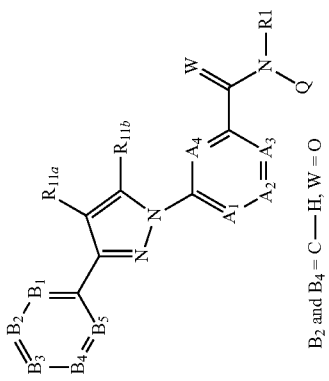

$B_2$ and $B_4 = C-H$, $W = O$

| | $R_{11a}$ | $R_{11b}$ | $B_1$ | $B_2$ | $B_3$ | $B_4$ | $B_5$ | $A_1$ | $A_2$ | $A_3$ | $A_4$ | $W$ | $R_1$ | $Q$ | | |
|---|---|---|---|---|---|---|---|---|---|---|---|---|---|---|---|---|
| I-T3-26 | C—CH$_3$ | C-i-C$_3$F$_7$ | C—CH$_3$ | H | H | C—H | C—H | C—Cl | C—H | O | H | CH$_2$CH$_2$CF$_3$ | 4.7 | 630 |
| I-T3-27 | C—CH$_3$ | C—CF$_3$ | C—CH$_3$ | H | H | C—H | C—H | C—Cl | C—H | O | H | 1-(cyano)cyclopropyl | 3.4 | 499 |
| I-T3-28 | C—CH$_3$ | C-i-C$_3$F$_7$ | C—CH$_3$ | H | H | C—H | C—H | C—Cl | C—H | O | H | cyclopropyl | 3.5 | 474 |
| I-T3-29 | C—CH$_3$ | C-i-C$_3$F$_7$ | C—CH$_3$ | H | H | C—H | C—H | C—H | C—H | O | H | cyclopropyl | 3.3 | 541 |
| I-T3-30 | C—Cl | C-i-C$_3$F$_7$ | C—H | H | H | C—H | C—H | C—Cl | C—H | O | H | 1-(cyano)cyclopropyl | 3.2 | 566 |
| I-T3-31 | C—Cl | C-i-C$_3$F$_7$ | C—H | H | H | C—H | C—H | C—Cl | C—H | O | H | cyclopropyl | 4.3 | 540 |
| I-T3-32 | C—Cl | C-i-C$_3$F$_7$ | C—H | H | H | C—H | C—H | C—Cl | C—H | O | H | CH$_2$CH$_2$CF$_3$ | 4.7 | 582 |
| I-T3-33 | C—Cl | C-i-C$_3$F$_7$ | C—H | H | H | C—H | C—H | C—Cl | C—H | O | H | 1-(cyano)cyclopropyl | 4.7 | 596 |
| I-T3-34 | C—OCF$_3$ | C-i-C$_3$F$_7$ | C—H | H | H | C—H | C—H | C—Cl | C—H | O | H | cyclopropyl | 4.6 | 615 |
| I-T3-35 | C—OCF$_3$ | C-i-C$_3$F$_7$ | C—H | H | H | C—H | C—H | C—Cl | C—H | O | H | cyclopropyl | 4.7 | 590 |
| I-T3-36 | C—OCF$_3$ | C-i-C$_3$F$_7$ | C—H | H | H | C—H | C—H | C—Cl | C—H | O | H | thietan-3-yl | 5.0 | 632 |
| I-T3-37 | C—C$_2$H$_5$ | C-i-C$_3$F$_7$ | C—H | H | H | C—H | C—H | C—Cl | C—H | O | H | 1-(cyano)cyclopropyl | 4.9 | 622 |
| I-T3-38 | C—C$_2$H$_5$ | C-i-C$_3$F$_7$ | C—H | H | H | C—H | C—H | C—Cl | C—H | O | H | cyclopropyl | 4.5 | 559 |
| I-T3-39 | C—C$_2$H$_5$ | C-i-C$_3$F$_7$ | C—H | H | H | C—H | C—H | C—Cl | C—H | O | H | CH$_2$CF$_3$ | 4.6 | 534 |
| I-T3-40 | C—C$_2$H$_5$ | C-i-C$_3$F$_7$ | C—H | H | H | C—H | C—H | C—Cl | C—H | O | H | 1-(cyano)cyclopropyl | 4.9 | 576 |
| I-T3-41 | C—Cl | C-i-C$_3$F$_7$ | C—Cl | H | H | C—H | C—H | C—Cl | C—H | O | H | thietan-3-yl | 4.9 | 566 |
| I-T3-42 | C—Cl | C-i-C$_3$F$_7$ | C—Cl | H | H | C—H | C—H | C—Cl | C—H | O | H | cyclopropyl | 3.8 | 575 |
| I-T3-43 | C—Cl | C-i-C$_3$F$_7$ | C—Cl | H | H | N | C—H | C—Cl | C—H | O | H | 1-(cyano)cyclopropyl | 3.8 | 600 |
| I-T3-44 | C—Cl | C-i-C$_3$F$_7$ | C—Cl | H | H | N | C—H | C—Cl | C—H | O | H | cyclopropyl | 4.7 | 548 |
| I-T3-45 | C—C$_2$H$_5$ | C-i-C$_3$F$_7$ | C—Cl | H | H | C—H | C—H | C—Cl | C—H | O | H | CH$_2$CF$_3$ | 5.0 | 590 |
| I-T3-46 | C—C$_2$H$_5$ | C-i-C$_3$F$_7$ | C—F | H | H | C—H | C—H | C—Cl | C—H | O | H | 1-(cyano)cyclopropyl | 4.6 | 573 |
| I-T3-47 | C—F | C—CF$_3$ | C—F | H | H | C—H | C—H | C—Cl | C—H | O | H | thietan-3-yl | 5.0 | 580 |
| I-T3-48 | C—F | C—CF$_3$ | C—F | H | H | C—H | C—H | C—Cl | C—H | O | H | cyclopropyl | 3.2 | 442 |
| I-T3-49 | C—F | C—CF$_3$ | C—OCF$_3$ | H | H | C—H | C—H | C—Cl | C—H | O | H | cyclopropyl | 3.2 | 467 |
| I-T3-50 | C—F | C—CF$_3$ | C—OCF$_3$ | H | H | C—H | C—H | C—Cl | C—H | O | H | 1-(cyano)cyclopropyl | 3.1 | 454 |
| I-T3-51 | C—CF$_3$ | C—CF$_3$ | C—H | H | H | C—H | C—H | C—Cl | C—H | O | H | cyclopropyl | 3.1 | 479 |
| I-T3-52 | C—CF$_3$ | C—CF$_3$ | C—CH$_3$ | H | H | C—H | C—H | C—Cl | C—H | O | H | 1-(cyano)cyclopropyl | 4.3 | 574 |
| I-T3-53 | C—CF$_3$ | C—CF$_3$ | C—CH$_3$ | H | H | C—H | C—H | C—Cl | C—H | O | H | cyclopropyl | 4.3 | 599 |
| I-T3-54 | C—CF$_3$ | C—CF$_3$ | C—H | H | H | C—H | C—H | C—Cl | C—H | O | H | 1-(cyano)cyclopropyl | 4.4 | 588 |
| I-T3-55 | C—CF$_3$ | C—CF$_3$ | C—Cl | H | H | C—H | C—H | C—Cl | C—H | O | H | cyclopropyl | 4.3 | 613 |
| I-T3-56 | C—CF$_3$ | C—CF$_3$ | C—Cl | H | H | C—H | C—H | C—Cl | C—H | O | H | 1-(cyano)cyclopropyl | 4.4 | 608 |
| I-T3-57 | C—CF$_3$ | C-i-C$_3$F$_7$ | C—Cl | H | H | C—H | C—H | C—Cl | C—H | O | H | CH$_2$CF$_3$ | 4.7 | 633 |
| I-T3-58 | C—Cl | C—CF$_3$ | N | H | H | C—H | C—H | C—Cl | C—H | O | H | 1-(cyano)cyclopropyl | 4.7 | 650 |
| I-T3-59 | C—Cl | C—CF$_3$ | N | H | H | C—H | C—H | C—Cl | C—H | O | H | cyclopropyl | 3.1 | 466 |
| I-T3-60 | C—F | C—CF$_3$ | C—Cl | H | H | C—H | C—H | C—Cl | C—H | O | H | cyclopropyl | 3.2 | 441 |
| I-T3-61 | C—F | C-i-C$_3$F$_7$ | C—F | H | H | C—H | C—H | C—Cl | C—H | O | H | cyclopropyl | 4.0 | 542 |

TABLE I-T2-continued

B₂ and B₄ = C—H, W = O

| No. | B1 | B3 | B5 | R11a | R11b | A1 | A2 | A3 | A4 | Q | R1 | R | logP | MW |
|---|---|---|---|---|---|---|---|---|---|---|---|---|---|---|
| I-T3-62 | C—F | C-i-C₃F₇ | C—F | H | H | C—H | C—H | C—H | C—Cl | O | H | 1-(cyano)cyclopropyl | 3.9 | 567 |
| I-T3-63 | C—CH₃ | C-i-C₃F₇ | C—Cl | H | H | C—H | C—H | C—H | C—Cl | O | H | cyclopropyl | 4.4 | 554 |
| I-T3-64 | C—CH₃ | C-i-C₃F₇ | C—CH₃ | H | H | C—H | C—H | C—H | C—Cl | O | H | 1-(cyano)cyclopropyl | 4.2 | 579 |
| I-T3-65 | C—CH₃ | C-i-C₃F₇ | C—CH₃ | H | H | C—H | C—H | C—F | C—Cl | O | H | 1-(cyano)cyclopropyl | 4.4 | 577 |
| I-T3-66 | C—C₂H₅ | C-i-C₃F₇ | C—CH₃ | H | H | C—H | C—H | C—F | C—Cl | O | H | 1-(cyano)cyclopropyl | 4.6 | 591 |
| I-T3-67 | C—C₂H₅ | C-i-C₃F₇ | C—CH₃ | H | H | C—H | C—H | C—F | C—Cl | O | H | cyclopropyl | 4.4 | 552 |
| I-T3-68 | C—C₂H₅ | C-i-C₃F₇ | C—CH₃ | H | H | C—H | C—H | C—F | C—Cl | O | H | cyclopropyl | 4.6 | 566 |
| I-T3-69 | C—C₂H₅ | C-i-C₃F₇ | C—CH₃ | H | H | C—H | C—H | C—F | C—Cl | O | H | 1-(cyano)cyclopropyl | 4.3 | 557 |
| I-T3-70 | C—C₂H₅ | C-i-C₃F₇ | C—CH₃ | H | H | C—H | C—H | C—H | C—Cl | O | H | cyclopropyl | 4.5 | 532 |
| I-T3-71 | C—C₂H₅ | C-i-C₃F₇ | C—CH₃ | H | H | C—H | C—H | C—H | C—Cl | O | H | 1-(cyano)cyclopropyl | 4.5 | 593 |
| I-T3-72 | C—C₂H₅ | C-i-C₃F₇ | C—Cl | H | H | C—H | C—H | C—H | C—Cl | O | H | cyclopropyl | 4.6 | 568 |
| I-T3-73 | C—Cl | C-i-C₃F₇ | C—H | H | H | C—H | C—H | C—H | C—Cl | O | H | cyclopropyl | 4.5 | 592 |
| I-T3-74 | C—C₂H₅ | C-i-C₃F₇ | C—H | H | H | C—H | C—H | C—H | C—Cl | O | H | 1-(cyano)cyclopropyl | 4.1 | 543 |
| I-T3-75 | C—C₂H₅ | C-i-C₃F₇ | C—H | H | H | C—H | C—H | C—H | C—Cl | O | H | cyclopropyl | 4.2 | 518 |
| I-T3-76 | C—C₂H₅ | C-i-C₃F₇ | C—CH₃ | H | H | C—H | N | C—H | C—Cl | O | H | 1-(cyano)cyclopropyl | 3.4 | 540 |
| I-T3-77 | C—C₂H₅ | C-i-C₃F₇ | C—CH₃ | H | H | C—H | N | C—H | C—Cl | O | H | cyclopropyl | 3.4 | 515 |
| I-T3-78 | C—C₂H₅ | C-i-C₃F₇ | C—CH₃ | H | H | C—H | N | C—H | C—Cl | O | H | 1-(cyano)cyclopropyl | 3.2 | 526 |
| I-T3-79 | C—C₂H₅ | C-i-C₃F₇ | C—CH₃ | H | H | C—H | C—H | C—H | C—Cl | O | H | 1-(cyano)cyclopropyl | 3.3 | 501 |
| I-T3-80 | C—C₂H₅ | C—C₂F₅ | C—CH₃ | H | H | C—H | C—H | C—H | C—Cl | O | H | cyclopropyl | 4.2 | 523 |
| I-T3-81 | C—C₂H₅ | C—C₂F₅ | C—CH₃ | H | H | C—H | C—H | C—H | C—Cl | O | H | 1-(cyano)cyclopropyl | 4.3 | 498 |
| I-T3-82 | C—C₂H₅ | C—C₂F₅ | C—CH₃ | H | H | C—H | C—H | C—H | C—Cl | O | H | CH₂CF₃ | 4.0 | 540 |
| I-T3-83 | C—CF₃ | C-i-C₃F₇ | C—CH₃ | H | H | C—H | C—H | C—H | C—Cl | O | H | thietan-3-yl | 4.6 | 530 |
| I-T3-84 | C—CF₃ | C-i-C₃F₇ | C—CH₃ | H | H | C—H | C—H | C—H | C—Cl | O | H | CH₂CF₃ | 4.7 | 630 |
| I-T3-85 | C—CH₃ | C-i-C₃F₇ | C—Br | H | H | C—H | C—H | C—H | C—Cl | O | H | thietan-3-yl | 4.7 | 620 |
| I-T3-86 | C—Cl | C-i-C₃F₇ | C—CH₃ | H | H | C—H | C—H | C—H | C—Cl | O | H | cyclopropyl | 4.5 | 598 |
| I-T3-87 | C—Cl | C—OCF₃ | C—CH₃ | H | H | C—H | C—H | C—H | C—Cl | O | H | 1-(cyano)cyclopropyl | 3.6 | 515 |
| I-T3-88 | C—Cl | C—OCF₃ | C—Cl | H | H | C—H | C—H | C—H | C—Cl | O | H | cyclopropyl | 3.6 | 490 |
| I-T3-89 | C—Cl | C—OCF₃ | C—Cl | H | H | C—H | N | C—H | C—Cl | O | H | cyclopropyl | 3.5 | 481 |
| I-T3-90 | C—Cl | C-i-C₃F₇ | C—Cl | H | H | C—H | N | C—H | C—H | O | H | cyclopropyl | 3.6 | 456 |
| I-T3-91 | C—Cl | C-i-C₃F₇ | C—H | H | H | C—H | C—H | C—H | C—CH₃ | O | H | cyclopropyl | 3.3 | 555 |
| I-T3-92 | C—Cl | C-i-C₃F₇ | C—CH₃ | H | H | C—H | N | C—H | C—CH₃ | O | H | 1-(cyano)cyclopropyl | 3.4 | 580 |
| I-T3-93 | C—CH₃ | C-i-C₃F₇ | C—CH₃ | H | H | C—H | C—H | C—H | C—CH₃ | O | H | 1-(tert.butyl)cyclopropyl | 4.7 | 588 |
| I-T3-94 | C—CH₃ | C-i-C₃F₇ | C—CH₃ | H | H | C—H | C—H | C—H | C—CH₃ | O | H | 1-(tert.butyl)cyclopropyl | 4.7 | 602 |
| I-T3-95 | C—CF₃ | C—CF₃ | C—CH₃ | H | H | C—H | C—H | C—H | C—Cl | O | H | 1-(cyano)cyclopropyl | 3.1 | 500 |
| I-T3-96 | C—Cl | C-i-C₃F₇ | C—CH₃ | H | H | C—H | C—H | C—H | C—CH₃ | O | H | cyclopropyl | 3.3 | 515 |
| I-T3-97 | C—CH₃ | C-i-C₃F₇ | C—CH₃ | H | H | C—H | C—H | C—H | C—CH₃ | O | H | 1-(cyano)cyclopropyl | 3.4 | 540 |

TABLE I-T2-continued

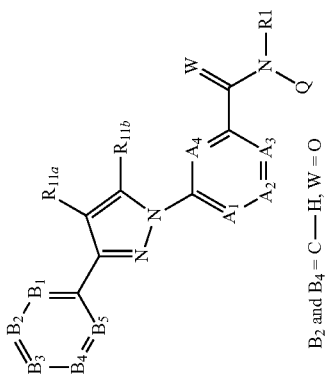

$B_2$ and $B_4 = C-H$, $W = O$

| No. | (a) | (b) | (c) | R11b | R11a | A1 | A2 | A3 | A4 | W | R1 | Q | logP | MW |
|---|---|---|---|---|---|---|---|---|---|---|---|---|---|---|
| I-T3-98 | C—Cl | C—CF3 | C—Cl | H | H | C—H | N | C—Cl | C—H | O | H | cyclopropyl | 3.1 | 475 |
| I-T3-99 | C—Cl | C—CF3 | C—Cl | H | H | C—H | N | C—Cl | C—H | O | CH3 | cyclopropyl | 3.5 | 489 |
| I-T3-100 | C—Cl | C—i-C3F7 | C—Cl | H | H | C—H | N | C—Cl | C—H | O | CH3 | cyclopropyl | 4.4 | 589 |
| I-T3-101 | C—CH3 | C—i-C3F7 | C—CH3 | H | H | C—H | N | C—CH3 | C—H | O | CH3 | cyclopropyl | 4.4 | 549 |
| I-T3-102 | C—Cl | C—i-C3F7 | C—CH3 | H | H | C—H | N | C—CH3 | C—H | O | CH3 | 1-(cyano)cyclopropyl | 4.3 | 614 |
| I-T3-103 | C—CH3 | C—i-C3F7 | C—CH3 | H | H | C—H | N | C—CH3 | C—H | O | CH3 | 1-(cyano)cyclopropyl | 4.3 | 574 |
| I-T3-104 | C—C2H5 | C—i-C3F7 | C—CH3 | H | H | C—H | N | C—CH3 | C—H | O | H | 1-(cyano)cyclopropyl | 4.2 | 535 |
| I-T3-105 | C—CH3 | C—i-C3F7 | C—H | H | H | C—H | N | C—CH3 | C—H | O | H | cyclopropyl | 4.1 | 560 |
| I-T3-106 | C—CF3 | C—CF3 | C—CH3 | H | H | C—H | N | C—CH3 | C—H | O | H | cyclopropyl | 4.0 | 589 |
| I-T3-107 | C—CF3 | C—CF3 | C—CH3 | H | H | C—H | N | C—CH3 | C—H | O | CH3 | cyclopropyl | 4.5 | 603 |
| I-T3-108 | C—CF3 | C—CF3 | C—CH3 | H | H | C—H | N | C—CH3 | C—H | O | H | 1-(cyano)cyclopropyl | 4.0 | 614 |
| I-T3-109 | C—CF3 | C—CF3 | C—CH3 | H | H | C—H | N | C—CH3 | C—H | O | CH3 | cyclopropyl | 4.2 | 549 |
| I-T3-110 | C—C2H5 | C—CF3 | C—CH3 | H | H | C—H | N | C—CH3 | C—H | O | H | 1-(cyano)cyclopropyl | 4.1 | 574 |
| I-T3-111 | C—CF3 | C—CF3 | C—CH3 | H | H | C—H | N | C—CH3 | C—H | O | CH3 | 1-(cyano)cyclopropyl | 4.4 | 628 |
| I-T3-112 | C—CF3 | C—CF3 | C—CH3 | H | H | C—H | N | C—CH3 | C—H | O | H | cyclopropyl | 4.0 | 609 |
| I-T3-113 | C—CF3 | C—CF3 | C—CH3 | H | H | C—H | N | C—CH3 | C—H | O | CH3 | cyclopropyl | 4.0 | 623 |
| I-T3-114 | C—CF3 | C—CF3 | C—CH3 | H | H | C—H | N | C—CH3 | C—H | O | H | 1-(cyano)cyclopropyl | 4.0 | 634 |
| I-T3-115 | C—CF3 | C—CF3 | C—CH3 | H | H | C—H | N | C—CH3 | C—H | O | CH3 | 1-(cyano)cyclopropyl | 3.8 | 554 |
| I-T3-116 | C—CF3 | C—CF3 | C—CH3 | H | H | C—H | N | C—CH3 | C—H | O | H | 1-(cyano)cyclopropyl | 4.3 | 648 |
| I-T3-117 | C—CF3 | C—CF3 | C—CH3 | CN | H | C—H | N | C—CH3 | C—H | O | H | cyclopropyl | 3.5 | 569 |
| I-T3-118 | C—CF3 | C—CF3 | C—CH3 | H | H | C—H | N | C—CH3 | C—H | O | CH3 | cyclopropyl | 3.8 | 583 |
| I-T3-119 | C—CF3 | C—CF3 | C—CH3 | H | H | C—H | N | C—CH3 | C—H | O | H | 1-(cyano)cyclopropyl | 3.6 | 594 |
| I-T3-120 | C—CF3 | C—CF3 | C—CH3 | H | H | C—H | N | C—CH3 | C—H | O | CH3 | cyclopropyl | 3.6 | 529 |
| I-T3-121 | C—CF3 | C—CF3 | N—CH3 | H | H | C—H | C—H | C—CH3 | C—H | O | H | cyclopropyl | 4.5 | 536 |
| I-T3-122 | C—Cl | C—CF3 | C—H | H | H | C—H | C—H | C—Cl | C—H | O | H | cyclopropyl | 3.0 | 407 |
| I-T3-123 | C—CF3 | C—CF3 | C—CH3 | H | H | C—H | N | C—CH3 | C—H | O | CH3 | 1-(cyano)cyclopropyl | 3.9 | 608 |
| I-T3-124 | C—CF3 | C—CF3 | C—CH3 | H | H | C—H | N | C—CH3 | C—H | O | H | 1-(cyano)cyclopropyl | 3.5 | 589 |
| I-T3-125 | C—CF3 | C—CF3 | C—CH3 | H | H | C—H | N | C—CH3 | C—H | O | CH3 | 1-(cyano)cyclopropyl | 3.8 | 614 |
| I-T3-126 | C—Cl | C—CF3 | C—Cl | H | H | C—H | N | C—Cl | C—H | O | H | cyclopropyl | 4.1 | 639 |
| I-T3-127 | C—CF3 | C—CF3 | C—CH3 | H | H | C—H | N | C—CH3 | C—H | O | H | cyclopropyl | 2.5 | 455 |
| I-T3-128 | C—Cl | C—CF3 | C—Cl | H | H | C—H | N | C—Cl | C—H | O | CH3 | 1-(cyano)cyclopropyl | 2.8 | 469 |
| I-T3-129 | C—Cl | C—CF3 | C—Cl | H | H | C—H | N | C—Cl | C—H | O | H | 1-(cyano)cyclopropyl | 2.6 | 480 |
| I-T3-130 | C—CF3 | C—CF3 | C—CH3 | H | H | C—H | N | C—CH3 | C—H | O | CH3 | cyclopropyl | 3.8 | 603 |
| I-T3-131 | C—Cl | C—CF3 | C—Cl | H | H | C—H | N | C—Cl | C—H | O | H | 1-(cyano)cyclopropyl | 3.9 | 628 |
| I-T3-132 | C—CF3 | C—CF3 | C—CH3 | H | H | C—H | N | C—CH3 | C—H | O | CH3 | cyclopropyl | 2.9 | 494 |
| I-T3-133 | C—Cl | C—CF3 | C—Cl | H | H | C—H | N | C—Cl | C—H | O | CH3 | cyclopropyl | 3.7 | 569 |

TABLE I-T2-continued

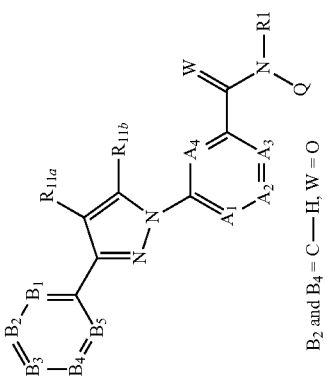

$B_2$ and $B_4$ = C—H, W = O

| | | | | | | | | | | | |
|---|---|---|---|---|---|---|---|---|---|---|---|
| I-T3-134 | C—CF$_3$ | C-i-C$_3$F$_7$ | C—H | H | H | C—H | C—H | C—Cl | C—H | O | CH$_3$ | cyclopropyl | 4.9 | 588 |
| I-T3-135 | C—Cl | C-i-C$_3$F$_7$ | C—Cl | H | H | C—H | N | C—Cl | C—H | O | H | cyclopropyl | 4.3 | 610 |
| I-T3-136 | C—Cl | C-i-C$_3$F$_7$ | C—Cl | H | H | C—H | N | C-(1-pyrrolidinyl) | C—H | O | H | cyclopropyl | 3.5 | 570 |
| I-T3-137 | C—Cl | C-i-C$_3$F$_7$ | C—Cl | H | H | C—H | N | C—NHCH$_3$ | C—H | O | H | cyclopropyl | 3.4 | 596 |
| I-T3-138 | C—Cl | C-i-C$_3$F$_7$ | C—Cl | H | H | C—H | N | C—NH-cyclopropyl | C—H | O | H | cyclopropyl | 4.1 | 614 |
| I-T3-139 | C—CH$_3$ | C-i-C$_3$F$_7$ | C—CH$_3$ | H | H | C—H | N | C—NH—CH$_2$CH$_2$OCH$_3$ | C—H | O | H | 1-(cyano)cyclopropyl | 4.1 | 566 |
| I-T3-140 | C—CH$_3$ | C-i-C$_3$F$_7$ | C—CH$_3$ | H | H | C—H | N | C-cyclopropyl | C—H | O | H | cyclopropyl | 4.2 | 541 |
| I-T3-141 | C—CH$_3$ | C-i-C$_3$F$_7$ | C—CH$_3$ | H | H | C—H | N | C-cyclopropyl | C—H | O | CH$_3$ | 1-(cyano)cyclopropyl | 4.4 | 556 |
| I-T3-142 | C—CH$_3$ | C-i-C$_3$F$_7$ | C—CH$_3$ | H | H | C—H | N | C-cyclopropyl | C—H | O | H | cyclopropyl | 4.6 | 555 |
| I-T3-143 | C—CH$_3$ | C-i-C$_3$F$_7$ | C—CH$_3$ | H | H | C—H | N | C—OCH$_3$ | C—H | O | CH$_3$ | cyclopropyl | 4.6 | 531 |
| I-T3-144 | C—CH$_3$ | C-i-C$_3$F$_7$ | C—CH$_3$ | H | H | C—H | N | C—OCH$_3$ | C—H | O | C$_2$H$_5$ | cyclopropyl | 4.4 | 545 |
| I-T3-145 | C—Cl | C-i-C$_3$F$_7$ | C—Cl | H | H | C—H | N | C—OCH$_3$ | C—H | O | H | cyclopropyl | 3.8 | 503 |
| I-T3-146 | C—Cl | C-i-C$_3$F$_7$ | C—Cl | H | H | C—H | C—H | C—Cl | C—H | O | H | N-methyl-pyrazole-3-yl | 2.8 | 515 |
| I-T3-147 | C—CF$_3$ | C-i-C$_3$F$_7$ | C—CH$_3$ | H | H | C—H | C—H | C—CH$_3$ | C—H | O | H | C$_2$H$_5$ | 4.0 | 443 |
| I-T3-148 | C—CF$_3$ | C-i-C$_3$F$_7$ | C—Br | H | H | C—H | C—H | C—Cl | C—H | O | H | cyclopropyl | 4.5 | 652 |
| I-T3-149 | C—Cl | C-i-C$_3$F$_7$ | N | H | H | C—H | C—H | C—Cl | C—H | O | H | 1-(cyano)cyclopropyl | 3.5 | 500 |
| I-T3-150 | C—CF$_3$ | C-i-C$_3$F$_7$ | N | H | H | C—H | C—H | C—Cl | C—H | O | H | cyclopropyl | 3.6 | 475 |
| I-T3-151 | C—Cl | C-i-C$_3$F$_7$ | N | H | H | C—H | C—H | C—Cl | C—H | O | H | 1-(cyano)cyclopropyl | 4.0 | 566 |
| I-T3-152 | C—CF$_3$ | C-i-C$_3$F$_7$ | C—Br | H | H | C—H | C—H | C—Cl | C—H | O | H | cyclopropyl | 4.1 | 541 |
| I-T3-153 | C—S(O)C$_2$H$_5$ | C-i-C$_3$F$_7$ | N | H | H | C—H | C—H | C—Cl | C—H | O | H | 1-(cyano)cyclopropyl | 3.7 | 608 |
| I-T3-154 | C—S(O)C$_2$H$_5$ | C-i-C$_3$F$_7$ | N | H | H | C—H | C—H | C—Cl | C—H | O | H | 1-(cyano)cyclopropyl | 3.8 | 624 |
| I-T3-155 | C—CF$_3$ | C-i-C$_3$F$_7$ | C—Br | H | H | C—H | C—H | C—Cl | C—H | O | H | 1-(cyano)cyclopropyl | 4.4 | 677 |
| I-T3-156 | C—CF$_3$ | C-i-C$_3$F$_7$ | N | H | H | C—H | N | C—Cl | C—H | O | H | cyclopropyl | 4.7 | 567 |
| I-T3-157 | C—S(O)C$_2$H$_5$ | C-i-C$_3$F$_7$ | N | H | H | C—H | N | C—Cl | C—H | O | H | cyclopropyl | 3.8 | 583 |
| I-T3-158 | C—S(O)C$_2$H$_5$ | C-i-C$_3$F$_7$ | C—CH$_3$ | H | H | C—H | C—H | C—Cl | C—H | S | H | cyclopropyl | 3.9 | 599 |
| I-T3-159 | C—CF$_3$ | C-i-C$_3$F$_7$ | C—Cl | H | H | C—H | C—H | C—Cl | C—H | O | H | 1-(thiocarbamoyl)-cyclopropyl | 3.8 | 668 |
| I-T3-160 | C—CF$_3$ | C-i-C$_3$F$_7$ | C—Br | H | H | C—H | C—H | C—Cl | C—H | O | H | cyclopropyl | 4.0 | 653 |
| I-T3-161 | C—CF$_3$ | C-i-C$_3$F$_7$ | C—CH$_3$ | H | H | C—H | C—H | C—Cl | C—H | O | H | cyclopropyl | 5.0 | 604 |
| I-T3-162 | C—OCF$_3$ | C-i-C$_3$F$_7$ | C—Cl | H | H | C—H | C—H | C—Cl | C—H | O | H | cyclopropyl | 4.6 | 624 |
| I-T3-163 | C—OCF$_3$ | C-i-C$_3$F$_7$ | C—Cl | H | H | C—H | C—H | C—Cl | C—H | O | H | 1-(cyano)cyclopropyl | 4.5 | 649 |

TABLE I-T3

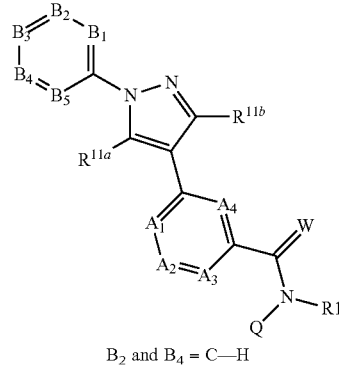

B$_2$ and B$_4$ = C—H

| Ex. No. | B$_1$ | B$_2$ | B$_3$ | B$_4$ | B$_5$ | R$^{11a}$ | R$^{11b}$ | A$_1$ | A$_2$ | A$_3$ | A$_4$ | W | R1 | Q | logP$^{a)}$ | Mass [m/z]$^{a)1)}$ |
|---|---|---|---|---|---|---|---|---|---|---|---|---|---|---|---|---|
| I-T3-1 | C—CH$_3$ | C—H | C—i-C$_3$F$_7$ | C—H | C—CH$_3$ | H | H | C—H | C—H | C—Cl | C—H | O | H | cyclopropyl | 4.4 | 534 |
| I-T3-2 | C—CH$_3$ | C—H | C—i-C$_3$F$_7$ | C—H | C—CH$_3$ | H | H | C—H | C—H | C—Cl | C—H | O | H | CH$_2$CF$_3$ | 4.7 | 577 |
| I-T3-3 | C—CH$_3$ | C—H | C—i-C$_3$F$_7$ | C—H | C—CH$_3$ | H | H | C—H | C—H | C—Cl | C—H | O | H | 1-(cyano)cyclo-propyl | 4.2 | 559 |
| I-T3-4 | C—CH$_3$ | C—H | C—i-C$_3$F$_7$ | C—H | C—CH$_3$ | H | H | C—H | C—H | C—Cl | C—H | O | H | thietan-3-yl | 4.7 | 566 |
| I-T3-5 | C—CH$_3$ | C—H | C—i-C$_3$F$_7$ | C—H | C—CH$_3$ | H | H | C—H | C—H | C—Cl | C—H | O | H | 1-(trifluoro-methyl)-cyclopropyl | 4.6 | 602 |
| I-T3-6 | C—CH$_3$ | C—H | C—i-C$_3$F$_7$ | C—H | C—CH$_3$ | H | H | C—H | C—H | C—Cl | C—H | O | H | 2-oxo-2-(2,2,2-trifluoroethyl-amino)-ethyl | 4.1 | 633 |
| I-T3-7 | C—CH$_3$ | C—H | C—i-C$_3$F$_7$ | C—H | C—CH$_3$ | H | H | C—H | N | C—H | C—H | O | H | cyclopropyl | 3.4 | 501 |
| I-T3-8 | C—CH$_3$ | C—H | C—i-C$_3$F$_7$ | C—H | C—CH$_3$ | H | H | C—H | N | C—H | C—H | O | H | 1-(cyano)cyclo-propyl | 3.4 | 526 |
| I-T3-9 | C—CH$_3$ | C—H | C—i-C$_3$F$_7$ | C—H | C—CH$_3$ | H | H | C—H | C—H | C—H | C—F | O | H | cyclopropyl | 4.3 | 518 |
| I-T3-10 | C—CH$_3$ | C—H | C—i-C$_3$F$_7$ | C—H | C—CH$_3$ | H | H | C—H | C—H | C—H | C—F | O | H | 1-(cyano)cyclo-propyl | 4.2 | 543 |
| I-T3-11 | C—CH$_3$ | C—H | C—i-C$_3$F$_7$ | C—H | C—CH$_3$ | H | H | C—Cl | C—H | C—F | C—H | O | H | cyclopropyl | 4.9 | 552 |
| I-T3-12 | C—CH$_3$ | C—H | C—i-C$_3$F$_7$ | C—H | C—CH$_3$ | H | H | C—Cl | C—H | C—F | C—H | O | H | 1-(cyano)cyclo-propyl | 4.7 | 577 |
| I-T3-13 | C—CH$_3$ | C—H | C—i-C$_3$F$_7$ | C—H | C—CH$_3$ | H | H | C—F | C—H | C—H | C—H | O | H | cyclopropyl | 4.5 | 518 |
| I-T3-14 | C—CH$_3$ | C—H | C—i-C$_3$F$_7$ | C—H | C—CH$_3$ | H | H | C—F | C—H | C—Cl | C—H | O | H | cyclopropyl | 4.5 | 552 |
| I-T3-15 | C—CH$_3$ | C—H | C—i-C$_3$F$_7$ | C—H | C—CH$_3$ | H | H | C—H | C—CF$_3$ | C—H | C—H | O | H | cyclopropyl | 4.9 | 568 |
| I-T3-16 | C—CH$_3$ | C—H | C—i-C$_3$F$_7$ | C—H | C—CH$_3$ | H | H | C—CH$_3$ | C—H | C—H | C—H | O | H | cyclopropyl | 4.4 | 514 |
| I-T3-17 | C—CH$_3$ | C—H | C—i-C$_3$F$_7$ | C—H | C—CH$_3$ | H | H | C—F | C—H | C—Cl | C—H | O | H | 1-(cyano)cyclo-propyl | 4.4 | 577 |
| I-T3-18 | C—CH$_3$ | C—H | C—i-C$_3$F$_7$ | C—H | C—CH$_3$ | H | H | C—H | C—CF$_3$ | C—H | C—H | O | H | 1-(cyano)cyclo-propyl | 4.7 | 593 |
| I-T3-19 | C—CH$_3$ | C—H | C—i-C$_3$F$_7$ | C—H | C—CH$_3$ | H | H | C—F | C—H | C—H | C—H | O | H | 1-(cyano)cyclo-propyl | 4.3 | 543 |
| I-T3-20 | C—CH$_3$ | C—H | C—i-C$_3$F$_7$ | C—H | C—CH$_3$ | H | H | C—H | N | C—Cl | C—H | O | H | cyclopropyl | 3.8 | 535 |
| I-T3-21 | C—CH$_3$ | C—H | C—i-C$_3$F$_7$ | C—H | C—CH$_3$ | H | H | C—H | N | C—Cl | C—H | O | H | 1-(cyano)cyclo-propyl | 3.7 | 560 |
| I-T3-22 | C—Cl | C—H | C—i-C$_3$F$_7$ | C—H | C—Cl | H | H | C—H | C—H | C—H | C—F | O | H | 1-(cyano)cyclo-propyl | 4.1 | 583 |
| I-T3-23 | C—CH$_3$ | C—H | C—i-C$_3$F$_7$ | C—H | C—CH$_3$ | H | H | C—H | C—H | C—Cl | C—H | O | H | 1-(cyano)cyclo-propyl | 4.2 | 599 |
| I-T3-24 | C—CH$_3$ | C—H | C—i-C$_3$F$_7$ | C—H | C—CH$_3$ | H | H | C—H | C—H | C—Cl | C—H | O | H | cyclopropyl | 4.3 | 574 |
| I-T3-25 | C—CH$_3$ | C—H | C—i-C$_3$F$_7$ | C—H | C—CH$_3$ | H | H | C—H | C—H | C—Cl | C—H | O | H | CH$_2$CF$_3$ | 4.7 | 616 |
| I-T3-26 | C—CH$_3$ | C—H | C—i-C$_3$F$_7$ | C—H | C—CH$_3$ | H | H | C—H | C—H | C—Cl | C—H | O | H | CH$_2$CH$_2$CF$_3$ | 4.7 | 630 |
| I-T3-27 | C—CH$_3$ | C—H | C—CF$_3$ | C—H | C—CH$_3$ | H | H | C—H | C—H | C—Cl | C—H | O | H | 1-(cyano)cyclo-propyl | 3.4 | 499 |

TABLE I-T3-continued

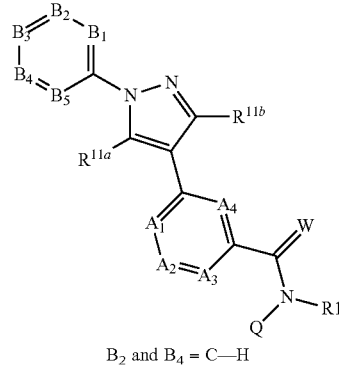

B2 and B4 = C—H

| Ex. No. | B1 | B2 | B3 | B4 | B5 | R11a | R11b | A1 | A2 | A3 | A4 | W | R1 | Q | logP | Mass [m/z] |
|---|---|---|---|---|---|---|---|---|---|---|---|---|---|---|---|---|
| I-T3-28 | C—CH3 | C—H | C—CF3 | C—H | C—CH3 | H | H | C—H | C—H | C—Cl | C—H | O | H | cyclopropyl | 3.5 | 474 |
| I-T3-29 | C—CH3 | C—H | C—i-C3F7 | C—H | C—CH3 | H | H | C—H | N | C—H | C—H | O | H | cyclopropyl | 3.3 | 541 |
| I-T3-30 | C—CH3 | C—H | C—i-C3F7 | C—H | C—CH3 | H | H | C—H | N | C—H | C—H | O | H | 1-(cyano)cyclopropyl | 3.2 | 566 |
| I-T3-31 | C—Cl | C—H | C—i-C3F7 | C—H | C—H | H | H | C—H | C—H | C—Cl | C—H | O | H | cyclopropyl | 4.3 | 540 |
| I-T3-32 | C—Cl | C—H | C—i-C3F7 | C—H | C—H | H | H | C—H | C—H | C—Cl | C—H | O | H | CH2CF3 | 4.7 | 582 |
| I-T3-33 | C—Cl | C—H | C—i-C3F7 | C—H | C—H | H | H | C—H | C—H | C—Cl | C—H | O | H | CH2CH2CF3 | 4.7 | 596 |
| I-T3-34 | C—OCF3 | C—H | C—i-C3F7 | C—H | C—H | H | H | C—H | C—H | C—Cl | C—H | O | H | 1-(cyano)cyclopropyl | 4.6 | 615 |
| I-T3-35 | C—OCF3 | C—H | C—i-C3F7 | C—H | C—H | H | H | C—H | C—H | C—Cl | C—H | O | H | cyclopropyl | 4.7 | 590 |
| I-T3-36 | C—OCF3 | C—H | C—i-C3F7 | C—H | C—H | H | H | C—H | C—H | C—Cl | C—H | O | H | CH2CF3 | 5.0 | 632 |
| I-T3-37 | C—OCF3 | C—H | C—i-C3F7 | C—H | C—H | H | H | C—H | C—H | C—Cl | C—H | O | H | thietan-3-yl | 4.9 | 622 |
| I-T3-38 | C—C2H5 | C—H | C—i-C3F7 | C—H | C—H | H | H | C—H | C—H | C—Cl | C—H | O | H | 1-(cyano)cyclopropyl | 4.5 | 559 |
| I-T3-39 | C—C2H5 | C—H | C—i-C3F7 | C—H | C—H | H | H | C—H | C—H | C—Cl | C—H | O | H | cyclopropyl | 4.6 | 534 |
| I-T3-40 | C—C2H5 | C—H | C—i-C3F7 | C—H | C—H | H | H | C—H | C—H | C—Cl | C—H | O | H | CH2CF3 | 4.9 | 576 |
| I-T3-41 | C—C2H5 | C—H | C—i-C3F7 | C—H | C—H | H | H | C—H | C—H | C—Cl | C—H | O | H | thietan-3-yl | 4.9 | 566 |
| I-T3-42 | C—Cl | C—H | C—i-C3F7 | C—H | C—Cl | H | H | C—H | N | C—Cl | C—H | O | H | cyclopropyl | 3.8 | 575 |
| I-T3-43 | C—Cl | C—H | C—i-C3F7 | C—H | C—Cl | H | H | C—H | N | C—Cl | C—H | O | H | 1-(cyano)cyclopropyl | 3.8 | 600 |
| I-T3-44 | C—C2H5 | C—H | C—i-C3F7 | C—H | C—CH3 | H | H | C—H | C—H | C—Cl | C—H | O | H | cyclopropyl | 4.7 | 548 |
| I-T3-45 | C—C2H5 | C—H | C—i-C3F7 | C—H | C—CH3 | H | H | C—H | C—H | C—Cl | C—H | O | H | CH2CF3 | 5.0 | 590 |
| I-T3-46 | C—C2H5 | C—H | C—i-C3F7 | C—H | C—CH3 | H | H | C—H | C—H | C—Cl | C—H | O | H | 1-(cyano)cyclopropyl | 4.6 | 573 |
| I-T3-47 | C—C2H5 | C—H | C—i-C3F7 | C—H | C—CH3 | H | H | C—H | C—H | C—Cl | C—H | O | H | thietan-3-yl | 5.0 | 580 |
| I-T3-48 | C—F | C—H | C—CF3 | C—H | C—F | H | H | C—H | C—H | C—Cl | C—H | O | H | cyclopropyl | 3.2 | 442 |
| I-T3-49 | C—F | C—H | C—CF3 | C—H | C—F | H | H | C—H | C—H | C—Cl | C—H | O | H | 1-(cyano)cyclopropyl | 3.2 | 467 |
| I-T3-50 | C—F | C—H | C—CF3 | C—H | C—OCH3 | H | H | C—H | C—H | C—Cl | C—H | O | H | cyclopropyl | 3.1 | 454 |
| I-T3-51 | C—F | C—H | C—CF3 | C—H | C—OCH3 | H | H | C—H | C—H | C—Cl | C—H | O | H | 1-(cyano)cyclopropyl | 3.1 | 479 |
| I-T3-52 | C—CF3 | C—H | C—i-C3F7 | C—H | C—H | H | H | C—H | C—H | C—Cl | C—H | O | H | cyclopropyl | 4.3 | 574 |
| I-T3-53 | C—CF3 | C—H | C—i-C3F7 | C—H | C—H | H | H | C—H | C—H | C—Cl | C—H | O | H | 1-(cyano)cyclopropyl | 4.3 | 599 |
| I-T3-54 | C—CF3 | C—H | C—i-C3F7 | C—H | C—CH3 | H | H | C—H | C—H | C—Cl | C—H | O | H | cyclopropyl | 4.4 | 588 |
| I-T3-55 | C—CF3 | C—H | C—i-C3F7 | C—H | C—CH3 | H | H | C—H | C—H | C—Cl | C—H | O | H | 1-(cyano)cyclopropyl | 4.3 | 613 |

TABLE I-T3-continued

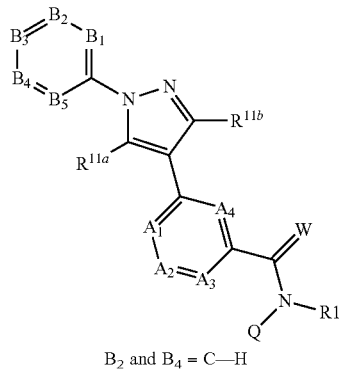

B2 and B4 = C—H

| Ex. No. | B1 | B2 | B3 | B4 | B5 | R11a | R11b | A1 | A2 | A3 | A4 | W | R1 | Q | logP<sup>a)</sup> | Mass [m/z]<sup>a)1)</sup> |
|---|---|---|---|---|---|---|---|---|---|---|---|---|---|---|---|---|
| I-T3-56 | C—CF3 | C—H | C—i-C3F7 | C—H | C—Cl | H | H | C—H | C—H | C—Cl | C—H | O | H | cyclopropyl | 4.4 | 608 |
| I-T3-57 | C—CF3 | C—H | C—i-C3F7 | C—H | C—Cl | H | H | C—H | C—H | C—Cl | C—H | O | H | 1-(cyano)cyclo-propyl | 4.3 | 633 |
| I-T3-58 | C—CF3 | C—H | C—i-C3F7 | C—H | C—Cl | H | H | C—H | C—H | C—Cl | C—H | O | H | CH2CF3 | 4.7 | 650 |
| I-T3-59 | C—Cl | C—H | C—CF3 | C—H | N | H | H | C—H | C—H | C—Cl | C—H | O | H | 1-(cyano)cyclo-propyl | 3.1 | 466 |
| I-T3-60 | C—Cl | C—H | C—CF3 | C—H | N | H | H | C—H | C—H | C—Cl | C—H | O | H | cyclopropyl | 3.2 | 441 |
| I-T3-61 | C—F | C—H | C—i-C3F7 | C—H | C—F | H | H | C—H | C—H | C—Cl | C—H | O | H | cyclopropyl | 4.0 | 542 |
| I-T3-62 | C—F | C—H | C—i-C3F7 | C—H | C—F | H | H | C—H | C—H | C—Cl | C—H | O | H | 1-(cyano)cyclo-propyl | 3.9 | 567 |
| I-T3-63 | C—CH3 | C—H | C—i-C3F7 | C—H | C—Cl | H | H | C—H | C—H | C—Cl | C—H | O | H | cyclopropyl | 4.4 | 554 |
| I-T3-64 | C—CH3 | C—H | C—i-C3F7 | C—H | C—Cl | H | H | C—H | C—H | C—Cl | C—H | O | H | 1-(cyano)cyclo-propyl | 4.2 | 579 |
| I-T3-65 | C—CH3 | C—H | C—i-C3F7 | C—H | C—CH3 | H | H | C—H | C—H | C—Cl | C—F | O | H | 1-(cyano)cyclo-propyl | 4.3 | 577 |
| I-T3-66 | C—C2H5 | C—H | C—i-C3F7 | C—H | C—CH3 | H | H | C—H | C—H | C—Cl | C—F | O | H | 1-(cyano)cyclo-propyl | 4.6 | 591 |
| I-T3-67 | C—CH3 | C—H | C—i-C3F7 | C—H | C—CH3 | H | H | C—H | C—H | C—Cl | C—F | O | H | cyclopropyl | 4.4 | 552 |
| I-T3-68 | C—C2H5 | C—H | C—i-C3F7 | C—H | C—CH3 | H | H | C—H | C—H | C—Cl | C—F | O | H | cyclopropyl | 4.8 | 566 |
| I-T3-69 | C—C2H5 | C—H | C—i-C3F7 | C—H | C—CH3 | H | H | C—H | C—H | C—H | C—F | O | H | 1-(cyano)cyclo-propyl | 4.5 | 557 |
| I-T3-70 | C—C2H5 | C—H | C—i-C3F7 | C—H | C—CH3 | H | H | C—H | C—H | C—H | C—F | O | H | cyclopropyl | 4.7 | 532 |
| I-T3-71 | C—C2H5 | C—H | C—i-C3F7 | C—H | C—Cl | H | H | C—H | C—H | C—Cl | C—H | O | H | 1-(cyano)cyclo-propyl | 4.5 | 593 |
| I-T3-72 | C—C2H5 | C—H | C—i-C3F7 | C—H | C—Cl | H | H | C—H | C—H | C—Cl | C—H | O | H | cyclopropyl | 4.6 | 568 |
| I-T3-73 | C—Cl | C—H | C—i-C3F7 | C—H | C—Cl | H | H | C—H | C—H | C—Cl | C—F | O | H | cyclopropyl | 4.5 | 592 |
| I-T3-74 | C—C2H5 | C—H | C—i-C3F7 | C—H | C—H | H | H | C—H | C—H | C—H | C—F | O | H | 1-(cyano)cyclo-propyl | 4.5 | 543 |
| I-T3-75 | C—C2H5 | C—H | C—i-C3F7 | C—H | C—H | H | H | C—H | C—H | C—H | C—F | O | H | cyclopropyl | 4.7 | 518 |
| I-T3-76 | C—C2H5 | C—H | C—i-C3F7 | C—H | C—CH3 | H | H | C—H | N | C—H | C—H | O | H | 1-(cyano)cyclo-propyl | 3.4 | 540 |
| I-T3-77 | C—C2H5 | C—H | C—i-C3F7 | C—H | C—CH3 | H | H | C—H | N | C—H | C—H | O | H | cyclopropyl | 3.4 | 515 |
| I-T3-78 | C—C2H5 | C—H | C—i-C3F7 | C—H | C—H | H | H | C—H | N | C—H | C—H | O | H | 1-(cyano)cyclo-propyl | 3.8 | 526 |
| I-T3-79 | C—C2H5 | C—H | C—i-C3F7 | C—H | C—H | H | H | C—H | N | C—H | C—H | O | H | cyclopropyl | 3.3 | 501 |
| I-T3-80 | C—C2H5 | C—H | C—C2F5 | C—H | C—CH3 | H | H | C—H | C—H | C—Cl | C—H | O | H | 1-(cyano)cyclo-propyl | 4.2 | 523 |
| I-T3-81 | C—C2H5 | C—H | C—C2F5 | C—H | C—CH3 | H | H | C—H | C—H | C—Cl | C—H | O | H | cyclopropyl | 4.3 | 498 |
| I-T3-82 | C—C2H5 | C—H | C—C2F5 | C—H | C—CH3 | H | H | C—H | C—H | C—Cl | C—H | O | H | CH2CF3 | 4.0 | 540 |
| I-T3-83 | C—C2H5 | C—H | C—C2F5 | C—H | C—CH3 | H | H | C—H | C—H | C—Cl | C—H | O | H | thietan-3-yl | 4.6 | 530 |

TABLE I-T3-continued

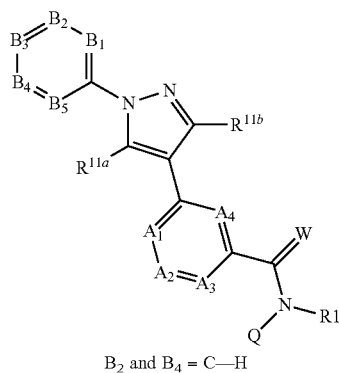

$B_2$ and $B_4$ = C—H

| Ex. No. | $B_1$ | $B_2$ | $B_3$ | $B_4$ | $B_5$ | $R^{11a}$ | $R^{11b}$ | $A_1$ | $A_2$ | $A_3$ | $A_4$ | W | R1 | Q | logP[a)] | Mass [m/z][a)1] |
|---|---|---|---|---|---|---|---|---|---|---|---|---|---|---|---|---|
| I-T3-84 | C—CF$_3$ | C—H | C—i-C$_3$F$_7$ | C—H | C—CH$_3$ | H | H | C—H | C—H | C—Cl | C—H | O | H | CH$_2$CF$_3$ | 4.7 | 630 |
| I-T3-85 | C—CF$_3$ | C—H | C—i-C$_3$F$_7$ | C—H | C—CH$_3$ | H | H | C—H | C—H | C—Cl | C—H | O | H | thietan-3-yl | 4.7 | 620 |
| I-T3-86 | C—CH$_3$ | C—H | C—i-C$_3$F$_7$ | C—H | C—Br | H | H | C—H | C—H | C—Cl | C—H | O | H | cyclopropyl | 4.5 | 598 |
| I-T3-87 | C—Cl | C—H | C—OCF$_3$ | C—H | C—Cl | H | H | C—H | C—H | C—Cl | C—H | O | H | 1-(cyano)cyclopropyl | 3.6 | 515 |
| I-T3-88 | C—Cl | C—H | C—OCF$_3$ | C—H | C—Cl | H | H | C—H | C—H | C—Cl | C—H | O | H | cyclopropyl | 3.6 | 490 |
| I-T3-89 | C—Cl | C—H | C—OCF$_3$ | C—H | C—H | H | H | C—H | C—H | C—Cl | C—H | O | H | 1-(cyano)cyclopropyl | 3.5 | 481 |
| I-T3-90 | C—Cl | C—H | C—OCF$_3$ | C—H | C—H | H | H | C—H | C—H | C—Cl | C—H | O | H | cyclopropyl | 3.6 | 456 |
| I-T3-91 | C—Cl | C—H | C—i-C$_3$F$_7$ | C—H | C—Cl | H | H | C—H | N | C—CH$_3$ | C—H | O | H | cyclopropyl | 3.3 | 555 |
| I-T3-92 | C—Cl | C—H | C—i-C$_3$F$_7$ | C—H | C—Cl | H | H | C—H | N | C—CH$_3$ | C—H | O | H | 1-(cyano)cyclopropyl | 3.4 | 580 |
| I-T3-93 | C—Cl | C—H | C—i-C$_3$F$_7$ | C—H | C—Cl | H | H | C—H | C—H | C—Cl | C—H | O | H | 1-(tert.butyl)cyclopropyl | 4.7 | 588 |
| I-T3-94 | C—CF$_3$ | C—H | C—i-C$_3$F$_7$ | C—H | C—CH$_3$ | H | H | C—H | C—H | C—Cl | C—H | O | H | 1-(tert.butyl)cyclopropyl | 4.7 | 602 |
| I-T3-95 | C—Cl | C—H | C—CF$_3$ | C—H | C—Cl | H | H | C—H | N | C—Cl | C—H | O | H | 1-(cyano)cyclopropyl | 3.1 | 500 |
| I-T3-96 | C—CH$_3$ | C—H | C—i-C$_3$F$_7$ | C—H | C—CH$_3$ | H | H | C—H | N | C—CH$_3$ | C—H | O | H | cyclopropyl | 3.3 | 515 |
| I-T3-97 | C—CH$_3$ | C—H | C—i-C$_3$F$_7$ | C—H | C—CH$_3$ | H | H | C—H | N | C—CH$_3$ | C—H | O | H | 1-(cyano)cyclopropyl | 3.4 | 540 |
| I-T3-98 | C—Cl | C—H | C—CF$_3$ | C—H | C—Cl | H | H | C—H | N | C—Cl | C—H | O | H | cyclopropyl | 3.1 | 475 |
| I-T3-99 | C—Cl | C—H | C—CF$_3$ | C—H | C—Cl | H | H | C—H | N | C—Cl | C—H | O | CH$_3$ | cyclopropyl | 3.5 | 489 |
| I-T3-100 | C—Cl | C—H | C—i-C$_3$F$_7$ | C—H | C—Cl | H | H | C—H | N | C—Cl | C—H | O | CH$_3$ | cyclopropyl | 4.4 | 589 |
| I-T3-101 | C—CH$_3$ | C—H | C—i-C$_3$F$_7$ | C—H | C—CH$_3$ | H | H | C—H | N | C—Cl | C—H | O | CH$_3$ | cyclopropyl | 4.4 | 549 |
| I-T3-102 | C—Cl | C—H | C—i-C$_3$F$_7$ | C—H | C—Cl | H | H | C—H | N | C—Cl | C—H | O | CH$_3$ | 1-(cyano)cyclopropyl | 4.3 | 614 |
| I-T3-103 | C—CH$_3$ | C—H | C—i-C$_3$F$_7$ | C—H | C—CH$_3$ | H | H | C—H | N | C—Cl | C—H | O | CH$_3$ | 1-(cyano)cyclopropyl | 4.3 | 574 |
| I-T3-104 | C—C$_2$H$_5$ | C—H | C—i-C$_3$F$_7$ | C—H | C—H | H | H | C—H | N | C—Cl | C—H | O | H | cyclopropyl | 4.2 | 535 |
| I-T3-105 | C—C$_2$H$_5$ | C—H | C—i-C$_3$F$_7$ | C—H | C—H | H | H | C—H | N | C—Cl | C—H | O | H | 1-(cyano)cyclopropyl | 4.1 | 560 |
| I-T3-106 | C—CF$_3$ | C—H | C—i-C$_3$F$_7$ | C—H | C—CH$_3$ | H | H | C—H | N | C—Cl | C—H | O | H | cyclopropyl | 4.0 | 589 |
| I-T3-107 | C—CF$_3$ | C—H | C—i-C$_3$F$_7$ | C—H | C—CH$_3$ | H | H | C—H | N | C—Cl | C—H | O | CH$_3$ | cyclopropyl | 4.5 | 603 |
| I-T3-108 | C—CF$_3$ | C—H | C—i-C$_3$F$_7$ | C—H | C—CH$_3$ | H | H | C—H | N | C—Cl | C—H | O | H | 1-(cyano)cyclopropyl | 4.0 | 614 |
| I-T3-109 | C—C$_2$H$_5$ | C—H | C—i-C$_3$F$_7$ | C—H | C—CH$_3$ | H | H | C—H | N | C—Cl | C—H | O | H | cyclopropyl | 4.2 | 549 |

TABLE I-T3-continued

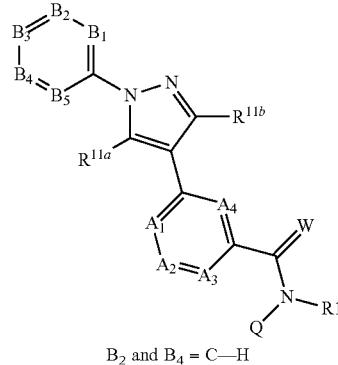

B₂ and B₄ = C—H

| Ex. No. | B₁ | B₂ | B₃ | B₄ | B₅ | $R^{11a}$ | $R^{11b}$ | A₁ | A₂ | A₃ | A₄ | W | R1 | Q | logP$^{a)}$ | Mass [m/z]$^{a)1)}$ |
|---|---|---|---|---|---|---|---|---|---|---|---|---|---|---|---|---|
| I-T3-110 | C—C₂H₅ | C—H | C—i-C₃F₇ | C—H | C—CH₃ | H | H | C—H | N | C—Cl | C—H | O | H | 1-(cyano)cyclopropyl | 4.1 | 574 |
| I-T3-111 | C—CF₃ | C—H | C—i-C₃F₇ | C—H | C—CH₃ | H | H | C—H | N | C—Cl | C—H | O | CH₃ | 1-(cyano)cyclopropyl | 4.4 | 628 |
| I-T3-112 | C—CF₃ | C—H | C—i-C₃F₇ | C—H | C—Cl | H | H | C—H | N | C—Cl | C—H | O | H | cyclopropyl | 4.0 | 609 |
| I-T3-113 | C—CF₃ | C—H | C—i-C₃F₇ | C—H | C—Cl | H | H | C—H | N | C—Cl | C—H | O | CH₃ | cyclopropyl | 4.0 | 623 |
| I-T3-114 | C—CF₃ | C—H | C—i-C₃F₇ | C—H | C—Cl | H | H | C—H | N | C—Cl | C—H | O | H | 1-(cyano)cyclopropyl | 4.0 | 634 |
| I-T3-115 | C—CH₃ | C—H | C—i-C₃F₇ | C—H | C—CH₃ | H | H | C—H | N | C—CH₃ | C—H | O | CH₃ | 1-(cyano)cyclopropyl | 3.8 | 554 |
| I-T3-116 | C—CF₃ | C—H | C—i-C₃F₇ | C—H | C—Cl | H | H | C—H | N | C—Cl | C—H | O | CH₃ | 1-(cyano)cyclopropyl | 4.3 | 648 |
| I-T3-117 | C—CF₃ | C—H | C—i-C₃F₇ | C—H | C—CH₃ | H | H | C—H | N | C—CH₃ | C—H | O | H | cyclopropyl | 3.5 | 569 |
| I-T3-118 | C—CF₃ | C—H | C—i-C₃F₇ | C—H | C—CH₃ | H | H | C—H | N | C—CH₃ | C—H | O | CH₃ | cyclopropyl | 3.8 | 583 |
| I-T3-119 | C—CF₃ | C—H | C—i-C₃F₇ | C—H | C—CH₃ | H | H | C—H | N | C—CH₃ | C—H | O | H | 1-(cyano)cyclopropyl | 3.6 | 594 |
| I-T3-120 | C—CH₃ | C—H | C—i-C₃F₇ | C—H | C—CH₃ | H | H | C—H | N | C—CH₃ | C—H | O | CH₃ | cyclopropyl | 3.6 | 529 |
| I-T3-121 | C—CH₃ | C—H | C—i-C₃F₇ | C—H | C—CH₃ | H | H | N | C—H | C—Cl | N | O | H | cyclopropyl | 4.5 | 536 |
| I-T3-122 | C—Cl | C—H | C—CF₃ | C—H | N | H | H | C—H | C—H | C—H | C—H | O | H | cyclopropyl | 3.0 | 407 |
| I-T3-123 | C—CF₃ | C—H | C—i-C₃F₇ | C—H | C—CH₃ | H | H | C—H | N | C—CH₃ | C—H | O | CH₃ | 1-(cyano)cyclopropyl | 3.9 | 608 |
| I-T3-124 | C—CF₃ | C—H | C—i-C₃F₇ | C—H | C—Cl | H | H | C—H | N | C—CH₃ | C—H | O | H | cyclopropyl | 3.5 | 589 |
| I-T3-125 | C—CF₃ | C—H | C—i-C₃F₇ | C—H | C—Cl | H | H | C—H | N | C—CH₃ | C—H | O | H | 1-(cyano)cyclopropyl | 3.8 | 614 |
| I-T3-126 | C—Cl | C—H | C—i-C₃F₇ | C—H | C—Cl | CN | NH₂ | C—H | C—H | C—Cl | C—H | O | H | 1-(cyano)cyclopropyl | 4.1 | 639 |
| I-T3-127 | C—Cl | C—H | C—CF₃ | C—H | C—Cl | H | H | C—H | N | C—CH₃ | C—H | O | H | cyclopropyl | 2.5 | 455 |
| I-T3-128 | C—Cl | C—H | C—CF₃ | C—H | C—Cl | H | H | C—H | N | C—CH₃ | C—H | O | CH₃ | cyclopropyl | 2.8 | 469 |
| I-T3-129 | C—Cl | C—H | C—CF₃ | C—H | C—Cl | H | H | C—H | N | C—CH₃ | C—H | O | H | 1-(cyano)cyclopropyl | 2.6 | 480 |
| I-T3-130 | C—CF₃ | C—H | C—i-C₃F₇ | C—H | C—Cl | H | H | C—H | N | C—CH₃ | C—H | O | CH₃ | cyclopropyl | 3.8 | 603 |
| I-T3-131 | C—CF₃ | C—H | C—i-C₃F₇ | C—H | C—Cl | H | H | C—H | N | C—CH₃ | C—H | O | CH₃ | 1-(cyano)cyclopropyl | 3.9 | 628 |
| I-T3-132 | C—Cl | C—H | C—CF₃ | C—H | C—Cl | H | H | C—H | N | C—CH₃ | C—H | O | CH₃ | 1-(cyano)cyclopropyl | 2.9 | 494 |
| I-T3-133 | C—Cl | C—H | C—i-C₃F₇ | C—H | C—Cl | H | H | C—H | N | C—CH₃ | C—H | O | CH₃ | cyclopropyl | 3.7 | 569 |
| I-T3-134 | C—CF₃ | C—H | C—i-C₃F₇ | C—H | C—H | H | H | C—H | C—H | C—Cl | C—H | O | CH₃ | cyclopropyl | 4.9 | 588 |
| I-T3-135 | C—Cl | C—H | C—i-C₃F₇ | C—H | C—Cl | H | H | C—H | N | C-(1-pyrrolidinyl) | C—H | O | H | cyclopropyl | 4.3 | 610 |
| I-T3-136 | C—Cl | C—H | C—i-C₃F₇ | C—H | C—Cl | H | H | C—H | N | C—NHCH₃ | C—H | O | H | cyclopropyl | 3.5 | 570 |

TABLE I-T3-continued

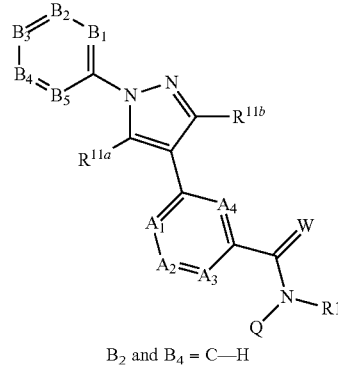

B₂ and B₄ = C—H

| Ex. No. | B₁ | B₂ | B₃ | B₄ | B₅ | $R^{11a}$ | $R^{11b}$ | A₁ | A₂ | A₃ | A₄ | W | R1 | Q | logP$^{a)}$ | Mass [m/z]$^{a)1)}$ |
|---|---|---|---|---|---|---|---|---|---|---|---|---|---|---|---|---|
| I-T3-137 | C—Cl | C—H | C—i-C₃F₇ | C—H | C—Cl | H | H | C—H | N | C—NH-cyclopropyl | C—H | O | H | cyclopropyl | 3.4 | 596 |
| I-T3-138 | C—Cl | C—H | C—i-C₃F₇ | C—H | C—Cl | H | H | C—H | N | C—NH—CH₂CH₂OCH₃ | C—H | O | H | cyclopropyl | 4.1 | 614 |
| I-T3-139 | C—CH₃ | C—H | C—i-C₃F₇ | C—H | C—CH₃ | H | H | C—H | N | C-cyclopropyl | C—H | O | H | 1-(cyano)cyclopropyl | 4.1 | 566 |
| I-T3-140 | C—CH₃ | C—H | C—i-C₃F₇ | C—H | C—CH₃ | H | H | C—H | N | C-cyclopropyl | C—H | O | H | cyclopropyl | 4.2 | 541 |
| I-T3-141 | C—CH₃ | C—H | C—i-C₃F₇ | C—H | C—CH₃ | H | H | C—H | N | C—OCH₃ | C—H | O | H | 1-(cyano)cyclopropyl | 4.4 | 556 |
| I-T3-142 | C—CH₃ | C—H | C—i-C₃F₇ | C—H | C—CH₃ | H | H | C—H | N | C-cyclopropyl | C—H | O | CH₃ | cyclopropyl | 4.6 | 555 |
| I-T3-143 | C—CH₃ | C—H | C—i-C₃F₇ | C—H | C—CH₃ | H | H | C—H | N | C—OCH₃ | C—H | O | H | cyclopropyl | 4.6 | 531 |
| I-T3-144 | C—CH₃ | C—H | C—i-C₃F₇ | C—H | C—CH₃ | H | H | C—H | N | C—OCH₃ | C—H | O | CH₃ | cyclopropyl | 4.4 | 545 |
| I-T3-145 | C—Cl | C—H | C—CF₃ | C—H | C—Cl | H | H | C—H | N | C—Cl | C—H | O | C₂H₅ | cyclopropyl | 3.8 | 503 |
| I-T3-146 | C—Cl | C—H | C—CF₃ | C—H | C—Cl | H | H | C—H | N | C—Cl | C—H | O | H | N-methyl-pyrazol-3-yl | 2.8 | 515 |
| I-T3-147 | C—Cl | C—H | C—CF₃ | C—H | C—Cl | H | H | C—H | N | C—CH₃ | C—H | O | H | C₂H₅ | 4.0 | 443 |
| I-T3-148 | C—CF₃ | C—H | C—i-C₃F₇ | C—H | C—Br | H | H | C—H | C—H | C—Cl | C—H | O | H | cyclopropyl | 4.5 | 652 |
| I-T3-149 | C—CF₃ | C—H | C—CF₃ | C—H | N | H | H | C—H | C—H | C—Cl | C—H | O | H | 1-(cyano)cyclopropyl | 3.5 | 500 |
| I-T3-150 | C—CF₃ | C—H | C—CF₃ | C—H | N | H | H | C—H | C—H | C—Cl | C—H | O | H | cyclopropyl | 3.6 | 475 |
| I-T3-151 | C—Cl | C—H | C—i-C₃F₇ | C—H | N | H | H | C—H | C—H | C—Cl | C—H | O | H | 1-(cyano)cyclopropyl | 4.0 | 566 |
| I-T3-152 | C—Cl | C—H | C—i-C₃F₇ | C—H | N | H | H | C—H | C—H | C—Cl | C—H | O | H | cyclopropyl | 4.1 | 541 |
| I-T3-153 | C—S(O)C₂H₅ | C—H | C—i-C₃F₇ | C—H | N | H | H | C—H | C—H | C—Cl | C—H | O | H | 1-(cyano)cyclopropyl | 3.7 | 608 |
| I-T3-154 | C—S(O₂)C₂H₅ | C—H | C—i-C₃F₇ | C—H | N | H | H | C—H | C—H | C—Cl | C—H | O | H | 1-(cyano)cyclopropyl | 3.8 | 624 |
| I-T3-155 | C—CF₃ | C—H | C—i-C₃F₇ | C—H | C—Br | H | H | C—H | C—H | C—Cl | C—H | O | H | 1-(cyano)cyclopropyl | 4.4 | 677 |
| I-T3-156 | C—SC₂H₅ | C—H | C—i-C₃F₇ | C—H | N | H | H | C—H | C—H | C—Cl | C—H | O | H | cyclopropyl | 4.7 | 567 |
| I-T3-157 | C—S(O)C₂H₅ | C—H | C—i-C₃F₇ | C—H | N | H | H | C—H | C—H | C—Cl | C—H | O | H | cyclopropyl | 3.8 | 583 |
| I-T3-158 | C—S(O₂)C₂H₅ | C—H | C—i-C₃F₇ | C—H | N | H | H | C—H | C—H | C—Cl | C—H | O | H | cyclopropyl | 3.9 | 599 |
| I-T3-159 | C—CF₃ | C—H | C—i-C₃F₇ | C—H | C—Cl | H | H | C—H | N | C—Cl | C—H | O | H | 1-(thiocarbamoyl)-cyclopropyl | 3.8 | 668 |
| I-T3-160 | C—CF₃ | C—H | C—i-C₃F₇ | C—H | C—Br | H | H | C—H | N | C—Cl | C—H | O | H | cyclopropyl | 4.0 | 653 |
| I-T3-161 | C—CF₃ | C—H | C—i-C₃F₇ | C—H | C—CH₃ | H | H | C—H | N | C—Cl | C—H | O | H | cyclopropyl | 5.0 | 604 |
| I-T3-162 | C—OCF₃ | C—H | C—i-C₃F₇ | C—H | C—Cl | H | H | C—H | N | C—Cl | C—H | O | H | cyclopropyl | 4.6 | 624 |

TABLE I-T3-continued

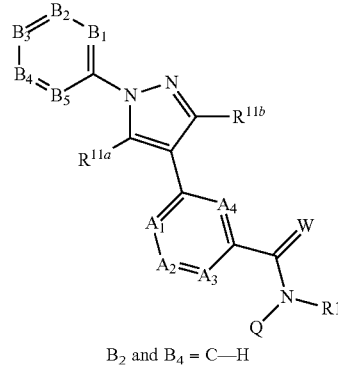

B2 and B4 = C—H

| Ex. No. | B1 | B2 | B3 | B4 | B5 | R11a | R11b | A1 | A2 | A3 | A4 | W | R1 | Q | logP[a] | Mass [m/z][a)1] |
|---|---|---|---|---|---|---|---|---|---|---|---|---|---|---|---|---|
| I-T3-163 | C—OCF3 | C—H | C—i-C3F7 | C—H | C—Cl | H | H | C—H | C—H | C—Cl | C—H | O | H | 1-(cyano)cyclopropyl | 4.5 | 649 |
| I-T3-164 | C—Cl | C—H | C—i-C3F7 | C—H | C—CN | H | H | C—H | C—H | C—Cl | C—H | O | H | 1-(cyano)cyclopropyl | 3.1 | 490 |
| I-T3-165 | C—CF3 | C—H | C—i-C3F7 | C—H | C—Br | H | H | C—H | N | C—Cl | C—H | O | H | 1-(cyano)cyclopropyl | 3.9 | 678 |
| I-T3-166 | C—SCH3 | C—H | C—i-C3F7 | C—H | N | H | H | C—H | C—H | C—Cl | C—H | O | H | 1-(cyano)cyclopropyl | 4.3 | 578 |
| I-T3-167 | C—Cl | C—H | C—i-C3F7 | C—H | N | H | H | C—H | C—H | C—Cl | C—H | O | H | 1-(cyano)cyclopropyl | 4.6 | 592 |
| I-T3-168 | C—Cl | C—H | C—CF3 | C—H | C—NO2 | H | H | C—H | C—H | C—Cl | C—H | O | H | 1-(cyano)cyclopropyl | 3.3 | 485 |
| I-T3-169 | C—Cl | C—H | C—CF3 | C—H | C—NO2 | H | H | C—H | C—H | C—Cl | C—H | O | H | 1-(cyano)cyclopropyl | 3.2 | 510 |
| I-T3-170 | C—SC2H5 | C—H | C—CF3 | C—H | C—Cl | H | H | C—H | C—H | C—Cl | C—H | O | H | 1-(cyano)cyclopropyl | 3.7 | 525 |
| I-T3-171 | C—SCH2CF3 | C—H | C—i-C3F7 | C—H | N | H | H | C—H | C—H | C—Cl | C—H | O | H | 1-(cyano)cyclopropyl | 4.5 | 646 |
| I-T3-172 | C—SC2H5 | C—H | C—CF3 | C—H | C—Cl | H | H | C—H | C—H | C—Cl | C—H | O | H | cyclopropyl | 3.9 | 500 |
| I-T3-173 | C—Cl | C—H | C—CF3 | C—H | C—Cl | H | H | C—H | N | C—OCH3 | C—H | O | CH3 | cyclopropyl | 4.4 | 585 |
| I-T3-174 | C—Cl | C—H | C—CF3 | C—H | C—CN | H | H | C—H | C—H | C—Cl | C—H | O | H | cyclopropyl | 3.1 | 465 |
| I-T3-175 | C—CH3 | C—H | C—i-C3F7 | C—H | C—I | H | H | C—H | C—H | C—Cl | C—H | O | H | cyclopropyl | 4.5 | 646 |
| I-T3-176 | C—CH3 | C—H | C—i-C3F7 | C—H | C—I | H | H | C—H | C—H | C—Cl | C—H | O | H | 1-(cyano)cyclopropyl | 4.4 | 671 |
| I-T3-177 | C—SC2H5 | C—H | C—CF3 | C—H | C—CN | H | H | C—H | C—H | C—Cl | C—H | O | H | 1-(cyano)cyclopropyl | 3.4 | 516 |
| I-T3-178 | C—S(O2)C2H5 | C—H | C—CF3 | C—H | C—Cl | H | H | C—H | C—H | C—Cl | C—H | O | H | cyclopropyl | 3.2 | 532 |
| I-T3-179 | C—S(O)C2H5 | C—H | C—CF3 | C—H | C—Cl | H | H | C—H | C—H | C—Cl | C—H | O | H | cyclopropyl | 3.0 | 516 |
| I-T3-180 | C—S(O2)C2H5 | C—H | C—CF3 | C—H | C—CN | H | H | C—H | C—H | C—Cl | C—H | O | H | cyclopropyl | 2.8 | 523 |
| I-T3-181 | C—S(O)C2H5 | C—H | C—CF3 | C—H | C—CN | H | H | C—H | C—H | C—Cl | C—H | O | H | cyclopropyl | 2.7 | 507 |
| I-T3-182 | C—S(O)C2H5 | C—H | C—CF3 | C—H | C—CN | H | H | C—H | C—H | C—Cl | C—H | O | H | 1-(cyano)cyclopropyl | 3.0 | 541 |
| I-T3-183 | C—S(O2)C2H5 | C—H | C—CF3 | C—H | C—Cl | H | H | C—H | C—H | C—Cl | C—H | O | H | 1-(cyano)cyclopropyl | 3.1 | 557 |
| I-T3-184 | C—Cl | C—F | C—CF3 | C—H | C—Cl | H | H | C—H | C—H | C—Cl | C—H | O | H | cyclopropyl | 3.6 | 492 |
| I-T3-185 | C—Cl | C—F | C—CF3 | C—H | C—Cl | H | H | C—H | C—H | C—Cl | C—H | O | H | 1-(cyano)cyclopropyl | 3.6 | 517 |
| I-T3-186 | C—Cl | C—H | C—CF3 | C—H | C—F | H | H | C—H | C—H | C—Cl | C—H | O | H | cyclopropyl | 3.6 | 458 |
| I-T3-187 | C—Cl | C—H | C—CF3 | C—H | C—F | H | H | C—H | C—H | C—Cl | C—H | O | H | 1-(cyano)cyclopropyl | 3.3 | 483 |
| I-T3-188 | C—F | C—F | C—CF3 | C—F | C—F | H | H | C—H | C—H | C—Cl | C—H | O | H | 1-(cyano)cyclopropyl | 3.4 | 503 |
| I-T3-189 | C—OCF3 | C—H | C—i-C3F7 | C—H | Cl | H | H | C—H | N | C—Cl | C—H | O | H | cyclopropyl | 4.3 | 625 |
| I-T3-190 | C—S(O2)C2H5 | C—H | C—CF3 | C—H | C—CN | H | H | C—H | C—H | C—Cl | C—H | O | H | 1-(cyano)cyclopropyl | 2.9 | 548 |

TABLE I-T3-continued

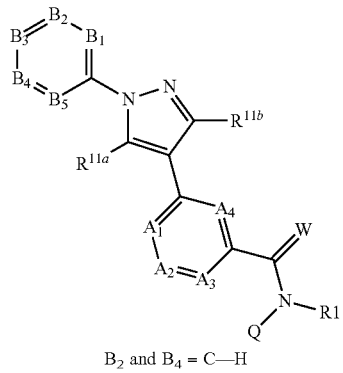

$B_2$ and $B_4$ = C—H

| Ex. No. | $B_1$ | $B_2$ | $B_3$ | $B_4$ | $B_5$ | $R^{11a}$ | $R^{11b}$ | $A_1$ | $A_2$ | $A_3$ | $A_4$ | W | R1 | Q | logP$^{a)}$ | Mass [m/z]$^{a)1)}$ |
|---|---|---|---|---|---|---|---|---|---|---|---|---|---|---|---|---|
| I-T3-191 | C—SC$_2$H$_5$ | C—H | C—i-C$_3$F$_7$ | C—H | C—SC$_2$H$_5$ | H | H | C—H | C—H | C—Cl | C—H | O | H | 1-(cyano)cyclo-propyl | 4.7 | 651 |
| I-T3-192 | C—SC$_2$H$_5$ | C—H | C—i-C$_3$F$_7$ | C—H | C—Cl | H | H | C—H | C—H | C—Cl | C—H | O | H | 1-(cyano)cyclo-propyl | 4.5 | 625 |
| I-T3-193 | C—CHF$_2$ | C—H | C—i-C$_3$F$_7$ | C—H | C—Cl | H | H | C—H | C—H | C—Cl | C—H | O | H | cyclopropyl | 4.4 | 590 |
| I-T3-194 | C—F | C—F | C—CF$_3$ | C—F | C—F | H | H | C—H | C—H | C—Cl | C—H | O | H | 1-(carbamoyl)-cyclopropyl | 2.8 | 521 |
| I-T3-195 | C—S(O)C$_2$H$_5$ | C—H | C—i-C$_3$F$_7$ | C—H | C—Cl | H | H | C—H | C—H | C—Cl | C—H | O | H | 1-(cyano)cyclo-propyl | 3.8 | 641 |
| I-T3-196 | C—OCHF$_2$ | C—H | C—i-C$_3$F$_7$ | C—H | Cl | H | H | C—H | N | C—Cl | C—H | O | H | cyclopropyl | 3.9 | 607 |
| I-T3-197 | C—CF$_3$ | C—H | C—i-C$_3$F$_7$ | C—H | C—CH$_3$ | H | H | C—H | N | C—Cl | C—H | O | H | 1-(cyano)cyclo-propyl)methyl | 4.0 | 628 |
| I-T3-198 | C—S(O$_2$)C$_2$H$_5$ | C—H | C—i-C$_3$F$_8$ | C—H | C—S(O$_2$)C$_2$H$_5$ | H | H | C—H | C—H | C—Cl | C—H | O | H | 1-(cyano)cyclo-propyl | 3.7 | 715 |
| I-T3-199 | C—CF$_3$ | C—H | C—i-C$_3$F$_7$ | C—H | C—Cl | H | H | C—H | C—H | C—Cl | C—H | O | H | 1-cyano-cyclo-propyl)methyl | 1.17 min$^{b)}$ | 648 |
| I-T3-200 | C—OCF$_3$ | C—H | C—i-C$_3$F$_7$ | C—H | C—Cl | H | H | C—H | C—H | C—Cl | C—H | O | H | 1-(cyano)cyclo-propyl | 4.1 | 650 |
| I-T3-201 | C—S(O$_2$)C$_2$H$_5$ | C—H | C—i-C$_3$F$_8$ | C—H | C—Cl | H | H | C—H | C—H | C—Cl | C—H | O | H | 1-(cyano)cyclo-propyl | 4.0 | 657 |
| I-T3-202 | C—SC$_2$H$_5$ | C—H | C—i-C$_3$F$_8$ | C—H | C—CH$_3$ | H | H | C—H | C—H | C—Cl | C—H | O | H | 1-(cyano)cyclo-propyl | 4.5 | 605 |
| I-T3-203 | C—SC$_2$H$_5$ | C—H | C—i-C$_3$F$_8$ | C—H | C—CH$_3$ | H | H | C—H | C—H | C—Cl | C—H | O | H | cyclopropyl | 4.6 | 580 |
| I-T3-204 | C—CN | C—H | C—i-C$_3$F$_7$ | C—H | C—Cl | H | H | C—H | N | C—Cl | C—H | O | CH$_3$ | cyclopropyl | 3.9 | 580 |
| I-T3-205 | C—CN | C—H | C—i-C$_3$F$_7$ | C—H | C—Cl | H | H | C—H | N | C—Cl | C—H | O | H | cyclopropyl | 3.5 | 566 |
| I-T3-206 | C—S(O)C$_2$H$_5$ | C—H | C—i-C$_3$F$_8$ | C—H | C—CH$_3$ | H | H | C—H | C—H | C—Cl | C—H | O | H | 1-(cyano)cyclo-propyl | 3.6 | 621 |
| I-T3-207 | C—CN | C—H | C—i-C$_3$F$_7$ | C—H | C—Cl | H | H | C—H | N | C—Cl | C—H | O | H | 1-(cyano)cyclo-propyl | 3.5 | 591 |
| I-T3-208 | C—OCF$_3$ | C—H | C—i-C$_3$F$_7$ | C—H | C—Cl | H | H | C—H | N | C—Cl | C—H | O | CH$_3$ | cyclopropyl | 4.6 | 639 |
| I-T3-209 | C—S(O$_2$)C$_2$H$_5$ | C—H | C—i-C$_3$F$_8$ | C—H | C—CH$_3$ | H | H | C—H | C—H | C—Cl | C—H | O | H | 1-(cyano)cyclo-propyl | 3.8 | 637 |
| I-T3-210 | C—S(O$_2$)C$_2$H$_5$ | C—H | C—i-C$_3$F$_8$ | C—H | C—CH$_3$ | H | H | C—H | C—H | C—Cl | C—H | O | H | cyclopropyl | 3.9 | 612 |
| I-T3-211 | C—OC$_2$H$_5$ | C—H | C—i-C$_3$F$_9$ | C—H | C—OC$_2$H$_5$ | H | H | C—H | N | C—Cl | C—H | O | CH$_3$ | cyclopropyl | 4.7 | 609 |
| I-T3-212 | C—I | C—H | C—i-C$_3$F$_7$ | C—H | C—Cl | H | H | C—H | C—H | C—Cl | C—H | O | H | 1-(cyano)cyclo-propyl | 4.3 | 691 |
| I-T3-213 | C—I | C—H | C—i-C$_3$F$_7$ | C—H | C—Cl | H | H | C—H | C—H | C—Cl | C—H | O | H | cyclopropyl | 4.4 | 666 |
| I-T3-214 | C—OCHF$_2$ | C—H | C—i-C$_3$F$_7$ | C—H | C—Cl | H | H | C—H | C—H | C—Cl | C—H | O | H | cyclopropyl | 4.3 | 606 |
| I-T3-215 | C—OCHF$_2$ | C—H | C—i-C$_3$F$_7$ | C—H | C—Cl | H | H | C—H | C—H | C—Cl | C—H | O | H | 1-(cyano)cyclo-propyl | 4.1 | 631 |
| I-T3-216 | C—OCHF$_2$ | C—H | C—i-C$_3$F$_7$ | C—H | C—Cl | H | H | C—H | C—H | C—Cl | C—H | O | CH$_3$ | cyclopropyl | 4.7 | 620 |
| I-T3-217 | C—OCHF$_2$ | C—H | C—i-C$_3$F$_7$ | C—H | C—Cl | H | H | C—H | N | C—Cl | C—H | O | CH$_3$ | cyclopropyl | 4.2 | 621 |
| I-T3-218 | C—OCHF$_2$ | C—H | C—i-C$_3$F$_7$ | C—H | C—Cl | H | H | C—H | N | C—Cl | C—H | O | H | 1-(cyano)cyclo-propyl | 3.7 | 632 |

TABLE I-T3-continued

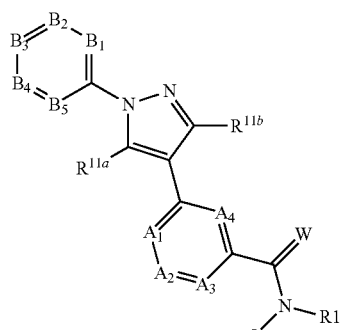

$B_2$ and $B_4$ = C—H

| Ex. No. | $B_1$ | $B_2$ | $B_3$ | $B_4$ | $B_5$ | $R^{11a}$ | $R^{11b}$ | $A_1$ | $A_2$ | $A_3$ | $A_4$ | W | R1 | Q | logP$^{a)}$ | Mass [m/z]$^{a)1)}$ |
|---|---|---|---|---|---|---|---|---|---|---|---|---|---|---|---|---|
| I-T3-219 | C—OCF$_3$ | C—H | C—i-C$_3$F$_7$ | C—H | C—Cl | H | H | C—H | C—H | C—Cl | C—H | O | CH$_3$ | cyclopropyl | 5.1 | 638 |
| I-T3-220 | C—Cl | C—H | C—C(CF$_3$)$_2$OH | C—H | C—Cl | H | H | C—H | N | C—Cl | C—H | O | CH$_3$ | cyclopropyl | 3.4 | 587 |
| I-T3-221 | C—Cl | C—H | C—C(CF$_3$)$_2$OH | C—H | C—Cl | H | H | C—H | N | C—Cl | C—H | O | H | cyclopropyl | 3.0 | 573 |
| I-T3-222 | C—Cl | C—H | C—C(CF$_3$)$_2$OH | C—H | C—Cl | H | H | C—H | N | C—Cl | C—H | O | H | 1-(cyano)cyclopropyl | 3.0 | 598 |
| I-T3-223 | C—Cl | C—H | C—C(CF$_3$)$_2$OH | C—H | C—Cl | H | H | C—H | N | C—Cl | C—H | O | CH$_3$ | 1-(cyano)cyclopropyl | 3.3 | 612 |
| I-T3-224 | C—OCF$_3$ | C—H | C—i-C$_3$F$_7$ | C—H | C—I | H | H | C—H | C—H | C—Cl | C—H | O | H | cyclopropyl | 4.7 | 716 |
| I-T3-225 | C—OCF$_3$ | C—H | C—i-C$_3$F$_7$ | C—H | C—I | H | H | C—H | C—H | C—Cl | C—H | O | CH$_3$ | cyclopropyl | 5.2 | 729 |
| I-T3-226 | C—OCF$_3$ | C—H | C—i-C$_3$F$_7$ | C—H | C—I | H | H | C—H | C—H | C—Cl | C—H | O | H | 1-(cyano)cyclopropyl | 4.6 | 740 |
| I-T3-227 | C—CF$_3$ | C—H | C—i-C$_3$F$_7$ | C—H | C—I | H | H | C—H | C—H | C—Cl | C—H | O | H | cyclopropyl | 4.5 | 700 |
| I-T3-228 | C—CF$_3$ | C—H | C—i-C$_3$F$_7$ | C—H | C—I | H | H | C—H | C—H | C—Cl | C—H | O | H | 1-(cyano)cyclopropyl | 4.4 | 725 |
| I-T3-229 | C—CF$_3$ | C—H | C—i-C$_3$F$_7$ | C—H | C—I | H | H | C—H | C—H | C—Cl | C—H | O | CH$_3$ | cyclopropyl | 5.1 | 714 |

*$^{b)}$Retention time measured with:

Instrument: Waters ACQUITY SQD UPLC system;

Column: Waters Acquity UPLC HSS T3 1.8 μ 50 × 1 mm;

Eluent A: 1l water + 0.25 ml 99% strength formic acid;

Eluent B: 1l acetonitrile + 0.25 ml 99% strength formic acid;

Gradient: 0.0 min 90% A → 1.2 min 5% A → 2.0 min 5% A;

Furnace: 50° C.;

Flow rate: 0.40 ml/min;

UV Detection: 208-400 am.

TABLE I-T4

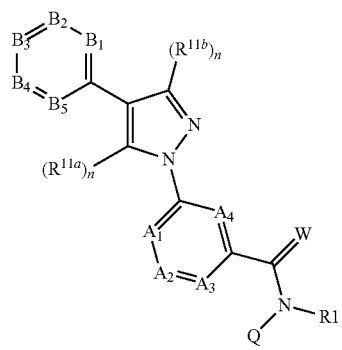

I-T4

$B_2$ and $B_4$ = C—H

| Ex. No. | $B_1$ | $B_3$ | $B_5$ | $R_1$ | $R^{11a}$ | $R^{11b}$ | $A_1$ | $A_2$ | $A_3$ | $A_4$ | W | $R_1$ | Q | logP[a] | Mass [m/z][a)1) |
|---|---|---|---|---|---|---|---|---|---|---|---|---|---|---|---|
| I-T4-1 | C—CH$_3$ | C—i-C$_3$F$_7$ | C—CH$_3$ | H | H | H | C—H | C—H | C—Cl | C—H | O | H | cyclopropyl | 4.7 | 534 |
| I-T4-2 | C—CH$_3$ | C—i-C$_3$F$_7$ | C—CH$_3$ | H | H | H | C—H | C—H | C—Cl | C—H | O | H | 1-(cyano)cyclopropyl | 4.6 | 559 |
| I-T4-3 | C—CH$_3$ | C—i-C$_3$F$_7$ | C—CH$_3$ | H | H | H | C—H | N | C—Cl | C—H | O | H | cyclopropyl | 4.4 | 535 |
| I-T4-4 | C—CH$_3$ | C—i-C$_3$F$_7$ | C—CH$_3$ | H | H | H | C—H | N | C—Cl | C—H | O | H | 1-(cyano)cyclopropyl | 4.3 | 560 |

TABLE I-T22

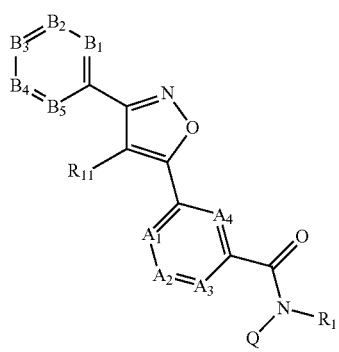

I-T22

$B_2$ and $B_4$ = C—H, W = O

| Ex. No. | $B_1$ | $B_3$ | $B_5$ | $R_1$ | $R_{11}$ | $A_1$ | $A_2$ | $A_3$ | $A_4$ | Q | logP[a] | Mass [m/z][a)1) |
|---|---|---|---|---|---|---|---|---|---|---|---|---|
| I-T22-1 | C—CH3 | C—i-C$_3$F$_7$ | C—CH3 | H | H | C—H | C—H | C—Cl | C—H | cyclopropyl | 4.8 | 535 |
| I-T22-2 | C—CH3 | C—i-C$_3$F$_7$ | C—CH3 | H | H | C—H | C—H | C—Cl | C—H | 1-(cyano)cyclopropyl | 4.6 | 560 |
| I-T22-3 | C—CH3 | C—i-C$_3$F$_7$ | C—CH3 | H | H | C—H | C—H | C—Cl | C—H | CH2CF3 | 5 | 577 |
| I-T22-4 | C—CF3 | C—i-C$_3$F$_7$ | C—CH3 | H | H | C—H | N | C—Cl | C—H | 1-(cyano)cyclopropyl | 4.4 | 615 |
| I-T22-5 | C—CF3 | C—i-C$_3$F$_7$ | C—CH3 | H | H | C—H | C—H | C—Cl | C—H | cyclopropyl | 4.9 | 589 |
| I-T22-6 | C—CF3 | C—i-C$_3$F$_7$ | C—CH3 | H | H | C—H | N | C—Cl | C—H | cyclopropyl | 4.5 | 590 |
| I-T22-7 | C—CF3 | C—i-C$_3$F$_7$ | C—CH3 | H | H | C—H | C—H | C—Cl | C—H | 1-(cyano)cyclopropyl | 4.7 | 614 |

TABLE I-T23

B₂ and B₄ = C—H

| Ex. No. | B₁ | B₃ | B₅ | R¹ | R¹¹ | A₁ | A₂ | A₃ | A₄ | Q | logP$^{a)}$ | Mass [m/z]$^{a)1)}$ |
|---|---|---|---|---|---|---|---|---|---|---|---|---|
| I-T23-1 | C—Cl | C—i-C₃F₇ | C—Cl | H | H | C—H | C—H | C—Cl | C—H | cyclopropyl | 5.0 | 575 |
| I-T23-2 | C—Cl | C—i-C₃F₇ | C—Cl | H | H | C—H | C—H | C—Cl | C—H | 1-(cyano)cyclopropyl | 4.8 | 600 |

TABLE I-T46

I-T46

B₂ and B₄ = C—H

| Ex. No. | B₁ | B₃ | B₅ | R¹¹$^a$ | R¹¹$^b$ | R¹¹$^c$ | A₁ | A₂ | A₃ | A₄ | W | R₁ | Q | logP$^{a)}$ | Mass [m/z]$^{a)1)}$ |
|---|---|---|---|---|---|---|---|---|---|---|---|---|---|---|---|
| I-T46-1 | C—CH₃ | C—i-C₃F₇ | C—CH₃ | H | H | H | C—H | C—H | C—Cl | C—H | O | H | 1-(cyano)cyclopropyl | 4.9 | 558 |
| I-T46-2 | C—CH₃ | C—i-C₃F₇ | C—CH₃ | H | H | H | C—H | C—H | C—Cl | C—H | O | H | cyclopropyl | 5.0 | 533 |
| I-T46-3 | C—Cl | C—i-C₃F₇ | C—Cl | H | H | H | C—H | N | C—Cl | C—H | O | CH₃ | cyclopropyl | 5.0 | 588 |
| I-T46-4 | C—Cl | C—i-C₃F₇ | C—Cl | H | H | H | C—H | N | C—Cl | C—H | O | H | cyclopropyl | 4.5 | 574 |
| I-T46-5 | C—Cl | C—i-C₃F₇ | C—Cl | H | H | H | C—H | N | C—Cl | C—H | O | H | 1-(cyano)cyclopropyl | 4.4 | 599 |
| I-T46-6 | C—Cl | C—i-C₃F₇ | C—Cl | H | H | H | C—H | N | C—Cl | C—H | O | CH₃ | 1-(cyano)cyclopropyl | 4.8 | 613 |

NMR Data of Selected Examples

The ¹H NMR data of selected examples are reported in the form of ¹H NMR peak lists. For each signal peak, first the δ value in ppm and then the signal intensity in round brackets are listed. The δ value—signal intensity number pairs for different signal peaks are listed with separation from one another by semicolons.

The peak list for one example therefore has the form of:

$\delta_1$ (intensity₁); $\delta_2$ (intensity₂); . . . ; $\delta_i$ (intensity$_i$); . . . ; $\delta_n$ (intensity$_n$)

The intensity of sharp signals correlates with the height of the signals in a printed example of an NMR spectrum in cm and shows the true ratios of the signal intensities. In the case of broad signals, several peaks or the middle of the signal and the relative intensity thereof may be shown in comparison to the most intense signal in the spectrum.

For calibration of the chemical shift of the ¹H NMR spectra we use tetramethylsilane and/or the chemical shift of the solvent, particularly in the case of spectra measured in DMSO. Therefore, the tetramethylsilane peak may but need not occur in NMR peak lists.

The lists of the ¹H NMR peaks are similar to the conventional ¹H NMR printouts and thus usually contain all peaks listed in conventional ¹H NMR interpretations.

In addition, like conventional ¹H NMR printouts, they may show solvent signals, signals of stereoisomers of the target compounds, which likewise form part of the subject-matter of the invention, and/or peaks of impurities.

In the reporting of compound signals in the delta range of solvents and/or water, our lists of 1H NMR peaks show the usual solvent peaks, for example peaks of DMSO in DMSO-D6 and the peak of water, which usually have a high intensity on average.

The peaks of stereoisomers of the target compounds and/or peaks of impurities usually have a lower intensity on average than the peaks of the target compounds (for example with a purity of >90%).

Such stereoisomers and/or impurities may be typical of the particular preparation process. Their peaks can thus help in this case to identify reproduction of our preparation process with reference to "by-product fingerprints".

An expert calculating the peaks of the target compounds by known methods (MestreC, ACD simulation, but also with empirically evaluated expected values) can, if required, isolate the peaks of the target compounds, optionally using additional intensity filters. This isolation would be similar to the relevant peak picking in conventional 1H NMR interpretation.

Further details of 1H NMR peak lists can be found in Research Disclosure Database Number 564025.

Beispiel I-T2-1: $^1$H-NMR (400.0 MHz, CD3CN):
δ = 8.297 (5.2); 8.291 (5.1); 7.846 (9.6); 7.825 (3.3); 7.818 (2.0); 7.545 (3.5); 7.525 (2.9); 7.523 (2.8); 7.443 (9.1); 6.977 (1.2); 6.544 (5.1); 6.538 (4.9); 4.085 (0.4); 4.068 (1.3); 4.050 (1.4); 4.032 (0.5); 3.440 (0.4); 3.374 (0.4); 2.862 (0.8); 2.853 (1.2); 2.844 (1.9); 2.834 (1.8); 2.826 (1.3); 2.816 (0.9); 2.240 (41.5); 2.150 (23.6); 2.086 (3.2); 1.972 (6.1); 1.965 (1.2); 1.958 (2.9); 1.953 (13.9); 1.947 (24.8); 1.941 (32.9); 1.934 (22.7); 1.928 (11.7); 1.436 (16.0); 1.269 (0.5); 1.221 (1.6); 1.204 (3.1); 1.186 (1.5); 0.790 (1.0); 0.778 (3.2); 0.773 (4.1); 0.760 (4.2); 0.755 (3.2); 0.743 (1.4); 0.614 (1.3); 0.604 (3.7); 0.597 (3.9); 0.593 (3.4); 0.588 (3.3); 0.575 (1.0); 0.000 (3.0)
Beispiel I-T2-2: $^1$H-NMR (400.0 MHz, CD3CN):
δ = 8.311 (4.9); 8.304 (5.0); 7.898 (10.0); 7.878 (3.3); 7.872 (2.0); 7.624 (2.0); 7.583 (3.2); 7.561 (2.8); 7.444 (9.7); 6.555 (4.9); 6.549 (4.9); 5.447 (0.7); 4.086 (0.5); 4.068 (1.6); 4.050 (1.6); 4.032 (0.6); 2.240 (45.7); 2.146 (80.1); 2.114 (0.7); 2.108 (0.7); 2.102 (0.5); 1.972 (7.1); 1.964 (3.1); 1.958 (8.0); 1.953 (36.5); 1.946 (65.9); 1.940 (87.5); 1.934 (62.1); 1.928 (33.1); 1.775 (0.4); 1.769 (0.6); 1.763 (0.4); 1.591 (2.0); 1.576 (5.7); 1.569 (5.7); 1.556 (2.8); 1.516 (0.4); 1.437 (16.0); 1.410 (0.4); 1.369 (2.8); 1.356 (5.7); 1.349 (6.0); 1.334 (2.1); 1.296 (0.3); 1.269 (1.9); 1.222 (1.9); 1.204 (3.6); 1.186 (1.8); 0.000 (4.5)
Beispiel I-T3-1: $^1$H-NMR (400.0 MHz, CD3CN):
δ = 8.118 (11.7); 8.061 (12.6); 7.689 (7.9); 7.683 (8.6); 7.667 (0.7); 7.652 (4.9); 7.646 (3.5); 7.631 (5.5); 7.625 (4.3); 7.535 (16.0); 7.463 (7.8); 7.442 (6.2); 6.895 (2.5); 4.068 (0.8); 4.050 (0.8); 3.912 (0.7); 2.881 (0.5); 2.871 (1.5); 2.862 (2.1); 2.853 (3.2); 2.844 (3.2); 2.835 (2.2); 2.826 (1.5); 2.816 (0.5); 2.270 (0.5); 2.261 (0.3); 2.143 (107.9); 2.138 (145.5); 2.111 (71.2); 1.972 (5.1); 1.964 (10.3); 1.958 (27.0); 1.952 (94.0); 1.946 (160.4); 1.940 (199.1); 1.934 (136.5); 1.928 (68.3); 1.780 (0.5); 1.774 (0.9); 1.768 (1.1); 1.762 (0.8); 1.756 (0.4); 1.437 (13.0); 1.271 (1.0); 1.222 (1.0); 1.204 (1.9); 1.186 (0.9); 0.794 (1.7); 0.782 (6.4); 0.777 (7.2); 0.764 (7.9); 0.759 (5.7); 0.747 (2.4); 0.725 (0.3); 0.610 (2.4); 0.600 (7.1); 0.592 (7.5); 0.588 (6.7); 0.584 (5.9); 0.571 (1.7); 0.146 (0.4); 0.000 (86.0); −0.008 (5.2); −0.150 (0.4)
Beispiel I-T3-2: $^1$H-NMR (400.0 MHz, CD3CN):
δ = 8.131 (12.6); 8.084 (13.3); 7.735 (7.6); 7.729 (9.9); 7.710 (5.2); 7.704 (3.5); 7.689 (5.8); 7.683 (4.6); 7.537 (16.0); 7.514 (8.9); 7.493 (7.4); 7.458 (1.9); 4.140 (1.8); 4.124 (2.1); 4.117 (5.8); 4.100 (5.9); 4.093 (6.2); 4.077 (5.9); 4.069 (2.6); 4.053 (2.1); 3.914 (0.6); 2.891 (0.7); 2.773 (0.6); 2.480 (0.7); 2.475 (1.3); 2.470 (1.8); 2.466 (1.3); 2.461 (0.7); 2.325 (0.4); 2.273 (1.9); 2.221 (979.0); 2.115 (79.7); 2.097 (1.4); 1.973 (3.4); 1.966 (10.4); 1.960 (22.6); 1.954 (102.7); 1.948 (182.7); 1.942 (241.3); 1.936 (167.3); 1.930 (87.0); 1.783 (0.7); 1.777 (1.1); 1.770 (1.5); 1.764 (1.1); 1.758 (0.6); 1.437 (15.2); 1.296 (0.5); 1.270 (1.7); 1.222 (0.7); 1.204 (1.3); 1.186 (0.6); 0.146 (0.3); 0.008 (2.7); 0.000 (69.9); −0.008 (3.3)
Beispiel I-T3-3: $^1$H-NMR (400.0 MHz, CD3CN):
δ = 8.129 (2.6); 8.075 (2.6); 7.738 (1.6); 7.732 (2.0); 7.701 (1.1); 7.696 (0.8); 7.681 (1.2); 7.675 (1.1); 7.572 (0.5); 7.536 (3.2); 7.496 (1.8); 7.475 (1.5); 2.146 (33.6); 2.113 (16.5); 1.972 (0.4); 1.964 (2.4); 1.958 (5.6); 1.953 (29.5); 1.946 (53.8); 1.940 (72.5); 1.934 (50.1); 1.928 (25.8); 1.769 (0.4); 1.599 (0.8); 1.585 (1.9); 1.578 (2.0); 1.564 (1.1); 1.437 (16.0); 1.359 (1.1); 1.345 (2.0); 1.338 (2.0); 1.324 (0.8); 1.269 (0.6); 0.008 (1.9); 0.000 (51.3); −0.009 (2.0)
Beispiel I-T3-4: $^1$H-NMR (400.0 MHz, CD3CN):
δ = 8.132 (5.7); 8.077 (6.1); 7.719 (3.4); 7.714 (4.3); 7.678 (2.2); 7.673 (1.8); 7.657 (2.6); 7.652 (2.3); 7.537 (7.8); 7.515 (1.0); 7.495 (1.0); 7.486 (4.3); 7.465 (3.3); 5.338 (0.9); 5.316 (1.8); 5.296 (1.8); 5.274 (1.0); 3.544 (2.3); 3.521 (4.7); 3.499 (3.1); 3.370 (3.0); 3.349 (4.6); 3.346 (4.3); 3.325 (2.4); 2.469 (0.4); 2.274 (0.4); 2.206 (300.4); 2.154 (0.5); 2.115 (36.2); 1.973 (1.3); 1.966 (3.0); 1.960 (6.3); 1.954 (30.3); 1.948 (55.1); 1.942 (73.7); 1.935 (52.5); 1.929 (28.5); 1.776 (0.4); 1.770 (0.5); 1.764 (0.4); 1.437 (16.0); 1.269 (1.6); 1.222 (0.3); 1.204 (0.6); 0.008 (0.7); 0.000 (20.8)
Beispiel I-T3-5: $^1$H-NMR (601.6 MHz, CD3CN):
δ = 8.125 (8.3); 8.124 (8.5); 8.072 (9.3); 8.071 (9.2); 7.680 (16.0); 7.677 (5.7); 7.668 (5.3); 7.664 (3.0); 7.537 (9.4); 7.485 (4.7); 7.482 (2.1); 7.473 (1.9); 7.470 (4.3); 7.461 (2.3); 2.146 (139.0); 2.113 (53.4); 2.060 (0.5); 2.056 (0.9); 2.052 (1.3); 2.048 (0.9); 2.044 (0.4); 1.966 (5.4); 1.958 (14.4); 1.953 (16.2); 1.950 (93.5); 1.945 (166.6); 1.941 (244.5); 1.937 (162.8); 1.933 (81.9); 1.924 (1.3); 1.835 (0.5); 1.831 (0.9); 1.827 (1.4); 1.822 (0.9); 1.818 (0.5); 1.393 (2.4); 1.383 (5.5); 1.380 (5.9); 1.370 (3.2); 1.343 (0.4); 1.269 (0.6); 1.251 (1.3); 1.248 (1.4); 1.238 (4.5); 1.228 (1.0); 1.225 (1.0); 0.096 (0.4); 0.005 (3.0); 0.000 (105.8); −0.006 (3.3); −0.100 (0.4)
Beispiel I-T3-6: $^1$H-NMR (601.6 MHz, CD3CN):
δ = 8.130 (11.9); 8.129 (12.8); 8.082 (13.1); 8.081 (13.4); 7.809 (8.6); 7.805 (9.0); 7.697 (5.1); 7.693 (4.8); 7.683 (5.9); 7.679 (5.7); 7.538 (13.6); 7.508 (9.3); 7.494 (8.0); 7.304 (1.1); 7.295 (1.9); 7.286 (1.1); 7.069 (1.2); 4.045 (16.0); 4.036 (15.9); 3.973 (1.6); 3.962 (1.8); 3.957 (5.2); 3.946 (5.2); 3.941 (5.5); 3.930 (5.3); 3.926 (2.0); 3.915 (1.8); 2.220 (0.4); 2.153 (19.3); 2.115 (73.8); 2.104 (1.0); 2.052 (0.4); 2.006 (0.4); 1.966 (1.4); 1.958 (3.8); 1.953 (4.5); 1.950 (25.7); 1.945 (45.5); 1.941 (67.9); 1.937 (46.1); 1.933 (22.7); 1.827 (0.4); 1.268 (1.1); 0.005 (0.8); 0.000 (28.7); −0.006 (0.9)
Beispiel I-T3-7: $^1$H-NMR (400.0 MHz, d$_6$-DMSO):
δ = 9.043 (1.2); 9.038 (1.2); 8.803 (1.3); 8.798 (1.3); 8.672 (3.2); 8.648 (0.9); 8.638 (0.9); 8.405 (3.2); 8.390 (1.1); 8.384 (1.9); 8.379 (1.0); 8.316 (0.3); 7.602 (3.5); 3.902 (9.7); 3.330 (83.7); 3.243 (0.6); 3.169 (0.4); 2.903 (0.3); 2.893 (0.5); 2.885 (0.7); 2.875 (0.7); 2.867 (0.4); 2.857 (0.3); 2.676 (0.4); 2.672 (0.5); 2.667 (0.4); 2.525 (1.4); 2.512 (30.7); 2.507 (61.4); 2.503 (80.2); 2.498 (57.8); 2.494 (27.6); 2.334 (0.3); 2.329 (0.5); 2.325 (0.3); 2.131 (16.0); 1.909 (0.3); 0.763 (0.4); 0.750 (1.1); 0.745 (1.6); 0.733 (1.5); 0.727 (1.3); 0.716 (0.6); 0.619 (0.6); 0.608 (1.7); 0.602 (1.4); 0.598 (1.4); 0.593 (1.2); 0.580 (0.4); 0.000 (9.2)
Beispiel I-T3-8: $^1$H-NMR (400.0 MHz, d$_6$-DMSO):
δ = 9.538 (2.0); 9.102 (1.4); 9.097 (1.4); 8.827 (1.4); 8.823 (1.5); 8.695 (3.2); 8.444 (1.1); 8.439 (1.9); 8.434 (1.2); 8.424 (3.3); 7.605 (3.8); 3.902 (6.0); 3.374 (0.4); 3.330 (90.4); 3.243 (0.4); 3.169 (2.1); 2.676 (0.4); 2.672 (0.6); 2.667 (0.5); 2.542 (0.5); 2.507 (75.8); 2.503 (97.5); 2.498 (74.7); 2.334 (0.4); 2.329 (0.6); 2.325 (0.5); 2.132 (16.0); 1.628 (0.7); 1.614 (2.0); 1.607 (2.1); 1.594 (0.9); 1.347 (0.9); 1.334 (2.1); 1.327 (2.1); 1.313 (0.7); 0.000 (8.2)
Beispiel I-T3-9: $^1$H-NMR (400.0 MHz, d$_6$-DMSO):
δ = 8.508 (2.0); 8.506 (2.0); 8.473 (1.0); 8.463 (1.0); 8.276 (2.2); 7.895 (0.5); 7.876 (1.0); 7.861 (0.5); 7.592 (4.1); 7.399 (0.5); 7.383 (1.0); 7.368 (0.7); 7.305 (1.1); 7.286 (1.7); 7.266 (0.7); 3.902 (5.7); 3.330 (72.5); 3.243 (0.4); 3.175 (0.4); 3.162 (0.3); 2.875 (0.4); 2.865 (0.5); 2.857 (0.7); 2.847 (0.7); 2.838 (0.5); 2.828 (0.3); 2.672 (0.5); 2.507 (63.9); 2.503 (80.2); 2.329 (0.5); 2.114 (16.0); 0.725 (0.4); 0.707 (1.8); 0.695 (1.7); 0.689 (1.5); 0.678 (0.6); 0.556 (0.6); 0.545 (1.8); 0.539 (1.8); 0.530 (1.6); 0.518 (0.5); 0.000 (6.1)

Beispiel I-T3-10: ¹H-NMR (400.0 MHz, d₆-DMSO):
δ = 9.369 (2.0); 8.535 (1.8); 8.532 (1.9); 8.290 (2.0); 7.968 (0.4); 7.965 (0.5); 7.949 (0.9); 7.946 (0.9); 7.931 (0.5); 7.927 (0.5); 7.595 (3.9); 7.479 (0.4); 7.475 (0.4); 7.459 (0.9); 7.443 (0.6); 7.440 (0.5); 7.352 (1.0); 7.333 (1.7); 7.314 (0.8); 3.903 (8.2); 3.372 (0.4); 3.329 (104.6); 3.243 (0.6); 3.175 (0.3); 2.675 (0.4); 2.671 (0.5); 2.667 (0.4); 2.541 (0.5); 2.507 (70.8); 2.502 (89.6); 2.498 (66.7); 2.333 (0.4); 2.329 (0.5); 2.324 (0.4); 2.115 (16.0); 1.598 (0.8); 1.584 (2.0); 1.577 (2.1); 1.564 (0.9); 1.292 (0.9); 1.278 (2.1); 1.272 (2.2); 1.257 (0.8); 1.169 (0.3); 1.068 (0.4); 0.007 (0.4); 0.000 (7.5); −0.008 (0.4)
Beispiel I-T3-11: ¹H-NMR (400.0 MHz, d₆-DMSO):
δ = 8.522 (0.9); 8.512 (0.9); 8.500 (3.3); 8.211 (3.2); 7.818 (1.8); 7.799 (1.8); 7.646 (1.8); 7.621 (1.8); 7.590 (3.5); 3.902 (3.1); 3.330 (117.7); 3.304 (0.3); 2.861 (0.3); 2.851 (0.4); 2.842 (0.7); 2.832 (0.4); 2.824 (0.7); 2.676 (0.4); 2.671 (0.5); 2.667 (0.3); 2.525 (1.5); 2.511 (29.4); 2.507 (58.1); 2.502 (75.7); 2.498 (54.9); 2.493 (26.6); 2.334 (0.3); 2.329 (0.5); 2.324 (0.3); 2.127 (16.0); 0.733 (0.7); 0.720 (1.2); 0.715 (1.7); 0.703 (1.6); 0.697 (1.3); 0.685 (0.6); 0.575 (0.6); 0.564 (1.7); 0.558 (1.5); 0.554 (1.4); 0.548 (1.3); 0.536 (0.4); 0.000 (7.9)
Beispiel I-T3-12: ¹H-NMR (400.0 MHz, d₆-DMSO):
δ = 9.396 (1.8); 8.522 (3.2); 8.223 (3.2); 7.906 (1.6); 7.887 (1.6); 7.712 (1.6); 7.687 (1.6); 7.593 (3.7); 3.903 (2.7); 3.332 (98.2); 2.672 (0.5); 2.542 (0.4); 2.507 (67.0); 2.503 (83.7); 2.498 (62.0); 2.334 (0.4); 2.329 (0.5); 2.325 (0.4); 2.129 (16.0); 1.604 (0.8); 1.590 (2.0); 1.583 (2.1); 1.570 (0.9); 1.312 (0.9); 1.299 (2.0); 1.292 (2.0); 1.278 (0.8); 0.000 (7.1)
Beispiel I-T3-13: ¹H-NMR (400.0 MHz, d₆-DMSO):
δ = 8.514 (1.8); 8.510 (1.9); 8.480 (0.9); 8.470 (0.9); 8.285 (2.1); 8.226 (0.8); 8.220 (0.8); 8.207 (0.8); 8.202 (0.8); 7.767 (0.4); 7.762 (0.5); 7.755 (0.5); 7.749 (0.6); 7.746 (0.6); 7.740 (0.5); 7.734 (0.5); 7.728 (0.4); 7.595 (3.7); 7.402 (0.9); 7.380 (0.9); 7.375 (1.0); 7.354 (0.8); 3.902 (1.5); 3.444 (0.4); 3.425 (0.6); 3.405 (1.1); 3.353 (438.8); 3.292 (0.5); 3.273 (0.3); 2.864 (0.5); 2.855 (0.7); 2.846 (0.7); 2.837 (0.5); 2.827 (0.3); 2.678 (0.4); 2.673 (0.5); 2.669 (0.4); 2.509 (61.5); 2.504 (78.8); 2.500 (57.5); 2.335 (0.4); 2.331 (0.5); 2.327 (0.4); 2.121 (16.0); 0.746 (0.4); 0.733 (1.2); 0.728 (1.7); 0.716 (1.6); 0.710 (1.3); 0.699 (0.6); 0.602 (0.6); 0.592 (1.7); 0.585 (1.6); 0.576 (1.3); 0.564 (0.4)
Beispiel I-T3-14: ¹H-NMR (400.0 MHz, d₆-DMSO):
δ = 8.600 (1.8); 8.596 (1.8); 8.536 (1.1); 8.525 (1.1); 8.352 (1.9); 7.977 (1.6); 7.960 (1.6); 7.594 (3.7); 7.437 (1.7); 7.411 (1.7); 3.902 (4.8); 3.332 (129.0); 2.826 (0.4); 2.817 (0.7); 2.807 (0.7); 2.799 (0.4); 2.789 (0.3); 2.676 (0.4); 2.672 (0.5); 2.667 (0.4); 2.511 (32.0); 2.507 (61.8); 2.503 (79.3); 2.498 (57.6); 2.494 (28.2); 2.334 (0.3); 2.329 (0.5); 2.325 (0.4); 2.115 (16.0); 0.733 (0.4); 0.720 (1.2); 0.715 (1.6); 0.703 (1.5); 0.697 (1.3); 0.685 (0.5); 0.567 (0.5); 0.557 (1.7); 0.551 (1.5); 0.547 (1.4); 0.541 (1.3); 0.529 (0.4); 0.000 (6.1)
Beispiel I-T3-15: ¹H-NMR (400.0 MHz, d₆-DMSO):
δ = 8.711 (3.3); 8.694 (1.1); 8.684 (1.0); 8.450 (3.3); 8.369 (1.8); 8.174 (1.8); 7.971 (1.8); 7.601 (3.9); 3.903 (1.0); 3.331 (150.2); 2.910 (0.3); 2.901 (0.5); 2.892 (0.7); 2.882 (0.7); 2.874 (0.5); 2.865 (0.4); 2.672 (0.5); 2.507 (59.3); 2.503 (74.7); 2.499 (55.2); 2.334 (0.4); 2.330 (0.5); 2.133 (16.0); 0.769 (0.4); 0.755 (1.3); 0.751 (1.7); 0.738 (1.6); 0.733 (1.4); 0.721 (0.6); 0.630 (0.6); 0.620 (1.8); 0.613 (1.7); 0.604 (1.4); 0.592 (0.4)
Beispiel I-T3-16: ¹H-NMR (601.6 MHz, d₆-DMSO):
δ = 8.439 (0.8); 8.433 (0.9); 8.344 (3.1); 8.343 (3.2); 8.082 (3.2); 8.081 (3.3); 7.912 (1.7); 7.909 (1.7); 7.670 (0.9); 7.667 (0.9); 7.657 (1.0); 7.654 (1.0); 7.600 (3.4); 7.368 (1.3); 7.354 (1.2); 3.376 (0.5); 3.367 (1.1); 3.351 (401.9); 3.328 (0.5); 3.324 (0.5); 2.997 (3.2); 2.856 (0.4); 2.850 (0.7); 2.844 (0.7); 2.838 (0.4); 2.831 (0.3); 2.618 (0.4); 2.615 (0.6); 2.612 (0.4); 2.543 (5.5); 2.524 (1.0); 2.521 (1.3); 2.518 (1.2); 2.509 (30.4); 2.506 (67.4); 2.503 (93.3); 2.500 (68.5); 2.497 (31.5); 2.438 (7.5); 2.390 (0.4); 2.387 (0.6); 2.384 (0.4); 2.146 (16.0); 0.715 (0.4); 0.707 (1.2); 0.703 (1.6); 0.695 (1.5); 0.692 (1.3); 0.684 (0.5); 0.590 (0.6); 0.583 (1.6); 0.579 (1.4); 0.576 (1.3); 0.572 (1.3); 0.564 (0.4); 0.000 (2.6)
Beispiel I-T3-17: ¹H-NMR (400.0 MHz, d₆-DMSO):
δ = 9.576 (0.4); 9.437 (2.3); 8.736 (0.7); 8.625 (1.7); 8.621 (1.8); 8.472 (0.7); 8.411 (0.4); 8.375 (1.8); 8.372 (1.9); 8.316 (0.5); 8.243 (0.4); 8.030 (1.7); 8.013 (1.6); 7.993 (0.3); 7.597 (3.8); 7.547 (1.7); 7.521 (1.9); 4.036 (1.1); 3.903 (6.7); 3.630 (0.4); 3.623 (0.4); 3.614 (0.4); 3.608 (0.3); 3.597 (0.3); 3.392 (0.7); 3.332 (259.6); 3.287 (0.3); 3.175 (0.4); 3.162 (0.5); 3.155 (0.4); 3.145 (0.5); 3.138 (0.4); 3.127 (0.5); 3.056 (0.4); 3.022 (4.3); 2.751 (0.4); 2.690 (1.7); 2.676 (0.8); 2.672 (1.1); 2.667 (0.9); 2.525 (3.7); 2.511 (72.5); 2.507 (143.5); 2.503 (187.7); 2.498 (136.4); 2.494 (66.3); 2.338 (0.4); 2.334 (0.8); 2.329 (1.1); 2.325 (0.8); 2.134 (3.5); 2.116 (16.0); 1.614 (0.5); 1.607 (1.1); 1.593 (1.9); 1.586 (2.0); 1.573 (0.8); 1.344 (0.5); 1.337 (0.5); 1.310 (0.9); 1.296 (1.9); 1.289 (2.1); 1.274 (3.8); 1.259 (6.5); 1.244 (6.0); 1.225 (1.2); 0.008 (0.5); 0.000 (16.5); −0.009 (0.5)
Beispiel I-T3-18: ¹H-NMR (400.0 MHz, d₆-DMSO):
δ = 9.576 (2.0); 8.736 (3.2); 8.472 (3.3); 8.411 (1.7); 8.316 (0.3); 8.243 (1.6); 7.994 (1.6); 7.605 (3.6); 3.903 (10.2); 3.372 (0.7); 3.333 (152.4); 3.243 (1.3); 3.175 (0.4); 3.162 (0.4); 2.690 (0.4); 2.676 (0.4); 2.672 (0.6); 2.667 (0.4); 2.542 (0.6); 2.525 (1.9); 2.512 (39.2); 2.507 (77.8); 2.503 (101.6); 2.498 (73.7); 2.494 (35.7); 2.334 (0.4); 2.330 (0.6); 2.325 (0.4); 2.134 (16.0); 2.116 (0.5); 1.629 (0.7); 1.614 (1.8); 1.607 (2.0); 1.594 (0.9); 1.358 (0.9); 1.345 (1.9); 1.338 (2.0); 1.323 (0.7); 1.259 (0.5); 1.244 (0.4); 1.017 (0.6); 1.001 (0.6); 0.000 (9.1)
Beispiel I-T3-19: ¹H-NMR (400.0 MHz, d₆-DMSO):
δ = 9.367 (1.9); 8.537 (1.8); 8.534 (1.9); 8.300 (2.2); 8.277 (0.8); 8.271 (0.9); 8.259 (0.9); 8.253 (0.8); 7.796 (0.4); 7.791 (0.5); 7.784 (0.5); 7.778 (0.6); 7.775 (0.6); 7.769 (0.6); 7.763 (0.5); 7.757 (0.5); 7.598 (3.8); 7.457 (0.8); 7.435 (0.8); 7.430 (1.0); 7.409 (0.7); 3.903 (4.8); 3.335 (104.3); 2.672 (0.4); 2.542 (0.3); 2.507 (54.0); 2.503 (69.3); 2.499 (52.7); 2.330 (0.4); 2.122 (16.0); 1.609 (0.8); 1.595 (2.0); 1.588 (2.1); 1.575 (0.9); 1.323 (0.9); 1.309 (2.0); 1.303 (2.1); 1.288 (0.8); 0.000 (5.6)
Beispiel I-T3-20: ¹H-NMR (400.0 MHz, d₆-DMSO):
δ = 8.816 (2.3); 8.810 (2.3); 8.695 (3.4); 8.681 (1.1); 8.670 (1.1); 8.451 (3.4); 8.184 (2.3); 8.178 (2.2); 7.601 (3.8); 3.903 (7.0); 3.333 (173.9); 3.289 (0.4); 3.242 (0.9); 3.175 (0.6); 3.162 (0.5); 2.859 (0.4); 2.850 (0.7); 2.840 (0.7); 2.832 (0.4); 2.822 (0.3); 2.676 (0.4); 2.671 (0.5); 2.667 (0.4); 2.542 (0.4); 2.511 (34.1); 2.507 (66.3); 2.502 (85.9); 2.498 (63.0); 2.494 (31.0); 2.333 (0.4); 2.329 (0.5); 2.325 (0.4); 2.132 (0.7); 2.117 (16.0); 1.016 (0.4); 1.001 (0.4); 0.755 (0.5); 0.742 (1.3); 0.737 (1.7); 0.725 (1.6); 0.719 (1.4); 0.707 (0.5); 0.564 (0.6); 0.553 (1.7); 0.547 (1.6); 0.543 (1.5); 0.538 (1.4); 0.526 (0.4); 0.000 (7.1)
Beispiel I-T3-21: ¹H-NMR (600.1 MHz, d₆-DMSO):
δ = 9.593 (1.8); 8.868 (2.3); 8.864 (2.3); 8.709 (3.3); 8.456 (3.4); 8.262 (2.3); 8.258 (2.2); 7.603 (3.7); 3.388 (0.4); 3.383 (0.4); 3.381 (0.5); 3.369 (0.8); 3.340 (1164.0); 2.994 (0.7); 2.617 (0.6); 2.615 (0.8); 2.612 (0.6); 2.542 (39.9); 2.523 (1.4); 2.520 (1.7); 2.517 (1.8); 2.508 (48.7); 2.505 (103.1); 2.502 (140.8); 2.499 (100.9); 2.497 (46.2); 2.389 (0.6); 2.386 (0.8); 2.383 (0.6); 2.117 (16.0); 1.636 (0.8); 1.627 (2.0); 1.622 (2.1); 1.613 (0.8); 1.288 (0.9); 1.278 (1.9); 1.274 (2.1); 1.264 (0.8); 0.005 (0.8); 0.000 (21.9); −0.006 (0.7)
Beispiel I-T3-22: ¹H-NMR (400.1 MHz, d₆-DMSO):
δ = 9.397 (6.5); 8.682 (5.3); 8.677 (5.1); 8.405 (7.9); 8.366 (0.3); 8.087 (16.0); 8.060 (0.3); 8.041 (0.7); 7.981 (1.7); 7.966 (2.6); 7.963 (2.7); 7.948 (1.5); 7.944 (1.4); 7.763 (0.3); 7.505 (1.2); 7.501 (1.3); 7.486 (2.7); 7.470 (1.8); 7.466 (1.6); 7.384 (0.6); 7.374 (3.1); 7.365 (1.1); 7.355 (5.1); 7.345 (0.8); 7.336 (2.3); 5.761 (0.8); 3.348 (68.6); 3.028 (1.2); 2.875 (1.0); 2.712 (0.4); 2.671 (0.3); 2.542 (99.6); 2.507 (38.4); 2.502 (50.3); 2.498 (38.2); 2.368 (0.4); 2.087 (0.8); 1.601 (2.4); 1.587 (6.3); 1.580 (6.5); 1.567 (2.8); 1.288 (3.1); 1.275 (6.2); 1.268 (6.6); 1.254 (2.5); 1.234 (0.8); 1.169 (0.9); 0.146 (0.3); 0.000 (72.5); −0.008 (4.9); −0.150 (0.4)
Beispiel I-T3-23: ¹H-NMR (400.0 MHz, CD3CN):
δ = 8.202 (5.5); 8.187 (0.5); 8.161 (5.9); 8.146 (0.5); 7.931 (0.4); 7.900 (9.0); 7.886 (0.8); 7.739 (3.5); 7.734 (4.4); 7.720 (0.5); 7.707 (2.6); 7.701 (1.9); 7.686 (3.0); 7.680 (2.5); 7.648 (1.5); 7.507 (4.1); 7.486 (3.4); 4.360 (0.5); 4.342 (0.5); 4.086 (1.0); 4.068 (2.9); 4.050 (3.0); 4.032 (1.1); 2.162 (61.1); 2.149 (10.3); 2.120 (0.4); 2.114 (0.4); 2.108 (0.5); 2.102 (0.4); 1.972 (13.4); 1.965 (4.8); 1.959 (8.2); 1.953 (30.5);

1.947 (52.3); 1.940 (68.1); 1.934 (48.2); 1.928 (27.3); 1.769 (0.4); 1.596 (1.8); 1.581 (4.5); 1.574 (4.4); 1.561 (2.8); 1.437 (16.0); 1.422 (1.2); 1.401 (0.5); 1.371 (0.6); 1.361 (2.6); 1.353 (1.9); 1.347 (4.6); 1.341 (4.6); 1.336 (1.5); 1.326 (2.3); 1.268 (1.6); 1.222 (3.7); 1.204 (7.2); 1.186 (3.8); 0.000 (2.2)

Beispiel I-T3-24: $^1$H-NMR (600.1 MHz, CD3CN):
δ = 8.189 (6.2); 8.144 (6.7); 7.897 (10.1); 7.690 (3.8); 7.687 (4.5); 7.652 (2.6); 7.648 (2.1); 7.638 (2.8); 7.634 (2.4); 7.471 (4.4); 7.457 (3.7); 6.891 (1.0); 5.446 (2.0); 4.077 (2.0); 4.065 (6.2); 4.053 (6.2); 4.041 (2.1); 2.864 (0.8); 2.857 (1.1); 2.852 (1.7); 2.845 (1.7); 2.839 (1.1); 2.833 (0.8); 2.129 (55.4); 2.054 (0.5); 2.050 (0.7); 2.046 (0.5); 1.971 (27.5); 1.963 (6.3); 1.955 (8.8); 1.951 (10.1); 1.947 (46.9); 1.943 (78.2); 1.939 (115.2); 1.935 (77.9); 1.931 (39.3); 1.922 (0.5); 1.828 (0.4); 1.824 (0.6); 1.820 (0.4); 1.437 (16.0); 1.270 (0.4); 1.216 (7.4); 1.204 (14.6); 1.192 (7.3); 0.786 (1.0); 0.777 (2.8); 0.774 (3.6); 0.765 (3.6); 0.762 (2.7); 0.754 (1.2); 0.606 (1.1); 0.599 (2.9); 0.598 (2.9); 0.595 (3.0); 0.591 (2.8); 0.588 (2.8); 0.580 (0.9); 0.005 (2.1); 0.000 (69.9); −0.006 (2.2)

Beispiel I-T3-25: $^1$H-NMR (601.6 MHz, CD3CN):
δ = 8.201 (9.9); 8.163 (10.8); 7.899 (16.0); 7.738 (5.9); 7.734 (7.4); 7.710 (4.2); 7.706 (3.3); 7.696 (4.6); 7.693 (4.0); 7.522 (6.8); 7.508 (5.8); 7.328 (1.4); 7.265 (0.6); 7.251 (1.5); 7.239 (1.1); 7.195 (1.4); 7.183 (1.0); 7.162 (0.5); 7.150 (0.7); 5.446 (1.0); 4.127 (1.3); 4.116 (1.5); 4.111 (4.2); 4.100 (4.3); 4.095 (4.5); 4.085 (4.3); 4.080 (1.7); 4.069 (1.4); 2.328 (5.9); 2.134 (32.5); 2.132 (53.6); 2.058 (0.4); 2.054 (0.6); 2.050 (1.0); 2.046 (0.7); 1.971 (1.2); 1.964 (7.9); 1.955 (12.2); 1.951 (13.8); 1.947 (67.1); 1.943 (113.1); 1.939 (165.4); 1.935 (111.4); 1.931 (56.0); 1.833 (0.5); 1.829 (0.7); 1.825 (0.9); 1.821 (0.7); 1.437 (5.7); 1.269 (0.8); 1.204 (0.6); 1.192 (0.3); 0.000 (1.4)

Beispiel I-T3-26: $^1$H-NMR (601.6 MHz, CD3CN):
δ = 8.222 (8.5); 8.184 (9.2); 8.183 (8.4); 7.933 (13.8); 7.743 (5.6); 7.739 (6.7); 7.712 (3.8); 7.709 (3.0); 7.699 (4.2); 7.695 (3.6); 7.530 (6.3); 7.516 (5.4); 7.228 (0.3); 7.216 (0.4); 7.172 (1.1); 5.481 (0.5); 4.022 (0.9); 3.653 (2.8); 3.641 (6.5); 3.631 (6.6); 3.620 (2.9); 2.605 (0.6); 2.594 (1.2); 2.586 (2.0); 2.582 (0.9); 2.575 (3.7); 2.568 (2.2); 2.564 (2.1); 2.556 (3.9); 2.549 (0.9); 2.545 (2.0); 2.538 (1.3); 2.527 (0.6); 2.505 (0.6); 2.502 (1.0); 2.499 (1.4); 2.496 (1.0); 2.361 (1.2); 2.216 (233.1); 2.214 (233.8); 2.213 (216.8); 2.211 (239.7); 2.210 (216.4); 2.206 (358.9); 2.092 (0.7); 2.088 (1.2); 2.084 (1.6); 2.080 (1.2); 2.076 (0.6); 2.005 (1.3); 1.998 (14.1); 1.990 (21.9); 1.985 (26.7); 1.982 (121.7); 1.978 (205.2); 1.973 (304.1); 1.969 (210.4); 1.965 (107.9); 1.867 (0.7); 1.863 (1.2); 1.859 (1.7); 1.855 (1.2); 1.850 (0.6); 1.470 (16.0); 1.303 (0.4); 1.237 (0.6); 0.033 (1.8)

Beispiel I-T3-27: $^1$H-NMR (400.0 MHz, d$_6$-DMSO):
δ = 9.439 (6.6); 8.693 (9.5); 8.441 (9.4); 8.274 (16.0); 7.807 (2.2); 7.802 (3.8); 7.792 (5.8); 7.786 (9.9); 7.569 (5.1); 7.553 (1.2); 7.546 (4.2); 4.020 (0.3); 3.568 (10.9); 3.328 (401.1); 2.675 (2.2); 2.671 (2.9); 2.666 (2.2); 2.506 (372.0); 2.502 (465.0); 2.497 (338.4); 2.333 (2.3); 2.328 (2.9); 2.324 (2.1); 1.989 (1.3); 1.615 (2.4); 1.601 (6.2); 1.594 (6.2); 1.581 (2.5); 1.398 (5.4); 1.287 (2.8); 1.274 (6.1); 1.267 (6.2); 1.253 (2.2); 1.235 (0.4); 1.192 (0.4); 1.175 (0.7); 1.157 (0.4); 0.146 (0.7); 0.000 (164.4); −0.008 (7.8); −0.150 (0.8)

Beispiel I-T3-28: $^1$H-NMR (400.0 MHz, d$_6$-DMSO):
δ = 8.684 (0.4); 8.672 (9.5); 8.535 (3.2); 8.524 (3.2); 8.453 (0.3); 8.427 (9.5); 8.271 (16.0); 7.749 (2.3); 7.744 (3.3); 7.723 (12.2); 7.519 (4.6); 7.498 (3.9); 4.056 (0.5); 4.038 (1.4); 4.020 (1.4); 4.002 (0.5); 3.568 (7.8); 3.329 (74.2); 2.857 (0.9); 2.848 (1.3); 2.839 (1.9); 2.829 (2.0); 2.820 (1.3); 2.811 (0.9); 2.801 (0.3); 2.676 (0.4); 2.671 (0.6); 2.667 (0.4); 2.524 (1.5); 2.511 (34.6); 2.507 (68.9); 2.502 (89.7); 2.498 (64.3); 2.493 (30.8); 2.333 (0.4); 2.329 (0.6); 2.324 (0.4); 1.989 (6.1); 1.397 (15.9); 1.193 (1.6); 1.175 (3.1); 1.157 (1.6); 0.728 (1.3); 0.716 (3.7); 0.711 (4.9); 0.698 (4.7); 0.693 (3.9); 0.681 (1.6); 0.561 (1.7); 0.551 (5.1); 0.544 (4.7); 0.535 (4.1); 0.523 (1.2); 0.008 (1.4); 0.000 (37.7); −0.008 (1.4)

Beispiel I-T3-29: $^1$H-NMR (400.1 MHz, d$_6$-DMSO):
δ = 9.042 (6.2); 9.036 (6.0); 8.962 (0.4); 8.831 (6.4); 8.826 (6.3); 8.807 (9.8); 8.678 (3.3); 8.668 (3.2); 8.507 (9.6); 8.478 (0.5); 8.385 (3.9); 8.379 (6.4); 8.374 (3.5); 8.111 (16.0); 3.368 (0.3); 3.367 (0.3); 3.365 (0.4); 3.362 (0.5); 3.361 (0.6); 3.360 (0.6); 3.357 (0.7); 3.356 (0.8); 3.350 (1.8); 3.330 (278.8); 3.313 (3.5); 3.309 (2.7); 3.308 (2.6); 3.306 (2.5); 3.297 (1.0); 3.295 (1.0); 3.294 (0.9); 3.287 (0.6); 3.284 (0.5); 3.281 (0.4); 3.279 (0.4); 3.277 (0.4); 2.915 (0.4); 2.905 (1.0); 2.896 (1.5); 2.887 (2.2); 2.877 (2.3); 2.869 (1.5); 2.859 (1.1); 2.849 (0.4); 2.711 (0.4); 2.671 (0.3); 2.565 (0.4); 2.564 (0.5); 2.563 (0.5); 2.562 (0.6); 2.560 (0.7); 2.559 (0.8); 2.558 (0.9); 2.557 (1.1); 2.555 (1.4); 2.542 (109.1); 2.533 (2.6); 2.532 (2.3); 2.530 (2.0); 2.529 (1.9); 2.528 (1.8); 2.527 (1.8); 2.525 (1.9); 2.524 (2.0); 2.523 (2.0); 2.511 (15.9); 2.507 (30.0); 2.502 (38.9); 2.498 (28.5); 2.494 (14.2); 2.368 (0.4); 2.130 (0.7); 1.234 (0.5); 0.765 (1.4); 0.752 (4.2); 0.747 (5.5); 0.735 (5.4); 0.729 (4.4); 0.717 (2.0); 0.696 (0.3); 0.618 (2.1); 0.608 (5.9); 0.602 (5.4); 0.592 (4.5); 0.580 (1.5); 0.146 (0.5); 0.022 (0.4); 0.021 (0.5); 0.020 (0.6); 0.019 (0.7); 0.017 (0.7); 0.016 (0.9); 0.008 (6.5); 0.000 (110.7); −0.009 (5.4); −0.013 (2.0); −0.014 (1.7); −0.015 (1.6); −0.016 (1.4); −0.018 (1.3); −0.019 (1.2); −0.020 (1.1); −0.021 (1.0); −0.023 (1.0); −0.024 (0.9); −0.025 (0.9); −0.026 (0.8); −0.027 (0.7); −0.029 (0.7); −0.031 (0.5); −0.034 (0.5); −0.035 (0.4); −0.036 (0.4); −0.150 (0.5)

Beispiel I-T3-30: $^1$H-NMR (400.1 MHz, d$_6$-DMSO):
δ = 9.562 (6.5); 9.101 (6.1); 9.095 (6.1); 8.989 (0.4); 8.855 (6.3); 8.850 (6.4); 8.829 (9.9); 8.5253 (9.7); 8.5245 (9.7); 8.496 (0.5); 8.438 (3.7); 8.432 (6.4); 8.427 (3.6); 8.115 (16.0); 5.759 (0.5); 3.361 (0.8); 3.329 (283.9); 2.712 (0.5); 2.671 (0.4); 2.568 (0.3); 2.567 (0.4); 2.565 (0.4); 2.564 (0.5); 2.563 (0.5); 2.562 (0.6); 2.560 (0.7); 2.559 (0.7); 2.558 (0.9); 2.557 (1.0); 2.555 (1.2); 2.554 (1.5); 2.542 (137.6); 2.533 (2.7); 2.532 (2.2); 2.530 (2.0); 2.529 (1.9); 2.528 (1.8); 2.527 (1.7); 2.525 (1.8); 2.524 (1.8); 2.523 (1.9); 2.511 (16.2); 2.507 (31.6); 2.502 (41.8); 2.498 (30.6); 2.493 (15.2); 2.368 (0.5); 1.631 (2.6); 1.617 (6.5); 1.610 (6.6); 1.597 (3.0); 1.348 (3.1); 1.334 (6.6); 1.328 (6.6); 1.313 (2.5); 1.234 (0.4); 0.146 (0.5); 0.026 (0.3); 0.025 (0.4); 0.024 (0.4); 0.022 (0.5); 0.021 (0.6); 0.020 (0.6); 0.019 (0.7); 0.016 (0.9); 0.008 (5.8); 0.000 (109.7); −0.008 (4.9); −0.014 (1.3); −0.015 (1.2); −0.016 (1.1); −0.018 (1.0); −0.019 (0.9); −0.020 (0.9); −0.023 (0.7); −0.024 (0.6); −0.025 (0.6); −0.027 (0.5); −0.029 (0.4); −0.031 (0.4); −0.150 (0.5)

Beispiel I-T3-31: $^1$H-NMR (601.6 MHz, CD3CN):
δ = 19.953 (0.4); 8.476 (0.6); 8.461 (16.0); 8.193 (0.3); 8.170 (0.6); 8.156 (14.9); 8.148 (0.5); 8.052 (0.3); 7.934 (7.1); 7.931 (7.2); 7.901 (0.6); 7.866 (5.7); 7.852 (8.0); 7.779 (4.3); 7.765 (3.1); 7.707 (9.8); 7.703 (11.5); 7.689 (0.7); 7.669 (6.5); 7.665 (5.3); 7.655 (7.3); 7.651 (6.3); 7.609 (0.4); 7.477 (11.0); 7.463 (9.5); 6.905 (2.4); 3.912 (2.1); 2.873 (0.6); 2.866 (1.9); 2.860 (2.7); 2.854 (4.1); 2.848 (4.3); 2.842 (2.7); 2.836 (2.0); 2.830 (0.7); 2.145 (513.7); 2.068 (0.6); 2.064 (0.3); 2.060 (0.5); 2.052 (8.1); 2.048 (5.6); 2.044 (2.9); 1.966 (31.6); 1.958 (83.8); 1.953 (98.4); 1.950 (560.5); 1.945 (964.6); 1.941 (1429.4); 1.937 (989.8); 1.933 (503.8); 1.925 (8.1); 1.843 (0.3); 1.835 (3.0); 1.831 (5.4); 1.827 (7.9); 1.823 (5.4); 1.818 (2.7); 1.340 (0.3); 1.285 (0.7); 1.269 (2.9); 1.123 (0.4); 0.882 (0.7); 0.790 (2.5); 0.782 (6.8); 0.779 (9.4); 0.770 (9.0); 0.767 (7.4); 0.759 (3.0); 0.744 (0.4); 0.732 (0.4); 0.636 (0.4); 0.609 (2.9); 0.601 (7.4); 0.598 (7.8); 0.595 (7.3); 0.592 (7.5); 0.583 (2.4); 0.097 (2.5); 0.005 (17.5); 0.000 (598.4); −0.006 (20.1); −0.100 (2.5)

Beispiel I-T3-32: $^1$H-NMR (601.6 MHz, CD3CN):
δ = 19.978 (0.8); 8.505 (16.0); 8.234 (0.7); 8.197 (15.1); 7.962 (7.3); 7.933 (1.0); 7.901 (6.0); 7.887 (8.2); 7.812 (4.3); 7.798 (3.2); 7.785 (9.1); 7.781 (11.3); 7.755 (6.0); 7.752 (4.8); 7.742 (6.5); 7.738 (5.8); 7.557 (10.5); 7.543 (9.3); 7.451 (1.9); 7.284 (1.2); 7.272 (0.9); 7.228 (1.1); 7.216 (0.9); 7.183 (0.6); 5.481 (0.6); 4.162 (2.0); 4.151 (2.3); 4.147 (6.6); 4.136 (6.5); 4.131 (7.2); 4.120 (6.5); 4.115 (3.0); 4.104 (2.2); 3.946 (0.8); 2.497 (1.3); 2.361 (4.7); 2.211 (114.1); 2.208 (135.0); 2.203 (158.6); 2.200 (140.9); 2.198 (164.0); 2.092 (0.8); 2.088 (1.1); 2.084 (1.6); 2.080 (1.1); 1.997 (12.7); 1.989 (19.6); 1.985 (22.3); 1.981 (108.3); 1.977 (181.4); 1.973 (268.0); 1.969 (184.4); 1.965 (94.6); 1.862 (1.0); 1.858 (1.5); 1.854 (1.1); 1.303 (1.1); 0.033 (2.1)

Beispiel I-T3-33: $^1$H-NMR (601.6 MHz, CD3CN):
δ = 8.489 (10.8); 8.221 (0.7); 8.184 (10.0); 7.966 (4.8); 7.932 (1.1); 7.902 (4.0); 7.888 (5.4); 7.813 (3.0); 7.799 (2.1); 7.759 (6.4); 7.755 (7.3); 7.725 (4.1); 7.722 (3.2); 7.712 (4.4); 7.708 (3.5); 7.533 (7.0); 7.519 (5.9); 7.111 (1.4); 3.659 (3.4); 3.648 (7.7); 3.637 (7.6); 3.626 (3.3); 2.609 (0.8); 2.598 (1.4); 2.591 (2.3); 2.579 (4.4); 2.572 (2.5); 2.568 (2.5); 2.561 (4.4); 2.549 (2.4); 2.542 (1.5); 2.531 (0.8); 2.184 (375.5); 2.182 (324.4); 2.181 (324.2); 2.177 (394.7); 2.173 (444.9); 2.092 (1.2); 2.088 (2.1); 2.084 (3.3); 2.080 (2.2); 2.076 (1.1); 1.998

(27.5); 1.990 (42.2); 1.985 (47.1); 1.981 (234.7); 1.977 (393.2); 1.973 (581.0); 1.969 (400.8); 1.965 (207.8); 1.867 (1.2); 1.863 (2.2); 1.859 (3.3); 1.855 (2.2); 1.850 (1.2); 1.471 (16.0); 1.303 (1.3); 0.033 (3.4)

Beispiel I-T3-34: $^1$H-NMR (400.0 MHz, CD3CN):
δ = 8.493 (16.0); 8.193 (15.4); 8.099 (0.4); 8.087 (6.7); 8.065 (8.0); 7.850 (4.4); 7.827 (4.3); 7.815 (7.2); 7.752 (9.3); 7.747 (11.6); 7.720 (6.3); 7.715 (4.4); 7.699 (7.2); 7.694 (5.8); 7.569 (4.2); 7.514 (10.8); 7.493 (8.8); 4.012 (0.8); 3.891 (0.5); 3.458 (0.5); 3.452 (0.5); 3.236 (1.8); 3.067 (0.5); 3.056 (0.5); 2.848 (0.4); 2.140 (115.1); 2.120 (1.0); 2.114 (1.4); 2.108 (1.6); 2.102 (1.2); 2.095 (0.6); 1.972 (1.7); 1.965 (8.4); 1.958 (21.0); 1.953 (103.8); 1.947 (185.9); 1.940 (245.9); 1.934 (166.9); 1.928 (84.5); 1.781 (0.6); 1.775 (1.1); 1.769 (1.5); 1.763 (1.0); 1.756 (0.6); 1.605 (4.6); 1.591 (11.9); 1.584 (11.8); 1.570 (6.0); 1.530 (0.8); 1.437 (6.2); 1.407 (0.7); 1.367 (6.3); 1.353 (11.8); 1.346 (12.0); 1.332 (4.7); 1.294 (0.6); 1.269 (5.1); 1.204 (0.6); 0.882 (0.6); 0.146 (1.2); 0.008 (11.5); 0.000 (282.0); −0.009 (9.7); −0.150 (1.3)

Beispiel I-T3-35: $^1$H-NMR (400.0 MHz, CD3CN):
δ = 8.496 (0.7); 8.480 (16.0); 8.182 (15.3); 8.181 (14.8); 8.087 (6.6); 8.065 (7.9); 7.848 (4.7); 7.825 (4.8); 7.812 (7.7); 7.702 (9.9); 7.697 (11.9); 7.670 (6.9); 7.664 (4.9); 7.649 (7.8); 7.643 (6.3); 7.481 (10.8); 7.460 (8.6); 6.929 (2.9); 2.887 (0.7); 2.877 (2.1); 2.868 (2.9); 2.859 (4.5); 2.849 (4.5); 2.841 (2.9); 2.831 (2.1); 2.822 (0.7); 2.467 (0.4); 2.463 (0.5); 2.458 (0.4); 2.153 (188.6); 2.120 (0.8); 2.114 (1.1); 2.108 (1.3); 2.102 (0.9); 2.096 (0.5); 1.972 (2.2); 1.965 (8.7); 1.959 (23.3); 1.953 (95.7); 1.947 (167.7); 1.941 (215.6); 1.934 (146.4); 1.928 (73.1); 1.781 (0.5); 1.775 (0.9); 1.769 (1.2); 1.763 (0.8); 1.757 (0.4); 1.437 (6.9); 1.269 (0.6); 1.204 (0.5); 0.800 (2.4); 0.788 (7.7); 0.783 (9.7); 0.770 (10.2); 0.765 (7.3); 0.753 (3.1); 0.731 (0.4); 0.713 (0.4); 0.656 (0.4); 0.646 (0.4); 0.617 (3.3); 0.605 (8.7); 0.599 (9.2); 0.595 (8.3); 0.590 (7.6); 0.577 (2.2); 0.522 (0.3); 0.146 (1.0); 0.000 (233.4); −0.009 (9.6); −0.150 (1.0)

Beispiel I-T3-36: $^1$H-NMR (400.0 MHz, CD3CN):
δ = 8.496 (16.0); 8.192 (15.3); 8.093 (6.4); 8.071 (7.7); 7.850 (4.3); 7.827 (4.3); 7.814 (7.1); 7.749 (9.1); 7.743 (11.5); 7.726 (6.8); 7.721 (4.1); 7.706 (7.6); 7.700 (5.6); 7.532 (10.3); 7.511 (8.3); 7.340 (2.4); 4.149 (2.3); 4.132 (2.8); 4.125 (7.1); 4.109 (7.4); 4.102 (7.4); 4.085 (7.2); 4.078 (2.6); 4.061 (2.3); 2.137 (51.6); 2.120 (0.6); 2.114 (0.9); 2.108 (1.0); 2.102 (0.7); 2.095 (0.4); 1.965 (6.7); 1.958 (18.2); 1.953 (74.7); 1.946 (129.6); 1.940 (165.9); 1.934 (111.8); 1.928 (55.4); 1.781 (0.4); 1.775 (0.7); 1.769 (1.0); 1.763 (0.6); 1.437 (3.7); 1.270 (0.3); 0.146 (0.8); 0.008 (11.2); 0.000 (188.1); −0.009 (6.3); −0.150 (0.8)

Beispiel I-T3-37: $^1$H-NMR (400.0 MHz, CD3CN):
δ = 8.518 (0.5); 8.490 (16.0); 8.238 (0.5); 8.193 (14.9); 8.090 (6.7); 8.069 (7.7); 7.850 (4.2); 7.827 (4.0); 7.814 (6.7); 7.735 (9.2); 7.729 (11.3); 7.717 (0.4); 7.696 (6.1); 7.690 (4.5); 7.675 (7.0); 7.569 (7.9); 7.587 (0.6); 7.536 (0.3); 7.514 (11.0); 7.494 (0.6); 7.483 (9.1); 7.459 (1.7); 7.445 (1.6); 6.694 (0.4); 6.666 (0.3); 5.364 (0.6); 5.343 (2.4); 5.322 (4.7); 5.301 (4.6); 5.280 (2.4); 5.259 (0.7); 4.006 (0.5); 3.589 (0.4); 3.567 (0.4); 3.549 (6.1); 3.545 (3.8); 3.525 (11.4); 3.507 (4.3); 3.503 (7.9); 3.379 (8.1); 3.375 (5.1); 3.358 (11.5); 3.355 (10.8); 3.338 (3.6); 3.334 (6.2); 3.067 (0.5); 2.848 (0.5); 2.472 (0.5); 2.468 (1.0); 2.463 (1.3); 2.458 (1.0); 2.453 (0.5); 2.264 (0.3); 2.245 (0.4); 2.151 (305.9); 2.120 (1.6); 2.114 (2.3); 2.107 (2.8); 2.101 (2.0); 2.095 (1.0); 2.022 (1.9); 2.003 (0.5); 1.964 (14.6); 1.958 (33.8); 1.952 (185.3); 1.946 (333.6); 1.940 (449.3); 1.934 (307.4); 1.928 (157.3); 1.915 (1.9); 1.781 (1.0); 1.775 (1.8); 1.768 (2.5); 1.762 (1.7); 1.756 (0.8); 1.269 (2.1); 0.146 (3.1); 0.025 (0.7); 0.008 (22.9); 0.000 (696.9); −0.009 (23.3); −0.150 (3.1)

Beispiel I-T3-38: $^1$H-NMR (400.0 MHz, CD3CN):
δ = 8.238 (7.9); 8.119 (7.5); 7.748 (4.6); 7.742 (5.7); 7.729 (4.0); 7.711 (3.1); 7.706 (2.3); 7.690 (3.5); 7.685 (2.8); 7.666 (1.4); 7.644 (2.6); 7.595 (5.4); 7.574 (4.0); 7.500 (5.1); 7.479 (4.2); 4.068 (1.0); 4.050 (1.0); 4.032 (0.3); 2.800 (1.9); 2.781 (5.9); 2.762 (6.0); 2.744 (2.0); 2.139 (27.7); 2.120 (0.5); 2.113 (0.5); 2.107 (0.6); 2.101 (0.4); 1.972 (4.6); 1.964 (2.9); 1.958 (7.5); 1.952 (33.5); 1.946 (58.9); 1.940 (77.3); 1.933 (53.2); 1.927 (27.2); 1.774 (0.4); 1.768 (0.5); 1.762 (0.3); 1.601 (2.2); 1.587 (6.0); 1.580 (6.0); 1.566 (3.0); 1.526 (0.4); 1.402 (0.3); 1.362 (3.0); 1.348 (6.0); 1.342 (6.1); 1.327 (2.3); 1.270 (1.6); 1.221 (1.2); 1.204 (2.3); 1.186 (1.1); 1.113 (7.7); 1.095 (16.0); 1.076 (7.4); 0.146 (1.1); 0.008 (13.7); 0.000 (231.5); −0.009 (10.7); −0.150 (1.1)

Beispiel I-T3-39: $^1$H-NMR (400.0 MHz, CD3CN):
δ = 8.226 (8.7); 8.120 (0.4); 8.108 (8.2); 7.726 (4.1); 7.700 (4.7); 7.694 (5.9); 7.680 (0.5); 7.663 (4.5); 7.657 (3.5); 7.642 (6.1); 7.637 (5.3); 7.593 (5.2); 7.572 (2.8); 7.467 (5.6); 7.447 (4.6); 6.927 (1.4); 3.874 (0.7); 3.051 (0.4); 2.938 (0.4); 2.875 (0.9); 2.865 (1.4); 2.857 (2.1); 2.847 (2.1); 2.838 (1.4); 2.829 (1.0); 2.819 (0.3); 2.780 (6.2); 2.761 (6.4); 2.742 (2.2); 2.463 (0.4); 2.160 (108.1); 2.120 (0.8); 2.114 (0.9); 2.108 (1.0); 2.101 (0.7); 2.095 (0.4); 1.972 (0.6); 1.964 (3.4); 1.958 (8.7); 1.952 (47.6); 1.946 (86.2); 1.940 (115.8); 1.934 (80.2); 1.928 (41.7); 1.781 (0.4); 1.775 (0.5); 1.768 (0.7); 1.762 (0.5); 1.437 (6.6); 1.270 (1.4); 1.112 (7.8); 1.102 (1.0); 1.093 (16.0); 1.074 (7.6); 0.797 (1.2); 0.784 (3.7); 0.779 (4.7); 0.766 (4.9); 0.761 (3.7); 0.749 (1.7); 0.614 (1.6); 0.602 (4.5); 0.596 (4.5); 0.592 (4.0); 0.587 (4.0); 0.574 (1.2); 0.146 (1.3); 0.008 (10.2); 0.007 (10.2); 0.000 (266.8); −0.008 (11.5); −0.150 (1.3)

Beispiel I-T3-40: $^1$H-NMR (400.0 MHz, CD3CN):
δ = 8.241 (8.2); 8.240 (8.8); 8.117 (8.2); 7.746 (4.6); 7.741 (6.2); 7.727 (4.2); 7.718 (3.5); 7.712 (2.4); 7.697 (3.6); 7.691 (3.1); 7.664 (1.4); 7.642 (2.6); 7.597 (5.2); 7.576 (2.7); 7.516 (5.5); 7.495 (4.5); 7.352 (0.9); 4.144 (1.2); 4.128 (1.3); 4.121 (3.6); 4.104 (3.6); 4.097 (3.8); 4.081 (3.6); 4.074 (1.4); 4.057 (1.2); 2.800 (2.0); 2.781 (5.9); 2.763 (6.1); 2.744 (2.1); 2.153 (11.7); 2.149 (14.3); 1.971 (0.5); 1.964 (1.3); 1.958 (3.1); 1.952 (16.8); 1.946 (30.8); 1.940 (41.6); 1.934 (28.7); 1.927 (14.8); 1.436 (10.4); 1.268 (0.4); 1.114 (7.8); 1.095 (16.0); 1.076 (7.6); 0.146 (0.6); 0.008 (4.4); 0.000 (116.7); −0.008 (5.1); −0.150 (0.6)

Beispiel I-T3-41: $^1$H-NMR (400.0 MHz, CD3CN):
δ = 8.239 (7.9); 8.122 (7.5); 7.732 (8.1); 7.727 (9.3); 7.689 (3.0); 7.684 (2.4); 7.668 (4.6); 7.663 (4.2); 7.644 (2.6); 7.598 (4.8); 7.577 (2.6); 7.491 (5.3); 7.470 (4.9); 5.342 (1.2); 5.320 (2.4); 5.300 (2.4); 5.279 (1.2); 3.548 (3.0); 3.524 (6.0); 3.502 (4.1); 3.374 (4.1); 3.371 (2.6); 3.354 (6.0); 3.351 (5.6); 3.330 (3.2); 2.803 (1.9); 2.784 (5.9); 2.765 (6.0); 2.746 (2.1); 2.468 (0.8); 2.464 (0.9); 2.459 (0.7); 2.156 (336.8); 2.120 (1.6); 2.114 (2.0); 2.107 (2.3); 2.101 (1.6); 2.095 (1.0); 1.964 (10.5); 1.958 (27.4); 1.952 (132.9); 1.946 (239.9); 1.940 (318.6); 1.934 (221.8); 1.928 (114.5); 1.781 (0.8); 1.775 (1.4); 1.769 (1.9); 1.762 (1.3); 1.756 (0.7); 1.437 (0.8); 1.269 (2.2); 1.115 (7.6); 1.096 (16.0); 1.078 (7.4); 0.146 (3.8); 0.008 (39.2); 0.000 (832.6); −0.008 (44.8); −0.150 (4.0)

Beispiel I-T3-42: $^1$H-NMR (400.0 MHz, d$_6$-DMSO):
δ = 8.830 (5.8); 8.821 (4.0); 8.815 (4.0); 8.694 (1.8); 8.683 (1.8); 8.548 (5.3); 8.547 (5.5); 8.315 (0.6); 8.192 (4.1); 8.186 (3.9); 8.107 (8.4); 3.902 (16.0); 3.333 (334.0); 3.243 (1.4); 3.175 (0.9); 3.162 (0.9); 2.870 (0.5); 2.861 (0.7); 2.852 (1.1); 2.842 (1.1); 2.833 (0.7); 2.824 (0.5); 2.680 (0.3); 2.676 (0.7); 2.672 (0.9); 2.667 (0.7); 2.662 (0.7); 2.542 (0.5); 2.525 (2.7); 2.511 (58.6); 2.507 (116.6); 2.502 (152.6); 2.498 (110.8); 2.493 (53.8); 2.338 (0.3); 2.334 (0.7); 2.329 (0.9); 2.325 (0.7); 1.909 (0.5); 1.016 (0.6); 1.001 (0.6); 0.757 (0.7); 0.744 (2.0); 0.739 (2.8); 0.727 (2.6); 0.721 (2.2); 0.709 (0.9); 0.566 (0.9); 0.555 (2.6); 0.549 (2.4); 0.545 (2.3); 0.540 (2.2); 0.528 (0.7); 0.008 (0.5); 0.000 (16.2); −0.009 (0.5)

Beispiel I-T3-43: $^1$H-NMR (400.0 MHz, d$_6$-DMSO):
δ = 9.603 (7.1); 8.876 (6.9); 8.870 (6.9); 8.843 (10.4); 8.833 (0.4); 8.554 (10.3); 8.315 (0.8); 8.280 (7.0); 8.274 (6.8); 8.110 (16.0); 3.903 (14.5); 3.434 (0.4); 3.333 (565.4); 3.045 (0.5); 2.869 (0.5); 2.676 (1.3); 2.671 (1.7); 2.667 (1.3); 2.662 (0.7); 2.542 (1.5); 2.524 (5.6); 2.511 (106.6); 2.507 (206.6); 2.502 (266.2); 2.498 (191.5); 2.493 (91.5); 2.338 (0.5); 2.334 (1.1); 2.329 (1.5); 2.325 (1.1); 1.643 (2.4); 1.629 (5.7); 1.622 (6.0); 1.609 (2.6); 1.298 (2.9); 1.284 (5.7); 1.277 (6.1); 1.263 (2.3); 1.249 (0.4); 1.236 (0.4); 0.008 (0.8); 0.000 (22.4); −0.009 (0.7)

Beispiel I-T3-44: $^1$H-NMR (400.0 MHz, CD3CN):
δ = 8.115 (9.4); 8.071 (10.0); 7.690 (6.4); 7.685 (6.3); 7.668 (1.1); 7.653 (3.9); 7.632 (4.2); 7.586 (0.3); 7.549 (8.1); 7.509 (0.4); 7.463 (5.6); 7.442 (4.5); 6.896 (2.5); 4.068 (0.5); 4.051 (0.5); 2.871 (1.3); 2.862 (1.9); 2.853 (2.6); 2.844 (2.5); 2.835 (1.9); 2.826 (1.2); 2.816 (0.5); 2.452 (2.7); 2.434 (7.4); 2.415 (7.5); 2.396 (2.8); 2.251 (0.5); 2.143 (127.4); 2.113 (3.7); 2.092 (29.0); 1.971 (7.1); 1.952 (73.0); 1.946 (111.8); 1.943 (112.2); 1.940 (130.1); 1.937 (90.9); 1.934 (90.5); 1.928 (48.4); 1.774 (0.6); 1.768 (0.7); 1.437 (3.1); 1.221 (0.7); 1.204 (1.2); 1.186 (0.6); 1.082 (8.3); 1.063 (16.0); 1.044 (7.9); 0.794 (1.7); 0.780 (6.1); 0.777 (6.2); 0.764 (6.6); 0.747 (2.1); 0.726 (0.4); 0.610 (2.4); 0.600 (6.7); 0.592 (7.0); 0.572 (1.7); 0.535 (0.4); 0.528 (0.3); 0.524 (0.3); 0.147 (1.4); 0.000 (240.4); −0.149 (1.3)

Beispiel I-T3-45: ¹H-NMR (400.0 MHz, CD3CN):
δ = 8.126 (9.0); 8.092 (9.4); 7.735 (4.9); 7.730 (6.5); 7.710 (3.2); 7.705 (2.4); 7.689 (3.6); 7.684 (3.1); 7.549 (5.9); 7.542 (5.8); 7.513 (5.6); 7.492 (4.6); 7.422 (1.5); 4.140 (1.2); 4.123 (1.5); 4.116 (3.7); 4.100 (3.9); 4.093 (4.1); 4.076 (3.7); 4.069 (1.6); 4.052 (1.2); 3.545 (1.6); 2.464 (1.4); 2.455 (2.7); 2.436 (6.7); 2.417 (6.9); 2.398 (2.4); 2.378 (0.9); 2.253 (0.5); 2.221 (1.4); 2.176 (369.0); 2.126 (0.6); 2.120 (0.7); 2.114 (1.0); 2.108 (1.5); 2.094 (27.0); 1.953 (71.9); 1.947 (129.9); 1.941 (173.4); 1.935 (125.8); 1.928 (67.7); 1.781 (0.4); 1.775 (0.7); 1.769 (1.1); 1.763 (0.7); 1.757 (0.4); 1.436 (9.9); 1.269 (0.4); 1.102 (0.5); 1.084 (8.0); 1.065 (16.0); 1.046 (7.7); 1.025 (0.5); 0.146 (2.0); 0.000 (393.0); −0.150 (2.0)

Beispiel I-T3-46: ¹H-NMR (400.0 MHz, CD3CN):
δ = 8.127 (4.1); 8.085 (4.4); 7.738 (2.5); 7.732 (3.1); 7.702 (1.6); 7.697 (1.2); 7.681 (1.8); 7.676 (1.5); 7.625 (0.9); 7.551 (2.4); 7.543 (2.3); 7.495 (2.9); 7.474 (2.3); 2.453 (1.1); 2.435 (3.1); 2.416 (3.2); 2.397 (1.1); 2.158 (61.0); 2.114 (0.4); 2.108 (0.5); 2.092 (12.6); 1.964 (2.0); 1.958 (4.9); 1.953 (25.4); 1.946 (45.6); 1.940 (61.1); 1.934 (42.3); 1.928 (21.8); 1.769 (0.4); 1.598 (1.2); 1.583 (3.1); 1.576 (3.1); 1.563 (1.6); 1.437 (16.0); 1.358 (1.6); 1.345 (3.1); 1.338 (3.2); 1.323 (1.3); 1.269 (1.8); 1.083 (4.2); 1.064 (8.8); 1.045 (4.0); 0.146 (0.7); 0.017 (0.4); 0.008 (5.9); 0.000 (150.8); −0.009 (6.1); −0.150 (0.7)

Beispiel I-T3-47: ¹H-NMR (400.0 MHz, CD3CN):
δ = 8.128 (3.6); 8.084 (3.8); 7.721 (2.0); 7.715 (2.5); 7.678 (1.2); 7.673 (1.0); 7.657 (1.4); 7.652 (1.2); 7.551 (2.1); 7.544 (2.1); 7.485 (2.4); 7.464 (2.2); 5.338 (0.6); 5.316 (1.1); 5.296 (1.1); 5.275 (0.6); 3.544 (1.4); 3.520 (2.8); 3.498 (1.8); 3.370 (1.7); 3.349 (2.6); 3.346 (2.4); 3.325 (1.4); 2.456 (0.9); 2.437 (2.6); 2.418 (2.7); 2.399 (0.9); 2.166 (9.4); 2.153 (19.8); 2.107 (0.4); 2.095 (10.7); 1.964 (1.2); 1.958 (3.1); 1.952 (15.2); 1.946 (27.1); 1.940 (36.2); 1.934 (25.2); 1.928 (13.1); 1.437 (16.0); 1.085 (3.2); 1.066 (6.7); 1.047 (3.1); 0.146 (0.4); 0.008 (3.9); 0.000 (86.8); −0.008 (4.3); −0.150 (0.5)

Beispiel I-T3-48: ¹H-NMR (400.0 MHz, CD3CN):
δ = 8.261 (10.8); 8.206 (0.8); 8.193 (16.0); 7.692 (9.7); 7.686 (12.3); 7.675 (1.0); 7.657 (6.5); 7.652 (4.9); 7.637 (9.5); 7.630 (13.3); 7.608 (11.0); 7.475 (11.5); 7.455 (9.1); 6.940 (2.5); 3.911 (0.6); 2.882 (0.7); 2.872 (2.0); 2.863 (2.8); 2.854 (4.4); 2.845 (4.3); 2.836 (2.9); 2.827 (2.0); 2.817 (0.7); 2.467 (0.3); 2.463 (0.4); 2.163 (117.4); 2.120 (0.3); 2.114 (0.5); 2.108 (0.7); 2.102 (0.5); 1.972 (1.7); 1.965 (3.3); 1.959 (8.5); 1.953 (43.3); 1.947 (77.6); 1.941 (103.6); 1.934 (71.4); 1.928 (36.7); 1.775 (0.4); 1.769 (0.6); 1.763 (0.4); 1.437 (2.0); 1.269 (0.7); 1.221 (0.4); 1.204 (0.7); 1.186 (0.3); 0.795 (2.4); 0.783 (7.5); 0.778 (9.7); 0.765 (10.2); 0.760 (7.3); 0.748 (3.3); 0.726 (0.4); 0.708 (0.4); 0.654 (0.4); 0.644 (0.4); 0.614 (3.3); 0.604 (8.6); 0.597 (9.0); 0.593 (7.8); 0.588 (7.7); 0.575 (2.3); 0.514 (0.4); 0.146 (1.3); 0.026 (0.4); 0.008 (10.5); 0.000 (259.4); −0.009 (10.3); −0.150 (1.2)

Beispiel I-T3-49: ¹H-NMR (400.0 MHz, CD3CN):
δ = 8.277 (10.6); 8.206 (16.0); 7.740 (9.1); 7.735 (12.1); 7.709 (6.2); 7.704 (4.7); 7.688 (7.6); 7.683 (7.1); 7.669 (3.6); 7.645 (1.5); 7.631 (10.9); 7.611 (10.7); 7.574 (0.5); 7.510 (11.0); 7.500 (0.6); 7.489 (9.0); 7.475 (0.4); 7.221 (0.6); 5.448 (8.3); 4.053 (4.3); 4.034 (0.9); 3.914 (1.0); 3.906 (0.7); 3.897 (0.5); 2.469 (1.1); 2.464 (1.5); 2.460 (1.1); 2.243 (0.4); 2.175 (509.2); 2.120 (1.2); 2.114 (1.7); 2.108 (2.3); 2.102 (1.5); 2.096 (0.9); 1.965 (8.1); 1.959 (21.5); 1.953 (116.7); 1.947 (211.5); 1.941 (284.4); 1.934 (197.6); 1.928 (103.4); 1.781 (0.8); 1.775 (1.3); 1.769 (1.8); 1.763 (1.3); 1.757 (0.7); 1.635 (0.4); 1.598 (4.6); 1.584 (12.3); 1.577 (12.3); 1.563 (6.3); 1.523 (0.8); 1.437 (0.7); 1.403 (0.8); 1.363 (6.4); 1.349 (12.1); 1.342 (12.8); 1.328 (4.9); 1.290 (0.6); 1.270 (2.7); 1.206 (1.3); 1.190 (1.2); 0.882 (0.3); 0.146 (3.5); 0.008 (26.4); 0.000 (693.0); −0.008 (31.4); −0.048 (0.4); −0.150 (3.5)

Beispiel I-T3-50: ¹H-NMR (400.0 MHz, CD3CN):
δ = 8.131 (3.8); 8.120 (0.3); 8.108 (3.8); 7.670 (2.4); 7.664 (2.9); 7.636 (1.7); 7.630 (1.2); 7.615 (1.9); 7.609 (1.6); 7.462 (2.8); 7.441 (2.1); 7.320 (3.0); 7.300 (1.2); 6.909 (0.6); 4.085 (0.5); 4.068 (1.4); 4.050 (1.4); 4.032 (0.5); 3.901 (16.0); 2.870 (0.5); 2.861 (0.7); 2.852 (1.1); 2.843 (1.1); 2.834 (0.7); 2.825 (0.5); 2.147 (64.0); 2.114 (0.3); 2.107 (0.4); 1.972 (6.8); 1.964 (3.1); 1.958 (6.8); 1.952 (27.1); 1.946 (46.5); 1.940 (60.6); 1.934 (41.2); 1.928 (20.8); 1.768 (0.3); 1.437 (1.1); 1.221 (1.7); 1.204 (3.2); 1.186 (1.6); 0.793 (0.6); 0.781 (1.8); 0.776 (2.3); 0.763 (2.4); 0.758 (1.7); 0.746 (0.8); 0.610 (0.9); 0.599 (2.1); 0.593 (2.1); 0.589 (1.9); 0.584 (1.8); 0.571 (0.5); 0.146 (0.7); 0.008 (9.0); 0.000 (144.6); −0.009 (5.4); −0.150 (0.7)

Beispiel I-T3-51: ¹H-NMR (400.0 MHz, CD3CN):
δ = 8.206 (0.4); 8.147 (3.5); 8.120 (3.6); 7.717 (2.2); 7.712 (2.8); 7.686 (1.6); 7.680 (1.3); 7.675 (0.4); 7.665 (2.0); 7.659 (1.9); 7.654 (0.6); 7.644 (0.5); 7.630 (0.5); 7.610 (0.3); 7.503 (0.4); 7.495 (2.6); 7.482 (3.0); 7.474 (2.1); 7.321 (2.8); 7.302 (1.3); 4.068 (1.8); 4.050 (0.9); 3.902 (16.0); 2.170 (60.8); 2.114 (0.4); 2.108 (0.5); 2.102 (0.3); 1.972 (4.1); 1.965 (2.3); 1.959 (5.7); 1.953 (31.1); 1.947 (56.0); 1.940 (74.9); 1.934 (51.0); 1.928 (25.9); 1.775 (0.3); 1.769 (0.4); 1.595 (1.1); 1.581 (2.7); 1.574 (2.7); 1.560 (1.5); 1.437 (1.0); 1.359 (1.5); 1.346 (2.7); 1.339 (2.8); 1.324 (1.1); 1.222 (1.1); 1.204 (2.1); 1.186 (1.0); 1.140 (0.5); 1.132 (0.6); 0.928 (0.6); 0.921 (0.6); 0.146 (0.8); 0.008 (7.0); 0.000 (187.7); −0.009 (6.3); −0.150 (0.8)

Beispiel I-T3-52: ¹H-NMR (400.0 MHz, CD3CN):
δ = 8.276 (6.4); 8.163 (0.3); 8.151 (6.6); 8.149 (7.0); 8.128 (3.5); 8.104 (1.6); 8.082 (1.8); 7.863 (2.9); 7.842 (2.4); 7.694 (4.0); 7.689 (5.1); 7.680 (0.5); 7.660 (3.0); 7.654 (2.2); 7.639 (3.3); 7.633 (2.8); 7.474 (4.9); 7.454 (3.9); 6.935 (1.1); 4.086 (0.7); 4.068 (2.0); 4.050 (2.1); 4.032 (0.7); 2.873 (0.8); 2.863 (1.2); 2.855 (1.8); 2.845 (1.9); 2.836 (1.2); 2.827 (0.9); 2.165 (66.0); 2.163 (75.8); 1.972 (9.5); 1.965 (1.3); 1.959 (3.0); 1.953 (16.9); 1.947 (30.5); 1.941 (41.0); 1.935 (28.3); 1.928 (14.5); 1.436 (16.0); 1.269 (0.5); 1.221 (2.5); 1.204 (4.8); 1.186 (2.4); 0.796 (1.0); 0.784 (2.9); 0.778 (3.9); 0.766 (4.1); 0.761 (3.0); 0.748 (1.4); 0.613 (1.4); 0.602 (3.5); 0.596 (3.5); 0.592 (3.2); 0.587 (3.2); 0.574 (1.0); 0.008 (2.1); 0.000 (62.9); −0.009 (2.3)

Beispiel I-T3-53: ¹H-NMR (400.0 MHz, CD3CN):
δ = 8.291 (3.8); 8.162 (4.2); 8.130 (2.0); 8.108 (0.9); 8.086 (1.0); 7.866 (1.8); 7.844 (1.5); 7.742 (2.5); 7.736 (3.2); 7.709 (2.0); 7.703 (1.5); 7.688 (2.7); 7.682 (2.4); 7.506 (3.0); 7.485 (2.4); 2.196 (8.5); 2.183 (24.4); 1.972 (1.1); 1.965 (0.6); 1.959 (1.4); 1.954 (7.8); 1.947 (14.2); 1.941 (19.1); 1.935 (13.1); 1.929 (6.7); 1.599 (1.3); 1.585 (3.1); 1.578 (3.1); 1.564 (1.7); 1.436 (16.0); 1.362 (1.7); 1.349 (3.0); 1.342 (3.1); 1.327 (1.3); 1.204 (0.6); 0.008 (1.6); 0.000 (44.8); −0.009 (1.6)

Beispiel I-T3-54: ¹H-NMR (400.0 MHz, CD3CN):
δ = 8.162 (0.9); 8.153 (15.7); 8.108 (12.4); 7.996 (6.8); 7.952 (7.0); 7.683 (9.7); 7.678 (12.2); 7.666 (0.8); 7.650 (6.7); 7.644 (4.9); 7.629 (7.9); 7.624 (6.4); 7.513 (0.4); 7.469 (11.7); 7.448 (9.3); 6.931 (2.4); 5.448 (0.6); 4.235 (0.4); 4.218 (0.4); 4.086 (0.6); 4.068 (1.8); 4.057 (0.4); 4.050 (1.8); 4.032 (0.6); 2.879 (0.8); 2.870 (2.2); 2.860 (2.8); 2.852 (4.7); 2.842 (4.7); 2.834 (2.9); 2.824 (2.2); 2.814 (0.7); 2.473 (0.6); 2.468 (1.4); 2.463 (1.4); 2.459 (1.4); 2.454 (0.5); 2.276 (0.4); 2.264 (0.4); 2.245 (0.6); 2.226 (0.8); 2.159 (388.9); 2.116 (47.5); 2.108 (3.9); 2.101 (1.9); 2.095 (1.0); 2.050 (0.8); 2.035 (0.7); 2.017 (1.1); 1.998 (1.0); 1.972 (9.4); 1.964 (12.6); 1.958 (30.5); 1.953 (165.9); 1.946 (298.2); 1.940 (398.5); 1.934 (272.4); 1.928 (139.0); 1.915 (1.9); 1.781 (0.9); 1.775 (1.6); 1.769 (2.3); 1.762 (1.6); 1.756 (0.8); 1.509 (0.3); 1.437 (13.5); 1.341 (0.4); 1.307 (1.0); 1.289 (1.9); 1.269 (16.0); 1.222 (2.4); 1.204 (4.5); 1.186 (2.2); 0.898 (0.7); 0.881 (2.2); 0.864 (1.0); 0.793 (2.4); 0.780 (7.3); 0.775 (9.5); 0.762 (10.1); 0.757 (6.9); 0.745 (3.2); 0.723 (0.5); 0.705 (0.5); 0.650 (0.4); 0.640 (0.5); 0.631 (0.5); 0.626 (0.6); 0.610 (3.5); 0.600 (7.9); 0.598 (7.8); 0.593 (8.2); 0.588 (7.1); 0.583 (7.2); 0.571 (2.4); 0.523 (0.3); 0.393 (0.5); 0.385 (0.5); 0.381 (0.5); 0.376 (0.5); 0.146 (3.4); 0.008 (28.7); 0.000 (825.5); −0.009 (28.8); −0.030 (0.5); −0.150 (3.4)

Beispiel I-T3-55: ¹H-NMR (601.6 MHz, CD3CN):
δ = 8.166 (3.1); 8.165 (3.2); 8.124 (2.4); 8.000 (1.2); 7.954 (1.2); 7.732 (2.0); 7.729 (2.3); 7.697 (1.3); 7.693 (1.1); 7.683 (1.5); 7.679 (1.3); 7.499 (2.3); 7.485 (2.0); 2.180 (8.0); 2.177 (8.1); 2.175 (8.7); 2.172 (9.0); 2.169 (10.1); 2.167 (8.6); 2.163 (12.2); 2.117 (8.6); 1.973 (0.6); 1.966 (0.7); 1.958 (1.9); 1.954 (2.1); 1.950 (12.7); 1.946 (22.2); 1.942 (32.1); 1.938 (21.1); 1.934 (10.5); 1.591 (1.0); 1.581 (2.2); 1.577 (2.2); 1.568 (1.1); 1.436 (16.0); 1.354 (1.2); 1.345 (2.2); 1.341 (2.3); 1.331 (1.0); 1.204 (0.4); 0.005 (1.3); 0.000 (42.8); −0.006 (1.2)

Beispiel I-T3-56: ¹H-NMR (400.0 MHz, CD3CN):
δ = 8.210 (7.6); 8.194 (0.9); 8.186 (15.9); 8.185 (16.0); 8.161 (0.7); 8.149 (14.1); 8.059 (7.6); 7.686 (9.6); 7.681 (12.3); 7.653 (6.8); 7.647 (5.0); 7.632 (7.9); 7.626 (6.5); 7.517 (0.3); 7.473 (11.6); 7.452 (9.1); 6.900 (2.7); 2.878 (0.7); 2.869 (2.1); 2.859 (2.9); 2.851 (4.6); 2.841 (4.6); 2.832 (2.9); 2.823 (2.2); 2.813 (0.7); 2.136 (41.9); 2.120 (0.5); 2.113 (0.6); 2.107 (0.8); 2.101 (0.5); 2.086 (0.4); 1.964 (15.3); 1.958 (9.2); 1.952 (49.0); 1.946 (88.5); 1.940 (118.3); 1.934 (80.8); 1.927 (41.2); 1.915 (0.5); 1.774 (0.5); 1.768 (0.7); 1.762 (0.5); 1.270 (0.4); 0.792 (2.4); 0.780 (7.2); 0.775 (9.6); 0.762 (10.1); 0.757 (7.0); 0.745 (3.3); 0.723 (0.4); 0.705 (0.4); 0.650 (0.4); 0.640 (0.4); 0.610 (3.3); 0.600 (8.0); 0.599 (8.0); 0.593 (8.4); 0.589 (7.4); 0.584 (7.5); 0.571 (2.4); 0.520 (0.4); 0.146 (0.9); 0.008 (7.4); 0.000 (218.3); −0.009 (7.6); −0.150 (0.9)

Beispiel I-T3-57: ¹H-NMR (400.0 MHz, CD3CN):
δ = 8.211 (2.2); 8.197 (4.2); 8.163 (3.5); 8.060 (2.1); 7.735 (2.4); 7.730 (3.0); 7.704 (1.6); 7.699 (1.1); 7.683 (1.8); 7.678 (1.5); 7.553 (1.2); 7.508 (2.8); 7.487 (2.3); 2.133 (61.2); 2.113 (0.8); 2.107 (0.9); 2.101 (0.7); 2.095 (0.4); 1.964 (4.3); 1.958 (11.3); 1.952 (55.5); 1.946 (99.8); 1.940 (134.0); 1.934 (93.4); 1.927 (48.7); 1.774 (0.6); 1.768 (0.8); 1.762 (0.5); 1.596 (1.1); 1.582 (3.0); 1.575 (3.1); 1.561 (1.6); 1.437 (16.0); 1.361 (1.6); 1.348 (3.0); 1.341 (3.1); 1.326 (1.2); 1.269 (0.3); 0.146 (1.1); 0.008 (9.0); 0.000 (233.2); −0.009 (12.0); −0.150 (1.0)

Beispiel I-T3-58: ¹H-NMR (400.0 MHz, CD3CN):
δ = 8.212 (1.1); 8.196 (2.4); 8.168 (2.0); 8.062 (1.1); 7.732 (1.4); 7.727 (2.0); 7.710 (1.1); 7.704 (0.7); 7.689 (1.2); 7.683 (1.0); 7.523 (1.8); 7.502 (1.4); 4.139 (0.4); 4.123 (0.4); 4.116 (1.2); 4.099 (1.2); 4.092 (1.3); 4.076 (1.2); 4.068 (0.5); 4.052 (0.4); 2.154 (2.8); 2.152 (3.0); 1.958 (0.6); 1.952 (3.2); 1.946 (5.8); 1.940 (7.8); 1.934 (5.3); 1.928 (2.7); 1.436 (16.0); 0.008 (0.5); 0.000 (14.4); −0.009 (0.5)

Beispiel I-T3-59: ¹H-NMR (601.6 MHz, d6-DMSO):
δ = 19.976 (2.1); 9.451 (11.5); 9.045 (16.0); 8.978 (7.7); 8.792 (7.9); 8.789 (7.8); 8.502 (16.0); 8.320 (2.2); 7.918 (8.4); 7.914 (11.9); 7.904 (7.1); 7.900 (4.5); 7.890 (6.8); 7.886 (5.6); 7.573 (10.3); 7.560 (9.7); 4.034 (1.6); 4.022 (1.5); 3.338 (576.9); 2.615 (4.0); 2.524 (5.6); 2.521 (7.1); 2.518 (8.3); 2.509 (220.0); 2.506 (474.2); 2.503 (654.0); 2.500 (473.2); 2.497 (216.3); 2.387 (3.5); 1.990 (4.8); 1.615 (4.4); 1.606 (10.1); 1.602 (10.7); 1.593 (4.6); 1.398 (2.2); 1.300 (4.9); 1.291 (9.5); 1.286 (10.1); 1.277 (4.3); 1.175 (3.1); 0.096 (2.5); 0.005 (23.7); 0.000 (635.1); −0.006 (20.4); −0.100 (2.7)

Beispiel I-T3-60: ¹H-NMR (400.0 MHz, CDCl3):
δ = 8.687 (8.6); 8.685 (8.5); 8.596 (15.9); 8.577 (0.6); 8.173 (8.6); 8.168 (8.5); 8.114 (16.0); 7.901 (10.7); 7.896 (11.0); 7.567 (5.3); 7.561 (5.3); 7.555 (1.2); 7.546 (7.0); 7.540 (6.9); 7.483 (0.4); 7.426 (11.9); 7.406 (8.9); 7.264 (25.7); 6.415 (3.4); 5.301 (12.8); 2.991 (0.6); 2.982 (1.7); 2.973 (3.0); 2.964 (4.1); 2.955 (4.1); 2.946 (3.1); 2.937 (1.8); 2.928 (0.7); 1.601 (5.6); 1.378 (1.1); 1.333 (0.6); 1.327 (0.4); 1.285 (1.1); 1.255 (5.4); 0.938 (2.5); 0.921 (10.0); 0.907 (9.8); 0.903 (8.2); 0.890 (3.5); 0.880 (1.2); 0.868 (0.9); 0.862 (0.7); 0.850 (0.9); 0.836 (0.6); 0.742 (0.4); 0.733 (0.4); 0.703 (3.0); 0.689 (8.1); 0.685 (8.5); 0.680 (8.2); 0.676 (7.9); 0.662 (2.4); 0.557 (0.5); 0.551 (0.5); 0.008 (0.6); 0.000 (19.7); −0.008 (1.0)

Beispiel I-T3-61: ¹H-NMR (400.0 MHz, CD3CN):
δ = 8.266 (6.2); 8.208 (0.5); 8.195 (8.9); 7.692 (5.7); 7.687 (6.8); 7.678 (0.7); 7.658 (3.7); 7.652 (2.8); 7.637 (4.3); 7.632 (3.5); 7.593 (5.8); 7.572 (5.8); 7.475 (6.2); 7.454 (4.9); 6.962 (1.7); 5.449 (0.9); 4.086 (0.3); 4.068 (1.1); 4.050 (1.1); 4.032 (0.4); 2.882 (0.4); 2.873 (1.2); 2.863 (1.6); 2.855 (2.6); 2.845 (2.6); 2.837 (1.7); 2.827 (1.2); 2.817 (0.4); 2.181 (57.5); 1.972 (4.8); 1.965 (1.5); 1.959 (3.8); 1.953 (16.3); 1.947 (29.0); 1.941 (37.9); 1.935 (26.4); 1.929 (13.7); 1.436 (16.0); 1.268 (0.8); 1.221 (1.3); 1.204 (2.5); 1.186 (1.2); 0.795 (1.3); 0.783 (4.5); 0.777 (5.6); 0.765 (5.9); 0.760 (4.4); 0.747 (1.8); 0.615 (1.8); 0.605 (5.0); 0.603 (5.0); 0.598 (5.5); 0.593 (4.9); 0.588 (4.6); 0.576 (1.4); 0.000 (58.7); −0.009 (3.0)

Beispiel I-T3-62: ¹H-NMR (601.6 MHz, CD3CN):
δ = 8.282 (5.8); 8.209 (9.7); 7.742 (5.2); 7.738 (6.1); 7.705 (3.5); 7.702 (2.9); 7.692 (4.0); 7.688 (3.5); 7.644 (0.8); 7.594 (5.2); 7.580 (5.1); 7.506 (6.4); 7.493 (5.6); 2.197 (13.4); 2.194 (14.8); 2.191 (16.6); 2.188 (16.2); 2.186 (16.6); 2.184 (16.2); 2.181 (15.5); 2.179 (16.7); 1.973 (1.0); 1.967 (1.1); 1.959 (2.7); 1.954 (3.0); 1.951 (18.5); 1.947 (31.7); 1.942 (46.4); 1.938 (30.9); 1.934 (15.5); 1.594 (2.6); 1.584 (6.6); 1.580 (6.4); 1.571 (3.2); 1.544 (0.3); 1.436 (16.0); 1.359 (3.2); 1.350 (6.2); 1.345 (6.8); 1.336 (2.7); 1.266 (0.4); 1.204 (0.5); 0.005 (1.2); 0.000 (39.8); −0.006 (1.3)

Beispiel I-T3-63: ¹H-NMR (400.0 MHz, d6-DMSO):
δ = 8.666 (5.1); 8.523 (1.9); 8.512 (2.0); 8.389 (5.2); 7.850 (2.9); 7.814 (2.7); 7.736 (1.2); 7.730 (1.9); 7.710 (7.1); 7.511 (2.5); 7.490 (2.1); 3.327 (42.2); 2.856 (0.5); 2.846 (0.8); 2.838 (1.2); 2.828 (1.2); 2.819 (0.8); 2.810 (0.5); 2.671 (0.4); 2.506 (46.0); 2.502 (59.6); 2.498 (46.8); 2.438 (0.6); 2.329 (0.4); 2.203 (0.6); 2.188 (12.9); 1.398 (16.0); 0.727 (0.7); 0.714 (2.3); 0.709 (3.0); 0.697 (2.8); 0.691 (2.5); 0.680 (0.9); 0.560 (0.9); 0.549 (3.0); 0.543 (3.1); 0.534 (2.7); 0.522 (0.7); 0.000 (42.2)

Beispiel I-T3-64: ¹H-NMR (400.0 MHz, d6-DMSO):
δ = 9.432 (2.1); 8.689 (2.8); 8.404 (2.9); 7.853 (1.5); 7.816 (1.5); 7.795 (0.6); 7.789 (1.2); 7.780 (1.7); 7.775 (2.6); 7.560 (1.6); 7.552 (0.4); 7.538 (1.4); 3.327 (22.2); 2.507 (17.7); 2.502 (23.3); 2.498 (17.9); 2.436 (0.3); 2.189 (6.9); 1.989 (0.4); 1.615 (0.7); 1.600 (1.8); 1.594 (1.9); 1.581 (0.8); 1.398 (16.0); 1.284 (0.8); 1.270 (1.8); 1.264 (2.0); 1.249 (0.7); 0.008 (0.7); 0.000 (19.4)

Beispiel I-T3-65: ¹H-NMR (500.1 MHz, d6-DMSO):
δ = 9.726 (2.4); 8.559 (1.7); 8.556 (1.8); 8.306 (2.2); 7.930 (0.7); 7.914 (1.5); 7.897 (0.8); 7.588 (3.9); 7.467 (1.5); 7.450 (1.4); 3.305 (13.5); 2.508 (2.9); 2.504 (6.0); 2.501 (8.2); 2.497 (6.1); 2.494 (3.0); 2.106 (16.0); 1.645 (0.8); 1.634 (2.0); 1.628 (2.1); 1.617 (0.8); 1.239 (1.1); 1.228 (2.0); 1.222 (2.1); 1.211 (0.8); 0.000 (5.4)

Beispiel I-T3-66: ¹H-NMR (400.2 MHz, d6-DMSO):
δ = 9.726 (4.5); 8.587 (3.6); 8.583 (3.6); 8.305 (4.5); 7.934 (1.5); 7.913 (3.1); 7.892 (1.7); 7.597 (3.1); 7.562 (3.1); 7.468 (3.1); 7.447 (2.9); 5.753 (0.4); 3.427 (0.5); 3.307 (130.4); 3.283 (0.9); 3.236 (0.8); 2.669 (0.5); 2.504 (61.2); 2.500 (82.9); 2.496 (61.6); 2.431 (1.1); 2.412 (3.4); 2.394 (3.5); 2.375 (1.2); 2.327 (0.5); 2.322 (0.4); 2.087 (16.0); 1.987 (0.6); 1.648 (1.6); 1.634 (4.0); 1.628 (4.2); 1.614 (1.7); 1.463 (0.4); 1.240 (2.1); 1.227 (4.0); 1.220 (4.2); 1.206 (1.5); 1.174 (0.4); 1.031 (5.0); 1.012 (10.6); 0.993 (4.8); 0.146 (0.6); 0.008 (5.8); 0.000 (128.9); −0.150 (0.6)

Beispiel I-T3-67: ¹H-NMR (400.0 MHz, d6-DMSO):
δ = 8.778 (1.2); 8.767 (1.2); 8.544 (1.7); 8.539 (1.8); 8.297 (2.1); 7.876 (0.8); 7.855 (1.5); 7.834 (0.8); 7.593 (3.9); 7.418 (1.5); 7.397 (1.4); 3.903 (3.9); 3.331 (120.3); 2.855 (0.5); 2.846 (0.7); 2.836 (0.7); 2.827 (0.5); 2.818 (0.3); 2.676 (0.5); 2.671 (0.7); 2.667 (0.6); 2.524 (2.0); 2.511 (45.1); 2.507 (87.8); 2.502 (113.1); 2.498 (83.2); 2.333 (0.5); 2.329 (0.7); 2.324 (0.5); 2.120 (0.9); 2.105 (16.0); 0.752 (0.4); 0.739 (1.3); 0.734 (1.7); 0.721 (1.7); 0.716 (1.4); 0.704 (0.5); 0.522 (0.6); 0.511 (1.6); 0.505 (1.6); 0.501 (1.5); 0.496 (1.5); 0.483 (0.5); 0.000 (6.3)

Beispiel I-T3-68: ¹H-NMR (500.1 MHz, d6-DMSO):
δ = 8.752 (2.4); 8.743 (2.4); 8.561 (3.4); 8.558 (3.7); 8.289 (4.4); 7.868 (1.5); 7.851 (3.0); 7.834 (1.6); 7.597 (3.0); 7.563 (3.0); 7.411 (3.0); 7.394 (2.9); 3.304 (38.0); 2.861 (0.6); 2.854 (0.9); 2.847 (1.4); 2.839 (1.4); 2.831 (0.9); 2.824 (0.7); 2.507 (6.9); 2.504 (14.1); 2.500 (19.4); 2.497 (14.5); 2.493 (7.2); 2.426 (1.2); 2.411 (3.5); 2.396 (3.6); 2.381 (1.2); 2.101 (1.1); 2.089 (16.0); 1.029 (5.5); 1.013 (11.1); 0.998 (5.0); 0.746 (0.9); 0.736 (2.7); 0.732 (3.5); 0.722 (3.4); 0.718 (2.8); 0.708 (1.0); 0.521 (1.1); 0.512 (3.3); 0.508 (3.3); 0.505 (3.1); 0.500 (3.1); 0.490 (0.9); 0.006 (0.7); 0.000 (14.7); −0.007 (0.6)

Beispiel I-T3-69: ¹H-NMR (400.2 MHz, d6-DMSO):
δ = 9.352 (4.3); 8.553 (4.2); 8.286 (4.4); 7.965 (1.0); 7.946 (2.0); 7.927 (1.1); 7.601 (3.3); 7.567 (3.5); 7.478 (0.9); 7.460 (2.0); 7.444 (1.3); 7.350 (2.0); 7.331 (3.4); 7.312 (1.5); 3.342 (0.4); 3.308 (118.1); 3.290 (0.6); 2.669 (0.3); 2.504 (47.2); 2.500 (55.9); 2.496 (39.1); 2.443 (1.2); 2.425 (3.6); 2.406 (3.6); 2.387 (1.2); 2.327 (0.3); 2.097 (16.0); 1.595 (1.7); 1.581 (4.8); 1.574 (4.3); 1.561 (1.8); 1.293 (2.0); 1.279 (4.8); 1.273 (4.3); 1.258 (1.6); 1.236 (0.8); 1.041 (4.9); 1.022 (10.0); 1.003 (4.6); 0.000 (32.0); −0.008 (1.3)

-continued

Beispiel I-T3-70: ¹H-NMR (400.2 MHz, d₆-DMSO):
δ = 8.528 (3.4); 8.524 (3.6); 8.456 (1.7); 8.445 (1.7); 8.270 (4.0); 7.896 (0.9); 7.891 (0.9); 7.877 (1.7); 7.873 (1.8); 7.858 (1.0); 7.854 (0.9); 7.598 (2.8); 7.565 (2.8); 7.403 (0.8); 7.399 (0.8); 7.384 (1.7); 7.368 (1.2); 7.364 (1.1); 7.303 (2.5); 7.284 (3.9); 7.265 (1.7); 3.309 (77.4); 2.875 (0.6); 2.866 (0.8); 2.857 (1.3); 2.847 (1.4); 2.839 (0.8); 2.829 (0.6); 2.509 (11.1); 2.505 (23.7); 2.500 (33.3); 2.496 (24.3); 2.491 (11.5); 2.442 (1.1); 2.423 (3.4); 2.404 (3.5); 2.386 (1.2); 2.096 (16.0); 1.236 (0.6); 1.040 (5.1); 1.021 (11.2); 1.002 (5.0); 0.725 (0.9); 0.712 (2.5); 0.707 (3.5); 0.695 (3.3); 0.689 (2.7); 0.677 (1.2); 0.557 (1.2); 0.546 (3.4); 0.540 (3.0); 0.536 (2.8); 0.530 (2.8); 0.518 (0.9); 0.008 (0.7); 0.000 (21.2); −0.009 (0.8)

Beispiel I-T3-71: ¹H-NMR (400.0 MHz, CD3CN):
δ = 8.160 (3.6); 8.139 (3.7); 7.764 (2.0); 7.739 (2.0); 7.733 (2.7); 7.704 (1.3); 7.699 (1.2); 7.683 (3.4); 7.678 (2.3); 7.553 (1.2); 7.502 (2.4); 7.481 (1.9); 3.060 (0.5); 2.851 (0.5); 2.520 (0.8); 2.501 (2.5); 2.482 (2.5); 2.463 (0.9); 2.134 (30.8); 2.114 (0.4); 2.107 (0.5); 2.101 (0.4); 1.964 (2.0); 1.958 (4.9); 1.952 (28.1); 1.946 (52.7); 1.940 (72.6); 1.934 (52.6); 1.928 (28.4); 1.768 (0.4); 1.762 (0.3); 1.598 (1.0); 1.583 (2.5); 1.577 (2.7); 1.563 (1.4); 1.437 (16.0); 1.361 (1.3); 1.347 (2.7); 1.340 (2.9); 1.326 (1.1); 1.102 (3.5); 1.083 (7.4); 1.064 (3.4); 0.146 (0.4); 0.008 (3.1); 0.000 (97.3); −0.150 (0.4)

Beispiel I-T3-72: ¹H-NMR (400.0 MHz, CD3CN):
δ = 8.150 (5.4); 8.130 (5.6); 7.764 (2.7); 7.689 (4.2); 7.684 (6.5); 7.655 (1.9); 7.650 (1.5); 7.634 (2.2); 7.629 (1.9); 7.469 (3.6); 7.448 (2.9); 6.939 (0.9); 2.871 (0.6); 2.862 (0.9); 2.853 (1.4); 2.843 (1.4); 2.834 (1.0); 2.825 (0.6); 2.518 (1.2); 2.499 (3.7); 2.480 (3.8); 2.462 (1.4); 2.168 (77.5); 2.114 (0.3); 2.108 (0.4); 1.965 (1.9); 1.959 (4.8); 1.953 (25.8); 1.947 (47.0); 1.941 (63.4); 1.935 (44.6); 1.929 (23.7); 1.769 (0.4); 1.437 (16.0); 1.100 (5.0); 1.081 (10.2); 1.062 (4.8); 0.794 (0.8); 0.781 (2.3); 0.776 (2.4); 0.763 (3.2); 0.758 (2.4); 0.746 (1.1); 0.611 (1.0); 0.600 (2.8); 0.594 (2.9); 0.590 (2.6); 0.585 (2.6); 0.572 (0.8); 0.146 (0.3); 0.008 (2.6); 0.000 (69.9); −0.008 (4.3); −0.149 (0.3)

Beispiel I-T3-73: ¹H-NMR (400.1 MHz, d₆-DMSO):
☐ = 8.77 (0.0325); 8.76 (0.0329); 8.67 (0.0447); 8.40 (0.0688); 8.07 (0.1396); 7.89 (0.0039); 7.88 (0.0202); 7.87 (0.0405); 7.43 (0.0406); 7.42 (0.0383); 3.78 (0.0029); 3.59 (0.0071); 3.30 (1.0000); 3.17 (0.0044); 3.16 (0.0042); 2.85 (0.0123); 2.84 (0.0187); 2.83 (0.0088); 2.64 (0.0025); 2.50 (0.4120); 2.37 (0.0016); 1.24 (0.0054); 0.73 (0.0482); 0.72 (0.0467); 0.71 (0.0149); 0.52 (0.0154); 0.50 (0.0420); 0.49 (0.0128); 0.12 (0.0012); 0.00 (0.2886); −0.12 (0.0012)

Beispiel I-T3-74: ¹H-NMR (400.0 MHz, d₆-DMSO):
δ = 9.381 (5.5); 8.653 (5.5); 8.317 (0.7); 8.293 (5.6); 7.988 (1.2); 7.984 (1.3); 7.969 (2.4); 7.965 (2.4); 7.950 (1.4); 7.946 (1.3); 7.747 (4.4); 7.734 (1.5); 7.713 (7.2); 7.706 (4.3); 7.683 (0.7); 7.493 (1.1); 7.489 (1.2); 7.474 (2.5); 7.458 (1.6); 7.454 (1.5); 7.362 (3.0); 7.343 (5.1); 7.324 (2.2); 3.903 (11.7); 3.333 (264.8); 3.267 (0.3); 3.174 (0.6); 3.162 (0.6); 2.802 (1.7); 2.783 (5.4); 2.765 (5.5); 2.746 (1.8); 2.676 (1.4); 2.672 (1.9); 2.667 (1.4); 2.542 (1.1); 2.525 (5.6); 2.511 (121.2); 2.507 (238.9); 2.503 (309.3); 2.498 (228.5); 2.494 (115.5); 2.334 (1.3); 2.329 (1.8); 2.325 (1.4); 1.603 (2.2); 1.589 (5.6); 1.582 (6.0); 1.569 (2.6); 1.298 (2.8); 1.285 (5.7); 1.278 (6.1); 1.264 (2.3); 1.237 (0.5); 1.060 (7.3); 1.042 (16.0); 1.023 (7.2); 0.008 (0.6); 0.000 (17.6); −0.008 (0.7)

Beispiel I-T3-75: ¹H-NMR (400.2 MHz, d₆-DMSO):
δ = 8.621 (4.9); 8.618 (5.3); 8.463 (2.4); 8.452 (2.4); 8.277 (5.0); 8.274 (5.4); 7.913 (1.3); 7.909 (1.4); 7.894 (2.4); 7.890 (2.5); 7.875 (1.4); 7.871 (1.3); 7.742 (4.3); 7.730 (1.5); 7.709 (7.2); 7.702 (4.2); 7.679 (0.7); 7.416 (1.1); 7.412 (1.2); 7.397 (2.4); 7.381 (1.7); 7.377 (1.6); 7.313 (3.4); 7.294 (5.4); 7.275 (2.3); 3.333 (0.6); 3.324 (0.5); 3.307 (125.1); 3.285 (0.5); 2.879 (0.8); 2.870 (1.2); 2.861 (1.9); 2.851 (1.9); 2.842 (1.2); 2.833 (0.9); 2.822 (0.4); 2.798 (1.7); 2.780 (5.3); 2.761 (5.5); 2.742 (1.8); 2.509 (17.8); 2.505 (38.4); 2.500 (54.1); 2.496 (39.8); 2.491 (19.1); 2.327 (0.3); 1.235 (0.5); 1.061 (7.3); 1.042 (16.0); 1.023 (7.1); 0.729 (1.2); 0.716 (3.4); 0.711 (4.8); 0.699 (4.5); 0.693 (3.7); 0.682 (1.6); 0.562 (1.6); 0.552 (4.7); 0.546 (4.2); 0.542 (4.0); 0.536 (3.9); 0.524 (1.2); 0.008 (1.4); 0.000 (45.5); −0.009 (1.9)

Beispiel I-T3-76: ¹H-NMR (400.1 MHz, d₆-DMSO):
δ = 9.531 (3.2); 9.102 (3.2); 9.096 (3.3); 8.822 (3.2); 8.817 (3.3); 8.727 (5.1); 8.442 (1.9); 8.436 (3.4); 8.428 (5.4); 7.617 (2.1); 7.582 (2.1); 5.759 (16.0); 3.568 (2.8); 3.437 (0.3); 3.424 (0.4); 3.326 (355.3); 3.303 (1.2); 2.711 (0.5); 2.675 (0.6); 2.670 (0.7); 2.667 (0.5); 2.557 (0.4); 2.554 (0.7); 2.552 (0.9); 2.551 (1.1); 2.541 (159.1); 2.530 (1.2); 2.528 (1.0); 2.527 (1.0); 2.524 (1.3); 2.510 (33.8); 2.506 (67.9); 2.502 (90.5); 2.497 (63.3); 2.493 (29.5); 2.458 (0.9); 2.440 (2.5); 2.421 (2.5); 2.402 (0.9); 2.338 (0.6); 2.333 (0.6); 2.329 (0.7); 2.324 (0.6); 2.111 (12.0); 2.086 (1.1); 1.629 (1.2); 1.615 (2.9); 1.608 (3.2); 1.595 (1.5); 1.346 (1.4); 1.332 (2.9); 1.325 (3.2); 1.311 (1.1); 1.072 (0.6); 1.055 (1.3); 1.048 (4.1); 1.037 (0.9); 1.029 (8.8); 1.010 (3.8); 0.008 (2.0); 0.000 (66.6); −0.008 (2.4); −0.014 (0.4)

Beispiel I-T3-77: ¹H-NMR (400.1 MHz, d₆-DMSO):
δ = 9.043 (4.2); 9.038 (4.3); 8.798 (4.2); 8.793 (4.4); 8.705 (6.6); 8.645 (1.9); 8.635 (2.0); 8.409 (6.8); 8.389 (2.6); 8.384 (4.6); 8.379 (2.6); 7.613 (2.8); 7.580 (2.9); 5.759 (4.7); 3.327 (158.6); 2.902 (0.6); 2.892 (1.0); 2.884 (1.5); 2.874 (1.5); 2.866 (1.0); 2.856 (0.7); 2.671 (0.4); 2.541 (65.9); 2.511 (20.9); 2.506 (42.9); 2.502 (59.0); 2.498 (43.4); 2.493 (22.4); 2.458 (2.1); 2.438 (3.5); 2.419 (3.4); 2.401 (1.3); 2.367 (0.3); 2.329 (0.4); 2.110 (16.0); 2.086 (1.2); 1.989 (0.4); 1.072 (0.4); 1.055 (1.0); 1.048 (5.3); 1.029 (11.6); 1.010 (5.3); 0.763 (0.9); 0.750 (2.3); 0.745 (3.4); 0.733 (3.3); 0.727 (2.8); 0.716 (1.4); 0.617 (1.2); 0.607 (3.5); 0.600 (3.1); 0.591 (2.8); 0.579 (1.0); 0.008 (1.3); 0.000 (40.7); −0.008 (2.2)

Beispiel I-T3-78: ¹H-NMR (400.1 MHz, d₆-DMSO):
δ = 9.542 (5.5); 9.127 (5.7); 9.122 (5.9); 8.857 (8.8); 8.834 (5.6); 8.829 (5.9); 8.472 (3.3); 8.467 (5.7); 8.461 (3.2); 8.434 (8.9); 7.757 (4.0); 7.724 (7.7); 7.699 (0.6); 5.759 (5.9); 4.020 (0.4); 3.611 (0.6); 3.568 (1.5); 3.426 (0.9); 3.326 (364.4); 3.303 (1.4); 3.235 (1.3); 2.821 (1.6); 2.802 (5.1); 2.783 (5.1); 2.765 (1.7); 2.711 (0.6); 2.670 (0.9); 2.666 (0.7); 2.541 (164.7); 2.510 (48.8); 2.506 (100.5); 2.502 (137.3); 2.497 (98.8); 2.493 (47.9); 2.367 (0.6); 2.329 (0.8); 1.989 (1.5); 1.633 (2.1); 1.619 (5.2); 1.612 (5.6); 1.599 (2.4); 1.350 (2.6); 1.337 (5.3); 1.330 (5.5); 1.316 (2.0); 1.234 (0.4); 1.192 (0.4); 1.174 (0.8); 1.156 (0.5); 1.146 (0.5); 1.069 (7.2); 1.050 (16.0); 1.032 (7.1); 0.146 (0.4); 0.008 (2.9); 0.000 (90.5); −0.008 (3.5)

Beispiel I-T3-79: ¹H-NMR (500.1 MHz, d₆-DMSO):
δ = 9.064 (5.0); 9.059 (5.1); 8.821 (8.9); 8.811 (5.2); 8.807 (5.3); 8.630 (2.5); 8.622 (2.5); 8.413 (3.8); 8.408 (13.3); 7.748 (4.3); 7.738 (1.8); 7.721 (6.6); 7.712 (3.8); 7.695 (0.9); 5.752 (1.0); 3.305 (76.3); 3.281 (0.9); 2.910 (0.4); 2.902 (0.9); 2.895 (1.3); 2.888 (2.0); 2.880 (1.3); 2.873 (1.3); 2.865 (1.0); 2.858 (0.7); 2.813 (1.7); 2.798 (5.5); 2.783 (5.6); 2.768 (1.9); 2.508 (13.7); 2.504 (28.5); 2.501 (39.3); 2.497 (29.3); 2.494 (14.5); 1.908 (2.7); 1.236 (0.5); 1.068 (7.4); 1.053 (16.0); 1.038 (7.3); 0.761 (1.2); 0.751 (3.5); 0.747 (4.8); 0.737 (4.6); 0.733 (3.8); 0.723 (1.6); 0.620 (1.6); 0.612 (4.7); 0.607 (4.4); 0.604 (4.2); 0.599 (4.0); 0.589 (1.2); 0.006 (1.3); 0.000 (30.6); −0.007 (1.4)

Beispiel I-T3-80: ¹H-NMR (400.0 MHz, CD3CN):
δ = 8.128 (2.6); 8.082 (2.8); 7.736 (1.6); 7.731 (2.1); 7.701 (1.1); 7.696 (0.8); 7.680 (1.2); 7.675 (1.1); 7.608 (0.4); 7.562 (1.4); 7.549 (1.4); 7.494 (1.9); 7.473 (1.5); 2.448 (0.6); 2.429 (1.9); 2.410 (2.0); 2.391 (0.7); 2.164 (9.8); 2.155 (20.2); 2.088 (7.6); 1.965 (1.0); 1.959 (2.5); 1.953 (13.9); 1.946 (25.4); 1.940 (34.2); 1.934 (24.1); 1.928 (12.6); 1.598 (0.8); 1.583 (2.0); 1.577 (2.0); 1.563 (1.1); 1.437 (16.0); 1.358 (1.0); 1.345 (2.0); 1.338 (2.1); 1.323 (0.8); 1.268 (0.7); 1.092 (2.7); 1.073 (5.7); 1.054 (2.6); 0.008 (1.1); 0.000 (34.6); −0.009 (1.5)

Beispiel I-T3-81: ¹H-NMR (400.0 MHz, CD3CN):
δ = 8.115 (7.2); 8.067 (7.4); 7.688 (4.4); 7.683 (5.6); 7.667 (0.5); 7.652 (3.0); 7.646 (2.4); 7.631 (3.5); 7.625 (3.0); 7.560 (4.1); 7.546 (4.1); 7.462 (5.2); 7.441 (4.2); 6.903 (1.2); 2.880 (0.3); 2.871 (0.9); 2.861 (1.3); 2.853 (2.1); 2.843 (2.1); 2.835 (1.3); 2.825 (1.0); 2.815 (0.4); 2.447 (1.8); 2.428 (5.5); 2.409 (5.7); 2.390 (1.9); 2.141 (55.3); 2.120 (1.0); 2.113 (0.9); 2.107 (1.0); 2.101 (0.9); 2.086 (21.5); 1.964 (4.2); 1.958 (10.5); 1.952 (54.5); 1.946 (98.5); 1.940 (132.1); 1.934 (92.1); 1.927 (48.4); 1.774 (0.5); 1.768 (0.8); 1.762 (0.5); 1.437 (1.3); 1.270 (1.0); 1.090 (7.7); 1.071 (16.0); 1.052 (7.4); 0.794 (1.1); 0.781 (3.3); 0.776 (4.4); 0.763 (4.7); 0.758 (3.4); 0.746 (1.6); 0.610 (1.5); 0.598 (3.8); 0.592 (4.0); 0.588 (3.6); 0.583 (3.6); 0.571 (1.1); 0.146 (1.8); 0.031 (0.4); 0.030 (0.4); 0.0272 (0.4); 0.0265 (0.4); 0.026 (0.4); 0.022 (0.6); 0.008 (16.0); 0.000 (381.4); −0.009 (18.6); −0.150 (1.8)

Beispiel I-T3-82: ¹H-NMR (400.0 MHz, CD3CN):
δ = 8.127 (7.5); 8.085 (7.7); 7.734 (4.3); 7.729 (5.7); 7.708 (3.2); 7.703 (2.2); 7.688 (3.6); 7.682 (2.9); 7.561 (3.9); 7.548 (3.8); 7.512 (5.3); 7.491 (4.4); 7.365 (0.9); 4.141 (1.1); 4.124 (1.2); 4.117 (3.5); 4.100 (3.5); 4.093 (3.7); 4.077 (3.5); 4.070 (1.3); 4.053 (1.2); 2.462 (0.4); 2.457 (0.4); 2.450 (1.8); 2.431 (5.5); 2.412 (5.7); 2.393 (1.9); 2.150 (76.9); 2.120 (0.5); 2.113 (0.7); 2.107 (0.8); 2.101 (0.8); 2.090 (21.3); 1.964 (3.5); 1.958 (8.4); 1.952 (45.7); 1.946 (82.9); 1.940 (111.8); 1.934 (77.5); 1.927 (40.4); 1.774 (0.4); 1.768 (0.6); 1.762 (0.4); 1.437 (1.0); 1.269 (1.0); 1.093 (7.7); 1.074 (16.0); 1.055 (7.4); 0.146 (1.4); 0.008 (11.1); 0.000 (291.0); −0.009 (12.7); −0.150 (1.4)

Beispiel I-T3-83: ¹H-NMR (400.0 MHz, CD3CN):
δ = 8.128 (7.9); 8.079 (8.4); 7.719 (4.9); 7.713 (6.1); 7.677 (3.1); 7.671 (2.5); 7.656 (3.5); 7.650 (3.1); 7.562 (4.8); 7.548 (4.7); 7.484 (5.6); 7.463 (5.1); 7.436 (1.2); 5.447 (1.2); 5.337 (1.3); 5.316 (2.5); 5.295 (2.5); 5.274 (1.3); 4.068 (0.4); 4.050 (0.4); 3.543 (3.2); 3.540 (2.1); 3.520 (6.4); 3.498 (4.2); 3.370 (4.2); 3.367 (2.8); 3.350 (6.2); 3.346 (5.9); 3.326 (3.3); 2.462 (0.3); 2.451 (2.0); 2.432 (6.0); 2.413 (6.2); 2.394 (2.1); 2.150 (115.6); 2.120 (0.5); 2.114 (0.7); 2.107 (0.9); 2.091 (23.5); 1.972 (1.9); 1.964 (3.0); 1.958 (7.9); 1.952 (39.4); 1.946 (71.5); 1.940 (96.0); 1.934 (68.4); 1.928 (36.7); 1.774 (0.4); 1.768 (0.6); 1.762 (0.4); 1.437 (2.7); 1.268 (1.0); 1.221 (0.4); 1.204 (0.8); 1.186 (0.4); 1.094 (7.8); 1.075 (16.0); 1.056 (7.5); 0.146 (1.1); 0.008 (9.8); 0.000 (220.9); −0.150 (1.1)

Beispiel I-T3-84: ¹H-NMR (400.0 MHz, CD3CN):
δ = 8.162 (9.4); 8.125 (7.5); 7.997 (4.3); 7.952 (4.4); 7.729 (4.8); 7.724 (6.8); 7.707 (3.5); 7.701 (2.3); 7.686 (3.9); 7.680 (3.2); 7.519 (6.1); 7.498 (4.9); 7.348 (1.3); 4.140 (1.3); 4.123 (1.4); 4.116 (3.9); 4.100 (3.9); 4.092 (4.2); 4.076 (3.9); 4.069 (1.7); 4.052 (1.4); 2.146 (92.5); 2.120 (27.2); 2.108 (1.6); 2.101 (0.9); 2.095 (0.5); 1.971 (0.9); 1.964 (3.5); 1.958 (9.1); 1.952 (47.9); 1.946 (87.4); 1.940 (118.0); 1.934 (83.5); 1.928 (44.7); 1.774 (0.5); 1.768 (0.7); 1.762 (0.5); 1.437 (16.0); 1.270 (0.6); 0.146 (0.9); 0.008 (6.8); 0.000 (179.6); −0.008 (10.9); −0.150 (0.9)

Beispiel I-T3-85: ¹H-NMR (400.0 MHz, CD3CN):
δ = 8.163 (5.2); 8.118 (4.2); 7.998 (2.5); 7.953 (2.5); 7.716 (3.0); 7.710 (3.7); 7.675 (1.9); 7.669 (1.5); 7.654 (2.2); 7.648 (1.9); 7.490 (3.5); 7.469 (2.8); 7.418 (0.8); 7.400 (0.8); 5.335 (0.8); 5.314 (1.6); 5.293 (1.5); 5.272 (0.8); 3.542 (2.0); 3.538 (1.3); 3.518 (4.0); 3.496 (2.2); 3.370 (2.6); 3.367 (1.7); 3.349 (3.8); 3.346 (3.6); 3.326 (2.0); 2.133 (15.0); 2.120 (15.4); 2.101 (0.5); 1.971 (1.1); 1.964 (1.7); 1.958 (4.3); 1.952 (19.7); 1.946 (35.3); 1.940 (47.2); 1.934 (33.6); 1.927 (18.1); 1.437 (16.0); 1.204 (0.4); 0.146 (0.4); 0.008 (3.9); 0.000 (78.7); −0.150 (0.4)

Beispiel I-T3-86: ¹H-NMR (400.0 MHz, CD3CN):
δ = 8.252 (0.3); 8.146 (2.7); 8.110 (0.4); 8.102 (2.9); 7.899 (1.3); 7.708 (1.4); 7.690 (1.7); 7.685 (2.2); 7.655 (1.2); 7.649 (0.9); 7.634 (1.5); 7.628 (1.4); 7.468 (2.2); 7.447 (1.8); 6.891 (0.5); 2.871 (0.4); 2.862 (0.5); 2.853 (0.8); 2.843 (0.8); 2.835 (0.5); 2.825 (0.4); 2.415 (1.0); 2.171 (8.3); 2.132 (10.6); 1.971 (0.5); 1.964 (1.1); 1.958 (2.6); 1.952 (13.9); 1.946 (25.2); 1.940 (34.0); 1.933 (23.7); 1.927 (12.5); 1.437 (16.0); 1.269 (0.4); 0.794 (0.4); 0.781 (1.3); 0.776 (1.7); 0.764 (1.8); 0.758 (1.3); 0.746 (0.6); 0.611 (0.6); 0.599 (1.5); 0.593 (1.6); 0.589 (1.4); 0.584 (1.4); 0.571 (0.5); 0.008 (2.3); 0.000 (63.9); −0.009 (3.1)

Beispiel I-T3-87: ¹H-NMR (400.0 MHz, CD3CN):
δ = 8.171 (11.0); 8.170 (11.0); 8.122 (12.2); 8.120 (11.4); 7.729 (6.8); 7.724 (8.7); 7.697 (4.9); 7.691 (3.7); 7.676 (5.6); 7.670 (4.6); 7.606 (16.0); 7.604 (15.8); 7.551 (3.2); 7.500 (8.3); 7.479 (6.7); 5.446 (1.2); 4.085 (0.6); 4.068 (2.0); 4.050 (2.0); 4.032 (0.7); 3.240 (0.6); 2.132 (42.8); 2.119 (0.5); 2.113 (0.7); 2.107 (0.9); 2.101 (0.6); 2.095 (0.3); 1.971 (9.0); 1.964 (4.0); 1.958 (10.1); 1.952 (56.8); 1.946 (103.2); 1.940 (138.6); 1.933 (95.2); 1.927 (49.0); 1.914 (0.7); 1.780 (0.3); 1.774 (0.6); 1.768 (0.8); 1.762 (0.6); 1.595 (3.6); 1.581 (8.5); 1.574 (8.5); 1.560 (4.6); 1.520 (0.5); 1.437 (11.1); 1.400 (0.6); 1.360 (4.7); 1.346 (8.6); 1.340 (8.8); 1.325 (3.6); 1.317 (0.8); 1.287 (0.4); 1.269 (1.4); 1.221 (2.5); 1.204 (4.7); 1.186 (2.3); 0.146 (1.8); 0.008 (14.1); 0.000 (400.9); −0.009 (15.1); −0.150 (1.8)

Beispiel I-T3-88: ¹H-NMR (400.0 MHz, CD3CN):
δ = 8.160 (10.6); 8.111 (11.3); 7.681 (6.2); 7.675 (7.9); 7.647 (3.9); 7.642 (3.1); 7.627 (4.5); 7.621 (4.0); 7.605 (16.0); 7.467 (7.2); 7.447 (5.7); 6.936 (2.0); 5.448 (0.4); 4.067 (0.5); 4.049 (0.5); 2.879 (0.4); 2.869 (1.3); 2.860 (2.0); 2.851 (2.8); 2.842 (2.9); 2.833 (2.0); 2.824 (1.4); 2.814 (0.5); 2.467 (1.2); 2.462 (1.7); 2.458 (1.3); 2.253 (0.6); 2.226 (0.4); 2.158 (239.6); 2.120 (1.0); 2.113 (1.3); 2.107 (1.6); 2.101 (1.2); 2.095 (0.7); 1.971 (3.4); 1.964 (8.0); 1.958 (20.3); 1.952 (98.7); 1.946 (178.8); 1.940 (240.6); 1.934 (170.9); 1.928 (91.2); 1.781 (0.5); 1.774 (1.0); 1.768 (1.3); 1.762 (1.0); 1.756 (0.5); 1.437 (3.0); 1.269 (0.9); 1.221 (0.5); 1.203 (1.0); 1.185 (0.5); 0.792 (1.7); 0.779 (4.8); 0.774 (6.6); 0.761 (6.5); 0.756 (5.1); 0.744 (2.2); 0.610 (2.2); 0.599 (6.0); 0.592 (6.3); 0.583 (5.4); 0.571 (1.6); 0.146 (3.3); 0.007 (29.1); 0.000 (640.2); −0.150 (3.3)

Beispiel I-T3-89: ¹H-NMR (400.0 MHz, d₆-DMSO):
δ = 9.437 (11.1); 8.788 (15.9); 8.367 (16.0); 8.317 (0.8); 7.986 (0.4); 7.903 (6.6); 7.897 (6.7); 7.824 (9.1); 7.810 (13.0); 7.805 (11.4); 7.802 (13.2); 7.797 (8.0); 7.791 (3.7); 7.614 (3.7); 7.610 (3.5); 7.591 (2.9); 7.588 (2.9); 7.560 (9.0); 7.551 (1.7); 7.546 (1.5); 7.537 (7.7); 3.903 (8.5); 3.332 (418.5); 3.174 (0.7); 3.162 (0.6); 2.676 (2.0); 2.671 (2.7); 2.667 (2.1); 2.541 (1.6); 2.507 (359.7); 2.502 (464.1); 2.498 (346.7); 2.333 (2.1); 2.329 (2.9); 2.325 (2.2); 1.618 (3.7); 1.604 (9.3); 1.597 (9.9); 1.584 (4.2); 1.543 (0.4); 1.327 (0.4); 1.287 (4.3); 1.274 (9.4); 1.267 (9.9); 1.253 (3.8); 1.234 (1.5); 1.215 (0.5); 1.181 (0.4); 1.177 (0.4); 0.861 (0.4); 0.853 (0.4); 0.843 (0.4); 0.834 (0.4); 0.824 (0.4); 0.813 (0.3); 0.008 (0.9); 0.000 (24.6); −0.008 (1.1)

Beispiel I-T3-90: ¹H-NMR (400.0 MHz, CD3CN):
δ = 8.565 (0.4); 8.349 (0.6); 8.333 (14.0); 8.123 (0.6); 8.109 (13.1); 8.096 (0.6); 7.904 (0.4); 7.881 (0.4); 7.712 (8.7); 7.689 (16.0); 7.683 (10.7); 7.672 (1.0); 7.654 (5.5); 7.648 (4.2); 7.633 (6.1); 7.627 (5.3); 7.617 (5.0); 7.611 (5.5); 7.475 (0.5); 7.467 (9.7); 7.454 (0.7); 7.446 (9.4); 7.438 (3.3); 7.422 (2.4); 7.419 (2.6); 7.416 (2.5); 6.891 (2.1); 5.446 (0.4); 3.899 (0.6); 2.881 (0.6); 2.872 (1.7); 2.862 (2.4); 2.854 (3.8); 2.844 (3.9); 2.835 (2.5); 2.826 (1.8); 2.816 (0.6); 2.132 (62.2); 2.113 (1.1); 2.107 (1.3); 2.101 (0.9); 2.095 (0.5); 1.996 (0.3); 1.971 (0.9); 1.964 (5.7); 1.958 (14.2); 1.952 (81.0); 1.946 (147.9); 1.940 (200.1); 1.933 (139.4); 1.927 (72.6); 1.780 (0.5); 1.774 (0.8); 1.768 (1.1); 1.762 (0.8); 1.756 (0.4); 1.268 (2.3); 0.881 (0.3); 0.796 (2.0); 0.783 (5.8); 0.778 (7.9); 0.765 (8.2); 0.760 (6.0); 0.748 (2.8); 0.726 (0.4); 0.709 (0.4); 0.653 (0.3); 0.643 (0.3); 0.613 (2.8); 0.601 (6.7); 0.595 (7.1); 0.591 (6.3); 0.586 (6.3); 0.574 (2.0); 0.146 (2.4); 0.008 (17.6); 0.000 (508.1); −0.009 (24.9); −0.150 (2.4)

Beispiel I-T3-91: ¹H-NMR (400.0 MHz, d₆-DMSO):
δ = 8.837 (3.4); 8.831 (3.6); 8.747 (6.3); 8.532 (1.9); 8.521 (2.0); 8.474 (6.2); 8.100 (9.7); 7.954 (3.3); 7.949 (3.5); 4.109 (0.4); 4.095 (0.4); 3.904 (16.0); 3.335 (287.0); 3.267 (0.5); 3.243 (0.4); 3.174 (2.4); 3.162 (2.5); 2.877 (0.6); 2.868 (0.9); 2.859 (1.3); 2.849 (1.3); 2.840 (0.9); 2.831 (0.6); 2.676 (1.0); 2.671 (1.3); 2.667 (1.0); 2.507 (156.9); 2.502 (206.2); 2.498 (158.4); 2.334 (0.9); 2.329 (1.2); 2.325 (0.9); 1.258 (0.4); 1.002 (1.3); 0.986 (1.2); 0.740 (0.8); 0.727 (2.3); 0.722 (3.1); 0.710 (2.9); 0.704 (2.4); 0.693 (1.0); 0.568 (1.0); 0.558 (3.1); 0.552 (2.9); 0.548 (2.7); 0.542 (2.5); 0.530 (0.7); 0.000 (1.8)

Beispiel I-T3-92: ¹H-NMR (400.0 MHz, d₆-DMSO):
δ = 9.415 (4.9); 8.892 (4.2); 8.886 (4.4); 8.765 (7.6); 8.488 (7.3); 8.104 (11.7); 8.044 (4.2); 8.039 (4.3); 3.904 (16.0); 3.593 (0.4); 3.336 (427.9); 3.173 (1.6); 3.163 (1.6); 2.676 (1.4); 2.672 (1.7); 2.667 (1.3); 2.518 (32.9); 2.511 (114.6); 2.507 (211.5); 2.503 (266.6); 2.498 (196.7); 2.334 (1.1); 2.329 (1.5); 2.325 (1.1); 1.613 (1.8); 1.599 (4.5); 1.592 (4.8); 1.579 (2.0); 1.315 (2.1); 1.301 (4.6); 1.295 (4.7); 1.280 (1.7); 1.235 (0.3); 0.000 (2.1)

Beispiel I-T3-93: ¹H-NMR (400.0 MHz, CD3CN):
δ = 8.187 (3.1); 8.146 (3.3); 7.899 (4.8); 7.653 (1.3); 7.648 (2.7); 7.639 (0.5); 7.624 (1.5); 7.618 (1.0); 7.462 (1.9); 7.441 (1.5); 7.115 (0.7); 5.449 (1.2); 4.068 (0.5); 4.050 (0.5); 2.174 (33.4); 1.972 (2.4); 1.965 (0.8); 1.959 (1.9); 1.953 (10.3); 1.947 (18.6); 1.941 (24.9); 1.934 (16.9); 1.928 (8.7); 1.448 (9.5); 1.437 (16.0); 1.270 (0.5); 1.221 (0.6); 1.204 (1.2); 1.186 (0.6); 0.837 (0.7); 0.824 (2.1); 0.820 (2.2); 0.808 (0.9); 0.673 (1.1); 0.661 (2.4); 0.656 (2.5); 0.644 (0.8); 0.008 (0.4); 0.000 (10.3); −0.009 (0.3)

Beispiel I-T3-94: ¹H-NMR (400.0 MHz, CD3CN):
δ = 8.149 (5.3); 8.106 (4.3); 7.996 (2.3); 7.951 (2.4); 7.645 (2.3); 7.639 (5.5); 7.632 (0.8); 7.618 (2.7); 7.612 (1.8); 7.457 (3.0); 7.436 (2.4); 7.098 (1.2); 2.468 (0.4); 2.464 (0.5); 2.459 (0.4); 2.165 (184.2); 2.116 (15.3); 2.102 (0.5); 1.972 (1.1); 1.965 (3.0); 1.959 (7.6); 1.953 (41.5); 1.947 (74.8); 1.940 (100.0); 1.934 (68.4); 1.928 (35.0); 1.775 (0.4); 1.769 (0.6); 1.763 (0.4); 1.447 (16.0); 1.437 (3.0); 1.270 (2.2); 1.204 (0.3); 0.835 (1.1); 0.822 (3.7); 0.818 (3.8); 0.807 (1.5); 0.673 (1.8); 0.662 (4.3); 0.656 (4.3); 0.644 (1.3); 0.008 (1.2); 0.000 (38.1); −0.009 (1.4)

Beispiel I-T3-95: ¹H-NMR (400.0 MHz, $d_6$-DMSO):
δ = 9.596 (2.3); 8.893 (2.0); 8.887 (2.0); 8.791 (3.3); 8.545 (3.3); 8.315 (0.5); 8.300 (2.2); 8.294 (2.3); 8.283 (5.7); 4.038 (0.4); 4.020 (0.4); 3.322 (38.3); 2.671 (0.6); 2.502 (83.6); 2.328 (0.6); 1.989 (1.8); 1.643 (0.8); 1.628 (2.2); 1.621 (2.3); 1.609 (0.9); 1.398 (16.0); 1.298 (1.0); 1.285 (2.2); 1.278 (2.3); 1.264 (0.8); 1.193 (0.5); 1.175 (0.9); 1.157 (0.5); 0.146 (0.4); 0.000 (75.9); −0.150 (0.4)

Beispiel I-T3-96: ¹H-NMR (400.0 MHz, $d_6$-DMSO):
δ = 8.838 (2.0); 8.833 (2.0); 8.618 (3.2); 8.513 (1.0); 8.502 (1.0); 8.377 (3.3); 7.954 (1.9); 7.949 (1.9); 7.596 (3.6); 4.104 (0.3); 3.903 (10.1); 3.409 (0.5); 3.350 (346.6); 3.302 (0.5); 3.175 (1.8); 3.162 (1.8); 2.865 (0.4); 2.857 (0.7); 2.847 (0.8); 2.838 (0.4); 2.677 (0.4); 2.672 (0.6); 2.668 (0.4); 2.526 (1.8); 2.512 (37.4); 2.508 (74.7); 2.503 (97.3); 2.499 (71.2); 2.494 (35.6); 2.489 (12.6); 2.335 (0.4); 2.330 (0.6); 2.325 (0.5); 2.117 (16.0); 1.003 (0.6); 0.987 (0.6); 0.739 (0.5); 0.726 (1.2); 0.721 (1.7); 0.709 (1.6); 0.703 (1.3); 0.692 (0.6); 0.568 (0.6); 0.557 (1.7); 0.551 (1.5); 0.547 (1.4); 0.542 (1.4); 0.529 (0.4); 0.000 (0.7)

Beispiel I-T3-97: ¹H-NMR (400.0 MHz, $d_6$-DMSO):
δ = 9.395 (2.2); 8.892 (2.0); 8.886 (2.0); 8.640 (3.3); 8.391 (3.4); 8.040 (1.9); 8.035 (1.9); 7.599 (3.7); 4.108 (0.5); 4.095 (0.5); 3.904 (10.2); 3.333 (130.8); 3.174 (2.4); 3.161 (2.4); 2.676 (0.4); 2.671 (0.6); 2.667 (0.5); 2.541 (0.4); 2.525 (1.8); 2.511 (39.6); 2.507 (81.0); 2.502 (95.3); 2.498 (69.0); 2.493 (34.2); 2.334 (0.4); 2.329 (0.6); 2.324 (0.4); 2.118 (16.0); 1.613 (0.8); 1.599 (1.9); 1.592 (2.1); 1.579 (0.9); 1.311 (0.9); 1.297 (2.0); 1.291 (2.1); 1.276 (0.8); 1.002 (0.5); 0.987 (0.5); 0.000 (1.2)

Beispiel I-T3-98: ¹H-NMR (400.0 MHz, $d_6$-DMSO):
δ = 8.839 (6.0); 8.833 (6.2); 8.791 (0.5); 8.781 (9.8); 8.692 (3.1); 8.681 (3.2); 8.549 (0.5); 8.540 (9.8); 8.282 (16.0); 8.217 (6.2); 8.210 (6.1); 5.756 (1.1); 3.326 (37.2); 2.871 (0.8); 2.861 (1.2); 2.852 (1.8); 2.842 (1.9); 2.833 (1.2); 2.824 (0.9); 2.814 (0.3); 2.671 (0.4); 2.525 (0.9); 2.511 (20.9); 2.507 (43.3); 2.502 (58.6); 2.498 (44.1); 2.494 (22.5); 2.329 (0.4); 1.989 (0.4); 1.397 (0.4); 0.757 (1.2); 0.744 (3.4); 0.739 (4.7); 0.726 (4.5); 0.721 (3.8); 0.709 (1.5); 0.568 (1.5); 0.557 (4.5); 0.551 (4.2); 0.548 (4.1); 0.542 (3.9); 0.530 (1.2); 0.146 (0.5); 0.008 (3.4); 0.000 (97.0); −0.008 (4.2); −0.150 (0.5)

Beispiel I-T3-99: ¹H-NMR (400.0 MHz, $d_6$-DMSO):
δ = 8.851 (0.6); 8.845 (0.8); 8.840 (3.5); 8.834 (3.6); 8.770 (6.0); 8.525 (5.8); 8.337 (3.6); 8.331 (3.5); 8.283 (11.0); 8.226 (0.6); 8.220 (0.6); 3.328 (25.7); 3.030 (16.0); 2.798 (0.7); 2.790 (0.8); 2.781 (1.3); 2.771 (0.9); 2.758 (2.9); 2.543 (55.4); 2.525 (0.6); 2.508 (28.1); 2.503 (37.2); 2.499 (27.6); 0.814 (0.3); 0.773 (0.4); 0.604 (0.5); 0.585 (2.1); 0.576 (2.8); 0.566 (1.0); 0.543 (1.2); 0.532 (2.2); 0.514 (2.0); 0.501 (0.4); 0.495 (0.4); 0.008 (1.0); 0.000 (28.2); −0.008 (1.0)

Beispiel I-T3-100: ¹H-NMR (400.0 MHz, $d_6$-DMSO):
δ = 8.826 (5.3); 8.817 (2.9); 8.811 (2.9); 8.531 (4.2); 8.320 (2.7); 8.314 (2.7); 8.206 (0.4); 8.200 (0.4); 8.111 (7.7); 3.904 (16.0); 3.395 (0.6); 3.337 (288.3); 3.257 (0.4); 3.243 (0.4); 3.175 (0.9); 3.162 (1.0); 3.029 (12.3); 2.795 (0.5); 2.788 (0.6); 2.778 (1.0); 2.768 (0.8); 2.757 (2.2); 2.676 (0.8); 2.672 (1.1); 2.668 (0.8); 2.512 (73.1); 2.507 (138.1); 2.503 (175.3); 2.499 (129.8); 2.334 (0.7); 2.330 (1.0); 2.325 (0.7); 1.002 (1.0); 0.987 (1.0); 0.833 (0.4); 0.815 (0.3); 0.603 (0.4); 0.584 (1.7); 0.574 (2.2); 0.565 (0.8); 0.542 (0.9); 0.531 (1.7); 0.513 (1.5); 0.000 (1.8)

Beispiel I-T3-101: ¹H-NMR (400.0 MHz, $d_6$-DMSO):
δ = 8.828 (0.4); 8.823 (0.4); 8.815 (2.1); 8.809 (2.2); 8.690 (3.8); 8.442 (0.7); 8.435 (3.3); 8.293 (2.2); 8.287 (2.1); 8.190 (0.4); 8.184 (0.3); 7.603 (4.3); 3.904 (8.8); 3.339 (233.4); 3.175 (0.6); 3.162 (0.6); 3.027 (9.9); 2.795 (0.4); 2.787 (0.5); 2.778 (0.8); 2.768 (0.6); 2.756 (1.8); 2.676 (0.6); 2.672 (0.8); 2.667 (0.6); 2.512 (51.7); 2.507 (99.0); 2.503 (126.8); 2.498 (93.4); 2.494 (47.1); 2.334 (0.6); 2.330 (0.8); 2.325 (0.6); 2.130 (16.0); 2.122 (3.6); 1.002 (0.4); 0.987 (0.4); 0.583 (1.3); 0.574 (1.7); 0.565 (0.6); 0.543 (0.7); 0.531 (1.3); 0.514 (1.1); 0.000 (0.9)

Beispiel I-T3-102: ¹H-NMR (400.0 MHz, $d_6$-DMSO):
δ = 8.908 (0.7); 8.879 (2.4); 8.874 (2.4); 8.833 (4.2); 8.820 (1.2); 8.538 (3.8); 8.496 (1.0); 8.431 (0.7); 8.427 (0.7); 8.288 (2.4); 8.283 (2.4); 8.111 (9.5); 3.904 (16.0); 3.591 (0.4); 3.341 (514.4); 3.175 (1.0); 3.162 (1.0); 3.136 (2.9); 2.914 (11.4); 2.676 (1.1); 2.672 (1.5); 2.668 (1.1); 2.507 (189.0); 2.503 (242.9); 2.499 (186.3); 2.334 (1.1); 2.330 (1.5); 2.326 (1.1); 1.713 (2.7); 1.489 (2.0); 0.000 (2.0)

Beispiel I-T3-103: ¹H-NMR (400.0 MHz, $d_6$-DMSO):
δ = 8.907 (0.4); 8.878 (1.3); 8.872 (1.3); 8.702 (2.2); 8.685 (0.6); 8.443 (2.1); 8.406 (0.9); 8.270 (1.3); 8.264 (1.3); 7.604 (4.3); 3.904 (12.6); 3.395 (0.4); 3.338 (210.6); 3.270 (0.4); 3.256 (0.3); 3.175 (0.8); 3.162 (0.9); 3.133 (1.6); 2.915 (6.3); 2.676 (0.6); 2.672 (0.8); 2.668 (0.6); 2.525 (2.1); 2.507 (102.9); 2.503 (131.5); 2.498 (97.6); 2.334 (0.7); 2.330 (0.9); 2.325 (0.6); 2.122 (16.0); 1.718 (1.3); 1.713 (1.4); 1.484 (1.0); 1.002 (0.8); 0.987 (0.8); 0.000 (1.9)

Beispiel I-T3-104: ¹H-NMR (400.0 MHz, $d_6$-DMSO):
δ = 8.865 (9.2); 8.857 (0.5); 8.845 (6.3); 8.839 (6.4); 8.694 (3.1); 8.683 (3.1); 8.470 (0.5); 8.459 (9.4); 8.229 (6.5); 8.223 (6.4); 7.751 (4.6); 7.728 (0.3); 7.710 (11.3); 4.457 (0.4); 4.403 (0.4); 4.392 (0.4); 4.121 (0.3); 4.108 (1.0); 4.095 (1.0); 4.082 (0.4); 3.904 (15.4); 3.395 (0.4); 3.334 (355.6); 3.243 (0.4); 3.175 (4.8); 3.161 (4.8); 2.883 (0.3); 2.873 (0.9); 2.864 (1.2); 2.855 (1.9); 2.845 (1.9); 2.836 (1.2); 2.827 (0.9); 2.816 (0.5); 2.807 (1.7); 2.788 (5.3); 2.769 (5.4); 2.751 (1.8); 2.680 (0.6); 2.676 (1.1); 2.671 (1.4); 2.667 (1.1); 2.542 (1.0); 2.525 (4.5); 2.511 (90.6); 2.507 (178.4); 2.502 (231.0); 2.498 (168.2); 2.494 (82.9); 2.334 (1.0); 2.329 (1.4); 2.325 (1.0); 1.056 (7.2); 1.038 (16.0); 1.019 (7.1); 1.002 (1.6); 0.987 (1.5); 0.759 (1.2); 0.746 (3.5); 0.741 (4.8); 0.729 (4.5); 0.723 (3.7); 0.711 (1.5); 0.568 (1.5); 0.557 (4.5); 0.551 (4.3); 0.547 (4.0); 0.542 (3.9); 0.529 (1.2); 0.000 (3.5)

Beispiel I-T3-105: ¹H-NMR (400.0 MHz, $d_6$-DMSO):
δ = 9.606 (5.9); 8.899 (6.1); 8.893 (6.2); 8.882 (8.7); 8.466 (9.0); 8.308 (6.0); 8.302 (5.8); 7.753 (4.6); 7.730 (0.3); 7.712 (11.2); 3.904 (12.3); 3.332 (328.2); 3.175 (1.4); 3.161 (1.4); 3.047 (0.5); 2.866 (0.5); 2.807 (1.7); 2.789 (5.3); 2.770 (5.4); 2.751 (1.8); 2.676 (1.1); 2.671 (1.5); 2.667 (1.1); 2.524 (4.8); 2.511 (97.8); 2.507 (190.1); 2.502 (244.3); 2.498 (178.1); 2.493 (87.7); 2.333 (1.1); 2.329 (1.5); 2.324 (1.1); 1.650 (2.1); 1.636 (5.3); 1.629 (5.6); 1.616 (2.3); 1.295 (2.5); 1.281 (5.3); 1.275 (5.7); 1.260 (2.1); 1.055 (7.3); 1.037 (16.0); 1.018 (7.1); 0.000 (3.2)

Beispiel I-T3-106: ¹H-NMR (400.0 MHz, $d_6$-DMSO):
δ = 8.824 (4.0); 8.818 (4.1); 8.781 (4.7); 8.694 (1.9); 8.683 (1.9); 8.515 (6.0); 8.223 (2.4); 8.196 (4.1); 8.190 (4.0); 7.937 (2.5); 4.456 (0.3); 4.402 (0.4); 4.391 (0.4); 4.107 (0.7); 4.094 (0.8); 3.904 (16.0); 3.332 (223.1); 3.243 (0.4); 3.174 (4.3); 3.161 (4.4); 2.868 (0.5); 2.859 (0.8); 2.850 (1.2); 2.840 (1.2); 2.831 (0.8); 2.822 (0.6); 2.676 (0.9); 2.671 (1.2); 2.667 (0.9); 2.541 (0.7); 2.525 (3.7); 2.511 (78.4); 2.507 (154.9); 2.502 (201.4); 2.498 (148.3); 2.493 (74.4); 2.334 (0.9); 2.329 (1.2); 2.325 (0.9); 2.147 (13.7); 1.002 (1.6); 0.987 (1.6); 0.755 (0.8); 0.742 (2.2); 0.737 (3.1); 0.725 (2.9); 0.719 (2.4); 0.708 (1.0); 0.563 (1.0); 0.552 (2.9); 0.546 (2.7); 0.542 (2.6); 0.536 (2.5); 0.524 (0.8); 0.000 (2.7)

Beispiel I-T3-107: ¹H-NMR (400.0 MHz, $d_6$-DMSO):
δ = 8.833 (0.5); 8.826 (0.6); 8.819 (2.8); 8.813 (2.8); 8.770 (3.5); 8.503 (0.9); 8.495 (4.3); 8.312 (2.8); 8.306 (2.6); 8.223 (2.0); 8.207 (0.5); 8.201 (0.4); 7.939 (2.1); 3.904 (16.0); 3.332 (177.8); 3.175 (1.5); 3.162 (1.6); 3.027 (12.7); 2.794 (0.5); 2.787 (0.6); 2.778 (1.0); 2.767 (0.8); 2.760 (2.8); 2.751 (0.4); 2.676 (0.8); 2.672 (1.0); 2.667 (0.7); 2.525 (3.3); 2.511 (67.3); 2.507 (128.5); 2.503 (163.4); 2.498 (118.9); 2.494

(59.0); 2.334 (0.7); 2.329 (1.0); 2.325 (0.7); 2.158 (9.9); 1.002 (1.1); 0.987 (1.1); 0.830 (0.3); 0.813 (0.3); 0.606 (0.4); 0.586 (1.6); 0.577 (2.2); 0.568 (0.8); 0.545 (1.0); 0.534 (1.7); 0.516 (1.5); 0.000 (2.1)

Beispiel I-T3-108: $^1$H-NMR (400.0 MHz, d$_6$-DMSO):
δ = 9.604 (5.0); 8.878 (4.1); 8.872 (4.2); 8.793 (5.7); 8.519 (7.0); 8.277 (4.3); 8.271 (4.2); 8.225 (3.2); 7.938 (3.2); 4.458 (0.3); 4.404 (0.4); 4.393 (0.4); 4.123 (0.4); 4.110 (1.1); 4.097 (1.1); 4.083 (0.4); 3.904 (16.0); 3.433 (0.3); 3.337 (510.1); 3.270 (0.6); 3.256 (0.6); 3.242 (0.4); 3.175 (4.2); 3.162 (4.3); 3.043 (0.4); 2.872 (0.4); 2.672 (1.4); 2.506 (184.9); 2.503 (232.7); 2.499 (181.4); 2.329 (1.4); 2.148 (15.6); 1.643 (1.6); 1.629 (4.1); 1.622 (4.4); 1.609 (1.8); 1.293 (1.8); 1.280 (4.1); 1.273 (4.3); 1.259 (1.6); 1.002 (1.2); 0.987 (1.2); 0.000 (0.9)

Beispiel I-T3-109: $^1$H-NMR (400.0 MHz, d$_6$-DMSO):
δ = 8.821 (4.5); 8.815 (4.5); 8.727 (6.7); 8.683 (2.3); 8.672 (2.3); 8.456 (6.9); 8.191 (4.6); 8.185 (4.4); 7.611 (3.0); 7.577 (3.0); 4.112 (0.4); 4.099 (0.5); 3.904 (16.0); 3.433 (0.3); 3.422 (0.4); 3.341 (478.8); 3.283 (0.5); 3.272 (0.4); 3.269 (0.4); 3.257 (0.4); 3.243 (0.3); 3.175 (2.2); 3.162 (2.3); 2.868 (0.6); 2.858 (0.9); 2.850 (1.4); 2.840 (1.4); 2.831 (0.9); 2.821 (0.7); 2.676 (0.9); 2.672 (1.2); 2.667 (0.9); 2.542 (0.7); 2.525 (3.9); 2.511 (83.9); 2.507 (159.5); 2.503 (202.9); 2.498 (149.6); 2.443 (1.3); 2.424 (3.5); 2.405 (3.5); 2.387 (1.2); 2.334 (0.9); 2.330 (1.2); 2.325 (0.9); 2.096 (16.0); 1.169 (1.4); 1.035 (5.1); 1.016 (10.9); 1.002 (2.2); 0.997 (5.0); 0.987 (1.4); 0.755 (0.9); 0.742 (2.7); 0.737 (3.5); 0.725 (3.4); 0.719 (2.8); 0.708 (1.1); 0.563 (1.1); 0.553 (3.4); 0.547 (3.3); 0.543 (3.1); 0.537 (3.0); 0.525 (0.9); 0.000 (2.0)

Beispiel I-T3-110: $^1$H-NMR (400.0 MHz, d$_6$-DMSO):
δ = 9.594 (4.6); 8.875 (3.8); 8.869 (3.9); 8.742 (6.3); 8.462 (6.5); 8.272 (3.9); 8.266 (3.9); 7.613 (3.3); 7.578 (3.3); 4.108 (0.5); 4.095 (0.5); 3.904 (12.4); 3.405 (0.3); 3.334 (307.0); 3.269 (0.5); 3.256 (0.4); 3.242 (0.4); 3.175 (2.2); 3.161 (2.3); 3.043 (0.4); 2.871 (0.4); 2.671 (1.3); 2.502 (210.6); 2.445 (1.6); 2.426 (3.6); 2.407 (3.7); 2.329 (1.3); 2.097 (16.0); 1.645 (1.5); 1.630 (4.1); 1.624 (4.4); 1.610 (1.8); 1.291 (1.8); 1.277 (4.2); 1.271 (4.6); 1.256 (1.7); 1.235 (0.5); 1.169 (1.0); 1.036 (4.8); 1.018 (10.0); 0.999 (5.0); 0.987 (1.2); 0.000 (2.4)

Beispiel I-T3-111: $^1$H-NMR (400.0 MHz, d$_6$-DMSO):
δ = 8.917 (0.5); 8.913 (0.5); 8.882 (1.9); 8.876 (1.9); 8.782 (2.6); 8.753 (0.7); 8.503 (3.1); 8.461 (0.8); 8.419 (0.5); 8.414 (0.5); 8.284 (1.9); 8.279 (1.8); 8.223 (2.2); 7.938 (2.3); 3.904 (16.0); 3.334 (271.2); 3.175 (0.9); 3.162 (1.0); 3.131 (2.1); 2.919 (9.2); 2.676 (0.8); 2.672 (1.0); 2.667 (0.8); 2.525 (3.1); 2.511 (66.1); 2.507 (129.1); 2.503 (166.9); 2.498 (121.9); 2.494 (60.4); 2.334 (0.8); 2.329 (1.0); 2.325 (0.8); 2.149 (11.9); 1.718 (1.7); 1.712 (1.9); 1.487 (1.3); 0.000 (2.6)

Beispiel I-T3-112: $^1$H-NMR (400.0 MHz, d$_6$-DMSO):
δ = 8.843 (5.5); 8.825 (4.0); 8.819 (4.0); 8.701 (2.1); 8.690 (2.0); 8.561 (6.3); 8.513 (3.0); 8.198 (3.9); 8.192 (3.8); 8.094 (2.9); 4.109 (0.4); 4.096 (0.5); 3.904 (16.0); 3.333 (218.4); 3.267 (0.4); 3.174 (2.5); 3.162 (2.6); 2.870 (0.6); 2.860 (0.9); 2.851 (1.3); 2.841 (1.3); 2.833 (0.9); 2.823 (0.6); 2.676 (0.9); 2.671 (1.2); 2.667 (0.9); 2.524 (3.8); 2.507 (149.9); 2.502 (194.0); 2.498 (144.0); 2.333 (0.9); 2.329 (1.2); 2.325 (0.9); 1.002 (1.2); 0.987 (1.2); 0.756 (0.8); 0.743 (2.5); 0.738 (3.3); 0.726 (3.1); 0.720 (2.6); 0.709 (1.0); 0.564 (1.0); 0.553 (3.2); 0.547 (3.1); 0.544 (2.9); 0.538 (2.8); 0.526 (0.8); 0.000 (2.3)

Beispiel I-T3-113: $^1$H-NMR (400.0 MHz, d$_6$-DMSO):
δ = 8.831 (3.5); 8.818 (2.5); 8.812 (2.5); 8.547 (0.8); 8.540 (3.7); 8.512 (1.9); 8.325 (2.4); 8.319 (2.4); 8.213 (0.4); 8.207 (0.4); 8.096 (1.8); 3.904 (16.0); 3.381 (0.4); 3.332 (195.5); 3.175 (1.3); 3.161 (1.4); 3.028 (11.1); 2.794 (0.5); 2.787 (0.5); 2.777 (0.9); 2.767 (0.7); 2.760 (2.4); 2.676 (0.7); 2.672 (0.9); 2.667 (0.7); 2.525 (2.8); 2.511 (58.6); 2.507 (114.3); 2.502 (147.1); 2.498 (107.3); 2.494 (52.8); 2.334 (0.6); 2.329 (0.9); 2.325 (0.6); 1.002 (1.0); 0.987 (0.9); 0.585 (1.4); 0.577 (1.9); 0.568 (0.7); 0.545 (0.8); 0.534 (1.4); 0.516 (1.3); 0.000 (2.0)

Beispiel I-T3-114: $^1$H-NMR (400.0 MHz, d$_6$-DMSO):
δ = 9.607 (2.4); 8.880 (2.4); 8.874 (2.4); 8.854 (3.1); 8.566 (3.7); 8.515 (1.6); 8.282 (2.4); 8.276 (2.4); 8.095 (1.6); 4.108 (0.4); 4.095 (0.4); 3.904 (16.0); 3.334 (175.5); 3.175 (2.1); 3.161 (2.1); 3.044 (0.5); 2.872 (0.5); 2.676 (0.6); 2.672 (0.8); 2.667 (0.6); 2.541 (0.5); 2.525 (2.4); 2.511 (50.8); 2.507 (99.8); 2.502 (129.1); 2.498 (94.9); 2.494 (47.4); 2.329 (0.7); 2.325 (0.6); 1.643 (0.8); 1.629 (2.0); 1.622 (2.2); 1.608 (0.9); 1.298 (1.0); 1.284 (2.0); 1.278 (2.2); 1.263 (0.8); 1.002 (0.9); 0.987 (0.8); 0.000 (1.0)

Beispiel I-T3-115: $^1$H-NMR (400.0 MHz, d$_6$-DMSO):
δ = 8.898 (1.1); 8.630 (1.1); 8.376 (0.7); 7.972 (0.4); 7.595 (4.0); 3.903 (4.3); 3.328 (177.7); 2.876 (1.2); 2.675 (0.9); 2.671 (1.2); 2.667 (0.9); 2.541 (0.9); 2.506 (159.0); 2.502 (205.8); 2.498 (157.5); 2.385 (2.8); 2.333 (1.0); 2.329 (1.3); 2.324 (1.0); 2.122 (16.0); 1.686 (0.6); 1.487 (0.8); 0.000 (1.2)

Beispiel I-T3-116: $^1$H-NMR (400.0 MHz, d$_6$-DMSO):
δ = 8.911 (1.0); 8.880 (3.4); 8.874 (3.4); 8.842 (5.1); 8.810 (1.3); 8.548 (5.6); 8.512 (4.5); 8.423 (0.9); 8.292 (3.4); 8.286 (3.4); 8.093 (4.3); 3.904 (4.9); 3.327 (229.2); 3.133 (3.9); 2.918 (16.0); 2.675 (1.2); 2.671 (1.6); 2.667 (1.3); 2.541 (1.5); 2.506 (202.4); 2.502 (261.5); 2.498 (200.6); 2.333 (1.1); 2.329 (1.5); 2.325 (1.2); 1.711 (3.8); 1.488 (2.6); −0.001 (1.3)

Beispiel I-T3-117: $^1$H-NMR (400.0 MHz, d$_6$-DMSO):
δ = 8.837 (3.9); 8.832 (3.9); 8.696 (5.5); 8.528 (2.3); 8.517 (2.3); 8.440 (6.7); 8.213 (3.3); 7.955 (3.9); 7.949 (3.9); 7.929 (3.4); 3.904 (3.8); 3.328 (223.0); 2.875 (0.7); 2.865 (1.0); 2.857 (1.5); 2.847 (1.5); 2.838 (1.1); 2.828 (0.7); 2.671 (1.5); 2.502 (230.7); 2.329 (1.4); 2.145 (16.0); 0.738 (0.9); 0.720 (3.6); 0.708 (3.4); 0.702 (3.0); 0.691 (1.1); 0.566 (1.2); 0.555 (3.7); 0.549 (3.6); 0.540 (3.2); 0.527 (0.9); 0.000 (1.2)

Beispiel I-T3-118: $^1$H-NMR (400.0 MHz, d$_6$-DMSO):
δ = 8.825 (3.2); 8.820 (3.1); 8.700 (5.9); 8.438 (7.3); 8.213 (3.4); 8.037 (3.0); 8.031 (3.0); 7.930 (3.5); 7.908 (0.5); 3.904 (11.1); 3.330 (239.1); 3.022 (14.7); 2.779 (0.4); 2.764 (0.9); 2.753 (1.3); 2.743 (1.0); 2.737 (1.0); 2.723 (2.0); 2.676 (1.0); 2.671 (1.3); 2.667 (1.0); 2.542 (1.0); 2.524 (4.1); 2.511 (78.7); 2.507 (153.6); 2.502 (199.9); 2.498 (148.4); 2.392 (13.3); 2.364 (1.8); 2.333 (0.9); 2.329 (1.2); 2.325 (0.9); 2.154 (16.0); 0.817 (0.5); 0.802 (0.5); 0.755 (0.6); 0.484 (4.8); 0.466 (2.5); 0.000 (1.4)

Beispiel I-T3-119: $^1$H-NMR (400.0 MHz, d$_6$-DMSO):
δ = 9.408 (4.7); 8.892 (3.9); 8.886 (3.9); 8.716 (5.6); 8.452 (7.3); 8.217 (2.9); 8.041 (3.8); 8.035 (3.8); 7.932 (3.0); 3.904 (9.3); 3.330 (168.1); 3.175 (1.1); 3.162 (1.1); 2.676 (0.7); 2.671 (1.0); 2.667 (0.8); 2.541 (0.9); 2.511 (82.5); 2.507 (129.7); 2.502 (165.2); 2.498 (122.9); 2.333 (0.7); 2.329 (1.0); 2.325 (0.7); 2.147 (16.0); 1.612 (1.5); 1.598 (4.0); 1.591 (4.3); 1.578 (1.8); 1.312 (1.8); 1.299 (4.1); 1.292 (4.2); 1.278 (1.5); 0.000 (1.1)

Beispiel I-T3-120: $^1$H-NMR (400.0 MHz, d$_6$-DMSO):
δ = 8.826 (1.6); 8.821 (1.6); 8.621 (4.1); 8.375 (3.7); 8.025 (1.5); 8.020 (1.6); 7.593 (4.8); 3.903 (7.6); 3.331 (235.6); 3.022 (7.6); 2.756 (0.7); 2.743 (0.5); 2.720 (1.0); 2.671 (1.1); 2.541 (0.9); 2.507 (130.2); 2.502 (168.8); 2.498 (127.0); 2.386 (6.8); 2.359 (0.9); 2.329 (1.0); 2.129 (16.0); 0.482 (2.7); 0.465 (1.4); 0.000 (1.0)

Beispiel I-T3-121: $^1$H-NMR (400.0 MHz, CD3CN):
δ = 8.836 (16.0); 8.460 (13.4); 8.441 (12.5); 7.871 (1.5); 7.554 (14.8); 2.909 (0.5); 2.899 (1.4); 2.890 (2.1); 2.881 (3.1); 2.871 (3.2); 2.862 (2.1); 2.853 (1.6); 2.843 (0.5); 2.469 (0.5); 2.464 (0.6); 2.460 (0.5); 2.287 (0.5); 2.263 (0.4); 2.245 (0.8); 2.226 (0.6); 2.164 (134.4); 2.128 (74.2); 2.108 (1.2); 2.102 (0.8); 2.096 (0.5); 1.976 (0.8); 1.965 (34.9); 1.959 (10.4); 1.953 (53.7); 1.947 (97.8); 1.941 (132.8); 1.935 (92.8); 1.928 (48.6); 1.829 (0.7); 1.781 (0.4); 1.775 (0.6); 1.769 (0.8); 1.763 (0.5); 1.540 (0.4); 1.470 (0.3); 1.429 (0.3); 1.320 (1.0); 1.269 (9.8); 1.135 (0.4); 0.897 (0.4); 0.881 (1.1); 0.864 (0.5); 0.834 (1.8); 0.821 (4.8); 0.816 (6.9); 0.803 (6.8); 0.798 (5.3); 0.786 (2.4); 0.764 (0.4); 0.746 (0.4); 0.721 (0.4); 0.710 (0.4); 0.681 (2.4); 0.669 (6.3); 0.663 (6.5); 0.659 (5.7); 0.653 (5.3); 0.641 (1.6); 0.000 (1.3)

Beispiel I-T3-122: $^1$H-NMR (400.0 MHz, CD3CN):
δ = 8.795 (7.1); 8.792 (7.1); 8.712 (16.0); 8.398 (7.3); 8.393 (7.2); 8.249 (14.8); 8.230 (0.4); 8.035 (5.4); 8.031 (10.0); 8.027 (5.8); 7.832 (3.6); 7.830 (4.9); 7.826 (3.7); 7.821 (2.0); 7.814 (5.0); 7.810 (5.4); 7.716 (5.3); 7.700 (3.9); 7.697 (5.2); 7.585 (0.4); 7.519 (5.8); 7.500 (9.9); 7.480 (4.3); 7.146 (1.9); 4.086 (0.4); 4.068 (1.3); 4.050 (1.3); 4.033 (0.5); 2.907 (0.6); 2.897 (1.9); 2.888 (2.8); 2.879 (4.2); 2.869 (4.1); 2.861 (2.8); 2.851 (2.0); 2.842 (0.7); 2.468 (0.7); 2.463 (0.9); 2.459 (0.7); 2.266 (0.3); 2.250 (0.4); 2.144 (668.5); 2.120 (3.2); 2.114

(4.0); 2.108 (5.1); 2.101 (3.3); 2.095 (1.7); 2.016 (0.5); 2.014 (0.5); 1.972 (7.8); 1.964 (22.3); 1.958 (55.1); 1.952 (312.9); 1.946 (568.6); 1.940 (766.2); 1.934 (526.3); 1.928 (270.3); 1.787 (0.4); 1.781 (1.7); 1.775 (3.2); 1.769 (4.4); 1.762 (3.0); 1.756 (1.5); 1.437 (5.8); 1.356 (0.3); 1.338 (0.6); 1.319 (0.4); 1.285 (0.5); 1.270 (2.2); 1.222 (1.6); 1.204 (3.0); 1.186 (1.6); 1.089 (0.9); 0.881 (0.4); 0.793 (2.2); 0.781 (6.2); 0.775 (8.7); 0.763 (8.9); 0.757 (6.5); 0.746 (3.2); 0.724 (0.5); 0.707 (0.5); 0.687 (0.5); 0.677 (0.4); 0.647 (3.3); 0.637 (8.3); 0.630 (8.0); 0.626 (7.0); 0.620 (6.8); 0.608 (2.2); 0.008 (1.7); 0.000 (60.4); −0.009 (2.1)

Beispiel I-T3-123: $^{1}$H-NMR (400.0 MHz, $d_6$-DMSO):

δ = 8.894 (2.1); 8.708 (1.4); 8.439 (1.2); 8.213 (2.9); 7.984 (0.8); 7.930 (3.0); 3.904 (15.2); 3.331 (445.1); 3.174 (0.5); 3.161 (0.5); 3.121 (0.5); 2.877 (2.5); 2.675 (1.3); 2.671 (1.8); 2.667 (1.4); 2.542 (1.7); 2.506 (224.4); 2.502 (292.1); 2.498 (219.8); 2.389 (5.1); 2.333 (1.3); 2.329 (1.8); 2.325 (1.4); 2.148 (16.0); 1.687 (1.2); 1.492 (1.5); 1.416 (0.6); 1.249 (0.4); 1.235 (0.4); 0.000 (1.8)

Beispiel I-T3-124: $^{1}$H-NMR (400.0 MHz, $d_6$-DMSO):

δ = 8.836 (5.2); 8.831 (5.2); 8.756 (7.5); 8.544 (2.8); 8.534 (2.9); 8.502 (4.3); 8.488 (8.8); 8.087 (4.0); 7.952 (5.0); 7.946 (5.0); 4.467 (0.8); 4.454 (2.0); 4.440 (0.8); 4.113 (0.5); 4.100 (0.5); 3.904 (16.0); 3.507 (0.4); 3.482 (0.5); 3.468 (0.5); 3.456 (0.5); 3.395 (5.7); 3.388 (4.9); 3.381 (6.3); 3.340 (838.4); 3.174 (2.4); 3.161 (2.3); 2.877 (0.8); 2.876 (0.9); 2.867 (1.2); 2.858 (1.9); 2.848 (1.9); 2.840 (1.3); 2.830 (0.9); 2.820 (0.4); 2.676 (1.6); 2.672 (2.1); 2.667 (1.7); 2.507 (264.8); 2.503 (344.8); 2.498 (274.4); 2.334 (1.5); 2.329 (2.0); 2.325 (1.5); 1.273 (0.4); 1.258 (0.8); 1.242 (0.8); 0.873 (0.4); 0.739 (1.2); 0.726 (3.4); 0.721 (4.6); 0.709 (4.3); 0.703 (3.7); 0.692 (1.5); 0.567 (1.5); 0.556 (4.6); 0.550 (4.3); 0.546 (4.1); 0.540 (3.8); 0.528 (1.1); 0.008 (2.2); 0.000 (60.2); −0.008 (2.5)

Beispiel I-T3-125: $^{1}$H-NMR (400.1 MHz, $d_6$-DMSO):

δ = 9.41 (0.0144); 8.89 (0.0123); 8.83 (0.0014); 8.77 (0.0184); 8.49 (0.0301); 8.23 (0.0012); 8.09 (0.0103); 8.03 (0.0119); 3.31 (1.0000); 2.54 (0.6709); 2.50 (0.2387); 1.59 (0.0138); 1.30 (0.0136); 0.15 (0.0007); 0.00 (0.1822); −0.16 (0.0004)

Beispiel I-T3-126: $^{1}$H-NMR (400.0 MHz, $d_6$-DMSO):

δ = 9.406 (0.9); 8.069 (2.0); 7.667 (0.4); 7.646 (1.1); 7.621 (0.6); 7.616 (0.6); 7.538 (0.8); 7.533 (0.7); 6.479 (0.9); 3.322 (20.1); 2.524 (0.4); 2.519 (0.7); 2.511 (11.8); 2.506 (24.6); 2.502 (33.4); 2.497 (24.8); 2.493 (12.4); 1.989 (0.8); 1.608 (0.4); 1.594 (0.8); 1.587 (0.9); 1.574 (0.4); 1.398 (16.0); 1.291 (0.4); 1.278 (0.7); 1.271 (0.8); 1.257 (0.3); 1.175 (0.5); 0.008 (0.6); 0.000 (18.6); −0.009 (0.7)

Beispiel I-T3-127: $^{1}$H-NMR (400.0 MHz, $d_6$-DMSO):

δ = 8.850 (5.1); 8.845 (5.4); 8.692 (9.2); 8.530 (3.1); 8.520 (3.2); 8.464 (9.2); 8.273 (16.0); 7.973 (5.1); 7.967 (5.3); 4.105 (0.5); 4.091 (0.5); 3.903 (5.0); 3.329 (87.9); 3.175 (1.9); 3.162 (1.8); 2.877 (0.8); 2.868 (1.2); 2.859 (1.9); 2.849 (1.9); 2.840 (1.3); 2.831 (0.9); 2.820 (0.3); 2.672 (0.6); 2.667 (0.5); 2.507 (79.2); 2.502 (111.9); 2.463 (0.7); 2.334 (0.5); 2.329 (0.6); 0.740 (1.1); 0.727 (3.5); 0.722 (4.8); 0.710 (4.4); 0.704 (4.0); 0.693 (1.5); 0.571 (1.5); 0.561 (4.6); 0.555 (4.7); 0.551 (4.6); 0.545 (4.2); 0.533 (1.1); 0.000 (0.4)

Beispiel I-T3-128: $^{1}$H-NMR (400.0 MHz, $d_6$-DMSO):

δ = 8.840 (3.6); 8.835 (3.5); 8.698 (8.9); 8.465 (8.7); 8.272 (15.4); 8.058 (3.3); 8.053 (3.4); 7.922 (0.5); 3.903 (5.1); 3.328 (66.8); 3.175 (1.0); 3.162 (1.0); 3.026 (16.0); 2.891 (0.3); 2.784 (0.4); 2.767 (0.9); 2.756 (1.4); 2.746 (1.0); 2.721 (1.9); 2.676 (0.5); 2.672 (0.6); 2.667 (0.5); 2.542 (0.7); 2.511 (37.1); 2.507 (71.3); 2.503 (93.3); 2.498 (71.7); 2.395 (14.5); 2.369 (1.9); 2.334 (0.4); 2.329 (0.6); 2.325 (0.4); 0.819 (0.5); 0.803 (0.5); 0.758 (0.6); 0.481 (5.4); 0.463 (2.8); 0.000 (0.4)

Beispiel I-T3-129: $^{1}$H-NMR (400.0 MHz, $d_6$-DMSO):

δ = 9.412 (6.2); 8.906 (4.7); 8.900 (5.0); 8.710 (9.0); 8.478 (8.5); 8.276 (16.0); 8.063 (4.7); 8.058 (4.9); 3.903 (5.3); 3.434 (0.4); 3.334 (71.6); 3.169 (3.4); 2.672 (0.8); 2.520 (27.6); 2.507 (94.6); 2.503 (122.2); 2.499 (100.6); 2.329 (0.7); 1.612 (1.9); 1.598 (5.2); 1.591 (5.7); 1.578 (2.3); 1.317 (2.3); 1.304 (5.3); 1.297 (5.6); 1.283 (1.9); 0.000 (0.4)

Beispiel I-T3-130: $^{1}$H-NMR (400.0 MHz, $d_6$-DMSO):

δ = 8.821 (3.6); 8.815 (3.5); 8.760 (6.9); 8.499 (4.1); 8.484 (8.5); 8.085 (3.9); 8.046 (3.3); 8.040 (3.3); 7.911 (0.5); 3.904 (10.2); 3.327 (87.7); 3.176 (0.7); 3.163 (0.7); 3.025 (16.0); 2.890 (0.3); 2.780 (0.4); 2.768 (0.7); 2.762 (0.9); 2.753 (1.5); 2.742 (1.1); 2.736 (1.1); 2.724 (2.2); 2.676 (0.5); 2.672 (0.7); 2.667 (0.5); 2.525 (2.4); 2.512 (41.2); 2.507 (81.2); 2.503 (106.8); 2.498 (80.2); 2.494 (41.1); 2.398 (14.3); 2.369 (1.8); 2.334 (0.5); 2.330 (0.7); 2.325 (0.5); 0.820 (0.5); 0.803 (0.5); 0.757 (0.6); 0.485 (4.9); 0.467 (2.7); 0.000 (0.5)

Beispiel I-T3-131: $^{1}$H-NMR (400.0 MHz, $d_6$-DMSO):

δ = 8.891 (3.3); 8.768 (2.3); 8.499 (5.4); 8.485 (2.0); 8.085 (4.9); 7.990 (1.3); 3.903 (16.0); 3.327 (119.4); 3.175 (0.8); 3.162 (0.9); 3.122 (0.7); 2.879 (3.8); 2.676 (0.7); 2.672 (1.0); 2.667 (0.8); 2.542 (0.7); 2.525 (3.3); 2.511 (61.8); 2.507 (121.8); 2.503 (160.9); 2.498 (122.6); 2.494 (64.2); 2.396 (8.3); 2.334 (0.8); 2.329 (1.0); 2.325 (0.8); 1.686 (1.8); 1.497 (2.2); 1.420 (0.8); 0.000 (0.7)

Beispiel I-T3-132: $^{1}$H-NMR (400.1 MHz, $d_6$-DMSO):

δ = 8.907 (3.3); 8.699 (3.2); 8.461 (1.9); 8.269 (16.0); 8.002 (1.1); 4.088 (0.5); 4.075 (0.5); 3.311 (245.5); 3.269 (0.3); 3.175 (2.1); 3.162 (2.1); 3.123 (0.6); 2.875 (3.1); 2.710 (0.5); 2.674 (0.4); 2.670 (0.5); 2.540 (120.2); 2.505 (48.9); 2.501 (64.0); 2.497 (45.6); 2.464 (0.3); 2.396 (8.6); 2.367 (0.8); 2.328 (0.5); 2.323 (0.4); 1.686 (1.6); 1.495 (2.0); 1.431 (0.8); 1.423 (0.8); 0.146 (0.4); 0.008 (3.2); 0.000 (89.8); −0.008 (4.5); −0.150 (0.4)

Beispiel I-T3-133: $^{1}$H-NMR (400.1 MHz, $d_6$-DMSO):

δ = 8.822 (3.7); 8.817 (3.4); 8.750 (9.7); 8.470 (9.1); 8.094 (15.1); 8.040 (3.3); 8.035 (3.3); 7.903 (0.4); 3.311 (86.3); 3.287 (0.3); 3.026 (16.0); 2.781 (0.4); 2.765 (1.0); 2.754 (1.5); 2.743 (1.1); 2.738 (1.1); 2.721 (1.6); 2.711 (0.7); 2.555 (0.4); 2.554 (0.5); 2.553 (0.6); 2.552 (0.7); 2.550 (0.8); 2.549 (1.0); 2.540 (89.5); 2.529 (0.7); 2.528 (0.6); 2.527 (0.6); 2.525 (0.6); 2.524 (0.6); 2.523 (0.6); 2.522 (0.6); 2.510 (12.1); 2.505 (23.8); 2.501 (31.3); 2.497 (21.3); 2.492 (9.9); 2.395 (14.5); 2.371 (1.7); 0.819 (0.4); 0.804 (0.5); 0.755 (0.6); 0.482 (5.8); 0.464 (3.0); 0.013 (0.3); 0.011 (0.4); 0.008 (2.1); 0.007 (1.4); 0.000 (61.4); −0.006 (1.7); −0.009 (2.2); −0.013 (0.4); −0.014 (0.3)

Beispiel I-T3-134: $^{1}$H-NMR (400.0 MHz, $d_6$-DMSO):

δ = 8.823 (4.4); 8.427 (4.3); 8.403 (0.4); 8.263 (1.3); 8.242 (1.6); 8.112 (2.9); 8.071 (2.1); 8.050 (1.8); 7.818 (2.7); 7.813 (2.7); 7.760 (1.6); 7.755 (1.5); 7.747 (1.0); 7.739 (1.8); 7.734 (1.5); 7.724 (0.9); 7.560 (1.0); 7.553 (2.6); 7.540 (1.0); 7.532 (2.1); 3.327 (28.9); 3.321 (6.8); 3.015 (11.5); 2.766 (0.4); 2.756 (0.8); 2.748 (1.0); 2.740 (1.3); 2.730 (1.2); 2.716 (2.7); 2.676 (0.4); 2.673 (0.4); 2.507 (45.7); 2.503 (53.0); 2.499 (41.0); 2.330 (0.4); 2.076 (16.0); 2.068 (2.0); 1.170 (0.4); 0.820 (0.4); 0.812 (0.4); 0.804 (0.4); 0.757 (0.5); 0.748 (0.5); 0.559 (2.6); 0.551 (2.5); 0.503 (0.4); 0.472 (2.1); 0.455 (2.2); 0.000 (51.7); −0.009 (7.9)

Beispiel I-T3-135: $^{1}$H-NMR (400.1 MHz, $d_6$-DMSO):

δ = 8.547 (0.5); 8.505 (10.0); 8.454 (9.8); 8.448 (8.1); 8.442 (4.1); 8.281 (10.0); 8.068 (16.0); 7.686 (6.9); 7.680 (6.8); 3.568 (0.4); 3.410 (4.1); 3.394 (11.2); 3.378 (4.3); 3.309 (165.8); 3.286 (0.7); 2.832 (0.3); 2.822 (0.9); 2.812 (1.3); 2.804 (2.0); 2.794 (2.0); 2.785 (1.3); 2.776 (0.9); 2.765 (0.4); 2.710 (0.9); 2.674 (0.5); 2.669 (0.6); 2.665 (0.5); 2.560 (0.6); 2.540 (226.8); 2.523 (1.6); 2.509 (31.4); 2.505 (60.7); 2.500 (78.7); 2.496 (53.0); 2.492 (24.2); 2.366 (0.8); 2.332 (0.4); 2.327 (0.6); 2.323 (0.4); 1.887 (4.2); 1.871 (11.1); 1.854 (3.9); 1.235 (0.4); 0.704 (1.4); 0.691 (3.7); 0.686 (5.2); 0.674 (4.8); 0.668 (4.0); 0.657 (1.7); 0.547 (1.8); 0.536 (5.3); 0.530 (4.6); 0.526 (4.3); 0.520 (4.2); 0.508 (1.3); 0.146 (0.5); 0.008 (4.2); 0.000 (120.8); −0.008 (4.5); −0.150 (0.5)

Beispiel I-T3-136: $^{1}$H-NMR (400.0 MHz, $d_6$-DMSO):

δ = 8.510 (2.6); 8.502 (7.1); 8.497 (6.4); 8.441 (8.5); 8.259 (8.4); 8.129 (2.2); 8.117 (2.5); 8.106 (1.0); 8.088 (5.7); 8.080 (16.0); 4.467 (1.4); 4.453 (4.0); 4.439 (1.5); 4.111 (0.4); 4.099 (0.4); 3.904 (15.8); 3.804 (0.4); 3.483 (0.4); 3.470 (0.5); 3.455 (0.4); 3.395 (8.9); 3.388 (7.6); 3.381 (9.5); 3.338 (810.3); 3.174 (1.7); 3.161 (1.6); 2.953 (0.4); 2.932 (11.5); 2.920 (11.5); 2.847 (0.4); 2.837 (0.9); 2.828 (1.3); 2.819 (1.9); 2.810 (1.9); 2.801 (1.3); 2.792 (0.9); 2.783 (0.4); 2.671 (2.2); 2.616 (0.3); 2.506 (280.8); 2.502 (354.5); 2.498 (275.8); 2.329 (2.2); 1.234 (0.6); 0.873 (0.6); 0.854 (0.5); 0.742 (1.0); 0.724 (4.4); 0.711 (4.1); 0.706 (3.6); 0.694 (1.4); 0.587 (1.5); 0.576 (4.6); 0.570 (4.4); 0.561 (3.8); 0.548 (1.1); 0.000 (48.0)

Beispiel I-T3-137: ¹H-NMR (400.0 MHz, d₆-DMSO):
δ = 8.543 (6.9); 8.537 (7.0); 8.455 (8.0); 8.364 (2.9); 8.356 (3.0); 8.268 (8.1); 8.118 (4.5); 8.113 (4.5); 8.083 (13.0); 4.467 (0.5); 4.453 (1.5); 4.439 (0.6); 4.112 (0.4); 4.099 (0.4); 3.904 (16.0); 3.483 (0.3); 3.469 (0.4); 3.433 (0.5); 3.407 (0.8); 3.395 (4.1); 3.388 (3.4); 3.381 (4.6); 3.338 (731.2); 3.174 (1.7); 3.161 (1.6); 2.955 (0.8); 2.852 (0.8); 2.844 (1.2); 2.835 (1.8); 2.826 (2.0); 2.818 (2.0); 2.809 (2.0); 2.800 (2.0); 2.791 (1.8); 2.782 (1.2); 2.772 (0.8); 2.676 (1.4); 2.672 (1.9); 2.667 (1.5); 2.507 (235.5); 2.502 (302.0); 2.498 (229.6); 2.333 (1.4); 2.329 (1.8); 2.325 (1.4); 1.237 (0.4); 0.873 (0.4); 0.854 (0.3); 0.765 (1.1); 0.753 (3.5); 0.748 (4.4); 0.736 (5.1); 0.731 (4.0); 0.718 (5.1); 0.706 (3.9); 0.700 (3.5); 0.689 (1.4); 0.582 (1.4); 0.571 (4.3); 0.565 (4.0); 0.556 (3.5); 0.544 (1.0); 0.466 (1.3); 0.455 (4.0); 0.450 (4.1); 0.445 (4.0); 0.440 (3.9); 0.428 (1.1); 0.000 (39.5)

Beispiel I-T3-138: ¹H-NMR (400.0 MHz, d₆-DMSO):
δ = 8.524 (1.8); 8.515 (1.9); 8.487 (3.8); 8.482 (3.9); 8.443 (6.4); 8.432 (1.1); 8.419 (1.9); 8.405 (1.0); 8.274 (0.4); 8.262 (6.3); 8.120 (4.0); 8.114 (3.6); 8.081 (10.3); 4.453 (0.7); 3.904 (16.0); 3.606 (1.0); 3.592 (3.0); 3.579 (3.7); 3.566 (1.8); 3.523 (3.7); 3.511 (4.9); 3.498 (1.9); 3.473 (0.5); 3.449 (0.3); 3.395 (2.5); 3.387 (2.3); 3.381 (2.9); 3.338 (556.7); 3.299 (28.1); 3.286 (1.6); 3.262 (0.8); 3.256 (0.7); 3.174 (0.9); 3.161 (0.9); 2.840 (0.6); 2.831 (0.9); 2.822 (1.3); 2.812 (1.4); 2.804 (0.9); 2.795 (0.6); 2.676 (1.4); 2.672 (2.0); 2.667 (1.4); 2.507 (219.1); 2.503 (282.2); 2.498 (210.9); 2.334 (1.2); 2.329 (1.7); 2.325 (1.3); 1.235 (0.5); 0.747 (0.8); 0.734 (2.3); 0.729 (3.2); 0.717 (2.9); 0.711 (2.6); 0.700 (1.0); 0.589 (1.1); 0.579 (3.3); 0.573 (3.0); 0.569 (3.0); 0.563 (2.7); 0.551 (0.9); 0.008 (1.7); 0.000 (45.2); −0.008 (1.8)

Beispiel I-T3-139: ¹H-NMR (400.0 MHz, d₆-DMSO):
δ = 9.474 (2.4); 8.837 (1.9); 8.831 (2.1); 8.602 (3.2); 8.355 (3.4); 7.970 (2.0); 7.965 (2.2); 7.596 (4.3); 4.467 (0.4); 4.453 (1.0); 4.440 (0.4); 3.904 (6.3); 3.423 (0.3); 3.395 (2.3); 3.387 (2.3); 3.381 (2.8); 3.340 (340.7); 3.174 (0.4); 3.161 (0.3); 3.063 (0.6); 2.880 (0.6); 2.672 (0.9); 2.668 (0.7); 2.507 (107.5); 2.503 (142.8); 2.498 (119.4); 2.329 (1.2); 2.325 (1.2); 2.312 (0.8); 2.299 (0.6); 2.292 (0.5); 2.110 (16.0); 1.615 (0.8); 1.601 (2.0); 1.594 (2.3); 1.581 (1.0); 1.324 (0.9); 1.310 (2.1); 1.304 (2.3); 1.289 (0.8); 1.257 (0.4); 1.243 (0.4); 1.168 (0.4); 0.993 (2.1); 0.982 (3.3); 0.962 (1.9); 0.000 (10.4)

Beispiel I-T3-140: ¹H-NMR (400.0 MHz, d₆-DMSO):
δ = 8.785 (2.0); 8.780 (1.9); 8.595 (1.3); 8.584 (4.5); 8.345 (3.4); 7.890 (2.0); 7.885 (1.9); 7.594 (4.2); 4.455 (0.3); 3.904 (3.2); 3.408 (0.5); 3.394 (1.3); 3.382 (1.7); 3.342 (322.7); 3.174 (0.4); 3.162 (0.4); 2.892 (0.5); 2.883 (0.7); 2.873 (0.7); 2.865 (0.5); 2.855 (0.4); 2.672 (0.7); 2.503 (110.1); 2.352 (0.4); 2.345 (0.5); 2.334 (1.3); 2.314 (0.5); 2.111 (16.0); 0.973 (1.9); 0.961 (1.8); 0.951 (1.9); 0.931 (1.6); 0.740 (0.4); 0.723 (1.7); 0.710 (1.7); 0.705 (1.4); 0.694 (0.6); 0.582 (0.6); 0.571 (1.8); 0.564 (1.8); 0.555 (1.5); 0.543 (0.4); 0.000 (8.3)

Beispiel I-T3-141: ¹H-NMR (400.0 MHz, d₆-DMSO):
δ = 9.093 (2.2); 8.668 (2.1); 8.662 (2.2); 8.577 (3.2); 8.327 (3.3); 8.314 (2.3); 8.308 (2.2); 7.593 (3.8); 3.969 (10.4); 3.904 (3.5); 3.409 (0.5); 3.343 (332.3); 3.285 (0.3); 2.676 (0.5); 2.672 (0.7); 2.668 (0.6); 2.525 (2.4); 2.512 (45.6); 2.507 (89.1); 2.503 (116.0); 2.498 (87.1); 2.334 (0.5); 2.330 (0.7); 2.325 (0.5); 2.121 (16.0); 1.602 (0.8); 1.587 (2.0); 1.581 (2.2); 1.567 (0.9); 1.305 (1.0); 1.292 (2.1); 1.285 (2.2); 1.271 (0.8); 0.008 (0.4); 0.000 (11.6); −0.008 (0.5)

Beispiel I-T3-142: ¹H-NMR (400.0 MHz, d₆-DMSO):
δ = 8.767 (2.0); 8.582 (3.2); 8.343 (3.2); 7.948 (2.0); 7.851 (0.3); 7.591 (5.1); 4.454 (0.8); 3.904 (4.5); 3.381 (3.9); 3.341 (346.8); 3.218 (0.4); 3.175 (0.5); 3.162 (0.4); 3.043 (7.9); 2.791 (1.0); 2.781 (0.9); 2.766 (1.5); 2.672 (1.0); 2.503 (159.1); 2.330 (1.0); 2.122 (16.0); 1.926 (0.6); 1.915 (0.9); 1.901 (0.7); 1.882 (0.4); 0.992 (1.5); 0.961 (2.3); 0.943 (2.0); 0.824 (0.4); 0.809 (0.4); 0.764 (0.5); 0.540 (2.1); 0.482 (1.7); 0.467 (1.6); 0.000 (14.1)

Beispiel I-T3-143: ¹H-NMR (400.0 MHz, d₆-DMSO):
δ = 8.608 (2.1); 8.602 (2.1); 8.556 (3.2); 8.308 (3.3); 8.266 (1.0); 8.256 (1.0); 8.227 (2.2); 8.221 (2.1); 7.590 (3.9); 3.948 (10.3); 3.904 (3.5); 3.395 (0.9); 3.343 (295.8); 3.175 (0.3); 2.873 (0.3); 2.863 (0.5); 2.855 (0.7); 2.845 (0.7); 2.837 (0.5); 2.827 (0.3); 2.676 (0.5); 2.672 (0.7); 2.668 (0.5); 2.507 (88.5); 2.503 (112.5); 2.498 (84.8); 2.334 (0.5); 2.329 (0.7); 2.325 (0.5); 2.120 (16.0); 0.740 (0.4); 0.727 (1.3); 0.722 (1.8); 0.709 (1.6); 0.704 (1.4); 0.692 (0.6); 0.580 (0.6); 0.570 (1.8); 0.564 (1.7); 0.554 (1.4); 0.542 (0.4); 0.008 (0.7); 0.000 (14.6)

Beispiel I-T3-144: ¹H-NMR (400.0 MHz, d₆-DMSO):
δ = 8.563 (2.0); 8.558 (2.0); 8.526 (3.6); 8.302 (3.3); 8.005 (1.9); 7.999 (2.0); 7.590 (4.6); 4.468 (0.3); 4.454 (0.8); 4.440 (0.3); 3.915 (9.8); 3.904 (7.4); 3.425 (0.4); 3.395 (2.6); 3.388 (2.3); 3.381 (3.0); 3.341 (345.9); 3.282 (0.4); 2.981 (8.7); 2.748 (0.5); 2.738 (0.8); 2.724 (0.6); 2.711 (0.3); 2.700 (0.9); 2.676 (0.7); 2.672 (0.9); 2.668 (0.8); 2.507 (111.1); 2.503 (144.6); 2.499 (113.9); 2.334 (0.6); 2.329 (0.8); 2.127 (16.0); 0.466 (3.1); 0.449 (1.7); 0.000 (11.6)

Beispiel I-T3-145: ¹H-NMR (400.0 MHz, d₆-DMSO):
δ = 8.848 (0.6); 8.841 (0.8); 8.835 (4.1); 8.829 (4.2); 8.781 (6.9); 8.537 (7.1); 8.316 (0.4); 8.283 (13.4); 8.274 (4.6); 8.257 (0.6); 8.251 (0.5); 3.424 (0.3); 3.409 (0.3); 3.398 (0.4); 3.387 (0.3); 3.371 (0.4); 3.324 (185.3); 2.776 (0.4); 2.764 (0.8); 2.759 (0.9); 2.750 (1.6); 2.739 (1.0); 2.733 (0.9); 2.722 (0.5); 2.675 (1.1); 2.671 (1.5); 2.667 (1.1); 2.524 (4.5); 2.506 (173.0); 2.502 (225.3); 2.497 (167.2); 2.333 (1.1); 2.329 (1.5); 2.324 (1.1); 1.398 (16.0); 1.238 (4.1); 1.220 (8.5); 1.202 (3.9); 1.120 (0.5); 1.102 (1.0); 1.085 (0.5); 0.951 (0.4); 0.935 (0.5); 0.577 (2.8); 0.549 (2.5); 0.532 (2.1); 0.146 (0.9); 0.008 (7.2); 0.000 (188.0); −0.008 (8.4); −0.150 (0.9)

Beispiel I-T3-146: ¹H-NMR (400.0 MHz, d₆-DMSO):
δ = 10.752 (3.5); 8.900 (3.6); 8.894 (3.7); 8.806 (5.3); 8.571 (5.2); 8.570 (5.2); 8.393 (3.7); 8.387 (3.6); 8.284 (8.3); 8.283 (8.3); 8.028 (4.8); 7.502 (4.8); 7.501 (5.0); 5.756 (5.9); 4.056 (0.5); 4.038 (1.6); 4.020 (1.6); 4.002 (0.5); 3.837 (16.0); 3.324 (33.1); 2.671 (0.4); 2.524 (1.0); 2.520 (1.4); 2.511 (20.1); 2.507 (41.3); 2.502 (54.9); 2.497 (40.1); 2.493 (19.7); 2.329 (0.4); 1.989 (6.9); 1.193 (1.9); 1.175 (3.8); 1.157 (1.9); 0.008 (1.9); 0.000 (58.8); −0.009 (2.2)

Beispiel I-T3-147: ¹H-NMR (400.0 MHz, d₆-DMSO):
δ = 8.999 (3.5); 8.993 (3.6); 8.778 (6.5); 8.384 (3.5); 8.378 (3.5); 8.279 (10.7); 5.757 (1.1); 4.384 (1.6); 4.366 (5.0); 4.348 (5.1); 4.331 (1.7); 3.894 (0.5); 3.324 (128.6); 2.714 (16.0); 2.675 (0.9); 2.671 (1.3); 2.666 (1.0); 2.524 (3.3); 2.511 (69.0); 2.506 (138.7); 2.502 (184.5); 2.498 (139.2); 2.333 (0.8); 2.329 (1.1); 2.325 (0.9); 1.989 (0.7); 1.377 (5.4); 1.360 (11.3); 1.342 (5.4); 1.234 (0.5); 1.175 (0.4); 0.146 (0.9); 0.008 (6.9); 0.000 (189.8); −0.150 (0.9)

Beispiel I-T3-148: ¹H-NMR (400.0 MHz, CD3CN):
δ = 8.344 (1.0); 8.180 (2.1); 8.179 (2.0); 8.138 (1.8); 8.094 (1.0); 7.688 (1.2); 7.683 (1.6); 7.655 (0.9); 7.650 (0.6); 7.634 (1.0); 7.629 (0.8); 7.474 (1.5); 7.454 (1.2); 6.895 (0.4); 6.892 (0.4); 2.860 (0.4); 2.851 (0.6); 2.842 (0.6); 2.833 (0.4); 2.132 (17.4); 2.107 (0.3); 1.964 (1.5); 1.958 (3.8); 1.952 (20.1); 1.946 (36.2); 1.940 (48.4); 1.933 (33.3); 1.927 (17.3); 1.437 (16.0); 0.781 (1.0); 0.776 (1.2); 0.763 (1.3); 0.758 (0.9); 0.746 (0.4); 0.611 (0.4); 0.601 (1.1); 0.594 (1.2); 0.590 (1.0); 0.584 (1.0); 0.000 (2.5)

Beispiel I-T3-149: ¹H-NMR (400.0 MHz, d₆-DMSO):
δ = 18.228 (0.3); 18.070 (0.4); 11.873 (0.3); 9.464 (0.4); 9.435 (13.6); 9.407 (0.4); 9.265 (9.2); 9.168 (16.0); 8.869 (9.9); 8.544 (15.8); 8.514 (0.4); 8.316 (1.1); 8.148 (0.4); 8.012 (0.4); 7.945 (12.0); 7.931 (6.4); 7.910 (6.2); 7.905 (5.4); 7.850 (0.4); 7.843 (0.4); 7.839 (0.4); 7.702 (0.4); 7.639 (0.4); 7.582 (9.8); 7.561 (9.0); 7.543 (0.4); 3.637 (0.4); 3.591 (0.4); 3.572 (0.4); 3.547 (0.4); 3.535 (0.6); 3.512 (0.5); 3.469 (0.6); 3.434 (0.9); 3.392 (2.8); 3.344 (1316.4); 3.339 (765.9); 3.331 (992.7); 3.218 (1.0); 3.211 (0.9); 3.178 (0.5); 3.121 (0.3); 3.058 (0.3); 2.731 (0.4); 2.671 (5.7); 2.638 (0.4); 2.584 (0.4); 2.506 (689.3); 2.502 (847.8); 2.417 (1.1); 2.381 (0.8); 2.333 (4.7); 2.328 (5.7); 2.288 (0.4); 2.283 (0.4); 1.658 (0.3); 1.620 (4.0); 1.606 (11.5); 1.599 (12.3); 1.586 (5.4); 1.546 (0.6); 1.489 (0.4); 1.370 (0.3); 1.350 (0.7); 1.310 (5.0); 1.296 (11.9); 1.290 (12.3); 1.275 (4.4); 1.237 (0.5); 0.146 (2.0); 0.000 (404.8); −0.150 (2.2); −3.146 (0.3)

Beispiel I-T3-150: ¹H-NMR (400.0 MHz, d₆-DMSO):
δ = 9.265 (5.5); 9.179 (0.4); 9.144 (12.1); 9.086 (0.6); 8.868 (5.9); 8.863 (6.0); 8.554 (0.6); 8.536 (16.0); 8.525 (4.5); 8.504 (0.7); 8.316 (0.8); 8.292 (0.4); 7.872 (14.1); 7.866 (7.0); 7.855 (6.0); 7.850 (3.3); 7.569 (0.3); 7.534 (7.4); 7.527 (1.7); 7.518 (1.6); 7.511 (6.7); 3.568 (0.6); 3.468 (0.4); 3.455 (0.4); 3.444 (0.5); 3.341 (576.1); 3.339 (590.5); 3.331 (552.2); 2.875 (0.5); 2.864 (1.2); 2.855 (1.6); 2.846 (2.6);

2.836 (2.6); 2.828 (1.7); 2.818 (1.3); 2.807 (0.5); 2.676 (2.6); 2.672 (3.7); 2.667 (2.8); 2.662 (1.4); 2.580 (0.4); 2.525 (9.0); 2.520 (13.1); 2.511 (197.7); 2.507 (411.4); 2.502 (559.2); 2.498 (423.2); 2.493 (212.6); 2.458 (0.5); 2.334 (2.7); 2.329 (3.7); 2.325 (2.7); 0.736 (1.7); 0.724 (4.5); 0.718 (6.6); 0.706 (6.1); 0.700 (5.1); 0.689 (2.3); 0.650 (0.3); 0.608 (0.4); 0.578 (2.2); 0.568 (6.4); 0.562 (5.7); 0.558 (5.5); 0.552 (5.2); 0.540 (1.7); 0.146 (1.7); 0.030 (0.4); 0.024 (0.4); 0.017 (0.6); 0.008 (12.6); 0.000 (401.4); −0.009 (15.0); −0.150 (1.7)

Beispiel I-T3-151: $^1$H-NMR (400.0 MHz, d$_6$-DMSO):
δ = 9.444 (12.0); 9.048 (16.0); 8.890 (7.0); 8.886 (7.3); 8.610 (8.1); 8.605 (7.8); 8.506 (15.9); 8.495 (0.3); 8.317 (4.4); 7.899 (6.5); 7.894 (13.4); 7.885 (2.6); 7.870 (6.7); 7.865 (4.8); 7.579 (9.1); 7.559 (8.2); 3.410 (0.4); 3.383 (0.7); 3.364 (1.2); 3.327 (1576.2); 3.293 (1.2); 2.694 (0.5); 2.676 (8.0); 2.671 (11.2); 2.667 (8.3); 2.643 (0.4); 2.630 (0.4); 2.623 (0.5); 2.599 (0.7); 2.524 (28.8); 2.520 (43.4); 2.511 (594.8); 2.507 (1217.9); 2.502 (1623.1); 2.498 (1195.4); 2.493 (589.7); 2.419 (0.6); 2.338 (3.7); 2.333 (7.9); 2.329 (11.1); 2.324 (8.1); 2.320 (4.0); 1.620 (3.9); 1.606 (9.5); 1.599 (10.3); 1.586 (4.4); 1.546 (0.4); 1.342 (0.4); 1.303 (4.6); 1.289 (9.5); 1.282 (10.2); 1.268 (3.8); 1.234 (0.6); 1.148 (0.9); 0.146 (8.7); 0.049 (0.4); 0.039 (0.7); 0.008 (63.6); 0.000 (1893.8); −0.009 (67.7); −0.035 (1.3); −0.045 (0.8); −0.088 (0.3); −0.150 (8.7)

Beispiel I-T3-152: $^1$H-NMR (400.0 MHz, d$_6$-DMSO):
δ = 9.046 (0.6); 9.022 (16.0); 8.893 (8.5); 8.608 (9.0); 8.604 (8.5); 8.543 (6.0); 8.532 (6.0); 8.515 (0.9); 8.496 (15.9); 8.453 (0.3); 8.317 (2.0); 7.901 (0.4); 7.896 (0.4); 7.828 (8.6); 7.823 (11.4); 7.818 (11.0); 7.812 (8.2); 7.682 (0.3); 7.532 (8.5); 7.521 (2.4); 7.510 (7.5); 3.508 (0.4); 3.327 (1034.9); 3.230 (0.5); 3.210 (0.4); 2.874 (0.7); 2.864 (1.6); 2.854 (2.4); 2.846 (3.5); 2.836 (3.5); 2.827 (2.5); 2.817 (1.7); 2.807 (0.8); 2.671 (8.3); 2.622 (0.7); 2.608 (0.8); 2.506 (980.0); 2.502 (1179.0); 2.329 (8.1); 2.297 (0.4); 2.281 (0.3); 1.236 (0.7); 1.149 (0.6); 0.735 (2.2); 0.717 (8.7); 0.705 (8.5); 0.699 (7.0); 0.688 (2.9); 0.666 (0.5); 0.648 (0.4); 0.615 (0.3); 0.603 (0.4); 0.574 (3.0); 0.563 (9.1); 0.556 (9.0); 0.548 (7.5); 0.535 (2.1); 0.525 (0.5); 0.488 (0.3); 0.146 (5.2); 0.000 (1050.7); −0.150 (5.5)

Beispiel I-T3-153: $^1$H-NMR (400.0 MHz, d$_6$-DMSO):
δ = 9.441 (7.1); 9.380 (9.1); 8.960 (4.8); 8.954 (5.0); 8.641 (9.2); 8.581 (3.9); 8.577 (3.9); 8.317 (0.9); 8.166 (1.1); 8.002 (5.1); 7.997 (6.5); 7.969 (3.3); 7.963 (2.5); 7.948 (3.5); 7.942 (3.0); 7.589 (6.2); 7.568 (5.7); 3.430 (0.6); 3.411 (1.9); 3.393 (2.3); 3.378 (2.6); 3.359 (2.8); 3.328 (240.7); 2.950 (0.6); 2.932 (2.1); 2.913 (2.4); 2.898 (2.1); 2.880 (1.9); 2.862 (0.5); 2.676 (1.9); 2.671 (2.7); 2.667 (2.0); 2.542 (1.0); 2.525 (6.6); 2.520 (10.2); 2.511 (145.4); 2.507 (298.6); 2.502 (396.9); 2.498 (292.6); 2.493 (144.6); 2.334 (1.9); 2.329 (2.6); 2.325 (1.9); 2.320 (1.0); 2.075 (0.6); 1.908 (0.5); 1.627 (2.3); 1.613 (5.6); 1.606 (6.0); 1.593 (2.7); 1.314 (2.6); 1.301 (5.6); 1.294 (5.9); 1.279 (2.3); 1.106 (7.4); 1.088 (16.0); 1.069 (7.2); 0.146 (2.3); 0.008 (17.1); 0.000 (509.3); −0.009 (19.8); −0.031 (0.4); −0.034 (0.4); −0.150 (2.3)

Beispiel I-T3-154: $^1$H-NMR (400.0 MHz, d$_6$-DMSO):
δ = 9.448 (6.4); 9.231 (4.3); 9.226 (4.3); 9.186 (8.2); 8.634 (4.2); 8.629 (4.2); 8.596 (8.2); 8.317 (3.6); 7.954 (4.3); 7.949 (6.0); 7.934 (3.1); 7.929 (2.0); 7.913 (3.2); 7.908 (2.5); 7.595 (5.2); 7.574 (4.7); 4.152 (1.7); 4.133 (5.6); 4.115 (5.6); 4.096 (1.8); 3.459 (0.4); 3.445 (0.3); 3.436 (0.3); 3.328 (1346.5); 2.694 (0.4); 2.676 (6.7); 2.671 (9.0); 2.667 (6.9); 2.629 (0.5); 2.524 (24.4); 2.506 (1009.7); 2.502 (1305.6); 2.498 (988.2); 2.405 (0.6); 2.389 (0.6); 2.333 (6.4); 2.329 (8.7); 2.325 (6.5); 1.623 (2.1); 1.608 (5.2); 1.602 (5.6); 1.589 (2.4); 1.575 (0.5); 1.326 (6.4); 1.308 (16.0); 1.289 (11.7); 1.274 (2.1); 1.258 (0.6); 1.247 (0.5); 1.236 (0.7); 1.158 (0.5); 1.147 (0.4); 1.068 (0.8); 0.146 (6.9); 0.008 (62.7); 0.000 (1428.7); −0.059 (0.5); −0.080 (0.4); −0.101 (0.4); −0.150 (7.0)

Beispiel I-T3-155: $^1$H-NMR (400.0 MHz, CD3CN):
δ = 8.345 (0.9); 8.192 (1.8); 8.153 (1.5); 8.094 (0.9); 7.738 (1.0); 7.732 (1.3); 7.706 (0.6); 7.700 (0.5); 7.685 (0.7); 7.680 (0.6); 7.563 (0.4); 7.507 (1.1); 7.486 (0.9); 2.144 (6.2); 2.114 (0.5); 2.108 (0.4); 1.972 (1.1); 1.964 (1.1); 1.958 (2.8); 1.952 (14.4); 1.946 (26.2); 1.940 (35.3); 1.934 (25.1); 1.928 (13.6); 1.596 (0.5); 1.582 (1.3); 1.575 (1.3); 1.561 (0.7); 1.437 (16.0); 1.362 (0.6); 1.349 (1.3); 1.342 (1.4); 1.327 (0.5); 1.204 (0.5); 0.146 (0.8); 0.008 (7.0); 0.000 (147.1); −0.008 (10.2); −0.150 (0.7)

Beispiel I-T3-156: $^1$H-NMR (400.0 MHz, d$_6$-DMSO):
δ = 9.077 (8.4); 9.076 (8.4); 8.593 (4.1); 8.589 (4.2); 8.540 (3.1); 8.529 (3.2); 8.471 (8.5); 8.469 (8.4); 8.317 (0.7); 8.019 (4.1); 8.015 (4.0); 7.848 (1.5); 7.843 (5.5); 7.839 (7.4); 7.834 (5.9); 7.826 (4.6); 7.820 (2.2); 7.526 (5.7); 7.517 (1.0); 7.513 (0.9); 7.504 (5.1); 3.328 (238.4); 3.109 (1.9); 3.091 (6.4); 3.072 (6.5); 3.054 (2.0); 2.874 (0.4); 2.864 (0.9); 2.854 (1.2); 2.846 (1.9); 2.836 (2.0); 2.827 (1.2); 2.818 (1.0); 2.808 (0.4); 2.676 (1.5); 2.671 (2.2); 2.667 (1.6); 2.662 (0.8); 2.520 (8.4); 2.511 (110.7); 2.507 (227.2); 2.502 (302.7); 2.498 (222.3); 2.493 (109.6); 2.338 (0.6); 2.334 (1.4); 2.329 (1.9); 2.324 (1.4); 2.320 (0.7); 1.398 (1.0); 1.235 (8.0); 1.217 (16.0); 1.198 (7.0); 0.736 (1.2); 0.723 (3.4); 0.718 (4.9); 0.706 (4.5); 0.700 (3.8); 0.688 (1.6); 0.577 (1.6); 0.566 (4.8); 0.560 (4.3); 0.556 (4.1); 0.550 (3.9); 0.538 (1.2); 0.146 (0.6); 0.008 (4.5); 0.000 (140.4); −0.009 (5.1); −0.150 (0.6)

Beispiel I-T3-157: $^1$H-NMR (400.0 MHz, d$_6$-DMSO):
δ = 9.389 (0.4); 9.355 (9.8); 8.964 (5.4); 8.959 (5.4); 8.642 (0.5); 8.627 (9.7); 8.577 (4.7); 8.540 (3.8); 8.529 (3.8); 8.317 (1.2); 7.913 (12.3); 7.893 (4.1); 7.887 (2.8); 7.541 (4.9); 7.520 (4.4); 4.038 (0.9); 4.020 (0.8); 4.002 (0.4); 3.454 (0.4); 3.425 (0.9); 3.406 (2.4); 3.387 (2.9); 3.372 (3.7); 3.353 (5.7); 3.329 (694.0); 2.952 (0.7); 2.934 (2.2); 2.915 (2.5); 2.900 (2.2); 2.882 (2.0); 2.864 (1.6); 2.855 (1.6); 2.846 (2.3); 2.836 (2.3); 2.827 (2.8); 2.818 (1.1); 2.807 (0.5); 2.676 (3.2); 2.671 (4.1); 2.667 (3.2); 2.507 (462.3); 2.502 (589.8); 2.498 (442.8); 2.333 (2.8); 2.329 (3.8); 2.325 (2.8); 1.989 (3.4); 1.398 (1.9); 1.234 (0.7); 1.193 (1.0); 1.175 (1.8); 1.157 (1.7); 1.099 (7.6); 1.081 (16.0); 1.063 (7.3); 0.741 (1.3); 0.728 (4.0); 0.723 (5.4); 0.711 (5.1); 0.705 (4.3); 0.694 (1.7); 0.583 (1.8); 0.573 (5.5); 0.566 (5.3); 0.557 (4.5); 0.545 (1.3); 0.146 (0.3); 0.008 (3.2); 0.000 (63.6)

Beispiel I-T3-158: $^1$H-NMR (400.0 MHz, d$_6$-DMSO):
δ = 9.234 (1.6); 9.229 (1.6); 9.165 (3.1); 8.632 (1.6); 8.627 (1.6); 8.584 (3.2); 8.547 (1.2); 8.536 (1.2); 7.875 (4.5); 7.871 (1.9); 7.857 (1.5); 7.852 (0.9); 7.548 (1.5); 7.543 (0.7); 7.529 (0.6); 7.525 (1.4); 4.151 (0.7); 4.132 (2.2); 4.114 (2.2); 4.095 (0.7); 3.329 (71.4); 2.867 (0.3); 2.857 (0.4); 2.849 (0.7); 2.839 (0.7); 2.830 (0.5); 2.821 (0.3); 2.676 (0.4); 2.672 (0.6); 2.667 (0.4); 2.525 (1.6); 2.511 (33.5); 2.507 (66.9); 2.502 (87.7); 2.498 (64.8); 2.494 (32.5); 2.334 (0.4); 2.329 (0.6); 2.325 (0.4); 1.398 (16.0); 1.324 (2.6); 1.306 (5.7); 1.287 (2.6); 1.236 (0.3); 0.738 (0.6); 0.725 (1.3); 0.720 (1.8); 0.708 (1.6); 0.702 (1.4); 0.691 (0.6); 0.580 (0.6); 0.569 (1.8); 0.563 (1.6); 0.554 (1.4); 0.541 (0.4); 0.008 (0.4); 0.000 (10.6); −0.008 (0.4)

Beispiel I-T3-159: $^1$H-NMR (400.0 MHz, d$_6$-DMSO):
δ = 9.812 (2.8); 9.173 (7.1); 8.904 (2.9); 8.880 (0.5); 8.874 (0.4); 8.852 (1.7); 8.845 (2.6); 8.822 (6.9); 8.816 (7.2); 8.765 (9.2); 8.566 (0.7); 8.554 (1.9); 8.512 (5.8); 8.484 (11.2); 8.455 (6.7); 8.449 (6.6); 8.318 (0.7); 8.263 (1.1); 8.257 (1.1); 8.237 (0.4); 8.093 (5.7); 3.903 (16.0); 3.680 (2.8); 3.593 (0.6); 3.582 (0.9); 3.570 (0.7); 3.388 (0.9); 3.333 (306.9); 3.276 (1.0); 3.267 (1.3); 3.168 (13.0); 3.044 (0.4); 2.980 (0.9); 2.891 (2.0); 2.732 (1.7); 2.676 (1.9); 2.672 (2.6); 2.667 (1.9); 2.542 (0.9); 2.525 (6.2); 2.511 (158.8); 2.507 (322.0); 2.503 (423.2); 2.498 (311.3); 2.494 (156.1); 2.334 (2.0); 2.329 (2.7); 2.325 (2.1); 2.083 (0.4); 2.065 (0.3); 1.877 (2.4); 1.867 (5.7); 1.857 (6.2); 1.848 (2.6); 1.718 (0.4); 1.709 (0.4); 1.435 (0.4); 1.355 (0.6); 1.298 (0.6); 1.284 (0.5); 1.276 (0.6); 1.259 (3.3); 1.249 (6.9); 1.239 (9.7); 1.236 (9.6); 1.001 (0.6); 0.991 (0.5); 0.986 (0.5); 0.871 (0.5); 0.862 (0.6); 0.854 (1.3); 0.843 (0.5); 0.837 (0.7); 0.827 (0.3); 0.008 (0.7); 0.000 (25.7); −0.008 (1.0)

Beispiel I-T3-160: $^1$H-NMR (400.0 MHz, CD3CN):
δ = 8.728 (0.3); 8.722 (0.5); 8.704 (9.5); 8.698 (9.6); 8.524 (0.3); 8.353 (7.7); 8.234 (15.1); 8.219 (12.8); 8.100 (7.8); 8.052 (10.3); 8.046 (10.1); 7.603 (0.4); 7.592 (0.6); 7.560 (0.5); 7.537 (0.5); 7.495 (0.5); 7.490 (0.5); 7.342 (0.5); 7.067 (2.6); 5.449 (0.7); 4.054 (1.4); 3.893 (0.3); 3.441 (0.7); 3.375 (0.6); 3.241 (1.1); 3.154 (3.0); 3.070 (0.6); 2.886 (0.9); 2.876 (1.5); 2.867 (2.7); 2.858 (3.9); 2.849 (3.9); 2.840 (2.7); 2.831 (1.9); 2.821 (0.7); 2.600 (0.3); 2.590 (0.4); 2.531 (0.4); 2.470 (3.6); 2.465 (5.0); 2.460 (3.7); 2.432 (0.4); 2.425 (0.4); 2.394 (0.4); 2.368 (0.5); 2.359 (0.5); 2.329 (0.6); 2.316 (0.6); 2.289 (0.8); 2.261 (1.3); 2.257 (1.3); 2.255 (1.3); 2.243 (1.9); 2.178 (1072.5); 2.127 (0.9); 2.121 (1.9); 2.114 (3.1); 2.108 (4.0); 2.102 (2.8); 2.096 (1.6); 2.087 (0.7); 2.057 (0.4); 2.036 (0.7); 2.017 (1.1); 1.998 (1.2); 1.965 (20.6); 1.959 (52.5); 1.953 (270.7); 1.947 (487.5); 1.941 (651.6); 1.935 (450.7); 1.929 (234.0); 1.782 (1.4); 1.775 (2.7); 1.769 (3.6); 1.763 (2.5); 1.757 (1.3); 1.711 (2.4); 1.384 (0.4); 1.380 (0.8); 1.269 (16.0); 0.897 (0.7); 0.881 (1.8); 0.864 (0.9); 0.808 (2.2); 0.795 (6.8); 0.790

(8.9); 0.778 (9.1); 0.772 (6.9); 0.760 (3.0); 0.738 (0.4); 0.721 (0.4); 0.661 (0.4); 0.651 (0.4); 0.621 (3.0); 0.609 (8.1); 0.603 (8.3); 0.599 (7.4); 0.594 (7.1); 0.581 (2.1); 0.543 (0.5); 0.390 (0.4); 0.385 (0.5); 0.146 (8.5); 0.085 (0.4); 0.078 (0.5); 0.065 (0.5); 0.008 (68.5); 0.000 (1708.3); −0.009 (75.1); −0.049 (0.5); −0.058 (0.4); −0.150 (8.4)

Beispiel I-T3-161: $^1$H-NMR (400.0 MHz, CD3CN):
δ = 8.626 (2.2); 8.153 (1.1); 8.140 (16.0); 8.100 (13.1); 7.994 (7.6); 7.949 (7.7); 7.629 (9.3); 7.624 (11.5); 7.596 (6.2); 7.591 (4.8); 7.585 (2.3); 7.575 (7.4); 7.570 (6.0); 7.488 (0.5); 7.467 (0.4); 7.436 (11.0); 7.415 (8.4); 4.085 (1.8); 4.068 (5.5); 4.050 (5.6); 4.032 (1.9); 3.435 (0.7); 3.425 (1.5); 3.416 (1.9); 3.407 (3.0); 3.394 (2.9); 3.383 (1.8); 3.376 (1.3); 3.365 (0.6); 3.033 (0.5); 2.905 (0.4); 2.683 (0.6); 2.665 (0.6); 2.467 (0.8); 2.143 (2313.8); 2.117 (49.9); 2.108 (11.0); 2.101 (6.8); 2.095 (3.7); 1.972 (32.2); 1.964 (49.2); 1.958 (118.9); 1.953 (611.9); 1.946 (1099.9); 1.940 (1474.5); 1.934 (1019.6); 1.928 (525.2); 1.781 (2.8); 1.775 (5.7); 1.769 (7.9); 1.762 (5.4); 1.756 (2.4); 1.437 (7.6); 1.270 (1.1); 1.222 (6.5); 1.204 (13.0); 1.186 (6.4); 0.951 (2.0); 0.939 (6.4); 0.934 (8.6); 0.921 (8.9); 0.915 (6.5); 0.902 (2.8); 0.881 (0.8); 0.863 (0.6); 0.821 (0.5); 0.811 (0.4); 0.782 (2.8); 0.770 (7.8); 0.764 (8.1); 0.760 (6.9); 0.754 (6.8); 0.741 (1.9); 0.192 (0.4); 0.146 (19.2); 0.087 (1.0); 0.063 (1.5); 0.008 (155.4); 0.000 (3971.4); −0.009 (173.7); −0.068 (0.4); −0.150 (18.8)

Beispiel I-T3-162: $^1$H-NMR (400.0 MHz, CD3CN):
δ = 8.194 (6.9); 8.179 (6.7); 7.972 (3.4); 7.759 (3.0); 7.688 (3.5); 7.682 (4.6); 7.655 (2.4); 7.650 (1.8); 7.635 (2.7); 7.629 (2.4); 7.477 (4.3); 7.456 (3.4); 6.951 (1.1); 2.872 (0.7); 2.862 (1.1); 2.854 (1.6); 2.844 (1.6); 2.835 (1.1); 2.826 (0.8); 2.471 (0.3); 2.466 (0.5); 2.461 (0.3); 2.180 (199.2); 2.134 (0.5); 2.115 (0.5); 2.109 (0.6); 2.102 (0.4); 1.965 (2.7); 1.959 (6.7); 1.953 (37.6); 1.947 (69.0); 1.941 (93.6); 1.935 (65.6); 1.929 (34.4); 1.776 (0.4); 1.770 (0.5); 1.763 (0.4); 1.437 (16.0); 1.269 (0.4); 0.795 (0.9); 0.782 (2.6); 0.777 (3.6); 0.765 (3.7); 0.759 (2.8); 0.747 (1.2); 0.612 (1.2); 0.601 (3.3); 0.595 (3.4); 0.591 (3.1); 0.586 (3.0); 0.573 (0.9); 0.146 (1.5); 0.008 (10.7); 0.000 (294.5); −0.150 (1.5)

Beispiel I-T3-163: $^1$H-NMR (400.0 MHz, CD3CN):
δ = 8.205 (4.0); 8.190 (4.1); 7.973 (2.2); 7.760 (2.0); 7.736 (2.0); 7.731 (2.6); 7.704 (1.2); 7.700 (1.0); 7.684 (1.4); 7.679 (1.2); 7.600 (0.8); 7.509 (2.3); 7.488 (1.9); 2.121 (0.5); 2.114 (0.5); 2.108 (0.6); 2.102 (0.4); 1.963 (2.5); 1.952 (29.4); 1.946 (52.9); 1.941 (70.8); 1.934 (50.0); 1.928 (26.6); 1.769 (0.4); 1.598 (1.0); 1.583 (2.9); 1.576 (2.8); 1.563 (1.3); 1.436 (16.0); 1.362 (1.3); 1.348 (2.9); 1.341 (3.0); 1.327 (1.0); 1.269 (0.5); 0.145 (1.2); 0.000 (226.5); −0.150 (1.2)

Beispiel I-T3-164: $^1$H-NMR (400.0 MHz, d$_6$-DMSO):
δ = 9.460 (5.0); 8.854 (7.4); 8.671 (4.0); 8.535 (7.4); 7.846 (1.3); 7.840 (3.0); 7.833 (4.3); 7.827 (5.4); 7.824 (4.4); 7.818 (1.5); 7.594 (4.1); 7.584 (0.8); 7.582 (0.8); 7.572 (3.6); 4.056 (1.2); 4.038 (3.7); 4.020 (3.7); 4.002 (1.3); 3.934 (1.6); 3.329 (39.1); 2.671 (0.4); 2.525 (1.1); 2.507 (42.6); 2.502 (56.3); 2.498 (42.6); 2.329 (0.4); 1.989 (16.0); 1.619 (1.7); 1.605 (4.3); 1.598 (4.6); 1.585 (1.9); 1.397 (5.6); 1.295 (2.0); 1.281 (4.2); 1.275 (4.5); 1.260 (1.6); 1.193 (4.2); 1.175 (8.4); 1.157 (4.1); 1.069 (10.8); 0.008 (1.8); 0.000 (48.4); −0.008 (2.3)

Beispiel I-T3-165: $^1$H-NMR (400.0 MHz, CD3CN):
δ = 8.748 (1.7); 8.742 (1.8); 8.353 (1.5); 8.243 (2.8); 8.228 (2.4); 8.116 (1.9); 8.110 (2.1); 8.101 (1.5); 7.706 (0.5); 3.236 (0.9); 3.070 (0.4); 2.883 (0.4); 2.284 (0.3); 2.154 (118.3); 2.120 (0.8); 2.114 (0.9); 2.108 (0.9); 2.102 (0.7); 2.095 (0.4); 1.972 (0.7); 1.965 (3.4); 1.958 (8.8); 1.953 (47.0); 1.946 (85.3); 1.940 (114.8); 1.934 (80.1); 1.928 (41.8); 1.775 (0.5); 1.769 (0.7); 1.763 (0.5); 1.612 (0.8); 1.597 (2.0); 1.591 (2.0); 1.577 (1.0); 1.437 (16.0); 1.370 (1.0); 1.356 (2.0); 1.349 (2.1); 1.334 (0.8); 1.269 (0.9); 0.146 (1.9); 0.008 (15.7); 0.000 (390.9); −0.009 (19.9); −0.150 (2.0)

Beispiel I-T3-166: $^1$H-NMR (400.0 MHz, d$_6$-DMSO):
δ = 9.440 (11.8); 9.127 (15.9); 8.569 (7.7); 8.491 (16.0); 8.318 (2.5); 7.965 (7.6); 7.961 (7.7); 7.926 (7.5); 7.921 (12.0); 7.912 (6.7); 7.906 (3.4); 7.891 (6.2); 7.885 (4.8); 7.573 (10.1); 7.553 (9.2); 3.459 (0.4); 3.399 (0.7); 3.365 (1.8); 3.331 (1516.7); 3.298 (1.6); 2.701 (0.4); 2.694 (0.3); 2.676 (6.5); 2.671 (9.1); 2.667 (6.9); 2.638 (0.4); 2.576 (1.1); 2.529 (53.9); 2.520 (35.9); 2.511 (509.9); 2.507 (1041.8); 2.502 (1375.8); 2.498 (1016.8); 2.417 (0.5); 2.351 (0.6); 2.334 (6.6); 2.329 (9.1); 2.325 (6.8); 2.302 (0.3); 1.621 (3.9); 1.607 (9.8); 1.600 (10.6); 1.587 (4.4); 1.547 (0.4); 1.348 (0.4); 1.307 (4.5); 1.294 (9.7); 1.287 (10.6); 1.273 (3.7); 1.237 (0.4); 0.146 (3.4); 0.024 (0.3); 0.008 (24.7); 0.000 (766.8); −0.008 (29.5); −0.032 (0.8); −0.150 (3.5)

Beispiel I-T3-167: $^1$H-NMR (400.0 MHz, d$_6$-DMSO):
δ = 9.440 (6.2); 9.103 (8.3); 9.094 (0.8); 8.587 (4.2); 8.479 (8.5); 8.317 (1.1); 8.021 (4.5); 7.917 (3.9); 7.911 (6.2); 7.903 (3.6); 7.898 (1.8); 7.882 (3.2); 7.877 (2.5); 7.597 (0.4); 7.574 (5.4); 7.554 (4.7); 3.329 (494.7); 3.110 (1.9); 3.092 (6.3); 3.074 (6.4); 3.056 (2.0); 2.871 (0.3); 2.676 (3.0); 2.671 (4.2); 2.667 (3.1); 2.524 (9.6); 2.507 (478.6); 2.502 (637.0); 2.498 (477.3); 2.408 (0.8); 2.333 (2.9); 2.329 (4.1); 2.325 (3.1); 1.621 (2.0); 1.607 (5.2); 1.600 (5.6); 1.587 (2.3); 1.306 (2.4); 1.293 (5.3); 1.286 (5.7); 1.272 (2.1); 1.261 (0.6); 1.235 (7.6); 1.217 (16.0); 1.199 (7.1); 0.146 (1.6); 0.008 (11.5); 0.000 (362.6); −0.008 (14.5); −0.026 (0.6); −0.150 (1.6)

Beispiel I-T3-168: $^1$H-NMR (400.0 MHz, d$_6$-DMSO):
δ = 8.917 (4.0); 8.676 (2.2); 8.612 (2.2); 8.554 (1.4); 8.543 (1.4); 8.439 (4.1); 7.783 (0.8); 7.777 (1.6); 7.770 (2.3); 7.764 (3.0); 7.539 (2.1); 7.527 (0.4); 7.517 (1.8); 4.038 (0.4); 4.020 (0.4); 3.936 (2.3); 3.333 (264.0); 2.864 (0.4); 2.854 (0.6); 2.846 (0.8); 2.836 (0.8); 2.827 (0.6); 2.818 (0.4); 2.507 (26.6); 2.503 (34.6); 2.498 (26.4); 1.989 (1.7); 1.296 (0.7); 1.193 (0.5); 1.175 (0.9); 1.157 (0.5); 1.069 (16.0); 0.733 (0.5); 0.720 (1.6); 0.716 (2.1); 0.703 (2.0); 0.698 (1.8); 0.686 (0.7); 0.566 (0.7); 0.555 (2.1); 0.549 (2.0); 0.540 (1.8); 0.527 (0.6); 0.000 (11.0)

Beispiel I-T3-169: $^1$H-NMR (400.0 MHz, d$_6$-DMSO):
δ = 9.461 (11.1); 9.416 (0.4); 8.936 (15.7); 8.681 (8.8); 8.616 (8.7); 8.450 (16.0); 7.833 (11.0); 7.827 (9.7); 7.820 (7.2); 7.652 (0.3); 7.589 (8.1); 7.578 (1.9); 7.567 (7.0); 7.556 (0.5); 4.038 (0.8); 4.020 (0.8); 3.937 (0.6); 3.333 (133.2); 2.672 (0.7); 2.503 (110.4); 2.330 (0.7); 1.989 (3.2); 1.622 (3.6); 1.607 (9.7); 1.601 (10.5); 1.587 (4.3); 1.563 (0.4); 1.556 (0.4); 1.547 (0.5); 1.334 (0.4); 1.314 (0.5); 1.300 (4.8); 1.294 (5.2); 1.281 (9.9); 1.274 (10.4); 1.259 (3.7); 1.235 (0.6); 1.193 (0.9); 1.175 (1.7); 1.157 (0.9); 1.069 (3.7); 0.000 (35.7)

Beispiel I-T3-170: $^1$H-NMR (400.0 MHz, d$_6$-DMSO):
δ = 9.441 (1.5); 9.436 (2.4); 8.694 (1.7); 8.619 (3.2); 8.443 (1.7); 8.398 (3.2); 8.274 (2.8); 7.960 (1.6); 7.956 (1.6); 7.810 (0.9); 7.804 (2.1); 7.797 (2.3); 7.792 (2.9); 7.787 (3.1); 7.782 (0.9); 7.742 (1.6); 7.739 (1.6); 7.569 (1.0); 7.557 (2.1); 7.546 (1.3); 7.535 (1.8); 4.056 (1.2); 4.038 (3.6); 4.020 (3.7); 4.002 (1.2); 3.332 (35.6); 3.116 (0.7); 3.097 (2.3); 3.079 (2.4); 3.061 (0.7); 2.525 (0.5); 2.512 (10.5); 2.507 (21.4); 2.503 (28.1); 2.498 (20.5); 2.494 (9.9); 1.990 (16.0); 1.615 (1.1); 1.601 (2.8); 1.594 (2.9); 1.581 (1.3); 1.289 (1.3); 1.276 (2.8); 1.269 (3.0); 1.255 (1.1); 1.208 (2.7); 1.193 (9.2); 1.190 (6.2); 1.175 (4.2); 0.000 (3.5)

Beispiel I-T3-171: $^1$H-NMR (400.0 MHz, d$_6$-DMSO):
δ = 9.443 (12.6); 9.162 (16.0); 8.676 (8.2); 8.530 (16.0); 8.412 (7.8); 8.317 (4.0); 7.937 (8.0); 7.932 (12.0); 7.921 (6.8); 7.915 (3.8); 7.900 (6.4); 7.895 (5.0); 7.716 (0.4); 7.584 (10.3); 7.563 (9.1); 4.358 (2.5); 4.332 (7.5); 4.306 (7.8); 4.280 (2.7); 4.104 (0.5); 4.079 (0.4); 3.496 (0.5); 3.480 (0.4); 3.466 (0.4); 3.452 (0.4); 3.396 (0.8); 3.329 (1584.1); 3.287 (1.0); 2.676 (8.0); 2.671 (11.1); 2.667 (8.6); 2.645 (0.6); 2.525 (28.7); 2.511 (614.7); 2.507 (1266.3); 2.502 (1687.1); 2.498 (1264.2); 2.389 (0.6); 2.380 (0.6); 2.333 (7.8); 2.329 (11.0); 2.325 (8.3); 2.256 (0.4); 2.075 (1.4); 1.623 (4.0); 1.608 (10.0); 1.601 (10.8); 1.588 (4.6); 1.548 (0.5); 1.347 (0.4); 1.306 (4.7); 1.293 (10.0); 1.286 (10.8); 1.272 (3.9); 1.234 (0.7); 0.146 (0.5); 0.017 (0.4); 0.008 (3.6); 0.000 (115.1); −0.008 (5.1); −0.150 (0.6)

Beispiel I-T3-172: $^1$H-NMR (400.0 MHz, d$_6$-DMSO):
δ = 8.613 (0.3); 8.596 (8.4); 8.529 (2.9); 8.518 (3.0); 8.492 (0.7); 8.381 (8.5); 8.333 (0.6); 7.956 (4.4); 7.953 (4.4); 7.749 (2.3); 7.743 (4.8); 7.739 (5.0); 7.725 (13.2); 7.507 (4.3); 7.488 (2.3); 7.485 (3.1); 4.055 (1.2); 4.038 (3.6); 4.020 (3.7); 4.002 (1.2); 3.329 (51.5); 3.112 (1.9); 3.094 (6.1); 3.076 (6.1); 3.057 (2.0); 3.048 (0.4); 3.029 (0.9); 3.011 (0.9); 2.856 (0.8); 2.847 (1.1); 2.838 (1.8); 2.828 (1.8); 2.819 (1.1); 2.809 (0.9); 2.676 (0.4); 2.671 (0.5); 2.667 (0.4); 2.524 (1.3); 2.511 (30.4); 2.507 (60.9); 2.502 (79.7); 2.498 (58.7); 2.494 (29.4); 2.333 (0.4); 2.329 (0.5); 2.324 (0.4); 1.989 (16.0); 1.235 (0.4); 1.207 (6.8); 1.192 (7.1); 1.189 (14.7); 1.175 (10.4); 1.170 (7.2); 1.157 (4.7); 1.068 (0.4); 0.727 (1.1); 0.714 (3.3); 0.709 (4.6); 0.697 (4.3); 0.691 (3.7); 0.680 (1.5); 0.563 (1.5); 0.552 (4.6); 0.546 (4.3); 0.536 (3.8); 0.524 (1.1); 0.008 (2.2); 0.000 (61.3); −0.008 (2.4)

Beispiel I-T3-173: $^1$H-NMR (400.0 MHz, d$_6$-DMSO):
δ = 8.653 (6.0); 8.567 (3.1); 8.561 (3.2); 8.401 (5.7); 8.091 (10.1); 8.013 (3.1); 8.007 (3.2); 7.957 (0.4); 6.579 (0.7); 5.409 (0.3); 3.923 (16.0); 3.592 (0.3); 3.367 (923.7); 2.985 (14.3); 2.767 (0.4); 2.740 (1.3); 2.725 (0.9); 2.704 (1.4); 2.674 (0.9); 2.509 (96.0); 2.505 (123.6); 2.501 (91.6); 2.332 (0.8); 2.074 (1.6); 1.271 (0.8); 1.169 (5.1); 0.467 (4.6); 0.450 (2.4); 0.008 (1.4); 0.000 (28.9)

Beispiel I-T3-174: $^1$H-NMR (400.0 MHz, d$_6$-DMSO):
δ = 8.835 (7.5); 8.672 (3.0); 8.669 (4.0); 8.650 (3.9); 8.649 (3.9); 8.645 (2.9); 8.556 (2.5); 8.545 (2.5); 8.525 (7.6); 7.787 (1.7); 7.781 (2.9); 7.766 (4.0); 7.763 (11.3); 7.546 (3.2); 7.542 (1.7); 7.527 (1.5); 7.524 (2.8); 4.056 (1.2); 4.038 (3.6); 4.020 (3.7); 4.002 (1.2); 3.329 (59.6); 2.865 (0.7); 2.856 (0.9); 2.847 (1.4); 2.836 (1.5); 2.828 (0.9); 2.818 (0.7); 2.671 (0.4); 2.525 (1.0); 2.520 (1.6); 2.511 (21.0); 2.507 (42.8); 2.502 (56.7); 2.498 (41.2); 2.493 (19.8); 2.329 (0.4); 1.989 (16.0); 1.193 (4.3); 1.175 (8.7); 1.157 (4.2); 0.733 (1.0); 0.720 (2.7); 0.715 (3.8); 0.703 (3.5); 0.697 (2.9); 0.686 (1.3); 0.566 (1.3); 0.555 (3.7); 0.549 (3.3); 0.545 (3.1); 0.540 (3.0); 0.527 (0.9); 0.008 (1.4); 0.000 (40.4); −0.009 (1.3)

Beispiel I-T3-175: $^1$H-NMR (400.0 MHz, CD3CN):
δ = 8.146 (3.1); 8.082 (4.8); 7.714 (1.6); 7.697 (2.0); 7.692 (2.5); 7.663 (1.3); 7.658 (1.0); 7.642 (1.5); 7.637 (1.3); 7.472 (2.3); 7.451 (1.8); 6.931 (0.6); 2.873 (0.4); 2.864 (0.6); 2.855 (0.9); 2.845 (0.9); 2.837 (0.6); 2.827 (0.4); 2.165 (79.0); 2.115 (0.4); 2.108 (0.5); 2.102 (0.3); 1.965 (1.5); 1.959 (4.0); 1.953 (28.1); 1.947 (52.6); 1.941 (72.5); 1.935 (50.5); 1.929 (26.2); 1.769 (0.4); 1.437 (16.0); 0.796 (0.5); 0.783 (1.5); 0.778 (2.0); 0.765 (2.0); 0.760 (1.5); 0.748 (0.7); 0.613 (0.6); 0.601 (1.7); 0.595 (1.8); 0.591 (1.6); 0.586 (1.6); 0.574 (0.5); 0.000 (0.6)

Beispiel I-T3-176: $^1$H-NMR (400.0 MHz, CD3CN):
δ = 19.983 (0.4); 8.920 (0.7); 8.270 (0.3); 8.158 (11.0); 8.124 (0.4); 8.095 (11.8); 8.083 (6.1); 8.035 (0.7); 7.746 (6.2); 7.741 (7.8); 7.713 (9.2); 7.692 (4.8); 7.686 (4.4); 7.669 (3.3); 7.590 (0.6); 7.505 (6.9); 7.484 (5.7); 3.901 (3.1); 2.470 (2.5); 2.466 (3.4); 2.461 (2.6); 2.417 (1.0); 2.179 (1701.9); 2.153 (39.9); 2.121 (2.8); 2.115 (3.6); 2.109 (4.3); 2.103 (3.2); 2.096 (1.9); 2.034 (0.5); 1.965 (12.0); 1.954 (216.5); 1.947 (401.4); 1.941 (546.5); 1.935 (384.1); 1.929 (201.2); 1.782 (1.6); 1.776 (2.6); 1.770 (3.4); 1.764 (2.5); 1.599 (3.1); 1.584 (8.5); 1.577 (8.4); 1.564 (4.1); 1.524 (0.7); 1.437 (16.0); 1.401 (0.7); 1.362 (3.9); 1.349 (8.6); 1.342 (8.8); 1.327 (3.1); 1.268 (2.7); 0.882 (0.4); 0.000 (4.2)

Beispiel I-T3-177: $^1$H-NMR (400.0 MHz, d$_6$-DMSO):
δ = 9.462 (7.5); 8.855 (1.9); 8.790 (8.8); 8.673 (1.1); 8.536 (1.9); 8.483 (8.9); 8.391 (4.5); 8.388 (4.6); 8.105 (4.5); 8.102 (4.5); 7.846 (0.5); 7.840 (1.0); 7.833 (2.8); 7.827 (5.2); 7.820 (5.9); 7.814 (7.0); 7.810 (5.4); 7.804 (1.9); 7.595 (1.3); 7.586 (5.5); 7.573 (1.8); 7.564 (4.6); 4.055 (0.5); 4.038 (1.4); 4.020 (1.4); 4.002 (0.5); 3.331 (91.4); 3.168 (2.0); 3.150 (6.5); 3.131 (6.6); 3.113 (2.0); 2.676 (0.5); 2.672 (0.7); 2.667 (0.5); 2.525 (1.8); 2.511 (39.2); 2.507 (78.6); 2.502 (103.0); 2.498 (76.1); 2.494 (38.1); 2.334 (0.5); 2.329 (0.7); 2.325 (0.5); 1.989 (6.1); 1.619 (2.5); 1.604 (6.8); 1.598 (5.6); 1.585 (2.8); 1.397 (5.9); 1.293 (2.9); 1.279 (6.3); 1.273 (6.7); 1.258 (2.4); 1.203 (7.5); 1.193 (2.5); 1.184 (16.0); 1.175 (4.1); 1.166 (7.2); 1.157 (2.0); 1.069 (0.5); 0.008 (2.2); 0.000 (62.2); −0.008 (2.5)

Beispiel I-T3-178: $^1$H-NMR (400.0 MHz, d$_6$-DMSO):
δ = 8.730 (5.4); 8.726 (5.4); 8.701 (10.4); 8.556 (3.7); 8.545 (3.7); 8.483 (0.5); 8.463 (10.3); 8.318 (0.6); 8.268 (5.5); 8.264 (5.4); 7.760 (2.4); 7.754 (3.8); 7.736 (14.8); 7.524 (4.5); 7.502 (3.8); 4.055 (1.2); 4.037 (3.6); 4.020 (3.7); 4.002 (1.2); 3.460 (1.7); 3.442 (5.0); 3.424 (5.0); 3.405 (1.7); 3.329 (124.3); 2.868 (0.4); 2.858 (1.0); 2.848 (1.4); 2.840 (2.2); 2.830 (2.1); 2.821 (1.4); 2.811 (1.0); 2.802 (0.4); 2.675 (1.1); 2.671 (1.5); 2.667 (1.2); 2.541 (6.3); 2.506 (175.4); 2.502 (223.8); 2.498 (167.1); 2.333 (1.1); 2.329 (1.4); 2.324 (1.1); 1.989 (15.7); 1.235 (0.4); 1.193 (4.2); 1.175 (8.3); 1.157 (5.1); 1.150 (7.5); 1.132 (16.0); 1.113 (7.2); 0.728 (1.4); 0.715 (4.2); 0.710 (5.5); 0.698 (5.2); 0.692 (4.4); 0.681 (1.7); 0.561 (1.8); 0.551 (5.6); 0.545 (5.4); 0.535 (4.6); 0.523 (1.3); 0.146 (0.4); 0.000 (94.7); −0.008 (4.3); −0.150 (0.4)

Beispiel I-T3-179: $^1$H-NMR (400.0 MHz, d$_6$-DMSO):
δ = 8.862 (9.5); 8.701 (0.4); 8.548 (3.2); 8.537 (3.2); 8.504 (0.4); 8.487 (10.0); 8.482 (5.1); 8.477 (4.7); 8.463 (0.4); 8.317 (1.4); 8.095 (4.8); 8.091 (4.8); 7.769 (2.1); 7.764 (3.9); 7.753 (5.3); 7.748 (11.5); 7.736 (0.7); 7.540 (5.3); 7.533 (1.3); 7.524 (1.3); 7.517 (4.5); 4.055 (1.0); 4.037 (3.2); 4.020 (3.2); 4.002 (1.1); 3.507 (0.3); 3.443 (0.4); 3.424 (0.4); 3.396 (0.5); 3.373 (0.8); 3.332 (779.0); 3.293 (0.7); 3.061 (0.9); 3.042 (1.8); 3.024 (2.1); 3.008 (2.2); 2.995 (0.5); 2.990 (2.0); 2.971 (0.6); 2.870 (0.4); 2.860 (0.9); 2.850 (1.3); 2.842 (2.0); 2.831 (2.1); 2.822 (1.3); 2.813 (1.0); 2.803 (0.4); 2.680 (1.3); 2.676 (2.7); 2.671 (3.7); 2.667 (2.8); 2.584 (1.0); 2.565 (2.6); 2.547 (3.3); 2.542 (5.6); 2.525 (10.0); 2.520 (15.4); 2.511 (205.0); 2.507 (417.5); 2.502 (550.6); 2.498 (403.5); 2.493 (198.2); 2.333 (2.6); 2.329 (3.6); 2.325 (2.7); 1.989 (13.8); 1.298 (0.3); 1.259 (0.5); 1.235 (0.9); 1.193 (2.9); 1.175 (7.6); 1.157 (3.8); 1.132 (0.6); 1.047 (7.2); 1.029 (16.0); 1.010 (6.9); 0.733 (1.3); 0.720 (3.5); 0.715 (5.2); 0.703 (4.7); 0.697 (4.1); 0.685 (1.7); 0.563 (1.7); 0.552 (5.0); 0.546 (4.7); 0.542 (4.4); 0.536 (4.2); 0.524 (1.3); 0.146 (1.1); 0.008 (8.8); 0.000 (281.7); −0.009 (10.6); −0.150 (1.1)

Beispiel I-T3-180: $^1$H-NMR (400.0 MHz, d$_6$-DMSO):
δ = 9.105 (5.5); 9.100 (4.5); 8.889 (0.7); 8.871 (9.2); 8.581 (4.6); 8.570 (6.0); 8.564 (6.8); 8.559 (5.5); 8.545 (9.1); 8.317 (0.9); 7.817 (0.3); 7.812 (0.3); 7.774 (3.3); 7.768 (4.2); 7.755 (7.5); 7.751 (13.2); 7.553 (4.7); 7.548 (2.1); 7.535 (2.4); 7.530 (3.5); 4.055 (0.8); 4.037 (2.1); 4.020 (2.1); 4.002 (0.7); 3.559 (2.3); 3.541 (6.5); 3.523 (6.4); 3.504 (2.1); 3.334 (39.2); 3.328 (131.0); 2.866 (1.3); 2.856 (1.8); 2.847 (2.5); 2.837 (2.3); 2.829 (1.5); 2.819 (1.0); 2.809 (0.4); 2.676 (2.3); 2.671 (2.5); 2.667 (1.8); 2.621 (0.4); 2.507 (343.0); 2.502 (380.1); 2.498 (256.9); 2.333 (2.1); 2.329 (2.4); 2.324 (1.6); 1.995 (2.3); 1.989 (8.7); 1.298 (0.4); 1.258 (0.6); 1.249 (0.7); 1.236 (1.2); 1.193 (3.8); 1.181 (8.8); 1.175 (7.3); 1.163 (16.0); 1.157 (4.7); 1.144 (6.8); 1.114 (0.6); 0.731 (1.9); 0.719 (5.2); 0.714 (5.7); 0.702 (5.8); 0.696 (4.2); 0.684 (1.6); 0.593 (0.3); 0.563 (2.7); 0.553 (6.7); 0.547 (6.1); 0.538 (4.5); 0.525 (1.3); 0.006 (15.8); 0.000 (61.8); −0.008 (2.7)

Beispiel I-T3-181: $^1$H-NMR (400.0 MHz, d$_6$-DMSO):
δ = 9.108 (0.4); 9.087 (10.3); 8.892 (5.1); 8.888 (5.2); 8.613 (0.4); 8.591 (10.7); 8.579 (3.8); 8.568 (3.7); 8.407 (5.3); 8.403 (5.3); 7.787 (2.0); 7.781 (4.5); 7.775 (6.6); 7.769 (7.7); 7.765 (6.0); 7.759 (2.3); 7.575 (6.0); 7.564 (1.5); 7.552 (5.0); 4.056 (1.1); 4.038 (3.4); 4.020 (3.4); 4.002 (1.2); 3.330 (39.4); 3.101 (0.5); 3.083 (1.8); 3.065 (2.2); 3.049 (2.3); 3.031 (2.1); 3.012 (0.6); 2.879 (0.4); 2.869 (1.0); 2.860 (1.4); 2.851 (2.1); 2.841 (2.1); 2.833 (1.4); 2.823 (1.0); 2.813 (0.4); 2.676 (0.5); 2.672 (0.6); 2.667 (0.5); 2.601 (2.3); 2.583 (2.1); 2.564 (2.5); 2.549 (2.3); 2.530 (2.5); 2.525 (2.1); 2.507 (69.4); 2.503 (90.4); 2.498 (68.1); 2.334 (0.4); 2.329 (0.6); 2.325 (0.4); 1.989 (14.7); 1.193 (3.9); 1.175 (7.7); 1.158 (3.8); 1.081 (0.4); 1.067 (7.5); 1.048 (16.0); 1.030 (7.2); 0.738 (1.3); 0.725 (4.0); 0.720 (5.5); 0.708 (5.1); 0.702 (4.4); 0.691 (1.8); 0.566 (1.8); 0.555 (5.4); 0.549 (5.2); 0.539 (4.6); 0.527 (1.3); 0.008 (0.6); 0.000 (16.1)

Beispiel I-T3-182: $^1$H-NMR (400.0 MHz, d$_6$-DMSO):
δ = 9.454 (7.2); 8.884 (10.2); 8.500 (2.3); 8.482 (4.9); 8.478 (5.0); 8.317 (0.4); 8.098 (5.0); 8.093 (5.0); 7.829 (1.5); 7.823 (5.9); 7.821 (7.8); 7.815 (6.3); 7.807 (4.8); 7.801 (2.4); 7.588 (5.9); 7.579 (1.0); 7.574 (1.0); 7.566 (5.1); 4.056 (1.2); 4.038 (3.6); 4.020 (3.6); 4.002 (1.2); 3.329 (62.1); 3.069 (0.5); 3.051 (1.8); 3.032 (2.1); 3.017 (2.3); 2.998 (2.1); 2.980 (0.6); 2.676 (0.6); 2.672 (0.8); 2.667 (0.6); 2.594 (0.6); 2.575 (2.1); 2.557 (2.5); 2.541 (2.4); 2.523 (3.8); 2.520 (3.9); 2.511 (46.1); 2.507 (93.1); 2.503 (122.1); 2.498 (89.1); 2.494 (44.0); 2.334 (0.6); 2.329 (0.8); 2.325 (0.6); 1.989 (15.8); 1.622 (2.4); 1.607 (5.9); 1.601 (6.4); 1.588 (2.7); 1.290 (2.8); 1.276 (5.9); 1.270 (6.4); 1.255 (2.4); 1.235 (0.5); 1.193 (4.2); 1.175 (8.3); 1.157 (4.1); 1.134 (0.3); 1.051 (7.3); 1.033 (16.0); 1.014 (7.1); 0.008 (0.8); 0.000 (23.6); −0.008 (0.9)

Beispiel I-T3-183: $^1$H-NMR (400.0 MHz, d$_6$-DMSO):
δ = 9.464 (4.6); 8.733 (3.3); 8.729 (3.6); 8.723 (6.9); 8.477 (6.6); 8.270 (3.3); 8.266 (3.3); 7.820 (1.3); 7.814 (3.0); 7.808 (4.3); 7.803 (4.8); 7.798 (3.7); 7.792 (1.4); 7.573 (4.0); 7.562 (0.9); 7.551 (3.4); 4.055 (1.2); 4.038 (3.6); 4.020 (3.7); 4.002 (1.2); 3.465 (0.9); 3.447 (2.9); 3.429 (3.0); 3.410 (1.0); 3.329 (48.5); 2.676 (0.4); 2.671 (0.6); 2.667 (0.5); 2.525 (1.6); 2.511 (35.4); 2.507 (71.4); 2.502 (93.1); 2.498 (68.1); 2.494 (33.4); 2.333 (0.4); 2.329 (0.6); 2.325 (0.4); 1.989 (16.0); 1.614 (1.6); 1.600 (3.9); 1.593 (4.1); 1.580 (1.7); 1.290 (1.9); 1.277

(4.0); 1.270 (4.3); 1.256 (1.6); 1.235 (0.5); 1.193 (4.4); 1.175 (8.8); 1.157 (4.9); 1.152 (5.1); 1.134 (10.7); 1.115 (4.8); 0.008 (0.6); 0.000 (19.6); −0.009 (0.7)

Beispiel I-T3-184: $^1$H-NMR (400.0 MHz, CD3CN):
δ = 8.222 (1.1); 8.212 (14.6); 8.193 (0.9); 8.163 (0.7); 8.151 (14.2); 8.150 (13.6); 7.984 (5.6); 7.968 (5.6); 7.937 (0.6); 7.860 (0.5); 7.837 (0.5); 7.699 (8.7); 7.694 (11.4); 7.666 (5.9); 7.660 (4.9); 7.645 (6.7); 7.639 (6.1); 7.588 (0.8); 7.523 (0.3); 7.480 (10.7); 7.459 (8.5); 6.928 (2.6); 5.448 (5.4); 2.881 (0.7); 2.871 (1.9); 2.862 (2.7); 2.853 (4.3); 2.844 (4.3); 2.835 (2.8); 2.825 (2.1); 2.816 (0.7); 2.474 (0.9); 2.469 (1.8); 2.464 (2.4); 2.460 (1.9); 2.455 (1.0); 2.293 (0.4); 2.270 (0.7); 2.266 (0.7); 2.246 (1.0); 2.227 (1.0); 2.160 (875.2); 2.121 (3.1); 2.114 (4.2); 2.108 (5.3); 2.102 (3.8); 2.096 (2.1); 2.036 (0.6); 2.018 (0.8); 1.998 (0.9); 1.965 (19.7); 1.959 (49.7); 1.953 (311.9); 1.947 (575.9); 1.941 (786.4); 1.935 (548.9); 1.929 (287.9); 1.883 (0.6); 1.782 (1.8); 1.775 (3.4); 1.769 (4.7); 1.763 (3.2); 1.757 (1.8); 1.525 (0.4); 1.385 (0.3); 1.372 (0.5); 1.359 (0.4); 1.340 (1.4); 1.335 (0.8); 1.285 (2.9); 1.270 (16.0); 1.204 (0.3); 0.918 (0.4); 0.899 (0.9); 0.882 (2.1); 0.864 (1.1); 0.832 (0.4); 0.795 (2.4); 0.783 (7.1); 0.777 (9.7); 0.765 (9.8); 0.760 (7.5); 0.747 (3.3); 0.726 (0.5); 0.708 (0.5); 0.652 (0.5); 0.643 (0.5); 0.627 (0.4); 0.613 (3.3); 0.601 (8.2); 0.595 (8.8); 0.591 (7.8); 0.586 (7.8); 0.573 (2.3); 0.536 (0.3); 0.520 (0.4); 0.478 (0.3); 0.392 (0.4); 0.387 (0.4); 0.008 (0.7); 0.000 (20.9); −0.009 (1.0)

Beispiel I-T3-185: $^1$H-NMR (400.0 MHz, CD3CN):
δ = 17.517 (0.4); 15.219 (0.3); 14.973 (0.3); 13.920 (0.3); 8.404 (0.4); 8.394 (0.4); 8.224 (16.0); 8.208 (0.8); 8.165 (12.9); 7.986 (5.2); 7.970 (5.1); 7.938 (1.2); 7.864 (0.5); 7.840 (0.4); 7.747 (7.8); 7.741 (10.5); 7.715 (5.2); 7.710 (4.3); 7.694 (6.0); 7.689 (5.7); 7.654 (3.5); 7.624 (1.2); 7.601 (2.1); 7.594 (1.3); 7.590 (2.0); 7.564 (1.9); 7.541 (1.1); 7.513 (9.5); 7.492 (7.5); 7.292 (0.7); 7.282 (0.4); 7.270 (0.7); 7.201 (0.4); 7.176 (1.6); 7.168 (0.4); 7.151 (0.4); 7.064 (0.5); 7.045 (0.4); 6.914 (0.4); 6.892 (0.4); 6.881 (0.8); 6.859 (0.6); 6.178 (0.3); 6.160 (0.4); 6.111 (0.4); 6.099 (0.4); 6.067 (0.4); 6.042 (0.4); 6.038 (0.4); 6.017 (0.4); 5.640 (0.4); 5.594 (0.3); 5.540 (0.4); 5.516 (0.4); 5.485 (0.4); 5.427 (0.3); 5.373 (0.3); 4.507 (0.6); 4.491 (0.6); 4.068 (1.3); 4.050 (1.1); 4.032 (0.5); 3.789 (0.5); 3.776 (1.0); 3.758 (2.9); 3.656 (0.4); 3.149 (0.4); 3.128 (0.4); 2.720 (13.7); 2.656 (0.5); 2.492 (0.9); 2.475 (2.8); 2.470 (6.1); 2.465 (9.0); 2.461 (6.7); 2.456 (3.4); 2.285 (0.4); 2.264 (0.7); 2.247 (1.5); 2.237 (1.1); 2.171 (2483.4); 2.121 (7.1); 2.114 (9.5); 2.108 (11.9); 2.102 (8.8); 2.096 (5.2); 2.075 (1.8); 2.032 (0.9); 2.020 (0.7); 2.011 (0.6); 1.972 (8.4); 1.965 (39.5); 1.959 (102.1); 1.953 (642.3); 1.947 (1199.8); 1.941 (1645.9); 1.935 (1167.9); 1.929 (619.1); 1.818 (1.3); 1.782 (4.2); 1.775 (7.5); 1.769 (10.3); 1.763 (7.4); 1.757 (4.5); 1.722 (0.9); 1.708 (0.9); 1.696 (0.9); 1.688 (0.9); 1.674 (0.7); 1.638 (0.8); 1.597 (4.8); 1.583 (11.6); 1.576 (12.0); 1.562 (6.3); 1.543 (0.8); 1.522 (1.2); 1.501 (0.6); 1.472 (0.6); 1.437 (9.0); 1.402 (1.2); 1.361 (6.2); 1.348 (11.9); 1.341 (12.8); 1.327 (7.6); 1.311 (3.5); 1.269 (8.7); 1.222 (1.9); 1.204 (3.2); 1.186 (1.7); 1.164 (0.6); 1.154 (0.6); 1.145 (0.5); 1.131 (0.6); 1.109 (0.6); 1.095 (0.6); 1.091 (0.6); 1.047 (0.5); 1.040 (0.4); 1.031 (0.4); 1.009 (0.4); 0.987 (0.4); 0.976 (0.4); 0.952 (0.4); 0.945 (0.5); 0.897 (0.8); 0.881 (1.6); 0.855 (1.3); 0.838 (0.9); 0.824 (0.5); 0.806 (0.5); 0.797 (0.4); 0.776 (0.4); 0.766 (0.5); 0.739 (0.4); 0.636 (0.3); 0.526 (0.3); 0.147 (0.4); 0.008 (2.5); 0.000 (80.2); −0.020 (0.5); −0.121 (0.3); −0.149 (0.4); −0.213 (0.4); −2.478 (0.3); −3.017 (0.3)

Beispiel I-T3-186: $^1$H-NMR (400.0 MHz, CD3CN):
δ = 8.202 (8.0); 8.190 (8.4); 7.927 (0.7); 7.858 (4.8); 7.731 (2.7); 7.708 (2.9); 7.690 (4.8); 7.685 (6.1); 7.657 (2.8); 7.652 (2.5); 7.637 (3.4); 7.632 (3.2); 7.590 (0.8); 7.477 (5.0); 7.456 (4.0); 6.984 (0.3); 6.951 (1.9); 6.041 (0.3); 5.521 (0.4); 5.491 (0.4); 5.466 (0.3); 3.874 (0.9); 3.056 (0.3); 2.890 (4.6); 2.872 (1.0); 2.863 (1.5); 2.853 (2.1); 2.844 (2.2); 2.835 (1.7); 2.825 (1.1); 2.799 (0.4); 2.772 (4.2); 2.711 (0.4); 2.684 (0.4); 2.671 (0.4); 2.662 (0.4); 2.619 (0.4); 2.601 (1.1); 2.583 (0.4); 2.543 (0.5); 2.522 (0.5); 2.505 (0.6); 2.466 (6.3); 2.351 (0.9); 2.310 (1.3); 2.298 (1.3); 2.179 (2377.2); 2.121 (5.6); 2.115 (6.3); 2.108 (7.1); 2.102 (5.6); 2.043 (0.8); 2.018 (0.9); 1.953 (344.9); 1.947 (623.4); 1.941 (840.7); 1.935 (641.3); 1.929 (374.2); 1.827 (0.6); 1.781 (2.1); 1.776 (3.6); 1.770 (4.8); 1.763 (3.6); 1.758 (2.2); 1.437 (16.0); 1.311 (0.4); 1.283 (0.5); 1.268 (0.9); 0.794 (1.2); 0.777 (5.1); 0.764 (5.1); 0.747 (1.8); 0.738 (0.4); 0.612 (1.5); 0.600 (4.9); 0.594 (5.3); 0.586 (4.9); 0.573 (1.5); 0.000 (28.5)

Beispiel I-T3-187: $^1$H-NMR (400.0 MHz, CD3CN):
δ = 19.987 (0.6); 8.214 (12.6); 8.200 (13.9); 7.859 (6.8); 7.738 (9.0); 7.733 (14.7); 7.707 (9.2); 7.701 (5.6); 7.686 (6.6); 7.680 (5.9); 7.610 (3.2); 7.587 (1.7); 7.510 (9.9); 7.489 (8.2); 7.448 (0.5); 2.469 (1.8); 2.464 (2.6); 2.459 (2.0); 2.157 (1156.2); 2.120 (5.2); 2.114 (6.3); 2.108 (7.5); 2.102 (5.6); 2.096 (3.3); 1.965 (26.5); 1.959 (71.5); 1.953 (401.8); 1.947 (750.3); 1.941 (1019.6); 1.935 (723.9); 1.928 (383.2); 1.781 (2.7); 1.775 (4.6); 1.769 (6.2); 1.763 (4.5); 1.757 (2.6); 1.634 (0.6); 1.597 (4.4); 1.583 (11.2); 1.576 (11.2); 1.563 (6.0); 1.523 (1.0); 1.437 (16.0); 1.401 (1.1); 1.361 (6.0); 1.347 (11.3); 1.341 (12.0); 1.326 (4.9); 1.270 (8.5); 0.882 (2.0); 0.857 (2.2); 0.000 (34.6)

Beispiel I-T3-188: $^1$H-NMR (400.0 MHz, CD3CN):
δ = 8.340 (9.9); 8.272 (16.0); 8.192 (0.3); 7.761 (9.7); 7.755 (12.3); 7.742 (0.4); 7.737 (0.3); 7.727 (6.7); 7.721 (5.0); 7.706 (7.8); 7.700 (6.5); 7.569 (4.5); 7.524 (11.5); 7.503 (9.3); 5.447 (0.8); 2.576 (0.8); 2.572 (0.8); 2.250 (0.4); 2.139 (89.4); 2.120 (0.7); 2.114 (0.7); 2.108 (0.9); 2.102 (0.6); 2.095 (0.3); 1.965 (3.2); 1.959 (8.4); 1.953 (52.4); 1.947 (96.8); 1.940 (132.2); 1.934 (91.5); 1.928 (47.5); 1.781 (0.3); 1.775 (0.6); 1.769 (0.8); 1.763 (0.6); 1.604 (5.0); 1.590 (12.7); 1.583 (12.8); 1.569 (6.7); 1.529 (0.9); 1.406 (0.8); 1.366 (6.8); 1.352 (12.5); 1.346 (13.2); 1.331 (5.3); 1.309 (0.5); 1.293 (0.9); 1.285 (1.5); 1.269 (7.2); 0.898 (0.3); 0.881 (0.9); 0.864 (0.4); 0.000 (3.9)

Beispiel I-T3-189: $^1$H-NMR (400.0 MHz, CD3CN):
δ = 8.726 (0.3); 8.720 (0.4); 8.701 (10.1); 8.694 (10.3); 8.265 (0.8); 8.253 (16.0); 8.246 (15.9); 8.062 (0.6); 8.051 (11.3); 8.045 (11.1); 7.978 (7.4); 7.766 (6.5); 7.051 (2.2); 5.449 (0.6); 4.068 (0.4); 4.050 (0.4); 3.024 (0.4); 2.888 (0.6); 2.878 (1.7); 2.869 (2.5); 2.860 (3.8); 2.851 (3.8); 2.842 (2.5); 2.833 (1.8); 2.823 (0.6); 2.729 (0.6); 2.473 (0.5); 2.468 (0.9); 2.464 (1.2); 2.459 (0.9); 2.454 (0.5); 2.166 (234.9); 2.121 (0.8); 2.114 (1.2); 2.108 (1.5); 2.102 (1.1); 2.096 (0.6); 2.087 (0.5); 2.035 (0.4); 2.017 (0.7); 1.998 (0.6); 1.972 (2.6); 1.965 (5.7); 1.959 (13.8); 1.953 (85.4); 1.947 (157.6); 1.941 (215.5); 1.935 (150.1); 1.928 (78.1); 1.782 (0.5); 1.775 (0.9); 1.769 (1.3); 1.763 (0.9); 1.757 (0.5); 1.437 (3.4); 1.308 (0.3); 1.268 (8.7); 1.222 (0.6); 1.204 (1.0); 1.186 (0.5); 0.898 (0.4); 0.881 (1.1); 0.864 (0.5); 0.810 (2.1); 0.797 (6.2); 0.792 (8.4); 0.779 (8.6); 0.774 (6.4); 0.762 (2.8); 0.740 (0.4); 0.722 (0.4); 0.662 (0.3); 0.652 (0.4); 0.622 (2.8); 0.610 (7.3); 0.604 (7.7); 0.600 (6.9); 0.595 (6.8); 0.582 (2.1); 0.543 (0.4); 0.391 (0.3); 0.386 (0.3); 0.008 (1.2); 0.000 (38.3); −0.009 (1.6)

Beispiel I-T3-190: $^1$H-NMR (400.0 MHz, d$_6$-DMSO):
δ = 9.487 (7.1); 9.105 (5.1); 9.102 (5.1); 8.887 (9.5); 8.557 (11.6); 8.317 (0.4); 7.826 (4.4); 7.820 (6.3); 7.815 (6.9); 7.810 (5.3); 7.602 (5.1); 7.591 (1.5); 7.580 (4.2); 4.055 (1.3); 4.038 (3.8); 4.020 (3.8); 4.002 (1.3); 3.560 (1.9); 3.542 (6.2); 3.523 (6.3); 3.505 (2.1); 3.328 (157.1); 2.671 (1.6); 2.506 (190.5); 2.502 (243.8); 2.329 (1.7); 1.989 (16.0); 1.617 (2.3); 1.602 (6.1); 1.596 (6.6); 1.583 (2.7); 1.296 (2.7); 1.282 (6.2); 1.276 (6.6); 1.261 (2.3); 1.193 (4.5); 1.181 (7.3); 1.175 (10.1); 1.163 (14.9); 1.158 (7.2); 1.145 (6.8); 0.000 (25.1)

Beispiel I-T3-191: $^1$H-NMR (400.0 MHz, d$_6$-DMSO):
δ = 9.426 (3.3); 8.594 (4.6); 8.359 (4.8); 8.317 (0.5); 7.785 (4.0); 7.779 (2.8); 7.770 (2.1); 7.765 (1.1); 7.545 (2.7); 7.537 (0.6); 7.530 (0.5); 7.522 (2.3); 7.351 (6.5); 3.331 (366.6); 3.015 (2.0); 2.997 (6.6); 2.979 (6.7); 2.960 (2.1); 2.676 (1.1); 2.671 (1.6); 2.667 (1.2); 2.524 (4.4); 2.511 (86.9); 2.507 (177.3); 2.502 (236.3); 2.498 (176.3); 2.493 (90.0); 2.333 (1.1); 2.329 (1.5); 2.324 (1.2); 1.611 (1.1); 1.597 (2.7); 1.590 (2.9); 1.577 (1.2); 1.398 (15.1); 1.285 (1.3); 1.271 (2.7); 1.264 (2.9); 1.250 (1.1); 1.195 (7.5); 1.177 (16.0); 1.158 (7.3); 0.146 (1.7); 0.008 (13.5); 0.000 (371.8); −0.008 (16.5); −0.150 (1.7)

Beispiel I-T3-192: $^1$H-NMR (400.0 MHz, d$_6$-DMSO):
δ = 9.435 (6.5); 8.687 (9.2); 8.408 (9.3); 8.317 (1.5); 7.796 (4.7); 7.787 (4.3); 7.780 (6.0); 7.775 (6.7); 7.770 (5.2); 7.764 (2.0); 7.559 (5.8); 7.548 (5.4); 7.537 (5.3); 3.330 (735.7); 3.123 (0.7); 3.082 (1.9); 3.063 (6.4); 3.045 (6.6); 3.027 (2.0); 2.838 (0.6); 2.676 (2.8); 2.671 (4.1); 2.667 (3.1); 2.525 (10.0); 2.520 (15.7); 2.511 (220.9); 2.507 (459.4); 2.502 (612.6); 2.498 (450.6); 2.493 (223.7); 2.333 (2.9); 2.329 (4.0); 2.324 (3.0); 1.614 (2.1); 1.600 (5.3); 1.593 (5.7); 1.580 (2.4); 1.284 (2.5); 1.271 (5.3); 1.264 (5.7); 1.250 (2.1); 1.205 (7.5); 1.187 (16.0); 1.168 (7.5); 0.146 (1.8); 0.008 (13.1); 0.000 (404.0); −0.009 (15.5); −0.150 (1.8)

Beispiel I-T3-193: $^1$H-NMR (400.0 MHz, d$_6$-DMSO):
δ = 9.458 (0.3); 8.777 (8.3); 8.542 (3.2); 8.531 (3.0); 8.504 (0.3); 8.462 (8.6); 8.337 (3.7); 8.317 (1.8); 7.962 (3.6); 7.750 (2.0); 7.745 (3.2); 7.738 (1.0); 7.726 (12.9); 7.717 (1.1); 7.710 (1.7); 7.692 (1.1); 7.659 (1.1); 7.653 (0.9); 7.569 (1.2); 7.548 (1.0); 7.529 (3.7); 7.526 (2.4); 7.510 (2.0); 7.507 (3.2); 7.484 (1.3); 7.465 (0.8); 7.420 (0.5); 7.402 (0.6); 7.058 (1.6); 6.924 (3.7); 6.789 (1.9); 4.055 (1.2); 4.037 (3.6); 4.020 (3.6); 4.002 (1.2); 3.328 (98.6); 3.305 (0.8); 2.858 (0.9); 2.849 (1.2); 2.840 (1.9); 2.830 (1.9); 2.821 (1.3); 2.812 (0.9); 2.801 (0.4); 2.676 (1.1); 2.671 (1.6); 2.667 (1.2); 2.662 (0.6); 2.524 (3.6); 2.511 (83.9); 2.507 (175.0); 2.502 (233.7); 2.498 (171.2); 2.493 (84.1); 2.338 (0.5); 2.333 (1.1); 2.329 (1.5); 2.324 (1.1); 1.989 (16.0); 1.234 (0.8); 1.193 (4.2); 1.175 (8.4); 1.157 (4.2); 0.729 (1.2); 0.716 (3.5); 0.711 (4.9); 0.699 (4.5); 0.693 (4.0); 0.682 (1.6); 0.568 (0.4); 0.559 (1.8); 0.549 (5.1); 0.543 (4.5); 0.534 (3.7); 0.522 (1.2); 0.146 (0.4); 0.008 (2.5); 0.000 (83.8); −0.009 (3.2); −0.150 (0.4)

Beispiel I-T3-194: $^1$H-NMR (400.0 MHz, CD3CN):
δ = 8.349 (9.1); 8.304 (0.4); 8.286 (14.8); 8.241 (0.3); 7.801 (9.7); 7.795 (11.3); 7.718 (6.0); 7.712 (5.6); 7.697 (7.3); 7.692 (6.9); 7.665 (0.5); 7.647 (0.7); 7.643 (0.7); 7.635 (0.5); 7.617 (0.6); 7.614 (0.7); 7.584 (1.1); 7.541 (0.6); 7.522 (11.4); 7.501 (9.2); 7.484 (0.5); 7.453 (4.1); 7.422 (0.4); 7.236 (0.4); 7.215 (0.3); 6.837 (0.4); 6.673 (0.4); 6.617 (1.3); 6.575 (0.4); 5.973 (0.3); 5.954 (0.3); 5.896 (1.4); 5.447 (5.8); 3.817 (0.8); 3.769 (0.4); 3.550 (1.0); 3.545 (0.9); 2.579 (0.4); 2.575 (0.5); 2.269 (0.4); 2.253 (0.5); 2.140 (512.8); 2.120 (7.2); 2.114 (6.9); 2.108 (7.9); 2.102 (5.5); 2.095 (3.1); 1.965 (25.3); 1.959 (63.5); 1.953 (411.4); 1.947 (768.8); 1.940 (1065.1); 1.934 (761.0); 1.928 (406.5); 1.849 (1.2); 1.799 (0.7); 1.781 (2.8); 1.775 (4.8); 1.769 (6.7); 1.763 (4.7); 1.756 (2.7); 1.728 (0.5); 1.714 (0.5); 1.699 (0.5); 1.677 (0.4); 1.666 (0.5); 1.649 (0.4); 1.628 (0.4); 1.580 (0.4); 1.570 (0.4); 1.556 (0.4); 1.515 (0.6); 1.477 (5.4); 1.466 (14.4); 1.457 (16.0); 1.447 (6.5); 1.407 (0.7); 1.398 (3.9); 1.386 (0.8); 1.366 (0.5); 1.340 (6.0); 1.305 (1.0); 1.285 (8.1); 1.270 (5.0); 1.247 (0.7); 1.230 (0.5); 1.217 (0.6); 1.199 (0.5); 1.190 (0.6); 1.185 (0.7); 1.145 (6.1); 1.135 (15.7); 1.126 (14.8); 1.115 (5.4); 1.076 (0.6); 1.063 (0.4); 0.994 (0.4); 0.976 (0.8); 0.958 (0.5); 0.951 (0.4); 0.930 (0.4); 0.923 (0.4); 0.882 (1.1); 0.856 (0.9); 0.842 (0.7); 0.783 (0.4); 0.771 (0.4); 0.764 (0.5); 0.735 (0.4); 0.597 (0.3); 0.564 (0.4); 0.008 (1.0); 0.000 (32.8)

Beispiel I-T3-195: $^1$H-NMR (400.0 MHz, d$_6$-DMSO):
δ = 9.457 (8.1); 8.920 (11.3); 8.511 (11.3); 8.325 (5.6); 8.319 (6.1); 8.030 (5.3); 7.802 (8.5); 7.797 (7.4); 7.789 (5.4); 7.784 (3.0); 7.591 (6.0); 7.582 (1.3); 7.569 (5.0); 4.037 (0.6); 4.019 (0.6); 3.329 (278.3); 3.090 (0.5); 3.071 (1.9); 3.053 (2.4); 3.037 (2.5); 3.019 (2.1); 3.000 (0.7); 2.675 (3.1); 2.671 (4.3); 2.667 (3.5); 2.597 (0.4); 2.506 (494.1); 2.502 (653.4); 2.498 (511.0); 2.470 (6.8); 2.452 (3.7); 2.434 (2.4); 2.416 (1.0); 2.333 (3.0); 2.329 (4.1); 2.325 (3.3); 1.989 (2.4); 1.621 (2.6); 1.607 (6.7); 1.600 (7.6); 1.587 (3.1); 1.397 (1.3); 1.335 (0.4); 1.327 (0.3); 1.297 (0.8); 1.286 (3.2); 1.273 (7.0); 1.266 (7.6); 1.252 (3.2); 1.235 (5.1); 1.193 (0.7); 1.175 (1.3); 1.157 (0.7); 1.107 (0.4); 0.982 (7.4); 0.964 (16.0); 0.945 (7.3); 0.854 (0.5); 0.835 (0.3); 0.000 (20.8)

Beispiel I-T3-196: $^1$H-NMR (601.6 MHz, CD3CN):
δ = 8.223 (0.5); 8.218 (0.5); 8.045 (0.3); 8.041 (0.3); 2.621 (0.7); 2.150 (4.8); 1.948 (1.3); 1.944 (2.2); 1.940 (3.2); 1.936 (2.2); 1.932 (1.1); 1.135 (16.0); 0.000 (0.9)

Beispiel I-T3-197: $^1$H-NMR (601.6 MHz, CD3CN):
δ = 8.765 (7.5); 8.761 (7.5); 8.2493 (9.5); 8.2486 (9.9); 8.230 (8.0); 8.115 (8.0); 8.111 (8.0); 8.038 (4.4); 7.992 (4.5); 7.394 (1.5); 3.844 (16.0); 3.552 (11.2); 3.542 (11.1); 3.312 (0.7); 3.303 (0.7); 2.172 (78.0); 2.155 (28.3); 2.088 (0.6); 2.084 (0.8); 2.080 (0.6); 1.998 (2.0); 1.989 (5.4); 1.985 (7.5); 1.982 (52.9); 1.977 (98.7); 1.973 (145.4); 1.969 (98.4); 1.965 (48.4); 1.956 (0.7); 1.863 (0.5); 1.859 (0.8); 1.854 (0.6); 1.312 (2.7); 1.303 (8.1); 1.299 (8.0); 1.291 (3.5); 1.266 (0.4); 1.192 (0.4); 1.166 (3.5); 1.158 (7.9); 1.154 (7.9); 1.146 (2.6)

Beispiel I-T3-198: $^1$H-NMR (400.0 MHz, d$_6$-DMSO):
δ = 9.484 (3.8); 9.467 (0.6); 8.776 (0.9); 8.753 (5.3); 8.574 (0.6); 8.561 (8.6); 8.509 (5.3); 8.491 (0.8); 8.317 (1.8); 8.178 (0.4); 7.782 (7.1); 7.778 (3.2); 7.765 (2.2); 7.759 (1.3); 7.579 (2.8); 7.557 (2.4); 4.049 (0.4); 3.497 (0.3); 3.479 (0.7); 3.461 (0.7); 3.413 (1.0); 3.395 (1.5); 3.377 (1.6); 3.329 (582.9); 3.287 (1.0); 2.676 (4.0); 2.671 (5.5); 2.667 (4.1); 2.524 (14.3); 2.507 (629.0); 2.502 (826.7); 2.498 (606.0); 2.333 (3.8); 2.329 (5.2); 2.324 (3.9); 1.614 (1.3); 1.600 (3.4); 1.593 (3.7); 1.580 (1.5); 1.289 (1.5); 1.276 (3.3); 1.269 (3.6); 1.255 (1.3); 1.237 (0.4); 1.150 (0.4); 1.126 (0.7); 1.108 (8.3); 1.089 (16.0); 1.071 (7.0); 0.008 (0.5); 0.000 (18.9); −0.008 (0.7)

Beispiel I-T3-199: $^1$H-NMR (400.1 MHz, d$_6$-DMSO):
d = 8.86 (0.0328); 8.85 (0.0664); 8.56 (0.0471); 8.51 (0.0250); 8.18 (0.0290); 8.17 (0.0298); 8.09 (0.0245); 3.47 (0.0401); 3.45 (0.0407); 3.31 (0.7767); 2.54 (0.3233); 2.50 (0.3250); 2.50 (0.4400); 2.50 (0.3578); 1.25 (0.0306); 1.25 (0.0369); 1.15 (0.0210); 1.14 (0.0347); 1.13 (0.0321); 0.00 (1.0000)

Beispiel I-T3-200: $^1$H-NMR (400.0 MHz, CD3CN):
δ = 8.745 (8.9); 8.739 (8.9); 8.566 (1.6); 8.560 (1.6); 8.264 (13.9); 8.256 (14.3); 8.244 (0.7); 8.115 (9.6); 8.109 (9.4); 8.056 (1.8); 8.050 (1.7); 7.998 (0.4); 7.983 (7.2); 7.980 (7.2); 7.767 (6.3); 7.690 (2.3); 7.666 (0.6); 7.587 (0.3); 5.448 (3.1); 3.724 (0.8); 3.071 (0.5); 2.882 (0.5); 2.626 (0.7); 2.603 (0.5); 2.468 (0.4); 2.463 (0.5); 2.458 (0.4); 2.152 (189.2); 2.120 (1.4); 2.114 (1.8); 2.108 (2.1); 2.102 (1.5); 2.096 (0.8); 1.965 (8.9); 1.959 (23.8); 1.953 (126.4); 1.947 (227.5); 1.941 (305.0); 1.935 (212.6); 1.928 (110.8); 1.868 (0.3); 1.781 (0.8); 1.775 (1.4); 1.769 (1.9); 1.763 (1.3); 1.757 (0.7); 1.615 (3.9); 1.600 (10.0); 1.593 (10.8); 1.580 (6.7); 1.571 (2.5); 1.557 (1.3); 1.540 (0.7); 1.410 (0.6); 1.386 (0.4); 1.370 (5.3); 1.356 (10.0); 1.350 (10.4); 1.335 (5.3); 1.325 (2.3); 1.310 (1.1); 1.297 (0.5); 1.285 (0.7); 1.270 (2.4); 1.202 (0.6); 1.134 (16.0); 0.882 (0.4); 0.008 (0.5); 0.000 (15.0); −0.008 (0.8)

Beispiel I-T3-201: $^1$H-NMR (400.0 MHz, d$_6$-DMSO):
δ = 9.467 (2.2); 8.775 (3.1); 8.578 (1.5); 8.573 (1.5); 8.490 (3.1); 8.177 (1.4); 7.800 (0.6); 7.795 (1.2); 7.787 (1.8); 7.782 (2.4); 7.778 (1.9); 7.578 (1.7); 7.555 (1.5); 3.498 (0.6); 3.479 (1.9); 3.461 (1.9); 3.443 (0.6); 3.330 (198.5); 2.676 (0.7); 2.671 (1.0); 2.667 (0.7); 2.524 (2.5); 2.507 (107.2); 2.502 (141.8); 2.498 (106.1); 2.333 (0.7); 2.329 (0.9); 2.325 (0.7); 1.989 (0.4); 1.614 (0.7); 1.600 (1.8); 1.593 (1.9); 1.580 (0.8); 1.398 (16.0); 1.287 (0.8); 1.274 (1.8); 1.267 (2.0); 1.253 (0.7); 1.235 (0.3); 1.126 (2.1); 1.108 (4.7); 1.089 (2.1); 0.146 (0.9); 0.008 (7.4); 0.000 (188.9); −0.008 (8.7); −0.150 (0.9)

Beispiel I-T3-202: $^1$H-NMR (400.0 MHz, d$_6$-DMSO):
δ = 9.428 (4.8); 8.626 (0.4); 8.603 (6.6); 8.357 (6.9); 8.316 (0.6); 7.790 (1.3); 7.785 (2.8); 7.777 (4.1); 7.772 (5.1); 7.768 (4.0); 7.562 (3.3); 7.548 (3.9); 7.537 (0.8); 7.525 (3.2); 7.428 (3.2); 3.343 (390.5); 2.991 (1.5); 2.973 (4.8); 2.955 (5.1); 2.937 (1.8); 2.676 (1.0); 2.672 (1.3); 2.668 (1.0); 2.507 (163.2); 2.503 (208.0); 2.499 (152.2); 2.334 (1.0); 2.330 (1.3); 2.325 (0.9); 2.188 (1.0); 2.100 (16.0); 2.075 (0.5); 1.613 (1.6); 1.598 (4.1); 1.592 (4.5); 1.579 (2.0); 1.284 (2.0); 1.270 (4.3); 1.263 (4.5); 1.249 (1.6); 1.232 (0.4); 1.214 (0.7); 1.192 (5.5); 1.173 (11.4); 1.155 (5.2); 0.146 (0.5); 0.008 (4.9); 0.000 (117.1); −0.008 (4.9); −0.150 (0.5)

Beispiel I-T3-203: $^1$H-NMR (400.0 MHz, d$_6$-DMSO):
δ = 8.601 (0.6); 8.581 (6.8); 8.520 (2.4); 8.509 (2.4); 8.343 (7.1); 8.137 (0.8); 7.732 (1.5); 7.726 (2.4); 7.707 (9.8); 7.561 (3.2); 7.499 (2.9); 7.477 (2.5); 7.427 (3.2); 3.329 (31.4); 2.989 (1.5); 2.971 (5.0); 2.952 (5.1); 2.940 (0.7); 2.934 (1.6); 2.922 (0.4); 2.854 (0.6); 2.844 (0.9); 2.836 (1.4); 2.826 (1.4); 2.818 (1.0); 2.808 (0.7); 2.676 (0.5); 2.671 (0.7); 2.667 (0.5); 2.524 (1.7); 2.511 (39.4); 2.507 (80.4); 2.502 (106.1); 2.498 (78.2); 2.333 (0.5); 2.329 (0.7); 2.324 (0.5); 2.187 (1.2); 2.116 (0.8); 2.101 (16.0); 2.075 (1.0); 1.909 (0.5); 1.230 (0.4); 1.212 (0.9); 1.190 (5.7); 1.172 (11.9); 1.154 (5.4); 0.726 (0.9); 0.713 (2.5); 0.708 (3.6); 0.696 (3.5); 0.690 (3.0); 0.679 (1.3); 0.560 (1.2); 0.550 (3.7); 0.544 (3.5); 0.534 (3.0); 0.522 (0.9); 0.008 (2.2); 0.000 (67.6); −0.008 (2.8)

Beispiel I-T3-204: $^1$H-NMR (400.0 MHz, d$_6$-DMSO):
δ = 8.968 (6.3); 8.871 (0.8); 8.864 (4.0); 8.858 (3.7); 8.617 (5.8); 8.558 (2.8); 8.554 (2.9); 8.469 (3.0); 8.464 (2.8); 8.379 (3.8); 8.373 (3.6); 8.318 (1.3); 8.261 (0.5); 8.255 (0.6); 4.155 (1.4); 3.332 (210.2); 3.309 (0.8); 3.036 (16.0); 3.014 (1.0); 2.886 (0.9); 2.809 (0.3); 2.798 (0.7); 2.791 (0.8); 2.782 (1.3); 2.772 (1.0); 2.762 (3.0); 2.727 (0.4); 2.676 (0.8); 2.672 (1.1); 2.667 (0.9); 2.541 (0.4); 2.525 (2.7); 2.511 (61.5);

Beispiel I-T3-205: ¹H-NMR (400.0 MHz, d₆-DMSO):
δ = 8.991 (0.5); 8.972 (14.8); 8.876 (0.4); 8.861 (9.9); 8.855 (10.1); 8.716 (4.8); 8.706 (5.3); 8.672 (0.4); 8.661 (0.4); 8.642 (0.8); 8.631 (14.8); 8.562 (7.0); 8.557 (7.2); 8.471 (7.3); 8.467 (6.8); 8.318 (8.7); 8.264 (0.7); 8.258 (0.8); 8.247 (9.6); 8.240 (9.4); 7.948 (0.4); 7.942 (0.4); 7.795 (0.4); 4.156 (4.3); 3.329 (163.2); 3.306 (4.7); 2.887 (0.6); 2.877 (1.4); 2.867 (2.0); 2.859 (3.0); 2.849 (3.2); 2.840 (2.2); 2.830 (1.7); 2.821 (0.8); 2.676 (1.6); 2.671 (2.1); 2.667 (1.6); 2.525 (5.4); 2.507 (239.7); 2.502 (316.6); 2.498 (235.7); 2.333 (1.4); 2.329 (2.0); 2.325 (1.5); 2.076 (16.0); 0.760 (1.9); 0.747 (5.6); 0.743 (7.6); 0.730 (7.4); 0.725 (6.3); 0.713 (2.8); 0.570 (2.3); 0.559 (7.1); 0.553 (7.0); 0.550 (6.7); 0.544 (6.4); 0.532 (2.3); 0.495 (0.4); 0.146 (0.8); 0.008 (5.8); 0.000 (177.1); −0.008 (8.0); −0.150 (0.8)

Beispiel I-T3-206: ¹H-NMR (400.0 MHz, d₆-DMSO):
δ = 9.449 (4.9); 8.859 (6.6); 8.459 (6.7); 8.318 (4.2); 8.038 (3.0); 7.936 (3.0); 7.803 (3.4); 7.799 (4.7); 7.793 (4.8); 7.787 (3.7); 7.781 (1.6); 7.581 (4.2); 7.570 (0.9); 7.558 (3.6); 3.733 (0.3); 3.690 (0.4); 3.329 (896.7); 3.282 (0.7); 2.981 (1.3); 2.963 (1.5); 2.947 (1.5); 2.929 (1.4); 2.910 (0.5); 2.676 (7.6); 2.671 (10.3); 2.667 (7.7); 2.525 (28.4); 2.511 (589.6); 2.507 (1188.5); 2.502 (1555.2); 2.498 (1146.1); 2.493 (578.6); 2.389 (1.6); 2.370 (1.8); 2.354 (1.8); 2.333 (8.0); 2.329 (10.4); 2.324 (7.7); 2.296 (16.0); 1.909 (0.6); 1.621 (1.6); 1.607 (4.0); 1.600 (4.3); 1.587 (2.0); 1.282 (2.1); 1.269 (3.9); 1.262 (4.2); 1.248 (1.6); 1.147 (0.8); 0.945 (4.8); 0.927 (10.5); 0.908 (4.6); 0.146 (3.6); 0.008 (30.4); 0.000 (880.4); −0.008 (42.5); −0.150 (3.7)

Beispiel I-T3-207: ¹H-NMR (400.0 MHz, d₆-DMSO):
δ = 9.624 (6.5); 9.586 (0.7); 8.984 (9.3); 8.916 (5.7); 8.910 (5.5); 8.728 (0.7); 8.636 (9.3); 8.571 (1.5); 8.560 (4.6); 8.473 (4.6); 8.469 (4.3); 8.330 (6.1); 8.324 (6.0); 7.943 (0.4); 7.798 (0.4); 7.793 (0.4); 4.156 (3.5); 3.332 (174.7); 3.051 (0.6); 2.875 (0.6); 2.672 (1.1); 2.667 (0.9); 2.507 (117.6); 2.503 (153.3); 2.499 (115.3); 2.330 (1.0); 2.325 (0.7); 2.076 (16.0); 1.648 (2.1); 1.634 (5.4); 1.627 (6.2); 1.614 (2.5); 1.304 (2.4); 1.291 (5.2); 1.284 (5.7); 1.269 (2.1); 1.262 (0.8); 1.254 (0.7); 1.240 (0.3); 0.146 (0.4); 0.008 (2.8); 0.000 (78.1); −0.150 (0.4)

Beispiel I-T3-208: ¹H-NMR (400.0 MHz, CD3CN):
δ = 8.696 (3.0); 8.690 (3.1); 8.249 (4.2); 8.240 (4.6); 8.003 (3.2); 7.997 (3.1); 7.982 (2.3); 7.978 (2.3); 7.946 (0.5); 7.940 (0.5); 7.766 (2.1); 3.068 (16.0); 2.800 (2.7); 2.783 (0.6); 2.776 (0.6); 2.767 (1.1); 2.756 (0.7); 2.748 (0.6); 2.465 (0.4); 2.170 (94.3); 2.115 (0.5); 2.109 (0.6); 2.102 (0.4); 1.965 (2.7); 1.959 (7.1); 1.954 (39.1); 1.947 (71.0); 1.941 (94.9); 1.935 (64.8); 1.929 (33.1); 1.776 (0.4); 1.770 (0.5); 1.763 (0.4); 0.855 (0.3); 0.789 (0.4); 0.579 (1.4); 0.535 (1.7); 0.525 (1.1); 0.518 (1.6); 0.000 (0.5)

Beispiel I-T3-209: ¹H-NMR (400.0 MHz, d₆-DMSO):
δ = 9.461 (4.8); 8.713 (6.6); 8.448 (6.8); 8.317 (1.4); 8.281 (3.0); 8.094 (3.1); 7.800 (1.3); 7.794 (2.8); 7.787 (4.1); 7.782 (5.1); 7.778 (4.1); 7.569 (3.8); 7.557 (0.8); 7.546 (3.2); 3.393 (0.4); 3.331 (347.0); 2.676 (2.0); 2.672 (2.7); 2.667 (2.1); 2.524 (7.4); 2.507 (323.5); 2.503 (427.2); 2.498 (324.8); 2.426 (0.4); 2.334 (1.9); 2.329 (2.7); 2.325 (2.1); 2.197 (0.8); 2.160 (16.0); 1.614 (1.5); 1.600 (4.0); 1.593 (4.4); 1.580 (1.8); 1.284 (1.8); 1.270 (4.0); 1.264 (4.4); 1.249 (1.5); 1.147 (0.6); 1.079 (4.6); 1.061 (10.1); 1.042 (4.5); 0.146 (0.9); 0.008 (6.6); 0.000 (197.0); −0.150 (1.0)

Beispiel I-T3-210: ¹H-NMR (400.0 MHz, d₆-DMSO):
δ = 8.835 (0.4); 8.692 (6.8); 8.552 (2.5); 8.540 (2.5); 8.513 (0.5); 8.435 (7.0); 8.318 (0.5); 8.278 (3.0); 8.094 (3.0); 7.873 (0.4); 7.742 (1.5); 7.736 (2.5); 7.718 (10.2); 7.520 (3.0); 7.502 (1.5); 7.498 (2.5); 3.357 (1.0); 3.329 (76.1); 3.304 (1.0); 2.857 (0.6); 2.847 (0.9); 2.839 (1.4); 2.829 (1.4); 2.820 (0.9); 2.811 (0.7); 2.676 (0.8); 2.671 (1.1); 2.667 (0.9); 2.524 (3.0); 2.511 (66.6); 2.507 (135.2); 2.502 (178.3); 2.498 (130.4); 2.493 (64.6); 2.333 (0.9); 2.329 (1.2); 2.324 (0.9); 2.193 (1.1); 2.159 (16.0); 2.075 (0.6); 1.153 (0.3); 1.135 (0.7); 1.078 (4.8); 1.060 (10.5); 1.041 (4.6); 0.727 (0.9); 0.714 (2.6); 0.709 (3.6); 0.697 (3.5); 0.691 (3.0); 0.680 (1.3); 0.559 (1.2); 0.548 (3.6); 0.542 (3.3); 0.539 (3.1); 0.533 (3.0); 0.521 (0.9); 0.146 (0.4); 0.008 (3.0); 0.000 (92.3); −0.008 (3.7); −0.150 (0.4)

Beispiel I-T3-211: ¹H-NMR (400.0 MHz, d₆-DMSO):
δ = 8.641 (0.5); 8.541 (0.8); 8.530 (3.2); 8.524 (3.1); 8.504 (5.0); 8.495 (0.7); 8.385 (0.5); 8.318 (1.5); 8.288 (5.2); 8.280 (0.8); 7.971 (3.1); 7.965 (3.0); 7.943 (0.5); 7.803 (0.8); 7.532 (2.9); 7.375 (2.7); 7.322 (0.3); 7.209 (0.3); 4.421 (0.8); 4.404 (2.1); 4.386 (2.3); 4.369 (1.0); 4.240 (1.1); 4.224 (3.6); 4.206 (3.6); 4.189 (1.2); 4.179 (0.5); 4.162 (0.4); 3.741 (0.4); 3.727 (0.4); 3.328 (176.8); 3.027 (0.8); 2.985 (16.0); 2.886 (0.8); 2.775 (0.5); 2.762 (1.0); 2.748 (1.4); 2.734 (1.2); 2.717 (2.0); 2.676 (2.7); 2.671 (3.8); 2.667 (2.8); 2.524 (10.0); 2.510 (212.4); 2.507 (426.0); 2.502 (559.5); 2.498 (412.6); 2.456 (0.7); 2.333 (2.6); 2.329 (3.5); 2.324 (2.7); 2.075 (1.5); 1.361 (0.8); 1.344 (1.7); 1.329 (5.1); 1.312 (10.0); 1.294 (5.0); 1.282 (0.6); 1.229 (0.6); 1.213 (4.5); 1.196 (8.4); 1.178 (4.2); 1.160 (0.4); 1.147 (0.4); 0.788 (0.3); 0.779 (0.4); 0.704 (0.4); 0.469 (4.1); 0.454 (2.9); 0.146 (1.0); 0.008 (7.5); 0.000 (219.5); −0.008 (9.3); −0.150 (1.0)

Beispiel I-T3-212: ¹H-NMR (400.0 MHz, d₆-DMSO):
δ = 9.450 (2.0); 8.714 (2.7); 8.433 (2.7); 8.220 (1.3); 8.083 (1.3); 7.802 (0.5); 7.796 (1.2); 7.790 (1.7); 7.785 (1.8); 7.780 (1.4); 7.774 (0.6); 7.567 (1.5); 7.556 (0.4); 7.545 (1.3); 3.329 (62.0); 2.675 (0.5); 2.671 (0.7); 2.667 (0.5); 2.506 (78.1); 2.502 (103.1); 2.498 (77.2); 2.329 (0.7); 1.615 (0.6); 1.601 (1.6); 1.594 (1.7); 1.581 (0.7); 1.398 (16.0); 1.287 (0.7); 1.274 (1.6); 1.267 (1.7); 1.253 (0.6); 0.008 (1.3); 0.000 (41.2); −0.008 (1.8)

Beispiel I-T3-213: ¹H-NMR (400.0 MHz, d₆-DMSO):
δ = 8.692 (2.3); 8.542 (0.8); 8.531 (0.8); 8.417 (2.3); 8.220 (1.0); 8.216 (1.1); 8.079 (1.1); 8.075 (1.0); 7.742 (0.5); 7.737 (0.8); 7.717 (3.3); 7.517 (1.0); 7.496 (0.9); 3.348 (0.4); 3.330 (73.9); 2.839 (0.5); 2.829 (0.5); 2.676 (0.3); 2.671 (0.5); 2.667 (0.4); 2.525 (1.2); 2.520 (1.9); 2.511 (26.1); 2.507 (54.6); 2.502 (72.8); 2.498 (52.8); 2.493 (25.6); 2.333 (0.3); 2.329 (0.5); 2.324 (0.3); 1.398 (16.0); 0.716 (0.8); 0.710 (1.2); 0.698 (1.1); 0.692 (0.9); 0.681 (0.4); 0.562 (0.4); 0.552 (1.2); 0.545 (1.1); 0.536 (0.9); 0.008 (1.1); 0.000 (33.4); −0.009 (1.1)

Beispiel I-T3-214: ¹H-NMR (400.0 MHz, CD3CN):
δ = 20.020 (0.4); 8.203 (15.1); 8.187 (0.8); 8.173 (15.3); 7.865 (8.4); 7.716 (8.3); 7.711 (10.7); 7.683 (5.4); 7.677 (4.2); 7.662 (6.4); 7.656 (5.5); 7.608 (8.3); 7.528 (0.3); 7.504 (10.0); 7.484 (7.9); 7.016 (4.8); 6.931 (3.0); 6.835 (9.8); 6.653 (5.0); 2.910 (0.6); 2.901 (1.7); 2.891 (2.6); 2.883 (3.9); 2.873 (4.0); 2.865 (2.6); 2.855 (1.8); 2.846 (0.8); 2.174 (590.6); 2.150 (3.3); 2.144 (3.9); 2.138 (4.9); 2.132 (3.3); 2.125 (2.0); 1.995 (20.3); 1.988 (51.7); 1.983 (284.0); 1.977 (520.7); 1.970 (703.8); 1.964 (488.9); 1.958 (254.0); 1.811 (1.6); 1.805 (1.9); 1.799 (4.0); 1.793 (2.8); 1.786 (1.4); 1.467 (16.0); 1.299 (0.7); 0.824 (2.1); 0.811 (6.5); 0.807 (8.8); 0.794 (8.9); 0.789 (6.8); 0.777 (2.9); 0.755 (0.4); 0.737 (0.4); 0.670 (0.4); 0.641 (2.8); 0.629 (8.1); 0.623 (8.3); 0.614 (7.3); 0.602 (2.1); 0.030 (2.9)

Beispiel I-T3-215: ¹H-NMR (400.0 MHz, CD3CN):
δ = 8.215 (15.4); 8.189 (16.0); 7.866 (9.4); 7.763 (8.8); 7.758 (11.3); 7.732 (5.7); 7.726 (4.7); 7.711 (6.6); 7.705 (5.9); 7.672 (4.3); 7.609 (9.4); 7.536 (9.6); 7.515 (7.8); 7.022 (4.7); 6.840 (9.6); 6.659 (4.7); 4.096 (0.8); 4.079 (0.8); 2.495 (1.5); 2.491 (1.3); 2.206 (651.9); 2.150 (2.6); 2.144 (2.8); 2.138 (3.0); 2.131 (2.4); 2.001 (6.5); 1.994 (14.1); 1.983 (141.8); 1.976 (255.1); 1.970 (340.8); 1.964 (252.4); 1.958 (142.1); 1.811 (1.0); 1.805 (1.6); 1.799 (2.1); 1.793 (1.6); 1.787 (1.0); 1.664 (0.3); 1.626 (4.3); 1.611 (12.2); 1.605 (12.9); 1.591 (6.2); 1.551 (0.7); 1.466 (4.4); 1.431 (0.8); 1.390 (5.7); 1.376 (12.2); 1.370 (13.2); 1.355 (4.7); 1.318 (0.5); 1.297 (1.2); 1.251 (1.0); 1.233 (1.9); 1.215 (1.0); 0.029 (1.1)

Beispiel I-T3-216: ¹H-NMR (400.0 MHz, CD3CN):
δ = 8.197 (4.6); 8.169 (4.8); 7.865 (3.0); 7.669 (1.3); 7.664 (1.9); 7.644 (6.9); 7.609 (3.0); 7.584 (0.6); 7.579 (0.6); 7.516 (2.2); 7.495 (1.7); 7.023 (1.3); 7.016 (0.4); 6.841 (2.7); 6.835 (0.7); 6.660 (1.3); 3.086 (16.0); 2.794 (3.5); 2.778 (0.8); 2.769 (1.2); 2.759 (0.9); 2.751 (0.7); 2.741 (0.3); 2.184 (18.2); 2.175 (42.1); 2.144 (0.3); 2.138 (0.4); 2.002 (1.1); 1.994 (1.5); 1.988 (3.9); 1.983 (19.8); 1.976 (36.2); 1.970 (48.7); 1.964 (34.4); 1.958 (18.2); 1.466 (8.2); 1.233 (0.5); 0.869 (0.5); 0.852 (0.5); 0.806 (0.6); 0.795 (0.5); 0.598 (1.8); 0.512 (1.7); 0.504 (1.6); 0.495 (1.8)

Beispiel I-T3-217: $^1$H-NMR (400.0 MHz, CD3CN):
δ = 8.724 (2.9); 8.717 (3.2); 8.247 (7.4); 8.240 (1.1); 8.028 (3.1); 8.022 (3.1); 7.971 (0.5); 7.965 (0.5); 7.869 (2.3); 7.615 (2.4); 7.034 (1.5); 6.852 (2.9); 6.846 (0.6); 6.671 (1.5); 3.097 (16.0); 2.828 (2.6); 2.812 (0.6); 2.805 (0.6); 2.797 (1.1); 2.786 (0.7); 2.778 (0.6); 2.179 (56.3); 2.150 (0.4); 2.144 (0.5); 2.138 (0.6); 2.131 (0.4); 1.994 (4.3); 1.988 (6.2); 1.982 (37.6); 1.976 (69.1); 1.970 (93.5); 1.964 (64.7); 1.958 (33.4); 1.805 (0.4); 1.799 (0.6); 1.792 (0.4); 0.817 (0.4); 0.608 (1.4); 0.573 (1.0); 0.565 (1.7); 0.556 (1.1); 0.548 (1.5)
Beispiel I-T3-218: $^1$H-NMR (400.0 MHz, CD3CN):
δ = 20.011 (0.4); 8.773 (8.6); 8.766 (9.0); 8.741 (1.2); 8.735 (1.2); 8.265 (14.9); 8.261 (16.0); 8.253 (3.2); 8.250 (2.9); 8.143 (9.4); 8.137 (9.5); 8.009 (1.3); 8.002 (1.3); 7.870 (7.3); 7.689 (3.7); 7.614 (8.2); 7.029 (4.5); 6.847 (9.1); 6.666 (4.5); 5.477 (0.5); 3.753 (3.4); 3.653 (0.4); 3.636 (0.8); 3.628 (0.6); 3.611 (0.4); 3.327 (0.4); 3.315 (0.8); 3.304 (0.7); 3.098 (0.7); 3.087 (0.6); 2.911 (0.4); 2.168 (284.6); 2.150 (2.8); 2.144 (3.6); 2.138 (4.5); 2.131 (3.1); 2.125 (1.7); 1.994 (21.0); 1.988 (48.8); 1.982 (280.0); 1.976 (513.9); 1.970 (694.8); 1.964 (480.4); 1.958 (247.2); 1.811 (1.5); 1.805 (2.9); 1.799 (4.1); 1.792 (2.9); 1.786 (1.4); 1.644 (3.6); 1.629 (9.1); 1.623 (9.3); 1.609 (4.8); 1.568 (0.6); 1.440 (0.5); 1.399 (4.9); 1.386 (9.0); 1.379 (9.4); 1.364 (3.7); 1.327 (0.4); 1.299 (0.5); 1.164 (0.7); 0.029 (2.4)
Beispiel I-T3-219: $^1$H-NMR (400.0 MHz, CD3CN):
δ = 8.186 (4.3); 8.170 (4.3); 7.971 (2.5); 7.758 (2.2); 7.641 (1.2); 7.636 (1.8); 7.616 (6.7); 7.558 (0.6); 7.552 (0.5); 7.490 (2.0); 7.488 (1.7); 7.483 (0.7); 7.470 (1.3); 7.468 (1.5); 7.462 (0.6); 3.057 (16.0); 2.765 (3.5); 2.755 (0.7); 2.747 (0.7); 2.738 (1.1); 2.728 (0.7); 2.720 (0.6); 2.139 (32.4); 2.114 (0.4); 2.108 (0.5); 2.102 (0.4); 1.965 (2.1); 1.959 (5.3); 1.953 (31.9); 1.947 (58.9); 1.941 (79.9); 1.934 (55.2); 1.928 (28.6); 1.775 (0.3); 1.769 (0.5); 1.437 (6.1); 0.840 (0.4); 0.822 (0.4); 0.777 (0.5); 0.766 (0.4); 0.568 (1.4); 0.482 (1.4); 0.474 (1.3); 0.464 (1.5)
Beispiel I-T3-220: $^1$H-NMR (400.0 MHz, CD3CN):
δ = 8.695 (3.0); 8.689 (3.2); 8.219 (7.0); 8.000 (3.0); 7.994 (3.0); 7.937 (8.6); 7.897 (0.6); 5.449 (12.1); 3.067 (16.0); 2.891 (0.7); 2.869 (0.3); 2.798 (2.8); 2.785 (0.6); 2.778 (0.7); 2.769 (1.2); 2.758 (0.8); 2.750 (0.7); 2.741 (0.4); 2.474 (0.3); 2.469 (0.5); 2.464 (0.4); 2.189 (56.5); 2.121 (0.4); 2.115 (0.4); 2.109 (0.5); 2.103 (0.4); 2.087 (3.4); 1.965 (1.9); 1.959 (4.3); 1.954 (23.2); 1.947 (42.6); 1.941 (57.3); 1.935 (40.0); 1.929 (20.9); 1.770 (0.3); 1.316 (1.1); 1.300 (0.9); 1.285 (0.9); 1.269 (1.0); 0.853 (0.4); 0.834 (0.4); 0.787 (0.4); 0.776 (0.4); 0.578 (1.6); 0.535 (1.9); 0.525 (1.3); 0.518 (1.7); 0.146 (0.6); 0.008 (4.9); 0.000 (131.9); −0.008 (6.9); −0.150 (0.6)
Beispiel I-T3-221: $^1$H-NMR (400.0 MHz, CD3CN):
δ = 8.693 (6.2); 8.687 (6.2); 8.225 (9.9); 8.212 (10.1); 8.053 (0.4); 8.042 (6.8); 8.036 (6.6); 7.932 (16.0); 7.011 (1.9); 5.447 (15.9); 2.886 (0.5); 2.876 (1.3); 2.867 (1.8); 2.858 (2.8); 2.848 (2.8); 2.840 (1.8); 2.830 (1.3); 2.821 (0.4); 2.149 (16.6); 2.121 (1.4); 2.114 (1.2); 2.108 (1.2); 2.102 (0.9); 2.096 (0.6); 1.965 (6.2); 1.959 (9.3); 1.953 (46.1); 1.947 (83.1); 1.941 (110.8); 1.934 (76.5); 1.928 (39.4); 1.775 (0.5); 1.769 (0.7); 1.763 (0.4); 1.269 (1.0); 1.259 (0.5); 0.809 (1.5); 0.796 (4.5); 0.791 (5.9); 0.778 (6.1); 0.773 (4.5); 0.761 (2.0); 0.620 (2.0); 0.608 (5.1); 0.603 (5.5); 0.599 (4.9); 0.593 (4.7); 0.581 (1.4); 0.146 (1.3); 0.008 (11.5); 0.000 (286.0); −0.009 (12.3); −0.150 (1.3)
Beispiel I-T3-222: $^1$H-NMR (400.0 MHz, CD3CN):
δ = 8.742 (7.6); 8.736 (7.9); 8.237 (11.7); 8.230 (10.9); 8.112 (8.3); 8.106 (8.3); 7.935 (16.0); 7.717 (1.6); 6.777 (0.5); 5.448 (3.1); 2.170 (68.6); 2.121 (0.4); 2.115 (0.6); 2.108 (0.7); 2.102 (0.5); 1.965 (4.0); 1.959 (7.1); 1.953 (42.0); 1.947 (76.9); 1.941 (104.1); 1.935 (72.7); 1.929 (37.9); 1.776 (0.5); 1.769 (0.6); 1.763 (0.5); 1.697 (0.5); 1.612 (3.1); 1.598 (7.6); 1.591 (7.8); 1.577 (4.2); 1.537 (2.0); 1.523 (1.3); 1.505 (1.2); 1.408 (0.5); 1.368 (4.3); 1.355 (7.7); 1.348 (8.0); 1.333 (3.2); 1.277 (0.4); 1.269 (0.9); 1.259 (1.1); 1.193 (0.9); 1.187 (0.6); 1.183 (0.4); 1.177 (1.0); 1.171 (0.6); 1.166 (0.4); 0.146 (1.1); 0.008 (9.5); 0.000 (259.4); −0.009 (11.5); −0.150 (1.1)
Beispiel I-T3-223: $^1$H-NMR (600.1 MHz, CD3CN):
δ = 8.772 (0.8); 8.732 (3.1); 8.728 (3.0); 8.222 (7.7); 8.215 (5.8); 8.200 (0.8); 8.021 (3.2); 8.017 (3.1); 7.943 (13.2); 6.642 (0.5); 4.077 (1.3); 4.065 (3.9); 4.053 (3.9); 4.042 (1.3); 3.752 (0.8); 3.165 (3.1); 3.069 (0.4); 2.934 (16.0); 2.880 (0.4); 2.245 (0.5); 2.240 (0.6); 2.222 (0.8); 2.146 (25.4); 2.078 (1.0); 2.059 (0.8); 2.055 (1.1); 2.050 (1.3); 2.046 (1.0); 2.042 (0.7); 1.972 (17.2); 1.964 (2.0); 1.956 (5.4); 1.952 (7.4); 1.948 (55.6); 1.944 (100.9); 1.940 (146.1); 1.936 (99.1); 1.931 (49.9); 1.833 (0.4); 1.829 (0.7); 1.825 (0.9); 1.821 (0.7); 1.816 (0.4); 1.664 (3.8); 1.661 (4.0); 1.505 (0.4); 1.473 (3.0); 1.443 (0.6); 1.425 (0.6); 1.422 (0.6); 1.409 (0.8); 1.406 (0.8); 1.390 (2.1); 1.388 (1.6); 1.372 (1.4); 1.363 (0.5); 1.358 (0.7); 1.341 (1.7); 1.316 (0.9); 1.303 (0.9); 1.285 (3.5); 1.277 (3.9); 1.271 (6.9); 1.221 (1.2); 1.216 (6.4); 1.214 (5.7); 1.204 (9.5); 1.201 (2.5); 1.192 (4.8); 1.180 (0.6); 1.175 (0.3); 0.948 (0.4); 0.893 (0.9); 0.882 (1.8); 0.870 (1.5); 0.863 (0.9); 0.860 (0.9); 0.856 (0.9); 0.846 (0.9); 0.000 (7.9)
Beispiel I-T3-224: $^1$H-NMR (400.0 MHz, CD3CN):
δ = 8.271 (7.9); 8.267 (7.8); 8.184 (15.8); 8.183 (15.9); 8.152 (0.7); 8.141 (16.0); 7.791 (6.9); 7.693 (9.4); 7.688 (12.0); 7.678 (0.8); 7.662 (6.6); 7.656 (4.7); 7.641 (7.7); 7.635 (6.2); 7.591 (0.7); 7.479 (11.5); 7.458 (9.1); 6.959 (2.7); 4.086 (0.9); 4.068 (2.7); 4.050 (2.8); 4.032 (0.9); 2.986 (0.4); 2.883 (0.8); 2.873 (2.2); 2.864 (3.0); 2.855 (4.6); 2.846 (4.6); 2.837 (2.9); 2.828 (2.2); 2.818 (0.9); 2.567 (0.7); 2.536 (0.3); 2.503 (0.4); 2.477 (1.2); 2.472 (1.9); 2.467 (2.6); 2.462 (1.9); 2.458 (1.1); 2.411 (0.5); 2.398 (0.5); 2.373 (0.6); 2.310 (0.9); 2.281 (1.2); 2.187 (1104.6); 2.121 (0.9); 2.115 (2.0); 2.109 (2.7); 2.103 (1.9); 2.096 (0.9); 1.993 (0.6); 1.973 (14.2); 1.966 (15.1); 1.960 (36.7); 1.954 (209.3); 1.948 (380.7); 1.941 (511.0); 1.935 (347.0); 1.929 (175.8); 1.916 (1.4); 1.782 (1.0); 1.776 (1.9); 1.770 (2.8); 1.764 (1.8); 1.757 (0.8); 1.437 (14.7); 1.340 (0.4); 1.285 (0.8); 1.270 (2.8); 1.222 (3.4); 1.204 (6.6); 1.186 (3.2); 0.882 (0.5); 0.857 (0.5); 0.841 (0.4); 0.796 (2.4); 0.784 (7.0); 0.779 (9.4); 0.766 (9.7); 0.761 (6.9); 0.749 (3.1); 0.727 (0.5); 0.709 (0.4); 0.654 (0.4); 0.644 (0.4); 0.614 (3.2); 0.602 (7.9); 0.597 (8.2); 0.593 (7.3); 0.587 (7.3); 0.575 (2.2); 0.526 (0.3); 0.146 (7.1); 0.138 (0.4); 0.079 (0.4); 0.069 (0.4); 0.066 (0.3); 0.058 (0.5); 0.054 (0.5); 0.049 (0.5); 0.045 (0.6); 0.037 (0.4); 0.023 (0.8); 0.008 (59.7); 0.000 (1582.5); −0.009 (57.5); −0.033 (0.5); −0.036 (0.5); −0.150 (7.0)
Beispiel I-T3-225: $^1$H-NMR (400.0 MHz, CD3CN):
δ = 8.269 (2.4); 8.266 (2.4); 8.170 (4.4); 8.126 (4.2); 7.787 (2.2); 7.644 (1.2); 7.639 (1.7); 7.624 (1.0); 7.618 (5.4); 7.613 (1.7); 7.561 (0.6); 7.556 (0.5); 7.490 (2.1); 7.489 (2.0); 7.482 (0.7); 7.470 (1.6); 7.468 (1.6); 7.462 (0.6); 3.058 (14.9); 3.006 (0.4); 2.778 (0.6); 2.771 (3.2); 2.761 (0.6); 2.753 (0.7); 2.744 (1.1); 2.734 (0.7); 2.726 (0.8); 2.127 (33.1); 2.113 (0.8); 2.106 (0.7); 2.100 (0.5); 1.971 (0.8); 1.963 (2.6); 1.957 (6.7); 1.951 (37.7); 1.945 (68.8); 1.939 (92.9); 1.933 (64.3); 1.927 (33.3); 1.774 (0.4); 1.767 (0.5); 1.761 (0.4); 1.437 (16.0); 1.270 (0.8); 1.204 (0.4); 0.841 (0.5); 0.823 (0.4); 0.780 (0.5); 0.769 (0.4); 0.581 (1.4); 0.575 (1.4); 0.487 (1.5); 0.479 (1.3); 0.470 (1.5); 0.146 (1.1); 0.008 (9.5); 0.000 (262.4); −0.009 (11.4); −0.150 (1.2)
Beispiel I-T3-226: $^1$H-NMR (400.0 MHz, CD3CN):
δ = 8.269 (7.2); 8.266 (7.5); 8.191 (16.0); 8.147 (15.3); 8.056 (0.9); 7.789 (6.5); 7.741 (8.2); 7.735 (10.5); 7.708 (5.2); 7.703 (4.0); 7.687 (6.0); 7.682 (5.1); 7.554 (4.5); 7.509 (10.0); 7.488 (8.2); 4.084 (0.6); 4.067 (1.9); 4.049 (1.9); 4.032 (0.6); 3.063 (0.7); 3.040 (5.6); 2.902 (4.9); 2.854 (0.6); 2.568 (0.4); 2.126 (170.0); 2.112 (2.8); 2.106 (2.7); 2.100 (1.9); 2.093 (1.2); 2.035 (0.4); 1.970 (10.0); 1.962 (11.5); 1.956 (26.7); 1.951 (152.2); 1.944 (278.1); 1.938 (376.5); 1.932 (259.9); 1.926 (134.2); 1.913 (1.4); 1.779 (0.8); 1.773 (1.5); 1.767 (2.1); 1.761 (1.4); 1.754 (0.7); 1.597 (4.0); 1.583 (10.7); 1.576 (10.4); 1.563 (5.3); 1.523 (0.7); 1.436 (8.2); 1.404 (0.7); 1.364 (5.4); 1.350 (10.4); 1.344 (11.2); 1.329 (4.1); 1.318 (0.3); 1.292 (0.5); 1.269 (2.7); 1.221 (2.2); 1.203 (4.2); 1.185 (2.1); 0.881 (0.4); 0.858 (0.3); 0.145 (5.2); 0.031 (0.9); 0.0071 (35.1); 0.0066 (35.1); −0.001 (985.7); −0.009 (44.0); −0.026 (0.9); −0.040 (0.4); −0.151 (5.1)
Beispiel I-T3-227: $^1$H-NMR (400.0 MHz, CD3CN):
δ = 8.511 (7.8); 8.508 (7.8); 8.174 (16.0); 8.118 (13.4); 8.099 (7.8); 7.694 (9.8); 7.688 (12.4); 7.662 (6.6); 7.656 (5.0); 7.641 (7.7); 7.635 (6.4); 7.499 (0.3); 7.476 (11.6); 7.455 (9.2); 6.938 (2.9); 3.062 (0.6); 2.880 (0.7); 2.870 (2.1); 2.861 (3.0); 2.852 (4.7); 2.843 (4.7); 2.834 (3.0); 2.825 (2.2); 2.815 (0.7); 2.543 (0.4); 2.468 (0.4); 2.463 (0.6); 2.459 (0.4); 2.163 (162.8); 2.120 (1.0); 2.114 (1.0); 2.108 (1.1); 2.102 (0.9); 2.087 (20.5); 1.972 (1.6); 1.965 (5.0); 1.959 (13.4); 1.953 (69.2); 1.947 (125.1); 1.941 (166.4); 1.935 (115.7); 1.928 (59.8); 1.781 (0.4); 1.775 (0.7); 1.769 (1.0); 1.763 (0.6); 1.757 (0.3); 1.285 (0.4); 1.269 (1.7); 1.204 (0.6); 1.186 (0.3); 1.179 (0.8); 0.794 (2.5); 0.781

-continued (7.3); 0.776 (9.8); 0.763 (10.2); 0.758 (7.4); 0.746 (3.4); 0.724 (0.4); 0.707 (0.4); 0.652 (0.4); 0.642 (0.4); 0.612 (3.3); 0.601 (8.5); 0.595 (8.9); 0.591 (8.1); 0.586 (7.9); 0.573 (2.5); 0.536 (0.4); 0.528 (0.3); 0.146 (2.7); 0.029 (0.4); 0.008 (25.1); 0.000 (580.3); −0.009 (29.4); −0.028 (0.7); −0.150 (2.7)
Beispiel I-T3-228: $^1$H-NMR (400.0 MHz, CD3CN):
δ = 8.508 (2.3); 8.184 (4.7); 8.130 (3.9); 8.099 (2.3); 7.741 (2.6); 7.735 (3.4); 7.711 (1.8); 7.705 (1.3); 7.690 (2.1); 7.684 (1.7); 7.644 (1.3); 7.509 (3.2); 7.488 (2.6); 2.545 (0.6); 2.468 (0.5); 2.463 (0.7); 2.459 (0.5); 2.159 (239.3); 2.119 (0.6); 2.113 (0.8); 2.107 (0.9); 2.101 (0.7); 2.095 (0.4); 1.971 (1.0); 1.964 (3.7); 1.958 (9.3); 1.952 (53.0); 1.946 (96.2); 1.940 (130.0); 1.933 (90.1); 1.927 (46.8); 1.780 (0.3); 1.774 (0.6); 1.768 (0.8); 1.762 (0.6); 1.595 (1.3); 1.581 (3.4); 1.574 (3.5); 1.560 (1.8); 1.437 (16.0); 1.363 (1.8); 1.349 (3.4); 1.343 (3.5); 1.328 (1.4); 1.270 (0.7); 1.204 (0.4); 0.146 (1.3); 0.008 (10.5); 0.000 (282.8); −0.009 (11.9); −0.150 (1.3)
Beispiel I-T3-229: $^1$H-NMR (400.0 MHz, CD3CN):
δ = 8.507 (1.6); 8.161 (3.4); 8.104 (3.1); 7.644 (0.8); 7.639 (1.1); 7.619 (3.9); 7.562 (0.4); 7.557 (0.4); 7.488 (1.4); 7.481 (0.5); 7.466 (1.1); 7.460 (0.4); 3.056 (10.5); 2.855 (0.4); 2.771 (2.3); 2.763 (0.5); 2.755 (0.5); 2.745 (0.8); 2.736 (0.5); 2.728 (0.4); 2.544 (0.4); 2.131 (16.7); 1.971 (0.5); 1.963 (1.1); 1.957 (2.7); 1.951 (15.4); 1.945 (28.4); 1.939 (38.5); 1.933 (26.5); 1.927 (13.7); 1.437 (16.0); 0.779 (0.4); 0.576 (1.0); 0.488 (1.0); 0.480 (0.9); 0.471 (1.0); 0.146 (0.4); 0.008 (3.0); 0.000 (85.2); −0.009 (3.4); −0.150 (0.4)
Beispiel I-T4-1: $^1$H-NMR (400.0 MHz, CD3CN):
δ = 8.170 (4.8); 7.860 (5.7); 7.840 (2.0); 7.833 (1.3); 7.687 (4.2); 7.561 (1.9); 7.539 (1.6); 7.436 (5.5); 6.972 (0.9); 2.871 (0.5); 2.862 (0.8); 2.853 (1.1); 2.843 (1.1); 2.835 (0.8); 2.825 (0.5); 2.251 (24.5); 2.140 (6.0); 1.971 (0.5); 1.964 (0.6); 1.958 (1.4); 1.952 (6.2); 1.946 (11.2); 1.940 (15.0); 1.934 (10.9); 1.928 (5.9); 1.436 (16.0); 0.796 (0.6); 0.784 (1.9); 0.779 (2.5); 0.766 (2.6); 0.761 (2.0); 0.749 (0.9); 0.619 (0.8); 0.608 (2.3); 0.601 (2.5); 0.592 (2.1); 0.580 (0.6); 0.000 (15.7)
Beispiel I-T4-2: $^1$H-NMR (400.0 MHz, CD3CN):
δ = 8.184 (6.7); 8.183 (6.5); 7.920 (2.5); 7.915 (8.6); 7.894 (3.0); 7.887 (1.9); 7.699 (6.2); 7.680 (1.6); 7.602 (3.0); 7.600 (2.8); 7.582 (2.4); 7.580 (2.6); 7.438 (7.8); 2.463 (0.3); 2.253 (39.2); 2.151 (134.8); 2.120 (0.5); 2.114 (0.7); 2.108 (0.9); 2.102 (0.6); 2.095 (0.4); 1.972 (1.2); 1.965 (4.2); 1.959 (10.5); 1.953 (54.2); 1.947 (98.7); 1.940 (132.9); 1.934 (93.2); 1.928 (48.4); 1.775 (0.6); 1.769 (0.8); 1.763 (0.6); 1.599 (1.8); 1.585 (4.6); 1.578 (4.7); 1.564 (2.4); 1.437 (16.0); 1.415 (0.4); 1.375 (2.4); 1.361 (4.7); 1.354 (4.9); 1.340 (1.8); 1.269 (1.5); 1.204 (0.4); 0.146 (0.7); 0.008 (5.3); 0.000 (150.3); −0.008 (7.3); −0.149 (0.7)
Beispiel I-T4-3: $^1$H-NMR (400.0 MHz, CD3CN):
δ = 8.929 (2.4); 8.922 (2.4); 8.231 (2.7); 8.224 (2.6); 8.205 (4.3); 7.754 (3.8); 7.444 (5.0); 7.072 (0.7); 2.881 (0.4); 2.872 (0.7); 2.863 (1.0); 2.853 (1.0); 2.845 (0.7); 2.835 (0.4); 2.252 (22.9); 2.140 (16.7); 1.964 (1.1); 1.952 (13.4); 1.946 (23.9); 1.940 (31.3); 1.934 (21.8); 1.928 (11.3); 1.436 (16.0); 0.814 (0.5); 0.800 (1.8); 0.796 (2.2); 0.783 (2.3); 0.778 (1.7); 0.766 (0.7); 0.633 (0.7); 0.622 (2.1); 0.616 (2.2); 0.612 (2.0); 0.607 (1.8); 0.594 (0.5); 0.146 (0.6); 0.000 (113.1); −0.150 (0.6)
Beispiel I-T4-4: $^1$H-NMR (400.0 MHz, CD3CN):
δ = 8.974 (3.9); 8.967 (3.9); 8.300 (4.1); 8.294 (4.0); 8.216 (6.7); 7.764 (6.3); 7.753 (0.6); 7.735 (1.8); 7.446 (7.8); 4.067 (0.9); 4.050 (0.9); 3.076 (1.0); 2.898 (1.0); 2.254 (38.8); 2.144 (39.1); 2.114 (0.6); 2.107 (0.6); 2.101 (0.4); 2.095 (0.4); 2.086 (0.4); 2.063 (0.4); 1.972 (4.1); 1.964 (2.3); 1.958 (6.0); 1.952 (30.2); 1.946 (53.9); 1.940 (71.6); 1.934 (48.9); 1.928 (25.1); 1.768 (0.4); 1.617 (1.7); 1.602 (4.5); 1.595 (4.4); 1.581 (2.2); 1.437 (16.0); 1.388 (2.3); 1.375 (4.5); 1.368 (4.5); 1.353 (1.7); 1.269 (0.9); 1.221 (1.0); 1.204 (2.0); 1.186 (1.0); 0.146 (1.1); 0.008 (8.7); 0.000 (211.3); −0.009 (8.7); −0.150 (1.1)
Beispiel I-T22-1: $^1$H-NMR (400.0 MHz, CD3CN):
δ = 7.934 (2.4); 7.928 (3.4); 7.908 (1.9); 7.902 (1.3); 7.887 (2.0); 7.882 (1.6); 7.615 (3.0); 7.594 (2.6); 7.486 (5.3); 7.037 (0.7); 6.864 (0.4); 6.858 (6.5); 2.877 (0.5); 2.867 (0.8); 2.858 (1.2); 2.849 (1.2); 2.840 (0.8); 2.831 (0.6); 2.258 (25.0); 2.168 (12.6); 1.965 (0.4); 1.959 (1.0); 1.953 (5.8); 1.947 (10.6); 1.941 (14.3); 1.935 (10.0); 1.928 (5.3); 1.436 (16.0); 0.800 (0.6); 0.788 (1.8); 0.783 (2.5); 0.770 (2.6); 0.765 (1.9); 0.753 (0.9); 0.624 (0.9); 0.613 (2.2); 0.606 (2.3); 0.602 (2.0); 0.597 (2.0); 0.585 (0.7); 0.008 (0.7); 0.000 (20.3); −0.009 (0.9)
Beispiel I-T22-2: $^1$H-NMR (400.0 MHz, CD3CN):
δ = 7.992 (6.1); 7.986 (8.0); 7.960 (4.3); 7.954 (3.3); 7.939 (4.6); 7.933 (4.0); 7.709 (2.2); 7.654 (7.3); 7.633 (6.4); 7.487 (13.6); 6.877 (16.0); 5.448 (2.4); 2.418 (0.4); 2.260 (66.3); 2.153 (49.7); 2.120 (0.4); 2.114 (0.4); 2.108 (0.5); 2.098 (0.5); 2.086 (1.9); 1.972 (0.6); 1.964 (1.9); 1.958 (4.9); 1.953 (28.0); 1.946 (51.5); 1.940 (70.2); 1.934 (49.9); 1.928 (27.0); 1.775 (0.3); 1.769 (0.4); 1.603 (3.1); 1.588 (8.0); 1.581 (8.3); 1.568 (4.3); 1.528 (0.5); 1.436 (0.9); 1.419 (0.5); 1.379 (4.2); 1.365 (8.0); 1.359 (8.7); 1.344 (3.3); 1.268 (0.4); 0.146 (0.5); 0.008 (3.8); 0.000 (117.9); −0.008 (7.0); −0.150 (0.6)
Beispiel I-T22-3: $^1$H-NMR (400.0 MHz, CD3CN):
δ = 7.982 (3.5); 7.977 (5.3); 7.966 (3.0); 7.960 (1.9); 7.945 (2.9); 7.939 (2.5); 7.669 (4.3); 7.648 (3.7); 7.487 (9.9); 6.883 (8.4); 4.152 (1.0); 4.136 (1.1); 4.129 (3.0); 4.112 (3.1); 4.105 (3.3); 4.089 (3.1); 4.082 (1.4); 4.065 (1.1); 2.262 (40.4); 2.156 (20.4); 2.101 (0.4); 1.972 (0.5); 1.964 (1.0); 1.958 (2.4); 1.953 (12.4); 1.946 (23.1); 1.940 (31.5); 1.934 (23.1); 1.928 (12.8); 1.436 (16.0); 0.008 (2.0); 0.000 (53.5)
Beispiel I-T22-4: $^1$H-NMR (400.0 MHz, CD3CN):
δ = 8.983 (1.2); 8.977 (1.3); 8.360 (1.3); 8.355 (1.3); 7.953 (1.3); 7.944 (1.4); 7.036 (2.1); 2.306 (6.0); 2.160 (8.1); 1.953 (4.2); 1.947 (7.8); 1.941 (10.6); 1.935 (7.9); 1.929 (4.3); 1.619 (0.6); 1.604 (1.6); 1.597 (1.6); 1.584 (0.8); 1.437 (16.0); 1.390 (0.8); 1.376 (1.6); 1.369 (1.7); 1.354 (0.6)
Beispiel I-T22-5: $^1$H-NMR (400.0 MHz, CD3CN):
δ = 7.942 (4.2); 7.936 (5.2); 7.918 (1.6); 7.912 (1.1); 7.897 (1.6); 7.892 (1.3); 7.619 (2.4); 7.598 (2.1); 7.045 (0.8); 6.922 (4.2); 2.874 (0.4); 2.865 (0.7); 2.856 (1.0); 2.847 (1.0); 2.838 (0.7); 2.828 (0.4); 2.305 (10.8); 2.183 (27.7); 1.960 (0.8); 1.954 (3.8); 1.948 (6.9); 1.942 (9.3); 1.936 (6.5); 1.930 (3.4); 1.436 (16.0); 0.799 (0.5); 0.786 (1.7); 0.781 (2.2); 0.769 (2.2); 0.764 (1.7); 0.751 (0.7); 0.624 (0.7); 0.613 (2.1); 0.607 (2.1); 0.603 (2.0); 0.597 (1.8); 0.585 (0.5); 0.000 (23.8)
Beispiel I-T22-6: $^1$H-NMR (400.0 MHz, CD3CN):
δ = 8.939 (1.4); 8.933 (1.5); 8.286 (1.4); 8.292 (1.4); 7.952 (1.1); 7.942 (1.1); 7.150 (0.3); 7.022 (2.3); 2.874 (0.4); 2.865 (0.5); 2.855 (0.5); 2.847 (0.6); 2.305 (5.7); 2.187 (7.7); 1.973 (0.7); 1.960 (0.4); 1.954 (2.8); 1.948 (5.1); 1.942 (7.0); 1.936 (4.8); 1.930 (2.5); 1.436 (16.0); 1.204 (0.3); 0.803 (0.9); 0.798 (1.1); 0.785 (1.2); 0.780 (0.9); 0.767 (0.4); 0.636 (0.4); 0.624 (1.0); 0.619 (1.1); 0.615 (0.9); 0.609 (0.9); 0.000 (5.3)
Beispiel I-T22-7: $^1$H-NMR (400.0 MHz, CD3CN):
δ = 7.999 (1.6); 7.994 (2.1); 7.970 (1.1); 7.965 (0.8); 7.949 (2.6); 7.944 (2.6); 7.937 (1.8); 7.659 (2.2); 7.638 (1.6); 6.939 (3.3); 2.306 (8.4); 2.155 (9.0); 1.972 (0.6); 1.965 (0.3); 1.953 (5.6); 1.947 (10.3); 1.941 (14.0); 1.935 (9.7); 1.929 (5.0); 1.602 (0.8); 1.587 (2.1); 1.581 (2.1); 1.567 (1.1); 1.436 (16.0); 1.380 (1.1); 1.366 (2.1); 1.360 (2.2); 1.345 (0.8)
Beispiel I-T23-1: $^1$H-NMR (400.0 MHz, CD3CN):
δ = 7.961 (5.3); 7.958 (2.0); 7.942 (1.7); 7.937 (1.0); 7.864 (5.1); 7.609 (1.6); 7.606 (1.0); 7.590 (1.0); 7.587 (1.4); 7.148 (5.1); 6.968 (0.5); 2.876 (0.4); 2.867 (0.6); 2.858 (0.9); 2.849 (0.9); 2.840 (0.6); 2.831 (0.4); 2.134 (6.5); 1.964 (1.6); 1.958 (2.5); 1.952 (11.3); 1.946 (20.0); 1.940 (26.1); 1.934 (17.8); 1.928 (9.0); 1.437 (16.0); 0.800 (0.5); 0.787 (1.5); 0.782 (1.9); 0.770 (2.0); 0.764 (1.4); 0.752 (0.7); 0.624 (0.7); 0.614 (1.6); 0.606 (1.7); 0.602 (1.5); 0.597 (1.2); 0.584 (0.5); 0.000 (0.7)
Beispiel I-T23-2: $^1$H-NMR (400.0 MHz, CD3CN):
δ = 8.014 (3.3); 8.010 (1.3); 7.997 (1.1); 7.991 (0.6); 7.866 (3.6); 7.648 (1.5); 7.642 (0.8); 7.630 (0.6); 7.625 (1.2); 7.162 (3.0); 5.447 (16.0); 2.140 (12.0); 1.972 (0.4); 1.964 (2.4); 1.958 (4.0); 1.952 (17.2); 1.946 (30.2); 1.940 (39.3); 1.934 (26.8); 1.928 (13.7); 1.600 (0.6); 1.586 (1.7); 1.579 (1.7); 1.565 (0.9); 1.437 (0.9); 1.380 (0.9); 1.367 (1.6); 1.360 (1.7); 1.345 (0.7); 0.000 (0.9)

Beispiel I-T46-1: ¹H-NMR (400.0 MHz, CD3CN):
δ = 7.669 (6.3); 7.664 (9.6); 7.654 (5.5); 7.648 (2.9); 7.633 (5.5); 7.627 (4.3); 7.582 (3.1); 7.509 (16.0); 7.426 (8.2); 7.405 (6.8); 7.166 (4.7); 7.161 (8.3); 7.156 (5.0); 6.767 (3.7); 6.760 (7.3); 6.754 (5.5); 6.735 (5.6); 6.730 (6.3); 6.723 (3.8); 2.468 (0.7); 2.463 (1.0); 2.459 (0.7); 2.298 (0.5); 2.161 (388.0); 2.139 (78.8); 2.121 (1.2); 2.114 (1.5); 2.108 (1.7); 2.102 (1.2); 2.096 (0.7); 1.993 (0.7); 1.977 (0.9); 1.965 (8.8); 1.959 (16.3); 1.953 (98.1); 1.947 (179.6); 1.941 (243.9); 1.935 (167.4); 1.928 (86.0); 1.856 (0.9); 1.842 (0.6); 1.782 (0.6); 1.775 (1.1); 1.769 (1.5); 1.763 (1.0); 1.757 (0.5); 1.585 (3.5); 1.570 (9.4); 1.563 (9.3); 1.550 (4.6); 1.510 (0.5); 1.394 (0.5); 1.354 (4.7); 1.340 (9.4); 1.333 (9.8); 1.319 (3.5); 0.146 (0.4); 0.008 (2.9); 0.000 (87.8); −0.008 (3.4); −0.150 (0.4)

Beispiel I-T46-2: ¹H-NMR (400.0 MHz, CD3CN):
δ = 7.682 (3.3); 7.677 (6.3); 7.676 (6.2); 7.673 (6.2); 7.668 (4.7); 7.665 (5.9); 7.653 (5.1); 7.647 (7.8); 7.628 (1.3); 7.623 (1.7); 7.606 (1.1); 7.600 (0.7); 7.585 (1.1); 7.579 (1.0); 7.518 (4.3); 7.517 (4.5); 7.507 (3.5); 7.496 (6.1); 7.478 (6.1); 7.475 (3.5); 7.459 (3.7); 7.422 (2.5); 7.419 (1.8); 7.409 (1.0); 7.403 (2.8); 7.394 (1.8); 7.385 (1.0); 7.373 (1.2); 7.153 (0.9); 7.148 (1.6); 7.143 (1.1); 6.961 (0.8); 6.900 (0.5); 6.760 (0.8); 6.753 (1.5); 6.747 (1.1); 6.724 (1.1); 6.720 (1.3); 6.717 (1.2); 6.713 (0.9); 3.855 (0.7); 3.051 (1.3); 2.881 (0.4); 2.871 (1.1); 2.862 (1.6); 2.853 (2.4); 2.843 (3.0); 2.834 (1.8); 2.826 (1.3); 2.816 (0.6); 2.476 (0.8); 2.472 (1.3); 2.467 (1.8); 2.462 (1.4); 2.427 (0.5); 2.391 (0.4); 2.383 (0.3); 2.359 (0.4); 2.327 (0.5); 2.182 (852.2); 2.138 (15.6); 2.121 (1.5); 2.115 (2.2); 2.109 (2.8); 2.102 (2.4); 2.096 (1.2); 1.992 (0.9); 1.966 (9.9); 1.959 (26.3); 1.954 (166.7); 1.947 (309.9); 1.941 (423.2); 1.935 (291.5); 1.929 (148.5); 1.782 (0.9); 1.776 (1.7); 1.770 (2.4); 1.764 (1.7); 1.757 (0.9); 1.437 (16.0); 1.270 (1.6); 0.790 (1.1); 0.778 (3.3); 0.773 (4.8); 0.766 (2.0); 0.760 (4.8); 0.755 (4.0); 0.743 (1.7); 0.736 (0.5); 0.614 (1.5); 0.602 (4.2); 0.593 (4.9); 0.587 (4.7); 0.575 (1.8); 0.000 (1.7)

Beispiel I-T46-3: ¹H-NMR (400.0 MHz, CD3CN):
δ = 8.649 (2.9); 8.643 (3.2); 7.935 (2.9); 7.929 (2.9); 7.873 (7.9); 7.322 (1.5); 7.318 (2.7); 7.313 (1.9); 6.923 (1.5); 6.917 (2.0); 6.916 (2.3); 6.910 (1.9); 6.802 (1.7); 6.798 (2.2); 6.795 (2.0); 6.790 (1.9); 3.058 (16.0); 2.790 (2.7); 2.783 (0.4); 2.772 (0.6); 2.765 (0.6); 2.757 (1.2); 2.745 (0.7); 2.738 (0.6); 2.170 (18.1); 1.966 (1.0); 1.960 (2.0); 1.954 (11.8); 1.948 (21.8); 1.941 (29.7); 1.935 (20.7); 1.929 (10.7); 1.269 (0.6); 0.844 (0.3); 0.826 (0.4); 0.783 (0.4); 0.573 (1.4); 0.528 (1.7); 0.518 (1.1); 0.511 (1.6); 0.000 (7.0); −0.008 (0.3)

Beispiel I-T46-4: ¹H-NMR (400.0 MHz, CD3CN):
δ = 8.649 (6.8); 8.643 (7.0); 7.990 (0.3); 7.976 (7.4); 7.970 (7.3); 7.871 (16.0); 7.320 (4.1); 7.315 (6.6); 7.310 (4.1); 6.976 (1.8); 6.920 (3.8); 6.914 (4.9); 6.912 (5.2); 6.907 (4.0); 6.805 (4.5); 6.801 (4.8); 6.798 (4.5); 6.794 (3.8); 5.448 (0.6); 2.876 (0.4); 2.867 (1.2); 2.857 (1.7); 2.849 (2.7); 2.839 (2.8); 2.831 (1.8); 2.821 (1.3); 2.811 (0.4); 2.143 (54.7); 2.114 (0.4); 2.108 (0.4); 1.965 (2.0); 1.959 (5.3); 1.953 (26.5); 1.947 (48.2); 1.941 (64.2); 1.934 (44.7); 1.928 (23.1); 1.769 (0.4); 1.269 (0.9); 1.200 (0.4); 0.799 (1.4); 0.786 (4.5); 0.781 (5.9); 0.769 (6.1); 0.763 (4.5); 0.751 (1.9); 0.614 (1.9); 0.602 (5.1); 0.597 (5.6); 0.593 (5.0); 0.587 (4.8); 0.575 (1.4); 0.008 (0.5); 0.000 (15.3)

Beispiel I-T46-5: ¹H-NMR (400.0 MHz, CD3CN):
δ = 8.693 (7.0); 8.687 (7.3); 8.034 (7.5); 8.028 (7.5); 7.873 (16.0); 7.693 (1.3); 7.335 (3.9); 7.330 (6.8); 7.325 (4.4); 6.927 (3.7); 6.922 (4.7); 6.920 (5.0); 6.914 (4.3); 6.816 (4.3); 6.812 (4.8); 6.808 (4.4); 6.804 (3.9); 5.449 (14.1); 2.173 (58.5); 2.115 (0.4); 2.109 (0.5); 2.103 (0.4); 1.966 (2.9); 1.960 (5.1); 1.954 (29.3); 1.948 (53.8); 1.941 (72.9); 1.935 (50.8); 1.929 (26.4); 1.776 (0.3); 1.770 (0.4); 1.764 (0.3); 1.602 (2.9); 1.588 (7.3); 1.581 (7.4); 1.567 (3.9); 1.551 (0.4); 1.523 (0.7); 1.505 (0.6); 1.405 (0.5); 1.365 (4.1); 1.351 (7.2); 1.345 (7.6); 1.330 (3.0); 1.269 (0.9); 1.259 (0.5); 1.200 (0.6); 1.193 (0.4); 1.187 (0.4); 1.177 (0.5); 1.171 (0.4); 0.008 (0.4); 0.000 (13.0)

Beispiel I-T46-6: ¹H-NMR (400.0 MHz, CD3CN):
δ = 8.729 (1.0); 8.692 (3.0); 8.687 (3.0); 8.145 (1.0); 7.954 (3.0); 7.949 (3.0); 7.871 (14.1); 7.325 (3.5); 7.071 (0.6); 6.926 (2.7); 6.920 (3.2); 6.914 (2.1); 6.808 (2.6); 6.803 (2.8); 6.643 (1.1); 6.496 (1.1); 3.751 (1.8); 3.659 (0.8); 3.649 (0.9); 3.643 (2.1); 3.624 (1.8); 3.159 (4.2); 3.076 (1.9); 3.062 (0.3); 2.927 (16.0); 2.905 (0.3); 2.887 (0.3); 2.874 (0.3); 2.240 (1.1); 2.176 (137.5); 2.121 (0.6); 2.115 (0.7); 2.109 (0.7); 2.103 (0.6); 2.097 (0.4); 1.966 (2.5); 1.960 (6.5); 1.954 (35.6); 1.948 (65.4); 1.942 (88.3); 1.935 (62.6); 1.929 (33.5); 1.819 (1.0); 1.811 (1.1); 1.803 (2.6); 1.794 (1.2); 1.786 (1.1); 1.776 (0.6); 1.770 (0.8); 1.764 (0.6); 1.758 (0.4); 1.698 (0.4); 1.653 (4.1); 1.599 (0.4); 1.586 (0.3); 1.548 (0.4); 1.541 (0.4); 1.523 (0.9); 1.505 (1.0); 1.468 (3.4); 1.453 (1.6); 1.415 (1.4); 1.405 (1.4); 1.389 (9.5); 1.358 (1.0); 1.340 (1.1); 1.315 (1.4); 1.303 (3.2); 1.285 (4.6); 1.270 (11.8); 1.221 (12.0); 1.214 (12.0); 1.200 (3.3); 1.193 (1.3); 1.190 (1.5); 1.177 (1.0); 1.172 (1.1); 1.161 (0.7); 1.121 (0.6); 1.107 (0.6); 1.093 (0.9); 1.057 (0.7); 0.974 (0.4); 0.957 (0.5); 0.947 (0.6); 0.934 (0.5); 0.923 (0.7); 0.898 (1.3); 0.882 (3.1); 0.876 (2.5); 0.858 (2.8); 0.840 (1.7); 0.815 (0.6); 0.000 (3.4)

[1])The stated mass is the peak of the isotope pattern of the [M + H]⁺ ion of the highest intensity; if the [M − H]⁻ ion was detected, the stated mass is identified with [2].
[2]The stated mass is the peak of the isotope pattern of the [M − H]⁻ ion of the highest intensity.
[a)] Note regarding the determination of the logP values and mass detection: The logP values were determined according to EEC Directive 79/831 Annex V.A8 by HPLC (high-performance liquid chromatography) on a reversed-phase column (C18) Agilent 1100 LC system; 50 * 4.6 Zorbax Eclipse Plus C18 1.8 micron; eluent A: acetonitrile (0.1% formic acid); eluent B: water (0.09% formic acid); linear gradient from 10% acetonitrile to 95% acetonitrile in 4.25 min, then 95% acetonitrile for a further 1.25 min; oven temperature 55° C.; flow rate: 2.0 ml/min. Mass detection is effected by means of an Agilent MSD system.

Biological Examples

*Rhipicephalus sanguineus*—In Vitro Contact Tests with Adult Brown Dog Ticks

For the coating of the test tubes, 9 mg of active ingredient are first dissolved in 1 ml of acetone p.a. and then diluted to the desired concentration with acetone p.a. 250 µl of the solution are distributed homogeneously on the inner walls and base of a 25 ml test tube by turning and rocking on an orbital shaker (rocking rotation at 30 rpm for 2 h). With 900 ppm active ingredient solution and internal surface 44.7 cm², given homogeneous distribution, an area-based dose of 5 µg/cm² is achieved.

After the solvent has evaporated off, the tubes are populated with 5-10 adult dog ticks (*Rhipicephalus sanguineus*), sealed with a perforated plastic lid and incubated in a horizontal position in the dark at room temperature and ambient humidity. After 48 h, efficacy is determined. To this end, the ticks are knocked to the floor of the tube and incubated on a hotplate at 45-50° C. for not more than 5 min. Ticks which remain motionless on the floor or move in such an uncoordinated manner that they are unable to deliberately avoid the heat by climbing upwards are considered to be dead or moribund.

A substance shows good efficacy against *Rhipicephalus sanguineus* if at least 80% efficacy was achieved in this test at an application rate of 5 µg/cm². An efficacy of 100% means that all the ticks were dead or moribund. 0% efficacy means that none of the ticks had been harmed.

In this test, for example, the following compounds from the preparation examples show an efficacy of 100% at an application rate of 5 µg/cm²: I-T3-1, I-T3-3, I-T3-20, I-T3-21, I-T3-23, I-T3-24, I-T3-42, I-T3-44, I-T3-46, I-T3-47, I-T3-52, I-T3-53, I-T3-54, I-T3-55, I-T3-56, I-T3-61, I-T3-63, I-T3-71, I-T3-72, I-T3-81, I-T3-90, I-T3-91, I-T3-96, I-T3-97, I-T3-98, I-T3-104, I-T3-106, I-T3-109, I-T3-110, I-T3-112, I-T3-117, I-T3-119, I-T3-148, I-T3-155, I-T3-160, I-T3-161, I-T3-162, I-T3-163, I-T3-165, I-T3-175, I-T3-176, I-T3-189, I-T3-196, I-T4-1, I-T4-2, I-T4-3, I-T4-4, I-T22-2, I-T22-1, I- T22-4, I-T22-5, I-T22-6, I-T22-7

In this test, for example, the following compounds from the preparation examples show an efficacy of 80% at an application rate of 5 µg/cm²: I-T3-38, I-T3-43, I-T3-80, I-T3-88, I-T3-92, I-T3-143

In this test, for example, the following compounds from the preparation examples show an efficacy of 100% at an application rate of 1 µg/cm²: I-T3-108, I-T3-114, I-T3-141

In this test, for example, the following compounds from the preparation examples show an efficacy of 80% at an application rate of 1 µg/cm²: I-T3-94, I-T3-123

In this test, for example, the following compounds from the preparation examples show an efficacy of 100% at an application rate of 0.2 µg/cm²: I-T3-105

In this test, for example, the following compounds from the preparation examples show an efficacy of 80% at an application rate of 0.2 µg/cm²: I-T3-64

*Ctenocephalides felis*—In Vitro Contact Tests with Adult Cat Fleas

For the coating of the test tubes, 9 mg of active ingredient are first dissolved in 1 ml of acetone p.a. and then diluted to the desired concentration with acetone p.a. 250 µl of the solution are distributed homogeneously on the inner walls and base of a 25 ml test tube by turning and rocking on an orbital shaker (rocking rotation at 30 rpm for 2 h). With 900 ppm active ingredient solution and internal surface area 44.7 cm², given homogeneous distribution, an area-based dose of 5 µg/cm² is achieved.

After the solvent has evaporated off, the tubes are populated with 5-10 adult cat fleas (*Ctenocephalides felis*), sealed with a perforated plastic lid and incubated in a horizontal position at room temperature and ambient humidity. After 48 h, efficacy is determined. To this end, the test tubes are stood upright and the fleas are knocked to the base of the tube. Fleas which remain motionless at the base or move in an uncoordinated manner are considered to be dead or moribund.

A substance shows good efficacy against *Ctenocephalides felis* if at least 80% efficacy was achieved in this test at an application rate of 5 µg/cm². 100% efficacy means that all the fleas were dead or moribund. 0% efficacy means that no fleas were harmed.

In this test, for example, the following compounds from the preparation examples show an efficacy of 100% at an application rate of 5 µg/cm² (=500 g/ha): I-T3-1, I-T3-3, I-T3-7, I-T3-9, I-T3-17, I-T3-20, I-T3-21, I-T3-23, I-T3-24, I-T3-25, I-T3-27, I-T3-28, I-T3-29, I-T3-30, I-T3-31, I-T3-42, I-T3-43, I-T3-44, I-T3-46, I-T3-54, I-T3-55, I-T3-56, I-T3-57, I-T3-61, I-T3-63, I-T3-64, I-T3-71, I-T3-72, I-T3-80, I-T3-81, I-T3-84, I-T3-85, I-T3-86, I-T3-87, I-T3-88, I-T3-91, I-T3-92, I-T3-93, I-T3-94, I-T3-95, I-T3-96, I-T3-97, I-T3-98, I-T3-99, I-T3-100, I-T3-101, I-T3-102, I-T3-103, I-T3-106, I-T3-107, I-T3-108, I-T3-109, I-T3-110, I-T3-111, I-T3-112, I-T3-113, I-T3-114, I-T3-115, I-T3-116, I-T3-117, I-T3-118, I-T3-119, I-T3-120, I-T3-123, I-T3-124, I-T3-125, I-T3-127, I-T3-128, I-T3-129, I-T3-130, I-T3-131, I-T3-132, I-T3-133, I-T3-136, I-T3-137, I-T3-138, I-T3-143, I-T3-145, I-T3-147, I-T3-148, I-T3-155, I-T3-160, I-T3-162, I-T3-163, I-T3-165, I-T3-175, I-T3-176, I-T3-189, I-T3-196, I-T3-199, I-T4-2, I-T4-3, I-T4-4, I-T22-1, I-T22-2, I-T22-3, I-T22-5, I-T22-7, I-T23-1, I-T23-2, I-T46-2

*Amblyomma hebaraeum* Test

Solvent: dimethyl sulphoxide

To produce an appropriate active ingredient formulation, 10 mg of active ingredient are mixed with 0.5 ml of dimethyl sulphoxide, and the concentrate is diluted with water to the desired concentration.

Tick nymphs (*Amblyomma hebraeum*) are placed into perforated plastic beakers and immersed in the desired concentration for one minute. The ticks are transferred on filter paper into a Petri dish and stored in a climate-controlled cabinet.

After 42 days, the kill in % is determined. 100% means that all of the ticks have been killed; 0% means that none of the ticks have been killed.

In this test, for example, the following compounds from the preparation examples show an efficacy of 100% at an application rate of 100 ppm: I-T3-1, I-T3-3, I-T3-20, I-T3-21, I-T3-24, I-T3-28, I-T3-42, I-T3-43, I-T3-44, I-T3-54, I-T3-55, I-T3-56, I-T3-57, I-T3-63, I-T3-64, I-T3-71, I-T3-72, I-T3-81, I-T3-86, I-T3-91, I-T3-92, I-T3-95, I-T3-96, I-T3-97, I-T3-98, I-T3-100, I-T3-104, I-T3-106, I-T3-107, I-T3-108, I-T3-109, I-T3-110, I-T3-112, I-T3-114, I-T3-116, I-T3-117, I-T3-119, I-T3-124, I-T3-125, I-T3-131, I-T3-148, I-T3-155, I-T3-162, I-T3-163, I-T22-1, I-T22-2, I-T23-1, I-T4-3, I-T4-4

In this test, for example, the following compounds from the preparation examples show an efficacy of 95% at an application rate of 100 ppm: I-T3-101

In this test, for example, the following compounds from the preparation examples show an efficacy of 90% at an application rate of 100 ppm: I-T3-102, I-T3-103

In this test, for example, the following compounds from the preparation examples show an efficacy of 85% at an application rate of 100 ppm: I-T3-105

In this test, for example, the following compounds from the preparation examples show an efficacy of 80% at an application rate of 100 ppm: I-T3-53, I-T3-61, I-T3-111, I-T3-123

*Boophilus microplus*—Injection Test

Solvent: dimethyl sulphoxide

To produce an appropriate active ingredient formulation, 10 mg of active ingredient are mixed with 0.5 ml of solvent and the concentrate is diluted with solvent to the desired concentration.

1 µl of the active ingredient solution is injected into the abdomen of 5 engorged adult female cattle ticks (*Boophilus microplus*). The animals are transferred into dishes and kept in a climate-controlled room.

Efficacy is assessed after 7 days by laying of fertile eggs. Eggs which are not visibly fertile are stored in a climate-controlled cabinet until the larvae hatch after about 42 days. An efficacy of 100% means that none of the ticks has laid any fertile eggs; 0% means that all the eggs are fertile.

In this test, for example, the following compounds from the preparation examples show an efficacy of 100% at an application rate of 20 µg/animal: I-T2-1, I-T2-2, I-T3-1, I-T3-2, I-T3-3, I-T3-4, I-T3-5, I-T3-6, I-T3-7, I-T3-8, I-T3-9, I-T3-10, I-T3-11, I-T3-12, I-T3-13, I-T3-15, I-T3-17, I-T3-18, I-T3-19, I-T3-20, I-T3-21, I-T3-23, I-T3-24, I-T3-25, I-T3-26, I-T3-27, I-T3-28, I-T3-29, I-T3-30, I-T3-31, I-T3-32, I-T3-33, I-T3-34, I-T3-35, I-T3-36, I-T3-37, I-T3-38, I-T3-39, I-T3-40, I-T3-41, I-T3-42, I-T3-43, I-T3-44, I-T3-45, I-T3-46, I-T3-47, I-T3-48, I-T3-49, I-T3-50, I-T3-51, I-T3-52, I-T3-53, I-T3-54, I-T3-55, I-T3-56, I-T3-57, I-T3-58, I-T3-59, I-T3-60, I-T3-61, I-T3-62, I-T3-63, I-T3-64, I-T3-65, I-T3-66, I-T3-67, I-T3-68, I-T3-69, I-T3-70, I-T3-71, I-T3-72, I-T3-73, I-T3-74, I-T3-76, I-T3-77, I-T3-78, I-T3-79, I-T3-80, I-T3-81, I-T3-82, I-T3-83, I-T3-84, I-T3-85, I-T3-86, I-T3-87, I-T3-88, I-T3-89, I-T3-90, I-T3-91, I-T3-92, I-T3-93, I-T3-94, I-T3-95, I-T3-96, I-T3-97, I-T3-98, I-T3-99, I-T3-100, I-T3-101, I-T3-102, I-T3-103, I-T3-104, I-T3-105, I-T3-106, I-T3-107, I-T3-108, I-T3-109, I-T3-110, I-T3-111, I-T3-112, I-T3-113, I-T3-114, I-T3-115, I-T3-116, I-T3-117, I-T3-118, I-T3-119, I-T3-120, I-T3-123, I-T3-124, I-T3-125, I-T3-126, I-T3-127, I-T3-128, I-T3-129, I-T3-130, I-T3-131, I-T3-132, I-T3-133, I-T3-136, I-T3-137, I-T3-145, I-T3-139, I-T3-140, I-T3-141, I-T3-142, I-T3-143, I-T3-144, I-T3-146, I-T3-148, I-T3-149, I-T3-150, I-T3-151, I-T3-155, I-T3-160, I-T3-161, I-T3-162, I-T3-163, I-23-165, I-T3-168, I-T3-175, I-T3-176, I-T3-89, I-T4-1, I-T4-2, I-T4-3, I-T4-4, I-T22-1, I-T22-2, I- T22-3, I-T22-4, I-T22-5, I-T22-6, I-T22-7, I-T23-1, I-T23-2, I-T46-2

In this test, for example, the following compounds from the preparation examples show an efficacy of 90% at an application rate of 20 μg/animal: I-T3-75

In this test, for example, the following compounds from the preparation examples show an efficacy of 80% at an application rate of 20 μg/animal: I-T3-121

Boophilus microplus—Dip Test

Test animals: cattle ticks (Boophilus microplus) Parkhurst strain, SP-resistant

Solvent: dimethyl sulphoxide 10 mg of active ingredient are dissolved in 0.5 ml of dimethyl sulphoxide. For the purpose of producing a suitable formulation, the active ingredient solution is diluted with water to the concentration desired in each case.

This active ingredient formulation is pipetted into tubes. 8-10 adult engorged female cattle ticks (Boophilus microplus) are transferred into a further tube with holes. The tube is immersed into the active ingredient formulation, and all the ticks are completely wetted. After the liquid has run out, the ticks are transferred on filter discs into plastic dishes and stored in a climate-controlled room.

Efficacy is assessed after 7 days by laying of fertile eggs. Eggs which are not visibly fertile are stored in a climate-controlled cabinet until the larvae hatch after about 42 days. An efficacy of 100% means that none of the ticks has laid any fertile eggs; 0% means that all the eggs are fertile.

In this test, for example, the following compounds from the preparation examples show an efficacy of 100% at an application rate of 100 ppm: I-T3-1, I-T3-3, I-T3-20, I-T3-21, I-T3-24, I-T3-28, I-T3-39, I-T3-42, I-T3-43, I-T3-44, I-T3-48, I-T3-53, I-T3-54, I-T3-55, I-T3-56, I-T3-57, I-T3-61, I-T3-63, I-T3-64, I-T3-71, I-T3-72, I-T3-81, I-T3-86, I-T3-91, I-T3-92, I-T3-95, I-T3-96, I-T3-97, I- T3-98, I-T3-100, I-T3-101, I-T3-102, I-T3-103, I-T3-104, I-T3-106, I-T3-107, I-T3-108, I-T3-109, I-T3-110, I-T3-112, I-T3-113, I-T3-114, I-T3-115, I-T3-116, I-T3-117, I-T3-118, I-T3-119, I-T3-120, I-T3-123, I-T3-124, I-T3-125, I-T3-130, I-T3-131, I-T3-133, I-T3-148, I-T3-155, I-T3-160, I-T3-162, I-T3-163, I-T3-165, I-T3-175, I-T3-176, I-T4-3, I-T4-4, I-T22-1, I-T22-2, I-T22-4, I-T22-5, I-T22-6, I-T22-7, I-T23-1

In this test, for example, the following compounds from the preparation examples show an efficacy of 98% at an application rate of 100 ppm: I-T3-111

In this test, for example, the following compounds from the preparation examples show an efficacy of 90% at an application rate of 100 ppm: I-T3-99

In this test, for example, the following compounds from the preparation examples show an efficacy of 80% at an application rate of 100 ppm: I-T3-27, I-T3-80

Ctenocephalides felis—Oral Test

Solvent: dimethyl sulphoxide

For the purpose of producing an appropriate active ingredient formulation, 10 mg of active ingredient are mixed with 0.5 ml of dimethyl sulphoxide. Dilution with citrated cattle blood gives the desired concentration.

About 20 unfed adult cat fleas (Ctenocephalides felis) are placed into a chamber which is closed at the top and bottom with gauze. A metal cylinder whose bottom end is closed with parafilm is placed onto the chamber. The cylinder contains the blood/active ingredient preparation, which can be imbibed by the fleas through the parafilm membrane.

After 2 days, the kill in % is determined. 100% means that all of the fleas have been killed; 0% means that none of the fleas have been killed.

In this test, for example, the following compounds from the preparation examples show an efficacy of 100% at an application rate of 100 ppm: I-T3-1, I-T3-2, I-T3-3, I-T3-4, I-T3-5, I-T3-7, I-T3-8, I-T3-9, I-T3-10, I-T3-12, I-T3-18, I-T3-20, I-T3-21, I-T3-23, I-T3-24, I-T3-25, I-T3-26, I-T3-27, I-T3-28, I-T3-29, I-T3-30, I-T3-31, I-T3-32, I-T3-33, I-T3-34, I-T3-35, I-T3-38, I-T3-39, I-T3-40, I-T3-42, I-T3-43, I-T3-44, I-T3-46, I-T3-47, I-T3-48, I-T3-49, I-T3-50, I-T3-51, I-T3-52, I-T3-53, I-T3-54, I-T3-55, I-T3-56, I-T3-57, I-T3-58, I-T3-59, I-T3-61, I-T3-62, I-T3-63, I-T3-64, I-T3-65, I-T3-66, I-T3-67, I- T3-68, I-T3-69, I-T3-71, I-T3-72, I-T3-73, I-T3-76, I-T3-77, I-T3-78, I-T3-80, I-T3-81, I-T3-84, I-T3-85, I-T3-86, I-T3-87, I-T3-88, I-T3-89, I-T3-90, I-T3-91, I-T3-92, I-T3-93, I-T3-94, I-T3-95, I-T3-96, I- T3-97, I-T3-98, I-T3-99, I-T3-100, I-T3-101, I-T3-102, I-T3-103, I-T3-104, I-T3-105, I-T3-106, I-T3-107, I-T3-108, I-T3-109, I-T3-110, I-T3-111, I-T3-112, I-T3-113, I-T3-114, I-T3-115, I-T3-116, I-T3-117, I-T3-118, I-T3-119, I-T3-120, I-T3-123, I-T3-124, I-T3-125, I-T3-127, I-T3-128, I-T3-129, I-T3-130, I-T3-131, I-T3-132, I-T3-133, I-T3-135, I-T3-136, I-T3-137, I-T3-139, I-T3-140, I-T3-141, I-T3-143, I-T3-145, I-T3-146, I-T3-148, I-T3-149, I-T3-150, I-T3-151, I-T3-155, I-T3-160, I-T3-161, I-T3-162, I-T3-163, I-T3-165, I-T3-168, I-T3-175, I-T3-176, I-T3-189, I-T4-1, I-T4-2, I-T4-3, I-T4-4, I-T22-1, I- T22-2, I-T22-3, I-T22-4, I-T22-5, I-T22-7, I-T23-1, I-T23-2, I-T46-2

In this test, for example, the following compounds from the preparation examples show an efficacy of 95% at an application rate of 100 ppm: I-T3-11, I-T3-17, I-T3-19, I-T3-41, I-T3-45, I-T3-70, I-T3-79, I-T3-82, I-T3-83, I-T22-6

In this test, for example, the following compounds from the preparation examples show an efficacy of 90% at an application rate of 100 ppm: I-T3-15, I-T3-37, I-T3-60, I-T3-126, I-T3-144

In this test, for example, the following compounds from the preparation examples show an efficacy of 80% at an application rate of 100 ppm: I-T3-13, I-T3-16, I-T3-36

Lucilia cuprina Test

Solvent: dimethyl sulphoxide

To produce an appropriate active ingredient formulation, 10 mg of active ingredient are mixed with 0.5 ml of dimethyl sulphoxide, and the concentrate is diluted with water to the desired concentration.

About 20 L1 larvae of the Australian sheep blowfly (Lucilia cuprina) are transferred into a test vessel containing minced horsemeat and the active ingredient preparation of the desired concentration.

After 2 days, the kill in % is determined. 100% means that all the larvae have been killed; 0% means that none of the larvae have been killed.

In this test, for example, the following compounds from the preparation examples show an efficacy of 100% at an application rate of 100 ppm: I-T3-1, I-T3-2, I-T3-3, I-T3-4, I-T3-5, I-T3-6, I-T3-7, I-T3-8, I-T3-9, I-T3-10, I-T3-15, I-T3-17, I-T3-18, I-T3-20, I-T3-21, I-T3-23, I-T3-24, I-T3-25, I-T3-26, I-T3-27, I-T3-28, I-T3-29, I-T3-30, I-T3-31, I-T3-32, I-T3-33, I-T3-34, I-T3-35, I-T3-36, I- T3-37, I-T3-38, I-T3-39, I-T3-40, I-T3-42, I-T3-43, I-T3-44, I-T3-45, I-T3-46, I-T3-47, I-T3-48, I-T3-49, I-T3-50, I-T3-51, I-T3-52, I-T3-53, I-T3-54, I-T3-55, I-T3-56, I-T3-57, I-T3-58, I-T3-59, I-T3-61, I- T3-62, I-T3-63, I-T3-64, I-T3-65, I-T3-66, I-T3-67, I-T3-68, I-T3-70, I-T3-71, I-T3-72, I-T3-73, I-T3-77, I-T3-78, I-T3-80, I-T3-81, I-T3-82, I-T3-83, I-T3-

84, I-T3-85, I-T3-86, I-T3-87, I-T3-88, I-T3-89, I- T3-90, I-T3-91, I-T3-92, I-T3-93, I-T3-94, I-T3-96, I-T3-97, I-T3-98, I-T3-99, I-T3-100, I-T3-101, I-T3-102, I-T3-103, I-T3-104, I-T3-105, I-T3-106, I-T3-107, I-T3-108, I-T3-109, I-T3-110, I-T3-111, I-T3-112, I-T3-113, I-T3-114, I-T3-115, I-T3-116, I-T3-117, I-T3-118, I-T3-119, I-T3-120, I-T3-123, I-T3-124, I-T3-125, I-T3-130, I-T3-131, I-T3-133, I-T3-136, I-T3-139, I-T3-140, I-T3-141, I-T3-143, I-T3-144, I-T3-145, I-T3-148, I-T3-149, I-T3-150, I-T3-151, I-T3-155, I-T3-160, I-T3-161, I-T3-162, I-T3-163, I-T3-165, I-T3-168, I-T3-175, I-T3-176, I-T3-189, I-T4-1, I-T4-2, I-T4-3, I-T4-4, I-T22-1, I-T22-2, I-T22-3, I-T22-5, I-T22-6, I-T22-7, I-T23-1, I-T23-2, I-T46-2

In this test, for example, the following compounds from the preparation examples show an efficacy of 95% at an application rate of 100 ppm: I-T3-69

In this test, for example, the following compounds from the preparation examples show an efficacy of 90% at an application rate of 100 ppm: I-T3-41, I-T3-60, I-T3-74, I-T3-76, I-T3-127, I-T3-146

In this test, for example, the following compounds from the preparation examples show an efficacy of 80% at an application rate of 100 ppm: I-T3-12, I-T3-75, I-T3-79, I-T3-121, I-T3-137

*Musca domestica* Test

Solvent: dimethyl sulphoxide

To produce an appropriate active ingredient formulation, 10 mg of active ingredient are mixed with 0.5 ml of dimethyl sulphoxide, and the concentrate is diluted with water to the desired concentration.

Vessels containing a sponge treated with sugar solution and the active ingredient formulation of the desired concentration are populated with 10 adult houseflies (*Musca domestica*).

After 2 days, the kill in % is determined. 100% means that all of the flies have been killed; 0% means that none of the flies have been killed.

In this test, for example, the following compounds from the preparation examples show an efficacy of 100% at an application rate of 100 ppm: I-T3-1, I-T3-2, I-T3-3, I-T3-4, I-T3-5, I-T3-8, I-T3-20, I-T3-21, I-T3-23, I-T3-24, I-T3-25, I-T3-26, I-T3-27, I-T3-29, I-T3-31, I-T3-34, I-T3-38, I-T3-42, I-T3-43, I-T3-46, I-T3-48, I-T3-52, I-T3-53, I-T3-54, I-T3-55, I-T3-56, I-T3-57, I-T3-58, I-T3-61, I-T3-62, I-T3-63, I-T3-64, I-T3-65, I-T3-71, I-T3-72, I-T3-73, I-T3-77, I-T3-80, I-T3-84, I-T3-85, I- T3-86, I-T3-87, I-T3-89, I-T3-91, I-T3-92, I-T3-93, I-T3-94, I-T3-96, I-T3-97, I-T3-100, I-T3-101, I-T3-102, I-T3-103, I-T3-104, I-T3-106, I-T3-107, I-T3-108, I-T3-109, I-T3-110, I-T3-111, I-T3-112, I-T3-113, I-T3-114, I-T3-115, I-T3-116, I-T3-117, I-T3-118, I-T3-119, I-T3-120, I-T3-123, I-T3-124, I-T3-125, I-T3-130, I-T3-131, I-T3-133, I-T3-136, I-T3-137, I-T3-141, I-T3-143, I-T3-144, I-T3-148, I-T3-149, I-T3-150, I-T3-151, I-T3-155, I-T3-160, I-T3-161, I-T3-162, I-T3-163, I-T3-165, I-T3-175, I-T3-176, I-T3-189, I-T4-2, I-T22-1, I-T22-2, I-T22-3, I-T22-5, I-T22-7, I-T23-1, I-T23-2

In this test, for example, the following compounds from the preparation examples show an efficacy of 95% at an application rate of 100 ppm: I-T3-51

In this test, for example, the following compounds from the preparation examples show an efficacy of 90% at an application rate of 100 ppm: I-T3-30, I-T3-67, I-T3-76, I-T3-81, I-T3-90, I-T3-98, I-T3-99, I-T3-139, I-T3-145, I-T22-6

In this test, for example, the following compounds from the preparation examples show an efficacy of 80% at an application rate of 100 ppm: I-T3-7, I-T3-66, I-T3-68, I-T3-79, I-T3-88, I-T3-105, I-T3-121, I-T3-129

In this test, for example, the following compounds from the preparation examples show an efficacy of 80% at an application rate of 20 ppm: I-T3-28

In this test, for example, the following compounds from the preparation examples show an efficacy of 80% at an application rate of 4 ppm: I-T3-35

*Meloidogyne incognita* Test

Solvent: 125.0 parts by weight of acetone

To produce an appropriate active ingredient formulation, 1 part by weight of active ingredient is mixed with the stated amount of solvent and the concentrate is diluted with water to the desired concentration.

Vessels are filled with sand, active ingredient solution, an egg/larvae suspension of the southern root-knot nematode (*Meloidogyne incognita*) and lettuce seeds. The lettuce seeds germinate and the plants develop. The galls develop on the roots.

After 14 days, the nematicidal efficacy in % is determined by the formation of galls. 100% means that no galls were found; 0% means that the number of galls on the treated plants corresponds to the untreated control.

In this test, for example, the following compounds from the preparation examples show efficacy of 90% at an application rate of 20 ppm: I-T3-27, I-T3-28, I-T3-184, I-T3-185

*Myzus persicae*—Spray Test

Solvent: 78 parts by weight of acetone and 1.5 parts by weight of dimethylformamide Emulsifier: alkylaryl polyglycol ether To produce an appropriate active ingredient formulation, 1 part by weight of active ingredient is dissolved using the specified parts by weight of solvent and made up with water containing an emulsifier concentration of 1000 ppm until the desired concentration is attained. To produce further test concentrations, the preparation is diluted with emulsifier-containing water.

Discs of Chinese cabbage leaves (*Brassica pekinensis*) infested by all stages of the green peach aphid (*Myzus persicae*) are sprayed with an active ingredient formulation of the desired concentration.

After 6 days, efficacy in % is determined. 100% means that all the aphids have been killed; 0% means that none of the aphids have been killed.

In this test, for example, the following compounds from the preparation examples show efficacy of 100% at an application rate of 500 g/ha: I-T3-7, I-T3-20, I-T3-43, I-T3-44, I-T3-46, I-T3-92, I-T3-100, I-T3-106, I-T3-107, I-T3-108, I-T3-110, I-T3-122, I-T3-185, I-T3-187

In this test, for example, the following compounds from the preparation examples show efficacy of 90% at an application rate of 500 g/ha: I-T3-8, I-T3-21, I-T3-29, I-T3-30, I-T3-42, I-T3-91, I-T3-97, I-T3-103, I-T3-105, I-T3-109, I-T3-114, I-T3-117, I-T3-119, I-T3-120, I-T3-186

In this test, for example, the following compounds from the preparation examples show efficacy of 100% at an application rate of 100 g/ha: I-T3-1, I-T3-3, I-T3-27, I-T3-54, I-T3-55, I-T3-77, I-T3-88, I-T3-99, I-T3-101, I-T3-112, I-T3-113, I-T3-115, I-T3-116, I-T3-118, I-T3-120, I-T3-123, I-T3-124, I- T3-125, I-T3-127, I-T3-128, I-T3-129, I-T3-130, I-T3-162, I-T3-165, I-T3-170, I-T3-174, I-T3-175, I-T3-176, I-T3-179, I-T3-184, I-T3-189, I-T22-1, I-T22-2, I-T22-5, I-T22-7

In this test, for example, the following compounds from the preparation examples show efficacy of 90% at an application rate of 100 g/ha: I-T3-28, I-T3-38, I-T3-39, I-T3-53, I-T3-64, I-T3-72, I-T3-76, I-T3-80, I-T3-81, I-T3-85, I-T3-

87, I-T3-95, I-T3-96, I-T3-98, I-T3-131, I-T3-132, I-T3-145, I-T3-160, I-T3-164, I-T3-163, I-T4-3

In this test, for example, the following compounds from the preparation examples show efficacy of 90% at an application rate of 20 g/ha: I-T3-182, I-T4-2

*Phaedon cochleariae*—Spray Test

Solvent: 78.0 parts by weight of acetone and 1.5 parts by weight of dimethylformamide Emulsifier: alkylaryl polyglycol ether To produce an appropriate active ingredient formulation, 1 part by weight of active ingredient is dissolved using the specified parts by weight of solvent and made up with water containing an emulsifier concentration of 1000 ppm until the desired concentration is attained. To produce further test concentrations, the preparation is diluted with emulsifier-containing water.

Discs of Chinese cabbage leaves (*Brassica pekinensis*) are sprayed with an active ingredient formulation of the desired concentration and, after drying, populated with larvae of the mustard beetle (*Phaedon cochleariae*).

After 7 days, efficacy in % is determined. 100% means that all the beetle larvae have been killed; 0% means that no beetle larvae have been killed.

In this test, for example, the following compounds from the preparation examples show efficacy of 100% at an application rate of 500 g/ha: I-T3-7, I-T3-8, I-T3-9, I-T3-10, I-T3-12, I-T3-15, I-T3-17, I-T3-18, I-T3-19, I-T3-20, I-T3-21, I-T3-22, I-T3-23, I-T3-24, I-T3-25, I-T3-26, I-T3-29, I-T3-30, I-T3-31, I-T3-34, I-T3-35, I-T3-36, I-T3-37, I-T3-42, I-T3-43, I-T3-44, I-T3-45, I-T3-46, I-T3-47, I- T3-65, I-T3-66, I-T3-67, I-T3-68, I-T3-69, I-T3-70, I-T3-73, I-T3-74, I-T3-75, I-T3-76, I-T3-77, I-T3-78, I-T3-79, I-T3-89, I-T3-90, I-T3-91, I-T3-92, I-T3-96, I-T3-97, I-T3-98, I-T3-100, I-T3-101, I-T3-102, I-T3-103, I-T3-104, I-T3-105, I-T3-106, I-T3-107, I-T3-108, I-T3-109, I-T3-110, I-T3-111, I-T3-112, I-T3-113, I-T3-114, I-T3-115, I-T3-116, I-T3-117, I-T3-118, I-T3-119, I-T3-120, I-T3-126, I-T3-184, I-T3-185, I-T3-186, I-T3-187, I-T3-188, I-T23-1, I-T23-2

In this test, for example, the following compounds from the preparation examples show efficacy of 100% at an application rate of 100 g/ha: I-T2-1, I-T2-2, I-T3-1, I-T3-2, I-T3-3, I-T3-4, I-T3-5, I-T3-6, I-T3-27, I-T3-28, I-T3-38, I-T3-39, I-T3-40, I-T3-41, I-T3-48, I-T3-49, I-T3-50, I-T3-51, I-T3- 52, I-T3-53, I-T3-54, I-T3-55, I-T3-56, I-T3-57, I-T3-58, I-T3-59, I-T3-61, I-T3-62, I-T3-63, I-T3-64, I-T3-71, I-T3-72, I-T3-80, I-T3-81, I-T3-82, I-T3-83, I-T3-84, I-T3-85, I-T3-86, I-T3-87, I-T3-88, I-T3-93, I-T3-94, I-T3-95, I-T3-99, I-T3-123, I-T3-124, I-T3-125, I-T3-127, I-T3-128, I-T3-129, I-T3-130, I-T3-131, I-T3-132, I-T3-133, I-T3-136, I-T3-137, I-T3-139, I-T3-140, I-T3-141, I-T3-143, I-T3-144, I-T3-145, I-T3-148, I-T3-149, I-T3-151, I-T3-152, I-T3-153, I-T3-155, I-T3-160, I-T3-161, I-T3-162, I-T3-163, I-T3-164, I-T3-165, I-T3-168, I-T3-169, I-T3-170, I-T3-171, I-T3-172, I-T3-174, I-T3-175, I-T3-176, I-T3-177, I-T3-178, I-T3-179, I-T3-180, I-T3-181, I-T3-182, I-T3-183, I-T3-189, I-T3-190, I-T3-191, I-T3-192, I-T3-195, I-T3-197, I-T3-198, I-T3-220, I-T3-221, I-T3-222, I-T3-223, I-T4-1, I-T4-2, I-T4- 3, I-T4-4, I-T22-1, I-T22-2, I-T22-3, I-T22-4, I-T22-5, I-T22-6, I-T22- 7, I-T46-2, I-T46-3, I-T46- 4, I-T46-5, I-T46-6

In this test, for example, the following compounds from the preparation examples show efficacy of 83% at an application rate of 100 g/ha: I-T3-138

*Spodoptera frugiperda*—Spray Test

Solvent: 78.0 parts by weight of acetone and 1.5 parts by weight of dimethylformamide Emulsifier: alkylaryl polyglycol ether To produce an appropriate active ingredient formulation, 1 part by weight of active ingredient is dissolved using the specified parts by weight of solvent and made up with water containing an emulsifier concentration of 1000 ppm until the desired concentration is attained. To produce further test concentrations, the preparation is diluted with emulsifier-containing water.

Leaf discs of maize (*Zea mays*) are sprayed with an active ingredient formulation of the desired concentration and, after drying, populated with caterpillars of the armyworm (*Spodoptera frugiperda*).

After 7 days, efficacy in % is determined. 100% means that all the caterpillars have been killed; 0% means that no caterpillars have been killed.

In this test, for example, the following compounds from the preparation examples show efficacy of 100% at an application rate of 500 g/ha: I-T3-7, I-T3-8, I-T3-9, I-T3-10, I-T3-12, I-T3-17, I-T3-18, I-T3-19, I-T3-20, I-T3-21, I-T3-22, I-T3-23, I-T3-24, I-T3-25, I-T3-26, I-T3-29, I-T3-30, I-T3-31, I-T3-34, I-T3-42, I-T3-43, I-T3-44, I-T3-45, I-T3-46, I-T3-47, I-T3-65, I-T3-66, I-T3-67, I-T3-68, I- T3-69, I-T3-70, I-T3-73, I-T3-74, I-T3-75, I-T3-76, I-T3-77, I-T3-78, I-T3-79, I-T3-89, I-T3-90, I-T3-91, I-T3-92, I-T3-96, I-T3-97, I-T3-98, I-T3-100, I-T3-102, I-T3-103, I-T3-104, I-T3-105, I-T3-106, I-T3-107, I-T3-108, I-T3-109, I-T3-110, I-T3-111, I-T3-112, I-T3-113, I-T3-114, I-T3-115, I-T3-116, I-T3-117, I-T3-118, I-T3-119, I-T3-120, I-T3-126, I-T3-184, I-T3-185, I-T3-186, I-T3-187, I-T23-1, I-T23-2

In this test, for example, the following compounds from the preparation examples show efficacy of 83% at an application rate of 500 g/ha: I-T3-101

In this test, for example, the following compounds from the preparation examples show efficacy of 100% at an application rate of 100 g/ha: I-T2-2, I-T3-1, I-T3-2, I-T3-3, I-T3-4, I-T3-27, I-T3-28, I-T3-38, I-T3-39, I-T3-40, I-T3-41, I-T3-48, I-T3-52, I-T3-53, I-T3-54, I-T3-55, I-T3-56, I-T3-57, I-T3-58, I-T3-61, I-T3-62, I-T3-63, I-T3-64, I-T3-71, I-T3-72, I-T3-80, I-T3-81, I-T3-82, I-T3-83, I- T3-84, I-T3-85, I-T3-86, I-T3-87, I-T3-88, I-T3-93, I-T3-94, I-T3-95, I-T3-99, I-T3-123, I-T3-124, I-T3-125, I-T3-130, I-T3-131, I-T3-133, I-T3-136, I-T3-137, I-T3-138, I-T3-139, I-T3-140, I-T3-141, I-T3-143, I-T3-145, I-T3-148, I-T3-151, I-T3-152, I-T3-155, I-T3-160, I-T3-161, I-T3-162, I-T3-163, I-T3-164, I-T3-165, I-T3-170, I-T3-174, I-T3-175, I-T3-176, I-T3-189, I-T3-191, I-T3-192, I-T3-197, I-T3-198, I-T4-1, I-T4-2, I-T4-3, I-T4-4, I-T22-1, I-T22-2, I-T22-3, I-T22-5, I-T22-7, I-T46-2, I-T46-3, I-T46-4, I-T46-5, I-T46-6

In this test, for example, the following compounds from the preparation examples show efficacy of 83% at an application rate of 100 g/ha: I-T3-35, I-T3-50, I-T3-169, I-T3-177

*Tetranychus urticae*—Spray Test, OP-Resistant

Solvent: 78.0 parts by weight of acetone and 1.5 parts by weight of dimethylformamide Emulsifier: alkylaryl polyglycol ether To produce an appropriate active ingredient formulation, 1 part by weight of active ingredient is dissolved using the specified parts by weight of solvent and made up with water containing an emulsifier concentration of 1000 ppm until the desired concentration is attained. To produce further test concentrations, the preparation is diluted with emulsifier-containing water.

Discs of bean leaves (*Phaseolus vulgaris*) infested by all stages of the greenhouse red spider mite (*Tetranychus urticae*) are sprayed with an active ingredient formulation of the desired concentration.

After 6 days, efficacy in % is determined. 100% means that all the spider mites have been killed; 0% means that none of the spider mites have been killed.

In this test, for example, the following compounds from the preparation examples show an efficacy of 100% at an application rate of 500 g/ha: I-T3-7, I-T3-8, I-T3-9, I-T3-10, I-T3-20, I-T3-21, I-T3-22, I-T3-23, I-T3-24, I-T3-26, I-T3-29, I-T3-30, I-T3-31, I-T3-34, I-T3-42, I-T3-43, I-T3-44, I-T3-45, I-T3-46, I-T3-47, I-T3-69, I-T3-75, I-T3-76, I-T3-77, I-T3-78, I-T3-91, I-T3-92, I-T3-96, I-T3-97, I-T3-98, I-T3-100, I-T3-101, I-T3-103, I-T3-106, I-T3-107, I-T3-108, I-T3-109, I-T3-110, I-T3-112, I-T3-113, I-T3-114, I-T3-115, I-T3-119, I-T3-120, I-T3-184, I-T3-185, I-T3-186, I-T3-187, I-T23-1, I-T23-2

In this test, for example, the following compounds from the preparation examples show an efficacy of 90% at an application rate of 500 g/ha: I-T3-25, I-T3-65, I-T3-70, I-T3-89, I-T3-90, I-T3-102, I-T3-104, I-T3-105, I-T3-116, I-T3-117, I-T3-118

In this test, for example, the following compounds from the preparation examples show an efficacy of 100% at an application rate of 100 g/ha: I-T3-1, I-T3-2, I-T3-3, I-T3-4, I-T3-27, I-T3-28, I-T3-38, I-T3-39, I-T3-41, I-T3-51, I-T3-53, I-T3-54, I-T3-55, I-T3-56, I-T3-57, I-T3-58, I-T3-61, I-T3-62, I-T3-63, I-T3-64, I-T3-72, I-T3-73, I-T3-80, I-T3-81, I-T3-82, I-T3-83, I-T3-84, I-T3-85, I-T3-86, I-T3-87, I-T3-88, I-T3-93, I-T3-94, I-T3-95, I-T3-99, I-T3-124, I-T3-125, I-T3-127, I-T3-129, I-T3-130, I-T3-131, I-T3-132, I-T3-133, I-T3-139, I-T3-145, I-T3-146, I-T3-155, I-T3-160, I-T3-161, I-T3-162, I-T3-163, I-T3-164, I-T3-165, I-T3-168, I-T3-169, I-T3-170, I-T3-174, I-T3-175, I-T3-176, I-T3-177, I-T3-178, I-T3-179, I-T3-180, I-T3-181, I-T3-182, I-T3-183, I-T3-189, I-T3-190, I-T3-192, I-T3-197, I-T3-221, I-T3-222, I-T3-223, I-T4-1, I-T4-2, I-T4-3, I-T4-4, I-T22-4, I-T22-5, I-T22-7, I-T46-4, I-T46-5, I-T46-6

In this test, for example, the following compounds from the preparation examples show an efficacy of 90% at an application rate of 100 g/ha: I-T3-50, I-T3-52, I-T3-71, I-T3-74, I-T3-111, I-T3-123, I-T3-137, I-T3-138, I-T3-147, I-T3-148, I-T3-151, I-T3-172, I-T3-195, I-T22-1, I-T22-2, I-T22-3

In this test, for example, the following compounds from the preparation examples show an efficacy of 100% at an application rate of 20 g/ha: I-T3-49

*Anopheles* Test (ANPHGB Surface Treatment)

Solvent: acetone+2000 ppm rapeseed oil methyl ester (RME)

To produce an appropriate active ingredient formulation, the active ingredient is dissolved in the solvent (2 mg/ml). The active ingredient formulation is pipetted onto a glazed tile and, after it has dried off, adult mosquitoes of the species *Anopheles gambiae* strain RSPH (homozygot kdr) are placed onto the treated tile. The exposure time is 30 minutes.

24 hours after contact with the treated surface, mortality in % is determined. 100% means that all mosquitoes have been killed; 0% means that none of the mosquitoes have been killed.

In this test, for example, the following compounds from the preparation examples show efficacy of 90-100% at an application rate of 100 mg/m$^2$: I-T3-20, I-T3-24, I-T3-27, I-T3-28, I-T3-43, I-T3-52, I-T3-53, I-T3-54, I-T3-56, I-T3-57, I-T3-61, I-T3-100, I-T3-102, I-T3-112, I-T3-123, I-T3-130, I-T3-133, I-T3-134, I-T3-136, I-T3-145, I-T3-148, I-T3-155, I-T3-160, I-T3-162, I-T3-173, I-T3-189, I-T22-1

In this test, for example, the following compounds from the preparation examples show efficacy of 90-100% at an application rate of 20 mg/m$^2$: I-T3-23, I-T3-24, I-T3-26, I-T3-27, I-T3-28, I-T3-43, I-T3-52, I-T3-53, I-T3-54, I-T3-57, I-T3-58, I-T3-61, I-T3-87, I-T3-91, I-T3-92, I-T3-100, I-T3-102, I-T3-106, I-T3-112, I-T3-116, I-T3-130, I-T3-133, I-T3-134, I-T3-136, I-T3-137, I-T3-145, I-T3-148, I-T3-155, I-T3-159, I-T3-160, I-T3-162, I-T3-189, I-T22-2

*Anopheles* Test (ANPHFU Surface Treatment)

Solvent: acetone+2000 ppm rapeseed oil methyl ester (RME)

To produce an appropriate active ingredient formulation, the active ingredient is dissolved in the solvent (2 mg/ml). The active ingredient formulation is pipetted onto a glazed tile and, after it has dried off, adult mosquitoes of the species *Anopheles funestus* strain FUMOZ-R (Hunt et al., Med Vet Entomol. 2005 September; 19(3):271-5) are placed onto the treated tile. The exposure time is 30 minutes.

24 hours after contact with the treated surface, mortality in % is determined. 100% means that all mosquitoes have been killed; 0% means that none of the mosquitoes have been killed.

In this test, for example, the following compounds from the preparation examples show efficacy of 90-100% at an application rate of 100 mg/m$^2$: I-T3-24, I-T3-25, I-T3-38, I-T3-43, I-T3-46, I-T3-54, I-T3-56, I-T3-58, I-T3-63, I-T3-86, I-T3-92, I-T3-99, I-T3-100, I-T3-102, I-T3-107, I-T3-112, I-T3-113, I-T3-115, I-T3-123, I-T3-133, I-T3-134, I-T3-136, I-T3-145, I-T3-148, I-T3-155, I-T3-159, I-T3-160, I-T3-162, I-T3-189, I-T22-1, I-T22-2

In this test, for example, the following compounds from the preparation examples show efficacy of 90-100% at an application rate of 20 mg/m$^2$: I-T3-3, I-T3-24, I-T3-25, I-3-26, I-T3-38, I-T3-42, I-T3-43, I-T3-46, I-T3-52, I-T3-53, I-T3-54, I-T3-55, I-T3-57, I-T3-61, I-T3-63, I-T3-92, I-T3-93, I-T3-99, I-T3-100, I-T3-102, I-T3-107, I-T3-112, I-T3-113, I-T3-116, I-T3-123, I-T3-134, I-T3-136, I-T3-145, I-T3-148, I-T3-155, I-T3-159, I-T3-160, I-T3-162, I-T3-189, I-T22-1, I-T22-2, I-T23-1, I-T23-2

*Aedes* Test (AEDSAE Surface Treatment)

Solvent: acetone+2000 ppm rapeseed oil methyl ester (RME)

To produce an appropriate active ingredient formulation, the active ingredient is dissolved in the solvent (2 mg/ml). The active ingredient formulation is pipetted onto a glazed tile and, after it has dried off, adult mosquitoes of the species *Aedes aegypti* strain MONHEIM are placed onto the treated tile. The exposure time is 30 minutes.

24 hours after contact with the treated surface, mortality in % is determined. 100% means that all mosquitoes have been killed; 0% means that none of the mosquitoes have been killed.

In this test, for example, the following compounds from the preparation examples show efficacy of 90-100% at an application rate of 100 mg/m$^2$: I-T3-1, I-T3-3, I-T3-8, I-T3-20, I-T3-21, I-T3-23, I-T3-24, I-T3-25, I-T3-27, I-T3-28, I-T3-38, I-T3-42, I-T3-43, I-T3-46, I-T3-52, I-T3-53, I-T3-54, I-T3-55, I-T3-56, I-T3-57, I-T3-58, I-T3-61, I-T3-63, I-T3-64, I-T3-86, I-T3-87, I-T3-91, I-T3-92, I-T3-93, I-T3-96, I-T3-98, I-T3-99, I-T3-100, I-T3-101, I-T3-102, I-T3-103, I-T3-106, I-T3-107, I-T3-108, I-T3-112, I-T3-113, I-T3-115, I-T3-117, I-T3-118, I-T3-120, I-T3-123, I-T3-130, I-T3-133, I-T3-134, I-T3-136, I-T3-145, I-T3-148, I-T3-155, I-T3-160, I-T3-162, I-T3-163, I-T3-173, I-T3-189, I-T22-1, I-T22-2, I-T23-1, I-T23-2

In this test, for example, the following compounds from the preparation examples show efficacy of 90-100% at an application rate of 20 mg/m$^2$: I-T3-1, I-T3-3, I-T3-8, I-T3-20, I-T3-21, I-T3-23, I-T3-24, I-T3-25, I-T3-27, I-T3-28, I-T3-38, I-T3-42, I-T3-43, I-T3-46, I-T3-52, I-T3-53, I-T3-54, I-T3-55, I-T3-56, I-T3-57, I-T3-58, I-T3-61, I-T3-63, I-T3-64, I-T3-86, I-T3-87, I-T3-91, I-T3-92, I-T-93, I-T3-95, I-T3-96, I-T3-98, I-T3-99, I-T3-100, I-T3-101, I-T3-102, I-T3-103, I-T3-106, I-T3-107, I-T3-108, I-T3-112, I-T3-113, I-T3-115, I-T3-116, I-T3-117, I-T3-118, I-T3-123, I-T3-130, I-T3-133, I-T3-134, I-T3-136, I-T3-145, I-T3-148, I-T3-155, I-T3-159, I-T3-160, I-T3-162, I-T3-163, I-T3-173, I-T3-189, I-T22-1, I-T22-2, I-T23-1, I-T23-2

The invention claimed is:

1. A compound of formula (Ia")

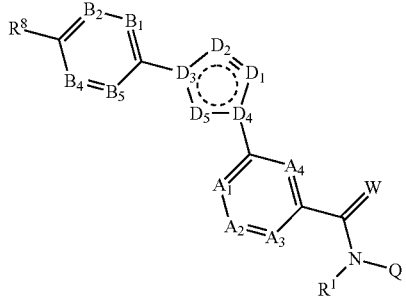

wherein
$D_1$ is C—R$^{11}$ or a heteroatom selected from N and O;
$D_2$ is C—R$^{11}$ or a heteroatom selected from N and O;
$D_3$ is C or N;
$D_4$ is C or N;
$D_5$ is C—R$^{11}$ or N;
where not more than one (1) or two moieties selected from $D_1$, $D_2$, $D_3$, $D_4$ and $D_5$ are a heteroatom;

is an aromatic system; and
$R^1$ is H, in each case optionally substituted $C_2$-$C_6$-alkenyl, $C_2$-$C_6$-alkynyl, $C_3$-$C_7$-cycloalkyl, $C_1$-$C_6$-alkylcarbonyl, $C_1$-$C_6$-alkoxycarbonyl, aryl($C_1$-$C_3$)-alkyl, or heteroaryl($C_1$-$C_3$)-alkyl;
the following moieties are as follows:
$A_1$ is CR$^2$ or N,
$A_2$ is CR$^3$ or N,
$A_3$ is CR$^4$ or N,
$A_4$ is CR$^5$ or N,
$B_1$ is CR$^6$ or N,
$B_2$ is CR$^7$ or N,
$B_4$ is CR$^9$ or N, and
$B_5$ is CR$^{10}$ or N,
but not more than three of the $A_1$ to $A_4$ moieties are N and not more than one moiety selected from $B_1$, $B_2$, $B_4$, and $B_5$ is N;
$R^2$, $R^3$, $R^4$, $R^5$, $R^6$, $R^7$, $R^9$ and $R^{10}$ are each independently H, halogen, cyano, nitro, in each case optionally substituted $C_1$-$C_6$-alkyl, $C_3$-$C_6$-cycloalkyl, $C_1$-$C_6$-alkoxy, N—$C_1$-$C_6$-alkoxyimino-$C_1$-$C_3$-alkyl, $C_1$-$C_6$-alkylsulphanyl, $C_1$-$C_6$-alkylsulphinyl, $C_1$-$C_6$-alkylsulphonyl, N—$C_1$-$C_6$-alkylamino, N,N-di-$C_1$-$C_6$-alkylamino or N—$C_1$-$C_3$-alkoxy-$C_1$-$C_4$-alkylamino or 1-pyrrolidinyl;
wherein R$^6$ and R$^{10}$ are not both H, if neither of the $A_2$ and $A_3$ moieties is N, R$^3$ and R$^4$ together with the carbon atom to which they are bonded may form a 5- or 6-membered ring containing 0, 1 or 2 nitrogen atoms and/or 0 or 1 oxygen atom and/or 0 or 1 sulphur atom, or if neither of the $A_1$ and $A_2$ moieties is N, R$^2$ and R$^3$ together with the carbon atom to which they are bonded may form a 6-membered ring containing 0, 1 or 2 nitrogen atoms;

R$^8$ is fluorine-substituted $C_1$-$C_4$-alkoxy or fluorine-substituted $C_1$-$C_4$-alkyl;

R$^{11}$ is independently H;

W is O or S;

Q is H, formyl, hydroxyl, amino or in each case optionally substituted $C_1$-$C_6$-alkyl, $C_2$-$C_6$-alkenyl, $C_2$-$C_6$-alkynyl, $C_3$-$C_6$-cycloalkyl, $C_1$-$C_5$-heterocycloalkyl, $C_1$-$C_4$-alkoxy, $C_1$-$C_6$-alkyl-$C_3$-$C_6$-cycloalkyl, $C_3$-$C_6$-cycloalkyl-$C_1$-$C_6$-alkyl, $C_6$-,$C_{10}$-$C_{14}$-aryl, $C_1$-$C_5$-heteroaryl, $C_6$-,$C_{10}$-,$C_{14}$-aryl-($C_1$-$C_3$)-alkyl, $C_1$-$C_5$-heteroaryl-($C_1$-$C_3$)-alkyl, N—$C_1$-$C_4$-alkylamino, N—$C_1$-$C_4$-alkylcarbonylamino, or N,N-di-$C_1$-$C_4$-alkylamino; or is an optionally poly-V-substituted unsaturated 6-membered carbocycle; or is an optionally poly-V-substituted unsaturated 4-, 5- or 6-membered heterocyclic ring, where V is independently halogen, cyano, nitro, in each case optionally substituted $C_1$-$C_6$-alkyl, $C_1$-$C_4$-alkenyl, $C_1$-$C_4$-alkynyl, $C_3$-$C_6$-cycloalkyl, $C_1$-$C_6$-alkoxy, N—$C_1$-$C_6$-alkoxyimino-$C_1$-$C_3$-alkyl, $C_1$-$C_6$-alkylsulphanyl, $C_1$-$C_6$-alkylsulphinyl, $C_1$-$C_6$-alkylsulphonyl, or N,N-di-($C_1$-$C_6$-alkyl)amino;

and/or one or more salts, N-oxides and/or tautomeric forms of the compounds of the formula (Ia").

2. A compound according to claim 1, wherein the compound of formula (Ia") is a compound of formula (I-T3)

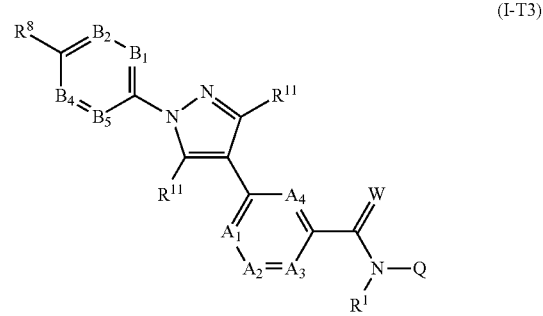

wherein,
not more than one moiety selected from $A_1$, $A_2$, $A_3$, $A_4$ is N.

3. A compound according to claim 1, wherein the compound of formula (Ia") is a compound of formula (I-T2)

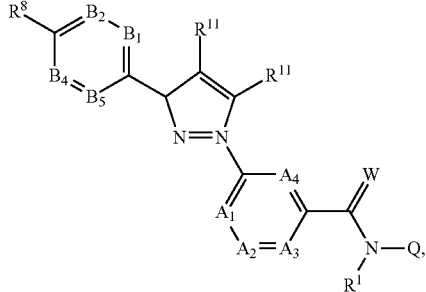

(I-T2)

where not more than one moiety selected from $A_1, A_2, A_3, A_4$ is N.

4. A compound according to claim 1, wherein the compound of formula (Ia") is a compound of formula (I-T4)

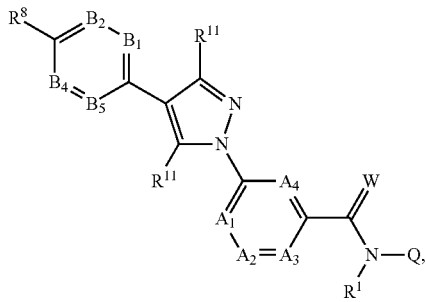

(I-T4)

where not more than one moiety selected from $A_1, A_2, A_3, A_4$ is N.

5. A compound according to claim 1, wherein the compound of the formula (Ia") is a compound of formula (I-T22)

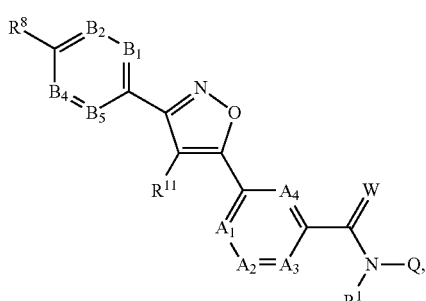

(T-22)

where not more than one moiety selected from $A_1, A_2, A_3, A_4$ is N.

6. A compound according to claim 1, wherein the compound of formula (Ia") is a compound of formula (I-T23)

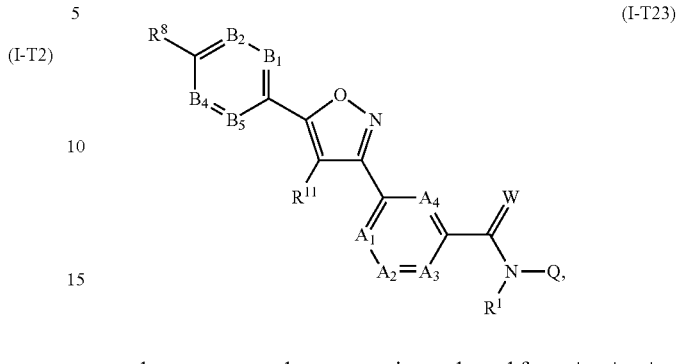

(I-T23)

where not more than one moiety selected from $A_1, A_2, A_3, A_4$ is N.

7. A compound according to claim 1, wherein the compound of formula (Ia") is a compound of formula (I-T46)

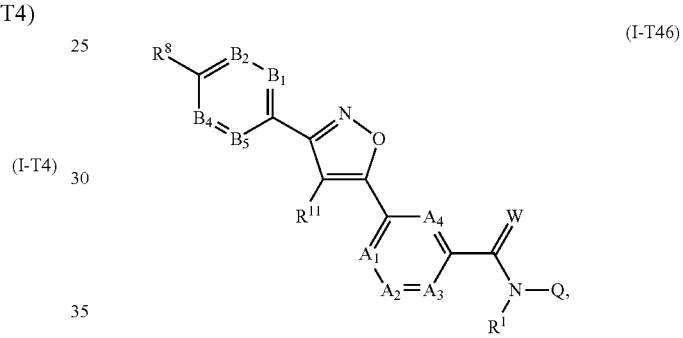

(I-T46)

where not more than one moiety selected from $A_1, A_2, A_3, A_4$ is N.

8. A compound according to claim 1, wherein W is O.

9. A compound according to claim 1, wherein W is O and, $R^8$ is fluorine-substituted $C_1$-$C_3$-alkyl or -substituted $C_1$-$C_3$-alkoxy.

10. A compound according to claim 1, wherein the $A_1$ to $A_4$ and $B_1$ to $B_5$ moieties are as follows:
$A_1$ is C—H,
$A_2$ is $CR^3$ or N,
$A_3$ is $CR^4$,
$A_4$ is C—H,
$B_1$ is $CR^6$ or N,
$B_2$ is C—H,
$B_4$ is C—H and
$B_5$ is $CR^{10}$ or N.

11. A compound according to claim 1, wherein $R^1$ is H.

12. A compound according to claim 1, wherein Q is $C_1$-$C_3$-alkyl, cyclopropyl, 1-(cyano)cyclopropyl, 1-(perfluorinated $C_1$-$C_3$-alkyl)cyclopropyl, 1-($C_1$-$C_4$-alkyl)cyclopropyl, 1-(thiocarbamoyl)cyclopropyl, halogen-substituted $C_1$-$C_3$-alkyl, thietan-3-yl, N-methylpyrazol-3-yl or 2-oxo-2 (2,2,2-trifluoroethylamino)ethyl.

13. An insecticidal composition, comprising a content of at least one compound according to claim 1 and an extender and/or a surface-active substance.

14. A method of controlling insects, arachnids and/or nematodes comprising allowing a compound according to claim 1 to act on the insects, arachnids and/or nematodes, and/or their habitat.

15. A method of controlling animal pests, comprising allowing a compound according to claim 1 to act on the pests and/or their habitat.

16. A method of controlling insects, arachnids and/or nematodes comprising allowing a composition according to claim 13 to act on the insects, arachnids or nematodes, and/or their habitat.

17. A method of controlling animal pests, comprising allowing a composition according to claim 13 to act on the pests and/or their habitat.

* * * * *